(12) United States Patent
Gersbach et al.

(10) Patent No.: US 11,970,710 B2
(45) Date of Patent: Apr. 30, 2024

(54) GENOME ENGINEERING WITH TYPE I CRISPR SYSTEMS IN EUKARYOTIC CELLS

(71) Applicants: Duke University, Durham, NC (US); North Carolina State University, Raleigh, NC (US)

(72) Inventors: Charles A. Gersbach, Durham, NC (US); Adrian Pickar Oliver, Durham, NC (US); Chase Beisel, Raleigh, NC (US)

(73) Assignees: Duke University, Durham, NC (US); North Carolina State University, Raleigh, NC (US)

( * ) Notice: Subject to any disclaimer, the term of this patent is extended or adjusted under 35 U.S.C. 154(b) by 414 days.

(21) Appl. No.: 15/766,912

(22) PCT Filed: Oct. 13, 2016

(86) PCT No.: PCT/US2016/056925
§ 371 (c)(1),
(2) Date: Apr. 9, 2018

(87) PCT Pub. No.: WO2017/066497
PCT Pub. Date: Apr. 20, 2017

(65) Prior Publication Data
US 2018/0334688 A1    Nov. 22, 2018

Related U.S. Application Data

(60) Provisional application No. 62/382,240, filed on Aug. 31, 2016, provisional application No. 62/240,716, filed on Oct. 13, 2015, provisional application No. 62/240,743, filed on Oct. 13, 2015.

(51) Int. Cl.
| | | |
|---|---|---|
| *C12N 15/90* | (2006.01) | |
| *C12N 9/22* | (2006.01) | |
| *C12N 15/10* | (2006.01) | |
| *C12N 15/11* | (2006.01) | |

(52) U.S. Cl.
CPC ............. *C12N 15/907* (2013.01); *C12N 9/22* (2013.01); *C12N 15/102* (2013.01); *C12N 15/11* (2013.01); *C07K 2319/00* (2013.01); *C07K 2319/09* (2013.01); *C07K 2319/21* (2013.01); *C07K 2319/41* (2013.01); *C07K 2319/43* (2013.01); *C07K 2319/80* (2013.01); *C12N 2310/20* (2017.05); *C12N 2740/15043* (2013.01); *C12N 2740/16043* (2013.01); *C12N 2800/22* (2013.01); *C12N 2830/001* (2013.01)

(58) Field of Classification Search
CPC .... C12N 15/907; C12N 15/102; C12N 15/11; C12N 9/22; C12N 2740/16043; C12N 2310/20; C12N 2800/22; C12N 2830/001; C12N 2740/15043; C07K 2319/21; C07K 2319/80; C07K 2319/41; C07K 2319/09; C07K 2319/43; C07K 2319/00
See application file for complete search history.

(56) References Cited

U.S. PATENT DOCUMENTS

| | | | |
|---|---|---|---|
| 3,687,808 | A | 8/1972 | Merigan, Jr. |
| 4,469,863 | A | 9/1984 | Ts'o et al. |
| 4,476,301 | A | 10/1984 | Imbach et al. |
| 4,501,729 | A | 2/1985 | Boucher et al. |
| 4,554,101 | A | 11/1985 | Hopp |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,737,323 | A | 4/1988 | Martin et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohtsuka et al. |
| 5,023,243 | A | 6/1991 | Tullis |
| 5,034,506 | A | 7/1991 | Summerton et al. |
| 5,082,830 | A | 1/1992 | Brakel et al. |

(Continued)

FOREIGN PATENT DOCUMENTS

| | | |
|---|---|---|
| CA | 2749305 A1 | 7/2010 |
| EP | 3009511 A2 | 4/2016 |

(Continued)

OTHER PUBLICATIONS

GenBank P38036.2. GenBank2013. p. 1-4 (Year: 2013).*

(Continued)

*Primary Examiner* — Paul J Holland

(74) *Attorney, Agent, or Firm* — Michael Best & Friedrich LLP

(57) ABSTRACT

Disclosed herein are Type I Clustered Regularly Interspaced Short Palindromic Repeats (CRISPR)/CRISPR-associated (Cas) system related compositions and methods of using said Type I CRISPR/Cas system related compositions for altering gene expression and genome engineering. The invention relates to compositions comprising Type I CRISPR-Cas polypeptides and CRISPR array nucleic acids designed for genome modification in eukaryotic cells and for targeted killing of eukaryotic cells.

17 Claims, 73 Drawing Sheets

Specification includes a Sequence Listing.

(56) References Cited

U.S. PATENT DOCUMENTS

| | | |
|---|---|---|
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,219,740 A | 6/1993 | Miller et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warren, III |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,473 A | 4/1996 | Camerini-otero et al. |
| 5,510,475 A | 4/1996 | Agrawal et al. |
| 5,512,439 A | 4/1996 | Horner et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,593,972 A | 1/1997 | Weiner et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,663,312 A | 9/1997 | Chaturvedula et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,773,700 A | 6/1998 | Van Grinsven et al. |
| 5,962,428 A | 10/1999 | Carrano et al. |
| 6,140,081 A | 10/2000 | Barbas |
| 6,207,453 B1 | 3/2001 | Maass et al. |
| 6,268,490 B1 | 7/2001 | Imanishi et al. |
| 6,287,860 B1 | 9/2001 | Monia et al. |
| 6,453,242 B1 | 9/2002 | Eisenberg et al. |
| 6,462,254 B1 | 10/2002 | Vernachio et al. |
| 6,534,261 B1 | 3/2003 | Cox, III et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,074,596 B2 | 7/2006 | Darzynkiewicz et al. |
| 7,084,125 B2 | 8/2006 | Wengel |
| 7,449,561 B1 | 11/2008 | Sommer et al. |
| 7,572,582 B2 | 8/2009 | Wengel et al. |
| 7,728,118 B2 | 6/2010 | Wood et al. |
| 7,745,651 B2 | 6/2010 | Heyes et al. |
| 7,799,565 B2 | 9/2010 | Maclachlan et al. |
| 8,278,036 B2 | 10/2012 | Kariko et al. |
| 8,450,107 B1 | 5/2013 | Zhang et al. |
| 8,586,526 B2 | 11/2013 | Gregory et al. |
| 8,889,356 B2 | 11/2014 | Zhang |
| 9,139,554 B2 | 9/2015 | Hope et al. |
| 9,458,205 B2 | 10/2016 | Gregory et al. |
| 9,890,364 B2 | 2/2018 | Joung et al. |
| 10,266,850 B2 | 4/2019 | Doudna et al. |
| 11,421,251 B2 | 8/2022 | Gersbach et al. |
| 11,427,817 B2 | 8/2022 | Josephs et al. |
| 11,898,176 B2 | 2/2024 | Gersbach et al. |
| 2002/0160940 A1 | 10/2002 | Case et al. |
| 2004/0142025 A1 | 7/2004 | Maclachlan et al. |
| 2004/0175727 A1 | 9/2004 | Draghia-Akli et al. |
| 2004/0192593 A1 | 9/2004 | Draghia-Akli et al. |

(56) References Cited

U.S. PATENT DOCUMENTS

| | | |
|---|---|---|
| 2004/0204345 A1 | 10/2004 | Case et al. |
| 2006/0068395 A1 | 3/2006 | Wood et al. |
| 2006/0211647 A1 | 9/2006 | Khan |
| 2007/0042031 A1 | 2/2007 | Maclachlan et al. |
| 2007/0042462 A1 | 2/2007 | Hildinger |
| 2007/0059795 A1 | 3/2007 | Moore et al. |
| 2007/0185042 A1 | 8/2007 | Tsai et al. |
| 2007/0192880 A1 | 8/2007 | Muyan et al. |
| 2008/0070299 A1 | 3/2008 | Wood et al. |
| 2008/0090291 A1 | 4/2008 | Wood et al. |
| 2009/0018031 A1 | 1/2009 | Trinklein et al. |
| 2010/0035968 A1 | 2/2010 | Rasmussen et al. |
| 2010/0076057 A1 | 3/2010 | Sontheimer et al. |
| 2010/0261175 A1 | 10/2010 | Rasmussen et al. |
| 2010/0267018 A1 | 10/2010 | Wengel et al. |
| 2011/0145940 A1 | 6/2011 | Voytas et al. |
| 2011/0197290 A1 | 8/2011 | Fahrenkrug et al. |
| 2011/0263682 A1 | 10/2011 | De Kimpe et al. |
| 2011/0301073 A1 | 12/2011 | Gregory et al. |
| 2012/0207744 A1 | 8/2012 | Mendlein et al. |
| 2013/0274129 A1 | 10/2013 | Katzen et al. |
| 2014/0179006 A1 | 6/2014 | Zhang |
| 2014/0234975 A1 | 8/2014 | Silva et al. |
| 2014/0295557 A1 | 10/2014 | Joung et al. |
| 2014/0315862 A1 | 10/2014 | Kaye |
| 2014/0356956 A1 | 12/2014 | Church et al. |
| 2015/0024499 A1 | 1/2015 | Brouns et al. |
| 2015/0044772 A1 | 2/2015 | Zhao |
| 2015/0045413 A1 | 2/2015 | De Visser et al. |
| 2015/0056705 A1 | 2/2015 | Conway et al. |
| 2015/0159178 A1 | 6/2015 | Green et al. |
| 2016/0002634 A1 | 1/2016 | Sazani et al. |
| 2016/0040189 A1 | 2/2016 | Kennedy et al. |
| 2016/0058889 A1 | 3/2016 | Olson et al. |
| 2016/0177278 A1 | 6/2016 | Wolfe et al. |
| 2016/0281166 A1 | 9/2016 | Bhattacharjee et al. |
| 2017/0204407 A1 | 7/2017 | Gilbert et al. |
| 2017/0283831 A1 | 10/2017 | Zhang et al. |
| 2018/0073012 A1 | 3/2018 | Liu et al. |
| 2018/0135109 A1 | 5/2018 | Jayaram et al. |
| 2018/0201951 A1 | 7/2018 | Guilak et al. |
| 2018/0251735 A1 | 9/2018 | Ko |
| 2018/0305719 A1 | 10/2018 | Perez-Pinera et al. |
| 2018/0327740 A1 | 11/2018 | Gifford et al. |
| 2019/0032049 A1 | 1/2019 | Naldini et al. |
| 2019/0038776 A1 | 2/2019 | Pyle et al. |
| 2019/0048337 A1 | 2/2019 | Hsu et al. |
| 2019/0062790 A1 | 2/2019 | Doudna et al. |
| 2019/0078119 A1 | 3/2019 | Wilson et al. |
| 2019/0106710 A1 | 4/2019 | Zhang et al. |
| 2019/0183932 A1 | 6/2019 | Mackall et al. |
| 2019/0201402 A1 | 7/2019 | Jiang et al. |
| 2019/0248854 A1 | 8/2019 | Tremblay et al. |
| 2019/0264232 A1 | 8/2019 | Hou et al. |
| 2019/0374655 A1 | 12/2019 | Kabadi et al. |
| 2020/0002731 A1 | 1/2020 | Frendewey et al. |
| 2020/0056206 A1 | 2/2020 | Tremblay et al. |
| 2020/0080108 A1 | 3/2020 | Jaskula-Ranga et al. |
| 2020/0123533 A1 | 4/2020 | Wang et al. |
| 2020/0216549 A1 | 7/2020 | Fukumura et al. |
| 2020/0216810 A1 | 7/2020 | Metelitsa et al. |
| 2020/0260698 A1 | 8/2020 | Kyrychenko et al. |
| 2021/0322577 A1 | 10/2021 | Lande et al. |
| 2022/0098561 A1 | 3/2022 | Gersbach et al. |
| 2022/0177879 A1 | 6/2022 | Gersbach et al. |
| 2022/0184229 A1 | 6/2022 | Gersbach et al. |
| 2022/0195406 A1 | 6/2022 | Gersbach et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2023/0201375 A1 | 6/2023 | Gersbach et al. |
| 2023/0348870 A1 | 11/2023 | Gersbach et al. |
| 2023/0349888 A1 | 11/2023 | Gersbach et al. |
| 2023/0383270 A1 | 11/2023 | Gersbach et al. |
| 2023/0383297 A1 | 11/2023 | Gersbach et al. |
| 2023/0392132 A1 | 12/2023 | Gersbach et al. |
| 2024/0026352 A1 | 1/2024 | Gersbach et al. |

FOREIGN PATENT DOCUMENTS

| | | | |
|---|---|---|---|
| EP | 3209783 B1 | 11/2021 | |
| EP | 3995584 A1 | 5/2022 | |
| JP | 2015-534817 A | 12/2015 | |
| JP | 2016-521452 A2 | 7/2016 | |
| JP | 2016-521975 A | 7/2016 | |
| JP | 2016-523082 A | 8/2016 | |
| KR | 20190134673 A | 12/2019 | |
| WO | WO1991/18114 A1 | 11/1991 | |
| WO | WO1992/0000387 A1 | 1/1992 | |
| WO | WO1993/007883 A1 | 4/1993 | |
| WO | WO 1993/024640 A2 | 12/1993 | |
| WO | WO 1994/016737 A1 | 8/1994 | |
| WO | WO1998/053058 A1 | 11/1998 | |
| WO | WO1998/053059 A1 | 11/1998 | |
| WO | WO1998/053060 A1 | 11/1998 | |
| WO | 2001/083793 A2 | 11/2001 | |
| WO | WO2001/083783 A2 | 11/2001 | |
| WO | WO2002/016536 A1 | 2/2002 | |
| WO | WO2003/016496 A2 | 2/2003 | |
| WO | WO2003/072788 A1 | 9/2003 | |
| WO | WO2007/019301 A2 | 2/2007 | |
| WO | WO2008/006028 A2 | 1/2008 | |
| WO | WO2008/070859 A2 | 6/2008 | |
| WO | WO-2010075424 A2 * | 7/2010 | ........... C12N 15/113 |
| WO | WO2010/144740 A1 | 12/2010 | |
| WO | WO2011/036640 A2 | 3/2011 | |
| WO | 2011/141820 A1 | 11/2011 | |
| WO | WO2011/154427 A1 | 12/2011 | |
| WO | WO2012/136476 A1 | 10/2012 | |
| WO | 2013/098244 A1 | 7/2013 | |
| WO | WO2014/018423 A2 | 1/2014 | |
| WO | WO2014/059255 A1 | 4/2014 | |
| WO | WO2014/065596 A1 | 5/2014 | |
| WO | WO2014/081855 A1 | 5/2014 | |
| WO | 2014/089290 A1 | 6/2014 | |
| WO | 2014/093622 A2 | 6/2014 | |
| WO | 2014/093712 A1 | 6/2014 | |
| WO | WO2014/093479 A1 | 6/2014 | |
| WO | WO2014/093595 A1 | 6/2014 | |
| WO | WO2014/093709 A1 | 6/2014 | |
| WO | WO2014/144592 A2 | 9/2014 | |
| WO | WO 2014/197748 A2 | 12/2014 | |
| WO | WO2014/204726 A1 | 12/2014 | |
| WO | WO 2015/006747 A2 | 1/2015 | |
| WO | WO2015/035136 A2 | 3/2015 | |
| WO | WO2015/048690 A1 | 4/2015 | |
| WO | WO2015/070083 A1 | 5/2015 | |
| WO | WO2015/089427 A1 | 6/2015 | |
| WO | WO 2015/155686 A2 | 10/2015 | |
| WO | WO2015/161276 A2 | 10/2015 | |
| WO | 2016/011080 A2 | 1/2016 | |
| WO | WO2016/011070 A2 | 1/2016 | |
| WO | WO2016/049258 A2 | 3/2016 | |
| WO | WO2016/063264 A1 | 4/2016 | |
| WO | WO2016/070070 A1 | 5/2016 | |
| WO | WO2016/081924 A1 | 5/2016 | |
| WO | WO2016/114972 A1 | 7/2016 | |
| WO | WO2016/123578 A1 | 8/2016 | |
| WO | WO2016/161380 A1 | 10/2016 | |
| WO | WO2016/187717 A1 | 12/2016 | |
| WO | WO2017/049266 A2 | 3/2017 | |
| WO | WO2017/049407 A1 | 3/2017 | |
| WO | 2017/066497 A2 | 4/2017 | |
| WO | WO2017/070632 A2 | 4/2017 | |
| WO | WO2017/072590 A1 | 5/2017 | |
| WO | WO2017/075478 A2 | 5/2017 | |
| WO | WO2017/139505 A2 | 8/2017 | |
| WO | WO2017/165859 A1 | 9/2017 | |
| WO | 2017/180976 A1 | 10/2017 | |
| WO | 2018/002812 A1 | 1/2018 | |
| WO | WO2018/017751 A1 | 1/2018 | |

(56) References Cited

FOREIGN PATENT DOCUMENTS

| | | |
|---|---|---|
| WO | WO2018/035388 A1 | 2/2018 |
| WO | WO2018/035495 A1 | 2/2018 |
| WO | WO2018/081504 A1 | 5/2018 |
| WO | WO2018/098480 A1 | 5/2018 |
| WO | WO2018/129296 A1 | 7/2018 |
| WO | 2018/162702 A1 | 9/2018 |
| WO | 2018/179578 A1 | 10/2018 |
| WO | WO2018/191388 A1 | 10/2018 |
| WO | 2019/023291 A2 | 1/2019 |
| WO | WO2019/002590 A1 | 1/2019 |
| WO | WO2019/067786 A1 | 4/2019 |
| WO | WO2019/077001 A1 | 4/2019 |
| WO | WO2019/079514 A1 | 4/2019 |
| WO | 2019/084050 A1 | 5/2019 |
| WO | WO2019/092505 A1 | 5/2019 |
| WO | 2019/113472 A1 | 6/2019 |
| WO | 2019/123014 A1 | 6/2019 |
| WO | 2019/204750 A1 | 10/2019 |
| WO | WO2019/232069 A1 | 12/2019 |
| WO | WO2020/124257 A1 | 6/2020 |
| WO | WO2020/163396 A1 | 8/2020 |
| WO | WO2020/257665 A1 | 12/2020 |
| WO | WO2021/0055956 A1 | 3/2021 |
| WO | WO2021/222328 A1 | 11/2021 |
| WO | 2022/038264 A1 | 2/2022 |
| WO | WO2022/087321 A1 | 4/2022 |
| WO | WO2022/104159 A1 | 5/2022 |
| WO | 2022/133062 A1 | 6/2022 |
| WO | WO2022/187288 A2 | 9/2022 |
| WO | WO2023/200998 A2 | 10/2023 |

OTHER PUBLICATIONS

Singh RK et al. Protein Engineering Approaches in the Post-Genomic Era. 2017. Current Protein and Peptide Science. 18, 1-11. (Year: 2017).*

Zhang M et al. Propagated Perturbations from a Peripheral Mutation Show Interactions Supporting WW Domain Thermostability. 2018. Structure. 26, 1474-1485. (Year: 2018).*

Mader et al., "CRISPR RNA-guided activation of endogenous human genes," Nature Methods, 2013, 10(10): 977-979.

Blakemore et al., "Editing of Human Genes May Begin by Year's End in the U.S." Smithsonian.com, <https://www.smithsonianmag.com/smart-news/editing-human-genes-may-begin-years-end-US-180959532/?no-ist> 2016.

Briner et al., "Lactobacillus buchneri genotyping on the basis of clustered regularly interspaced short palindromic repeat (CRISPR) locus diversity," Appl. Environ. Microbiol., 2014, 80: 994-1001.

Chen et al., "Targeted activation of diverse CRISPR-Cas systems for mammalian genome editing via proximal CRISPR targeting," Nature Communications, 2017, 8: 14958.

Crawford et al., "Genome-wide mapping of DNase hypersensitive sites using massively parallel signature sequencing (MPSS)," Genome Res, 2006, 16: 123-131.

Esvelt et al., "Orthogonal Cas9 proteins for RNA-guided gene regulation and editing," Nat. Methods, 2013, 10: 1116-1121.

Gasiunas et al., "Cas9-crRNA ribonucleoprotein complex mediates specific DNA cleavage for adaptive immunity in bacteria," Proc. Natl. Acad. Sci., 2012, 109: E2579-E2586.

Genbank Accenssion AP006627.1 (2016).
Genbank Accenssion BA000004.3 (2016).
Genbank Accenssion BAB04055.1 (2016).
GenBank Accession No. AAC75803.1 (2018).
GenBank Accession No. AIN33136.1 (2014).
GenBank Accession No. BAB04055.1 (2017).
GenBank Accession No. EOT14076.1 (2013).

Gomaa et al., "Programmable Removal of Bacterial Strains by Use of Genome-Targeting CRISPR-Cas Systems," 2014, mBio 5(1): e00928-13.

Gonda "Aerosols for delivery of therapeutic and diagnostic agents to the respiratory tract," Critical Reviews in Therapeutic Drug Carrier Systems, 1990 6:273-313.

Gong et al., "Molecular insights into DNA interference by CRISPR-associated nuclease-helicase Cas3," Proc Natl Acad Sci U S A, 2014, 111(46):16359-64.

Grissa et al., "CRISPRFinder: a web tool to identify clustered regularly interspaced short palindromic repeats," Nucleic Acids Res., 2007, 35(Web Server issue):W52-57.

Henikoff et al., "Amino acid substitution matrices from protein blocks," Proc. Natl. Acad. Sci. USA, 1992, 89: 10915-9.

Hilton et al., "Epigenome editing by a CRISPR-Cas9-based acetyltransferase activates genes from promoters and enhancers," Nat. Biotechnol, 2015, 33: 510-517.

Hsu et al., "Development and applications of CRISPR-Cas9 for genome engineering," Cell, 2014, 157(6):1262-78.

Jiang et al., "RNA-guided editing of bacterial genomes using CRISPR-Cas systems," Nat. Biotechnol., 2013, 31:233-239.

Karlin et al., "Applications and statistics for multiple high-scoring segments in molecular sequences," Proc. Natl. Acad. Sci. USA, 1993, 90: 5873-77.

Kyte et al., "A simple method for displaying the hydropathic character of a protein," J. Mol. Biol., 1982, 157:105-132.

Levskaya et al., "Synthetic biology: engineering *Escherichia coli*to see light," Nature, 2005, 438:441-442.

Makarova et al., "An updated evolutionary classification of CRISPR-Cas systems," Nature Reviews Microbiology, 2015, 13:722-736.

Mojica et al., "Short motif sequences determine the targets of the prokaryotic CRISPR defence system," Microbiology, 2009, 155: 733-740.

Murray et al., "Codon usage in plant genes," Nucl. Acids Res., 1989, 17:477-498.

Nam et al., "Cas5d protein processes pre-crRNA and assembles into a Cascade-like interference complex in Subtype I-C/Dvulg CRISPR-Cas system," Structure, 2012, 20:1574-1584.

Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23: 635-646.

Raeburn et al., "Techniques for drug delivery to the airways, and the assessment of lung function in animal models," J. Pharmacol. Toxicol. Meth., 1992, 27:143-159.

Semenova et al., "The Cas6e ribonuclease is not required for interference and adaptation by the E. colitype I-E CRISPR-Cas system," Nucleic Acids Res, 2015, 43(12):6049-61.

Seto et al., "Gene replacement therapies for duchenne muscular dystrophy using adeno-associated viral vectors," Current Gene Therapy, 2012, 12: 139-151.

Simpson, "Contacts between *Escherichia coli* RNA polymerase and thymines in the lac UV5 promoter," Proc. Natl. Acad. Sci. USA, 1979, 76: 3233-3237.

Spitz et al., "Transcription factors: from enhancer binding to developmental control," Nat Rev Genet, 2012, 13: 613-26.

Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.

Tyle, "Iontophoretic Devices for Drug Delivery," Pharm. Res., 1986, 3: 318-326.

Van der Oost et al., "Unravelling the structural and mechanistic basis of CRISPR-Cas systems," Nature Reviews Microbiology, 2014, 12: 479-492.

Wada et al., "Codon usage tabulated from the GenBank genetic sequence data," Nucl. Acids Res., 1990, 18: 2367-2411.

Wherry, "T cell exhaustion," Nat.Immunology, 2011, 12: 492-499.

Zhao et al., "High-efficiency transfection of primary human and mouse T lymphocytes using RNA electroporation," Mol. Ther., 2006, 13: 151-159.

International Search Report and Written Opinion for Application No. PCT/US2016/056925 dated Apr. 28, 2017 (30 pages).

European Patent Office Action for Application No. 16856228.8 dated Sep. 21, 2020 (6 pages).

Makarova et al., "Evolution and classification of the CRISPR-Cas systems," Nature Reviews Microbiology, 2011, pp. 467-477.

(56) References Cited

OTHER PUBLICATIONS

Russa et al. "The New State of the Art: Cas9 for Gene Activation and Repression," Molecular and Cellular Biology, 2015, 35(22):3800-3809.
European Patent Office Extended Search Report for Application No. 16856228.8 dated Jun. 13, 2019 (16 pages).
Ousterout et al., "Genetic Correction of Duchenne Muscular Dystrophy Using Zinc Finger Nucleases," Mol. Ther., 2013, vol. 21, Supplement 1, 292, p. S111-S112.
Rousseau et al., "New TALENs To Correct the Reading Frame of Exon 54 of the Dystrophin Gene," Mol. Ther., 2013, vol. 21, Supplement 1, 293, p. S112.
International Search Report and Written Opinion for Application No. PCT/US2019/014386 dated Jun. 26, 2019 (16 pages).
United States Patent Office Notice of Allowance for U.S. Appl. No. 16/837,395 dated Apr. 13, 2022 (12 pages).
United States Patent Office Supplemental Notice of Allowance for U.S. Appl. No. 16/837,395 dated May 12, 2022 (5 pages).
'T Hoen et al., "Generation and characterization of transgenic mice with the full-length human DMD gene," J. Biol. Chem., 2008, 283: 5899-5907.
Aartsma-Rus et al., "Antisense-mediated exon skipping: a versatile tool with therapeutic and research applications," RNA, 2007, 13: 1609-1624.
Aartsma-Rus et a., "Exploring the frontiers of the therapeutic exon skipping for Duchenne muscular dystrophy by double targeting within one or multiple exons," Mol Ther, 2006, 14: 401-407.
Aartsma-Rus et al., "Theoretic applicability of antisense-medaited exon skipping for Duchenne muscular dystrophy mutations," Hum Mutat, 2009, 30: 293-299.
Acosta et al., "Use of two gRNAs for CRISPR/Cas9 improves bi-allelic homologous recomgination efficiency in mouse embryonic stem cells," Genesis, 2018, 56(5): 1-8.
Adamson et al., "a Multiplexed Single-Cell CRISPR Screening Platform Enables Systematic Dissection of the Unfolded Protein Response," Cell, 2016, 167: 1867-1182 e1821.
Adamson et al., "A Multiplexed Single-Cell CRISPR Screening Platform Enables Systematic Dissection of the Unfolded Protein Response," Cell, 2016, 167: 1867-1882.e21.
Adler et al., "Nonviral direct conversion of primary mouse embryonic fibroblasts to neuronal cells," Molecular therapy, 2012 Nucleic acids 1, e32.
Aguilar et al., "Transcriptional and Chromatin Dynamics of Muscle Regeneration after Severe Trauma," Stem Cell Rep, 2016, 7: 983-997.
Ahlenius et al., "FoxO3 regulates neuronal reprogramming of cells from postnatal and aging mice," Proc Natl Acad Sci U S A, 2016, 113: 8514-8519.
Aiuti et al., "Lentiviral hematopoietic stem cell gene therapy in patients with Wiskott-Aldrich syndrome," Science, 2013, 341 (6148): 1233151.
Albuquerque et al., "Mammalian nicotinic acetylcholine receptors: from structure to function," Physiol Rev, 2009, 89: 73-120.
Aloia, "Epigenetic Regulation of Cell-Fate Changes That Determine Adult Liver Regeneration After Injury," Front. Cell Dev. Biol., 2021, 9: 643055.
Amabile et al., "Inheritable Silencing of Endogenous Genes by Hit-and-Run Targeted Epigenetic Editing," Cell, 2016, 167(1): 219-232.e14.
Amabile et al., "Permanent Epigenetic Silencing of Human Genes with Artificial Transcriptional Repressors,", Molecular Therapy, 2015, 23(Suppl. 1): S275.
Amoasii et al., "Gene editing restores dystrophin expression in a canine model of Duchenne muscular dystrophy," Science, 2018, 362: 86-91.
Amoasii et al., "Single-cut genome editing restores dystrophin expression in a new mouse model of muscular dystrophy," Sci Transl Med, Nov. 2017, 9(418): eaan8081.
Anders et al., "Differential expression analysis for sequence count data," Genome biology 11, 2010, R106.

Andersen et al., "Dual role of delta-like 1 homolog (DLK1) in skeletal muscle development and adult muscle regeneration," Development, 2013, 140: 3743-3753.
Anguela et al., "Robust ZFN-mediated genome editing in adult hemophilic mice," Blood, 2013, 122: 3283-3287.
Aoki et al., "Bodywide skipping of exons 45-55 in dystrophic mdx52 mice by systemic antisense delivery," Proc Natl Acad Sci USA, 2012, 109: 13763-13768.
Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.
Arnett et al., "Adeno-associated viral vectors do not efficiently target muscle satellite cells," Molecular Therapy Methods & Clinical Development, 2014, 1: 14038.
Asokan et al., "Reengineering a receptor footprint of adeno-associated virus enables selective and systemic gene transfer to muscle," Nat Biotechnol, 2010, 28: 79-82.
Asrani et al., "Burden of liver diseases in the world," J Hepatol, 2019, 70(1): 151-171.
Bae et al., "Cas-OFFinder: a fast and versatile algorithm that searches for potential off-target sites of Cas9 RNA-guided endonucleases," Bioinformatics, 2014, 30: 1473-1475.
Balboa et al., "Conditionally Stabilized dCas9 Activator for Controlling Gene Expression in Human Cell Reprogramming and Differentiation," Stem Cell Rep, 2015, 5: 448-459.
Baratta et al., "Cellular organization of normal mouse liver: a histological, quantitative immunocytochemical, and fine structural analysis," Histochem Cell Biol, 2009, 131(6): 713-726.
Barberi et al., "Derivation of engraftable skeletal myoblasts from human embryonic stem cells," Nat Med, 2007, 13: 642-648.
Barr et al., "Predominant Expression of Alternative PAX3 and PAX7 Forms in Myogenic and Neural Tumor Cell Lines," Cancer Res, 1999, 59: 5443-5448.
Barrangou et al., "CRISPR provides acquired resistance against viruses in prokaryotes," Science, 2007, 315(5819): 1709-1712.
Bartel et al., "Isolation of new ribozymes from a large pool of random sequences,"Science, 1993, 261(5127): 1411-1418.
Bartsevich et al., "Engineered zinc finger proteins for controlling stem cell fate,"Stem Cells, 2003, 21: 632-637.
Bauer et al., "An erythroid enhancer of BCL11A subject to genetic variation determines fetal hemoglobin level," Science 342, 2013, 253-257.
Beaudry et al., "Direction evolution of an RNA enzyme," Science, 1992, 257(5070: 635-641.
Beerli et al., "Chemically regulated zinc finger transcription factors," J Biol Chem, 2000, 275(42): 32617-27.
Beerli et al., "Engineering polydactyl zinc-finger transcription factors," Nat Biotechnol, 2002, 20: 135-141.
Beerli et al., "Positive and negative regulation of endogenous genes by designed transcription factors," Proc Natl Acad Sci USA, 2000, 97: 1495-1500.
Beerli et al., "Toward Controlling gene expression at will: specific regulation of the erbB-2/HER-2 promoter by using polydactyl zinc finger proteins constructed from modular building blocks," Proc Natl Acad Sci USA, 1998, 95: 14628-14633.
Beltran et al., "Reactivation of a dormant tumor suppressor gene maspin by designed transcription factors," Oncogene, 2007, 26: 2791-2798.
Benedetti et al., "Repair or Replace? Exploiting Novel Gene and Cell Therapy Strategies for Muscular Dystrophies," FEBS Journal, 2013, 280: 4263-4280.
Bengtsson et al., "Muscle-specific CRISPR/Cas9 dystrophin gene editing ameliorates pathophysiology in a mouse model for Duchenne muscular dystrophy," Nat Commun, 2017, 8: 1-10.
Berghella et al., "Reversible immortalization of human myogenic cells by site-specific excision of a retrovirally transferred onco-gene," Human gene therapy, 1999, 10: 1607-1617.
Bernstein et al., "An integrated encyclopedia of DNA elements in the human genome," Nature, 2012, 489: 57-74.
Bhakta et al., "Highly active zinc-finger nucleases by extended modular assembly," Genome Res, 2013, 530-538.

(56) References Cited

OTHER PUBLICATIONS

Bidou et al., "Sense from nonsense: therapies for premature stop codon diseases," Trends in Molecular Medicine, 2012, 18: 679-688.
Bieth et al., "Highly restricted deletion of the SNORD116 region is implicated in Prader-Willi Syndrome," Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.
Bladen et al., "The TREAT-NMD DMD Global Database: analysis of more than 7,000 Duchenne muscular dystrophy mutations," Human Mutation, 2015, 36(4):395-402.
Blancafort et al., "Scanning the human genome with combinatorial transcription factor libraries," Nat Biotechnol, 2003, 21 : 269-274.
Blancafort et al., "Writing and rewriting the epigenetic code of cancer cells: from engineered proteins to small molecules," Mol. Pharmacol., 2013, 83(3): 563-576.
Boch et al., "Breaking the code of DNA binding specificity of TAL-type III effectors," Science, 2009, 326: 1509.
Boldrin et al., "Donor satellite cell engraftment is significantly augmented when the host niche is preserved and endogenous satellite cells are incapacitated," Stem Cells, 2012, 30: 1971-1984.
Bolger et al., "Trimmomatic: a flexible trimmer for Illumina sequence data," Bioinformatics, 2014, 30: 2114-2120.
Bowles et al., "Phase 1 Gene Therapy for Duchenne Muscular Dystrophy Using a Translation Optimized AAV Vector," Molecular Therapy, 2012, 20: 443-455.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," TIBTECH, 1994, 12: 268-274.
Breaker, "Are engineered proteins getting competition from RNA?," Curr. Op. Biotech., 1996, 7(4): 442-448.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Brummelkamp et al., "A system for stable expression of short interfering RNAs in mammalian cells," Science, 2002, 296(5567): 550-553.
Brunet et al., "Chromosomal translocations induced at specific loci in human stem cells," Proc Natl Acad Sci USA, 2009, 106: 10620-10625.
Brunger et al., "CRISPR/Cas9 Editing of Murine Induced Pluripotent Stem Cells for Engineering Inflammation-Resistant Tissues," Arthritis Rheumatol, 2017, 69: 1111-1121.
Brunger et al., "Genome Engineering of Stem Cells for Autonomously Regulated, Close-Loop Delivery of Biologic Drugs," Stem Cell Reports, 2017, 8: 1202-1213.
Buenrostro et al., "Transposition of native chromatin for fast and sensitive epigenomic profiling of open chromatin, DNA-binding proteins and nucleosome position," Nat Methods, 2013, 10: 1213-1218.
Buiting, "Prader-Willi syndrome and Angelman syndrome," Am J Med Genet C Semin Med Genet, 2010, 154C(3): 365-376.
Buler et al., "Energy sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, 2012, 287(3): 1847-1860.
Bultmann et al., "Targeted transcriptional activation of silent oct4 pluripotency gene by combining designer TALEs and inhibition of epigenetic modifuers," Nucleic Acs Res, 2012, 40: 5368-5377.
Burnett et al., "Deficiency in prohormone convertase PC1 impairs prohormone processing in Prader-Willi syndrome," J Clin Invest, 2017, 127: 293-305.
Busskamp et al., "Rapid neurogenesis through transcriptional activation in human stem cells," Mol Syst Biol, 2014, 10: 760.
Cano-Rodriguez et al., "Writing of H3K4Me3 overcomes epigenetic silencing in a sustained but context dependent manner," Nat Commun, 2016, 7: 12284.
Canver et al., "BCL11A enhancer dissection by Cas9-meidated in situ saturating mutagenesis," Nature, 2015, 527: 192-197.
Carroll, "A CRISPR approach to gene targeting," Molecular Therapy, 2012, 20: 1658-1660.
Cassidy et al., "Prader-Willi syndrome,"Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Cerletti et al., "Highly efficient, functional engraftment of skeletal muscle stem cells in dystrophic muscles," Cell, 2008, 134: 37-47.
Cermak et al., "Efficient design and assembly of custom TALEN and other TAL effector-based constructs for DNA targeting," Nucleic Acids Res, 2011, 30: e82.
Chal et al., "Differentiation of pluripotent stem cells to muscle fiber to model Duchenne muscular dystrophy," Nat Biotechnol, 2015, 33: 962-969.
Chamberlain et al., "Progress toward Gene Therapy for Duchenne Muscular Dystrophy," Mol. Ther., 2017, 25: 1125-1131.
Chanda et al., "Generation of induced neuronal cells by the single reprogramming factor ASCL1," Stem Cell Reports, 2014, 3: 282-296.
Chang et al., "Integrating Combinatorial Lipid Nanoparticle and Chemically Modified Protein for Intracellular Delivery and Genome Editing," Acc. Chem. Res., 2019, 52: 665-675.
Chapdelaine et al., "Meganucleases can restore the reading frame of a mutual dystrophin," Gene therapy, 2010, 17: 846-858.
Cheloufi et al., "The histone chaperone CAF-1 safeguards somatic cell identify," Nature, 2015, 528: 218-224.
Chen et al., "Acetylation of ReIA at discrete sites regulates distinct nuclear functions of NF-kB," The EMBO Journal, 2002, 21(23): 6539-6548.
Chen et al., "Dynamic imaging of genomic loci in living human cells by an optimized CRISPR/Cas systemm," Cell, 2013, 155: 1479-1491.
Chen et al., "Enrichr: interactive and collaborative HTML5 gene list enrichment analysis tool," BMC Bioinformatics, 2013, 14: 128.
Chen et al., "Genome-wide CRISPR screen in a mosue model of tumor growth and metastasis," Cell, 2015, 160: 1246-1260.
Chen et al., "microRNA-1 and microRNA-206 regulate skeletal muscle satellite cell proliferation and differentiation by repressing Pax7," J Cell Biol, 2010, 190: 867-879.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Cheng et al., "Multiplexed activation of endogenous genes by CRISPR-on, an RNA-guided transcriptional activator system," Cell Res, 2013, 23(10): 1163-1171.
Childers et al., "Gene therapy prolongs survival and restores function in murine and canine models of myotubular myopathy," Sci Transl Med, 2014, 6: 220ra210.
Cho et al., "Analysis of off-target effects of CRISPR-Cas-derived RNA-guided endonucleases and nickases," Genome Res, 2014, 24: 132-141.
Cho et al., "Targeted genome engineering in human cells with the Cas9 RNA-guided endonuclease," nat Biotechnol 2013, 31: 230-232.
Christian et al., "Targeting DNA double-strand breaks with TAL effector nucleases," Genetics, 2010, 186: 757-761.
Christoffersen et al., "Ribozymes as human therapeutic agents," J. Med. Chem., 1995, 38(12): 2023-2037.

(56) References Cited

OTHER PUBLICATIONS

Chronis et al., "Cooperative Binding of Transcription Factors Orchestrates Reprogramming," Cell, 2017, 168: 442-459 e420.
Cirak et al., "Exon skipping and dystrophin restoration in patients with Duchenne muscular dystrophy after systemic phosphorodiamidate morpholino oligomer treatment: an open-label, phase 2, dose-escalation study," Lancet, 2011, 378: 595-605.
Concise Encyclopedia of Polymer Science and Engineering, 1990, pp. 858-859.
Cong et al., "Multiplex Genome Engineering Using CRISPR/Case Systems," Science, 2013, 339: 819-823.
Cooper et al., "Improved induction of immune tolerance to factor IX by hepatic AAV-8 gene transfer," Hum Gene Ther, 209, 20: 767-776.
Corces et al., "The chromatin accessibility landscape of primary human cancers," Science, 2018, 362(6413): eaav1898.
Cordier et al., "Muscle-specific promoters may be necessary for adeno-associated virus-meidated gene transfer in the treatment of muscular dystrophies," Hum. Gene Ther., 2001, 12: 205-215.
Cornu et al., "DNA-binding specificity is a major determinant of the activity and toxicity of zinc-finger nucleases," Mol Ther, 2008, 16: 352-358.
Cornu et al., "Quantification of zinc finger nuclease-associated toxicity," Meth Mol Biol, 2010, 649: 237-245.
Cradick et al., "CRISPR/Cas9 systems targeting betaglobin and CCR5 genes have substantial off-target activity," Nucleic Acids Res, 2013, 41(20): 9584-92.
Crooke et al., "Pharmacokinetic properties of several novel oligo-nucleotide analogs in mice," J. Pharmacol. Exp. Ther., 1996, 277(2): 923-937.
Cruvinel et al., "Reactivation of maternal SNORD116 cluster via SETDB1 knockdown in Prader-Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159.
Darabi et al., "Functional skeletal muscle regeneration from differentiating embryonic stem cells," Nat Med, 2008, 14: 134-143.
Darabi et al., "Human ES-and iPS-derived myogenic progenitors restore dystrophin and improve contractility upon transplantation in dystrophic mice," Cell Stem Cell, 2012, 10: 610-619.
Darmanis et al., "A survey of human brain transcriptome diversity at the single cell level," Proc Natl Acad Sci U S A, 2015, 112: 7285-7290.
Datlinger et al., "Pooled CRISPR screening with single-cell transcriptome readout," Nat. Methods, 2017, 14: 297-301.
De Mesmaeker et al., "Antisense Oligonucleotides," Ace. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257-3265.
Deconinck et al., "Utrophin-Dystrophin-Dystrophin-Deficient Mice as a Model for Duchenne Muscular Dystrophy," Cell, 1997, 90(4): 717-727.
Dempster et al., "Extracting Biological Insights from the Project Achilles Genome-Scale CRISPR Screens in Cancer Cell Lines," Cold Spring Harbor Laboratory, 2019, 35 pages.
Dezawa et al., "Bone marrow stromal cells generate muscle cells and repair muscle degeneration," Science Signaling, 2005, 309: 314-317.
Diao et al., "A new class of temporarily phenotypic enhancers identified by CRISPR/Cas9-mediated genetic screening," Genome Res, 2016, 26: 397-405.
Ding et al., "A TALEN Genome-Editing System for Generating Human Stem Cell-Based Disease Models," Cell Stem Cell, 2013, 12: 238-251.
Ding et al., "Enhanced efficiency of human pluripotent stem cell genome editing through replacing TALENs with CRISPRs," Cell Stem Cell, 2013, 12: 393-394.
Dirks et al., "Triggered amplification by hybridization chain reaction," Proceedings of the National Academy of Sciences of the United States of America, 2004, 101(43): 15275-15278.
Dixit et al., "Pertrub-Seq: Dissecting Molecular Circuits with Scalable Single-Cell RNA Profiling of Pooled Genetic Screens," Cell, 2016, 167: 1853-1866.e17.
Dobin et al., "STAR: ultrafast universal RNA-seq aligner," Bioinformatics, 2013, 29: 15-21.
Doyle et al., "TAL Effector-Nucleotide Targeter (TALE-NT) 2.0: tools for TAL effectors design and target prediction," Nucleic Acids Res, 2012, 40: W117-122.
Doyon et al., "Enhancing zinc-finger-nuclease activity with improved obligate heterodimeric architectures," Nat Methods, 2010, 8: 74-79.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison," Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dumont et al., "Dystrophin expression in muscle stem cells regulates their polarity and asymmetric division," Nat Med, 2015, 21: 1455-1463.
Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Dykeman, "An implementation of the Gillespie algorithm for RNA kinetics with logarithmic time update," Nucleic Acids Research, 2015, 45(12): 5708-5715.
Edelstein et al., "Gene therapy clinical trials worldwide 1989-2004——an overview," J. Gene Med., 2004, 6: 597-602.
Eguchi et al., "Reprogramming cell fate with a genome-scale library of artificial transcription factors," Proc Natl Acad Sci U S A, 2016, 113: E8257-E8266.
Encode Project Consortium, "Expanded encyclopaedias of DNA elements in the human and mouse genomes," Nature, 2020, 583: 699-710.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics," Nat. Rev. Genet., 2019, 20: 389-403.
Ernsberger, "Role of neurotrophin signalling in the differentiation of neurons from dorsal root ganglia and sympathetic ganglia," Cell Tissue Res, 2009, 336: 349-384.
Ernst et al., "ChromHMM: automating chromatin-state discovery and characterization," Nat. Methods, 2012, 9: 215-216.
Erwin et al., "Synthetic transcription elongation facotrs license transcription across repressive chromatin," Science, 2017, 358: 1617-1622.
Fagerlund et al., "The Cpf1 CRISPR-Cas protein expands genome-editing tools," Genome Biology, 2015, 16:251.
Fairclough et al., "Therapy for Duchenne muscular dystrophy: renewed optimism from genetic approaches," Nat. Rev. Genet., 2013, 14: 373-378.
Farasat et al., "A Biophysical Model of CRISPR/Cas9 Activity for Rational Deisgn of Genome Editing and Gene Regulation," PLOS Computationl Biology, 2016, 12(1):e1004724.
Farasat, "Sequence-to-Function Models for Efficient Optimization of Metabolic Pathways and Genetic Circuits," Ph. D. Thesis, 2015, 254 pages.
Farinelli et al., "Lentiviral vectors for the treatment of primary immunodeficiencies," J Inherit Metab Dis, 2014, 37: 525-533.

(56) References Cited

OTHER PUBLICATIONS

Farzadfard et al., "Tunable and Multifunctional Eukaryotic Transcription Factors Based on CRISPR/Cas," ACS Synth Biol, 2013, 604-613.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm>(Dec. 23, 2016).
FDA approves first-of-its kind targeted RNA-based therapy to treat a rare disease, <https://www.fda.gov/newsevents/newsroom/pressannouncements/ucm616518.htm> (Aug. 10, 2018).
FDA approves novel gene therapy to treat patients with a rare form of inherited vision loss, <https://www.fda.gov/newevents/newsroom/pressannouncements/ucm589467.htm> (Dec. 18, 2017).
FDA grants accelereated approval to first drug for Duchenne muscular dystrophy, <https://www.fda.gov/newsevents/newsroom/pressannouncements/ucm521263.htm> (Sep. 19, 2016).
Flamm et al., "RNA folding at elementary step resolution," Rna, 2000, 6: 325-338.
Flandin et al., "Lhx6 and Lhx8 coordinately induce neuronal expression of Shh that controls the generation of interneuron progenitors," Neuron, 2011, 70: 939-950.
Flanigan et al., "Mutational spectrum of DMD mutations in dystrophinopathy patients: application of modern diagnostic techniques to a large cohort," Human mutation, 2009, 30: 1657-1666.
Fluiter et al., "Filling the gap in LNA antisense oligo gapmers: the effects of unlocked nucleic acid (UNA) and 4'-C-hydroxymethyl-DNA modofications on RNase H recruitment and efficacy of an LNA gapmer," Mol. Biosyst., 2009, 5: 838-843.
Fonfara et al., "Phylogeny of Cas9 determines functional exchangeability of dual-RNA and Cas9 among orthologous type II CRISPR-Cas systems," Nucleic Acids Res, 2013, 42(4): 2577-2590.
Forget, "Molecular basis of hereditary persistence of fetal hemoglobin," Ann N Y Acad Sci, 1998, 850, 38-44.
Frank et al., "HDAC inhibitors cause site-specific chromatin remodeling at PU.1-bound enhancers in K562 cells," Epigenetics Chromatin, 2016, 9: 15.
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Molecular Therapy, 2015, 23(Suppl. 1):S224.
Friedland et al., "*Staphyloccocus aureus* Cas9: An Alternative Cas9 for Genome Editing Applications," Retrieved from the Internet: <http://www.editasmedicine.com/data/documents/ASGCT%20poster 2015 Ari.pdf> Retreived on Feb. 28, 2018.
Fu et al., "High-frequency off-target mutagenesis induced by CRISPR-Cas nucleases in human cells," Nat Biotechnol, 2013, 31(9): 822-826.
Fu et al., "Improving CRISPR-Cas nuclease specificity using truncated guide RNAs," Nat Biotechnol, 2014, 32: 279-284.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gaj et al., "Structure-Guided Reprogramming of Serine Recombinase DNA Sequence Specificity," Proc Natl Acad Sci U S A, 2011, 108(2): 498-503.
Gaj et al., "Targeted gene knockout by direct delivery of zinc-finger nuclease proteins," Nature Methods, 2012, 9(8): 805-807.
Gaj et al., "ZFN, TALEN, and CRISPR/Cas-based methods for genome engineering," Trends Biotechnol, 2013, 31:397-405.
Gao et al., "Complex transcriptional modulation with orthogonal and inducible dCas9 regulators," Nat Methods, 2016, 13: 1043-1049.
Garg et al., "Enginnering synthetic TAL effectors with orthogonal target sites," Nucleic Acids Res, 2012, 40: 7584-7595.
Gascon et al., "Direct Neuronal Reprogramming: Achievements, Hurdles, and New Roads to Success," Cell Stem Cell, 2017, 21: 18-34.
Gasperini et al., "A Genome-wide Framework for Mapping Gene Regulation via Cellular Genetic Screens," Cell, 2018, 176(1-2); 377-390.e19.
Gaudelli et al., "Direction evolution of adenine base editors with increased activity and therapeutic application," Nat Biotechnol, Jul. 2020, 38(7): 892-900.
Gaudelli et al., "Programmable based editing of A•T to G•C in genomic DNA without DNA cleavage," Nature, Nov. 2017, 551(7681): 464-471
Gebeyehu et al., "Novel biotinylated nucleotide——analogs for labeling and colorimetric detection of DNA," Nucl. Acids Res., 1987, 15(11): 4513-4534.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
GenBank Accession AF214528.1 (2000).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank Accession No. X51934.1 (1997).
Gersbach et al., "Targeted plasmid integration into the human genome by an engineered zinc-finger recombinase," Nucleic Acids REs, 2011, 39: 7868-7878.
Gertz et al., "Transposase mediated construction of RNA-seq libraries," Genome Res, 2012, 22: 134-141.
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gilbert et al., "CRISPR-mediated modular RNA-guided regulation of transcription in eukaryotes," Cell, 2013, 154: 442-451.
Gillespie, "A general method for numerically simulating the stochastic time evolution of coupled chemical reactions," Journal of computational physics, 1976, 22: 403-434.
Gilman et al., "Distal CCAAT box delection in the A gamma globin gene of two black adolescents with elevated fetal A gamma globin," Nucleic Acids Res 16, 1988, 10635-10642.
Goemans et al., "Systemic administration of PRO051 in Duchenne's muscular dystrophy," The New England journal of medicine, 2011, 364: 1513-1522.
Goldstein et al., "In Situ Modification of Tissue Stem and Progenitor Cell Genomes," Cell Reports, 2019, 27: 1254-1264.e7.
Gou et al., "A novel approach for the construction of multiple shRNA expression vectors," J Gene Med, 2007, 9(9): 751-63.
Gräslund et al., "Exploring strategies for the design of artificial transcription factors: targeting sites proximal to known regulatory regions for the induction of gamma-globin expression and the treatment of sickle cell disease," J Biol Chem, 2005, 280: 3707-3714.

(56) References Cited

OTHER PUBLICATIONS

Gray et al., "G quadruplexes are genomewide targets of transcriptional helicases XPB and XPD," Nat. Chem. Biol, 2014, 10: 313-318.
Gregorevic et al., "Systemic delivery of genes to striated muscles using adeno-associated viral vectors," Nat Med, 2004, 10: 828-834.
Gregorevic et al., "Systemic microdystrophin gene delivery improves skeletal muscle structure and function in old dystrophic mdx mice," Mol Ther, 2008, 16: 657-664.
Guo et al., "Directed evolution of an enhanced and highly efficient FokI cleavage domain for zinc finger nucleases," J Mol Biol, 2010, 400: 96-107.
Guo et al., "Harnessing accurate non-homologous end joining for efficient prease deletion in CRISPR/Cas9-mediated genome editing," Genome Biology, 2018, 19: 170, 20 pages.
Guo, J. et al., "Directed evolution of an enhanced and highly efficient FokI cleavage domain for zinc finger nucleases," J Mol Biol, 2010.
Guschin et al., "A rapid and general assay for monitoring endogenous gene modification," Methods Mol Biol, 2010, 649: 247-256.
Hacein-Bey-Abina et al., "LMO2-associated clonal T cell proliferation in two patients after gene therapy for SCID-X1," Science, 2003, 302: 415-419.
Hakim et al., "Evaluation of Muscle Functio nof the Extensor Digitorum Longus Muscle Ex vivo and Tibialis Anterior Muscle In situ in Mice," J. Vis. Exp., 2013, 1-8.
Hkaim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Hall et al., "Prevention of Muscle Aging by Myofiber-Associated Satellite Cell Transplantation," Sci Transl Med, 2010, 2: 57ra83.
Hardy et al., "Comparative Study of Injury Models for Studying Muscle Regeneration in Mice," PLoS ONE, 2016, 11: e0147198.
Harper et al., "Modular flexibility of dystrophin: implications for gene therapy of Duchenne muscular dystrophy," Nat. Med., 2002, 8: 253-261.
Harrow et al., "GENCODE: The reference human genome annotation for The ENCODE Project," Genome Res, 2012, 22: 1760-1744.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heagerty et al., "Time-dependent ROC curves for censored survival data and a diagnostic marker," Biometrics, 2000, 56(2): 337-344.
Heasman, "Morpholino oligos: making sense of antisense?," Dev. Biol., 2002, 243(2): 209-214.
Henning et al., "Epigenetic control of CD8 + T cell differentiation," Nat Rev Immunol, 2018, 18(5): 340-356.
Hilton et al., "Enabling functional genomics with genome engineering," Genome Research, 2015, 25(10):1442-1455.
Himeda et al., "Design and Testing of Regulatory Cassettes for Optimal Activity in Skeletal and Cardiac Muscles," Methods Mol Biol, 2011, 709: 3-19 (Published Online Dec. 2010).
Hockemeyer et al., "Efficient targeting of expressed and silent genes in human ESCs and iPSCs using zinc-finger nucleases," Nat Biotechnol, 2009, 27(9): 851-857.
Hockemeyer et al., "Genetic engineering of human pluripotent cells using TALE nucleases," Nat Biotechnol, 2011, 29: 731-734.
Hoffman et al., "Dystrophin: the protein product of the Duchenne muscular dystrophy locus," Cell, 1987, 51: 919.
Hori et al., "Simple and reproducible hepatectomy in the mouse using the clip technique," World J Gastroenterol, 2012, 18(22): 2767-2774.
Horlbeck et al., "Compact and highly active next-generation libraries for CRISPR-mediated gene repression and activation," eLife, 2016, 5: e19760.
Hou et al., "Efficient genome engineering in human pluripotent stem cells using Cas9 from *Neisseria meningitidis*," Proct Natl Acad Sci USA, 2013, 110: 15644-15649.
Howarth et al., "A monovalent streptavidin with a single femtomolar biotin binding site," Nature methods, 2006, 3(4): 267-273.
Hsu et al., "Dissecting Neural Function using Targeted Genome Engineering Technologies,", ASC Chem. Neurosci., 2012, 3: 603-610.
Hsu et al., "DNA targeting specificity of RNA-guided Cas9 nucleases," Nature Biotechnology, 2013, 31: 827-832.
Hsu et al., "Development and applications of CRISPR-Cas9 for genome engineering," Cell, 2014, 157: 1262-1278.
Huang et al., "Generation and comparison of CRISPR-Cas9 and Cre-mediated genetically engineered mouse models of sarcoma," Nature Communications, 2017, 8(15999): 1-11.
Huang et al., "Impaired respiratory function in mdx and mdx/utrn+/− mice," Muscle & Nerve, 2011, 43(2): 263-267.
Humbert et al., "Targeted gene therapies: tools, applications, optimization", Critical Reviews in Biochemistry and Molecular Biology, 2012, 47(3): 264-281.
Huntriss et al., "Imprinted expression of SNRPN in human preimplantation embryos," Am J Hum Genet, 1998, 63: 1009-1014.
Hwang et al., "Efficient genome editing in zebrafish using CRISPR-Cas system," Nat Biotechnol, 2013, 31(3): 227-9.
Inoue et al., "Runx transcription factors in neuronal development," Neural Dev, 2008, 3: 20.
Isaac et al., "Dystrophin and utrophin "double knockout" dystrophic mice exhibit a spectrum of degenerative musculoskeletal abnormalities," Journal of Orthopaedic Research, 2013, 31(3): 343-349.
Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.
Jansen et al., "Identification of genes that are associated with DNA repeats in prokaryotes," Mol Microbiol, 2002, 43(6): 1565-1575.
Jeltsch et al., "Application of DNA methyltransferases in targeted DNA methylation," Appl. Microbiol. Biotechnol., 2007, 75(6): 1233-1240.
Jepsen et al., "Locked nucleic acid: a potent nucleic acid analog in therapeutics and biotechnology," Oligonucleotides, 2004, 14(2): 130-146.
Jiang et al., "A Cas9-guide RNA complex preorganized for target DNA recognition," Science, 2015, 348, 1477-1481.
Jiang et al., "Notch signaling deficiency underlies age-dependent depletion of satellite cells in muscular dystrophy," Disease Models & Mechanisms, 2014, 7: 997-1004.
Jimenez et al., "Activation of the beta-globin locus control region precedes commitment ot hte erythroid lineage," Proceedings of the National Academy of Sciences, 1992, 89: 10618-10622.
Jinek et al., "A programmable dual-RNA-guided DNA endonuclease in adaptive bacterial immunity," Science, 2012, 337: 816-821.
Jinek et al., "RNA-programmed genome editing in human cells," eLife, 2013, 2: e00471.
Jinek et al., "Structures of Cas9 endonucleases reveal RNA-mediated conformational activation," Science, 2014, 343(6176): 1247997.
Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.
Jobling et al., "Chitayat-Hall and Schaaf-Yang syndromes:a common aetiology: expanding the phenotype of MAGEL2-related disorders," J Med Genet, 2018, 55: 316-321.
Jooss et al., "Transduction of dendritic cells by DNA viral vectors directs the immune response to transgene products in muscle fibers," J. Virol., 1998, 72: 4212-4223.
Josephs et al., "Structure and specificity of the RNA-guided endonuclease Cas9 during DNA interrogation, target binding and cleavage," Nucleic Acids Research, 2015, 43(18): 8924-8941.
Joung et al., "TALENS: a widely applicable technology for targeted genome editing," Nature Reviews Molecular Cell Biology, 2013, 14: 49-55.

(56) References Cited

OTHER PUBLICATIONS

Joyce, "Amplification, mutation and selection of catalytic RNA," Gene, 1989, 82(1): 83-87.
Joyce, "Directed molecular evolution," Scientific American, 1992, 267(6): 90-97.
Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259: 327-330.
Kauppinen et al., "Locked nucleic acid (LNA): high affinity targeting of RNA for diagnostics and therapeutics," Drug Discov Today Technol, 2005, 2(3): 287-290.
Kayali et al., "Site-directed gene repair of the dystrophin gene mediated by PNA-ssODNs," Human Molecular Genetics, 2010, 19(16):3266-3281.
Kearns et al., "Cas9 effector-mediated regulation of transcription and differentiation in human pluripotent stem cells," Development, 2014, 141(1): 219-23.
Keefe et al., "Muscle stem cells contribute to myofibers in sedentary adult mice," Nat Commun, 2015, 6: 7087.
Keil et al., "Brain transcriptome databases: a user's guide," J Neurosci, 2018, 38(10): 2399-2412.
Kempfer et al., "Methods for mapping 3D chromosome architecture," Nat. Rev. Genet., 2020, 21:207-226.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Khambata-Ford et al., "Identification of Promoter Regions in the Human Genome by Using a Retroviral Plasmid Library-Based Functional Reporter Gene Assay," Genome Research, 2003, 13: 1765-1774.
Kohodakov et al., "Protected DNA strand displacement for enhanced single nucleotide discrimination in double-stranded DNA," Scientific reports, 2015, 5: 8721.
Khurana et al., "Role of non-coding sequence variants in cancer," Nat. Rev. Genet., 2016, 17: 93-108.
Kim et al., "Epigenetic therapy of Prader-Willi Syndrome," Transl Res, 2019, 208: 105-118.
Kim et al., "Expansion and Purification Are Critical for the Therapeutic Application of Pluripotent Stem Cell-Derived Myogenic Progenitors," Stem Cell Rep, 2017, 9: 12-22.
Kim et al., "Histone acetylation contributes to chromatin looping between the locus control region and globin gene by influencing hypersensitive site formation," Biochim Biophys Acta, 2013, 1829: 963-969.
Kim et al., "Surrogate reporters for enrichment of cells with nuclease-induced mutations," Nat Methods, 2011, 8: 941-943.
Kim et al., "TALENS and ZFNs are associated with different mutation signatures," Nat Methods, 2013, 10(3): 185.
Kim et al., "Targeting the histone methyltransferase G9a activates imprinted genes and improves survival of a mouse model of Prader-Willi syndrome," Nat Med, 2017, 23: 213-222.
Kim et al., "Engineering and Application of Zinc Finger Proteins and TALEs for Biomedical Research," Mol Cells, 2017, 40(8): 533-541.
Kimura et al., "Cell-lineage regulated myogenesis for dystrophin replacement: a novel therapeutic approach for treatment of muscular dystrophy," Hum Mol Genet, 2008, 17: 2507-2517.
Klann et al., "CRISPR-based methods for high-throughput annotation of regulatory DNA," Curr Opin Biotechnol, 2018, 52: 32-41.
Klann et al., "CRISPR-Cas9 epigenome eidting enables high-throughput screening for functional regulatory elements in the human genome," Nat Biotechnol, 2017, 35: 561-568.
Klann et al., "Genome-wide annotation of gene regulatory elements linked to cell fitness," bioRxiv doi: 10.1101/2021.03.08.434470. Preprint posted Mar. 9, 2021, 42 pages.
Kleinstiver et al., "Broadening the targeting range of *Staphylococcus aureus* CRISPR-Cas9 by modifying PAM recognition," Nature Biotechnology, 2015, 33(12): 1293-1298.
Kleinstiver et al., "Engineered CRISPR-Cas9 nucleases with altered PAM specificities," Nature, 2015, 523 (7561): 481-485.
Kleinstiver et al., "Genome-wide specificities of CRISPR-Cas Cpf1 nucleases in human cells," Nature Biotechnology, 2016, 34(8):869-874.
Koblan et al., "Improving cytidine and adenine base editors by expression optimization and ancestral reconstruction," Oct. 2018, 36(9): 843-846.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graudate School of Duke University, 2013, p. 1-29.
Kocher et al., "Phylogenetic Analysis of the SNORD116 Locus," Genes, 2017, 8(12): 358.
Kodaka et al., "Skeletal Muscle Cell Induction from Pluripotent Stem Cells," Stem Cells Int, Apr. 2017, Article ID 1376151, 16 pages.
Koerber et al., "DNA shuffling of adeno-associated virus yields functionally diverse viral progeny," Mol Ther, 2008, 16: 1703-1709.
Komor et al., "Programmable editing of a target base in genomic DNA without double-stranded DNA cleavage," Nature, 2016, 533(7603): 420-424.
Konermann et al., "Optical control of mammalian endogenous transcription and epigenetic states," Nature, 2013, 500(7463): 472-6.
Konieczny et al., "Gene and cell-mediated therapies for muscular dystrophy," Muscle Nerve, 2013, 47: 649-663.
Koo et al., "Functional Rescue of Dystrophin Deficiency in Mice Cause by Frameshift Mutations Using Campylobacter jejuni Cas9," Molecular Therapy, 2018 26(6): 1529-1538.
Koopmans et al., "SynGO: An Evidence-Based, Expert-Curated Knowledge Base for the Synapse," Neuron, 2019, 103: 217-234 e214.
Koppanati et al., "Improvement of the mdx mouse dystrophic phenotype by systemic in utero AAV8 delivery of a minidystrophin gene," Gene Ther. 2010, 17: 1355-1362.
Korkmaz et al., "Functional genetic screens for enhancer elements in the human genome using CRISPR-Cas9," Nat Biotechnol, 2016, 34: 192-198
Kronberg et al., "DNA Replication," 1980, pp. 75-77.
Koshkin et al., "LNA (Locked Nucleic Acids): Synthesis of the adenine, cystosine, guanine, 5-methylcytosine, thymine and uracil bicyclonucleoside monomers, oligomerisation, and unprecedented nucleic acid recognition," Tetrahedron, 1998, 54(14): 3607-3630.
Kreis et al., "The Multifacted p21 (Cip1/Waf1/CDKN1A) in Cell Differentiation, Migration and Cancer Therapy," Cancers (Basel), 2019, 11(9): 1220.
Kubokawa et al., "Molecular characterization of the 5'-UTR of retinal dystrophin reveals a cryptic intron that regulates translational activity," Molecular Vision, 2010, 16: 2590-2597.
Kuhnel et al., "Tumor-specific adenoviral gene therapy: Transcriptional repression of gene expression by utilizing p53- signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kwa et al., "Chromatin modifying agents—the cutting edge of anticancer therapy," Drug Discovery Today, 2011, 16(13/14):543-547.
Kwon et al., "Myogenic Progenitor Cell Lineage Specification by CRISPR/Cas9-Based Transcriptional Activators," Stem cell reports, 2020, 14: 755-769.

(56) References Cited

OTHER PUBLICATIONS

Lacerra et al., "Restoration of hemoglobin A synthesis in erythroid cells from peripheral blood of thalassemic patients," Proc. Natl. Acad. Sci., 2000, 97(17): 9591-9596.

Lai et al., "Partial restoration of cardiac function with ΔPDZ nNOS in aged mdx model of Duchenne cardiomyopathy," Hum Mol Genet., 2014, 23(12): 3189-3199.

Lake et al., "Integrative single-cell analysis of transcriptional and epigenetic states in the human adult brain," Nat Biotechnol, 2018, 36: 70-80.

Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.

Lambert et al., "The Human Transcription Factors," Cell, 2018, 172: 650-665.

Lamey et al., "Pax genes in myogenesis: alternate transcripts add complexity," Histol Histopathol, 2004, 19: 1289-1300.

Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.

Langmead et al., "Ultrafast and memory-efficient alignment of short DNA sequences to the human genome," Genome biology, 2009, 10: R25.

Langouet et al., "Zinc finger protein 274 regulates imprinted expression of transcripts in Prader-Willi syndrome neurons," Hum Hol Genet, 2018, 27: 505-515.

Larson et al., "CRISPR interference (CRISPRi) for sequence-editing control of gene expression," Nat Protoc, 2013, 8(11): 2180-96.

Latta-Mahieu et al., "Gene transfer of a chimeric trans-activator is immunogenic and results in short-lived transgene expression," Human Gene Therapy, 2002, 13(13): 1611-1620.

Lattanzi et al., "High efficiency myogenic conversion of human fibroblasts by adenoviral vector-mediated MyoD gene transfer. An alternative strategy for ex vivo gene therapy of primary myopathies," The Journal of clinical investigation, 1998, 101: 2119-2128.

Laumont et al., "Noncoding regions are the main source of targetable tumor-specific antigens," Sci. Transl. Med., 2018, 10(470): eaau5516, 11 pages.

Lawrence et al., "Discovery and saturation analysis of cancer genes across 21 tumour types," Nature, 2014, 505: 495-501.

Lee et al., "Activation of innate immunity is required for efficient nuclear reprogramming," Cell, 2012, 151: 547-558.

Lee et al., "Expression of small interfering RNAs targeted against HIV-1 rev transcripts in human cells," Nature Biotechnol, 2002, 20(5): 500-505.

Lee et al., "Nanoparticle delivery of Cas9 ribonucleoprotien and donor DNA in vivo induces homology-directed DNA repair," Nat Biomed Eng, 2017, 1: 889-901.

Lee et al., "Targeted chromosomal deletions in human cells using zinc finger nucleases," Genome research, 2010, 20: 81-89.

Lenoir et al., "PICKLES: the database of pooled in-vitro CRISPR knockout library essentiality screens," Nucleic Acids Res, 2018, 46: D776-D780.

Lesnik et al., "Relative thermodynamic stability of DNA, RNA, and DNA: RNA hybrid duplexes: relationship with base composition and struction," Biochemistry, 1995, 34(34): 10807-10815.

Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.

Levin et al., "Position-dependent effects of locked nucleic acid (LNA) on DNA sequencing and PCR primers," Nuc. Acids. Res., 2006, 34: e142.

Li et al., "In vivo genome editing restores haemostasis in a mouse model of haemophilia," Nature, 2011, 475: 217-221.

Li et al., "Chimeric DNA methyltransferases target DNA methylation to specific DNA sequences and repress expression of target genes," Nucleic Acids Res., 2007, 35(1): 100-112.

Li et al., "Engineering and selection of shuffled AAV genomes: a new strategy for producing targeted biological nanoparticles," Mol Ther, 2008, 16: 1252-1260.

Li et al., "Ex vivo cell-based CRISPR/Cas9 genome editing for therapeutic applications," Biomaterials, 2020, 234: 119711.

Li et al., "Marginal level dystrophin expression improves clinical outcome in a strain of dystrophin/utrophin double knockout mice," PLoS One, 2010, 5: e15286.

Li et al., "Modularly assembled designer TAL effector nucleases for targeted gene knockout and gene replacement in eukaryotes," Nucleic Acids Research, 2011, 39(14): 6315-6325.

Li et al., "Precise correction of the dystrophin gene in duchenne muscular dystrophy patient induced pluripotent stem cells by TALEN and CRISPR-Cas9," Stem Cell Reports, 2015, 4: 143-154.

Li et al., "Preservation of muscle force in Mdx3cv mice correlates with low-level expression of a near full-length dystrophin protein," Am. J. Pathol., 2008, 172: 1332-1341.

Li et al., "RSEM: accurate transcript quantification from RNA-Seq data with or without a reference genome," BMC Bioinformatics, 2011, 12: 323.

Li et al., "Synthetic muscle promoters: activities exceeding naturally ocurring regulatory sequences," Nature Biotechnology, 1999, 17: 241-245.

Li et al., "The autism-related gene SNRPN regulates cortical and spine development via controlling nuclear receptor Nr4a1," Sci Rep, 2016, 6: 29878.

Li et al., "Transcription activator-like effector hybrids for conditional control and rewiring of chromosomal transgene expression," Scientific reports, 2012, 2: 897.

Lian et al., "Robust cardiomyocyte differentiation from human pluripotent stem cells via temporal modulation of canonical Wnt signaling," Proc Natl Acad Sci, 2012, 109: E1848-E1857.

Liang et al., "Engineering biological systems with synthetic RNA molecules," Mol Cell, 2011, 43: 915-926.

Liao et al., "In Vivo Target Gene Activation via CRISPR/Cas9-Mediated Trans-epigenetic Modulation," Cell, 2017, 171: 1495-1507.

Liao et al., "The Subread aligner: fast, accurate and scalable read mapping by seed-and-vote," Nucleic Acids Res, 2013, 41: e108.

Lim et al., "Application of CRISPR/Cas9 for the Treatment of Duchenne Muscular Dystrophy," Journal of Personalized Medicine, 2018, 8(4): 1-20.

Limberis et al., "Transduction efficiencies of novel AAV vectors in mouse airway epithelium in vivo and human ciliated airway epithelium in vitro," Molecular therapy: the journal of the American Society of Gene Thereapy, 2009, 17: 294-301.

Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.

Liu et al., "Adeno-associated virus-mediated microdystrophin expression protects young mdx muscle from contraction-induced injury," Mol. Ther., 2005, 11: 245-256.

Liu et al., "CRISPR Activation Screens Systematically Identify Factors that Drive Neuronal Fate and Reprogramming," Cell Stem Cell, 2018, 23: 758-771 e758.

Liu et al., "CRISPR-Based Chromatin Remodeling of the Endogenous Oct4 or Sox2 Locus Enables Reprogramming to Pluripotency," Cell Stem Cell, 2018, 22: 252-261 e254.

Liu et al., "Editing DNA Methylation in the Mammalian Genome," Cell, Sep. 2016, 167(1): 233-247.

Liu et al.,"Monte Carlo simulation for single RNA unfolding by force," Biophysical journal, 2005, 88(1): 76-84.

Lohmueller et al., "A tunable zinc finger-based framework for Boolean logic computation in mammalian cells," Nucleic Acids Res, 2012, 40: 5180-5187.

Long et al., "Postnatal genome editing partially restores dystrophin expression in a mouse model of muscular dystrophy," Science, 2016, 351 (6271): 400-403.

(56) References Cited

OTHER PUBLICATIONS

Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu et al., "The status of exon skipping as a therapeutic approach to duchenne muscular dystrophy," Molecular Therapy, 2011, 19: 9-15.
Lund et al. "Promoter-targeted phage display selections with preassembled synthetic zinc finger libraries for endogenous gene regulation." Journal of Molecular Biology, 2004, 340: 599-613.
Luo et al., "Repurposing endogenous type I CRISPR-Cas systems for programmable gene repression," Nucleic Acids Research, 2014, 43(1): 674-681.
Luo et al., "Synthetic DNA Delivery systems," Nature Biotechnology, 2000, 18: 33-37.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.
MacPherson et al., "Flexible guide-RNA design for CRISPR application using Protospacer Workbench," Nature biotechnology, 2015, 33(8): 805-806.
Madigan et al., "Engineering AAV Receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Maeder et al., "CRISPR RNA-guided activation of endogenous human genes," Nat Methods, 2013, 10: 977-979.
Maeder, "Targeted DNA demethylation and activation of endogenous genes using programmable TALE-TET1 fusion proteins," Nat Biotechnol, 2013, 31(12): 1137-42.
Magli et al., "PAX7 Targets, CD54, Integrin $\alpha 9\beta 1$, and SDC2, Allow Isolation of Human ESC/iPSC-Derived Myogenic Progenitors," Cell Rep, 2017, 19: 2867-2877.
Maheshri et al., "Directed evolution of adeno-associated virus yields enhanced gene delivery vectors," Nat Biotechnol, 2006, 24: 198-204.
Majzner et al., "Clinical lessons learned from the first leg of the CAR T cell journey," Nature Medicine, 2019, 25(9): 1341-1355.
Mali et al., "Cas9 as a versatile tool for engineering biology," Nat Methods, 2013, 10(10): 957-63.
Mali et al., "CAS9 transcriptional activators for target specificity screening and paired nickases for cooperative genome engineering," Nat Biotechnol, 2013, 31(9): 833-8.
Mali et al., "RNA-Guided Human Genome Engineering via Cas9," Science, 2013, 339: 823-826.
Mamchaoui et al., "Immortalized pathological human myoblasts: towards a universal tool for the study of neuromuscular disorders," Skelet Muscle, 2011, 1: 1-11.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease?, " Journal of Muscle Research and Cell Motility, 2015, 36: 155-167.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides," Helv. Chim. Acta, 1995, 78: 486-504.
Maruyama et al., "Epigenetic Regulation of Cell Type-Specific Expression Patterns in the Human Mammary Epithelium," PLoS Genetics, 2011, 7(4): e1001369, 15 pages.
Mastellos et al., "Inducing and characterizing liver regeneration in mice: Reliable models, essential "readouts" and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
McCarthy et al., "Schaaf-Yang syndrome overview: Report of 78 individuals," Am J Med Genet A 2018, 176(12): 2564-2574.
McFadden et al., "The Hand1 and Hand2 transcription factors regulate expansion of the embryonic cardiac ventricles in a gene dosage-dependent manner," Development, 2005, 132: 189-201.
McGreevy et al., "Animal models of Duchenne muscular dystrophy: from basic mechanisms to gene therapy," Disease Models Mechanisms, 2015, 8(3): 195-213.
McTigue et al., "Sequence-dependent thermodynamic parameters for locked nucleic acid (LNA)-DNA duplex formation," Biochemistry, 2004, 43(18): 5388-5405.
Mendell et al., "Dystrophin immunity in Duchenne's muscular dystrophy," New England Journal of Medicine, 2010, 363: 1429-1437.
Mendenhall et al., "Locus-specific editing of histone modification at endogenous enhancers," Nat Biotechnol, 2013, 31(12): 1133-6.
Mercer et al., "Regulation of Endogenous Human Gene Expression by Ligand-Inducible TALE Transcription Factors," ACS Synth Biol, 2013.
Mertens et al., "Evaluating cell reprogramming, differentiation and conversion technologies in neuroscience," Nat Rev Neurosci, 2016, 17: 424-437.
Mevissen et al., "Molecular basis of Lys11-polyubiquitin specificity in the deubiquitinase Cezanne," Nature, 2016, 538(7625): 402-405.
Meyers et al., "Computational correction of copy number effect imrpoves specificity of CRISPR-Cas9 essentiality screens in cancer cells," Nat. Genet., 2017, 49: 1779-1784.
Miller et al., "A TALE nuclease architecture for efficient genome editing," Nat Biotechnol, 2011, 29: 143-148.
Miller et al., "Transcriptional landscape of the prenatal human brain," Nature, 2014, 508: 199-206.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Miyagishi et al., "U6 promoter-driven siRNAs with four uridine 3'overhangs efficiently suppress targeted gene expression in mammalian cells," Nature Biotechnol, 2002, 20(5): 497-500.
Mojica et al., "Intervening sequences of regularly spaced prokaryotic repeats derive from foreign genetic elements," J Molec Evolution, 2005, 60(2): 174-182.
Montalbano et al., "High-Throughput Approaches to Pinpoint Function within the Noncoding Genome," Mol. Cell, 2017, 68: 44-59.
Montarras, "Direct Isolation of Satellite Cells for Skeletal Muscle Regeneration," Science, 2005, 309: 2064-2067.
Moore et al., "Transcription Activator-like Effectors: A Toolkit for Synthetic Biology," ACS Synth Biol, 2014, 3(10): 708-716.
Morris et al., "Dissecting engineered cell types and enhancing cell fate conversion via CellNet," Cell, 2014, 158: 889-902.
Moscou et al., "A simple cipher governs DNA recognition by TAL effectors," Science, 2009, 326: 1501.

(56) References Cited

OTHER PUBLICATIONS

Muir et al., "Engraftment potential of dermal fibroblasts following in vivo myogenic conversion in immunocompetent dystrophic skeletal muscle," Mol. Ther. Methods Clin. Dev., 2014, 1:14025.
Murphy et al., "The in vitro transcription of the 7SK RNA gene by RNA polymerase III is dependable only on the presence of an upstream promoter," Cell, 1987, 51: 81-87.
Mussolino et al., "A novel TALE nuclease scaffold enables high genome editing activity in combination with low toxicity," Nucleic Acids Res, 2011, 39: 9283-9293.
Myslinski et al., "An unusually compact external promoter for RNA polymerase III transcription of the human H1RNA gene," Nucleic Acids Res, 2001, 29: 2502-2509.
Naguibneva et al., "An LNA-based loss-of-function assay for micro-RNAs," Biomed Pharmacother, 2006, 60: 633-638.
Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nance et al., "AAV9 Edits Muscle Stem Cells in Normal and Dystrophic Adult Mice," Molecular Therapy, 2019, 27: 1568-1585.
Nasevicius et al., "Effective targeted gene 'knockdown' in zebrafish," Nat. Genet., 2000, 26(2): 216-220.
Negroni et al., "In Vivo Myogenic Potential of Human CD133+ Muscle-derived Stem Cells: A Quantitative Study," Molecular Therapy, 2009, 17: 1771-1778.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "Local and Systemic Gene Editing in a Mouse Model of Duchenne Muscular Dystrophy," Molecular Therapy, 2016, 24(Supp 1):S191.
Nelson et al., "Long-term evaluation of AAV-CRISPR gehome editing for Duchenne muscular dystrophy," Nature Medicine, 2019, 25(3): 427-432.
Nguyen et al., "Transcriptional Enhancers in the Regulation of T Cell Differentiation," Front. Immunol., 2015, 6: 462.
Nielsen et al., "Sequence-selective recognition of DNA by strand displacement with a thymine-substituted polyamide," Science, 1991, 254: 1497-1500.
Nikfarjam et al., "A Model of Partial Hepatectomy in Mice," Journal of Investigative Surgery, 2004, 17(5): 291-294.
Nishimasu et al., "Crystal structure of cas9 in complex with guide RNA and target DNA Cell," 2014, 156(5): 935-49.
Nowotny et al., "Crystal structures of RNase H bound to an RNA/DNA hybrid: substrate specificity and metal-dependent catalysis," Cell, 2005, 121(7): 1005-1016.
Nuñez et al., "Genome-wide programmable transcriptional memory by CRISPR-based epigenome editing," Cell, 2021, 184(9): P2503-2519.
O'Brien et al., "GT-Scan: identifying unique genomic targets," Bioinformatics, 2014, 30: 2673-2675.
Oberhauser et al., "Effective incorporation of 2'-Oomethyl-oligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-O,4'-C-methyleneribonucleosides," Tetrahedron Lett. 1998, 39(30): 5401-5404.
O'Connell et al., "Programmable RNA recognition and cleavage by CRISPR/Cas9," Nature, 2014, 516: 263-266.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.

O'Geen et al., "dCas9-based epigenome editing suggests acquisition of histone methylation is not sufficient for target gene repression," Nucleic Acids Res, 2017, 45: 9901-9916.
O'Geen et al., "Ezh2-dCas9 and KRAB-dCas9 enable engineering of epigenetic memory in a context-dependent manner," Epigenetics Chromatin, 2019, 12: 26.
Ohshima et al., "Nucleotide sequence of mouse genomic loci including a gene or pseudogene for U6 (4.85) nuclear RNA," Nucleic Acids Res, 1981, 9: 5145-5158.
Olguin et al., "Pax-7 up-regulation inhibits myogenesis and cell cycle prograssion in satellite cells: a potential mechanism for self-renewal," Dev Biol, 2004, 275: 375-388.
Orgel, "Selection in vitro," Proc. R. Soc. B, 1979, 205: 435-442.
Orlando et al., "Promoter capture Hi-C-based identification of recurrent noncoding mutations in colorectal cancer," Nat. Genet., 2018, 50: 1375-1380.
Orom et al., "LNA-modified oligonucleotides mediate specific inhibition of microRNA function," Gene, 2006, 372: 137-141.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR-Cas9-based gehome editing for correction of dystrophin mutations that cause Duchenne muscular dystrophy," Nature Communications, 2015, 6:6244.
Ousterout et al., "Reading frame correction by targeted gehome editing restores dystrophin expression in cells from Duchenne muscular dystrophy patients," Mol Ther, 2013, 21: 1718-1726.
Ousterout, "Genetic Correction of Duchenne Muscular Dystrophy using Engineered Nucleases," Dept. of Biomedical Engineering Duke University (Dissertation), 2014, pp. 1-204.
Paddison et al., "Short hairpin RNAs (shRNAs) induce sequence-specific silencing in mammalian cells," Genes & Dev, 2002, 16(8): 948-958.
Paez-Espino et al., "CRISPR immunity drives rapid phage genome evolution in *Steptococcus thermophilus*," mBio, 2015, 5(2): e00262-15.
Palu et al., "In pursuit of new developments for gene therapy of human diseases," J. Biotechnol., 1999, 68: 1-13.
Pang et al., "Induction of human neuronal cells by defined transcription factors," Nature, 2011, 476: 220-223.
Papapetrou, "Induced pluripotent stem cells, past and future," Science, 2016, 353: 991-992.
Papayannakos et al., "Understanding lentiviral vector chromatin targeting: working to reduce insertional mutagenic potential for gene therapy," Gene Ther, 2013, 20(6): 581-8.
Parekh et al., "Mapping Cellular Reprogramming via Pooled Overexpression Screens with Paired Fitness and Single-Cell RNA-Sequencing Readout," Cell Systems, 2018, 7: 548-555.e548.
Park et al., "Multiparametric MRI at 14T for Muscular Dystrophy Mice Treated with AAV Vector-Mediated Gene Therapy," PLoS ONE, 2015, 10(4): e0124914.
Park et al., "Phenotypic alteration of eukaryotic cells using randomized libraries of artificial transcription factors," Nat Biotechnol, 2003, 21: 1208-1214.
Pattanayak et al., "High-throughput profiling of off-target DNA cleavage reveals RNA-programmed Cas9 nuclease specificity," Nat Biotechnol, 2013, 31(9): 839-43.
Paul et al., "Effective expression of small interfering RNA in human cells," Nature Biotechnol, 2002, 20(5): 505-508.
Pawlikowski et al., "Regulation of skeletal muscle stem cells by fibroblast growth factors," Dev Dyn, 2017, 246: 359-367.
Peault et al., "Stem and progenitor cells in skeletal muscle devleopment, maintenance, and therapy, Molecular Therapy," 2007, 15: 867-877.
Penczek et al., "Three-dimensional reconstruction of single particles embedded in ice," Ultramicroscopy, 1992, 40, 33-53.
Perez et al., "Establishment of HIV-1 resistance in CD4+ T cells by gehome editing using zinc-finger nucleases," Nature biotechnology, 2008, 26: 808-816.
Perez-Pinera et al., "Advances in targeted genome editing," Current Opinion in Chemical Biology, 2012, 16: 268-277.

(56) References Cited

OTHER PUBLICATIONS

Perez-Pinera et al., "Gene targeting to the ROSA26 locus directed by engineered zinc finger nucleases," Nucleic Acids Research, 2012, 40: 3741-3752.
Perez-Pinera et al., "RNA-guided gene activation by CRISPR-Cas9-based transcription factors," Nat Methods, 2013, 10: 973-976.
Perez-Pinera et al., "Synergistic and tunable human gene activation by combinations of synthetic transcription factors," Nature Methods, 2013, 10(3): 239-244, including pp. 1/12-12-12 of Supplementary Material.
Perez-Pinera et al., "Synergistic Transcriptional Activation by Combinations of Engineered TALEs" presented at the American Society of Gene & Cell Therapy's 15th Annual Meeting in Philadelphia, Pennsylvania, May 19, 2012, Abstract 855.
Persons, "Lentiviral vector gene therapy: effective and safe?" Mol Ther, 2010, 18(5): 861-2.
Pichavant et al., "Current status of pharmaceutical and genetic therapeutic approaches to treat DMD," Molecular Therapy, 2011, 19: 830-840.
Pigozzo et al., "Revertant Fibers in the mdx Murine Model of Duchenne Muscular Dystrophy: An Age- and Muscle-Related Reappraisal," PLoS One, 2013, 8(8): e72147.
Pinello et al., "Analyzing CRISPR genome-editing experiments with CRISPResso," Nat Biotechnol, 2016, 34(7):695-697.
Polstein et al., "A light-inducible CRISPR-Cas9 system for control of endogenous gene activation," Nature Chemical Biology, 2015, 11: 198-200.
Polstein et al., "Light-inducible spatiotemporal control of gene activation by customizable zinc finger transcription factors," J Am Chem Soc, 2012, 134(40): 16480-3.
Ponting et al., "Evolution and functions of long noncoding RNAs," Cell, 2009, 136(4): 629-641.
Popplewell et al., "Gene correction of a duchenne muscular dystrophy mutation by meganuclease-enhanced exon knock-in," Hum Gene Ther, 2013, 24: 692-701.
Povero et al., "Lipid-induced toxicity stimulates hepatocytes to release angiogenic microparticles that require Vanin-1 for uptake by endothelial cells," Sci Signal, 2013, 6(296): ra88.
Powell et al., "A Prader-Willi locus lncRNA cloud modulates diurnal genes and energy expenditure," Hum Molec Genet, 2013, 22: 4318-4328.
Prykhozhij et al., "CRISPR MultiTargeter: A Web Tool to Find Common and Unique CRISPR Single Guide RNA Targets in a Set of Similar Sequences," PLoS One, 2015, 10(3): e0119372.
Puccini et al., "Colorectal cancer: epigenetic alterations and their clinical implications,", Biochim Biophys Acta, 2017, vol. 1868, No. 2, pp. 439-448.
Qi et al., "Repurposting CRISPR as an RNA-guided platform for sequence specific control of gene expression," Cell, 2013, 152: 1173-1183.
Rackham et al., "A predictive computational framework for direct reprogramming between human cell types," Nature Genetics, 2016, 48: 331-335.
Rajagopal et al., "High-throughput mapping of regulatory DNA," Nat. Biotechnol, 2016, 34: 167-174.
Ramachandran et al., "Nitric Oxide Signaling Pathway in Duchenne Muscular Dystrophy Mice: Upregulation of L-arginine Transport," Biochem. J., 2012, 449: 133-142.
Ran et al., "Double nicking by RNA-guided CRISPR Cas9 for enhanced genome editing specificity," Cell, 2013, 154(6): 1380-9.
Ran et al., "Genome engineering using the CRISPR-Cas9 system," Nature Protocols, 2013, 8(11): 2281-2308.
Rao et al., "Engineering human pluripotent stem cells into a functional skeletal muscle tissue," Nat Commun, 2018, 9: 126.
Ratcliff et al., "A novel single-molecule study to determine protein-protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rebar et al., "Induction of angiogenesis in a mouse model using engineered transcription factors," Nat Med, 2002, 8: 1427-1432.
Reyon et al., "FLASH assembly of TALENs for high-throughput genome editing," Nat Biotechnol, 2012, 30: 460-465.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Reg, 2015, 43: 8627-8637.
Richter et al., "Phage-assisted evolution of an adenine base editor with improved Cas domain compatibility and activity," Nat Biotechnol, Jul. 2020, 38(7): 883-891.
Riordan et al., "Application of CRISPR/Cas9 for biomedical discoveries," Cell & Bioscience, 2015, 5(1):11 pages.
Rmilah et al., "Understanding the marvels behind liver regeneration," Wiley Interdiscip Rev Dev Biol., 2019, 8(3): e340.
Roadmap Epigehomics Consortium, "Integrative analysis of 111 reference human epigenomes," Nature, 2015, 518: 317-330.
Rodriguez et al., "Clustering by fast search and find of density peaks," Science, 2014, 344)6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Rousseau et al., "Endonucleases: tools to correct the dystrophin gene" The Journal of Gene Medicine, 2011, 13: 522-537.
Rutkauskas et al., "Directional R-loop formation by the CRISPR-Cas surveillance complex cascase provides efficient off-target site rejection," Cell reports, 2015, 10, 1534-1543.
Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atoh1 drives highly efficient differentiation of human pluripotent stem cells into dopaminergic neurons," Stem Cells Transl Med, 2014, 3: 888-898.
Sahoo et al., "Prader-Willi phenotype caused by paternal deficiency for the HBII-85 C/D box small nucleolar RNA cluster," Nat Genet, 2008, 40: 719-721.
Saito et al., "Specific activation of microRNA-127 with downregulation of the proto-oncogene BCL6 by chromatin-modifying drugs in human cancer cells," Cancer Cell, 2006, 9: 435-443.
Saitoh et al., "Parent-of-Origin Histone Acetylation and Reactivation of a Key Imprinted Gene Locus in Prader-Willi Syndrome," Am J Hum Genet, 2000, 66: 1958-1962.
Salmon et al., "Production and titration of lentiviral vectors," Curr Protoc Hum Genet, 2007, Chapter 12, Unit 12.10, Supplement 54, 24 pages.
Salmon et al., "Production and titration of lentiviral vectors," Curr Protoc Neurosci, 2006, Chapter 4: Unit 4 21.
Salva et al., "Design of tissue-specific regulatory cassettes for high-level rAAV-mediated expression in skeletal and cardiac muscle," Mol. Ther., 2007, 15:320-329.
Sambasivan et al., "Embryonic founders of adult muscle stem cells are primed by the determination gene Mrf4," Development Biology, 2013, 381: 241-255.
Sambrook et al., "Molecular Cloning and Laboratory manual," Second Ed., Cold Spring Harbor, 1989, pp. 16.7-16.8.
Sanghvi et al., "Heterocyclic Base Modifications in Nucleic Acids and their Applications in Antisense Oligonucleotides," 1993, Antisense Research and Applications, Chapter 15, pp. 274-285.
Sanjana et al., "High-resolution interrogation of functional elements in the noncoding genome," Science, 2016, 353: 1545-1549.
Sanson et al., "Optimized libraries for CRISPR-Cas9 genetic screens with multiple modalities," Nat Commun, 2018, 9: 5416.
SantaLucia et al., "Improved nearest-neighbor parameters for predicting DNA duplex stability," Biochemistry, 1996, 35(11): 3555-3562.
Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.

(56) References Cited

OTHER PUBLICATIONS

Schmid-Burgk et al., "A ligation-independent cloning technique for high-throughput of transcription activator-like effector genes," Nat Biotechnol, 2012, 31: 76-81.
Schmidt et al., "GenomeRNAi: a database for cell-based and in vivo RNAi phenotypes, 2013 update," Nucleic Acids Res, 2013, 41: D1021-6.
Schmittgen et al., "Analyzing real-time PCR data by the comparative CT method," Nature Protocols, 2008, 3(6): 1101-1108.
Scholze et al., "TAL effectors are remote controls for gene activation," Current Opinion in Microbiology, 2011, 14: 47-53.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv:1408.4401.
Schultz et al., "Recombinant adeno-associated virus transduction and integration," Molecular Therapy, 2008, 16: 1189-1199.
Sebastiano et al., "In Situ Genetic Correction of the Sickle Cell Anemia Mutation in Human Induced Pluripotent Stem Cells Using Engineered Zinc Finger Nucleases," Stem Cells, 2011, 29: 1717-1726.
Segal and Meckler, "Genome Engineering at the Dawn of the Golden Age," Annu. Rev. Genomics Hum. Genet., 2013, 14: 135-158.
Seidel et al., "Chromatin-modifying agents in anti-cancer therapy," Biochimie, 2012, 94: 2264-2279.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Sequence alignment: SEQ ID No. 102920 (2019).
Sequence alignment: SEQ ID No. 102921 (2019).
Sequence alignment SEQ ID No. 103735 (2019).
Sequence alignment: SEQ ID No. 103736 (2019).
Serra et al., "Predicting thermodynamic properties of RNA," Methods in Enzymology, 1995, 259: 242-261.
Shalem et al., "Genome-scale CRISPR-Cas9 knockout screening in human cells," Science, 2014, 343: 84-87.
Sharma et al., "Efficiency of nonhomologous DNA end joining varies among somatic tissues, despite similarity in mechanism," Cellular and Molecular Life Science, 2011, 68: 661-676.
Sharma et al., "In vivo gehome editing of the albumin locus as a platform for protein replacement therapy," Blood, 2015, 126: 1777-1784.
Shea et al., "Synthesis, hybridization properties and antiviral activity of lipid-oligodeoxynucleotide conjugates," Nucl. Acids Res, 1990, 18: 3777-3783.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shen et al., "Engraftment of a galactose receptor footprint onto adeno-associated viral capsids improves transduction efficiency," J Biol Chem, 2013, 288(40): 28814-28823.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Silva et al., "Meganucleases and other tools for targeted genome engineering: perspective and challenges for gene therapy," Current gene therapy, 2011, 11: 11-27.
Skene et al., "Genetic identification of brain cell types underlying schizophrenia," Nat Genet, 2018, 50: 825-833.
Soejima et al., "Imprinting centers, chromatin structure, and disease," J Cell Biochem, 2005, 95(2): 226-233.
Şöllü et al., "Autonomous zinc-finger nuclease pairs for targeted chromosomal deletion," Nucleic acids research, 2010, 38: 8269-8276.
Song et al., "Dnase-seq: a high-resolution technique for mapping active generegulatory elements across the gehome from mammalian cells," Cold Spring Harbor protocols 2010, pdb prot5384.
Song et al., "Non-immunogenic utrophin gene therapy for the treatment of muscular dystrophy animal models," Nature Medicine, 2019, 25(10): 1505-1511.
Song et al., "Open chromatin defined by DnaseI and FAIRE identifies regulatory elements that shape cell-type identify," Genome Res, 2011, 21: 1757-1767.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediciton Tool," PLoS One, 2015, 10(4): e0124633.
Stephens, "False discovery rates: a new deal," Biostatistics, 2017, 18: 275-294.
Stepper et al., "Efficient targeted DNA methylation with chimeric dCas9—Dnmt3a—Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Stuelsatz et al., "A Contemporary Atlast of the Mouse Diaphragm: Myogenicity, Vascularity, and the Pax3 Connection" J Histochem Cytochem, 2012, 60(9): 638-657.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A DNA vector-based RNAi technology to suppress gene expression in mammalian cells," PNAS, 2002, 99(8): 5515-5520.
Sun et al., "Optimized TAL effector nucleases (TALENs) for use in treatment of sickle cell disease," Molecular bioSystems, 2012, 8: 1255-1263.
Sun et al., "Phage mutations in response to CRISPR diversification in a bacterial population," Environmental microbiology, 2013, 15(2): 463-470.
Sur et al., "The role of enhancers in cancer,"Nat. Rev. Cancer., 2016, 16: 483-493.
Sutcliffe et al., "Deletions of a differentially methylated CpG island at the SNRPN gene define a putative imprinting control region," Nature Genetics, 1994, 8: 52-58.
Suzuki et al., "In vivo genome editing via CRISPR/Cas9 mediated homology-independent targeted integration," Nature, 2016, 540: 144-149.
Svinarchuk et al., "Inhibition of HIV proliferation in MT-4 cells by antisense oligonucleotide conjugated to lipophilic groups," Biochimie, 1993, 75: 49-54.
Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 1993, 17: 89-93.
Szyf, "Epigenetics, DNA methylation and chromatin modifying drugs," Annual Review of Pharmacology and Toxicology, 2009, 49: 243-263.
Takahashi et al., "A decade of transcription factor-mediated reprogramming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.
Takeshima et al., "Mutation spectrum of the dystrophin gene in 442 Duchene/Becker muscular dystrophy cases from one Japanese referral center," Journal of Human Genetics, 2010, 55: 379-388.
Tam et al., "Benefits and limitations of genome-wide association studies," Nat. Rev. Genet., 2019, 20: 467-484.

(56) References Cited

OTHER PUBLICATIONS

Tan et al., "Efficient derivation of lateral plate and paraxial mesoderm subtypes from human embryonic stem cells through GSKi-mediated differentiation," Stem Cells Dev, 2013, 22: 1893-1906.
Tan et al., "Rationally engineered Staphylococcus aureus Cas9 nucleases with high genome-wide specificity," Proc. Nat. Acad. Sci. USA, 2019, 116(46): 20969-20976.
Taniguchi-Ikeda et al., "Pathogenic exon-trapping by SVA retrotransposon and rescue in Fukuyama muscular dystrophy," Nature, 2011, 478: 127-131.
Tebas et al., "Gene editing of CCR5 in autologous CD4 T cells of persons infected with HIV," N Engl J Med, 2014, 370: 901-910.
Tedesco et al., "Repairing skeletal muscle: regenerative potential of skeletal muscle stem cells," J Clin Invest, 2010, 120: 11-19.
Tedesco et al., "Stem Cell-Mediated Transfer of a Human Artificial Chromosome Ameliorates Musculat Dystrophy," Science Translational Medicine, 2011, 3(96): 96ra78.
Tedesco et al., "Transplantation of Genetically Corrected Human iPSC-Derived Progenitors in Mice with Limb-Girdle Muscular Dystrophy," Science Translational Medicine, 2012, 4; 140ra189.
Teratani-Ota et al., "Induction of specific neuron types by overexpression of single transcription factors," In Vitro Cell Dev Biol Anim, 2016, 52(9): 961-973.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetics Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Tsai et al., "GUIDE-seq enables genome-wide profiling of off-target cleavage by CRISPR-Cas nucleases," Nature biotechnology, 2015, 33(2): 187-197.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380.
Tycko et al., "Screening S. aureus CRISPR-Cas9 Paired Guide RNAs for Efficient Targeted Deletion in Duchenne Muscular Dystrophy," Editas, Poster presented on May 5, 2016.
U.S. Appl. No. 17/471,935, filed Sep. 10, 2021, by Gersbach et al.
U.S. Appl. No. 17/636,750, filed Feb. 18, 2022, Gersbach et al.
U.S. Appl. No. 17/636,754, filed Feb. 18, 2022, by Gersbach et al.
Urnov et al., "Highly efficient endogenous human gene correction using designed zinc-finger nucleases," Nature, 2005, 435: 646-651.
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.
Van Arensbergen et al., "Genome-wide mapping autnomous promoter activity in human cells," Nature Biotechnology, 2017, 35(2): 145-153.
Van Deutekom et al., "Advances in Duchenne muscular dystrophy gene therapy," Nat. Rev. Genet., 2003, 4: 774-783.
Van Putten et al., "Low dystrophin levels in heart can delay heart failure in mdx mice," J Mol Cell Cardiol, 2014, 69C: 17-23.
Van Putten et al., "Low dystrophin levels increase survival and improve muscle pathology and function in dystrophin/utrophin double-knockout mice," FASEB J, 2013, 27: 2484-2495.

Vaquerizas et al., "A census of human transcription factors: function, expression and evolution," Nat Rev Genet, 2009, 10: 252-263.
Veltrop et al., "A dystrophic Duchenne mouse model for testing human antisense oligonucleotides," PLoS One, 2018, 13(2): e0193289, 18 pages.
Verkhusha et al., "GFP-like flourescent proteins and chromoproteins of the class Anthozoa," Protein Structures: Kaleidoscope of Structural Properties and Functions, 2003, 405-439.
Verma et al., "Gene Therapy: Twenty-first century medicine," Annual Review of Biochemistry, 2005, 74: 711-738.
Verma et al., "Gene therapy-promises, problems and prospects," Nature, 1997, 389: 239-242.
Vierbuchen et al., "Direct conversion of fibroblasts to functional neurons by defined factors," Nature, 2010, 463: 1035-1041.
Vierbuchen et al., "Direct lineage conversions: unnatural but useful?," Nat Biotechnol, 2011, 29: 892-907.
Vierbuchen et al., "Molecular roadblocks for cellular reprogramming," Mol Cell, 2012, 47: 827-838.
Vorobyov et al., "Expression of two protein isoforms of PAX7 is controlled by competing cleavage-polyadenlation and splicing," Gene, 2004, 342: 107-112.
Waddell e tal., "Dlk1 Is Necessary for Proper Skeletal Muscle Development and Regeneration," PLoS ONE, 2010, 5(11): e15055.
Waldrop et al., "Updated in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Adeno-associated virus vector carrying human minidystrophin genes effectively amerliorates muscular dystrophy in mdx mouse model," Proc Natl Acad Sci USA, 2000, 97(25): 13714-13719.
Wang et al., "Construction and analysis of compact muscle-specific promoters for AAV vectors," Gene Ther, 2008, 15: 1489-1499.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Gene Essentiality Profiling Reveals Gene Networks and Synthetic Lethal Interactions with Oncogenic Ras," Cell, 2017, 168: 890-903.e15.
Wng et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wang et al., "One-Step Generation of Mice Carrying Mutations in Multiple Genes by CRISPR-Cas-Mediated Genome Engineering," Cell, 2013, 153(4): 910-8.
Wang et al., "Potential of Epigenetic Therapy for Pader-Willi Syndrome," Trends in Pharmacologial Sciences, 2019, 40(9): 605-608.
Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature biotechnology, 2015, 33(2): 175-8.
Wapinski et al., "Hierarchical mechanisms for direct reprogramming of fibroblasts to neurons," Cell, 2013, 155: 621-635.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targetin Regnase-1 programs long-lived effector T cells for cancer therapy," Nature, 2019, 576(7787): 471-476.
Wein et al., "Efficient bypass of mutations in dysferlin deficient patient cells by antisense-induced exon skipping," Hum Mutat, 2010, 31: 136-142.
Welch et al., "PTC124 targets genetic disorders caused by nonsense mutations," Nature, 2007, 447: 87-91.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.

(56) References Cited

OTHER PUBLICATIONS

Wienert et al., "Editing the genome to introduce a beneficial naturally occurring mutation associated with increased fetal globin," Nat Commun 6, 2015, 7085.

Wiggins et al., "High flexibility of DNA on short length scales probed by atomic force microscopy," Nature nanotechnology, 2006, 1(2): 137-141.

Wilbie et al., "Delivery Aspects of CRISPR/Cas for in Vivo Genome Editing," Acc Chem Res, 2019, 52(6): 1555-1564.

Wiles et al., "CRISPR-Cas9_mediated gehome editing and guide RNA design," Mammalian Gehome, 2015, 26(9): 501-510.

Willmann et al., "Mammalian animal models for Duchenne muscular dystrophy," Neuromuscular Disorders, 2009, 19(4): 241-249.

Wood, "Neuromuscular disease: CRISPR/Cas9 gene-editing platform corrects mutations associated with Duchenne muscular dystrophy," Nature Reviews Neurology, 2015, 11(4):184.

Wu et al., "A Myogenic Double-Reporter Human Pluripotent Stem Cell Line Allows Prospective Isolation of Skeletal Muscle Progenitors," Cell Rep, 2018, 25: 1966-1981.e4.

Wu et al., "Genome-wide binding of the CRISPR endonuclease Cas9 in mammalian cells," Nature biotechnology, 2014, 32(7): 670-6.

Wu et al., "Induction of anion exchanger-1 translation and its opposite roles in the carcinogenesis of gastric cancer cells and differentiation of K562 cells," Oncogene, 2010, 29: 1987-1996.

Wu et al., "Unusual Processing Generates SPA LncRNAs that Sequester Multiple RNA Binding Proteins," Mol Cell, 2016, 64: 534-548.

Wüst et al., "Metabolic Maturation during Muscle Stem Cell Differentiation Is Achieved by MiR-1/133a-Mediated Inhibition of the Dlk1-Dio3 Mega Gene Cluster," Cell Metab, 2018, 27: 1026-1039.e6.

Wylie et al., "Distinct transcriptomes define rostral and caudal serotonin neurons," J Neurosci, 2010, 30: 670-684.

Xie et al., "Multiplexed Engineering and Analysis of Combinatorial Enhancer Activity in Single Cells," Mol. Cell, 2017, 66: 285-299.e5.

Xie et al., "sgRNAcas9: a software package for designing CRISPR sgRNA and evaluationg potential off-target cleavage sites," PLoS One, 2014, 9(6): e100448.

Xu et al., "CRISPR-mediated Genome Editing Restores Dystrophin Expression and Function in mdx Mice," Molecular Therapy: The Journal of the American Society of Gene Therapy, 2016, 24(3):564-569.

Xu et al., "Direct lineage reprogramming: strategies, mechanisms, and applications," Cell Stem Cell, 2015, 16: 119-134.

Xu et al., "Human Satellite Cell Transplantation and Regeneration from Diverse Skeletal Muscles," Stem Cell Rep, 2015, 5: 419-434.

Xu et al., "Recent advances in neuroepigenetic editing," Curr Opin Neurobiol, 2019, 59: 26-33.

Xue et al., "Synthetic mRNAs Drive Highly Efficient iPS Cell Differentiation to Dopaminergic Neurons," Stem Cells Transl Med, 2019, 8: 112-123.

Yan et al., "Drugging the Undruggable: Transcription Therapy for Cancer," Biochim Biophys Acta, 2013, 1835(1): 76-85.

Yang et al., "Determination of protein-DNA binding constants and specificities from statistical analyses of single molecules: MutS-DNA interactions," Nucleic acids research, 2005, 33(13): 4322-4334.

Yang et al., "Gene Reactivation by 5-Aza-2'-Deoxycytidine-Induced Demethylation Requires SRCAP-Mediated NZA.Z Insertion to Establish Nucleosome Depleted Regions", PLoS Genetics, 2012, vol. 8, Issue 3, e1002604, 12 pages.

Yang et al., "Generation of pure GABAergic neurons by transcription factor programming," Nat Methods, 2017, 14: 621-628.

Yang et al., "Optimization of scarless human stem cell genome editing," Nucleic Acids Res, 2013, 41(19): 9049-9061.

Yin et al., "Long noncoding RNAs with snoRNA ends," Mol Cell, 2012, 48(2): 219-230.

Yin et al., "Programming biomolecular self-assembly pathways," Nature, 2008, 451 (7176):318-323.

You et al., "Design of LNA probes that imrpove mismatch discrimination," Nuc. Acids, Res., 2006, 34(8): e60.

Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.

Young et al., "Creation of a Novel Humanized Dystrophic Mouse Model of Duchenne Muscular Dystrophy and Application of a CRISPR/Cas9 Gene Editing Therapy," Journal of Neuromuscular Diseases, 2017, 4(2): 139-145.

Younossi et al., "Epidemiology of chronic liver diseases in the USA in the past three decades," Gut, 2020, 69(3): 564-568.

Yu et al., "RNA interference by expression of short-interfering RNAs and hairpin RNAs in mammalian cells," PNAS, 2002, 99(9): 6047-6052.

Yusa et al., "Targeted gene correction of α1-antitrypsin deficiency in induced pluripotent stem cells," Nature, 2011, 478: 391-394.

Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.

Zetsche et al., "Cpf1 Is a Single RNA-Guided Endonuclease of a Class 2 CRISPR-Cas System," Cell, 2015, 163(3):759-71.

Zhang et al., "Efficient construction of sequence-specific TAL effectors for modulating mammalian transcription," Nat Biotechnol, 2011, 29: 149-153.

Zhang et al., "Comprehensive Structure-Function Study of Neurogenin3 Disease-Causing Alleles during Human Pancreas and Intestinal Organoid Development," Dev Cell, 2019, 50(3): 367-380.e7.

Zhang et al., "Efficient precise knockin with a double cute HDR donor after CRISPR-Cas9-mediated double-stranded DNA cleavage," Genome Biol, 2017 18(35): 18 pages.

Zhang et al., "Gene activation in human cells using CRISPR/Cpf1-p300 and CRISPR/Cpf1-SunTag systems," Protein Cell, 2018, 9: 380-383.

Zhang et al., "Myoediting: Toward Prevention of Muscular Dystrophy by Therapeutic Genome Editing," Physiological Reviews, 2018, 98(3): 1205-1240.

Zhang et al., "Rapid single-step induction of functional neurons from human pluripotent stem cells," Neruon, 2013, 78: 785-798.

Zhao et al., "Intracelular delivery of artificial transcription factors fused to the protein transduction domain of HIV-1 Tat," Protein Expr Purif, 2013, 90(1):27-33.

Zhao et al., "The LIM-homeobox gene Lhx8 is required for the development of many cholinergic neurons in the mouse forebrain," Proc Natl Acad Sci U S A, 2003, 100: 9005-9010.

Zheng et al., "Foxp3 in control of the regulatory T cell lineage," Nat. Immunol. 2007, 8: 457-462.

Zhou et al., "Haploinsufficiency of utrophin gene worsens skeletal muscle inflammation and fibrosis in mdx mice," Journal of the Neurological Sciences, 264(1): 106-111.

Zhu et al., "Cellular senescence in human telomerase reverse transcriptase and cyclin-dependent kinase 4: consequences in aging muscle and therapeutic strategies for muscular dystrophies," Aging cell, 2007, 6: 515-523.

Zhu et al., "The role of histone deacetylase 7 (HDAC7) in cancer cell proliferation: regulation on c-Myc," J. Mol. Med, 2011, 89: 279-289.

Zou et al., "Site-specific gene correction of a point mutation in human iPS cells derived from an adult patient with sickle cell disease," Blood, 2011, 118: 4599-4608.

European Patent Office Extended Search Report for Application No. 22168794.0 dated Oct. 18, 2022 (12 pages).

Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.

Min et al., "CRISPR Correction of Duchene Muscular Dystrophy Exon 44 Deletion Mutations in Mice and Human Cells," Science Advances, 2019, 5: eaav4324.

NCBI Reference Sequence NG_028016.2 (2013).

(56) References Cited

OTHER PUBLICATIONS

NCBI Reference Sequence NM_004020.2 (2010).
NCBI Reference Sequence XM011532698.1 (2015).
Robinson-Hamm et al., "Gene therapies that restore dystrophin expression for the treatment of Duchenne muscular dystrophy," Human Genetics, 2016, 135(9): 1029-1040.
U.S. Appl. No. 17/879,506, filed Aug. 2, 2022, by Josephs et al.
U.S. Appl. No. 17/922,751, filed Nov. 1, 2022, by Iglesias et al.
Yu et al., "Dystrophin-deficient large animal models: translational research and exon skipping," Am J Transl Res, 2015, 7(8): 1314-1331.
Trinklein et al., "Identification and functional analysis of human transcriptional promoters," Genome Research, 2003, 13(2): 308-312.
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
Adikusuma et al., "Versatile single-step-assembly CRISPR/Cas9 vectors for dual gRNA expression," 2017, 12(12): e0187236.
Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999, 64(2): 397-413.
Yang et al., "A dual AAV system enables the Cas9-mediated correction of a metabolic liver disease in newborn mice," Nature Biotechnology, 2016, 34(3): 334-338.
United States Patent Office Action for U.S. Appl. No. 16/927,679 dated Sep. 21, 2023 (6 pages).
United States Patent Office Notice of Allowance for U.S. Appl. No. 15/789,348 dated Oct. 17, 2023 (7 pages).
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors,"Mol Ther Nucl Acids, 2013, 2: e93, 11 pages.
Azuma et al., "Robust expansion of human hepatocytes in Fah-/-/Rag2-/-/Il2rg-/- mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Buckingham, M. et al. "The role of Pax genes in the development of tissues and organs: Pax3 and Pax7 regulate muscle progenitor cell functions." Annu. Rev. Cell Dev. Biol. 23 (2007): 645-673.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.
Carlens et al., "Ex vivo T lymphocyte expansion for retroviral transduction: influence of serum-free media on variations in cell expansion rates and lymphocyte subset distribution," Exp Hemtol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Chakraborty et al., "553. AAV-fVlediated Delivery of HSV--Specific Homing Endonucleases To Neurons of the Trigeminal Ganglia for HSV-1 Inhibition." Molecular Therapy 22 (2014).
Chen et al., "Fusion protein linkers: property, design and functionality," Adv. Drug Deliv. Rev., 2013, 65(10): 1357-1369.
Chicaybam et al., "An efficient low cost method for gene transfer to T lymphocytes," PLoS ONE, 2013, 8(3): e60298, 11 pages.
Chylinski et al., "The tracrRNA and Cas9 families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortés-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Devleopment, 2005, 15(5): 490-495.
Gersbach et al., "Synthetic zinc finger proteins: the advent of targeted gene regulation and genome modification technologies," Acc. Chem. Res., 2014, 47(8): 2309-18.
Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Gowher et al., "Molecular enzymology of the catalytic domains of the Dnmt3a and Dnmt3b DNA methyltransferases," J. Biol. Chem., 2002, 277(23): 20409-20414.
Hochstrasser et al., "CasA mediates Cas3-catalyzed target degradation during CRISPR RNA-guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation," Nature, 2007, 449(7159): 248-251.
Johnston, "Biolistic transformation: microbes to mice," Nature, 1990, 346: 776-777.
Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (DNMT) 3B to enhance DNMT3B-mediated transcriptional repression," Biochemical and Biophysical Research Communications, 2007, 355(2): 318-323.
Koste et al., "T-cell receptor transfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun., 2017, 8: 16026, 10 pages.

(56) References Cited

OTHER PUBLICATIONS

Li et al., "Development of fluorescent methods for DNA methyltransferase assay," Methods Appl. Fluoresc., 2017, 5: 012002, 8 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Liu et al., "Design of polydactyl zinc-finger proteins for unique addressing within complex genomes," PNAS, 1997, 94(11): 5525-5530.
Ma et al., "Pol III Promoters to Express Small RNAs: Delineation of Transcription Initiation," Molecular Therapy—Nucleic Acids, 2014, 3: e161, 11 pages.
Makarova et al., "Annotation and Classification of CRISPR-Case Systems," Methods Mol. Biol, 2015, 1311: 47-75.
Manuri et al., "piggyBac transposon/transposase syste mto generate CD19-specific T cells for the treatment of B-lineage malignancies," Hum Gene Ther, 2010, 21(4): 427-437.
Mavrothalassitis et al., "Proteins of the ETS family with transcriptional repressor activity," Oncogene, 2000, 19: 6524-6532.
Miller et al., "Improved retroviral vectors for gene transfer and expression," BioTechniques, 1989, 7(9): 980-990.
Miller, "Retrovirus packaging cells," Human Gene Therapy, 1990, 1: 5-14.
Milone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130, 11 pages.
Moussa et al., "Here to stay: Writing lasting epigenetic memories," Cell, 2021, 184(9): 2281-2283.
Murphy et al., "The Transcriptional Repressive Activity of KRAB Zinc Finger Proteins Does Not Correlate with Their Ability to Recruit TRIM28," PLoS ONE, 2016, 11(9): e0163555, 19 pages.
O'Geen et al., "Determinants of heritable gene silencing for KRAB-dCas9 + DNMT3 and Ezh2-dCase9 + DNMT3 hit-and-run epigenome editing," Nucleic Acids Res, 2022, 50(6): 3239-3253.
Orth et al., "Structural basis of gene regulation by the tetracycline inducible Tet represor-operator system," natural structural biology, 2000, 7(3): 215-219.
Park et al., "Treating cancer with genetically engineered T cells," Trends Biotechnol, 2011, 29(11): 550-557.
Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.

Poh et al., "DNA Methyltransferase Activity Assays: Advances and Challenges," Theranostics, 2016, 6(3): 369-391.
Poirier et al., "The proprotein convertase PCSK9 induces the degradation of low density lipoprotein receptor (LDLR) and its closest family members VLDLR and ApoER2"J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.
Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.
Sharma et al., "Efficient Sleeping Beauty DNA Transposition From DNA Minicircles," Molec Ther Nucl Acids, 2013, 2(2): e74, 10 pages.
Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.
Thakore et al., "385. Inhibiting the Myostatin Signaling Pathway using CRISPR-Cas9-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adult bone marrow CD34+ cells via electroporation-mediated gene delivery," Gene Therapy, 2000, 7(16): 1434-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. Immunother, 2012, 35(9): 689-701.
Wright et al., "Rational design of a split-Cas9 enzyme complex," PNAS, 2015, 112(10): 2984-2989.
Wright et al., "Standardized reagents and protocols for engineering zinc finger nucleases by modular assembly," Nat. Protoc., 2006, 1(3): 1637-1652.
Zetsche et al., "A split-Cas9 architecture for inducible genome editing and transcription modulation," Nat. Biotechnol, 2015, 33(2): 139-142.
Echevarria et al., "Exon-skipping advances for Duchenne muscular dystrophy," Human Molecular Genetics, 2018, 27 (R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.

\* cited by examiner

FIG. 6

V1. 3x crRNA array (pAP05)

SEQ ID NO: 51

**GAGGGCCTATTTCCCATGATTCCTTCATATATTTGCATATACGATACAAGGCTGTTAGAGAGATAATTG
GAATTAATTTGACTGTAAACACAAAAGATATTAGTACAAAATACGTGACGTAGAAAGTAATAATTTCT
TGGGTAGTTGCAGTTTTAAAATTATGTTTAAAATGGACTATCATATGCTTACCGTAACTTGAAAG
TATTTCGATTTCTTGGCTTTATATCTTGTGGAAAGGACGAAACACC**GGTCGCACTCTTCATGGG
*TGCGTGGATTGAAAT*ACGGGTGAAATACCGGGTCGGACTCGGACTCTTCATGGG
*TGCGTGGATTGAAAT*AGGGTCAGCTTGCCGTAGGTGCGCATCCGGTCGCACTCTTCATGGG
*TGCGTGGATTGAAAT*AGCCGTACCCGACGACAGCAAGCAGGACAGTCGCACTCTTCATGGG
*TGCGTGGATTGAAAT*TTTTTT

U6 promoter = bold
+1 transcription site = underlined
Repeat = italicized and underlined
crRNA spacer sequence = italicized (crRNA-A, crRNA-I, crRNA-J)
Poly-T terminator sequence = bold and underlined

FIG. 13

V2. Individual crRNAs (pAP07-09)

SEQ ID NO: 52

**GAGGGCCTATTTCCCATGATTCCTTCATATTTGCATATACGATACAAGGCTGTTAGAGAGATAATTG
GAATTAATTTGACTGTAAACACAAAGATATTAGTACAAAATGTGACGTAGAAAGTAATAATTTCT
TGGGTAGTTTGCAGTTTTAAAATTATGTTTTAAAATGGACTATCATATGCTTACCGTAACTTGAAAG
TATTTCGATTTCTTGGCTTTATATATCTTGTGGAAGGACGAAACCG**<u>*TGGATTGAAAT*</u><u>ACGGG
*GTGGGTGCCCATCCTGGTCGAGCTGGA*</u>*GTCGGAGCTGGA*<u>GTCGGCACTCTTCATGGGTGGCGTTTTTT</u>

U6 promoter = bold
+1 transcription site = underlined
Repeat = italicized and underlined
    5' repeat = italicized and double underline
    3' repeat = italicized and single underline
crRNA spacer sequence = italicized (crRNA-A, crRNA-I, crRNA-J)
Poly=T terminator sequence = bold and underlined

FIG. 14

Generating GFP+ HEK293T cells

5ul transduction | 50ul transduction | 150ul transduction | GFP transfection

Flow results (% GFP positive)

5x transduction
13%

50x transduction
59%

150x transduction
91%

GFP transfection
N/A

FIG. 15

Type I-E Constructs

Cloned from *E. coli* genomic DNA

| System | Protein | Tag/ NLS side | Epitope tag | kb | Plasmid |
|---|---|---|---|---|---|
| I-E | CasA | NTD | myc | 59 | pAP46 |
| I-E | CasB | NTD | VSV | 22 | pAP47 |
| I-E | CasC | NTD | V5 | 43 | pAP48 |
| I-E | CasD | NTD | HA | 28 | pAP49 |
| I-E | CasE | NTD | E | 25 | pAP50 |
| I-E | Cas3 | NTD | 3xFlag | 105 | pAP45 |

Cloned using IDT's human codon optimization tool

| System | Protein | Tag/ NLS side | Epitope tag | kb | Plasmid |
|---|---|---|---|---|---|
| I-E | CasA | NTD | myc | 59 | pAP62 |
| I-E | CasB | NTD | VSV | 22 | pAP63 |
| I-E | CasC | NTD | V5 | 43 | pAP64 |
| I-E | CasD | NTD | HA | 28 | pAP65 |
| I-E | CasE | NTD | E | 25 | pAP66 |
| I-E | Cas3 | NTD | 3xFlag | 105 | pAP67 |

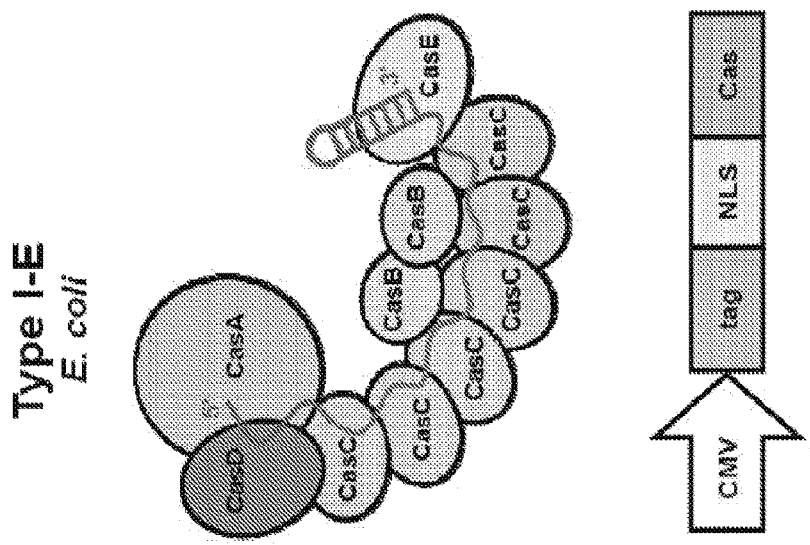

FIG. 37

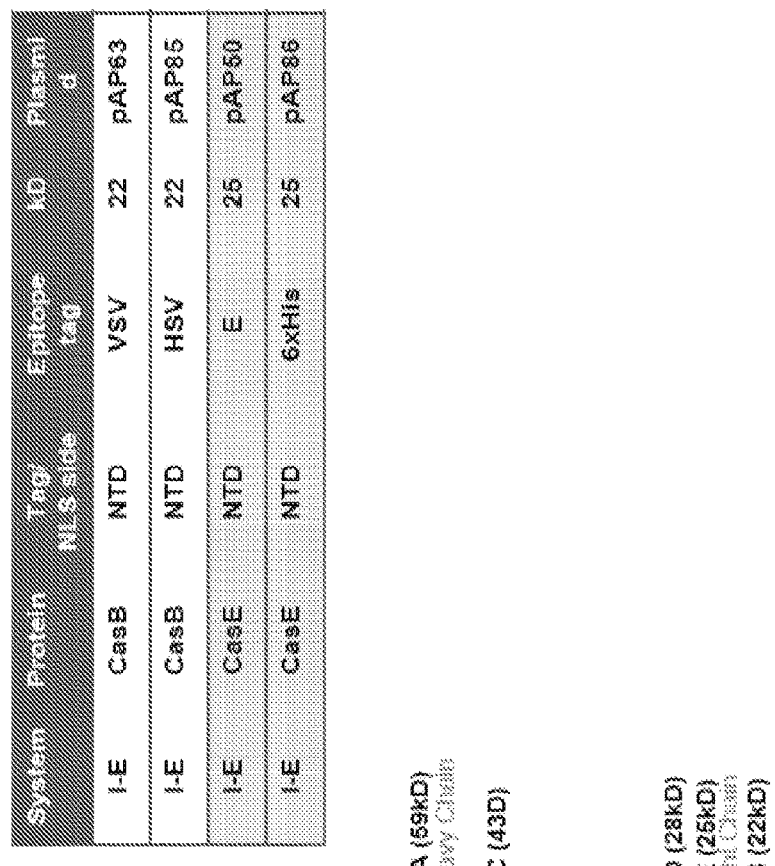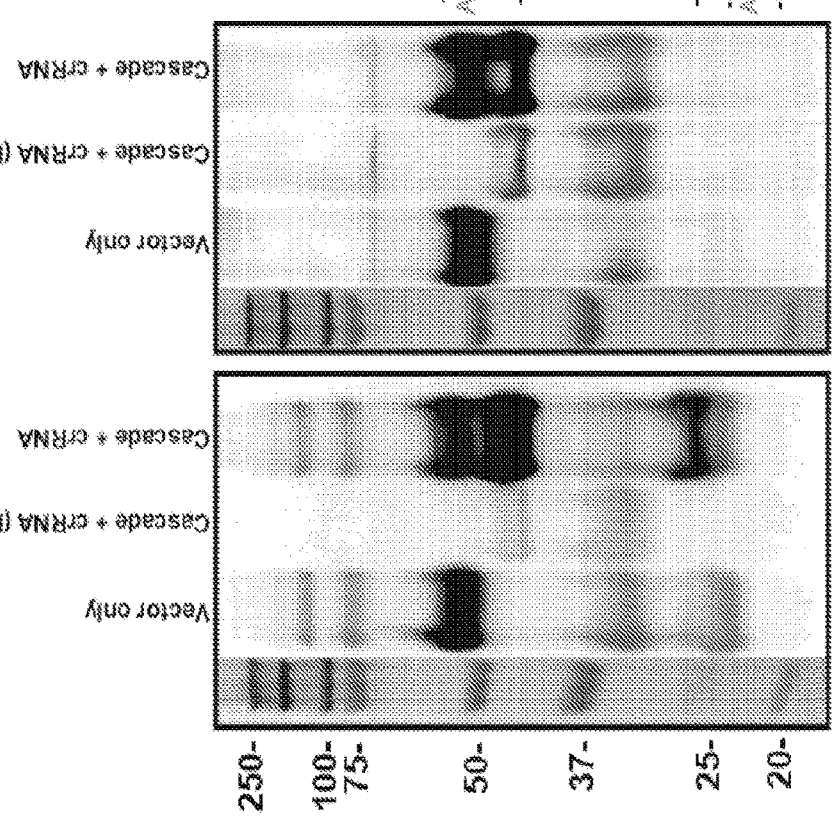
FIG. 42

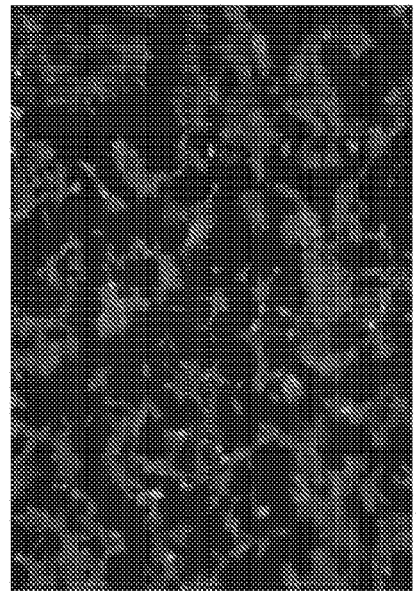
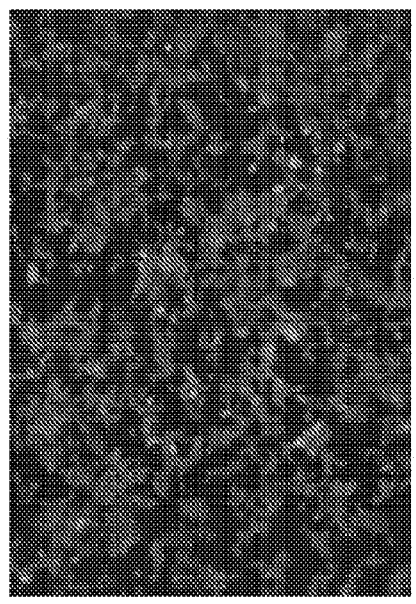
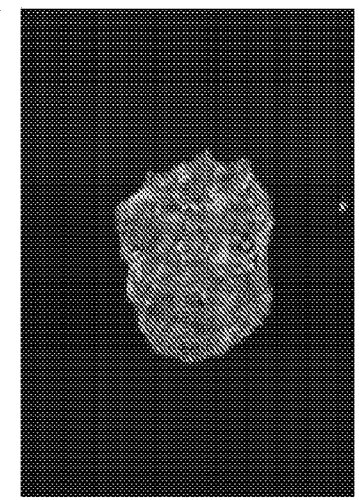
FIG. 45

Bacterial Protein Purification Duet System Constructs

| Plasmid | 1st MCS | 2nd MCS | Vector | Resistance |
|---|---|---|---|---|
| pAP76 | CasA | — | pRSF | Kan |
| pAP78 | CasB (6xHis) | CasC | pET | Amp/Carb |
| pAP83 | CasC (6xHis) | CasB | pET | Amp/Carb |
| pAP80 | CasD | CasE | pCDF | Sm |
| pAP71 | pAP57 3x crRNA (Targeting GFP) | | pACYC | CAM |
| pAP72 | APcr03 crRNA (Targeting CMV) | | pACYC | CAM |
| pAP73 | APcr04 crRNA (Targeting CMV) | | pACYC | CAM |
| pAP74 | APcr09 crRNA (Targeting GFP) | | pACYC | CAM |
| pAP75 | APcr10 crRNA (Targeting GFP) | | pACYC | CAM |
| pAP84 | CasC (6xHis) | — | pRSF | Kan |

FIG. 50

Type I-F Constructs

**Cloned from *P. aeruginosa* genomic DNA**

| System | Protein | Tag/NLS Side | Epitope tag | kb | Plasmid |
|---|---|---|---|---|---|
| I-F | Csy4 | NTD | HA | 24 | pAP85 |

Cloned using IDT's human codon optimization tool

| System | Protein | Tag/NLS Side | Epitope tag | kb | Plasmid |
|---|---|---|---|---|---|
| I-F | Csy1 | NTD | E | 52 | pAP51 |
| I-E | Csy2 | NTD | myc | 39 | pAP52 |
| I-E | Csy3 | NTD | V5 | 40 | pAP53 |
| I-E | Csy4 | NTD | HA | 24 | pAP54 |
| I-E | Cas3 | NTD | 3xFlag | 125 | pAP55** |

| | Plasmid | Transfection amount for each well (1600 ng total for 12-well) | | | | | | | | |
|---|---|---|---|---|---|---|---|---|---|---|
| | | 1 | 2 | 3 | 4 | 5 | 6 | 7 | 8 | 9 |
| crRNA | mCherry-Vec | AP94 | 1600 | | | | | | | | |
| crRNA | mCherry-CMV | cr013 | | 1600 | | | | | | | |
| crRNA | mCherry-CMV | cr014 | | | 1600 | | | | | | |
| crRNA | mCherry-3xGFP | AP95 | | | | 1600 | | | | | |
| crRNA | mCherry-GFP | cr015 | | | | | 1600 | | | | |
| crRNA | mCherry-GFP | cr016 | | | | | | 1600 | | | |
| | | Lenti-FlpIn c.8 (AP91+AP90 C.3) cells | | | | | | Lenti cells | 293T cells | 293T cells |

FIG. 56

SEQUENCE LISTING

<160> NUMBER OF SEQ ID NOS: 83

<210> SEQ ID NO 1
<211> LENGTH: 8
<212> TYPE: PRT
<213> ORGANISM: Artificial sequence
<220> FEATURE:
<223> OTHER INFORMATION: Synthetic

<400> SEQUENCE: 1

Asp Tyr Lys Asp Asp Asp Asp Lys
1               5

<210> SEQ ID NO 2
<211> LENGTH: 10
<212> TYPE: PRT
<213> ORGANISM: Artificial sequence
<220> FEATURE:
<223> OTHER INFORMATION: Synthetic

<400> SEQUENCE: 2

Tyr Pro Tyr Asp Val Pro Asp Tyr Ala Cys
1               5                   10

<210> SEQ ID NO 3
<211> LENGTH: 11
<212> TYPE: PRT
<213> ORGANISM: Artificial sequence
<220> FEATURE:
<223> OTHER INFORMATION: Synthetic

<400> SEQUENCE: 3

Glu Gln Lys Leu Ile Ser Glu Glu Asp Leu Cys
1               5                   10

<210> SEQ ID NO 4
<211> LENGTH: 14
<212> TYPE: PRT
<213> ORGANISM: Artificial sequence
<220> FEATURE:
<223> OTHER INFORMATION: Synthetic

<400> SEQUENCE: 4

Gly Lys Pro Ile Pro Asn Pro Leu Leu Gly Leu Asp Ser Thr
1               5                   10

<210> SEQ ID NO 5
<211> LENGTH: 13
<212> TYPE: PRT
<213> ORGANISM: Artificial sequence
<220> FEATURE:
<223> OTHER INFORMATION: Synthetic

<400> SEQUENCE: 5

```
Gly Ala Pro Val Pro Tyr Pro Asp Pro Leu Glu Pro Arg
1               5                   10
```

<210> SEQ ID NO 6
<211> LENGTH: 11
<212> TYPE: PRT
<213> ORGANISM: Artificial sequence
<220> FEATURE:
<223> OTHER INFORMATION: Synthetic

<400> SEQUENCE: 6

```
Tyr Thr Asp Ile Glu Met Asn Arg Leu Gly Lys
1               5                   10
```

<210> SEQ ID NO 7
<211> LENGTH: 6
<212> TYPE: PRT
<213> ORGANISM: Artificial sequence
<220> FEATURE:
<223> OTHER INFORMATION: Synthetic

<400> SEQUENCE: 7

```
His His His His His His
1               5
```

<210> SEQ ID NO 8
<211> LENGTH: 12
<212> TYPE: PRT
<213> ORGANISM: Artificial sequence
<220> FEATURE:
<223> OTHER INFORMATION: Synthetic

<400> SEQUENCE: 8

```
Gln Pro Glu Leu Ala Pro Glu Asp Pro Glu Asp Cys
1               5                   10
```

<210> SEQ ID NO 9
<211> LENGTH: 7
<212> TYPE: PRT
<213> ORGANISM: Artificial sequence
<220> FEATURE:
<223> OTHER INFORMATION: Synthetic

<400> SEQUENCE: 9

```
Pro Lys Lys Lys Arg Lys Val
1               5
```

<210> SEQ ID NO 10
<211> LENGTH: 20
<212> TYPE: PRT
<213> ORGANISM: Artificial sequence
<220> FEATURE:
<223> OTHER INFORMATION: Synthetic

<400> SEQUENCE: 10

```
Ala Val Lys Arg Pro Ala Ala Thr Lys Lys Ala Gly Gln Ala Lys Lys
1               5                   10                  15

Lys Lys Leu Asp
```

<210> SEQ ID NO 11
<211> LENGTH: 25
<212> TYPE: PRT
<213> ORGANISM: Artificial sequence
<220> FEATURE:
<223> OTHER INFORMATION: Synthetic

<400> SEQUENCE: 11

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 12
<211> LENGTH: 9
<212> TYPE: PRT
<213> ORGANISM: Artificial sequence
<220> FEATURE:
<223> OTHER INFORMATION: Synthetic

<400> SEQUENCE: 12

Pro Ala Ala Lys Arg Val Lys Leu Asp
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic

<400> SEQUENCE: 13

Lys Leu Lys Ile Lys Arg Pro Val Lys
1               5

<210> SEQ ID NO 14
<211> LENGTH: 2400
<212> TYPE: DNA
<213> ORGANISM: Artificial sequence
<220> FEATURE:
<223> OTHER INFORMATION: Synthetic

<400> SEQUENCE: 14

```
atgtacatcg cacatatccg ggaggttgat aaggtgattc aaaccttgaa ggagcatctg      60
tgtggggtgc agtgcctggc agagaccttc ggcgccaagc tgcggctcca gcatgtagcg     120
gggctcgccg ggctcctcca tgacctggga agtatactaa cgagttcaa ggactatata      180 tataaagctg tctttgagcc cgagcttgct gagaaaaagc gcggtcaagt tgaccattct     240
accgccggcg gtaggcttct gtatcaaatg ctccacgatc gcgaaaattc tttccacgaa     300
aagctcctgg ccgaggtcgt ggggaacgca attatatctc accactccaa cctgcaggat     360
tatatttccc ccacaataga gtcaaacttc ctgacacgcg tactcgagaa ggagctgcct     420
gagtatgagt cagctgtgga aaggtttttc aagaagtga tgacagaagc agaacttgcg      480
cgctatgtgg ccaaagctgt ggacgagata aagcaattta ccgataattc tcccacgcag     540
tctttttttc tcaccaagta tattttagc tgcttgatcg acgctgatag gaccaacacc      600
cggatgtttg acgagcaggc aagagaggag gaacccacac agcctcagca gctcttcgag     660
cactatcatc agcaactgct gaatcacctc gcttccctga aggaaagtga cagtgctcag     720
aagcctatta acgtgctccg gagcgccatg tcagagcaat gcgaatcctt tgcaatgcgc     780
```

-continued

```
cctagtggca tctataccct gtccattccc accggcggcg ggaaaacatt ggcgagtctg    840
cggtatgccc tcaaacacgc tcaggagtac aacaagcaga ggataattta cattgtcccc    900
ttcaccacca ttattgagca gaatgcccag gaagttagaa acatcctcgg ggatgatgag    960
aatattctgg agcaccactc caacgtcgtt gaagatagtg aaaatggcga tgagcaagaa   1020
gacggcgtca tcacaaagaa ggagcgcctc agactggcga gagataactg gacagacct    1080
atcatcttta ctactttggt ccagtttctg aacgtgtttt atgcaaaggg gaacaggaac   1140
acaagaaggt tgcataatct cagccactcc gtgctgatat tcgatgaggt gcagaaggtt   1200
cctactaaat gtgtgtcatt gtttaacgag gccctgaact ttcttaaaga gttcgcacat   1260
tgctccatcc tcctctgtac ggcaacccag ccgacacttg aaaacgttaa gcacagtctg   1320
ttgaaggata gggatgggga gatagtgcag aatctgaccg aggtctccga agcctttaaa   1380
cgcgtcgaaa tcctggacaa gaccgaccag ccaatgacga atgagcgact ggcagagtgg   1440
gttcgagatg aggcaccttc atggggctcc accttgatta tcctcaatac caagaaggtc   1500
gtgaaggatc tttatgagaa gcttgaggga ggacccctgc ccgtgtttca cctgtcaact   1560
tccatgtgtg ctgctcatcg caaagaccaa ctcgacgaaa tacgcgccct cctgaaggaa   1620
ggcacccctt tcatctgtgt gaccacccag ctgatcgagg ctggtgtgga cgtctccttt   1680
aaatgcgtga tacgctctct ggctggactg gatagcatag cgcaggctgc cggaagatgc   1740
aatagacatg gcgaagagca gttgcaatat gtgtacgtga ttgaccacgc cgaagaaact   1800
ctgagcaaat tgaaggagat agaggtgggc caggagatcg ctggaaacgt ccttgcacgc   1860
ttcaaaaaga aagcagaaaa atatgagggc aatttgctgt ctcaggctgc aatgcgagag   1920
tacttcaggt attattattc caagatggat gccaacctga actactttgt gaaagaggtg   1980
gacaaagaca tgactaagct gctcatgtcc catgcagttg aaaactccta tgtaacttat   2040
tatcagaaga acaccgggac tcacttccct cttctgttga atggcagcta caagaccgcc   2100
gctgaccact ttagagtaat cgatcagaac accacttccg ctatcgtccc atacggcgag   2160
ggacaagaca tcattgcaca gcttaatagc ggcgagtggg tggacgatct ttctaaagtg   2220
ctgaaaaagg ctcagcagta taccgttaat ctgtattccc aggagataga ccagctgaag   2280
aaagagggtg caatcgtgat gcatcttgac ggcatggtct acgaactgaa agaaagttgg   2340
tactcccacc agtacggggt ggatttcaag ggtgaagggg ggatggattt tatgagttttt  2400
```

<210> SEQ ID NO 15
<211> LENGTH: 800
<212> TYPE: PRT
<213> ORGANISM: Bacillus halodurans

<400> SEQUENCE: 15

```
Met Tyr Ile Ala His Ile Arg Glu Val Asp Lys Val Ile Gln Thr Leu
1               5                   10                  15

Lys Glu His Leu Cys Gly Val Gln Cys Leu Ala Glu Thr Phe Gly Ala
            20                  25                  30

Lys Leu Arg Leu Gln His Val Ala Gly Leu Ala Gly Leu Leu His Asp
        35                  40                  45

Leu Gly Lys Tyr Thr Asn Glu Phe Lys Asp Tyr Ile Tyr Lys Ala Val
    50                  55                  60

Phe Glu Pro Glu Leu Ala Glu Lys Lys Arg Gly Gln Val Asp His Ser
65                  70                  75                  80

Thr Ala Gly Gly Arg Leu Leu Tyr Gln Met Leu His Asp Arg Glu Asn
```

```
                85                  90                  95
Ser Phe His Glu Lys Leu Leu Ala Glu Val Gly Asn Ala Ile Ile
            100                 105                 110

Ser His His Ser Asn Leu Gln Asp Tyr Ile Ser Pro Thr Ile Glu Ser
115                 120                 125

Asn Phe Leu Thr Arg Val Leu Glu Lys Glu Leu Pro Glu Tyr Glu Ser
            130                 135                 140

Ala Val Glu Arg Phe Phe Gln Glu Val Met Thr Glu Ala Glu Leu Ala
145                 150                 155                 160

Arg Tyr Val Ala Lys Ala Val Asp Glu Ile Lys Gln Phe Thr Asp Asn
                165                 170                 175

Ser Pro Thr Gln Ser Phe Phe Leu Thr Lys Tyr Ile Phe Ser Cys Leu
            180                 185                 190

Ile Asp Ala Asp Arg Thr Asn Thr Arg Met Phe Asp Glu Gln Ala Arg
            195                 200                 205

Glu Glu Glu Pro Thr Gln Pro Gln Gln Leu Phe Glu His Tyr His Gln
            210                 215                 220

Gln Leu Leu Asn His Leu Ala Ser Leu Lys Glu Ser Asp Ser Ala Gln
225                 230                 235                 240

Lys Pro Ile Asn Val Leu Arg Ser Ala Met Ser Glu Gln Cys Glu Ser
                245                 250                 255

Phe Ala Met Arg Pro Ser Gly Ile Tyr Thr Leu Ser Ile Pro Thr Gly
            260                 265                 270

Gly Gly Lys Thr Leu Ala Ser Leu Arg Tyr Ala Leu Lys His Ala Gln
            275                 280                 285

Glu Tyr Asn Lys Gln Arg Ile Ile Tyr Ile Val Pro Phe Thr Thr Ile
            290                 295                 300

Ile Glu Gln Asn Ala Gln Glu Val Arg Asn Ile Leu Gly Asp Asp Glu
305                 310                 315                 320

Asn Ile Leu Glu His His Ser Asn Val Val Glu Asp Ser Glu Asn Gly
                325                 330                 335

Asp Glu Gln Glu Asp Gly Val Ile Thr Lys Lys Glu Arg Leu Arg Leu
            340                 345                 350

Ala Arg Asp Asn Trp Asp Arg Pro Ile Ile Phe Thr Thr Leu Val Gln
            355                 360                 365

Phe Leu Asn Val Phe Tyr Ala Lys Gly Asn Arg Asn Thr Arg Arg Leu
            370                 375                 380

His Asn Leu Ser His Ser Val Leu Ile Phe Asp Glu Val Gln Lys Val
385                 390                 395                 400

Pro Thr Lys Cys Val Ser Leu Phe Asn Glu Ala Leu Asn Phe Leu Lys
                405                 410                 415

Glu Phe Ala His Cys Ser Ile Leu Leu Cys Thr Ala Thr Gln Pro Thr
            420                 425                 430

Leu Glu Asn Val Lys His Ser Leu Leu Lys Asp Arg Asp Gly Glu Ile
            435                 440                 445

Val Gln Asn Leu Thr Glu Val Ser Glu Ala Phe Lys Arg Val Glu Ile
            450                 455                 460

Leu Asp Lys Thr Asp Gln Pro Met Thr Asn Glu Arg Leu Ala Glu Trp
465                 470                 475                 480

Val Arg Asp Glu Ala Pro Ser Trp Gly Ser Thr Leu Ile Ile Leu Asn
                485                 490                 495

Thr Lys Lys Val Val Lys Asp Leu Tyr Glu Lys Leu Glu Gly Gly Pro
            500                 505                 510
```

```
Leu Pro Val Phe His Leu Ser Thr Ser Met Cys Ala Ala His Arg Lys
        515                 520                 525

Asp Gln Leu Asp Glu Ile Arg Ala Leu Leu Lys Glu Gly Thr Pro Phe
    530                 535                 540

Ile Cys Val Thr Thr Gln Leu Ile Glu Ala Gly Val Asp Val Ser Phe
545                 550                 555                 560

Lys Cys Val Ile Arg Ser Leu Ala Gly Leu Asp Ser Ile Ala Gln Ala
                565                 570                 575

Ala Gly Arg Cys Asn Arg His Gly Glu Gln Leu Gln Tyr Val Tyr
                580                 585                 590

Val Ile Asp His Ala Glu Glu Thr Leu Ser Lys Leu Lys Glu Ile Glu
                595                 600                 605

Val Gly Gln Glu Ile Ala Gly Asn Val Leu Ala Arg Phe Lys Lys Lys
    610                 615                 620

Ala Glu Lys Tyr Glu Gly Asn Leu Leu Ser Gln Ala Ala Met Arg Glu
625                 630                 635                 640

Tyr Phe Arg Tyr Tyr Tyr Ser Lys Met Asp Ala Asn Leu Asn Tyr Phe
                645                 650                 655

Val Lys Glu Val Asp Lys Asp Met Thr Lys Leu Leu Met Ser His Ala
                660                 665                 670

Val Glu Asn Ser Tyr Val Thr Tyr Tyr Gln Lys Asn Thr Gly Thr His
                675                 680                 685

Phe Pro Leu Leu Leu Asn Gly Ser Tyr Lys Thr Ala Ala Asp His Phe
    690                 695                 700

Arg Val Ile Asp Gln Asn Thr Thr Ser Ala Ile Val Pro Tyr Gly Glu
705                 710                 715                 720

Gly Gln Asp Ile Ile Ala Gln Leu Asn Ser Gly Glu Trp Val Asp Asp
                725                 730                 735

Leu Ser Lys Val Leu Lys Lys Ala Gln Gln Tyr Thr Val Asn Leu Tyr
                740                 745                 750

Ser Gln Glu Ile Asp Gln Leu Lys Lys Glu Gly Ala Ile Val Met His
    755                 760                 765

Leu Asp Gly Met Val Tyr Glu Leu Lys Glu Ser Trp Tyr Ser His Gln
    770                 775                 780

Tyr Gly Val Asp Phe Lys Gly Glu Gly Gly Met Asp Phe Met Ser Phe
785                 790                 795                 800

<210> SEQ ID NO 16
<211> LENGTH: 2667
<212> TYPE: DNA
<213> ORGANISM: Artificial sequence
<220> FEATURE:
<223> OTHER INFORMATION: Synthetic

<400> SEQUENCE: 16
atggaaccat tcaagtacat ttgccattat tgggggaagt cctcaaaaag tctgacaaag      60
ggtaacgaca tccacctgct tatatatcac tgcctggacg tcgccgcggt agccgactgt     120
tggtgggacc aaagtgtcgt gcttcaaaat acctttttgcc gaaacgaaat gttgagtaag    180
cagcgcgtta agcttggct  cctttttcttt atagcgttgc atgacatcgg caagttcgat    240
ataagattcc aatacaaaag tgccgagagc tggctgaagc tcaaccctgc tactccttct    300
cttaacgggc cctcaacaca gatgtgtcgg aaatttaatc acggcgctgc agggttgtat    360
tggttcaatc aggactcact cagcgaacaa tcattgggcg attttttttc ttttttcgat    420
```

```
gctgctcctc atccatatga atcctggttt ccatgggtag aagccgttac agggcatcac    480
ggttttatac ttcatagcca agatcaggat aaatcacggt gggagatgcc ggcttctctt    540
gccagctatg ccgcccaaga taagcaggcc agggaagagt ggatttctgt tttggaagct    600
ttgtttctga ctccagccgg cctttccatc aatgacatac cccccgattg ttcatcactt    660
ctcgcagggt tctgcagttt ggctgattgg ttgggatctt ggaccacaac caacacattc    720
ttgtttaacg aggacgcccc cagcgacata aatgcgcttc gaacctattt ccaggaccgc    780
caacaagacg cttctcgggt tcttgaattg tcagggctcg ttagcaacaa aaggtgttac    840
gaaggagtcc atgctcttct cgataatgga taccagcccc ggcaacttca agttttggta    900
gacgccctcc ctgtggcgcc tggacttacg gtcatagagg ccccaaccgg atctggcaaa    960
accgagaccg cattggcata tgcgtggaag ttgatagatc aacaaatagc cgactctgtc   1020
attttttgcac ttccgacaca agcgacggct aacgccatgc ttactaggat ggaagcatct   1080
gcctctcacc tcttctcttc ccctaacctt atcctcgcgc atggaaactc cagatttaac   1140
catttgttcc aaagtatcaa gtcaagggct ataacagagc agggacaaga agaggcatgg   1200
gtacagtgtt gtcagtggct cagtcagtcc aacaagaagg tcttttttggg gcagattggc   1260
gtatgcacaa tcgaccaagt acttatttct gttctgcctg tcaagcatag attcattcgc   1320
ggcttgggaa taggacgctc cgtgctcata gtcgacgaag ttcacgctta tgatacgtat   1380
atgaacggac ttttggaagc ggttcttaag gctcaggccg atgtaggagg ctccgttatt   1440
ctgttgtctg caacactccc aatgaaacaa aacaaaagt tgctcgatac ctacggcctc   1500
catactgacc ccgtcgaaaa caattcagcc tacccactta ttaactggcg aggtgttaac   1560
ggagcccaaa gatttgatct cctcgcacac cccgaacagc tcccaccacg gttctccatt   1620
cagccggagc cgatatgtct tgcggacatg cttcctgatc ttaccatgct tgagcggatg   1680
attgcggcgg ctaatgctgg agctcaagta tgcctcattt gcaatctcgt ggatgtcgca   1740
caggtctgct atcaacgcct gaaggagttg aataacacgc aagtggatat agatctgttc   1800
catgctcgat tcacactcaa tgatcgacgc gaaaagaaa atcgggtgat tagtaatttc   1860
ggaaagaacg gcaagcgaaa cgttggcagg attctcgtag ccacccaagt tgtagaacag   1920
agtctggacg ttgattttga ttggctcata acgcaacact gtccggcaga ccttctgttc   1980
caaaggttgg ggagactcca ccgccatcat cggaaatacc ggcccgccgg gttcgagatt   2040
cctgttgcta ccattttgct cccggacggg gagggttatg gcaggcatga acatatttac   2100
tcaaatgtgc gggttatgtg gcggacgcaa caacatattg aagagctcaa cggggcctct   2160
ctgttctttc ctgacgcata taggcagtgg ttggatagta tatatgatga cgcggaaatg   2220
gacgaacccg agtgggttgg aaacggcatg gataaatttg agtccgctga gtgtgagaaa   2280
aggttcaagg ccagaaaggt attgcaatgg gcggaggagt attctctcca ggacaatgat   2340
gagactatcc tcgccgtaac gcgcgacgga gagatgtcat tgccgcttct cccgtacgtt   2400
caaacttcat caggtaagca acttttggat ggacaagtgt acgaggatct gagccacgag   2460
cagcagtacg aggcgctcgc actcaatcgc gtgaacgtgc ccttcacgtg gaagcggtca   2520
ttcagtgagg ttgtggatga agacggcctc ttgtggcttg aaggaaagca gaatttggat   2580
gggtgggtgt ggcaaggaaa tagcatcgtt ataacttata ctggagacga ggggatgaca   2640
cgcgtgatcc ctgcgaaccc taagtga                                      2667
```

<210> SEQ ID NO 17
<211> LENGTH: 888

<212> TYPE: PRT
<213> ORGANISM: Escherichia coli

<400> SEQUENCE: 17

```
Met Glu Pro Phe Lys Tyr Ile Cys His Tyr Trp Gly Lys Ser Ser Lys
1               5                   10                  15

Ser Leu Thr Lys Gly Asn Asp Ile His Leu Leu Ile Tyr His Cys Leu
            20                  25                  30

Asp Val Ala Val Ala Asp Cys Trp Trp Asp Gln Ser Val Val Leu
        35                  40                  45

Gln Asn Thr Phe Cys Arg Asn Glu Met Leu Ser Lys Gln Arg Val Lys
    50                  55                  60

Ala Trp Leu Leu Phe Phe Ile Ala Leu His Asp Ile Gly Lys Phe Asp
65                  70                  75                  80

Ile Arg Phe Gln Tyr Lys Ser Ala Glu Ser Trp Leu Lys Leu Asn Pro
                85                  90                  95

Ala Thr Pro Ser Leu Asn Gly Pro Ser Thr Gln Met Cys Arg Lys Phe
            100                 105                 110

Asn His Gly Ala Ala Gly Leu Tyr Trp Phe Asn Gln Asp Ser Leu Ser
        115                 120                 125

Glu Gln Ser Leu Gly Asp Phe Phe Ser Phe Phe Asp Ala Ala Pro His
    130                 135                 140

Pro Tyr Glu Ser Trp Phe Pro Trp Val Glu Ala Val Thr Gly His His
145                 150                 155                 160

Gly Phe Ile Leu His Ser Gln Asp Gln Asp Lys Ser Arg Trp Glu Met
                165                 170                 175

Pro Ala Ser Leu Ala Ser Tyr Ala Ala Gln Asp Lys Gln Ala Arg Glu
            180                 185                 190

Glu Trp Ile Ser Val Leu Glu Ala Leu Phe Leu Thr Pro Ala Gly Leu
        195                 200                 205

Ser Ile Asn Asp Ile Pro Pro Asp Cys Ser Ser Leu Leu Ala Gly Phe
    210                 215                 220

Cys Ser Leu Ala Asp Trp Leu Gly Ser Trp Thr Thr Thr Asn Thr Phe
225                 230                 235                 240

Leu Phe Asn Glu Asp Ala Pro Ser Asp Ile Asn Ala Leu Arg Thr Tyr
                245                 250                 255

Phe Gln Asp Arg Gln Gln Asp Ala Ser Arg Val Leu Glu Leu Ser Gly
            260                 265                 270

Leu Val Ser Asn Lys Arg Cys Tyr Glu Gly Val His Ala Leu Leu Asp
        275                 280                 285

Asn Gly Tyr Gln Pro Arg Gln Leu Gln Val Leu Val Asp Ala Leu Pro
    290                 295                 300

Val Ala Pro Gly Leu Thr Val Ile Glu Ala Pro Thr Gly Ser Gly Lys
305                 310                 315                 320

Thr Glu Thr Ala Leu Ala Tyr Ala Trp Lys Leu Ile Asp Gln Gln Ile
                325                 330                 335

Ala Asp Ser Val Ile Phe Ala Leu Pro Thr Gln Ala Thr Ala Asn Ala
            340                 345                 350

Met Leu Thr Arg Met Glu Ala Ser Ala Ser His Leu Phe Ser Ser Pro
        355                 360                 365

Asn Leu Ile Leu Ala His Gly Asn Ser Arg Phe Asn His Leu Phe Gln
    370                 375                 380

Ser Ile Lys Ser Arg Ala Ile Thr Glu Gln Gly Gln Glu Glu Ala Trp
385                 390                 395                 400
```

```
Val Gln Cys Cys Gln Trp Leu Ser Gln Ser Asn Lys Lys Val Phe Leu
            405                 410                 415

Gly Gln Ile Gly Val Cys Thr Ile Asp Gln Val Leu Ile Ser Val Leu
            420                 425                 430

Pro Val Lys His Arg Phe Ile Arg Gly Leu Gly Ile Gly Arg Ser Val
            435                 440                 445

Leu Ile Val Asp Glu Val His Ala Tyr Asp Thr Tyr Met Asn Gly Leu
        450                 455                 460

Leu Glu Ala Val Leu Lys Ala Gln Ala Asp Val Gly Gly Ser Val Ile
465                 470                 475                 480

Leu Leu Ser Ala Thr Leu Pro Met Lys Gln Lys Gln Lys Leu Leu Asp
            485                 490                 495

Thr Tyr Gly Leu His Thr Asp Pro Val Glu Asn Asn Ser Ala Tyr Pro
            500                 505                 510

Leu Ile Asn Trp Arg Gly Val Asn Gly Ala Gln Arg Phe Asp Leu Leu
            515                 520                 525

Ala His Pro Glu Gln Leu Pro Pro Arg Phe Ser Ile Gln Pro Glu Pro
            530                 535                 540

Ile Cys Leu Ala Asp Met Leu Pro Asp Leu Thr Met Leu Glu Arg Met
545                 550                 555                 560

Ile Ala Ala Ala Asn Ala Gly Ala Gln Val Cys Leu Ile Cys Asn Leu
                565                 570                 575

Val Asp Val Ala Gln Val Cys Tyr Gln Arg Leu Lys Glu Leu Asn Asn
                580                 585                 590

Thr Gln Val Asp Ile Asp Leu Phe His Ala Arg Phe Thr Leu Asn Asp
            595                 600                 605

Arg Arg Glu Lys Glu Asn Arg Val Ile Ser Asn Phe Gly Lys Asn Gly
            610                 615                 620

Lys Arg Asn Val Gly Arg Ile Leu Val Ala Thr Gln Val Val Glu Gln
625                 630                 635                 640

Ser Leu Asp Val Asp Phe Asp Trp Leu Ile Thr Gln His Cys Pro Ala
                645                 650                 655

Asp Leu Leu Phe Gln Arg Leu Gly Arg Leu His Arg His His Arg Lys
            660                 665                 670

Tyr Arg Pro Ala Gly Phe Glu Ile Pro Val Ala Thr Ile Leu Leu Pro
            675                 680                 685

Asp Gly Glu Gly Tyr Gly Arg His Glu His Ile Tyr Ser Asn Val Arg
690                 695                 700

Val Met Trp Arg Thr Gln Gln His Ile Glu Glu Leu Asn Gly Ala Ser
705                 710                 715                 720

Leu Phe Phe Pro Asp Ala Tyr Arg Gln Trp Leu Asp Ser Ile Tyr Asp
            725                 730                 735

Asp Ala Glu Met Asp Glu Pro Glu Trp Val Gly Asn Gly Met Asp Lys
            740                 745                 750

Phe Glu Ser Ala Glu Cys Glu Lys Arg Phe Lys Ala Arg Lys Val Leu
            755                 760                 765

Gln Trp Ala Glu Glu Tyr Ser Leu Gln Asp Asn Asp Glu Thr Ile Leu
            770                 775                 780

Ala Val Thr Arg Asp Gly Glu Met Ser Leu Pro Leu Leu Pro Tyr Val
785                 790                 795                 800

Gln Thr Ser Ser Gly Lys Gln Leu Leu Asp Gly Gln Val Tyr Glu Asp
            805                 810                 815
```

| | | | | | | | | | | | |
|---|---|---|---|---|---|---|---|---|---|---|---|
|Leu|Ser|His|Glu<br>820|Gln|Gln|Tyr|Glu<br>825|Ala|Leu|Ala|Leu|Asn|Arg<br>830|Val|Asn|

Leu Ser His Glu Gln Gln Tyr Glu Ala Leu Ala Leu Asn Arg Val Asn
              820                 825                 830

Val Pro Phe Thr Trp Lys Arg Ser Phe Ser Glu Val Val Asp Glu Asp
          835                 840                 845

Gly Leu Leu Trp Leu Glu Gly Lys Gln Asn Leu Asp Gly Trp Val Trp
    850                 855                 860

Gln Gly Asn Ser Ile Val Ile Thr Tyr Thr Gly Asp Glu Gly Met Thr
865                 870                 875                 880

Arg Val Ile Pro Ala Asn Pro Lys
                885

<210> SEQ ID NO 18
<211> LENGTH: 3231
<212> TYPE: DNA
<213> ORGANISM: Artificial sequence
<220> FEATURE:
<223> OTHER INFORMATION: Synthetic

<400> SEQUENCE: 18

```
atgaacatcc tgctggtgtc gcaatgcgaa aagcgcgccc tgagcgaaac ccgccgcatt      60
ctcgaccagt cgccgagcg ccgcggcgaa cggacctggc aaacgcccat cactcaagcc     120
ggactggata ccctgcgacg cctgctgaag aaaagcgcac ggcgcaacac cgccgtagcc     180
tgtcactgga tccgcggccg cgaccacagc gaactgctgt ggatcgtcgg tgatgccagc     240
cgcttcaacg cccagggtgc ggtgccgacc aacaggacct gccgcgacat cctgcgcaag     300
gaagacgaga acgactggca cagcgccgag gacatccgcc tgctgacggt gatggcagcg     360
ctgttccacg atatcggcaa ggccagccag gccttccagg ccaaactgcg gaaccgcggc     420
aaaccgatgg ccgatgccta tcgtcacgaa tgggtatcac tgcgcctgtt cgaagccttc     480
gttggcccag gcagcagcga cgaggactgg ctgaggcgcc tggcggacaa gcgagagacg     540
ggcgatgcct ggctgtcgca actggccagg gacgaccggc aatccgcgcc acccggcccg     600
ttccagaaaa gccggctacc gccgctcgcc caggcggtcg gctggttgat cgtcagccat     660
catcgcctgc caacggggga ccatcgcggc agcgcctcgc tggcacgctt gccggccccc     720
atccagagcc aatggtgcgg cgcacgcgac gcagacgcaa agaaaaaggc cgcctgctgg     780
cagttccccc acggcctgcc cttcgccagc gcccattggc gcgccaggac agcgctatgc     840
gcgcagagca tgctcgagcg tcccggcctg ctggctcggg accggccttt gttgcatgat     900
tcctacgtca tgcatgtgtc ccgactgatc ctgatgctcg cggaccacca ctattccagt     960
ctccctgccg actcccggct gggcgacccg aacttcccct gcacgccaa caccgaccgg    1020 gacagcggca aactaaagca gcgcctggac gaacacctgc tcggcgtcgc cctgcacagt    1080
cgcaagctcg ccggcaccct gccacgcctg gagcgacaac taccgcgcct gcccggcac    1140 aagggcttca cccgccgggt cgagcagccg cgcttccgct ggcaggacaa ggcctacgac    1200
tgcgcgatgg cctgccgcga gcaggctatg gagcatggat tcttcggcct caacctggcg    1260
tcgaccggtt gcggtaagac cctcgccaac ggccgtatcc tgtatgcgct ggccgatccg    1320
caacgcggcg cgcgtttcag catcgctctc ggcctgcgca gcttgaccct gcaaaccggg    1380
caggcctacc gcgagcggct cggcctgggc gacgacgacc tcgctatcct ggtcggcggc    1440
agcgccgccc gcgaactgtt cgaaaagcag caggagcgcc tggagcgcag cggtagcgag    1500
tcagcccagg agctgctggc ggaaaacagc catgtacact tcgccggcac gctcgaggac    1560
ggccctctac gcgagtggct cggcaggaac agcgcgggaa accgcctact ccaggcgccc    1620
```

-continued

| | | | | |
|---|---|---|---|---|
| atcctggcct | gcaccatcga | ccacctgatg | cccgccagcg | aaagcctgcg cggcggacac | 1680 |
| cagatagcgc | cactgctccg | cctgatgact | tccgacctgg | tgctcgacga ggtcgacgac | 1740 |
| ttcgatatcg | acgacctgcc | cgccctgtcg | cggctggtgc | actgggccgg cctgttcggc | 1800 |
| agccgcgtgc | tgctctcctc | cgcgaccctg | ccgccggcct | tggtgcaggg cctgttcgag | 1860 |
| gcctatcgca | gcggccggga | aatcttccag | cgccatcgtg | cgctcccgg acgcgctacg | 1920 |
| gaaatccgct | gtgcctggtt | cgacgagttc | tccagccaat | ccagcgccca cggcgccgta | 1980 |
| acctccttca | gcgaagcgca | tgcgaccttc | gtcgcccagc | gtctggcgaa gctcgagcaa | 2040 |
| ctgccgccac | gtcgccaggc | gcagctatgc | accgtgcatg | ccgctggcga ggcccgtccc | 2100 |
| gcgctgtgcc | gcgagttggc | cgggcagatg | aatacctgga | tggctgacct gcatcgctgc | 2160 |
| catcacaccg | aacaccaagg | acgtcgcatc | agtttcggcc | tgctacggct ggccaacatc | 2220 |
| gaacccctga | tcgaactggc | ccaggccatc | ctcgcccagg | gtgcgcccga ggggttgcat | 2280 |
| gtccatctgt | gtgtctacca | ttcgcggcat | ccccttctgg | tccgctcggc catcgagcga | 2340 |
| caactcgatg | aactgctgaa | gcgttcggac | gacgacgccg | ccgcgctgtt cgctcgtccg | 2400 |
| acgctggcca | aggcgctcca | ggccagcacg | gagcgggatc | atctgttcgt cgtactcgcc | 2460 |
| tcgccggtgg | cggaggtcgg | tcgcgaccac | gattacgact | gggccatcgt cgaaccctcc | 2520 |
| tccatgcgct | cgatcatcca | gttggccggg | cgaatccgcc | gccatcgctc cggcttcagc | 2580 |
| ggcgaggcca | acctatacct | gctatcgcgc | aatatccgct | cgctggaagg cagaatccg | 2640 |
| gcgttccagc | ggcccggctt | cgagaccccc | gacttccctc | ttgacagcca cgacctgcac | 2700 |
| gacctgctcg | accccgccct | actcgcccgc | atcgacgcca | gcccacgaat cgtcgaaccg | 2760 |
| ttcccactgt | tcccacgcag | ccggttggtc | gacctggaac | accgacgcct gcgcgcgctg | 2820 |
| atgcttgccg | acgacccacc | gtcgtccctg | ctcggcgtac | cgctctggtg gcaaaccccg | 2880 |
| gcatcgctca | gcggcgccct | gcaaaccagc | caaccatttc | gcgcaggcgc caaggagcga | 2940 |
| tgctacgccc | tgctgccgga | cgaggacgac | gaggagcgct | tgcatttcag ccgctacgaa | 3000 |
| gaagggacct | ggagcaacca | ggacaacctg | ttgcgcaacc | tcgacctcac ctatgccccg | 3060 |
| cgcatccaga | catggggcac | ggtcaactat | cgggaggagc | tagtcgcaat ggccggccgc | 3120 |
| gaggacctcg | acctgcgtca | atgcgccatg | cgctacggcg | aggtgagatt gcgagaaaac | 3180 |
| acccagggat | ggagctacca | cccttatttg | gggttcaaga | aatacaactg a | 3231 |

<210> SEQ ID NO 19
<211> LENGTH: 1076
<212> TYPE: PRT
<213> ORGANISM: Pseudomonas aeruginosa

<400> SEQUENCE: 19

Met Asn Ile Leu Leu Val Ser Gln Cys Glu Lys Arg Ala Leu Ser Glu
1               5                   10                  15

Thr Arg Arg Ile Leu Asp Gln Phe Ala Glu Arg Arg Gly Glu Arg Thr
            20                  25                  30

Trp Gln Thr Pro Ile Thr Gln Ala Gly Leu Asp Thr Leu Arg Arg Leu
        35                  40                  45

Leu Lys Lys Ser Ala Arg Arg Asn Thr Ala Val Ala Cys His Trp Ile
    50                  55                  60

Arg Gly Arg Asp His Ser Glu Leu Leu Trp Ile Val Gly Asp Ala Ser
65                  70                  75                  80

Arg Phe Asn Ala Gln Gly Ala Val Pro Thr Asn Arg Thr Cys Arg Asp
                85                  90                  95

```
Ile Leu Arg Lys Glu Asp Glu Asn Asp Trp His Ser Ala Glu Asp Ile
                100                 105                 110

Arg Leu Leu Thr Val Met Ala Ala Leu Phe His Asp Ile Gly Lys Ala
            115                 120                 125

Ser Gln Ala Phe Gln Ala Lys Leu Arg Asn Arg Gly Lys Pro Met Ala
        130                 135                 140

Asp Ala Tyr Arg His Glu Trp Val Ser Leu Arg Leu Phe Glu Ala Phe
145                 150                 155                 160

Val Gly Pro Gly Ser Ser Asp Glu Asp Trp Leu Arg Arg Leu Ala Asp
                165                 170                 175

Lys Arg Glu Thr Gly Asp Ala Trp Leu Ser Gln Leu Ala Arg Asp Asp
            180                 185                 190

Arg Gln Ser Ala Pro Pro Gly Pro Phe Gln Lys Ser Arg Leu Pro Pro
        195                 200                 205

Leu Ala Gln Ala Val Gly Trp Leu Ile Val Ser His His Arg Leu Pro
    210                 215                 220

Asn Gly Asp His Arg Gly Ser Ala Ser Leu Ala Arg Leu Pro Ala Pro
225                 230                 235                 240

Ile Gln Ser Gln Trp Cys Gly Ala Arg Asp Ala Asp Ala Lys Glu Lys
                245                 250                 255

Ala Ala Cys Trp Gln Phe Pro His Gly Leu Pro Phe Ala Ser Ala His
            260                 265                 270

Trp Arg Ala Arg Thr Ala Leu Cys Ala Gln Ser Met Leu Glu Arg Pro
        275                 280                 285

Gly Leu Leu Ala Arg Gly Pro Ala Leu Leu His Asp Ser Tyr Val Met
    290                 295                 300

His Val Ser Arg Leu Ile Leu Met Leu Ala Asp His His Tyr Ser Ser
305                 310                 315                 320

Leu Pro Ala Asp Ser Arg Leu Gly Asp Pro Asn Phe Pro Leu His Ala
                325                 330                 335

Asn Thr Asp Arg Asp Ser Gly Lys Leu Lys Gln Arg Leu Asp Glu His
            340                 345                 350

Leu Leu Gly Val Ala Leu His Ser Arg Lys Leu Ala Gly Thr Leu Pro
        355                 360                 365

Arg Leu Glu Arg Gln Leu Pro Arg Leu Ala Arg His Lys Gly Phe Thr
    370                 375                 380

Arg Arg Val Glu Gln Pro Arg Phe Arg Trp Gln Asp Lys Ala Tyr Asp
385                 390                 395                 400

Cys Ala Met Ala Cys Arg Glu Gln Ala Met Glu His Gly Phe Phe Gly
                405                 410                 415

Leu Asn Leu Ala Ser Thr Gly Cys Gly Lys Thr Leu Ala Asn Gly Arg
            420                 425                 430

Ile Leu Tyr Ala Leu Ala Asp Pro Gln Arg Gly Ala Arg Phe Ser Ile
        435                 440                 445

Ala Leu Gly Leu Arg Ser Leu Thr Leu Gln Thr Gly Gln Ala Tyr Arg
    450                 455                 460

Glu Arg Leu Gly Leu Gly Asp Asp Leu Ala Ile Leu Val Gly Gly
465                 470                 475                 480

Ser Ala Ala Arg Glu Leu Phe Glu Lys Gln Glu Arg Leu Glu Arg
                485                 490                 495

Ser Gly Ser Glu Ser Ala Gln Glu Leu Leu Ala Glu Asn Ser His Val
            500                 505                 510
```

```
His Phe Ala Gly Thr Leu Glu Asp Gly Pro Leu Arg Glu Trp Leu Gly
            515                 520                 525

Arg Asn Ser Ala Gly Asn Arg Leu Leu Gln Ala Pro Ile Leu Ala Cys
530                 535                 540

Thr Ile Asp His Leu Met Pro Ala Ser Glu Ser Leu Arg Gly Gly His
545                 550                 555                 560

Gln Ile Ala Pro Leu Leu Arg Leu Met Thr Ser Asp Leu Val Leu Asp
            565                 570                 575

Glu Val Asp Asp Phe Asp Ile Asp Asp Leu Pro Ala Leu Ser Arg Leu
            580                 585                 590

Val His Trp Ala Gly Leu Phe Gly Ser Arg Val Leu Leu Ser Ser Ala
            595                 600                 605

Thr Leu Pro Pro Ala Leu Val Gln Gly Leu Phe Glu Ala Tyr Arg Ser
610                 615                 620

Gly Arg Glu Ile Phe Gln Arg His Arg Gly Ala Pro Gly Arg Ala Thr
625                 630                 635                 640

Glu Ile Arg Cys Ala Trp Phe Asp Glu Phe Ser Ser Gln Ser Ser Ala
            645                 650                 655

His Gly Ala Val Thr Ser Phe Ser Glu Ala His Ala Thr Phe Val Ala
            660                 665                 670

Gln Arg Leu Ala Lys Leu Glu Gln Leu Pro Pro Arg Arg Gln Ala Gln
            675                 680                 685

Leu Cys Thr Val His Ala Ala Gly Glu Ala Arg Pro Ala Leu Cys Arg
    690                 695                 700

Glu Leu Ala Gly Gln Met Asn Thr Trp Met Ala Asp Leu His Arg Cys
705                 710                 715                 720

His His Thr Glu His Gln Gly Arg Arg Ile Ser Phe Gly Leu Arg
                725                 730                 735

Leu Ala Asn Ile Glu Pro Leu Ile Glu Leu Ala Gln Ala Ile Leu Ala
                740                 745                 750

Gln Gly Ala Pro Glu Gly Leu His Val His Leu Cys Val Tyr His Ser
            755                 760                 765

Arg His Pro Leu Leu Val Arg Ser Ala Ile Glu Arg Gln Leu Asp Glu
    770                 775                 780

Leu Leu Lys Arg Ser Asp Asp Ala Ala Leu Phe Ala Arg Pro
785                 790                 795                 800

Thr Leu Ala Lys Ala Leu Gln Ala Ser Thr Glu Arg Asp His Leu Phe
                805                 810                 815

Val Val Leu Ala Ser Pro Val Ala Glu Val Gly Arg Asp His Asp Tyr
            820                 825                 830

Asp Trp Ala Ile Val Glu Pro Ser Ser Met Arg Ser Ile Ile Gln Leu
            835                 840                 845

Ala Gly Arg Ile Arg Arg His Arg Ser Gly Phe Ser Gly Glu Ala Asn
850                 855                 860

Leu Tyr Leu Leu Ser Arg Asn Ile Arg Ser Leu Glu Gly Gln Asn Pro
865                 870                 875                 880

Ala Phe Gln Arg Pro Gly Phe Glu Thr Pro Asp Phe Pro Leu Asp Ser
            885                 890                 895

His Asp Leu His Asp Leu Leu Asp Pro Ala Leu Leu Ala Arg Ile Asp
                900                 905                 910

Ala Ser Pro Arg Ile Val Glu Pro Phe Pro Leu Phe Pro Arg Ser Arg
            915                 920                 925

Leu Val Asp Leu Glu His Arg Arg Leu Arg Ala Leu Met Leu Ala Asp
```

```
                   930                935                940
Asp Pro Pro Ser Ser Leu Leu Gly Val Pro Leu Trp Trp Gln Thr Pro
945                 950                955                960

Ala Ser Leu Ser Gly Ala Leu Gln Thr Ser Gln Pro Phe Arg Ala Gly
                965                970                975

Ala Lys Glu Arg Cys Tyr Ala Leu Leu Pro Asp Glu Asp Glu Glu
            980                985                990

Arg Leu His Phe Ser Arg Tyr Glu Glu Gly Thr Trp Ser Asn Gln Asp
        995                1000               1005

Asn Leu Leu Arg Asn Leu Asp Leu Thr Tyr Gly Pro Arg Ile Gln
    1010               1015               1020

Thr Trp Gly Thr Val Asn Tyr Arg Glu Glu Leu Val Ala Met Ala
    1025               1030               1035

Gly Arg Glu Asp Leu Asp Leu Arg Gln Cys Ala Met Arg Tyr Gly
    1040               1045               1050

Glu Val Arg Leu Arg Glu Asn Thr Gln Gly Trp Ser Tyr His Pro
    1055               1060               1065

Tyr Leu Gly Phe Lys Lys Tyr Asn
    1070               1075

<210> SEQ ID NO 20
<211> LENGTH: 711
<212> TYPE: DNA
<213> ORGANISM: Artificial sequence
<220> FEATURE:
<223> OTHER INFORMATION: Synthetic

<400> SEQUENCE: 20
atggcccgaa atgaggtgca gtttgaactt tcggcgatt acgccctctt cacggaccca      60
ctgaccaaaa ttggcggaga gaagctgagc tattcagtgc ctacgtacca ggcactgaaa     120
ggcatcgccg aatcaattta ttggaaacca accattgtct tcgtgatcga tgaactgcgg     180
gtgatgaagc caatccaaat ggagtccaag ggggtgcggc caattgaata cggaggcggc     240
aatacattgg ctcactacac ctacctgaaa gatgtccact atcaagtcaa agcgcatttt     300
gagtttaatc tccaccgccc cgacttggcc ttcgatagaa atgaggggaa gcattactcc     360
attcttcaga gatcactgaa gcgggggga aggagggaca tcttcctggg agcacgggag     420
tgccagggct acgtggcccc atgtgaattt ggttccggag acggctttta tgacggacaa     480
ggaaagtatc atcttggcac catggtgcac ggcttcaact ccccgatga actggccag      540 catcagttgg acgtgcggct gtggtcagct gtgatgaaa cgggtatat tcagttccca     600 agaccagagg actgccctat cgtcaggccc gtcaaagaaa tggaaccaaa gattttcaac     660
ccagataatg tgcagtccgc agaacaactc ctccatgacc tcggaggcga g              711

<210> SEQ ID NO 21
<211> LENGTH: 1884
<212> TYPE: DNA
<213> ORGANISM: Artificial sequence
<220> FEATURE:
<223> OTHER INFORMATION: Synthetic

<400> SEQUENCE: 21
atggccagtt ggctccttca cctgtacgag acttacgaag ccaatctgga tcaggtgggt      60
aaaaccgtca aaagggaga ggatcgggaa tacactctgc ttccaatctc ccacaccact      120
cagaacgctc acattgaagt gaccctggac gaggacggag attttctcag ggctaaagca     180
```

| | |
|---|---|
| ctgaccaaag agtctaccct gattccctgt actgaggaag ctgcgagtag atccggatcc | 240 |
| aaggtggcac cctaccccct ccacgataag ctgtcttacg ttgccggcga ctttgtcaag | 300 |
| tacggaggta agataaagaa ccaggacgat gcaccgtttg acacttacat caagaacctt | 360 |
| ggcgaatggg ccaatagtcc ctatgcgact gagaaggtga agtgcattta cacttacctc | 420 |
| aagaagggac ggctgattga ggacttggtg gacgctgggg tccttaagtt ggacgagaat | 480 |
| cagcagctta tagagaagtg ggagaaaagg tacgaggagc tgctgggaga aaagcccgca | 540 |
| atttttagca gcggggcaac cgatcaggct tccgcattcg tgagattcaa tgtcttccac | 600 |
| cccgaaagta ttgatgacgt gtggaaagac aaagaaatgt tgacagctt tatcagcttt | 660 |
| tataatgata agctcggtga ggaagacatt tgcttcgtca ccggtaatcg actcccgagc | 720 |
| accgaacggc atgctaataa aatacggcat gcagcagaca aggccaagct gatctccgca | 780 |
| aacgataact caggctttac cttccggggt cggttcaaaa caagtaggga agctgtcggc | 840 |
| atcagttacg aggtttccca aaaggctcat aatgctctga gtggctgat tcataggcag | 900 |
| agcaaatcaa tcgatgaccg ggtgttcctt gtctggagca atgataattc acttgtgccc | 960 |
| aacccagacg aggacgccgt tgacattatg aaacacgcaa accgagagct ggaacgcgac | 1020 |
| cctgataccg tcagattttt cgccggcgag gtgaagaaag ccatcggggg ataccgaagc | 1080 |
| gatttgaact accaacccga ggtccatatt cttgttcttg attctgcaac aactggccgg | 1140 |
| atggccgtgc tgtactatag aagcctgaat aaggaactgt atctgaacag actggaggcc | 1200 |
| tggcacgatt cttgcgcctg gaacaccgg tacaggcgcg atgagaaaga gttcattagc | 1260 |
| ttttatgggg caccggccac gaaggacatt gcctttgcag cttacgggcc aagagcttcc | 1320 |
| gaaaaagtga tcaaagacct tatggaacgg atgcttcctt gcatcgtgga cggacgccga | 1380 |
| gtcccaaaag acatagtacg gagtgctttt cagagagcgt ccaacccagt gtctatggaa | 1440 |
| cgctgggagt gggagaaaac tctgagcatt acttgtgccc tgattcggaa aatgcatatc | 1500 |
| gaacaaaaag aagaatgggg ggtgccctg acaaatcct caaccgatcg atcttatctt | 1560 |
| tttgggcgcc tccttgccgt tgctgacgtc ctggaagggg gcgccctggg aaaggacgaa | 1620 |
| actcgggcca caaacgctat tcggtatatg aatagctaca gcaaaaaccc cggaagaacc | 1680 |
| tggaaaacaa tacaggagtc attgcagccc taccaggcta agctgggaac aaaagccaca | 1740 |
| tacctgtcaa gcttgtgga tgagattggc gaccagtttg agcctggtga ctttaataac | 1800 |
| aatccattga ctgagcagta tctcttgggt ttttacagcc agcggcggga actttacaaa | 1860 |
| aaaaagagg aggagacaaa tcag | 1884 |

<210> SEQ ID NO 22
<211> LENGTH: 852
<212> TYPE: DNA
<213> ORGANISM: Artificial sequence
<220> FEATURE:
<223> OTHER INFORMATION: Synthetic

<400> SEQUENCE: 22

| | |
|---|---|
| atggccacca ttcttgatca caaaattgat ttcgccgtta ttctgagcgt cactaaggcg | 60 |
| aacccaaatg gtgacccact caatggcaac aggccgcgcc agaattatga tgggcatggc | 120 |
| gaaatttctg acgtcgccat aaaacgcaag atccgcaacc gcctgctcga catggaagag | 180 |
| cccattttg tccagtctga cgaccgcaaa gcagactctt ttaagtcact gcgggaccgc | 240 |
| gctgattcta accccgaact ggcaaaaatg ctgaggcca aaaatgctag tgtggacgaa | 300 |
| tttgccaaaa tagcttgcca ggaatggatg gacgtgagga gtttcgggca ggtgtttgcg | 360 |

| | |
|---|---:|
| ttcaaaggct caaatctgtc agtcggcgta cggggcccag ttagcattca cactgcgacc | 420 |
| tctatcgatc ctattgacat agtgagcacg cagatcacta agagtgtgaa tagtgtaacc | 480 |
| ggggacaaga gaagttccga cacaatgggt atgaagcacc gggttgactt cggcgtctat | 540 |
| gttttcaaag ggagcatcaa tacgcagctc gcagagaaga ctggcttcac aaacgaggac | 600 |
| gccgaaaaaa tcaagcgggc cctgattact ctgttcgaaa atgatagctc ttcagcccga | 660 |
| cccgatgggt caatggaggt gcacaaagtt tactggtggg aacactccag caagcttgga | 720 |
| cagtatagtt ctgctaaggt gcaccgcagc ctgaaaatcg aatctaagac cgacacgcct | 780 |
| aagagcttcg acgattacgc tgtcgaactg tatgaactgg acggcctcgg cgtggaagtg | 840 |
| atcgacggac ag | 852 |

<210> SEQ ID NO 23
<211> LENGTH: 1512
<212> TYPE: DNA
<213> ORGANISM: Artificial sequence
<220> FEATURE:
<223> OTHER INFORMATION: Synthetic

<400> SEQUENCE: 23

| | |
|---|---:|
| atggccaatc tcctgattga caattggatc cctgtgagac cgaggaacgg agggaaggtt | 60 |
| cagatcatca acctgcaaag tctctactgt agcagagatc aatggcgact ctcattgccc | 120 |
| agggatgata tggaattggc ggcacttgca ctcttggtat gtattgggca gatcatcgcc | 180 |
| cctgccaagg atgatgtcga gtttaggcac agaataatga ccctcttac tgaagatgaa | 240 |
| ttccagcaat tgatcgcgcc ttggatagat atgttctatt gaatcacgc cgaacatccc | 300 |
| ttcatgcaga caaaaggggt taaagcaaat gatgtcacac caatggagaa gcttttggca | 360 |
| ggtgtgtcag gagcaaccaa ctgcgctttc gttaaccaac caggccaagg tgaggcgttg | 420 |
| tgcggggggt gcacggccat agcgttgttt aatcaggcga accaggctcc tggctttgga | 480 |
| ggaggattca agtccggttt cgcgggggt acacccgtaa ccacattcgt tcgcggaatt | 540 |
| gacctccgat caacagtcct gttgaacgta ttgacgttgc ctagacttca gaagcaattt | 600 |
| ccaaacgagt ctcacactga gaatcaaccg acttggatta agcccatcaa gtcaaatgaa | 660 |
| agtatacccg cgtcttctat tggatttgtt agaggacttt tttggcagcc cgctcacata | 720 |
| gaactctgtg atcccatagg cattggaaag tgttcttgct gtggccaaga gtctaacctt | 780 |
| agatatacgg gctttctcaa ggagaagttc acgttcaccg tgaatggact ttggccacat | 840 |
| ccccatagcc cgtgcttggt cacggtcaag aaggggagg ttgaagagaa atttcttgcg | 900 |
| tttaccacat ccgccccatc ctggacgcaa atatctcgcg tcgttgtgga taaaatcatc | 960 |
| cagaacgaaa atggtaaccg cgttgccgcg gtagtgaatc aattcagaaa catagcacca | 1020 |
| cagagcccgt tggagttgat aatgggcggg taccgcaata tcaagcttc cattctcgag | 1080 |
| cgacgccatg acgtacttat gtttaaccag gggtggcagc aatatggtaa cgtgataaac | 1140 |
| gagatagtca cagtcggcct cggctacaaa actgcgttgc gcaaagctct gtatacgttc | 1200 |
| gcggagggtt ttaagaataa agactttaaa ggcgctgggg tgagtgtgca cgagacggca | 1260 |
| gaacgccatt tctatcgcca gtctgaactc ttgattcccg acgttctggc gaatgtcaat | 1320 |
| ttttcccagg ccgatgaggt cattgcggat ctgcgagata gcttcaccha gttgtgtgag | 1380 |
| atgctgttca accagtctgt ggctcctat gctcatcatc ccaaactgat ttcaactctc | 1440 |
| gctttggcaa gggctacgtt gtataaacac cttagagaac tgaagccaca gggtggtccc | 1500 |

| agcaatggct ga | 1512 |

<210> SEQ ID NO 24
<211> LENGTH: 483
<212> TYPE: DNA
<213> ORGANISM: Artificial sequence
<220> FEATURE:
<223> OTHER INFORMATION: Synthetic

<400> SEQUENCE: 24

| atggccgatg aaatagacgc aatggctctt taccgagcat ggcaacagct cgacaatgga | 60 |
| tcttgcgccc aaatacggcg ggtaagtgaa cccgatgaac tgcgagatat ccccgcattc | 120 |
| taccgattgg ttcagccgtt tggctgggag aacccacggc accagcaggc gcttcttagg | 180 |
| atggttttt gtcttagtgc cgggaaaaac gtaatccgcc atcaggataa gaagtccgaa | 240 |
| caaacaacag ggatttctct gggaagagcg cttgctaaca gcggcaggat caatgaacgc | 300 |
| cgcatatttc agttgatccg agcagatcgg actgctgata tggtccagct caggaggctc | 360 |
| cttacgcacg cagagccagt gttggattgg ccactcatgg caagaatgct tacgtggtgg | 420 |
| gggaagaggg aaaggcagca actgcttgaa gattttgtat tgacgacgaa caaaaacgcg | 480 |
| taa | 483 |

<210> SEQ ID NO 25
<211> LENGTH: 1092
<212> TYPE: DNA
<213> ORGANISM: Artificial sequence
<220> FEATURE:
<223> OTHER INFORMATION: Synthetic

<400> SEQUENCE: 25

| atgtcaaact tcattaatat ccacgtgctt atctcacact cccctagttg ccttaacaga | 60 |
| gacgatatga acatgcaaaa agacgcaatt tttggcggca aaaggagagt cagaattagt | 120 |
| agccagagcc tgaagcgcgc tatgaggaaa agcggctact atgctcaaaa cattggtgaa | 180 |
| agttcattgc ggaccatcca tctcgcgcag ttgagggacg tcctgcgaca aagcttggg | 240 |
| gaaagatttg atcagaagat catcgacaaa acgcttgccc ttctgtccgg taaatcagtg | 300 |
| gacgaagcgg agaagataag tgcggatgct gttacgccat gggtggtagg tgaaatcgcg | 360 |
| tggttttgcg agcaggtagc caaggccgaa gcggataatt tggatgataa gaaactgctc | 420 |
| aaagtcctca agaggacat cgcggcgatc cgggtgaacc ttcagcaggg tgttgatatt | 480 |
| gcgctctctg gtcggatggc cacgtctgga atgatgactg aactgggtaa ggtgacgga | 540 |
| gctatgtcta tagctcatgc tataactacc catcaggtgg attctgacat agactggttc | 600 |
| acggctgtcg acgatctcca ggaacaagga tccgcacacc tcggcacgca agaatttct | 660 |
| tctggagtgt tctataggta tgccaacatc aaccttgcac agctccagga aaacctcggt | 720 |
| ggggcaagcc gggaacaggc tcttgaaata gctacccatg tggttcacat gctggcgacc | 780 |
| gaagtgccag gggccaagca gagaacgtac gccgcattca atccggcgga catggtcatg | 840 |
| gtgaatttct ctgatatgcc cttgtctatg gcaaatgctt tcgagaaggc ggtcaaggca | 900 |
| aaggacggtt ttttgcaacc ctccatccaa gcctttaatc agtactggga tagagtagct | 960 |
| aacgggtatg gtctcaatgg cgcggctgct cagttttctt tgtccgatgt ggatccgata | 1020 |
| acggcgcagg ttaaacagat gcccaccttg gaacaactca atcctgggt tagaaacaat | 1080 |
| ggggaggcgt ga | 1092 |

<210> SEQ ID NO 26
<211> LENGTH: 675
<212> TYPE: DNA
<213> ORGANISM: Artificial sequence
<220> FEATURE:
<223> OTHER INFORMATION: Synthetic

<400> SEQUENCE: 26

```
atgcgatcat acttgatcct gcggcttgca ggtcctatgc aagcctgggg gcaacctacc      60
tttgaaggta ctcggccgac tggcaggttc cctacgcggt ctggtttgct cggactcctc     120
ggcgcctgtt tggggataca aaggatgac acttcttcct tgcaggcact ttccgaatca      180
gtccagttcg cagtgagatg tgatgaactc atactgacg acagacgggt gtccgtaact      240
ggactgaggg actatcatac tgtactcggc gcaagagaag attatcgagg tcttaagtca     300
catgagacta ttcagacatg gagggaatat ttgtgtgacg cctccttcac ggtgccctc      360
tggcttacac cacatgcaac tatggtgatc tcagagcttg agaaagccgt tcttaaacct     420
cggtacacac catatctggg gaggcggtct tgcccactta cccacccgct tttcttgggg     480
acttgtcagg ccagcgatcc acagaaggcc ttgctgaact atgaaccgt tggtggcgat      540
atatacagtg aagagagcgt cacgggccat cacttgaagt tcactgctag ggatgagccg     600
atgattacgc tcccgagaca gttcgctagt agggaatggt acgttattaa gggggggaatg   660
gacgtttccc aatga                                                    675
```

<210> SEQ ID NO 27
<211> LENGTH: 600
<212> TYPE: DNA
<213> ORGANISM: Escherichia coli

<400> SEQUENCE: 27

```
atgtatctca gtaaagtcat cattgccagg gcctggagca gggatcttta ccaacttcac      60
cagggattat ggcatttatt tccaaacaga ccggatgctg ctcgtgattt tcttttttcat    120
gttgagaagc gaaacacacc agaaggctgt catgttttat tgcagtcagc gcaaatgcct    180
gtttcaactg ccgttgcgac agtcattaaa actaaacagg ttgaatttca acttcaggtt    240
ggtgttccac tctattttcg gcttcgggca aatccgatca aaactattct cgacaatcaa    300
aagcgcctgg acagtaaagg gaatattaaa cgctgtcggg ttccgttaat aaaagaagca    360
gaacaaatcg cgtggttgca acgtaaattg gcaatgcgg cgcgcgttga agatgtgcat     420
cccatatcgg aacggccaca gtattttct ggtgatggta aaagtggaaa gatccaaacg     480
gtttgctttg aaggtgtgct caccatcaac gacgcgccag cgttaataga tcttgtacag    540
caaggtattg ggccagctaa atcgatggga tgtggcttgc tatctttggc tccactgtga    600
```

<210> SEQ ID NO 28
<211> LENGTH: 1305
<212> TYPE: DNA
<213> ORGANISM: Artificial sequence
<220> FEATURE:
<223> OTHER INFORMATION: Synthetic

<400> SEQUENCE: 28

```
atgacatctc cattgccgac gcctacctgg caggaactta acaatttat cgagagtttc       60
atccaggagc gcctccaggg gaagctggac aagttgcaac ctgatgagga cgataaacgg     120
caaactctgt tggctacaca caggcgagaa gcgtggcttg cagacgcggc ccgaagggtc     180
ggccaactcc aactggttac ccacacccct taaacccatcc accccgacgc ccggggcagt   240
```

```
aatctgcact ccctcccgca agcccctggt caacccgggt tggctggttc ccacgagctt    300
ggagacagac tggtatcaga cgttgtcggg aatgcagcag ctctcgatgt ttttaaattc    360
ctgtcacttc agtatcaagg aaagaatctc ctgaattggc tcacagaaga ctccgctgaa    420
gcgctgcaag cgcttagcga taacgctgag caggctcggg agtggcgcca ggcattcatc    480 ggataacta ccgtcaaagg ggccccggca agtcactctc ttgctaaaca actgtacttt    540
cccctgcccg ggagtggtta ccatttgttg gcacctctgt tccctacctc tcttgtccac    600
catgtccacg cattgctgcg agaagcacgc tttggcgacg ccgccaaggc agccagggaa    660
gctcgctcta gacaggagag ctggcctcac gggttctcag agtacccaaa tttggcgata    720
caaaaattcg gtggtacaaa gccgcagaac atttcccagc ttaataatga aaggcggggc    780
gagaattggc tcctgccatc cctgccgcct aattggcagc gccaaaatgt caatgcccca    840
atgagacatt cctcagtgtt tgaacatgac tttggaagaa cgccagaggt tagtcgcctc    900
accagaaccc ttcaacggtt ccttgccaag acagtccaca ataatcttgc gatacgccag    960
cgaagggctc agttggtggc gcagatatgc gatgaagcgc ttcagtacgc cgcccgcctg   1020
cgagaattgg aacccggatg gtccgccact cctggttgcc aactccatga tgcagagcag   1080
ttgtggcttg atcccttgcg cgcccagaca gatgaaacct tcctgcagcg ccggctccgg   1140
ggtgattggc ctgcggaagt tggcaaccgc tttgctaact ggttgaatag agcggtttct   1200
tcagacagcc aaatacttgg ttcacctgag gccgcccagt ggtcccagga gttgagtaag   1260
gagctgacga tgtttaagga gatacttgag gacgaaagag actga                   1305
```

<210> SEQ ID NO 29
<211> LENGTH: 984
<212> TYPE: DNA
<213> ORGANISM: Artificial sequence
<220> FEATURE:
<223> OTHER INFORMATION: Synthetic

<400> SEQUENCE: 29

```
atgagtgtca cagaccctga agccttgttg cttctccccc gactgagtat ccaaaatgcg     60
aacgctatat ctagccctct cacttgggga tttccctcac caggggcttt tactggattc    120
gtacatgcgt tgcagagaag ggtcggcata tcacttgaca tagagttgga tggtgtcggc    180
atcgtatgtc accgatttga agcacagata agccagcctg ctggtaaacg acaaaggta    240 tttaacttga cacgcaatcc acttaacaga gatggttcca ccgccgcgat cgttgaagag    300
gggcgagccc accttgaggt tagtcttttg ctcggagtcc atggcgatgg actcgatgac    360
catccggccc aggagatcgc caggcaggtg caagaacaag cgggagccat gaggttggct    420
ggaggtagca tacttccctg tgtaatgag cggtttcccg caccaaatgc agagctgctt    480
atgctcgggg ggagcgacga acagagaaga aagaatcaaa ggcgcctgac tcggaggctg    540
ttgcctggat ttgctcttgt tagcaggggag gctttgctcc aacagcacct ggagactctc    600
cggaccactc ttcccgaagc gacgacgctc gacgctcttc tggacctttg tcgaatcaac    660
tttgaacccc cagcgacatc aagtgaggaa gaggctagtc ccccagatgc agcatggcaa    720
gtacgagaca aaccaggctg gctcgttcct atccccgccg gatataatgc gctgagcccg    780
ctttatcttc ccggagaagt tcgcaacgca agagacagag agacaccgtt gaggttcgta    840 gagaaccctct ttgggcttgg cgaatggctt tctccacatc gagtagcggc cctgtctgat    900
ctcctgtggt atcaccatgc cgaaccggat aaggggcttt accggtggtc aacgcctcgg    960
tttgtagagc acgccattgc atga                                            984
```

<210> SEQ ID NO 30
<211> LENGTH: 1029
<212> TYPE: DNA
<213> ORGANISM: Artificial sequence
<220> FEATURE:
<223> OTHER INFORMATION: Synthetic

<400> SEQUENCE: 30

| | | | | | |
|---|---|---|---|---|---|
| atgagcaaac | cgatattgag | cacagcgtct | gtacttgcct | ttgaacgaaa | attggacccc | 60 |
| tcagacgcct | tgatgtctgc | cggcgcctgg | gcacaacgag | acgcgtccca | ggagtggcct | 120 |
| gcggtgactg | tacgggagaa | gagcgtgaga | gggactatct | ctaaccggct | gaagaccaaa | 180 |
| gatagagacc | ctgccaagct | ggatgcgtct | attcaaagcc | caaacttgca | aaccgtggac | 240 |
| gtggccaatc | ttccgagcga | cgctgataca | ctgaaggtaa | gatttacgct | tagggtactc | 300 |
| ggcggtgctg | ggactccgtc | tgcatgcaat | gatgcggcgt | atagggacaa | gctgttgcag | 360 |
| actgttgcaa | catacgtcaa | tgatcaaggc | tttgcagagc | ttgctaggcg | ctacgctcat | 420 |
| aatcttgcca | acgcaaggtt | cctgtggagg | aatcggttg | gtgcagaggc | cgtggaggtg | 480 |
| agaattaatc | acataagaca | aggcgaggtg | gcacgcgcgt | ggcggtttga | tgctttggcc | 540 |
| atcgggctgc | gggacttcaa | agcagacgcc | gagttggacg | cccttgccga | gctgattgca | 600 |
| tctggccttt | cagggagcgg | gcatgtgctt | cttgaagtcg | tggccttcgc | taggatagga | 660 |
| gacggccaag | aggtatttcc | atcacaagag | ttgattcttg | ataagggtga | taaaaaagga | 720 |
| caaaagtcca | agaccctcta | ctcagtgcgg | gatgcggctg | cgattcactc | ccagaaaata | 780 |
| ggaaacgcct | tgagaaccat | agacacttgg | tatccagatg | aggatggcct | tggacccatt | 840 |
| gcagtagaac | cttatggttc | cgtaactagc | caaggaaaag | cctatcggca | gccaaagcag | 900 |
| aaacttgact | tttataccct | ccttgacaac | tgggttctcc | gggatgaggc | accggcggtc | 960 |
| gaacagcaac | attacgtcat | cgctaatctc | atcagaggcg | cgtgtttgg | tgaagctgaa | 1020 |
| gagaaatga | | | | | 1029 |

<210> SEQ ID NO 31
<211> LENGTH: 564
<212> TYPE: DNA
<213> ORGANISM: Artificial sequence
<220> FEATURE:
<223> OTHER INFORMATION: Synthetic

<400> SEQUENCE: 31

| | | | | | |
|---|---|---|---|---|---|
| atggaccact | acttggacat | acgcctgaga | cctgatccag | agtttccacc | agcccaactg | 60 |
| atgtccgtat | tgttcggaaa | gctgcatcag | gcacttgtgg | cccagggtgg | agatcgaatt | 120 |
| ggcgtatcct | ttcctgattt | ggacgaatca | cgctcccgac | ttggcgagag | actccgaatc | 180 |
| catgccagcg | ccgacgactt | gcgggcgttg | ctcgccaggc | cctggctgga | gggactgagg | 240 |
| gatcaccttc | aatttggaga | acctgccgtc | gtaccgcatc | caactcccta | tagacaggtc | 300 |
| tccagagtcc | aggctaaaag | caatccagaa | agattgaggc | gccggttgat | gaggcggcac | 360 |
| gacctctccg | aagaagaagc | acgcaaaaga | atcccggaca | cggtggcaag | agcattggat | 420 |
| ctgccttttg | tcacactgcg | gagtcagagc | acggggcaac | acttccgact | ttttattcgc | 480 |
| cacggaccct | tgcaggtgac | agcagaagaa | ggagggttta | cttgttatgg | gctttccaaa | 540 |
| ggtgggtttg | ttccctggtt | ctga | | | 564 |

<210> SEQ ID NO 32

<211> LENGTH: 1929
<212> TYPE: DNA
<213> ORGANISM: Artificial sequence
<220> FEATURE:
<223> OTHER INFORMATION: Synthetic

<400> SEQUENCE: 32

| | | | | | |
|---|---|---|---|---|---|
| atggattaca | aggaccatga | cggagattat | aaggaccacg | acatagacta | aaggatgac | 60 |
| gatgacaaaa | tggcagatgc | taagtcactg | actgcctggt | cccggacact | ggtgaccttc | 120 |
| aaggatgtgt | ttgtggactt | caccagggag | gagtggaagc | tgctggacac | tgctcagcag | 180 |
| atcctgtaca | gaaatgtgat | gctggagaac | tataagaacc | tggtttcctt | gggttatcag | 240 |
| cttactaagc | cagatgtgat | cctccggttg | gagaagggag | aagagccctg | gctggtggag | 300 |
| agagaaattc | accaagagac | ccatcctgat | tcagagactg | catttgaaat | caaatcatca | 360 |
| gttccgaaaa | agaaacgcaa | agttggatcc | ccaaagaaga | acgcaaagt | gcggggcatg | 420 |
| gccaatctcc | tgattgacaa | ttggatccct | gtgagaccga | ggaacggagg | gaaggttcag | 480 |
| atcatcaacc | tgcaaagtct | ctactgtagc | agagatcaat | ggcgactctc | attgcccagg | 540 |
| gatgatatgg | aattggcggc | acttgcactc | ttggtatgta | ttgggcagat | catcgcccct | 600 |
| gccaaggatg | atgtcgagtt | taggcacaga | ataatgaacc | tcttactga | agatgaattc | 660 |
| cagcaattga | tcgcgccttg | gatagatatg | ttctatttga | atcacgccga | acatcccttc | 720 |
| atgcagacaa | aaggggttaa | agcaaatgat | gtcacaccaa | tggagaagct | tttggcaggt | 780 |
| gtgtcaggag | caaccaactg | cgctttcgtt | aaccaaccag | gccaaggtga | ggcgttgtgc | 840 |
| ggggggtgca | cggccatagc | gttgtttaat | caggcgaacc | aggctcctgg | ctttggagga | 900 |
| ggattcaagt | ccggtttgcg | cggggggtaca | cccgtaacca | cattcgttcg | cggaattgac | 960 |
| ctccgatcaa | cagtcctgtt | gaacgtattg | acgttgccta | gacttcagaa | gcaatttcca | 1020 |
| aacgagtctc | acactgagaa | tcaaccgact | tggattaagc | ccatcaagtc | aaatgaaagt | 1080 |
| ataccggcgt | cttctattgg | atttgttaga | ggactttttt | ggcagcccgc | tcacatagaa | 1140 |
| ctctgtgatc | ccataggcat | tggaaagtgt | tcttgctgtg | ccaagagtc | taaccttaga | 1200 |
| tatacgggct | ttctcaagga | gaagttcacg | ttcaccgtga | atggactttg | gccacatccc | 1260 |
| catagcccgt | gcttggtcac | ggtcaagaag | ggggaggttg | aagagaaatt | tcttgcgttt | 1320 |
| accacatccg | ccccatcctg | gacgcaaata | tctcgcgtcg | ttgtggataa | aatcatccag | 1380 |
| aacgaaaatg | gtaaccgcgt | tgccgcggta | gtgaatcaat | tcagaaacat | agcaccacag | 1440 |
| agcccgttgg | agttgataat | gggcgggtac | cgcaataatc | aagcttccat | tctcgagcga | 1500 |
| cgccatgacg | tacttatgtt | taaccagggg | tggcagcaat | atggtaacgt | gataaacgag | 1560 |
| atagtcacag | tcggcctcgg | ctacaaaact | gcgttgcgca | aagctctgta | tacgttcgcg | 1620 |
| gagggttta | agaataaaga | ctttaaaggc | gctggggtga | gtgtgcacga | gacggcagaa | 1680 |
| cgccatttct | atcgccagtc | tgaactcttg | attcccgacg | ttctggcgaa | tgtcaatttt | 1740 |
| tcccaggccg | atgaggtcat | tgcggatctg | cgagataagc | ttcaccagtt | gtgtgagatg | 1800 |
| ctgttcaacc | agtctgtggc | tccttatgct | catcatccca | aactgatttc | aactctcgct | 1860 |
| ttggcaaggg | ctacgttgta | taaacacctt | agagaactga | agccacaggg | tggtcccagc | 1920 |
| aatggctga | | | | | | 1929 |

<210> SEQ ID NO 33
<211> LENGTH: 642
<212> TYPE: PRT
<213> ORGANISM: Artificial sequence
<220> FEATURE:
<223> OTHER INFORMATION: Synthetic

<400> SEQUENCE: 33

```
Met Asp Tyr Lys Asp His Asp Gly Asp Tyr Lys Asp His Asp Ile Asp
1               5                   10                  15

Tyr Lys Asp Asp Asp Lys Met Ala Asp Ala Lys Ser Leu Thr Ala
            20                  25                  30

Trp Ser Arg Thr Leu Val Thr Phe Lys Asp Val Phe Val Asp Phe Thr
        35                  40                  45

Arg Glu Glu Trp Lys Leu Leu Asp Thr Ala Gln Gln Ile Leu Tyr Arg
    50                  55                  60

Asn Val Met Leu Glu Asn Tyr Lys Asn Leu Val Ser Leu Gly Tyr Gln
65                  70                  75                  80

Leu Thr Lys Pro Asp Val Ile Leu Arg Leu Glu Lys Gly Glu Glu Pro
                85                  90                  95

Trp Leu Val Glu Arg Glu Ile His Gln Glu Thr His Pro Asp Ser Glu
            100                 105                 110

Thr Ala Phe Glu Ile Lys Ser Ser Val Pro Lys Lys Arg Lys Val
        115                 120                 125

Gly Ser Pro Lys Lys Lys Arg Lys Val Arg Gly Met Ala Asn Leu Leu
130                 135                 140

Ile Asp Asn Trp Ile Pro Val Arg Pro Arg Asn Gly Gly Lys Val Gln
145                 150                 155                 160

Ile Ile Asn Leu Gln Ser Leu Tyr Cys Ser Arg Asp Gln Trp Arg Leu
                165                 170                 175

Ser Leu Pro Arg Asp Asp Met Glu Leu Ala Ala Leu Ala Leu Leu Val
            180                 185                 190

Cys Ile Gly Gln Ile Ile Ala Pro Ala Lys Asp Asp Val Glu Phe Arg
        195                 200                 205

His Arg Ile Met Asn Pro Leu Thr Glu Asp Glu Phe Gln Gln Leu Ile
    210                 215                 220

Ala Pro Trp Ile Asp Met Phe Tyr Leu Asn His Ala Glu His Pro Phe
225                 230                 235                 240

Met Gln Thr Lys Gly Val Lys Ala Asn Asp Val Thr Pro Met Glu Lys
                245                 250                 255

Leu Leu Ala Gly Val Ser Gly Ala Thr Asn Cys Ala Phe Val Asn Gln
            260                 265                 270

Pro Gly Gln Gly Glu Ala Leu Cys Gly Gly Cys Thr Ala Ile Ala Leu
        275                 280                 285

Phe Asn Gln Ala Asn Gln Ala Pro Gly Phe Gly Gly Phe Lys Ser
    290                 295                 300

Gly Leu Arg Gly Gly Thr Pro Val Thr Thr Phe Val Arg Gly Ile Asp
305                 310                 315                 320

Leu Arg Ser Thr Val Leu Leu Asn Val Leu Thr Leu Pro Arg Leu Gln
                325                 330                 335

Lys Gln Phe Pro Asn Glu Ser His Thr Glu Asn Gln Pro Thr Trp Ile
            340                 345                 350

Lys Pro Ile Lys Ser Asn Glu Ser Ile Pro Ala Ser Ser Ile Gly Phe
        355                 360                 365

Val Arg Gly Leu Phe Trp Gln Pro Ala His Ile Glu Leu Cys Asp Pro
    370                 375                 380

Ile Gly Ile Gly Lys Cys Ser Cys Cys Gly Gln Glu Ser Asn Leu Arg
385                 390                 395                 400
```

Tyr Thr Gly Phe Leu Lys Glu Lys Phe Thr Phe Thr Val Asn Gly Leu
            405                 410                 415

Trp Pro His Pro His Ser Pro Cys Leu Val Thr Val Lys Lys Gly Glu
            420                 425                 430

Val Glu Glu Lys Phe Leu Ala Phe Thr Thr Ser Ala Pro Ser Trp Thr
            435                 440                 445

Gln Ile Ser Arg Val Val Asp Lys Ile Ile Gln Asn Glu Asn Gly
    450                 455                 460

Asn Arg Val Ala Ala Val Val Asn Gln Phe Arg Asn Ile Ala Pro Gln
465                 470                 475                 480

Ser Pro Leu Glu Leu Ile Met Gly Gly Tyr Arg Asn Asn Gln Ala Ser
            485                 490                 495

Ile Leu Glu Arg Arg His Asp Val Leu Met Phe Asn Gln Gly Trp Gln
            500                 505                 510

Gln Tyr Gly Asn Val Ile Asn Glu Ile Val Thr Val Gly Leu Gly Tyr
            515                 520                 525

Lys Thr Ala Leu Arg Lys Ala Leu Tyr Thr Phe Ala Glu Gly Phe Lys
            530                 535                 540

Asn Lys Asp Phe Lys Gly Ala Gly Val Ser Val His Glu Thr Ala Glu
545                 550                 555                 560

Arg His Phe Tyr Arg Gln Ser Glu Leu Leu Ile Pro Asp Val Leu Ala
            565                 570                 575

Asn Val Asn Phe Ser Gln Ala Asp Glu Val Ile Ala Asp Leu Arg Asp
            580                 585                 590

Lys Leu His Gln Leu Cys Glu Met Leu Phe Asn Gln Ser Val Ala Pro
            595                 600                 605

Tyr Ala His His Pro Lys Leu Ile Ser Thr Leu Ala Leu Ala Arg Ala
            610                 615                 620

Thr Leu Tyr Lys His Leu Arg Glu Leu Lys Pro Gln Gly Gly Pro Ser
625                 630                 635                 640

Asn Gly

<210> SEQ ID NO 34
<211> LENGTH: 900
<212> TYPE: DNA
<213> ORGANISM: Artificial sequence
<220> FEATURE:
<223> OTHER INFORMATION: Synthetic

<400> SEQUENCE: 34
atggattaca aggaccatga cggagattat aaggaccacg acatagacta taaggatgac    60
gatgacaaaa tggcagatgc taagtcactg actgcctggt cccggacact ggtgaccttc   120
aaggatgtgt ttgtggactt caccagggag gagtggaagc tgctggacac tgctcagcag   180
atcctgtaca gaaatgtgat gctggagaac tataagaacc tggtttcctt gggttatcag   240
cttactaagc cagatgtgat cctccggttg gagaagggag aagagccctg gctggtggag   300
agagaaattc accaagagac ccatcctgat tcagagactg catttgaaat caaatcatca   360
gttccgaaaa agaaacgcaa agttggatcc ccaaagaaga acgcaaggt gcgcgggatg   420 gccgatgaaa tagacgcaat ggctctttac cgagcatggc aacagctcga caatggatct   480
tgcgcccaaa tacggcgggt aagtgaaccc gatgaactgc gagatatccc cgcattctac   540
cgattggttc agccgtttgg ctgggagaac ccacggcacc agcaggcgct tcttaggatg   600
gttttttgtc ttagtgccgg gaaaaacgta atccgccatc aggataagaa gtccgaacaa   660

```
acaacaggga tttctctggg aagagcgctt gctaacagcg gcaggatcaa tgaacgccgc    720
atatttcagt tgatccgagc agatcggact gctgatatgg tccagctcag gaggctcctt    780
acgcacgcag agccagtgtt ggattggcca ctcatggcaa gaatgcttac gtggtggggg    840
aagagggaaa ggcagcaact gcttgaagat tttgtattga cgacgaacaa aaacgcgtaa    900
```

<210> SEQ ID NO 35
<211> LENGTH: 299
<212> TYPE: PRT
<213> ORGANISM: Artificial sequence
<220> FEATURE:
<223> OTHER INFORMATION: Synthetic

<400> SEQUENCE: 35

```
Met Asp Tyr Lys Asp His Asp Gly Asp Tyr Lys Asp His Asp Ile Asp
1               5                   10                  15

Tyr Lys Asp Asp Asp Asp Lys Met Ala Asp Ala Lys Ser Leu Thr Ala
                20                  25                  30

Trp Ser Arg Thr Leu Val Thr Phe Lys Asp Val Phe Val Asp Phe Thr
            35                  40                  45

Arg Glu Glu Trp Lys Leu Leu Asp Thr Ala Gln Gln Ile Leu Tyr Arg
        50                  55                  60

Asn Val Met Leu Glu Asn Tyr Lys Asn Leu Val Ser Leu Gly Tyr Gln
65                  70                  75                  80

Leu Thr Lys Pro Asp Val Ile Leu Arg Leu Glu Lys Gly Glu Glu Pro
                85                  90                  95

Trp Leu Val Glu Arg Glu Ile His Gln Glu Thr His Pro Asp Ser Glu
            100                 105                 110

Thr Ala Phe Glu Ile Lys Ser Ser Val Pro Lys Lys Arg Lys Val
        115                 120                 125

Gly Ser Pro Lys Lys Lys Arg Lys Val Arg Gly Met Ala Asp Glu Ile
    130                 135                 140

Asp Ala Met Ala Leu Tyr Arg Ala Trp Gln Gln Leu Asp Asn Gly Ser
145                 150                 155                 160

Cys Ala Gln Ile Arg Arg Val Ser Glu Pro Asp Glu Leu Arg Asp Ile
                165                 170                 175

Pro Ala Phe Tyr Arg Leu Val Gln Pro Phe Gly Trp Glu Asn Pro Arg
            180                 185                 190

His Gln Gln Ala Leu Leu Arg Met Val Phe Cys Leu Ser Ala Gly Lys
        195                 200                 205

Asn Val Ile Arg His Gln Asp Lys Lys Ser Glu Gln Thr Thr Gly Ile
    210                 215                 220

Ser Leu Gly Arg Ala Leu Ala Asn Ser Gly Arg Ile Asn Glu Arg Arg
225                 230                 235                 240

Ile Phe Gln Leu Ile Arg Ala Asp Arg Thr Ala Asp Met Val Gln Leu
                245                 250                 255

Arg Arg Leu Leu Thr His Ala Glu Pro Val Leu Asp Trp Pro Leu Met
            260                 265                 270

Ala Arg Met Leu Thr Trp Trp Gly Lys Arg Glu Arg Gln Gln Leu Leu
        275                 280                 285

Glu Asp Phe Val Leu Thr Thr Asn Lys Asn Ala
    290                 295
```

<210> SEQ ID NO 36
<211> LENGTH: 1509

<212> TYPE: DNA
<213> ORGANISM: Artificial sequence
<220> FEATURE:
<223> OTHER INFORMATION: Synthetic

<400> SEQUENCE: 36

```
atggattaca aggaccatga cggagattat aaggaccacg acatagacta taaggatgac      60
gatgacaaaa tggcagatgc taagtcactg actgcctggt cccggacact ggtgaccttc     120
aaggatgtgt ttgtggactt caccagggag gagtggaagc tgctggacac tgctcagcag     180
atcctgtaca gaaatgtgat gctggagaac tataagaacc tggtttcctt gggttatcag     240
cttactaagc cagatgtgat cctccggttg gagaagggag aagagccctg gctggtggag     300
agagaaattc accaagagac ccatcctgat tcagagactg catttgaaat caaatcatca     360
gttccgaaaa agaaacgcaa agttggatcc caaagaagaa acgcaaggt gagaggaatg     420
tcaaacttca ttaatatcca cgtgcttatc tcacactccc ctagttgcct aacagagac     480
gatatgaaca tgcaaaaaga cgcaatttttt ggcggcaaaa ggagagtcag aattagtagc     540
cagagcctga agcgcgctat gaggaaaagc ggctactatg ctcaaaacat tggtgaaagt     600
tcattgcgga ccatccatct cgcgcagttg agggacgtcc tgcgacagaa gcttggggaa     660
agatttgatc agaagatcat cgacaaaacg cttgcccttc tgtccggtaa atcagtggac     720
gaagcggaga gataagtgc ggatgctgtt acgccatggg tggtaggtga atcgcgtgg     780
ttttgcgagc aggtagccaa ggccgaagcg gataatttgg atgataagaa actgctcaaa     840
gtcctcaaag aggacatcgc ggcgatccgg gtgaaccttc agcagggtgt tgatattgcg     900
ctctctggtc ggatggccac gtctggaatg atgactgaac tgggtaaggt ggacggagct     960
atgtctatag ctcatgctat aactacccat caggtggatt ctgacataga ctggttcacg    1020
gctgtcgacg atctccagga caaggatcc gcacacctcg gcacgcaaga ttttcttct    1080
ggagtgttct ataggtatgc caacatcaac cttgcacagc tccaggaaaa cctcggtggg    1140
gcaagccggg aacaggctct tgaaatagct acccatgtgg ttcacatgct ggcgaccgaa    1200
gtgccagggg ccaagcagag aacgtacgcc gcattcaatc cggcggacat ggtcatggtg    1260
aatttctctg atatgcccttt gtctatggca atgctttcg agaaggcggt caaggcaaag    1320
gacggttttt tgcaaccctc catccaagcc tttaatcagt actgggatag agtagctaac    1380
gggtatggtc tcaatggcgc ggctgctcag ttttctttgt ccgatgtgga tccgataacg    1440
gcgcaggtta acagatgcc caccttggaa caactcaaat cctgggttag aaacaatggg    1500
gaggcgtga                                                            1509
```

<210> SEQ ID NO 37
<211> LENGTH: 502
<212> TYPE: PRT
<213> ORGANISM: Artificial sequence
<220> FEATURE:
<223> OTHER INFORMATION: Synthetic

<400> SEQUENCE: 37

```
Met Asp Tyr Lys Asp His Asp Gly Asp Tyr Lys Asp His Asp Ile Asp
1               5                   10                  15
Tyr Lys Asp Asp Asp Lys Met Ala Asp Ala Lys Ser Leu Thr Ala
            20                  25                  30
Trp Ser Arg Thr Leu Val Thr Phe Lys Asp Val Phe Val Asp Phe Thr
        35                  40                  45
Arg Glu Glu Trp Lys Leu Leu Asp Thr Ala Gln Gln Ile Leu Tyr Arg
```

```
                50                  55                  60
Asn Val Met Leu Glu Asn Tyr Lys Asn Leu Val Ser Leu Gly Tyr Gln
 65                  70                  75                  80

Leu Thr Lys Pro Asp Val Ile Leu Arg Leu Glu Lys Gly Glu Glu Pro
                 85                  90                  95

Trp Leu Val Glu Arg Glu Ile His Gln Glu Thr His Pro Asp Ser Glu
                100                 105                 110

Thr Ala Phe Glu Ile Lys Ser Ser Val Pro Lys Lys Arg Lys Val
            115                 120                 125

Gly Ser Pro Lys Lys Arg Lys Val Arg Gly Met Ser Asn Phe Ile
        130                 135                 140

Asn Ile His Val Leu Ile Ser His Ser Pro Ser Cys Leu Asn Arg Asp
145                 150                 155                 160

Asp Met Asn Met Gln Lys Asp Ala Ile Phe Gly Gly Lys Arg Arg Val
                165                 170                 175

Arg Ile Ser Ser Gln Ser Leu Lys Arg Ala Met Arg Lys Ser Gly Tyr
            180                 185                 190

Tyr Ala Gln Asn Ile Gly Glu Ser Ser Leu Arg Thr Ile His Leu Ala
            195                 200                 205

Gln Leu Arg Asp Val Leu Arg Gln Lys Leu Gly Glu Arg Phe Asp Gln
210                 215                 220

Lys Ile Ile Asp Lys Thr Leu Ala Leu Leu Ser Gly Lys Ser Val Asp
225                 230                 235                 240

Glu Ala Glu Lys Ile Ser Ala Asp Ala Val Thr Pro Trp Val Val Gly
                245                 250                 255

Glu Ile Ala Trp Phe Cys Glu Gln Val Ala Lys Ala Glu Ala Asp Asn
            260                 265                 270

Leu Asp Asp Lys Lys Leu Leu Lys Val Leu Lys Glu Asp Ile Ala Ala
        275                 280                 285

Ile Arg Val Asn Leu Gln Gln Gly Val Asp Ile Ala Leu Ser Gly Arg
        290                 295                 300

Met Ala Thr Ser Gly Met Met Thr Glu Leu Gly Lys Val Asp Gly Ala
305                 310                 315                 320

Met Ser Ile Ala His Ala Ile Thr Thr His Gln Val Asp Ser Asp Ile
                325                 330                 335

Asp Trp Phe Thr Ala Val Asp Asp Leu Gln Glu Gln Gly Ser Ala His
            340                 345                 350

Leu Gly Thr Gln Glu Phe Ser Ser Gly Val Phe Tyr Arg Tyr Ala Asn
        355                 360                 365

Ile Asn Leu Ala Gln Leu Gln Glu Asn Leu Gly Gly Ala Ser Arg Glu
        370                 375                 380

Gln Ala Leu Glu Ile Ala Thr His Val Val His Met Leu Ala Thr Glu
385                 390                 395                 400

Val Pro Gly Ala Lys Gln Arg Thr Tyr Ala Ala Phe Asn Pro Ala Asp
                405                 410                 415

Met Val Met Val Asn Phe Ser Asp Met Pro Leu Ser Met Ala Asn Ala
            420                 425                 430

Phe Glu Lys Ala Val Lys Ala Lys Asp Gly Phe Leu Gln Pro Ser Ile
        435                 440                 445

Gln Ala Phe Asn Gln Tyr Trp Asp Arg Val Ala Asn Gly Tyr Gly Leu
        450                 455                 460

Asn Gly Ala Ala Ala Gln Phe Ser Leu Ser Asp Val Asp Pro Ile Thr
465                 470                 475                 480
```

Ala Gln Val Lys Gln Met Pro Thr Leu Glu Gln Leu Lys Ser Trp Val
            485                 490                 495

Arg Asn Asn Gly Glu Ala
            500

<210> SEQ ID NO 38
<211> LENGTH: 1092
<212> TYPE: DNA
<213> ORGANISM: Artificial sequence
<220> FEATURE:
<223> OTHER INFORMATION: Synthetic

<400> SEQUENCE: 38

```
atggattaca aggaccatga cggagattat aaggaccacg acatagacta taaggatgac      60
gatgacaaaa tggcagatgc taagtcactg actgcctggt cccggacact ggtgaccttc     120
aaggatgtgt ttgtggactt caccagggag gagtggaagc tgctggacac tgctcagcag     180
atcctgtaca gaaatgtgat gctggagaac tataagaacc tggtttcctt gggttatcag     240
cttactaagc cagatgtgat cctccggttg gagaagggag aagagccctg gctggtggag     300
agagaaattc accaagagac ccatcctgat tcagagactg catttgaaat caaatcatca     360
gttccgaaaa agaaacgcaa agttggatcc ccaaagaaga acgcaaagt acggggcatg      420
cgatcatact tgatcctgcg gcttgcaggt cctatgcaag cctgggggca acctaccttt     480
gaaggtactc ggccgactgg caggttccct acgcggtctg gtttgctcgg actcctcggc     540
gcctgtttgg ggatacaaag ggatgacact tcttccttgc aggcactttc gaatcagtc      600
cagttcgcag tgagatgtga tgaactcata ctggacgaca cgggtgtc cgtaactgga       660
ctgagggact atcatactgt actcggcgca agagaagatt atcgaggtct taagtcacat     720
gagactattc agacatggag ggaatatttg tgtgacgcct ccttcacggt ggccctctgg     780
cttacaccac atgcaactat ggtgatctca gagcttgaga agccgttct aaacctcgg      840
tacacaccat atctggggag gcggtcttgc ccacttaccc accgctttt cttggggact      900
tgtcaggcca gcgatccaca gaaggccttg ctgaactatg aacccgttgg tggcgatata     960
tacagtgaag agagcgtcac gggccatcac ttgaagttca ctgctaggga tgagccgatg    1020
attacgctcc cgagacagtt cgctagtagg gaatggtacg ttattaaggg gggaatggac    1080
gtttcccaat ga                                                        1092
```

<210> SEQ ID NO 39
<211> LENGTH: 363
<212> TYPE: PRT
<213> ORGANISM: Artificial sequence
<220> FEATURE:
<223> OTHER INFORMATION: Synthetic

<400> SEQUENCE: 39

Met Asp Tyr Lys Asp His Asp Gly Asp Tyr Lys Asp His Asp Ile Asp
1               5                   10                  15

Tyr Lys Asp Asp Asp Lys Met Ala Asp Ala Lys Ser Leu Thr Ala
            20                  25                  30

Trp Ser Arg Thr Leu Val Thr Phe Lys Asp Val Phe Val Asp Phe Thr
        35                  40                  45

Arg Glu Glu Trp Lys Leu Leu Asp Thr Ala Gln Gln Ile Leu Tyr Arg
    50                  55                  60

Asn Val Met Leu Glu Asn Tyr Lys Asn Leu Val Ser Leu Gly Tyr Gln
65                  70                  75                  80

Leu Thr Lys Pro Asp Val Ile Leu Arg Leu Glu Lys Gly Glu Glu Pro
            85                  90                  95

Trp Leu Val Glu Arg Glu Ile His Gln Glu Thr His Pro Asp Ser Glu
                100                 105                 110

Thr Ala Phe Glu Ile Lys Ser Ser Val Pro Lys Lys Arg Lys Val
        115                 120                 125

Gly Ser Pro Lys Lys Lys Arg Lys Val Arg Gly Met Arg Ser Tyr Leu
    130                 135                 140

Ile Leu Arg Leu Ala Gly Pro Met Gln Ala Trp Gly Gln Pro Thr Phe
145                 150                 155                 160

Glu Gly Thr Arg Pro Thr Gly Arg Phe Pro Thr Arg Ser Gly Leu Leu
                165                 170                 175

Gly Leu Leu Gly Ala Cys Leu Gly Ile Gln Arg Asp Asp Thr Ser Ser
            180                 185                 190

Leu Gln Ala Leu Ser Glu Ser Val Gln Phe Ala Val Arg Cys Asp Glu
        195                 200                 205

Leu Ile Leu Asp Asp Arg Arg Val Ser Val Thr Gly Leu Arg Asp Tyr
210                 215                 220

His Thr Val Leu Gly Ala Arg Glu Asp Tyr Arg Gly Leu Lys Ser His
225                 230                 235                 240

Glu Thr Ile Gln Thr Trp Arg Glu Tyr Leu Cys Asp Ala Ser Phe Thr
                245                 250                 255

Val Ala Leu Trp Leu Thr Pro His Ala Thr Met Val Ile Ser Glu Leu
            260                 265                 270

Glu Lys Ala Val Leu Lys Pro Arg Tyr Thr Pro Tyr Leu Gly Arg Arg
        275                 280                 285

Ser Cys Pro Leu Thr His Pro Leu Phe Leu Gly Thr Cys Gln Ala Ser
    290                 295                 300

Asp Pro Gln Lys Ala Leu Leu Asn Tyr Glu Pro Val Gly Gly Asp Ile
305                 310                 315                 320

Tyr Ser Glu Glu Ser Val Thr Gly His His Leu Lys Phe Thr Ala Arg
                325                 330                 335

Asp Glu Pro Met Ile Thr Leu Pro Arg Gln Phe Ala Ser Arg Glu Trp
            340                 345                 350

Tyr Val Ile Lys Gly Gly Met Asp Val Ser Gln
        355                 360

<210> SEQ ID NO 40
<211> LENGTH: 1017
<212> TYPE: DNA
<213> ORGANISM: Artificial sequence
<220> FEATURE:
<223> OTHER INFORMATION: Synthetic

<400> SEQUENCE: 40
atggattaca aggaccatga cggagattat aaggaccacg acatagacta taaggatgac      60
gatgacaaaa tggcagatgc taagtcactg actgcctggt cccggacact ggtgaccttc     120
aaggatgtgt tgtggactt caccagggag gagtggaagc tgctggacac tgctcagcag     180
atcctgtaca gaaatgtgat gctggagaac tataagaacc tggtttcctt gggttatcag     240
cttactaagc cagatgtgat cctccggttg gagaagggag aagagccctg gctggtggag     300
agagaaattc accaagagac ccatcctgat tcagagactg catttgaaat caatcatca     360 gttccgaaaa agaaacgcaa agttggatcc ccaaagaaga acgcaaggt gcggggcatg     420

-continued

```
tatctcagta aagtcatcat tgccagggcc tggagcaggg atctttacca acttcaccag    480
ggattatggc atttatttcc aaacagaccg gatgctgctc gtgattttct ttttcatgtt    540
gagaagcgaa acacaccaga aggctgtcat gttttattgc agtcagcgca aatgcctgtt    600
tcaactgccg ttgcgacagt cattaaaact aaacaggttg aatttcaact tcaggttggt    660
gttccactct attttcggct cgggcaaat ccgatcaaaa ctattctcga caatcaaaag     720
cgcctggaca gtaaagggaa tattaaacgc tgtcgggttc cgttaataaa agaagcagaa    780
caaatcgcgt ggttgcaacg taaattgggc aatgcggcgc gcgttgaaga tgtgcatccc    840
atatcggaac ggccacagta ttttctggt gatggtaaaa gtggaaagat ccaaacggtt     900
tgctttgaag gtgtgctcac catcaacgac gcgccagcgt taatagatct tgtacagcaa    960
ggtattgggc cagctaaatc gatgggatgt ggcttgctat ctttggctcc actgtga      1017
```

<210> SEQ ID NO 41
<211> LENGTH: 338
<212> TYPE: PRT
<213> ORGANISM: Artificial sequence
<220> FEATURE:
<223> OTHER INFORMATION: Synthetic

<400> SEQUENCE: 41

```
Met Asp Tyr Lys Asp His Asp Gly Asp Tyr Lys Asp His Asp Ile Asp
1               5                   10                  15

Tyr Lys Asp Asp Asp Lys Met Ala Asp Ala Lys Ser Leu Thr Ala
            20                  25                  30

Trp Ser Arg Thr Leu Val Thr Phe Lys Asp Val Phe Val Asp Phe Thr
        35                  40                  45

Arg Glu Glu Trp Lys Leu Leu Asp Thr Ala Gln Gln Ile Leu Tyr Arg
    50                  55                  60

Asn Val Met Leu Glu Asn Tyr Lys Asn Leu Val Ser Leu Gly Tyr Gln
65                  70                  75                  80

Leu Thr Lys Pro Asp Val Ile Leu Arg Leu Glu Lys Gly Glu Glu Pro
                85                  90                  95

Trp Leu Val Glu Arg Glu Ile His Gln Glu Thr His Pro Asp Ser Glu
            100                 105                 110

Thr Ala Phe Glu Ile Lys Ser Ser Val Pro Lys Lys Arg Lys Val
        115                 120                 125

Gly Ser Pro Lys Lys Lys Arg Lys Val Arg Gly Met Tyr Leu Ser Lys
    130                 135                 140

Val Ile Ile Ala Arg Ala Trp Ser Arg Asp Leu Tyr Gln Leu His Gln
145                 150                 155                 160

Gly Leu Trp His Leu Phe Pro Asn Arg Pro Asp Ala Ala Arg Asp Phe
                165                 170                 175

Leu Phe His Val Glu Lys Arg Asn Thr Pro Glu Gly Cys His Val Leu
            180                 185                 190

Leu Gln Ser Ala Gln Met Pro Val Ser Thr Ala Val Ala Thr Val Ile
        195                 200                 205

Lys Thr Lys Gln Val Glu Phe Gln Leu Gln Val Gly Val Pro Leu Tyr
    210                 215                 220

Phe Arg Leu Arg Ala Asn Pro Ile Lys Thr Ile Leu Asp Asn Gln Lys
225                 230                 235                 240

Arg Leu Asp Ser Lys Gly Asn Ile Lys Arg Cys Arg Val Pro Leu Ile
                245                 250                 255

Lys Glu Ala Glu Gln Ile Ala Trp Leu Gln Arg Lys Leu Gly Asn Ala
```

```
              260              265              270
Ala Arg Val Glu Asp Val His Pro Ile Ser Glu Arg Pro Gln Tyr Phe
            275                  280                  285

Ser Gly Asp Gly Lys Ser Gly Lys Ile Gln Thr Val Cys Phe Glu Gly
            290                  295                  300

Val Leu Thr Ile Asn Asp Ala Pro Ala Leu Ile Asp Leu Val Gln Gln
305                  310                  315                  320

Gly Ile Gly Pro Ala Lys Ser Met Gly Cys Gly Leu Leu Ser Leu Ala
                325                  330                  335

Pro Leu
```

<210> SEQ ID NO 42
<211> LENGTH: 6506
<212> TYPE: DNA
<213> ORGANISM: Artificial sequence
<220> FEATURE:
<223> OTHER INFORMATION: Synthetic

<400> SEQUENCE: 42

```
gggtctctct ggttagacca gatctgagcc tgggagctct ctggctaact agggaaccca    60
ctgcttaagc ctcaataaag cttgccttga gtgcttcaag tagtgtgtgc ccgtctgttg   120
tgtgactctg gtaactagag atccctcaga ccctttagt cagtgtggaa atctctagc    180
agtggcgccc gaacagggac ttgaaagcga aggggaaacc agaggagctc tctcgacgca   240
ggactcggct tgctgaagcg cgcacggcaa gaggcgaggg gcggcgactg gtgagtacgc   300
caaaaatttt gactagcgga ggctagaagg agagagatgg gtgcgagagc gtcagtatta   360
agcgggggag aattagatcg cgatgggaaa aaattcggtt aaggccaggg ggaaagaaaa   420
aatataaatt aaaacatata gtatgggcaa gcagggagct agaacgattc gcagttaatc   480
ctggcctgtt agaaacatca gaaggctgta gacaaatact gggacagcta caaccatccc   540
ttcagacagg atcagaagaa cttagatcat tatataatac agtagcaacc ctctattgtg   600
tgcatcaaag gatagagata aagacacca aggaagcttt agacaagata gaggaagagc   660
aaaacaaaag taagaccacc gcacagcaag cggccgctga tcttcagacc tggaggagga   720
gatatgaggg acaattggag aagtgaatta tataaatata agtagtaaaa aattgaacca   780
ttaggagtag cacccaccaa ggcaaagaga agagtggtgc agagagaaaa aagagcagtg   840
ggaataggag cttgttcct tgggttcttg ggagcagcag gaagcactat gggcgcagcg   900
tcaatgacgc tgacggtaca ggccagacaa ttattgtctg gtatagtgca gcagcagaac   960
aatttgctga gggctattga ggcgcaacag catctgttgc aactcacagt ctggggcatc  1020
aagcagctcc aggcaagaat cctggctgtg gaaagatacc taaaggatca acagctcctg  1080
gggatttggg gttgctctgg aaaactcatt tgcaccactg ctgtgccttg gaatgctagt  1140
tggagtaata atctctgga acagatttgg aatcacacga cctggatgga gtgggacaga  1200
gaaattaaca attacacaag cttaatacac tccttaattg aagaatcgca aaaccagcaa  1260
gaaaagaatg aacaagaatt attggaatta gataaatggg caagtttgtg gaattggttt  1320
aacataacaa attggctgtg gtatataaaa ttattcataa tgatagtagg aggcttggta  1380
ggtttaagaa tagttttgc tgtactttct atagtgaata gagttaggca gggatattca  1440
ccattatcgt ttcagaccca cctcccaacc ccgaggggac ccgacaggcc cgaaggaata  1500
gaagaagaag gtggagagag agacagagac agatccattc gattagtgaa cggatcggca  1560
ctgcgtgcgc caattctgca gacaaatggc agtattcatc cacaatttta aagaaaagg  1620
```

```
ggggattggg gggtacagtg caggggaaag aatagtagac ataatagcaa cagacataca     1680
aactaaagaa ttacaaaaac aaattacaaa aattcaaaat tttcgggttt attacaggga     1740
cagcagagat ccagtttggt taattaaggg tgcagcggcc tccgcgccgg gttttggcgc     1800
ctcccgcggg cgccccctc ctcacggcga gcgctgccac gtcagacgaa gggcgcagga     1860
gcgttcctga tccttccgcc cggacgctca ggacagcggc ccgctgctca taagactcgg     1920
ccttagaacc ccagtatcag cagaaggaca ttttaggacg ggacttgggt gactctaggg     1980
cactggtttt ctttccagag agcggaacag gcgaggaaaa gtagtccctt ctcggcgatt     2040
ctgcggaggg atctccgtgg ggcggtgaac gccgatgatt atataaggac gcgccgggtg     2100
tggcacagct agttccgtcg cagccgggat ttgggtcgcg gttcttgttt gtggatcgct     2160
gtgatcgtca cttggtgagt tgcgggctgc tgggctggcc ggggctttcg tggccgccgg     2220
gccgctcggt gggacggaag cgtgtggaga gaccgccaag ggctgtagtc tgggtccgcg     2280
agcaaggttg ccctgaactg gggggttgggg ggagcgcaca aaatggcggc tgttcccgag     2340
tcttgaatgg aagacgcttg taaggcgggc tgtgaggtcg ttgaaacaag gtgggggca     2400 tggtgggcgc caagaaccca aggtcttgag gccttcgcta atgcgggaaa gctcttattc     2460
gggtgagatg ggctggggca ccatctgggg accctgacgt gaagtttgtc actgactgga     2520
gaactcgggt ttgtcgtctg gttgcggggg cggcagttat gcggtgccgt tgggcagtgc     2580
acccgtacct ttgggagcgc cgcgcctcgtc gtgtcgtgac gtcacccgtt ctgttggctt     2640
ataatgcagg gtggggccac ctgccggtag gtgtgcggta ggcttttctc cgtcgcagga     2700
cgcagggttc gggcctaggg taggctctcc tgaatcgaca ggcgccggac ctctggtgag     2760
gggagggata agtgaggcgt cagtttcttt ggtcggtttt atgtacctat cttcttaagt     2820
agctgaagct ccggttttga actatgcgct cggggttggc gagtgtgttt tgtgaagttt     2880
tttaggcacc ttttgaaatg taatcatttg ggtcaatatg taattttcag tgttagacta     2940
gtaaattgtc cgctaaattc tggccgtttt tggcttttt gttagacgaa gcttgggctg     3000
caggtcgact ctagaggatc cccgggtacc ggtcgccacc gccgccacca tggcctatcc     3060
atatgatgtg ccagattatg ccatggcgcc gaagaaaaag aggaaagtac ggggcatgcg     3120
atcatacttg atcctgcggc ttgcaggtcc tatgcaagcc tgggggcaac ctacctttga     3180
aggtactcgg ccgactggca ggttccctac gcggtctggt ttgctcggac tcctcggcgc     3240
ctgtttgggg atacaaaggg atgacacttc ttccttgcag gcactttccg aatcagtcca     3300
gttcgcagtg agatgtgatg aactcatact ggacgacaga cgggtgtccg taactggact     3360
gagggactat catactgtac tcggcgcaag agaagattat cgaggtctta agtcacatga     3420
gactattcag acatggaggg aatatttgtg tgacgcctcc ttcacggtgg ccctctggct     3480
tacaccacat gcaactatgg tgatctcaga gcttgagaaa gccgttctta aacctcggta     3540
cacaccatat ctggggaggc ggtcttgccc acttacccac ccgcttttct tggggacttg     3600
tcaggccagc gatccacaga aggccttgct gaactatgaa cccgttggtg gcgatatata     3660
cagtgaagag agcgtcacgg gccatcactt gaagttcact gctagggatg agccgatgat     3720
tacgctcccg agacagttcg ctagtaggga atggtacgtt attaagggg gaatggacgt     3780 ttcccaagga agcggagcta ctaacttcag cctgctgaag caggctggag acgtggagga     3840
gaaccctgga cctatgggtg ccccagttcc ctatcccgac ccactggagc caaggatggc     3900
gcctaagaag aagcgcaagg tgcggggcat gtatctcagt aaagtcatca ttgccagggc     3960
```

-continued

```
ctggagcagg gatctttacc aacttcacca gggattatgg catttatttc caaacagacc    4020
ggatgctgct cgtgattttc tttttcatgt tgagaagcga aacacaccag aaggctgtca    4080
tgttttattg cagtcagcgc aaatgcctgt ttcaactgcc gttgcgacag tcattaaaac    4140
taaacaggtt gaatttcaac ttcaggttgg tgttccactc tattttcggc ttcgggcaaa    4200
tccgatcaaa actattctcg acaatcaaaa gcgcctggac agtaaaggga atattaaacg    4260
ctgtcgggtt ccgttaataa agaagcaga acaaatcgcg tggttgcaac gtaaattggg    4320
caatgcggcg cgcgttgaag atgtgcatcc catatcggaa cggccacagt attttttctgg   4380
tgatggtaaa agtggaaaga tccaaacggt ttgctttgaa ggtgtgctca ccatcaacga    4440
cgcgccagcg ttaatagatc ttgtacagca aggtattggg ccagctaaat cgatgggatg    4500
tggcttgcta tctttggctc cactgggaag cggagagggc agaggaagtc ttctcacatg    4560
cggtgacgtg gaggagaatc ctggacctat gaccgagtac aagcccacgg tgcgcctcgc    4620
cacccgcgac gacgtcccca gggccgtacg caccctcgcc gccgcgttcg ccgactaccc    4680
cgccacgcgc cacaccgtcg atccggaccg ccacatcgag cgggtcaccg agctgcaaga    4740
actcttcctc acgcgcgtcg ggctcgacat cggcaaggtg tgggtcgcgg acgacggcgc    4800
cgcggtggcg gtctggacca cgccggagag cgtcgaagcg ggggcggtgt cgccgagat    4860
cggcccgcgc atggccgagt tgagcggttc ccggctggcc gcgcagcaac agatggaagg    4920
cctcctggcg ccgcaccggc caaggagcc cgcgtggttc ctggccaccg tcggcgtctc    4980
gcccgaccac cagggcaagg gtctgggcag cgccgtcgtg ctccccggag tggaggcggc    5040
cgagcgcgcg ggggtgcccg ccttcctgga gacctccgcg ccccgcaacc tccccttcta    5100
cgagcggctc ggcttcaccg tcaccgccga cgtcgaggtg cccgaaggac cgcgcacctg    5160
gtgcatgacc cgcaagcccg gtgcctgaga attcgatatc aagcttatcg ataatcaacc    5220
tctggattac aaaatttgtg aaagattgac tggtattctt aactatgttg ctccttttac    5280
gctatgtgga tacgctgctt taatgccttt gtatcatgct attgcttccc gtatggcttt    5340
cattttctcc tccttgtata atcctggtt gctgtctctt tatgaggagt tgtggcccgt    5400
tgtcaggcaa cgtggcgtgg tgtgcactgt gtttgctgac gcaaccccca ctggttgggg    5460
cattgccacc acctgtcagc tcctttccgg gactttcgct ttccccctcc ctattgccac    5520
ggcggaactc atcgccgcct gccttgcccg ctgctggaca ggggctcggc tgttgggcac    5580
tgacaattcc gtggtgttgt cggggaaatc atcgtccttt ccttggctgc tcgcctgtgt    5640
tgccacctgg attctgcgcg gacgtccctt ctgctacgtc ccttcggccc tcaatccagc    5700
ggaccttcct tcccgcggcc tgctgccggc tctgcggcct cttccgcgtc ttcgccttcg    5760
ccctcagacg agtcggatct ccctttgggc cgcctccccg catcgatacc gtcgacctcg    5820
agacctagaa aaacatggag caatcacaag tagcaataca gcagctacca atgctgattg    5880
tgcctggcta aagcacaag aggaggagga ggtgggtttt ccagtcacac ctcaggtacc    5940
tttaagacca atgacttaca aggcagctgt agatcttagc cacttttaa aagaaaaggg    6000
gggactggaa gggctaattc actcccaacg aagacaagat atccttgatc tgtggatcta    6060
ccacacacaa ggctacttcc ctgattggca gaactacaca ccagggccag gatcagata    6120
tccactgacc tttggatggt gctacaagct agtaccagtt gagcaagaga aggtagaaga    6180
agccaatgaa ggagagaaca cccgcttgtt acaccctgtg agcctgcatg ggatggatga    6240
cccggagaga gaagtattag agtggaggtt tgacagccgc ctagcatttc atcacatggc    6300
ccgagagctg catccggact gtactgggtc tctctggtta gaccagatct gagcctggga    6360
```

```
gctctctggc taactaggga acccactgct taagcctcaa taaagcttgc cttgagtgct      6420
tcaagtagtg tgtgcccgtc tgttgtgtga ctctggtaac tagagatccc tcagacccett     6480 ttagtcagtg tggaaaatct ctagca                                           6506
```

<210> SEQ ID NO 43
<211> LENGTH: 8669
<212> TYPE: DNA
<213> ORGANISM: Artificial sequence
<220> FEATURE:
<223> OTHER INFORMATION: Synthetic

<400> SEQUENCE: 43

```
gggtctctct ggttagacca gatctgagcc tgggagctct ctggctaact agggaaccca        60
ctgcttaagc ctcaataaag cttgccttga gtgcttcaag tagtgtgtgc ccgtctgttg       120
tgtgactctg gtaactagag atccctcaga ccctttttagt cagtgtggaa aatctctagc     180
agtggcgccc gaacagggac ttgaaagcga aagggaaacc agaggagctc tctcgacgca       240
ggactcggct tgctgaagcg cgcacggcaa gaggcgaggg gcggcgactg gtgagtacgc       300
caaaaatttt gactagcgga ggctagaagg agagagatgg gtgcgagagc gtcagtatta       360
agcgggggag aattagatcg cgatgggaaa aaattcggtt aaggccaggg ggaaagaaaa       420
aatataaatt aaaacatata gtatgggcaa gcagggagct agaacgattc gcagttaatc       480
ctggcctgtt agaaacatca gaaggctgta gacaaatact gggacagcta caaccatccc      540
ttcagacagg atcagaagaa cttagatcat tatataatac agtagcaacc ctctattgtg      600
tgcatcaaag gatagagata aagacaccca aggaagcttt agacaagata gaggaagagc      660
aaaacaaaag taagaccacc gcacagcaag cggccgctga tcttcagacc tggaggagga      720
gatatgaggg acaattggag aagtgaatta tataaatata agtagtaaaa aattgaacca      780
ttaggagtag cacccaccaa ggcaaagaga agagtggtgc agagagaaaa aagagcagtg      840
ggaataggag ctttgttcct tgggttcttg ggagcagcag gaagcactat gggcgcagcg      900
tcaatgacgc tgacggtaca ggccagacaa ttattgtctg gtatagtgca gcagcagaac      960
aatttgctga gggctattga ggcgcaacag catctgttgc aactcacagt ctggggcatc     1020
aagcagctcc aggcaagaat cctggctgtg gaaagatacc taaaggatca acagctcctg     1080
gggatttggg gttgctctgg aaaactcatt tgcaccactg ctgtgccttg gaatgctagt     1140
tggagtaata aatctctgga acagatttgg aatcacacga cctggatgga gtgggacaga     1200
gaaattaaca attacacaag cttaatacac tccttaattg aagaatcgca aaaccagcaa     1260
gaaaagaatg aacaagaatt attggaatta gataaatggg caagtttgtg gaattggttt     1320
aacataacaa attggctgtg gtatataaaa ttattcataa tgatagtagg aggcttggta     1380
ggtttaagaa tagttttttgc tgtactttct atagtgaata gagttaggca gggatattca     1440
ccattatcgt ttcagaccca cctcccaacc ccgaggggac ccgacaggcc cgaaggaata     1500
gaagaagaag gtggagagag agacagagac agatccattc gattagtgaa cggatcggca     1560
ctgcgtgcgc caattctgca gacaaatggc agtattcatc cacaatttta aaagaaaagg     1620
ggggattggg gggtacagtg caggggaaag aatagtagac ataatagcaa cagacataca     1680
aactaaagaa ttacaaaaac aaattacaaa aattcaaaat ttttcgggttt attacaggga     1740 cagcagagat ccagtttggt taattaaggg tgcagcggcc tccgcgccgg gttttggcgc     1800
ctcccgcggg cgcccccctc ctcacggcga gcgctgccac gtcagacgaa gggcgcagga     1860
```

```
gcgttcctga tccttccgcc cggacgctca ggacagcggc ccgctgctca taagactcgg    1920
ccttagaacc ccagtatcag cagaaggaca ttttaggacg ggacttgggt gactctaggg    1980
cactggtttt ctttccagag agcggaacag gcgaggaaaa gtagtccctt ctcggcgatt    2040
ctgcggaggg atctccgtgg ggcggtgaac gccgatgatt atataaggac gcgccgggtg    2100
tggcacagct agttccgtcg cagccgggat ttgggtcgcg gttcttgttt gtggatcgct    2160
gtgatcgtca cttggtgagt tgcgggctgc tgggctggcc ggggcttttcg tggccgccgg    2220 gccgctcggt gggacggaag cgtgtggaga gaccgccaag ggctgtagtc tgggtccgcg    2280
agcaaggttg ccctgaactg ggggttgggg ggagcgcaca aaatggcggc tgttcccgag    2340
tcttgaatgg aagacgcttg taaggcgggc tgtgaggtcg ttgaaacaag gtgggggggca    2400 tggtgggcgg caagaaccca aggtcttgag gccttcgcta atgcgggaaa gctcttattc    2460
gggtgagatg ggctggggca ccatctgggg accctgacgt gaagtttgtc actgactgga    2520
gaactcgggt ttgtcgtctg gttgcggggg cggcagttat gcggtgccgt tgggcagtgc    2580
acccgtacct ttgggagcgc gcgcctcgtc gtgtcgtgac gtcacccgtt ctgttggctt    2640
ataatgcagg gtggggccac ctgccggtag gtgtgcggta ggcttttctc cgtcgcagga    2700
cgcagggttc gggcctaggg taggctctcc tgaatcgaca ggcgccggac ctctggtgag    2760
gggagggata agtgaggcgt cagtttcttt ggtcggtttt atgtacctat cttcttaagt    2820
agctgaagct ccggttttga actatgcgct cggggttggc gagtgtgttt tgtgaagttt    2880
tttaggcacc ttttgaaatg taatcatttg ggtcaatatg taattttcag tgttagacta    2940
gtaaattgtc cgctaaattc tggccgtttt tggcttttttt gttagacgaa gcttgggctg    3000
caggtcgact ctagaggatc cccgggtacc ggtcgccacc gccgccacca tggagcaaaa    3060
attgatcagt gaagaagacc tgatggcacc aaaaaagaaa cgcaaagtgc ggggcatggc    3120
caatctcctg attgacaatt ggatccctgt gagaccgagg aacggaggga aggttcagat    3180
catcaacctg caaagtctct actgtagcag agatcaatgg cgactctcat tgcccaggga    3240
tgatatggaa ttggcggcac ttgcactctt ggtatgtatt gggcagatca tcgcccctgc    3300
caaggatgat gtcgagttta ggcacagaat aatgaaccct cttactgaag atgaattcca    3360
gcaattgatc gcgccttgga tagatatgtt ctatttgaat cacgccgaac atccccttcat    3420 gcagacaaaa ggggttaaag caaatgatgt cacaccaatg gagaagcttt tggcaggtgt    3480
gtcaggagca accaactgcg ctttcgttaa ccaaccaggc caaggtgagg cgttgtgcgg    3540
ggggtgcacg gccatagcgt tgtttaatca ggcgaaccag gctcctggct ttggaggagg    3600
attcaagtcc ggtttgcgcg ggggtacacc cgtaaccaca ttcgttcgcg gaattgacct    3660
ccgatcaaca gtcctgttga acgtattgac gttgcctaga cttcagaagc aatttccaaa    3720
cgagtctcac actgagaatc aaccgacttg gattaagccc atcaagtcaa atgaaagtat    3780
acccgcgtct tctattggat ttgttagagg actttttttgg cagcccgctc acatagaact    3840
ctgtgatccc ataggcattg gaaagtgttc ttgctgtggc caagagtcta accttagata    3900
tacgggcttt ctcaaggaga agttcacgtt caccgtgaat ggactttggc cacatcccca    3960
tagcccgtgc ttggtcacgg tcaagaaggg ggaggttgaa gagaaatttc ttgcgtttac    4020
cacatccgcc ccatcctgga cgcaaatatc tcgcgtcgtt gtggataaaa tcatccagaa    4080
cgaaaatggt aaccgcgttg ccgcggtagt gaatcaattc agaaacatag caccacagag    4140
cccgttggag ttgataatgg gcgggtaccg caataatcaa gcttccattc tcgagcgacg    4200
ccatgacgta cttatgtttta accaggggtg gcagcaatat ggtaacgtga taaacgagat    4260
```

```
agtcacagtc ggcctcggct acaaaactgc gttgcgcaaa gctctgtata cgttcgcgga    4320
gggttttaag aataaagact ttaaaggcgc tggggtgagt gtgcacgaga cggcagaacg    4380
ccatttctat cgccagtctg aactcttgat tcccgacgtt ctggcgaatg tcaattttc    4440 ccaggccgat gaggtcattg cggatctgcg agataagctt caccagttgt gtgagatgct    4500
gttcaaccag tctgtggctc cttatgctca tcatcccaaa ctgatttcaa ctctcgcttt    4560
ggcaagggct acgttgtata acaccttag agaactgaag ccacagggtg gtcccagcaa    4620
tggcggaagc ggagctacta acttcagcct gctgaagcag gctggagacg tggaggagaa    4680
ccctggacct atggcccagc cagaattggc acctgaagat cccgaagata tggcgccgaa    4740
gaaaaagagg aaagtacgcg ggatggccga tgaaatagac gcaatggctc tttaccgagc    4800
atggcaacag ctcgacaatg gatcttgcgc ccaaatacgg cgggtaagtg aacccgatga    4860
actgcgagat atccccgcat tctaccgatt ggttcagccg tttggctggg agaacccacg    4920
gcaccagcag gcgcttctta ggatggtttt ttgtcttagt gccgggaaaa acgtaatccg    4980
ccatcaggat aagaagtccg aacaaacaac agggatttct ctgggaagag cgcttgctaa    5040
cagcggcagg atcaatgaac gccgcatatt tcagttgatc cgagcagatc ggactgctga    5100
tatggtccag ctcaggaggc tccttacgca cgcagagcca gtgttggatt ggccactcat    5160
ggcaagaatg cttacgtggt gggggaagag ggaaaggcag caactgcttg aagattttgt    5220
attgacgacg aacaagaacg cgggaagcgg agagggcaga ggaagtcttc tcacatgcgg    5280
tgacgtggag gagaatcctg gacctatggg caagcctata cctaacccct tgctcgggct    5340
ggactccacc atggctccta agaagaagcg caaggtgaga ggaatgtcaa acttcattaa    5400
tatccacgtg cttatctcac actccccctag ttgccttaac agagacgata tgaacatgca    5460
aaaagacgca atttttggcg gcaaaaggag agtcagaatt agtagccaga gcctgaagcg    5520
cgctatgagg aaaagcggct actatgctca aacattggt gaaagttcat tgcggaccat    5580
ccatctcgcg cagttgaggg acgtcctgcg acagaagctt ggggaaagat ttgatcagaa    5640
gatcatcgac aaaacgcttg cccttctgtc cggtaaatca gtggacgaag cggagaagat    5700
aagtgcggat gctgttacgc catgggtggt aggtgaaatc gcgtggtttt gcgagcaggt    5760
agccaaggcc gaagcggata atttggatga taagaaactg ctcaaagtcc tcaaagagga    5820
catcgcggcg atccgggtga accttcagca gggtgttgat attgcgctct ctggtcggat    5880
ggccacgtct ggaatgatga ctgaactggg taaggtggac ggagctatgt ctatagctca    5940
tgctataact acccatcagg tggattctga catagactgg ttcacggctg tcgacgatct    6000
ccaggaacaa ggatccgcac acctcggcac gcaagaattt tcttctggag tgttctatag    6060
gtatgccaac atcaaccttg cacagctcca ggaaaacctc ggtggggcaa gccgggaaca    6120
ggctcttgaa atagctaccc atgtggttca catgctggcg accgaagtgc caggggccaa    6180
gcagagaacg tacgccgcat tcaatccggc ggacatggtc atggtgaatt tctctgatat    6240
gcccttgtct atggcaaatg ctttcgagaa ggcggtcaag gcaaaggacg gttttttgca    6300
accctccatc caagcctttta atcagtactg ggatagagta gctaacgggt atggtctcaa    6360
tggcgcggct gctcagtttt cttttgtccga tgtggatccg ataacggcgc aggttaaaca    6420
gatgcccacc ttggaacaac tcaaatcctg ggttagaaac aatggggagg cgggaagcgg    6480
agtgaaacag actttgaact ttgacttgct caagttggca ggagacgtgg agtccaaccc    6540
tggacctatg ggatcggcca ttgaacaaga tggattgcac gcaggttctc cggccgcttg    6600
```

| | |
|---|---|
| ggtggagagg ctattcggct atgactgggc acaacagaca atcggctgct ctgatgccgc | 6660 |
| cgtgttccgg ctgtcagcgc aggggcgccc ggttcttttt gtcaagaccg acctgtccgg | 6720 |
| tgccctgaat gaactgcagg acgaggcagc gcggctatcg tggctggcca cgacgggcgt | 6780 |
| tccttgcgca gctgtgctcg acgttgtcac tgaagcggga agggactggc tgctattggg | 6840 |
| cgaagtgccg gggcaggatc tcctgtcatc tcaccttgct cctgccgaga agtatccat | 6900 |
| catggctgat gcaatgcggc ggctgcatac gcttgatccg gctacctgcc cattcgacca | 6960 |
| ccaagcgaaa catcgcatcg agcgagcacg tactcggatg gaagccggtc ttgtcgatca | 7020 |
| ggatgatctg gacgaagagc atcagggct cgcgccagcc gaactgttcg ccaggctcaa | 7080 |
| ggcgcgcatg cccgacggcg atgatctcgt cgtgacccat ggcgatgcct gcttgccgaa | 7140 |
| tatcatggtg gaaaatggcc gcttttctgg attcatcgac tgtggccggc tgggtgtggc | 7200 |
| ggaccgctat caggacatag cgttggctac ccgtgatatt gctgaagagc ttggcggcga | 7260 |
| atgggctgac cgcttcctcg tgctttacgg tatcgccgct cccgattcgc agcgcatcgc | 7320 |
| cttctatcgc cttcttgacg agttcttctg agaattcgat atcaagctta tcgataatca | 7380 |
| acctctggat tacaaaattt gtgaaagatt gactggtatt cttaactatg ttgctccttt | 7440 |
| tacgctatgt ggatacgctg cttttaatgc ctttgtatcat gctattgctt cccgtatggc | 7500 |
| tttcattttc tcctccttgt ataaatcctg gttgctgtct ctttatgagg agttgtggcc | 7560 |
| cgttgtcagg caacgtggcg tggtgtgcac tgtgtttgct gacgcaaccc ccactggttg | 7620 |
| gggcattgcc accacctgtc agctcctttc cgggactttc gctttccccc tccctattgc | 7680 |
| cacggcggaa ctcatcgccg cctgccttgc ccgctgctgg acaggggctc ggctgttggg | 7740 |
| cactgacaat tccgtggtgt tgtcggggaa atcatcgtcc tttccttggc tgctcgcctg | 7800 |
| tgttgccacc tggattctgc gcgggacgtc cttctgctac gtcccttcgg ccctcaatcc | 7860 |
| agcggacctt ccttcccgcg gcctgctgcc ggctctgcgg cctcttccgc gtcttcgcct | 7920 |
| tcgccctcag acgagtcgga tctcccttg ggccgcctcc ccgcatcgat accgtcgacc | 7980 |
| tcgagaccta gaaaaacatg gagcaatcac aagtagcaat acagcagcta ccaatgctga | 8040 |
| ttgtgcctgg ctagaagcac aagaggagga ggagtgggg tttccagtca cacctcaggt | 8100 |
| acctttaaga ccaatgactt acaaggcagc tgtagatctt agccactttt taaaagaaaa | 8160 |
| ggggggactg gaagggctaa ttcactccca acgaagacaa gatatccttg atctgtggat | 8220 |
| ctaccacaca caaggctact tccctgattg gcagaactac acaccagggc cagggatcag | 8280 |
| atatccactg acctttggat ggtgctacaa gctagtacca gttgagcaag agaaggtaga | 8340 |
| agaagccaat gaaggagaga acacccgctt gttacaccct gtgagcctgc atgggatgga | 8400 |
| tgacccggag agagaagtat tagagtggag gtttgacagc cgcctagcat ttcatcacat | 8460 |
| ggcccgagag ctgcatccgg actgtactgg gtctctctgg ttagaccaga tctgagcctg | 8520 |
| ggagctctct ggctaactag ggaacccact gcttaagcct caataaagct tgccttgagt | 8580 |
| gcttcaagta gtgtgtgccc gtctgttgtg tgactctggt aactagagat ccctcagacc | 8640 |
| cttttagtca gtgtggaaaa tctctagca | 8669 |

<210> SEQ ID NO 44
<211> LENGTH: 8669
<212> TYPE: DNA
<213> ORGANISM: Artificial sequence
<220> FEATURE:
<223> OTHER INFORMATION: Synthetic

<400> SEQUENCE: 44

```
gggtctctct ggttagacca gatctgagcc tgggagctct ctggctaact agggaaccca        60
ctgcttaagc ctcaataaag cttgccttga gtgcttcaag tagtgtgtgc ccgtctgttg       120
tgtgactctg gtaactagag atccctcaga ccctttagt cagtgtggaa aatctctagc        180
agtggcgccc gaacagggac ttgaaagcga aagggaaacc agaggagctc tctcgacgca       240
ggactcggct tgctgaagcg cgcacggcaa gaggcgaggg gcggcgactg gtgagtacgc       300
caaaaatttt gactagcgga ggctagaagg agagagatgg gtgcgagagc gtcagtatta       360
agcgggggag aattagatcg cgatgggaaa aaattcggtt aaggccaggg ggaaagaaaa       420
aatataaatt aaaacatata gtatgggcaa gcagggagct agaacgattc gcagttaatc       480
ctggcctgtt agaaacatca gaaggctgta gacaaatact gggacagcta caaccatccc       540
ttcagacagg atcagaagaa cttagatcat tatataatac agtagcaacc ctctattgtg       600
tgcatcaaag gatagagata aaagacacca aggaagcttt agacaagata gaggaagagc       660
aaaacaaaag taagaccacc gcacagcaag cggccgctga tcttcagacc tggaggagga       720
gatatgaggg acaattggag aagtgaatta tataaatata agtagtaaaa aattgaacca       780
ttaggagtag cacccaccaa ggcaaagaga agagtggtgc agagagaaaa aagagcagtg       840
ggaataggag ctttgttcct tgggttcttg ggagcagcag gaagcactat gggcgcagcg       900
tcaatgacgc tgacggtaca ggccagacaa ttattgtctg gtatagtgca gcagcagaac       960
aatttgctga gggctattga ggcgcaacag catctgttgc aactcacagt ctggggcatc      1020
aagcagctcc aggcaagaat cctggctgtg gaaagatacc taaaggatca acagctcctg      1080
gggatttggg gttgctctgg aaaactcatt tgcaccactg ctgtgccttg gaatgctagt      1140
tggagtaata aatctctgga acagatttgg aatcacacga cctggatgga gtgggacaga      1200
gaaattaaca attacacaag cttaatacac tccttaattg aagaatcgca aaaccagcaa      1260
gaaaagaatg aacaagaatt attggaatta gataaatggg caagtttgtg gaattggttt      1320
aacataacaa attggctgtg gtatataaaa ttattcataa tgatagtagg aggcttggta      1380
ggtttaagaa tagttttgc tgtactttct atagtgaata gagttaggca gggatattca      1440
ccattatcgt ttcagaccca cctcccaacc ccgaggggac ccgacaggcc cgaaggaata      1500
gaagaagaag gtggagagag agacagagac agatccattc gattagtgaa cggatcggca      1560
ctgcgtgcgc caattctgca gacaaatggc agtattcatc cacaattta aaagaaaagg       1620 ggggattggg gggtacagtg caggggaaag aatagtagac ataatagcaa cagacataca      1680
aactaaagaa ttacaaaaac aaattacaaa aattcaaaat tttcgggttt attacaggga      1740
cagcagagat ccagtttggt taattaaggg tgcagcggcc tccgcgccgg ttttggcgc       1800 ctcccgcggg cgcccccctc ctcacggcga gcgctgccac gtcagacgaa gggcgcagga      1860
gcgttcctga tccttccgcc cggacgctca ggacagcggc ccgctgctca taagactcgg      1920
ccttagaacc ccagtatcag cagaaggaca ttttaggacg ggacttgggt gactctaggg      1980
cactggtttt cttccagag agcggaacag gcgaggaaaa gtagtcctt ctcggcgatt       2040 ctgcggaggg atctccgtgg ggcggtgaac gccgatgatt atataaggac gcgccgggtg      2100
tggcacagct agttccgtcg cagccgggat ttggtcgcg gttcttgttt gtggatcgct       2160
gtgatcgtca cttggtgagt tgcgggctgc tgggctggcc ggggctttcg tggccgccgg      2220
gccgctcggt gggacggaag cgtgtggaga accgccaag ggctgtagtc tgggtccgcg      2280
agcaaggttg ccctgaactg ggggttgggg ggagcgcaca aaatggcggc tgttcccgag      2340
```

```
tcttgaatgg aagacgcttg taaggcgggc tgtgaggtcg ttgaaacaag gtgggggca      2400 tggtgggcgg caagaaccca aggtcttgag gccttcgcta atgcgggaaa gctcttattc    2460
gggtgagatg ggctggggca ccatctgggg accctgacgt gaagtttgtc actgactgga    2520
gaactcgggt ttgtcgtctg gttgcggggg cggcagttat gcggtgccgt tgggcagtgc    2580
acccgtacct ttgggagcgc gcgcctcgtc gtgtcgtgac gtcacccgtt ctgttggctt    2640
ataatgcagg gtggggccac ctgccggtag gtgtgcggta ggcttttctc cgtcgcagga    2700
cgcagggttc gggcctaggg taggctctcc tgaatcgaca ggcgccggac ctctggtgag    2760
gggagggata agtgaggcgt cagtttcttt ggtcggtttt atgtacctat cttcttaagt    2820
agctgaagct ccggttttga actatgcgct cggggttggc gagtgtgttt tgtgaagttt    2880
tttaggcacc ttttgaaatg taatcatttg ggtcaatatg taattttcag tgttagacta    2940
gtaaattgtc cgctaaattc tggccgtttt tggcttttttt gttagacgaa gcttgggctg    3000
caggtcgact ctagaggatc cccgggtacc ggtcgccacc gccgccacca tggagcaaaa    3060
attgatcagt gaagaagacc tgatggcacc aaaaaagaaa cgcaaagtgc ggggcatggc    3120
caatctcctg attgacaatt ggatccctgt gagaccgagg aacggaggga aggttcagat    3180
catcaacctg caaagtctct actgtagcag agatcaatgg cgactctcat tgcccaggga    3240
tgatatggaa ttggcggcac ttgcactctt ggtatgtatt gggcagatca tcgcccctgc    3300
caaggatgat gtcgagttta ggcacagaat aatgaaccct cttactgaag atgaattcca    3360
gcaattgatc gcgccttgga tagatatgtt ctatttgaat cacgccgaac atcccttcat    3420
gcagacaaaa ggggttaaag caaatgatgt cacaccaatg gagaagcttt tggcaggtgt    3480
gtcaggagca accaactgcg ctttcgttaa ccaaccaggc caaggtgagg cgttgtgcgg    3540
ggggtgcacg gccatagcgt tgtttaatca ggcgaaccag gctcctggct ttggaggagg    3600
attcaagtcc ggtttgcgcg ggggtacacc cgtaaccaca ttcgttcgcg gaattgacct    3660
ccgatcaaca gtcctgttga acgtattgac gttgcctaga cttcagaagc aatttccaaa    3720
cgagtctcac actgagaatc aaccgacttg gattaagccc atcaagtcaa atgaaagtat    3780
acccgcgtct tctattggat ttgttagagg acttttttgg cagcccgctc acatagaact    3840
ctgtgatccc ataggcattg gaaagtgttc ttgctgtggc caagagtcta accttagata    3900
tacgggcttt ctcaaggaga agttcacgtt caccgtgaat ggactttggc cacatcccca    3960
tagcccgtgc ttggtcacgg tcaagaaggg ggaggttgaa gagaaatttc ttgcgtttac    4020
cacatccgcc ccatcctgga cgcaaatatc tcgcgtcgtt gtggataaaa tcatccagaa    4080
cgaaaatggt aaccgcgttg ccgcggtagt gaatcaattc agaaacatag caccacagag    4140
cccgttggag ttgataatgg gcgggtaccg caataatcaa gcttccattc tcgagcgacg    4200
ccatgacgta cttatgttta accaggggtg gcagcaatat ggtaacgtga taaacgagat    4260
agtcacagtc ggcctcggct acaaaactgc gttgcgcaaa gctctgtata cgttcgcgga    4320
gggttttaag aataaagact ttaaaggcgc tggggtgagt gtgcacgaga cggcagaacg    4380
ccatttctat cgccagtctg aactcttgat tcccgacgtt ctggcgaatg tcaatttttc    4440
ccaggccgat gaggtcattg cggatctgcg agataagctt caccagttgt gtgagatgct    4500
gttcaaccag tctgtggctc cttatgctca tcatcccaaa ctgatttcaa ctctcgcttt    4560
ggcaagggct acgttgtata aacacccttag agaactgaag ccacagggtg gtcccagcaa    4620
tggcggaagc ggagctacta acttcagcct gctgaagcag gctggagacg tggaggagaa    4680
ccctggacct atggcccagc cagaattggc acctgaagat cccgaagata tggcgccgaa    4740
```

```
gaaaaagagg aaagtacgcg ggatggccga tgaaatagac gcaatggctc tttaccgagc    4800
atggcaacag ctcgacaatg gatcttgcgc ccaaatacgg cgggtaagtg aacccgatga    4860
actgcgagat atccccgcat tctaccgatt ggttcagccg tttggctggg agaacccacg    4920
gcaccagcag gcgcttctta ggatggtttt ttgtcttagt gccgggaaaa acgtaatccg    4980
ccatcaggat aagaagtccg aacaaacaac agggatttct ctgggaagag cgcttgctaa    5040
cagcggcagg atcaatgaac gccgcatatt tcagttgatc cgagcagatc ggactgctga    5100
tatggtccag ctcaggaggc tccttacgca cgcagagcca gtgttggatt ggccactcat    5160
ggcaagaatg cttacgtggt gggggaagag ggaaaggcag caactgcttg aagattttgt    5220
attgacgacg aacaagaacg cgggaagcgg agagggcaga ggaagtcttc tcacatgcgg    5280
tgacgtggag gagaatcctg gacctatggg caagcctata cctaacccct tgctcgggct    5340
ggactccacc atggctccta agaagaagcg caaggtgaga ggaatgtcaa acttcattaa    5400
tatccacgtg cttatctcac actccccctag ttgccttaac agagacgata tgaacatgca    5460
aaaagacgca atttttggcg gcaaaaggag agtcagaatt agtagccaga gcctgaagcg    5520
cgctatgagg aaaagcggct actatgctca aaacattggt gaaagttcat tgcggaccat    5580
ccatctcgcg cagttgaggg acgtcctgcg acagaagctt ggggaaagat ttgatcagaa    5640
gatcatcgac aaaacgcttg cccttctgtc cggtaaatca gtggacgaag cggagaagat    5700
aagtgcggat gctgttacgc catgggtggt aggtgaaatc gcgtggtttt gcgagcaggt    5760
agccaaggcc gaagcggata atttggatga taagaaactg ctcaaagtcc tcaaagagga    5820
catcgcggcg atccgggtga accttcagca gggtgttgat attgcgctct ctggtcggat    5880
ggccacgtct ggaatgatga ctgaactggg taaggtggac ggagctatgt ctatagctca    5940
tgctataact acccatcagg tggattctga catagactgg ttcacggctg tcgacgatct    6000
ccaggaacaa ggatccgcac acctcggcac gcaagaattt tcttctggag tgttctatag    6060
gtatgccaac atcaaccttg cacagctcca ggaaaacctc ggtggggcaa gccgggaaca    6120
ggctcttgaa atagctaccc atgtggttca catgctggcg accgaagtgc caggggccaa    6180
gcagagaacg tacgccgcat tcaatccggc ggacatggtc atggtgaatt tctctgatat    6240
gcccttgtct atggcaaatg cttttcgaga ggcggtcaag gcaaaggacg gttttttgca    6300
accctccatc caagccttta atcagtactg ggatagagta gctaacgggt atggtctcaa    6360
tggcgcggct gctcagtttt ctttgtccga tgtggatccg ataacggcgc aggttaaaca    6420
gatgcccacc ttgaacaac tcaaatcctg ggttagaaac aatggggagg cgggaagcgg    6480
agtgaaacag actttgaact ttgacttgct caagttggca ggagacgtgg agtccaaccc    6540
tggacctatg ggatcggcca ttgaacaaga tggattgcac gcaggttctc cggccgcttg    6600
ggtggagagg ctattcggct atgactgggc acaacagaca atcggctgct ctgatgccgc    6660
cgtgttccgg ctgtcagcgc aggggcgccc ggttcttttt gtcaagaccg acctgtccgg    6720
tgccctgaat gaactgcagg acgaggcagc gcggctatcg tggctggcca cgacgggcgt    6780
tccttgcgca gctgtgctcg acgttgtcac tgaagcggga agggactggc tgctattggg    6840
cgaagtgccg gggcaggatc tcctgtcatc tcaccttgct cctgccgaga agtatccat    6900 catggctgat gcaatgcggc ggctgcatac gcttgatccg gctacctgcc cattcgacca    6960
ccaagcgaaa catcgcatcg agcgagcacg tactcggatg gaagccggtc ttgtcgatca    7020
ggatgatctg gacgaagagc atcaggggct cgcgccagcc gaactgttcg ccaggctcaa    7080
```

-continued

| | |
|---|---|
| ggcgcgcatg cccgacggcg atgatctcgt cgtgacccat ggcgatgcct gcttgccgaa | 7140 |
| tatcatggtg gaaaatggcc gcttttctgg attcatcgac tgtggccggc tgggtgtggc | 7200 |
| ggaccgctat caggacatag cgttggctac ccgtgatatt gctgaagagc ttggcggcga | 7260 |
| atgggctgac cgcttcctcg tgctttacgg tatcgccgct cccgattcgc agcgcatcgc | 7320 |
| cttctatcgc cttcttgacg agttcttctg agaattcgat atcaagctta tcgataatca | 7380 |
| acctctggat tacaaaattt gtgaaagatt gactggtatt cttaactatg ttgctccttt | 7440 |
| tacgctatgt ggatacgctg ctttaatgcc tttgtatcat gctattgctt cccgtatggc | 7500 |
| tttcattttc tcctccttgt ataaatcctg gttgctgtct ctttatgagg agttgtggcc | 7560 |
| cgttgtcagg caacgtggcg tggtgtgcac tgtgtttgct gacgcaaccc ccactggttg | 7620 |
| gggcattgcc accacctgtc agctcctttc cgggactttc gctttccccc tccctattgc | 7680 |
| cacggcggaa ctcatcgccg cctgccttgc ccgctgctgg acaggggctc ggctgttggg | 7740 |
| cactgacaat tccgtggtgt tgtcggggaa atcatcgtcc tttccttggc tgctcgcctg | 7800 |
| tgttgccacc tggattctgc gcgggacgtc cttctgctac gtcccttcgg ccctcaatcc | 7860 |
| agcggacctt ccttcccgcg gcctgctgcc ggctctgcgg cctcttccgc gtcttcgcct | 7920 |
| tcgccctcag acgagtcgga tctccctttg gccgcctcc ccgcatcgat accgtcgacc | 7980 |
| tcgagaccta gaaaaacatg gagcaatcac aagtagcaat acagcagcta ccaatgctga | 8040 |
| ttgtgcctgg ctagaagcac aagaggagga ggaggtgggg tttccagtca cacctcaggt | 8100 |
| acctttaaga ccaatgactt acaaggcagc tgtagatctt agccactttt taaaagaaaa | 8160 |
| ggggggactg gaagggctaa ttcactccca acgaagacaa gatatccttg atctgtggat | 8220 |
| ctaccacaca caaggctact tccctgattg gcagaactac acaccagggc cagggatcag | 8280 |
| atatccactg acctttggat ggtgctacaa gctagtacca gttgagcaag agaaggtaga | 8340 |
| agaagccaat gaaggagaga acacccgctt gttacaccct gtgagcctgc atgggatgga | 8400 |
| tgacccggag agagaagtat tagagtggag gtttgacagc cgcctagcat tcatcacat | 8460 |
| ggcccgagag ctgcatccgg actgtactgg gtctctctgg ttagaccaga tctgagcctg | 8520 |
| ggagctctct ggctaactag ggaacccact gcttaagcct caataaagct tgccttgagt | 8580 |
| gcttcaagta gtgtgtgccc gtctgttgtg tgactctggt aactagagat ccctcagacc | 8640 |
| cttttagtca gtgtggaaaa tctctagca | 8669 |

<210> SEQ ID NO 45
<211> LENGTH: 9014
<212> TYPE: DNA
<213> ORGANISM: Artificial sequence
<220> FEATURE:
<223> OTHER INFORMATION: Synthetic

<400> SEQUENCE: 45

| | |
|---|---|
| gggtctctct ggttagacca gatctgagcc tgggagctct ctggctaact agggaaccca | 60 |
| ctgcttaagc ctcaataaag cttgccttga gtgcttcaag tagtgtgtgc ccgtctgttg | 120 |
| tgtgactctg gtaactagag atccctcaga ccctttttagt cagtgtggaa aatctctagc | 180 |
| agtggcgccc gaacagggac ttgaaagcga aagggaaacc agaggagctc tctcgacgca | 240 |
| ggactcggct tgctgaagcg cgcacggcaa gaggcgaggg gcggcgactg gtgagtacgc | 300 |
| caaaaatttt gactagcgga ggctagaagg agagagatgg gtgcgagagc gtcagtatta | 360 |
| agcggggag aattagatcg cgatgggaaa aaattcggtt aaggccaggg ggaaagaaaa | 420 |
| aatataaatt aaaacatata gtatgggcaa gcagggagct agaacgattc gcagttaatc | 480 |

-continued

```
ctggcctgtt agaaacatca gaaggctgta gacaaatact gggacagcta caaccatccc      540
ttcagacagg atcagaagaa cttagatcat tatataatac agtagcaacc ctctattgtg      600
tgcatcaaag gatagagata aaagacacca aggaagcttt agacaagata gaggaagagc      660
aaaacaaaag taagaccacc gcacagcaag cggccgctga tcttcagacc tggaggagga      720
gatatgaggg acaattggag aagtgaatta tataaatata aagtagtaaa aattgaacca      780
ttaggagtag cacccaccaa ggcaaagaga agagtggtgc agagagaaaa aagagcagtg      840
ggaataggag ctttgttcct tgggttcttg ggagcagcag gaagcactat gggcgcagcg      900
tcaatgacgc tgacggtaca ggccagacaa ttattgtctg gtatagtgca gcagcagaac      960
aatttgctga gggctattga ggcgcaacag catctgttgc aactcacagt ctggggcatc     1020
aagcagctcc aggcaagaat cctggctgtg gaaagatacc taaaggatca acagctcctg     1080
gggatttggg gttgctctgg aaaactcatt tgcaccactg ctgtgccttg gaatgctagt     1140
tggagtaata aatctctgga acagatttgg aatcacacga cctggatgga gtgggacaga     1200
gaaattaaca attacacaag cttaatacac tccttaattg aagaatcgca aaaccagcaa     1260
gaaaagaatg aacaagaatt attggaatta gataaatggg caagtttgtg gaattggttt     1320
aacataacaa attggctgtg gtatataaaa ttattcataa tgatagtagg aggcttggta     1380
ggtttaagaa tagttttgc tgtactttct atagtgaata gagttaggca gggatattca     1440
ccattatcgt ttcagaccca cctcccaacc ccgaggggac ccgacaggcc cgaaggaata     1500
gaagaagaag gtggagagag agacagagac agatccattc gattagtgaa cggatcggca     1560
ctgcgtgcgc caattctgca gacaaatggc agtattcatc cacaatttta aagaaaagg      1620 ggggattggg gggtacagtg cagggggaaag aatagtagac ataatagcaa cagacataca     1680
aactaaagaa ttacaaaaac aaattacaaa aattcaaaat tttcgggttt attacaggga     1740
cagcagagat ccagtttggt taattaaggg tgcagcggcc tccgcgccgg ttttggcgc      1800 ctcccgcggg cgcccccctc ctcacggcga gcgctgccac gtcagacgaa gggcgcagga     1860
gcgttcctga tccttccgcc cggacgctca ggacagcggc ccgctgctca taagactcgg     1920
ccttagaacc ccagtatcag cagaaggaca ttttaggacg ggacttgggt gactctaggg     1980
cactggtttt ctttccagag agcggaacag gcgaggaaaa gtagtccctt ctcggcgatt     2040
ctgcggaggg atctccgtgg ggcggtgaac gccgatgatt atataaggac gcgccgggtg     2100
tggcacagct agttccgtcg cagccgggat ttgggtcgcg gttcttgttt gtggatcgct     2160
gtgatcgtca cttggtgagt tgcgggctgc tgggctggcc ggggctttcg tggccgccgg     2220
gccgctcggt gggacggaag cgtgtggaga gaccgccaag ggctgtagtc tgggtccgcg     2280
agcaaggttg ccctgaactg gggggttggg ggagcgcaca aaatggcggc tgttcccgag     2340
tcttgaatgg aagacgcttg taaggcgggc tgtgaggtcg ttgaaacaag gtgggggca      2400 tggtgggcgg caagaaccca aggtcttgag gccttcgcta atgcgggaaa gctcttattc     2460
gggtgagatg ggctggggca ccatctgggg accctgacgt gaagtttgtc actgactgga     2520
gaactcgggt ttgtcgtctg gttgcggggg cggcagttat gcggtgccgt tgggcagtgc     2580
acccgtacct ttgggagcgc gcgcctcgtc gtgtcgtgac gtcacccgtt ctgttggctt     2640
ataatgcagg gtggggccac ctgccggtag gtgtgcggta ggcttttctc cgtcgcagga     2700
cgcagggttc gggcctaggg taggctctcc tgaatcgaca ggcgccggac ctctggtgag     2760
gggagggata agtgaggcgt cagtttctt ggtcggtttt atgtacctat cttcttaagt      2820
```

```
agctgaagct ccggttttga actatgcgct cggggttggc gagtgtgttt tgtgaagttt   2880
tttaggcacc ttttgaaatg taatcatttg ggtcaatatg taattttcag tgttagacta   2940
gtaaattgtc cgctaaattc tggccgtttt tggctttttt gttagacgaa gcttgggctg   3000
caggtcgact ctagaggatc cccgggtacc ggtcgccacc gccgccacca tggagcaaaa   3060
attgatcagt gaagaagacc tgatggcacc aaaaaagaaa cgcaaagtgc ggggcatggc   3120
caatctcctg attgacaatt ggatccctgt gagaccgagg aacggaggga aggttcagat   3180
catcaacctg caaagtctct actgtagcag agatcaatgg cgactctcat tgcccaggga   3240
tgatatggaa ttggcggcac ttgcactctt ggtatgtatt gggcagatca tcgcccctgc   3300
caaggatgat gtcgagttta ggcacagaat aatgaaccct cttactgaag atgaattcca   3360
gcaattgatc gcgccttgga tagatatgtt ctatttgaat cacgccgaac atcccttcat   3420
gcagacaaaa ggggttaaag caaatgatgt cacaccaatg gagaagcttt tggcaggtgt   3480
gtcaggagca accaactgcg ctttcgttaa ccaaccaggt caaggtgagg cgttgtgcgg   3540
ggggtgcacg gccatagcgt tgtttaatca ggcgaaccag gctcctggct ttggaggagg   3600
attcaagtcc ggtttgcgcg ggggtacacc cgtaaccaca ttcgttcgcg gaattgacct   3660
ccgatcaaca gtcctgttga acgtattgac gttgcctaga cttcagaagc aatttccaaa   3720
cgagtctcac actgagaatc aaccgacttg gattaagccc atcaagtcaa atgaaagtat   3780
acccgcgtct tctattggat ttgttagagg acttttttgg cagcccgctc acatagaact   3840
ctgtgatccc ataggcattg gaaagtgttc ttgctgtggc caagagtcta accttagata   3900
tacgggcttt ctcaaggaga agttcacgtt caccgtgaat ggactttggc cacatcccca   3960
tagcccgtgc ttggtcacgg tcaagaaggg ggaggttgaa gagaaatttc ttgcgtttac   4020
cacatccgcc ccatcctgga cgcaaatatc tcgcgtcgtt gtggataaaa tcatccagaa   4080
cgaaaatggt aaccgcgttg ccgcggtagt gaatcaattc agaaacatag caccacagag   4140
cccgttggag ttgataatgg gcgggtaccg caataatcaa gcttccattc tcgagcgacg   4200
ccatgacgta cttatgttta accaggggtg gcagcaatat ggtaacgtga taaacgagat   4260
agtcacagtc ggcctcggct acaaaactgc gttgcgcaaa gctctgtata cgttcgcgga   4320
gggttttaag aataaagact ttaaaggcgc tggggtgagt gtgcacgaga cggcagaacg   4380
ccatttctat cgccagtctg aactcttgat tcccgacgtt ctggcgaatg tcaattttc   4440 ccaggccgat gaggtcattg cggatctgcg agataagctt caccagttgt gtgagatgct   4500
gttcaaccag tctgtggctc cttatgctca tcatcccaaa ctgatttcaa ctctcgcttt   4560
ggcaagggct acgttgtata aacaccttag agaactgaag ccacagggtg gtcccagcaa   4620
tggcggaagc ggagctacta acttcagcct gctgaagcag gctggagacg tggaggagaa   4680
ccctggacct atggattaca aggaccatga cggagattat aaggaccacg acatagacta   4740
taaggatgac gatgacaaaa tggcagatgc taagtcactg actgcctggt cccggacact   4800
ggtgaccttc aaggatgtgt tgtggacttc accaggagag gagtggaagc tgctggacac   4860
tgctcagcag atcctgtaca gaaatgtgat gctggagaac tataagaacc tggtttcctt   4920
gggttatcag cttactaagc cagatgtgat cctccggttg gagaagggag aagagccctg   4980
gctggtggag agagaaattc accaagagac ccatcctgat tcagagactg catttgaaat   5040
caaatcatca gttccgaaaa agaaacgcaa agttggatcc ccaaagaaga acgcaaggt   5100 gcgcgggatg gccgatgaaa tagacgcaat ggctctttac cgagcatggc aacagctcga   5160
caatggatct tgcgcccaaa tacggcgggt aagtgaaccc gatgaactgc gagatatccc   5220
```

```
cgcattctac cgattggttc agccgtttgg ctgggagaac ccacggcacc agcaggcgct    5280
tcttaggatg gttttttgtc ttagtgccgg gaaaaacgta atccgccatc aggataagaa    5340
gtccgaacaa acaacaggga tttctctggg aagagcgctt gctaacagcg gcaggatcaa    5400
tgaacgccgc atatttcagt tgatccgagc agatcggact gctgatatgg tccagctcag    5460
gaggctcctt acgcacgcag agccagtgtt ggattggcca ctcatggcaa gaatgcttac    5520
gtggtggggg aagagggaaa ggcagcaact gcttgaagat tttgtattga cgacgaacaa    5580
gaacgcggga agcggagagg gcagaggaag tcttctcaca tgcggtgacg tggaggagaa    5640
tcctggacct atgggcaagc ctatacctaa ccctttgctc gggctggact ccaccatggc    5700
tcctaagaag aagcgcaagg tgagaggaat gtcaaacttc attaatatcc acgtgcttat    5760
ctcacactcc cctagttgcc ttaacagaga cgatatgaac atgcaaaaag acgcaatttt    5820
tggcggcaaa aggagagtca gaattagtag ccagagcctg aagcgcgcta tgaggaaaag    5880
cggctactat gctcaaaaca ttggtgaaag ttcattgcgg accatccatc tcgcgcagtt    5940
gagggacgtc ctgcgacaga agcttgggga aagatttgat cagaagatca tcgacaaaac    6000
gcttgccctt ctgtccggta atcagtggac gaagcggag aagataagtg cggatgctgt    6060
tacgccatgg gtggtaggtg aaatcgcgtg gttttgcgag caggtagcca aggccgaagc    6120
ggataatttg gatgataaga aactgctcaa agtcctcaaa gaggacatcg cggcgatccg    6180
ggtgaacctt cagcagggtg ttgatattgc gctctctggt cggatggcca cgtctggaat    6240
gatgactgaa ctgggtaagg tggacggagc tatgtctata gctcatgcta taactaccca    6300
tcaggtggat tctgacatag actggttcac ggctgtcgac gatctccagg aacaaggatc    6360
cgcacacctc ggcacgcaag aattttcttc tggagtgttc tataggtatg ccaacatcaa    6420
ccttgcacag ctccaggaaa acctcggtgg ggcaagccgg gaacaggctc ttgaaatagc    6480
tacccatgtg gttcacatgc tggcgaccga agtgccaggg gccaagcaga gaacgtacgc    6540
cgcattcaat ccggcggaca tggtcatggt gaatttctct gatatgccct tgtctatggc    6600
aaatgctttc gagaaggcgg tcaaggcaaa ggacggtttt ttgcaaccct ccatccaagc    6660 cttaatcag tactgggata gagtagctaa cgggtatggt ctcaatggcg cggctgctca    6720 gttttcctg tccgatgtgg atccgataac ggcgcaggtt aaacagatgc ccaccttgga    6780
acaactcaaa tcctgggtta gaaacaatgg ggaggcggga agcggagtga acagactttt    6840
gaactttgac ttgctcaagt tggcaggaga cgtggagtcc aaccctggac ctatgggatc    6900
ggccattgaa caagatggat tgcacgcagg ttctccggcc gcttgggtgg agaggctatt    6960
cggctatgac tgggcacaac agacaatcgg ctgctctgat ccgccgtgt tccggctgtc    7020 agcgcagggg cgcccggttc ttttgtcaa gaccgacctg tccggtgccc tgaatgaact    7080
gcaggacgag gcagcgcggc tatcgtggct ggccacgacg ggcgttcctt gcgcagctgt    7140
gctcgacgtt gtcactgaag cgggaaggga ctggctgcta ttgggcgaag tgccggggca    7200
ggatctcctg tcatctcacc ttgctcctgc cgagaaagta tccatcatgg ctgatgcaat    7260
gcggcggctg catacgcttg atccggctac ctgcccattc gaccaccaag cgaaacatcg    7320
catcgagcga gcacgtactc ggatggaagc cggtcttgtc gatcaggatg atctggacga    7380
agagcatcag gggctcgcgc cagccgaact gttcgccagg ctcaaggcgc gcatgcccga    7440
cggcgatgat ctcgtcgtga cccatggcga tgcctgcttg ccgaatatca tggtggaaaa    7500
tggccgcttt tctggattca tcgactgtgg ccggctgggt gtggcggacc gctatcagga    7560
```

| | |
|---|---|
| catagcgttg gctacccgtg atattgctga agagcttggc ggcgaatggg ctgaccgctt | 7620 |
| cctcgtgctt tacggtatcg ccgctcccga ttcgcagcgc atcgccttct atcgccttct | 7680 |
| tgacgagttc ttctgagaat tcgatatcaa gcttatcgat aatcaacctc tggattacaa | 7740 |
| aatttgtgaa agattgactg gtattcttaa ctatgttgct ccttttacgc tatgtggata | 7800 |
| cgctgcttta atgcctttgt atcatgctat tgcttcccgt atggctttca ttttctcctc | 7860 |
| cttgtataaa tcctggttgc tgtctcttta tgaggagttg tggcccgttg tcaggcaacg | 7920 |
| tggcgtggtg tgcactgtgt tgctgacgc accccccact ggttgggca ttgccaccac | 7980 |
| ctgtcagctc ctttccggga ctttcgcttt cccctccct attgccacgg cggaactcat | 8040 |
| cgccgcctgc cttgcccgct gctggacagg ggctcggctg ttgggcactg acaattccgt | 8100 |
| ggtgttgtcg gggaaatcat cgtccttcc ttggctgctc gcctgtgttg ccacctggat | 8160 |
| tctgcgcggg acgtccttct gctacgtccc ttcggccctc aatccagcgg accttccttc | 8220 |
| ccgcggcctg ctgccggctc tgcggcctct tccgcgtctt cgccttcgcc ctcagacgag | 8280 |
| tcggatctcc ctttgggccg cctccccgca tcgataccgt cgacctcgag acctagaaaa | 8340 |
| acatggagca atcacaagta gcaatacagc agctaccaat gctgattgtg cctggctaga | 8400 |
| agcacaagag gaggaggagg tgggttttcc agtcacacct caggtacctt taagaccaat | 8460 |
| gacttacaag gcagctgtag atcttagcca ctttttaaaa gaaaaggggg gactggaagg | 8520 |
| gctaattcac tcccaacgaa gacaagatat ccttgatctg tggatctacc acacacaagg | 8580 |
| ctacttccct gattggcaga actacacacc agggccaggg atcagatatc cactgacctt | 8640 |
| tggatggtgc tacaagctag taccagttga gcaagagaag gtagaagaag ccaatgaagg | 8700 |
| agagaacacc cgcttgttac accctgtgag cctgcatggg atggatgacc cggagagaga | 8760 |
| agtattagag tggaggtttg acagccgcct agcatttcat cacatggccc gagagctgca | 8820 |
| tccggactgt actgggtctc tctggttaga ccagatctga gcctgggagc tctctggcta | 8880 |
| actagggaac ccactgctta agcctcaata aagcttgcct tgagtgcttc aagtagtgtg | 8940 |
| tgcccgtctg ttgtgtgact ctggtaacta gagatccctc agacccttt agtcagtgtg | 9000 |
| gaaaatctct agca | 9014 |

```
<210> SEQ ID NO 46
<211> LENGTH: 6857
<212> TYPE: DNA
<213> ORGANISM: Artificial sequence
<220> FEATURE:
<223> OTHER INFORMATION: Synthetic

<400> SEQUENCE: 46
```

| | |
|---|---|
| gggtctctct ggttagacca gatctgagcc tgggagctct ctggctaact agggaaccca | 60 |
| ctgcttaagc ctcaataaag cttgccttga gtgcttcaag tagtgtgtgc ccgtctgttg | 120 |
| tgtgactctg gtaactagag atccctcaga cccttttagt cagtgtggaa aatctctagc | 180 |
| agtggcgccc gaacagggac ttgaaagcga aaggaaacc agaggagctc tctcgacgca | 240 |
| ggactcggct tgctgaagcg cgcacggcaa gaggcgaggg gcggcgactg gtgagtacgc | 300 |
| caaaaatttt gactagcgga ggctagaagg agagagatgg gtgcgagagc gtcagtatta | 360 |
| agcgggggag aattagatcg cgatgggaaa aaattcggtt aaggccaggg ggaaagaaaa | 420 |
| aatataaatt aaaacatata gtatgggcaa gcagggagct agaacgattc gcagttaatc | 480 |
| ctggcctgtt agaaacatca gaaggctgta gacaaatact gggacagcta caaccatccc | 540 |
| ttcagacagg atcagaagaa cttagatcat tatataatac agtagcaacc ctctattgtg | 600 |

```
tgcatcaaag gatagagata aaagacacca aggaagcttt agacaagata gaggaagagc      660
aaaacaaaag taagaccacc gcacagcaag cggccgctga tcttcagacc tggaggagga      720
gatatgaggg acaattggag aagtgaatta tataaatata agtagtaaa aattgaacca       780 ttaggagtag cacccaccaa ggcaaagaga agagtggtgc agagagaaaa aagagcagtg     840
ggaataggag ctttgttcct tgggttcttg ggagcagcag gaagcactat gggcgcagcg     900
tcaatgacgc tgacggtaca ggccagacaa ttattgtctg gtatagtgca gcagcagaac    960
aatttgctga gggctattga ggcgcaacag catctgttgc aactcacagt ctggggcatc    1020
aagcagctcc aggcaagaat cctggctgtg gaaagatacc taaaggatca acagctcctg    1080
gggatttggg gttgctctgg aaaactcatt tgcaccactg ctgtgccttg gaatgctagt    1140
tggagtaata atctctgga acagatttgg aatcacacga cctggatgga gtgggacaga     1200
gaaattaaca attacacaag cttaatacac tccttaattg aagaatcgca aaaccagcaa    1260
gaaaagaatg aacaagaatt attggaatta gataaatggg caagtttgtg gaattggttt    1320
aacataacaa attggctgtg gtatataaaa ttattcataa tgatagtagg aggcttggta    1380
ggtttaagaa tagttttttgc tgtactttct atagtgaata gagttaggca gggatattca    1440
ccattatcgt ttcagaccca cctcccaacc ccgaggggac ccgacaggcc cgaaggaata    1500
gaagaagaag gtggagagag agacagagac agatccattc gattagtgaa cggatcggca    1560
ctgcgtgcgc caattctgca gacaaatggc agtattcatc cacaatttta aagaaaagg     1620 ggggattggg gggtacagtg caggggaaag aatagtagac ataatagcaa cagacataca    1680
aactaaagaa ttacaaaaac aaattacaaa aattcaaaat tttcgggttt attacaggga    1740
cagcagagat ccagtttggt taattaaggg tgcagcggcc tccgcgccgg ttttggcgc     1800 ctcccgcggg cgcccccctc ctcacggcga gcgctgccac gtcagacgaa gggcgcagga    1860
gcgttcctga tccttccgcc cggacgctca ggacagcggc ccgctgctca taagactcgg    1920
ccttagaacc ccagtatcag cagaaggaca ttttaggacg ggacttgggt gactctaggg    1980
cactggtttt ctttccagag agcggaacag gcgaggaaaa gtagtcccct tccggcgatt    2040
ctgcggaggg atctccgtgg ggcggtgaac gccgatgatt atataaggac gcgccgggtg    2100
tggcacagct agttccgtcg cagccgggat ttgggtcgcg gttcttgttt gtggatcgct    2160
gtgatcgtca cttggtgagt tgcgggctgc tgggctggcc ggggctttcg tggccgccgg    2220
gccgctcggt gggacggaag cgtgtggaga gaccgccaag ggctgtagtc tgggtccgcg    2280
agcaaggttg ccctgaactg ggggttgggg ggagcgcaca aaatggcggc tgttcccgag    2340
tcttgaatgg aagacgcttg taaggcgggc tgtgaggtcg ttgaaacaag gtgggggca     2400 tggtgggcgg caagaaccca aggtcttgag gccttcgcta atgcgggaaa gctcttattc    2460
gggtgagatg ggctggggca ccatctgggg accctgacgt gaagtttgtc actgactgga    2520
gaactcgggt tgtcgtctg gttgcgggg cggcagttat gcggtgccgt tgggcagtgc      2580
acccgtacct ttgggagcgc gcgcctcgtc gtgtcgtgac gtcacccgtt ctgttggctt    2640
ataatgcagg gtggggccac ctgccggtag gtgtgcggta ggcttttctc cgtcgcagga    2700
cgcagggttc gggcctaggg taggctctcc tgaatcgaca ggcgccggac ctctggtgag    2760
gggagggata agtgaggcgt cagtttcttt ggtcggtttt atgtacctat cttcttaagt    2820
agctgaagct ccggttttga actatgcgct cggggtggc gagtgtgttt tgtgaagttt     2880
tttaggcacc ttttgaaatg taatcatttg ggtcaatatg taatttttcag tgttagacta   2940
```

-continued

```
gtaaattgtc cgctaaattc tggccgtttt tggctttttt gttagacgaa gcttgggctg    3000
caggtcgact ctagaggatc cccgggtacc ggtcgccacc gccgccacca tggattacaa    3060
ggaccatgac ggagattata aggaccacga catagactat aaggatgacg atgacaaaat    3120
ggcagatgct aagtcactga ctgcctggtc ccggacactg gtgaccttca aggatgtgtt    3180
tgtggacttc accagggagg agtggaagct gctggacact gctcagcaga tcctgtacag    3240
aaatgtgatg ctggagaact ataagaacct ggtttccttg ggttatcagc ttactaagcc    3300
agatgtgatc ctccggttgg agaagggaga agagccctgg ctggtggaga gagaaattca    3360
ccaagagacc catcctgatt cagagactgc atttgaaatc aaatcatcag ttccgaaaaa    3420
gaaacgcaaa gttggatccc caagaagaa acgcaaagta cggggcatgc gatcatactt    3480
gatcctgcgg cttgcaggtc ctatgcaagc ctgggggcaa cctacctttg aaggtactcg    3540
gccgactggc aggttcccta cgcggtctgg tttgctcgga ctcctcggcg cctgtttggg    3600
gatacaaagg gatgacactt cttccttgca ggcactttcc gaatcagtcc agttcgcagt    3660
gagatgtgat gaactcatac tggacgacag acgggtgtcc gtaactggac tgagggacta    3720
tcatactgta ctcggcgcaa gagaagatta tcgaggtctt aagtcacatg agactattca    3780
gacatggagg gaatatttgt gtgacgcctc cttcacggtg gccctctggc ttacaccaca    3840
tgcaactatg gtgatctcag agcttgagaa agccgttctt aaacctcggt acacaccata    3900
tctggggagg cggtcttgcc cacttaccca cccgcttttc ttggggactt gtcaggccag    3960
cgatccacag aaggccttgc tgaactatga acccgttggt ggcgatatat acagtgaaga    4020
gagcgtcacg ggccatcact tgaagttcac tgctagggat gagccgatga ttacgctccc    4080
gagacagttc gctagtaggg aatggtacgt tattaagggg ggaatggacg tttcccaagg    4140
aagcggagct actaacttca gcctgctgaa gcaggctgga gacgtggagg agaaccctgg    4200
acctatgggt gccccagttc cctatcccga cccactggag ccaaggatgg cgcctaagaa    4260
gaagcgcaag gtgcggggca tgtatctcag taaagtcatc attgccaggg cctggagcag    4320
ggatctttac caacttcacc agggattatg gcatttattt ccaaacagac cggatgctgc    4380
tcgtgatttt cttttttcatg ttgagaagcg aaacacacca gaaggctgtc atgttttatt    4440
gcagtcagcg caaatgcctg tttcaactgc cgttgcgaca gtcattaaaa ctaaacaggt    4500
tgaatttcaa cttcaggttg gtgttccact ctattttcgg cttcgggcaa atccgatcaa    4560
aactattctc gacaatcaaa agcgcctgga cagtaaaggg aatattaaac gctgtcgggt    4620
tccgttaata aaagaagcag aacaaatcgc gtggttgcaa cgtaaattgg caatgcggc    4680 gcgcgttgaa gatgtgcatc ccatatcgga acggccacag tatttttctg gtgatggtaa    4740
aagtggaaag atccaaacgg tttgctttga aggtgtgctc accatcaacg acgcgccagc    4800
gttaatagat cttgtacagc aaggtattgg gccagctaaa tcgatgggat gtggcttgct    4860
atctttggct ccactgggaa gcggagaggg cagaggaagt cttctcacat gcggtgacgt    4920
ggaggagaat cctggaccta tgaccgagta caagcccacg gtgcgcctcg ccacccgcga    4980
cgacgtcccc agggccgtac gcaccctcgc cgccgcgttc gccgactacc ccgccacgcg    5040
ccacaccgtc gatccggacc gccacatcga gcgggtcacc gagctgcaag aactcttcct    5100
cacgcgcgtc gggctcgaca tcggcaaggt gtgggtcgcg gacgacggcg ccgcggtggc    5160
ggtctggacc acgccggaga gcgtcgaagc gggggcggtg ttcgccgaga tcggcccgcg    5220 catgccgag ttgagcggtt cccggctggc cgcgcagcaa cagatggaag gcctcctggc    5280
gccgcaccgg cccaaggagc ccgcgtggtt cctggccacc gtcggcgtct cgcccgacca    5340
```

```
ccagggcaag ggtctgggca gcgccgtcgt gctccccgga gtggaggcgg ccgagcgcgc    5400
cggggtgccc gccttcctgg agacctccgc gccccgcaac ctccccttct acgagcggct    5460
cggcttcacc gtcaccgccg acgtcgaggt gcccgaagga ccgcgcacct ggtgcatgac    5520
ccgcaagccc ggtgcctgag aattcgatat caagcttatc gataatcaac ctctggatta    5580
caaaatttgt gaaagattga ctggtattct taactatgtt gctcctttta cgctatgtgg    5640
atacgctgct ttaatgcctt tgtatcatgc tattgcttcc cgtatggctt tcattttctc    5700
ctccttgtat aaatcctggt tgctgtctct ttatgaggag ttgtggcccg ttgtcaggca    5760
acgtggcgtg gtgtgcactg tgtttgctga cgcaaccccc actggttggg cattgccac     5820 cacctgtcag ctccttccg ggactttcgc tttccccctc cctattgcca cggcggaact     5880
catcgccgcc tgccttgccc gctgctgaca aggggctcgg ctgttgggca ctgacaattc    5940
cgtggtgttg tcgggaaat catcgtcctt ccttggctg ctcgcctgtg ttgccacctg     6000
gattctgcgc gggacgtcct tctgctacgt cccttcggcc ctcaatccag cggaccttcc    6060
ttcccgcggc ctgctgccgg ctctgcggcc tcttccgcgt cttcgccttc gccctcagac    6120
gagtcggatc tccctttggg ccgcctcccc gcatcgatac cgtcgacctc gagacctaga    6180
aaaacatgga gcaatcacaa gtagcaatac agcagctacc aatgctgatt gtgcctggct    6240
agaagcacaa gaggaggagg aggtgggttt tccagtcaca cctcaggtac ctttaagacc    6300
aatgacttac aaggcagctg tagatcttag ccactttta aaagaaaagg ggggactgga    6360
agggctaatt cactcccaac gaagacaaga tatccttgat ctgtggatct accacacaca    6420
aggctacttc cctgattggc agaactacac accagggcca gggatcagat atccactgac    6480
ctttggatgg tgctacaagc tagtaccagt tgagcaagag aaggtagaag aagccaatga    6540
aggagagaac accgcttgt tacaccctgt gagcctgcat gggatggatg acccggagag    6600
agaagtatta gagtggaggt ttgacagccg cctagcattt catcacatgg cccgagagct    6660
gcatccggac tgtactgggt ctctctggtt agaccagatc tgagcctggg agctctctgg    6720
ctaactaggg aacccactgc ttaagcctca ataaagcttg ccttgagtgc ttcaagtagt    6780
gtgtgcccgt ctgttgtgtg actctggtaa ctagagatcc ctcagaccct tttagtcagt    6840
gtggaaaatc tctagca                                                   6857
```

<210> SEQ ID NO 47
<211> LENGTH: 6848
<212> TYPE: DNA
<213> ORGANISM: Artificial sequence
<220> FEATURE:
<223> OTHER INFORMATION: Synthetic

<400> SEQUENCE: 47

```
gggtctctct ggttagacca gatctgagcc tgggagctct ctggctaact agggaaccca     60
ctgcttaagc ctcaataaag cttgccttga gtgcttcaag tagtgtgtgc ccgtctgttg    120
tgtgactctg gtaactagag atccctcaga ccctttagt cagtgtggaa atctctagc      180 agtggcgccc gaacagggac ttgaaagcga aagggaaacc agaggagctc tctcgacgca    240
ggactcggct tgctgaagcg cgcacggcaa gaggcgaggg gcggcgactg gtgagtacgc    300
caaaaatttt gactagcgga ggctagaagg agagagatgg gtgcgagagc gtcagtatta    360
agcgggggag aattagatcg cgatgggaaa aaattcggtt aaggccaggg ggaaagaaaa    420
aatataaatt aaaacatata gtatgggcaa gcagggagct agaacgattc gcagttaatc    480
```

| | | |
|---|---|---|
| ctggcctgtt agaaacatca gaaggctgta gacaaatact gggacagcta caaccatccc | 540 | |
| ttcagacagg atcagaagaa cttagatcat tatataatac agtagcaacc ctctattgtg | 600 | |
| tgcatcaaag gatagagata aaagacacca aggaagcttt agacaagata gaggaagagc | 660 | |
| aaaacaaaag taagaccacc gcacagcaag cggccgctga tcttcagacc tggaggagga | 720 | |
| gatatgaggg acaattggag aagtgaatta tataaatata aagtagtaaa aattgaacca | 780 | |
| ttaggagtag cacccaccaa ggcaaagaga agagtggtgc agagagaaaa aagagcagtg | 840 | |
| ggaataggag ctttgttcct tgggttcttg ggagcagcag gaagcactat gggcgcagcg | 900 | |
| tcaatgacgc tgacggtaca ggccagacaa ttattgtctg gtatagtgca gcagcagaac | 960 | |
| aatttgctga gggctattga ggcgcaacag catctgttgc aactcacagt ctggggcatc | 1020 | |
| aagcagctcc aggcaagaat cctggctgtg gaaagatacc taaaggatca acagctcctg | 1080 | |
| gggatttggg gttgctctgg aaaactcatt tgcaccactg ctgtgccttg gaatgctagt | 1140 | |
| tggagtaata aatctctgga acagatttgg aatcacacga cctggatgga gtgggacaga | 1200 | |
| gaaattaaca attacacaag cttaatacac tccttaattg aagaatcgca aaaccagcaa | 1260 | |
| gaaaagaatg aacaagaatt attggaatta gataaatggg caagtttgtg gaattggttt | 1320 | |
| aacataacaa attggctgtg gtatataaaa ttattcataa tgatagtagg aggcttggta | 1380 | |
| ggtttaagaa tagttttgc tgtactttct atagtgaata gagttaggca gggatattca | 1440 | |
| ccattatcgt ttcagaccca cctcccaacc ccgaggggac ccgacaggcc cgaaggaata | 1500 | |
| gaagaagaag gtggagagag agacagagac agatccattc gattagtgaa cggatcggca | 1560 | |
| ctgcgtgcgc caattctgca gacaaatggc agtattcatc cacaatttta aagaaaagg | 1620 | |
| ggggattggg gggtacagtg caggggaaag aatagtagac ataatagcaa cagacataca | 1680 | |
| aactaaagaa ttacaaaaac aaattacaaa aattcaaaat tttcgggttt attacaggga | 1740 | |
| cagcagagat ccagtttggt taattaaggg tgcagcggcc tccgcgccgg ttttggcgc | 1800 | |
| ctcccgcggg cgcccccctc ctcacggcga gcgctgccac gtcagacgaa gggcgcagga | 1860 | |
| gcgttcctga tccttccgcc cggacgctca ggacagcggc ccgctgctca taagactcgg | 1920 | |
| ccttagaacc ccagtatcag cagaaggaca ttttaggacg ggacttgggt gactctaggg | 1980 | |
| cactggtttt ctttccagag agcggaacag gcgaggaaaa gtagtccctt ctcggcgatt | 2040 | |
| ctgcggaggg atctccgtgg ggcggtgaac gccgatgatt atataaggac gcgccgggtg | 2100 | |
| tggcacagct agttccgtcg cagccgggat ttgggtcgcg gttcttgttt gtggatcgct | 2160 | |
| gtgatcgtca cttggtgagt tgcgggctgc tgggctggcc ggggctttcg tggccgccgg | 2220 | |
| gccgctcggt gggacggaag cgtgtggaga gaccgccaag ggctgtagtc tgggtccgcg | 2280 | |
| agcaaggttg ccctgaactg ggggttgggg ggagcgcaca aaatggcggc tgttcccgag | 2340 | |
| tcttgaatgg aagacgcttg taaggcgggc tgtgaggtcg ttgaaacaag gtgggggca | 2400 | |
| tggtgggcgg caagaaccca aggtcttgag gccttcgcta atgcgggaaa gctcttattc | 2460 | |
| gggtgagatg ggctggggca ccatctgggg accctgacgt gaagtttgtc actgactgga | 2520 | |
| gaactcgggt tgtcgtctg gttgcggggg cggcagttat gcggtgccgt tgggcagtgc | 2580 | |
| acccgtacct ttgggagcgc gcgcctcgtc gtgtcgtgac gtcacccgtt ctgttggctt | 2640 | |
| ataatgcagg gtggggccac ctgccggtag gtgtgcggta ggcttttctc cgtcgcagga | 2700 | |
| cgcagggttc gggcctaggg taggctctcc tgaatcgaca ggcgccggac ctctggtgag | 2760 | |
| gggagggata agtgaggcgt cagtttcttt ggtcggtttt atgtacctat cttcttaagt | 2820 | |
| agctgaagct ccggttttga actatgcgct cggggttggc gagtgtgttt tgtgaagttt | 2880 | |

```
tttaggcacc ttttgaaatg taatcatttg ggtcaatatg taattttcag tgttagacta    2940
gtaaattgtc cgctaaattc tggccgtttt tggcttttt gttagacgaa gcttgggctg     3000
caggtcgact ctagaggatc cccgggtacc ggtcgccacc gccgccacca tggcctatcc    3060
atatgatgtg ccagattatg ccatggcgcc gaagaaaaag aggaaagtac ggggcatgcg    3120
atcatacttg atcctgcggc ttgcaggtcc tatgcaagcc tgggggcaac ctacctttga    3180
aggtactcgg ccgactggca ggttccctac gcggtctggt ttgctcggac tcctcggcgc    3240
ctgtttgggg atacaaaggg atgacacttc ttccttgcag gcactttccg aatcagtcca    3300
gttcgcagtg agatgtgatg aactcatact ggacgacaga cgggtgtccg taactggact    3360
gagggactat catactgtac tcggcgcaag agaagattat cgaggtctta agtcacatga    3420
gactattcag acatggaggg aatatttgtg tgacgcctcc ttcacggtgg ccctctggct    3480
tacaccacat gcaactatgg tgatctcaga gcttgagaaa gccgttctta aacctcggta    3540
cacaccatat ctggggaggc ggtcttgccc acttacccac ccgcttttct tggggacttg    3600
tcaggccagc gatccacaga aggccttgct gaactatgaa cccgttggtg gcgatatata    3660
cagtgaagag agcgtcacgg ccatcactt gaagttcact gctagggatg agccgatgat    3720
tacgctcccg agacagttcg ctagtaggga atggtacgtt attaaggggg gaatggacgt    3780
ttcccaagga agcggagcta ctaacttcag cctgctgaag caggctggag acgtggagga    3840
gaaccctgga cctatggatt acaaggacca tgacggagat tataaggacc acgacataga    3900
ctataaggat gacgatgaca aaatggcaga tgctaagtca ctgactgcct ggtcccggac    3960
actggtgacc ttcaaggatg tgtttgtgga cttcaccagg gaggagtgga agctgctgga    4020
cactgctcag cagatcctgt acagaaatgt gatgctggag aactataaga acctggtttc    4080
cttgggttat cagcttacta agccagatgt gatcctccgg ttggagaagg gagaagagcc    4140
ctggctggtg gagagagaaa ttcaccaaga gacccatcct gattcagaga ctgcatttga    4200
aatcaaatca tcagttccga aaagaaacg caaagttgga tccccaaaga agaaacgcaa    4260 ggtgcgggc atgtatctca gtaaagtcat cattgccagg gcctggagca gggatcttta    4320
ccaacttcac cagggattat ggcatttatt tccaaacaga ccggatgctg ctcgtgattt    4380 tcttttcat gttgagaagc gaaacacacc agaaggctgt catgttttat tgcagtcagc    4440
gcaaatgcct gtttcaactg ccgttgcgac agtcattaaa actaaacagg ttgaatttca    4500
acttcaggtt ggtgttccac tctatttcg gcttcgggca aatccgatca aaactattct    4560
cgacaatcaa aagcgcctgg acagtaaagg gaatattaaa cgctgtcggg ttccgttaat    4620
aaaagaagca gaacaaatcg cgtggttgca acgtaaattg ggcaatgcgg cgcgcgttga    4680
agatgtgcat cccatatcgg aacgccaca gtattttct ggtgatggta aaagtggaaa    4740
gatccaaacg gtttgctttg aaggtgtgct caccatcaac gacgcgccag cgttaataga    4800
tcttgtacag caaggtattg gccagctaa atcgatggga tgtggcttgc tatctttggc    4860
tccactggga agcggagagg gcagaggaag tcttctcaca tgcggtgacg tggaggagaa    4920
tcctggacct atgaccgagt acaagcccac ggtcgcctc gccacccgcg acgacgtccc    4980
cagggccgta cgcaccctcg ccgccgcgtt cgccgactac cccgccacgc gccacaccgt    5040
cgatccggac cgccacatcg agcgggtcac cgagctgcaa gaactcttcc tcacgcgcgt    5100
cgggctcgac atcggcaagg tgtgggtcgc ggacgacggc gccgcggtgg cggtctggac    5160
cacgccggag agcgtcgaag cggggcggt gttcgccgag atcggccgc gcatggccga    5220
```

-continued

| | |
|---|---|
| gttgagcggt tcccggctgg ccgcgcagca acagatggaa ggcctcctgg cgccgcaccg | 5280 |
| gcccaaggag cccgcgtggt tcctggccac cgtcggcgtc tcgcccgacc accagggcaa | 5340 |
| gggtctgggc agcgccgtcg tgctccccgg agtggaggcg gccgagcgcg ccggggtgcc | 5400 |
| cgccttcctg gagacctccg cgcccgcaa cctccccttc tacgagcggc tcggcttcac | 5460 |
| cgtcaccgcc gacgtcgagg tgcccgaagg accgcgcacc tggtgcatga cccgcaagcc | 5520 |
| cggtgcctga gaattcgata tcaagcttat cgataatcaa cctctggatt acaaaatttg | 5580 |
| tgaaagattg actggtattc ttaactatgt tgctcctttt acgctatgtg gatacgctgc | 5640 |
| tttaatgcct ttgtatcatg ctattgcttc ccgtatggct ttcattttct cctccttgta | 5700 |
| taaatcctgg ttgctgtctc tttatgagga gttgtggccc gttgtcaggc aacgtggcgt | 5760 |
| ggtgtgcact gtgtttgctg acgcaacccc cactggttgg ggcattgcca ccacctgtca | 5820 |
| gctccttttcc gggactttcg ctttccccct ccctattgcc acggcggaac tcatcgccgc | 5880 |
| ctgccttgcc cgctgctgga caggggctcg gctgttgggc actgacaatt ccgtggtgtt | 5940 |
| gtcggggaaa tcatcgtcct ttccttggct gctcgcctgt gttgccacct ggattctgcg | 6000 |
| cgggacgtcc ttctgctacg tcccttcggc cctcaatcca gcggaccttc cttcccgcgg | 6060 |
| cctgctgccg gctctgcggc ctcttccgcg tcttcgcctt cgccctcaga cgagtcggat | 6120 |
| ctcccttttgg gccgcctccc cgcatcgata ccgtcgacct cgagacctag aaaaacatgg | 6180 |
| agcaatcaca agtagcaata cagcagctac caatgctgat tgtgcctggc tagaagcaca | 6240 |
| agaggaggag gaggtgggtt ttccagtcac acctcaggta cctttaagac caatgactta | 6300 |
| caaggcagct gtagatctta gccactttt aaaagaaaag gggggactgg aagggctaat | 6360 |
| tcactcccaa cgaagacaag atatccttga tctgtggatc taccacacac aaggctactt | 6420 |
| ccctgattgg cagaactaca caccagggcc agggatcaga tatccactga cctttggatg | 6480 |
| gtgctacaag ctagtaccag ttgagcaaga gaaggtagaa gaagccaatg aaggagagaa | 6540 |
| cacccgcttg ttcaccctg tgagcctgca tgggatggat gacccggaga gagaagtatt | 6600 |
| agagtggagg tttgacagcc gcctagcatt tcatcacatg gcccgagagc tgcatccgga | 6660 |
| ctgtactggg tctctctggt tagaccagat ctgagcctgg gagctctctg gctaactagg | 6720 |
| gaacccactg cttaagcctc aataaagctt gccttgagtg cttcaagtag tgtgtgcccg | 6780 |
| tctgttgtgt gactctggta actagagatc cctcagaccc ttttagtcag tgtggaaaat | 6840 |
| ctctagca | 6848 |

<210> SEQ ID NO 48
<211> LENGTH: 32
<212> TYPE: RNA
<213> ORGANISM: Artificial sequence
<220> FEATURE:
<223> OTHER INFORMATION: Synthetic

<400> SEQUENCE: 48

| | |
|---|---|
| gucgcacucu ucaugggugc guggauugaa au | 32 |

<210> SEQ ID NO 49
<211> LENGTH: 634
<212> TYPE: DNA
<213> ORGANISM: Artificial sequence
<220> FEATURE:
<223> OTHER INFORMATION: Synthetic

<400> SEQUENCE: 49

| | |
|---|---|
| taatacgact cactataggg tcgcactctt catgggtgcg tggattgaaa tattgaggta | 60 |

```
ggtattgatt cgttggacat gatcatgtcg cactcttcat gggtgcgtgg attgaaatat    120
tgaggtaggt attgattcgt tggacatgat catgtcgcac tcttcatggg tgcgtggatt    180
gaaatattga ggtaggtatt gattcgttgg acatgatcat gtcgcactct tcatgggtgc    240
gtggattgaa atattgaggt aggtattgat tcgttggaca tgatcatgtc gcactcttca    300
tgggtgcgtg gattgaaata ttgaggtagg tattgattcg ttggacatga tcatgtcgca    360
ctcttcatgg gtgcgtggat tgaaatattg aggtaggtat tgattcgttg gacatgatca    420
tgtcgcactc ttcatgggtg cgtggattga atattgagg taggtattga ttcgttggac    480
atgatcatgt cgcactcttc atgggtgcgt ggattgaaat attgaggtag gtattgattc    540
gttggacatg atcatgtcgc actcttcatg ggtgcgtgga ttgaaattag cataacccct    600
tggggcctct aaacgggtct gaggggtttt tttg                                634

<210> SEQ ID NO 50
<211> LENGTH: 67
<212> TYPE: RNA
<213> ORGANISM: Artificial sequence
<220> FEATURE:
<223> OTHER INFORMATION: Synthetic

<400> SEQUENCE: 50
uggauugaaa uauugaggua gguauugauu cguuggacau gaucaugucg cacucuucau    60
gggugcg                                                              67

<210> SEQ ID NO 51
<211> LENGTH: 484
<212> TYPE: DNA
<213> ORGANISM: Artificial sequence
<220> FEATURE:
<223> OTHER INFORMATION: Synthetic

<400> SEQUENCE: 51
gagggcctat ttcccatgat tccttcatat ttgcatatac gatacaaggc tgttagagag    60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg gtcgcactct tcatgggtgc gtggattgaa ataccggggt ggtgcccatc    300
ctggtcgagc tggacgtcgc actcttcatg ggtgcgtgga ttgaaatagg gtcagcttgc    360
cgtaggtggc atcgccctcg gtcgcactct tcatgggtgc gtggattgaa atagccgcta    420
ccccgaccac atgaagcagc acgacgtcgc actcttcatg ggtgcgtgga ttgaaatttt    480
tttt                                                                 484

<210> SEQ ID NO 52
<211> LENGTH: 322
<212> TYPE: DNA
<213> ORGANISM: Artificial sequence
<220> FEATURE:
<223> OTHER INFORMATION: Synthetic

<400> SEQUENCE: 52
gagggcctat ttcccatgat tccttcatat ttgcatatac gatacaaggc tgttagagag    60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
```

```
atgcttaccg taacttgaaa gtatttcgat tcttggctt tatatatctt gtggaaagga    240
cgaaacaccg tggattgaaa taccggggtg gtgcccatcc tggtcgagct ggacgtcgca    300
ctcttcatgg gtgcgttttt tt                                             322
```

<210> SEQ ID NO 53
<211> LENGTH: 7
<212> TYPE: DNA
<213> ORGANISM: Artificial sequence
<220> FEATURE:
<223> OTHER INFORMATION: Synthetic

<400> SEQUENCE: 53

```
tttttttt                                                               7
```

<210> SEQ ID NO 54
<211> LENGTH: 55
<212> TYPE: DNA
<213> ORGANISM: Artificial sequence
<220> FEATURE:
<223> OTHER INFORMATION: Synthetic

<400> SEQUENCE: 54

```
gaaacaccgc ggaccggtcg cactcttcat gggtgcgtgg attgaaattt ttttt          55
```

<210> SEQ ID NO 55
<211> LENGTH: 55
<212> TYPE: DNA
<213> ORGANISM: Artificial sequence
<220> FEATURE:
<223> OTHER INFORMATION: Synthetic

<400> SEQUENCE: 55

```
aaaaaaaatt tcaatccacg cacccatgaa gagtgcgacc ggtccgcggt gtttc          55
```

<210> SEQ ID NO 56
<211> LENGTH: 10
<212> TYPE: DNA
<213> ORGANISM: Artificial sequence
<220> FEATURE:
<223> OTHER INFORMATION: Synthetic

<400> SEQUENCE: 56

```
gaaacaccgc                                                             10
```

<210> SEQ ID NO 57
<211> LENGTH: 8
<212> TYPE: DNA
<213> ORGANISM: Artificial sequence
<220> FEATURE:
<223> OTHER INFORMATION: Synthetic

<400> SEQUENCE: 57

```
ctttgtgg                                                                8
```

<210> SEQ ID NO 58
<211> LENGTH: 42
<212> TYPE: DNA
<213> ORGANISM: Artificial sequence
<220> FEATURE:
<223> OTHER INFORMATION: Synthetic

<400> SEQUENCE: 58

```
ccggtcgcac tcttcatggg tgcgtggatt gaaattttttt tt                       42
```

```
<210> SEQ ID NO 59
<211> LENGTH: 38
<212> TYPE: DNA
<213> ORGANISM: Artificial sequence
<220> FEATURE:
<223> OTHER INFORMATION: Synthetic

<400> SEQUENCE: 59
aaaaaaaatt tcaatccacg cacccatgaa gagtgcga                            38

<210> SEQ ID NO 60
<211> LENGTH: 68
<212> TYPE: DNA
<213> ORGANISM: Artificial sequence
<220> FEATURE:
<223> OTHER INFORMATION: Synthetic

<400> SEQUENCE: 60
ggaccggtcg cactcttcat gggtgcgtgg attgaaatac cggggtggtg cccatcctgg    60
tcgagctg                                                            68

<210> SEQ ID NO 61
<211> LENGTH: 120
<212> TYPE: DNA
<213> ORGANISM: Artificial sequence
<220> FEATURE:
<223> OTHER INFORMATION: Synthetic

<400> SEQUENCE: 61
gaaacaccgc ggaccggtcg cactcttcat gggtgcgtgg attgaaatac cggggtggtg    60
cccatcctgg tcgagctgcc ggtcgcactc ttcatgggtg cgtggattga aattttttt   120

<210> SEQ ID NO 62
<211> LENGTH: 120
<212> TYPE: DNA
<213> ORGANISM: Artificial sequence
<220> FEATURE:
<223> OTHER INFORMATION: Synthetic

<400> SEQUENCE: 62
aaaaaaaatt tcaatccacg cacccatgaa gagtgcgacc ggcagctcga ccaggatggg    60
caccaccccg gtatttcaat ccacgcaccc atgaagagtg cgaccggtcc gcggtgtttc   120

<210> SEQ ID NO 63
<211> LENGTH: 51
<212> TYPE: DNA
<213> ORGANISM: Artificial sequence
<220> FEATURE:
<223> OTHER INFORMATION: Synthetic

<400> SEQUENCE: 63
gaaacaccgc ggctcgagtt ccccgcgcca gcggggataa accgtttttt t            51

<210> SEQ ID NO 64
<211> LENGTH: 51
<212> TYPE: DNA
<213> ORGANISM: Artificial sequence
<220> FEATURE:
<223> OTHER INFORMATION: Synthetic

<400> SEQUENCE: 64
aaaaaaacgg tttatccccg ctggcgcggg gaactcgagc cgcggtgttt c            51

<210> SEQ ID NO 65
```

```
<211> LENGTH: 39
<212> TYPE: DNA
<213> ORGANISM: Artificial sequence
<220> FEATURE:
<223> OTHER INFORMATION: Synthetic

<400> SEQUENCE: 65
ctcgagttcc ccgcgccagc ggggataaac cgtttttt                              39

<210> SEQ ID NO 66
<211> LENGTH: 36
<212> TYPE: DNA
<213> ORGANISM: Artificial sequence
<220> FEATURE:
<223> OTHER INFORMATION: Synthetic

<400> SEQUENCE: 66
aaaaaaacgg tttatccccg ctggcgcggg gaactc                               36

<210> SEQ ID NO 67
<211> LENGTH: 64
<212> TYPE: DNA
<213> ORGANISM: Artificial sequence
<220> FEATURE:
<223> OTHER INFORMATION: Synthetic

<400> SEQUENCE: 67
ggctcgagtt ccccgcgcca gcggggataa accgcgtgta cggtgggagg tctatataag     60
caga                                                                  64

<210> SEQ ID NO 68
<211> LENGTH: 113
<212> TYPE: DNA
<213> ORGANISM: Artificial sequence
<220> FEATURE:
<223> OTHER INFORMATION: Synthetic

<400> SEQUENCE: 68
gaaacaccgc ggactcgagt tccccgcgcc agcggggata accgcgtgt acggtgggag      60 gtctatataa gcagatcgag ttccccgcgc agcggggat aaaccgtttt ttt            113

<210> SEQ ID NO 69
<211> LENGTH: 113
<212> TYPE: DNA
<213> ORGANISM: Artificial sequence
<220> FEATURE:
<223> OTHER INFORMATION: Synthetic

<400> SEQUENCE: 69
aaaaaaacgg tttatccccg ctggcgcggg gaactcgatc tgcttatata gacctcccac     60
cgtacacgcg gttatcccc gctggcgcgg ggaactcgag tccgcggtgt ttc            113

<210> SEQ ID NO 70
<211> LENGTH: 51
<212> TYPE: DNA
<213> ORGANISM: Artificial sequence
<220> FEATURE:
<223> OTHER INFORMATION: Synthetic

<400> SEQUENCE: 70
gaaacaccgc ggaccggttc actgccgtgt aggcagctaa gaaatttttt t              51

<210> SEQ ID NO 71
<211> LENGTH: 51
```

```
<212> TYPE: DNA
<213> ORGANISM: Artificial sequence
<220> FEATURE:
<223> OTHER INFORMATION: Synthetic

<400> SEQUENCE: 71
aaaaaaattt cttagctgcc tacacggcag tgaaccggtc cgcggtgttt c        51

<210> SEQ ID NO 72
<211> LENGTH: 38
<212> TYPE: DNA
<213> ORGANISM: Artificial sequence
<220> FEATURE:
<223> OTHER INFORMATION: Synthetic

<400> SEQUENCE: 72
ccggttcact gccgtgtagg cagctaagaa attttttt                        38

<210> SEQ ID NO 73
<211> LENGTH: 35
<212> TYPE: DNA
<213> ORGANISM: Artificial sequence
<220> FEATURE:
<223> OTHER INFORMATION: Synthetic

<400> SEQUENCE: 73
aaaaaaattt cttagctgcc tacacggcag tgaac                           35

<210> SEQ ID NO 74
<211> LENGTH: 63
<212> TYPE: DNA
<213> ORGANISM: Artificial sequence
<220> FEATURE:
<223> OTHER INFORMATION: Synthetic

<400> SEQUENCE: 74
ggaccggttc actgccgtgt aggcagctaa gaaattttgg cagtacatca atgggcgtgg  60
atg                                                              63

<210> SEQ ID NO 75
<211> LENGTH: 111
<212> TYPE: DNA
<213> ORGANISM: Artificial sequence
<220> FEATURE:
<223> OTHER INFORMATION: Synthetic

<400> SEQUENCE: 75
gaaacaccgc ggaccggttc actgccgtgt aggcagctaa gaaattttgg cagtacatca  60
atgggcgtgg atgccggttc actgccgtgt aggcagctaa gaaattttt t          111

<210> SEQ ID NO 76
<211> LENGTH: 111
<212> TYPE: DNA
<213> ORGANISM: Artificial sequence
<220> FEATURE:
<223> OTHER INFORMATION: Synthetic

<400> SEQUENCE: 76
aaaaaaattt cttagctgcc tacacggcag tgaaccggca tccacgccca ttgatgtact  60
gccaaaattt cttagctgcc tacacggcag tgaaccggtc cgcggtgttt c          111

<210> SEQ ID NO 77
<211> LENGTH: 75
<212> TYPE: DNA
```

-continued

```
<213> ORGANISM: Artificial sequence
<220> FEATURE:
<223> OTHER INFORMATION: Synthetic

<400> SEQUENCE: 77
accggcagct cgaccaggat gggcaccacc ccggtatttc aatccacgca cccatgaaga    60
gtgcgaccgg tccgc                                                    75

<210> SEQ ID NO 78
<211> LENGTH: 70
<212> TYPE: DNA
<213> ORGANISM: Artificial sequence
<220> FEATURE:
<223> OTHER INFORMATION: Synthetic

<400> SEQUENCE: 78
tcgatctgct tatatagacc tcccaccgta cacgcggttt atccccgctg gcgcggggaa    60
ctcgagccgc                                                          70

<210> SEQ ID NO 79
<211> LENGTH: 74
<212> TYPE: DNA
<213> ORGANISM: Artificial sequence
<220> FEATURE:
<223> OTHER INFORMATION: Synthetic

<400> SEQUENCE: 79
ccggcatcca cgcccattga tgtactgcca aaatttctta gctgcctaca cggcagtgaa    60
ccggtccggt ccgc                                                     74

<210> SEQ ID NO 80
<211> LENGTH: 10
<212> TYPE: PRT
<213> ORGANISM: Artificial sequence
<220> FEATURE:
<223> OTHER INFORMATION: Synthetic

<400> SEQUENCE: 80

Val Gln Arg Lys Arg Gln Lys Leu Met Pro
1               5                   10

<210> SEQ ID NO 81
<211> LENGTH: 8
<212> TYPE: PRT
<213> ORGANISM: Artificial sequence
<220> FEATURE:
<223> OTHER INFORMATION: Synthetic

<400> SEQUENCE: 81

Ser Lys Lys Lys Lys Thr Lys Val
1               5

<210> SEQ ID NO 82
<211> LENGTH: 8
<212> TYPE: PRT
<213> ORGANISM: Artificial sequence
<220> FEATURE:
<223> OTHER INFORMATION: Synthetic

<400> SEQUENCE: 82

Gly Arg Lys Arg Lys Lys Arg Thr
1               5

<210> SEQ ID NO 83
```

```
<211> LENGTH: 5
<212> TYPE: PRT
<213> ORGANISM: Artificial sequence
<220> FEATURE:
<223> OTHER INFORMATION: Synthetic

<400> SEQUENCE: 83

Lys Ile Pro Ile Lys
1               5
```

GENOME ENGINEERING WITH TYPE I CRISPR SYSTEMS IN EUKARYOTIC CELLS

CROSS REFERENCE TO RELATED APPLICATIONS

This application is a national stage filing under 35 U.S.C. § 371 of International Patent Application No. PCT/US2016/056925, which claims priority to U.S. Provisional Application No. 62/382,240, filed Aug. 31, 2016, U.S. Provisional Application No. 62/240,743, Oct. 13, 2015, U.S. Provisional Application No. 62/240,716, filed Oct. 13, 2015, the entire contents of each of which are hereby incorporated by reference.

STATEMENT OF GOVERNMENT INTEREST

This invention was made with government support under federal grant numbers 1DP2-OD008586 awarded by NIH. The U.S. Government has certain rights to this invention.

SEQUENCE LISTING

The instant application includes a Sequence Listing which has been submitted electronically in ASCII format and is hereby incorporated by reference in its entirety. Said ASCII copy, created on Aug. 31, 2020, is named 028193-9237-US03_As_Filed_Sequence_Listing.txt and is 153,771 bytes in size.

TECHNICAL FIELD

The present disclosure relates to the field of gene expression alteration, genome engineering and genomic alteration of genes in eukaryotic cells using Type I Clustered Regularly Interspaced Short Palindromic Repeats (CRISPR)/CRISPR-associated (Cas) systems and viral delivery systems. The invention relates to compositions comprising Type I CRISPR-Cas polypeptides and CRISPR array nucleic acids designed for genome modification in eukaryotic cells and for targeted killing of eukaryotic cells.

BACKGROUND

CRISPR-Cas systems are naturally adaptive immune systems found in bacteria and archaea. The CRISPR (for clustered regularly interspaced short palindromic repeats) consists of alternating repeats and spacers and is often flanked by a set of cas (for CRISPR associated) genes. The CRISPR array is transcribed and processed into individual CRISPR RNAs that complex with the Cas proteins. The spacer portion of the CRISPR RNA then serves as a guide to recognize complementary foreign genetic material, which is cleaved by the Cas proteins.

Bioinformatics analyses have a revealed a diversity of CRISPR-Cas systems based on the set of cas genes and their phylogenetic relationship. The most recent classification system (Makarova et al. *Nat Rev Microbiol.* 2015 Sep. 28. doi: 10.1038/nrmicro3569) defines five different types (I through V) with many possessing multiple subtypes. The Type I systems represent the most common type of CRISPR-Cas systems, representing over 50% of all identified systems in both bacteria and archaea. Type I systems are further divided into six subtypes: I-A, I-B, I-C, I-D, I-E, and I-F. While the exact set of proteins between these systems varies, they share a common framework: all of the systems encode an endoribonuclease called Cas3, which is split into two proteins (Cas3', Cas3") for I-A and I-B systems. Most of the other proteins form a multi-subunit complex called Cascade (for complex associated with antiviral defense) that is responsible for processing the CRISPR RNAs and binding target DNA. The only requirements for DNA binding are that (1) the target substantially match the spacer portion of the CRISPR RNA and (2) the target is flanked on its 5' end by a protospacer-adjacent motif (PAM). The PAM is recognized by one of the Cas proteins within Cascade (e.g., the Cse1 protein in the Type I-E Cascade), which then unwinds the flanking DNA to evaluate the extent of base pairing between the target and the spacer portion of the CRISPR RNA. Sufficient recognition leads Cascade to recruit and activate Cas3. Cas3 then nicks the non-target strand and begins degrading the strand in a 3'-to-5' direction (Gong et al. *Proc Natl Acad Sci USA.* 111(46):16359-64 (2014)).

Despite the unique attributes and prevalence of Type I CRISPR-Cas systems, little work has been done to exploit these systems. In contrast, Type II CRISPR-Cas systems have been heavily exploited in the realms of biotechnology (Hsu et al. Cell 157(6):1262-78 (2014)). These systems rely on a single effector protein called Cas9 that introduces a double-stranded break within the target sequence. Cas9 has been used extensively in eukaryotic cells for genome editing, wherein the double-stranded break is repaired through either non-homologous end joining (i.e., formation of insertions or deletions (indels)) or homology-directed repair. Cas9 has also been used to generate large deletions by targeting at least two locations along a stretch of the chromosome. However, the frequency of obtaining a large deletion has been extremely low particularly in comparison to the formation of indels at each target site.

Prokaryotes have CRISPR (clustered regularly interspaced short palindromic repeats)/Cas (CRISPR-associated) systems to provide adaptive immune protection. Invaders are detected by CRISPR RNAs (crRNA) that also function to recruit Cas proteins for destruction of the foreign genetic material. Type II CRISPR/Cas systems have been used as a molecular tool for genome editing in prokaryotes, and has been adapted for use in eukaryotes as well. Type I CRISPR/Cas systems have been less extensively studied. There remains a need for the ability to precisely regulate any gene in a eukaryotic cell.

SUMMARY

The present invention is directed to a Type I CRISPR/Cas system composition for genome engineering at least one target gene in a eukaryotic cell. The composition comprises at least one polynucleotide sequence encoding: (a) a Cascade complex; (b) a Cas3 polypeptide; and/or (c) at least one crRNA, wherein the crRNA targets a target nucleotide sequence from the at least one target gene. The Cascade complex comprises three or more Type I Cascade polypeptides, or functional fragments thereof. The at least one polynucleotide sequence is operably linked to a eukaryotic promoter and comprises a nuclear localization signal. The at least one polynucleotide sequence is codon-optimized.

The present invention is directed to an expression cassette or a vector comprising the Type I CRISPR/Cas system described above or subcomponents thereof.

The present invention is directed to a host cell comprising the Type I CRISPR/Cas system described above or the expression cassette or vector described above.

The present invention is directed to pharmaceutical composition comprising the Type I CRISPR/Cas system described above, the expression cassette or vector described above, or the host cell described above.

The present invention is directed to a method of modulating the expression of a target gene in a eukaryotic cell. The method comprises introducing to a cell the Type I CRISPR/Cas system t or the expression cassette or vector described above.

The present invention is directed to a method of activating an endogenous gene in a cell. The method comprises contacting a cell with the Type I CRISPR/Cas system described above or the expression cassette or vector described above. The at least one Cascade polypeptide is fused to a second polypeptide domain having transcription activation activity.

The present invention is directed to a method of correcting a mutant gene in a eukaryotic cell. The method comprises administering to a cell the Type I CRISPR/Cas system described above or the expression cassette or vector described above.

The present invention is directed to a kit for modulating gene expression of at least one target gene in a eukaryotic cell. The kit comprises the Type I CRISPR/Cas system described above, the expression cassette or vector described above, or the host cell described above.

The present invention is directed to a method for introducing an insertion, deletion, or mutation in a chromosome or extrachromosomal element of a eukaryotic cell by homologous recombination, comprising: introducing into the eukaryotic cell (A) (i) at least one nucleic acid construct encoding polypeptides of a Type I CRISPR-Cas system; and (ii) a CRISPR array comprising at least one spacer sequence that is complementary to a target DNA on the chromosome or extrachromosomal element; or (B) a protein-RNA complex comprising polypeptides of a Type I CRISPR-Cas system and a CRISPR array comprising at least one spacer sequence that is complementary to a target DNA on the chromosome or extrachromosomal element; and (C) a template comprising a single stranded DNA sequence or a double stranded DNA sequence, thereby introducing an insertion, deletion, or mutation in the chromosome or extrachromosomal element of the eukaryotic cell by homologous recombination.

The present invention is directed to a method for introducing a deletion into a chromosome or extrachromosomal element of a eukaryotic cell, comprising: introducing into the eukaryotic cell (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary to different target DNAs located on opposite strands of the chromosome or extrachromosomal element of the eukaryotic cell; and (C) optionally, a template comprising a single stranded DNA sequence or a double stranded DNA sequence and an intervening sequence having zero nucleotides or base pairs, respectively, wherein the different target DNAs located on opposite strands of the chromosome or extrachromosomal element are each adjacent to a protospacer adjacent motif (PAM) and the at least two spacer sequences of the CRISPR array(s) guide the Type I CRISPR-Cas polypeptides to the two different target DNAs, thereby degrading the chromosome or extrachromosomal element between the two different target DNAs including the PAM adjacent to each of the two different target DNAs (convergent degradation) and introducing a deletion.

The present invention is directed to a method for introducing an insertion or mutation into a chromosome of a eukaryotic cell, comprising: introducing into the eukaryotic cell (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary or extrachromosomal element to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; and (C) a template comprising a single stranded DNA sequence or a double stranded DNA sequence, wherein the different target DNAs located on opposite strands of the chromosome or extrachromosomal element are each adjacent to a protospacer adjacent motif (PAM) and the at least two spacer sequences of the CRISPR array(s) guide the Type I CRISPR-Cas polypeptides to the two different target DNAs, thereby degrading the chromosome or extrachromosomal element between the two different target DNAs including the PAM adjacent to each of the two different target DNAs (convergent degradation) and introducing an insertion or mutation.

The present invention is directed to a method for treating a viral infection in a subject in need thereof, comprising: administering to the subject an effective amount of (A) (i) at least one nucleic acid construct encoding polypeptides of a Type I CRISPR-Cas system; and (ii) a CRISPR array comprising at least one spacer sequence that is complementary to a target DNA on the chromosome or extrachromosomal element; or (B) a protein-RNA complex comprising polypeptides of a Type I CRISPR-Cas system and a CRISPR array comprising at least one spacer sequence that is complementary to a target DNA on the chromosome or extrachromosomal element; and (C) a template comprising a single stranded DNA sequence or a double stranded DNA sequence and an intervening sequence having zero nucleotides or base pairs, respectively, wherein the target DNA is DNA of a virus infecting the subject, thereby introducing a deletion by homologous recombination in the chromosome or extrachromosomal element of the eukaryotic cell, thereby treating the viral infection in the subject in need thereof.

The present invention is directed to a method for treating a viral infection in a subject in need thereof, comprising: administering to the subject an effective amount of: (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; wherein the different target DNAs located on opposite strands of the chromosome or extrachromosomal element are each adjacent to a protospacer adjacent motif (PAM) and the at least two spacer sequences of the CRISPR array(s) are each complementary to DNA of a virus infecting the subject and guide the Type I CRISPR-Cas polypeptides to the two different target DNAs, thereby degrading the chromosome or extrachromosomal element between the two different target DNAs including the PAM adjacent to each of the two different target DNAs (convergent degradation) and introducing a deletion, thereby treating the viral infection in the subject in need thereof.

The present invention is directed to a method for disabling or deleting a chromosome in a eukaryotic cell comprising: introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA on the chromosome; or (B) a protein-RNA complex comprising polypeptides of a Type I CRISPR-Cas system and at least one CRISPR array comprising at least one spacer sequence that is complementary to a target DNA on the chromosome, thereby disabling or deleting the chromosome in the eukaryotic cell.

The present invention is directed to a method of killing of selected cells in a population of eukaryotic cells, comprising introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA present on a chromosome of a subset of cells within a population of cells and not present in a chromosome of the other cells of the population; or (B) a protein-RNA complex comprising polypeptides of a Type I CRISPR-Cas system and at least one CRISPR array comprising at least one spacer sequence that is complementary to a target DNA present in a subset of cells in a population of cells and not present in the other cells of the population, thereby killing the subset of cells within the population of cells.

The present invention is directed to a method of sequence-specific killing of a eukaryotic cell, comprising: introducing into the organism cell: (A) (i) at least one nucleic acid construct encoding polypeptides of a Type I CRISPR-Cas system; and (ii) at least one CRISPR array comprising at least one spacer sequence that is complementary to a target DNA in an essential gene; or (B) a protein-RNA complex comprising polypeptides of a Type I CRISPR-Cas system and at least one CRISPR array comprising at least one spacer sequence that is complementary to a target DNA in an essential gene, thereby disrupting or deleting the gene and killing the cell The present invention is directed to a method for deleting a target DNA in a chromosome or on an extrachromosomal element in a eukaryotic cell, the method comprising introducing into the eukaryotic cell: (A) (i) at least one nucleic acid construct encoding polypeptides of a Type I CRISPR-Cas system; and (ii) at least one CRISPR array comprising at least one spacer sequence that is complementary to the target DNA on the chromosome or on the extrachromosomal element; or (B) a protein-RNA complex comprising polypeptides of a Type I CRISPR-Cas system and at least one CRISPR array comprising at least one spacer sequence that is complementary to the target DNA in the chromosome or on the extrachromosomal element, thereby deleting the target DNA in the chromosome or on the extrachromosomal element.

The present invention is directed to a modified lentiviral construct comprising a polynucleotide sequence of any one of SEQ ID NO: 42, SEQ ID NO: 43, SEQ ID NO: 44, SEQ ID NO: 45, SEQ ID NO: 46, or SEQ ID NO: 47.

These and other aspects of the invention are set forth in more detail in the description of the invention below.

BRIEF DESCRIPTION OF THE DRAWINGS

FIG. 6 shows a schematic of surveillance and interference by crRNP complexes and proposed mechanisms of targeting for the different types of CRISPR-Cas (clustered regularly interspaced short palindromic repeats-CRISPR-associated proteins) systems (modified from van der Oost et al., Nature Reviews Microbiology (2014) 12:479-492). FIG. 6A shows that in type I systems, the Cascade complex searches for a complementary protospacer in the invader DNA via target scanning. The large subunit (Cse1 or Cas8) of the complex recognizes the protospacer adjacent motif (PAM) sequence by a 'non-self activation' strategy, which is followed by hybridization between the seed sequence and the target DNA. If these initial criteria are met, complete base pairing results in R-loop formation and a simultaneous conformational change in the Cascade complex, which probably triggers Cas3 recruitment and subsequent degradation of the displaced target DNA strand (red triangles indicate endonucleolytic cleavage). The dashed arrow indicates processivity by the concerted helicase (green triangle) and exonuclease activities in the 3' to 5' direction. FIG. 6B shows that in type II systems, the Cas9 complex, bound to the CRISPR RNA (crRNA)-transactivating crRNA (tracrRNA) duplex, follows a similar mechanism of PAM-dependent recognition of invading DNA. However, unlike type I systems, the PAM is located upstream (at the 5' end) of the protospacer and both target DNA strands are cleaved by Cas9-mediated nuclease activity.

FIG. 13 shows the V1. 3× crRNA array (pAP05).

FIG. 14 shows the V2. Individual crRNAs (pAP07-09).

FIG. 15 shows generated GFP+ HEK293T cells.

FIG. 37 shows Type I-E Constructs.

FIG. 42 shows Type I-E Cascade Co-IP optimizations.

FIG. 45 shows FlpIn293 GFP+ cells made with pAP35 (CMV-GFP).

FIG. 50 shows Bacterial Protein Purification Duet System Constructs.

FIG. 56 shows the transfection amount for each well for the Type I-E system.

DETAILED DESCRIPTION

Figure 1A:
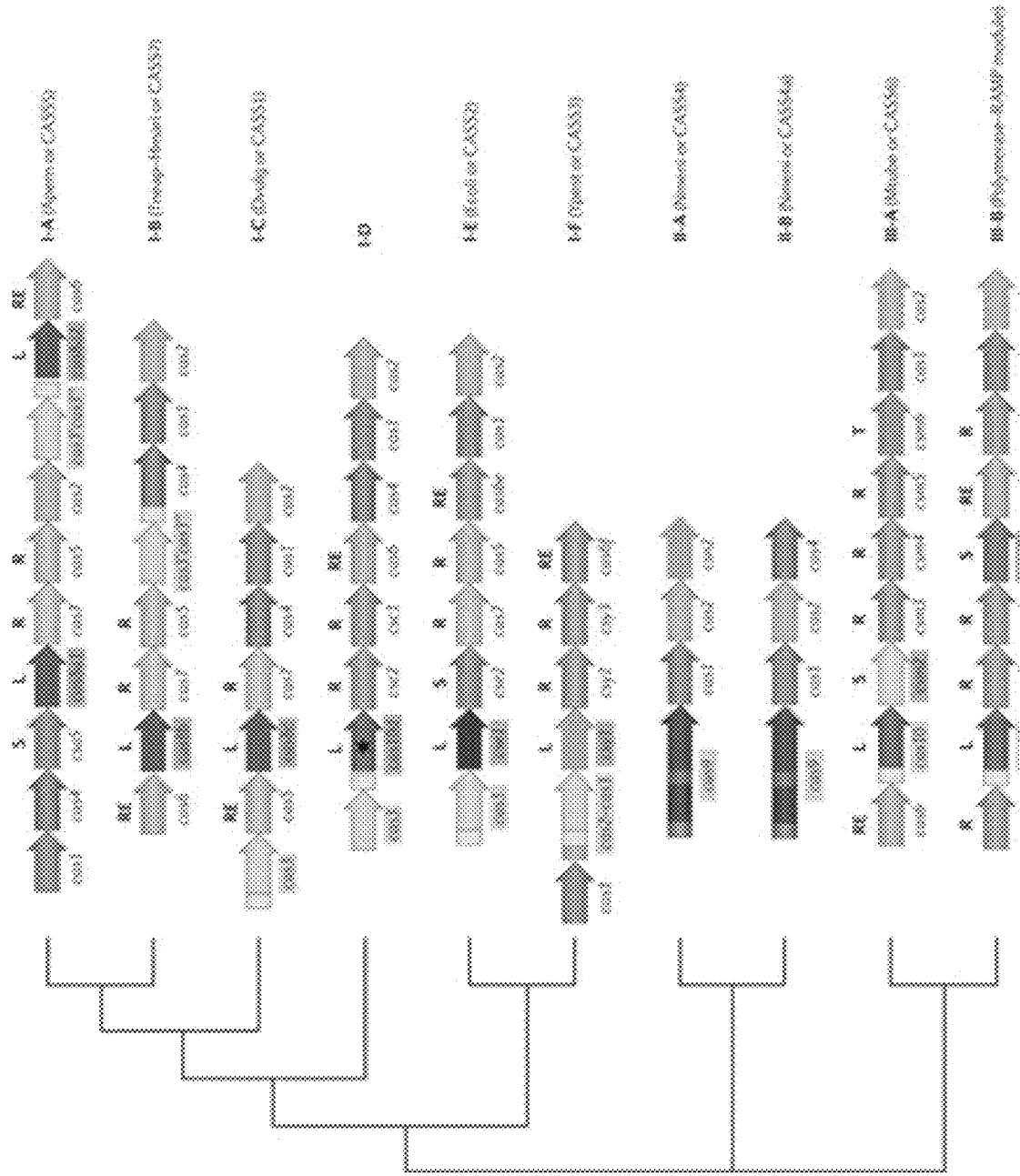
FIG. 1A shows the architectures of the genomic loci for the subtypes of CRISPR-Cas systems (modified from Makarova et al., Nature Reviews Microbiology (2015) 13:722-736).

As described herein, certain engineered Type I CRISPR/CRISPR-associated (Cas) system compositions have been discovered to be useful for altering the expression of genes and for genome engineering in eukaryotic cells. The Type I CRISPR/Cas system involves Cascade (a multimeric complex consisting of three to five proteins that processes crRNA arrays), Cas3 polypeptide, and at least one crRNA. Modifications of Type I systems for use in eukaryotes has exciting potential to be a novel molecular tool for genome editing with advantages over Type II systems.

One advantage of the Type I system is the potential for increased specificity/fewer off-target effects. Type II involves spCas9, a 20 bp spacer, where repression is observed with a gRNA possessing only 12 nt. Type I uses a 32 bp spacer and required a perfect match for 7-nt (or up to 5 nt) seed region. In Type I, mismatches are tolerated outside the seed region reducing the recognition region to 30 bp (including PAM).

Another advantage of Type I is that the Cascade complex is targeted to the target DNA with processed crRNA. There is possibility of transcriptional repression with the Type I system. There is strong binding of Cascade to target DNA and Cascade remains bound to DNA until released by Cas3-mediated DNA degradation. There is a greater steric hindrance because the Cascade complex is larger than Cas9. Type I can inhibit activation due to steric hindrance. Another possible additional advantage may be that it interferes with RNA polymerase-DNA interaction. Type I provides numerous protein components available to test fusions. The synergistic effect of fusions can be tested based on Cascade stoichiometry.

Another advantage of Type I is that Cas3 functional activity includes nuclease, helicase, and exonuclease activity. Type I has additional PAM sequences that can be used and has the potential for new or optimized targets. There is potential for deletions, as well as the degradation of an entire chromosome, chromosomal segment, or viral genome due to Cas3's exonuclease activity. Cascade binds to DNA until Cas3 binds and mediates DNA degradation. The present invention overcomes previous shortcomings in the art by providing compositions comprising Type I CRISPR-Cas systems and methods for their use in eukaryotes.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a target nucleotide sequence that is recognized and bound by the Cascade.

As used herein, "chimeric" may refer to a nucleic acid molecule and/or a polypeptide in which at least two components are derived from different sources (e.g., different organisms, different coding regions). Also as used herein, chimeric refers to a construct comprising a polypeptide linked to a nucleic acid.

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Complement" as used herein can mean 100% complementarity (fully complementary) with the comparator nucleotide sequence or it can mean less than 100% complementarity (e.g., substantial complementarity)(e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity). Complement may also be used in terms of a "complement" to or "complementing" a mutation.

The terms "complementary" or "complementarity," as used herein, refer to the natural binding of polynucleotides under permissive salt and temperature conditions by base-pairing. For example, the sequence "5'-A-G-T-3'" binds to the complementary sequence "5'-A-C-T-3'." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ. Genome editing, correction, or restoration may also occur by direct insertion of a linear DNA segment into a DNA break via the NHEJ mechanism.

A "CRISPR array" as used herein refers to a nucleic acid molecule that comprises at least two repeat nucleotide sequences, or portions thereof, and at least one spacer sequence, wherein one of the two repeat nucleotide sequences, or a portion thereof, is linked to the 5' end of the spacer nucleotide sequence and the other of the two repeat nucleotide sequences, or portion thereof, is linked to the 3' end of the spacer nucleotide sequence. In a recombinant CRISPR array, the combination of repeat nucleotide sequences and spacer nucleotide sequences is synthetic, made by man and not found in nature.

As used herein, the terms "delete," "deleted," and/or "deleting" in reference to a chromosome and/or a gene mean that the chromosome and/or the gene is removed from and therefore no longer present in the cell.

As used herein, the terms "disable," "disabled," and/or "disabling" in reference to a chromosome mean that the chromosome is degraded sufficiently such that it is no longer able to be replicated in the cell.

As used herein, the terms "disrupt," "disrupted," and/or "disrupting" in reference to a gene mean that the gene is degraded sufficiently such that it is no longer functional.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

As used herein, the terms "eliminate," "eliminated," and/or "eliminating" refer to complete cessation of the specified activity.

"Eukaryotic" or "eukaryotes" as used interchangeably herein refers to any organism whose cells contain a nucleus and other organelles enclosed within membranes. Eukaryotes have membrane-bound organelles, especially the nucleus, which contains the genetic material, and is enclosed by the nuclear envelope. Examples of eukaryotes include, but are not limited to, an animal, a mammal, an insect, a plant, a fungus, an insect, a bird, a fish, an amphibian, a reptile, or a cnidarian. in additional embodiments, a mammal can include, but is not limited to, a rodent, a horse, a dog a cat, a human, a non-human primate (e.g., monkeys, baboons, and chimpanzees), a goat, a pig, a cow (e.g., cattle), a sheep, laboratory animals (e.g., rats, mice, gerbils, hamsters, and the like) and the like. Non-limiting examples of birds useful with this invention include chickens, ducks, turkeys, geese, quails and birds kept as pets (e.g., parakeets, parrots, macaws, and the like). Additional embodiments can include, for example, mammalian and insect cell lines. Non-limiting examples of mammalian and insect cell lines include HEK293T cells, HeLa cells, CHO cells, MEF cells, 3T3 cells, Hi-5 cells, and Sf21 cells.

"Expression cassette" as used herein refers to a recombinant nucleic acid molecule comprising a nucleotide sequence of interest (e.g., a polynucleotide sequence encoding the Type I CRISPR/Cas system or subcomponents thereof), wherein said nucleotide sequence is operably associated with at least a control sequence (e.g., a promoter). Thus, some aspects of the invention provide expression cassettes designed to express the nucleotides sequences of the invention. An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). In some embodiments of this invention, terminators can be operably linked to the recombinant polynucleotide(s) encoding the Type I CRISPR/Cas system or subcomponents thereof.

An expression cassette also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

As used herein, an extrachromosomal element means a double stranded nucleic acid element that is residing in a eukaryotic cell and is not integrated into any of the eukaryotic cell's chromosomes.

A "fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. In some embodiments, a fragment of a polynucleotide can be a functional fragment that encodes a polypeptide that retains its function (e.g., a fragment of a Cas3 polypeptide retains one or more of the activities of a native Cas3 nuclease including, but not limited to, helicase and nuclease activity).

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but is not limited to DMD, hemophilia, cystic fibrosis, Huntington's chorea, familial hypercholesterolemia (LDL receptor defect), hepatoblastoma, Wilson's disease, congenital hepatic *porphyria*, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

The term "genome" as used herein includes an organism's chromosomal/nuclear genome as well as any mitochondrial, and/or plasmid genome.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

A "hairpin sequence" as used herein refers to a nucleotide sequence comprising hairpins (e.g., that forms one or more hairpin structures). A hairpin (e.g., stem-loop, fold-back) refers to a nucleic acid molecule having a secondary structure that includes a region of nucleotides that form a single strand that are further flanked on either side by a double stranded-region. Such structures are well known in the art. As known in the art, the double stranded region can comprise some mismatches in base pairing or can be perfectly complementary. In some embodiments, a repeat nucleotide sequence comprises, consists essentially of, consists of a hairpin sequence that is located within said repeat nucleotide sequence (i.e., at least one nucleotide (e.g., one, two, three, four, five, six, seven, eight, nine, ten, or more) of the repeat nucleotide sequence is present on either side of the hairpin that is within said repeat nucleotide sequence). In some embodiments, a hairpin sequence can be located at the 3'end of a transactivating CRISPR (tracr) sequence. In some embodiments, a repeat sequence comprises a hairpin sequence.

A "heterologous" or a "recombinant" nucleotide sequence as used interchangeably herein refers to a nucleotide sequence not naturally associated with a host cell into which it is introduced, including non-naturally occurring multiple copies of a naturally occurring nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence or polypeptide of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to the nucleotide sequence or polypeptide of the invention. Thus, for example, a homologue of a CRISPR array repeat sequence, a Cas 3 polypeptide/polynucleotide, a Cascade polypeptide/polynucleotide and the like, can be about 70% homologous or more to any known CRISPR array repeat sequence, Cas 3 polypeptide/polynucleotide, or Cascade polypeptide/polynucleotide, respectively.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the site specific nuclease, such as with a Type I CRISPR/Cas systems, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to treat disease by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

"Multicistronic" as used herein refers to a polynucleotide possessing more than one coding region to produce more than one protein from the same polynucleotide.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid is a nucleotide sequence naturally associated with a host cell into which it is introduced. Thus, for example, as used herein, the term "an endogenous restriction enzyme" means a restriction enzyme that is naturally occurring in (native to) the production host bacterium.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

A "synthetic" nucleic acid or polynucleotide, as used herein, refers to a nucleic acid or polynucleotide that is not found in nature but is constructed by the hand of man and as a consequence is not a product of nature.

A "nuclear localization signal," "nuclear localization sequence," or "NLS" as used interchangeably herein refers to an amino acid sequence that "tags" a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal, which targets proteins out of the nucleus.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

A "protospacer sequence" refers to the target double stranded DNA and specifically to the portion of the target DNA (e.g., or target region in the genome) that is fully or substantially complementary (and hybridizes) to the spacer sequence of the CRISPR arrays. The protospacer sequence in a Type I system is directly flanked at the 3' end by a PAM. A spacer is designed to be complementary to the protospacer.

A "protospacer adjacent motif (PAM)" is a short motif of 2-4 base pairs present immediately 3' to the protospacer.

As used herein, the terms "retarding the growth" or "retardation of growth" refers to reducing, delaying, inhibiting, and/or hindering the activity contributing to the growth and multiplication of, for example, a fungus or a virus.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

A "spacer nucleotide sequence" as used herein refers to a nucleotide sequence that is complementary to a target nucleotide sequence on a target gene. In some embodiments, a spacer nucleotide sequence of this invention can be about 15 nucleotides to about 150 nucleotides in length. In other embodiments, a spacer nucleotide sequence of this invention can be about 15 nucleotides to about 100 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides or more). In some particular embodiments, a spacer nucleotide sequence can be a length of about 8 to about 150 nucleotides, about 8 to about 100 nucleotides, about 8 to about 50 nucleotides, about 8 to about 40 nucleotides, about 8 to about 30 nucleotides, about 8 to about 25 nucleotides, about 8 to about 20 nucleotides, about 10 to about 50 nucleotides, about 10 to about 40, about 10 to about 30, about 10 to about 25, about 10 to about 20, about 15 to about 50, at least about 8, at least about 10, at least about 15, at least about 20, at least about 25, at least about 30, at least about 35, at least about 40, at least about 50, at least about 60, at least about 70, at least about 80, at least about 90, at least about 100, at least about 1 10, at least about 120, at least about 130, at least about 140, at least about 150 nucleotides in length, or more, and any value or range therein.

A "spacer sequence" as used herein is a nucleotide sequence that is complementary to a target DNA.

"Subject" and "patient" as used herein interchangeably refers to any vertebrate, including, but is not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus or rhesus monkey, chimpanzee, etc.) and a human). In some embodiments, the subject may be a human or a non-human. The subject or patient may be undergoing other forms of treatment.

A "sub-optimal protospacer sequence" refers to a target DNA to which a spacer is designed, wherein the spacer comprises greater than 50% complementarity and less than 100% complementarity to the protospacer sequence. The reduced complementarity can come from, for example, truncating the spacer sequence at the 5' end by up to about 5 nucleotides, introducing up to 5 mismatches within the non-seed region, or introducing up to 3 mismatches within the seed region.

A "sub-optimal PAM sequence" refers to a PAM sequence that allows DNA cleavage but at a rate that is below an optimal PAM. Sub-optimal PAMs are commonly identified when applying high-throughput techniques for PAM elucidation. For instance, a suboptimal PAM for the Type I-E system in *E. coli* is TTTC, while a suboptimal PAM for the I-C system in *B. halodurans* is AAA.

As used herein, the phrase "substantially identical," or "substantial identity" and grammatical variations thereof in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 70%, at least about 75%, at least about 80%, at least about 85%, at least about 90%, at least about 95, 96, 96, 97, 98, or 99% identity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

"Target gene" as used herein refers to any nucleotide sequence encoding a known or putative gene product. The target gene may be a mutated gene involved in a genetic disease.

"Target nucleotide sequence" as used herein refers to the region of the target gene to which the Type I CRISPR/Cas system is designed to bind.

The terms "transformation," "transfection," and "transduction" as used interchangeably herein refer to the introduction of a heterologous nucleic acid into a cell. Such introduction into a cell may be stable or transient. Thus, in some embodiments, a host cell or host organism is stably transformed with a polynucleotide of the invention. In other embodiments, a host cell or host organism is transiently transformed with a polynucleotide of the invention. "Transient transformation" in the context of a polynucleotide means that a polynucleotide is introduced into the cell and does not integrate into the genome of the cell. By "stably introducing" or "stably introduced" in the context of a polynucleotide introduced into a cell is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear, the plasmid and the plastid genome, and therefore includes integration of the nucleic acid construct into, for example, the chloroplast or mitochondrial genome. Stable transformation as used herein can also refer to a transgene that is maintained extrachromasomally, for example, as a minichromosome or a plasmid. In some embodiments, the nucleotide sequences, constructs, expression cassettes can be expressed transiently and/or they can be stably incorporated into the genome of the host organism.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

By the terms "treat," "treating," or "treatment," it is intended that the severity of the subject's condition is reduced or at least partially improved or modified and that some alleviation, mitigation or decrease in at least one clinical symptom is achieved, and/or there is a delay in the progression of the disease or condition, and/or delay of the onset of a disease or illness. With respect to an infection, a disease or a condition, the term refers to, e.g., a decrease in the symptoms or other manifestations of the infection, disease or condition. In some embodiments, treatment provides a reduction in symptoms or other manifestations of the infection, disease or condition by at least about 5%, e.g., about 10%, 15%, 20%, 25%, 30%, 35%, 40%, 45%, 50% or more.

"Type I CRISPR-associated complex for antiviral defense" or "Cascade" as used interchangeably herein refers to a complex of polypeptides involved in processing of pre-crRNAs and subsequent binding to the target DNA in type I CRISPR-Cas systems.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of 2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

2. TYPE I CRISPR/CAS SYSTEM

Figure 1B:
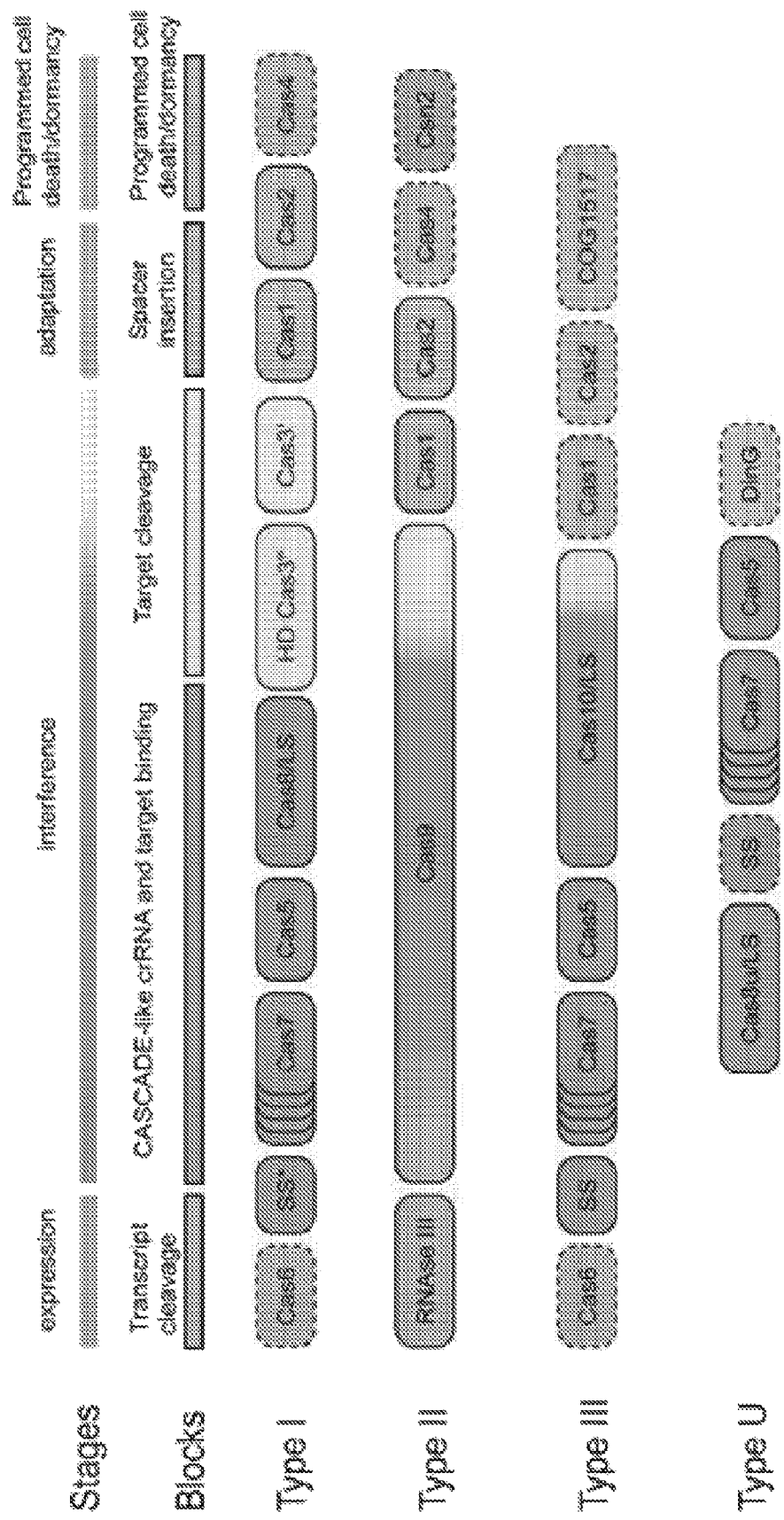
FIG. 1B shows the functional classification of Cas proteins (modified from Makarova et al., Nature Reviews Microbiology (2015) 13:722-736).
Figure 1C:
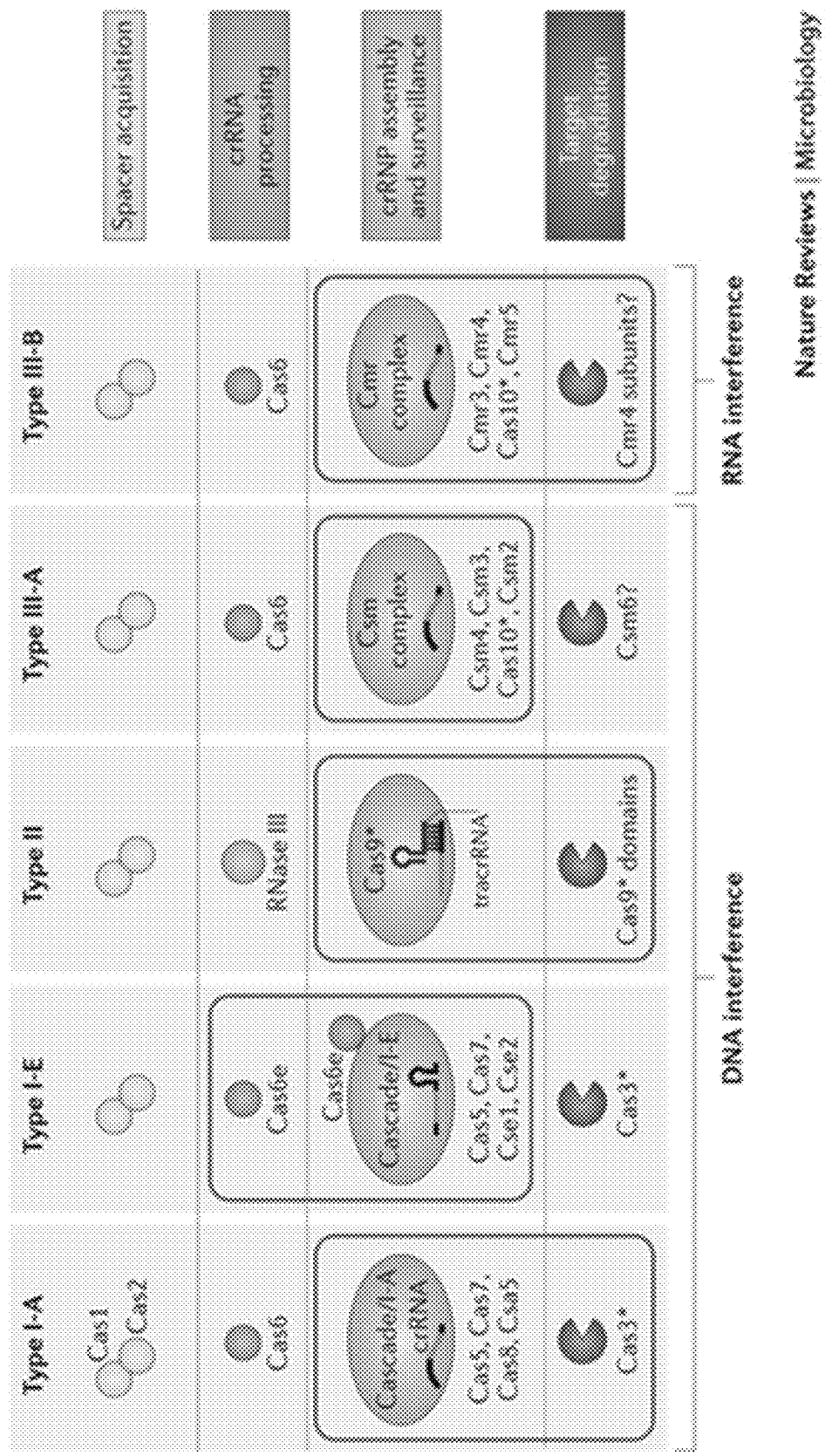
FIG. 1C shows the Diversity of CRISPR-Cas systems (modified from van der Oost et al., Nature Reviews Microbiology (2014) 12:479-492). The CRISPR-associated (Cas) proteins can be divided into distinct functional categories as shown. The three types of CRISPR-Cas systems are defined on the basis of a type-specific signature Cas protein (indicated by an asterisk) and are further subdivided into subtypes. The CRISPR ribonucleoprotein (crRNP) complexes of type I and type III systems contain multiple Cas subunits, whereas the type II system contains a single Cas9 protein. Boxes indicate components of the crRNP complexes for each system. The type III-B system is unique in that it targets RNA, rather than DNA, for degradation.
Figure 2:
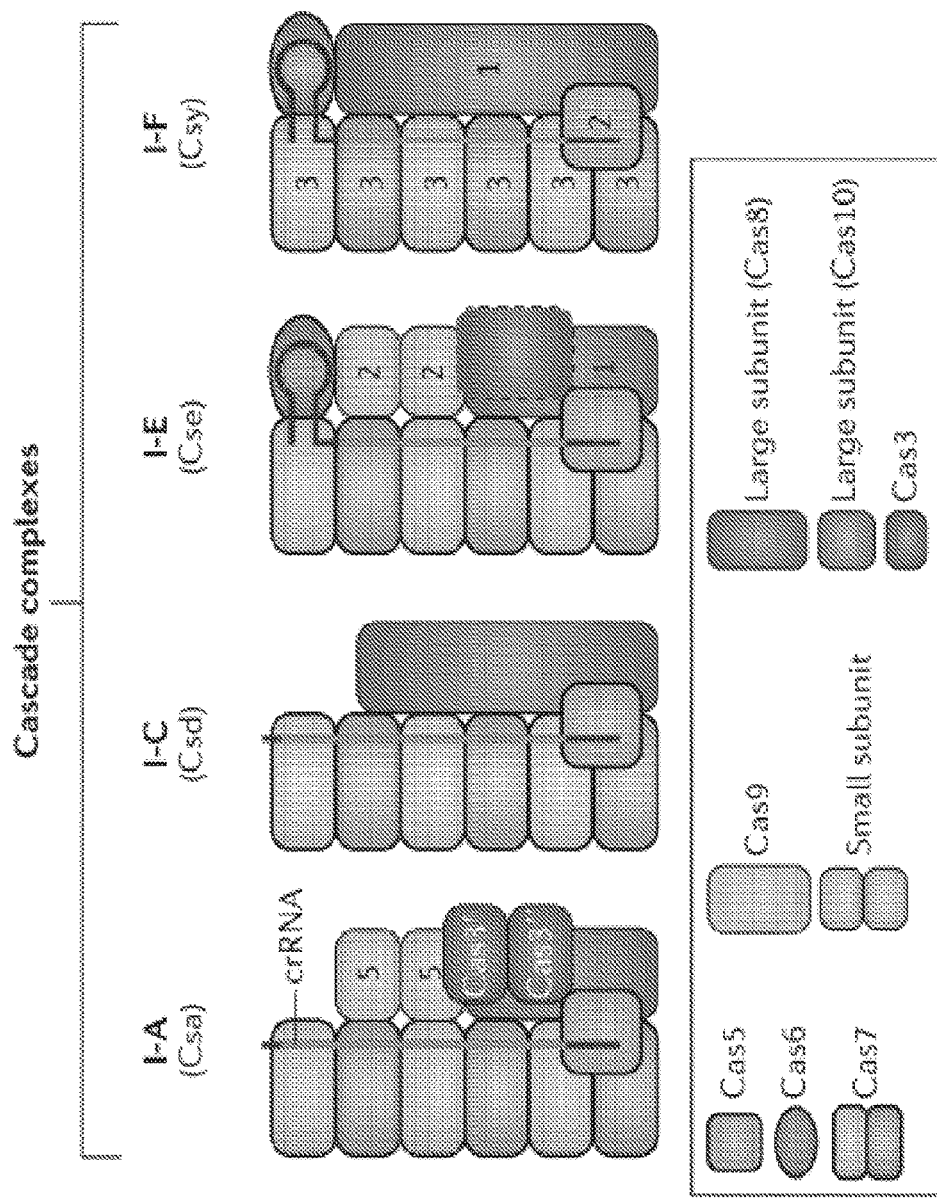
FIG. 2 shows the architecture of crRNP complexes (modified from van der Oost et al., Nature Reviews Microbiology (2014) 12:479-492). Schematic representation of the subunit composition of different CRISPR ribonucleoprotein (crRNP) complexes from all three CRISPR-Cas types. The colors indicate homology with conserved Cas proteins or defined components of the complexes, as shown in the key. The numbers refer to protein names that are typically used for individual subunits of each subtype (for example, subunit 5 of the type I-A (Csa) complex refers to Csa5, whereas subunit 2 of the type I-E (Cse) complex refers to Cse2, and so on). The CRISPR RNA (crRNA) is shown, including the spacer (green) and the flanking repeats (grey). Truncated Cas3 domains (Cas3' and Cas3") may be part of the type I-A complex, and fusions of Cas3 with Cascade subunits (for example, with Cse1) have been found in some type I-E systems (shown as a dashed Cas3 homologue).
Figure 3:
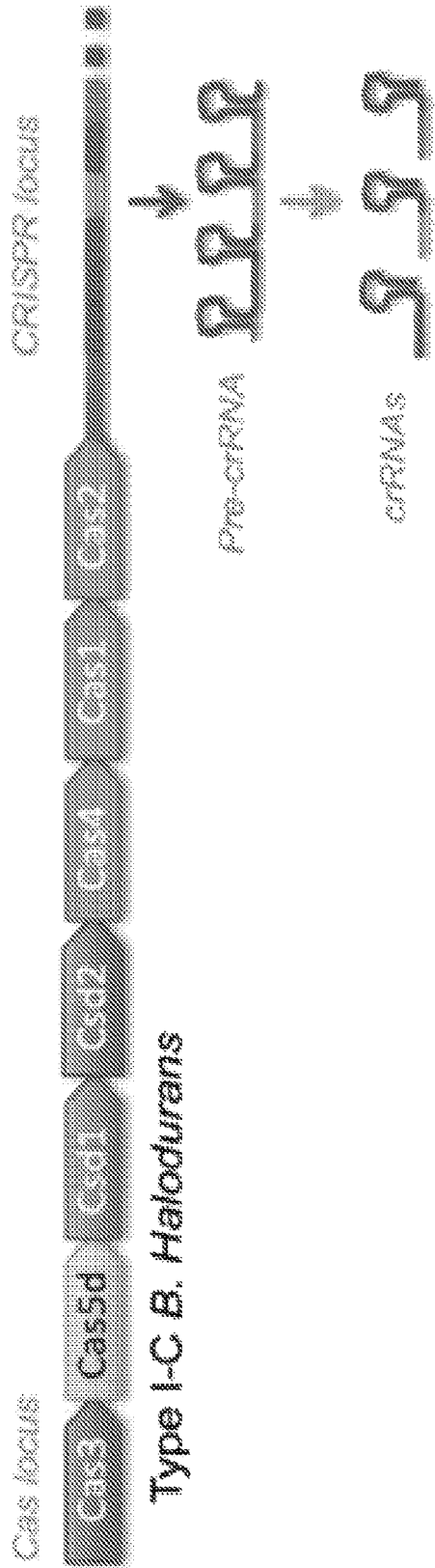
FIG. 3 shows the Type I CRISPR/Cas Locus.
Figure 4:
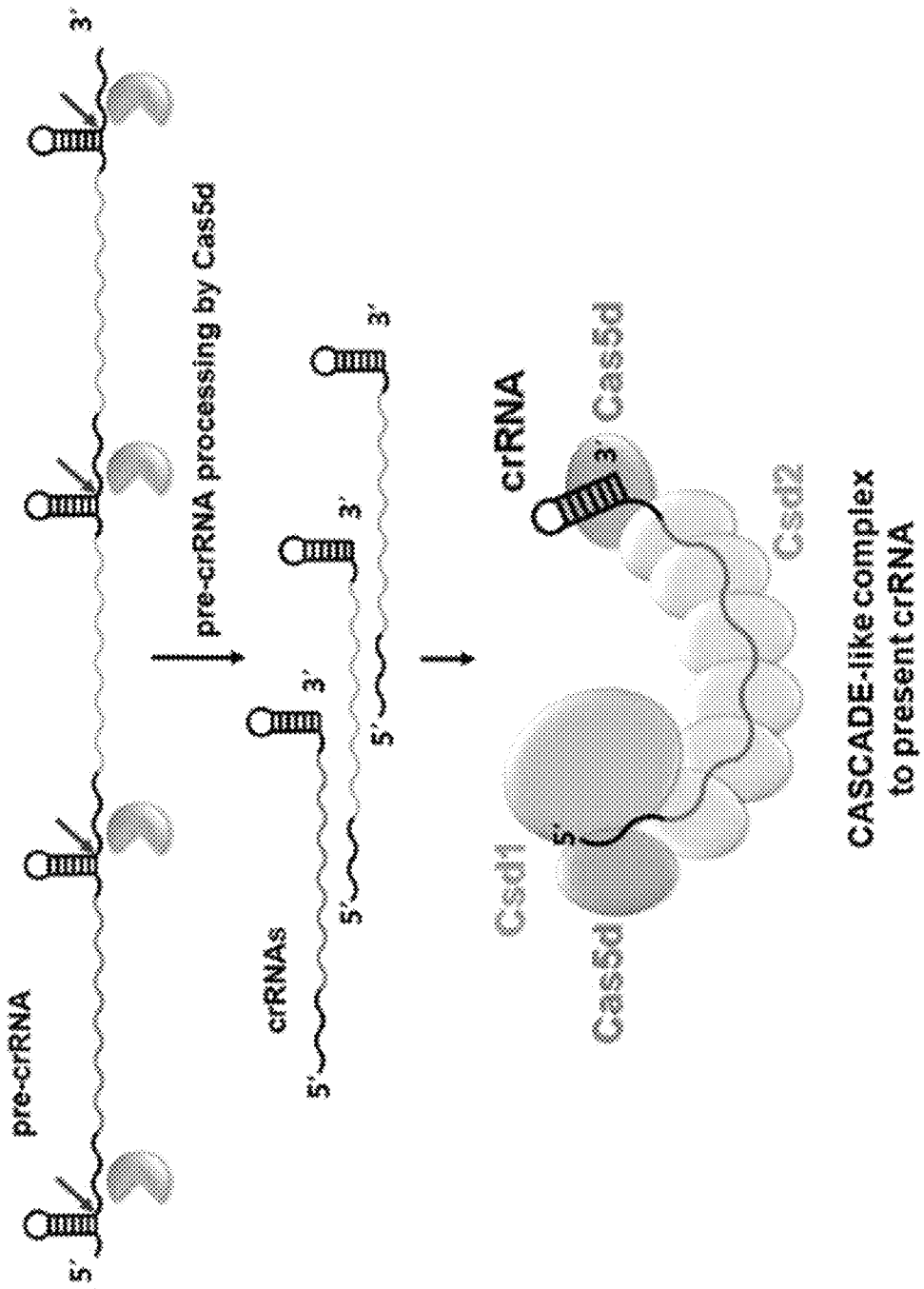
FIG. 4 shows the Type I-C CRISPR/Cas System and the mechanistic model for crRNA-mediated DNA silencing in subtype I-C CRISPR-Cas system (taken from Nam et al., Structure (2012) 20:1574-1584).
Figure 5:
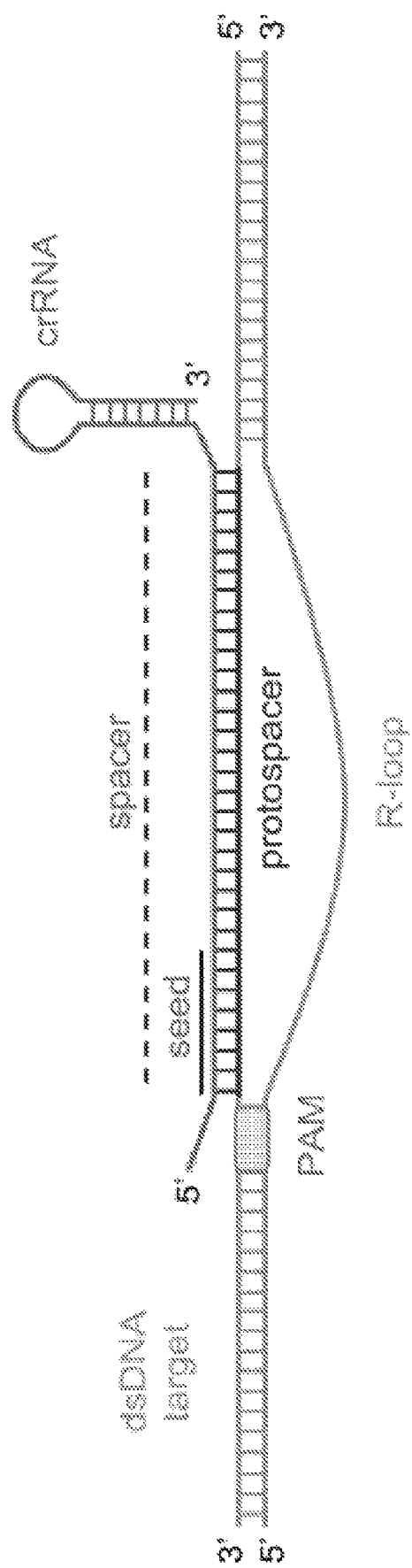
FIG. 5 shows a schematic of crRNA (green) and target DNA (sky blue). The PAM and protospacer of the target are depicted in orange and dark blue, respectively.
Figure 6:
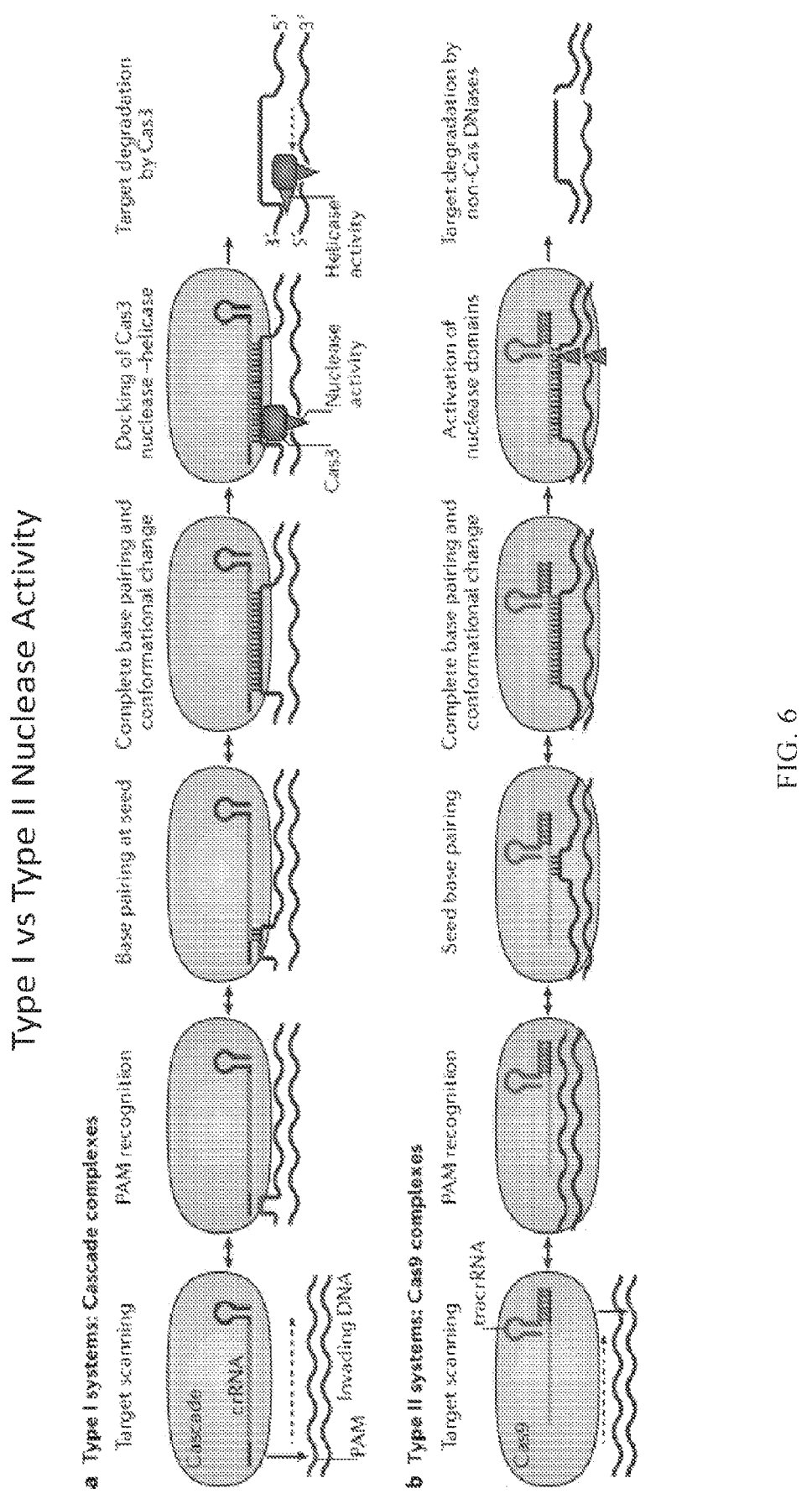
Figure 7:
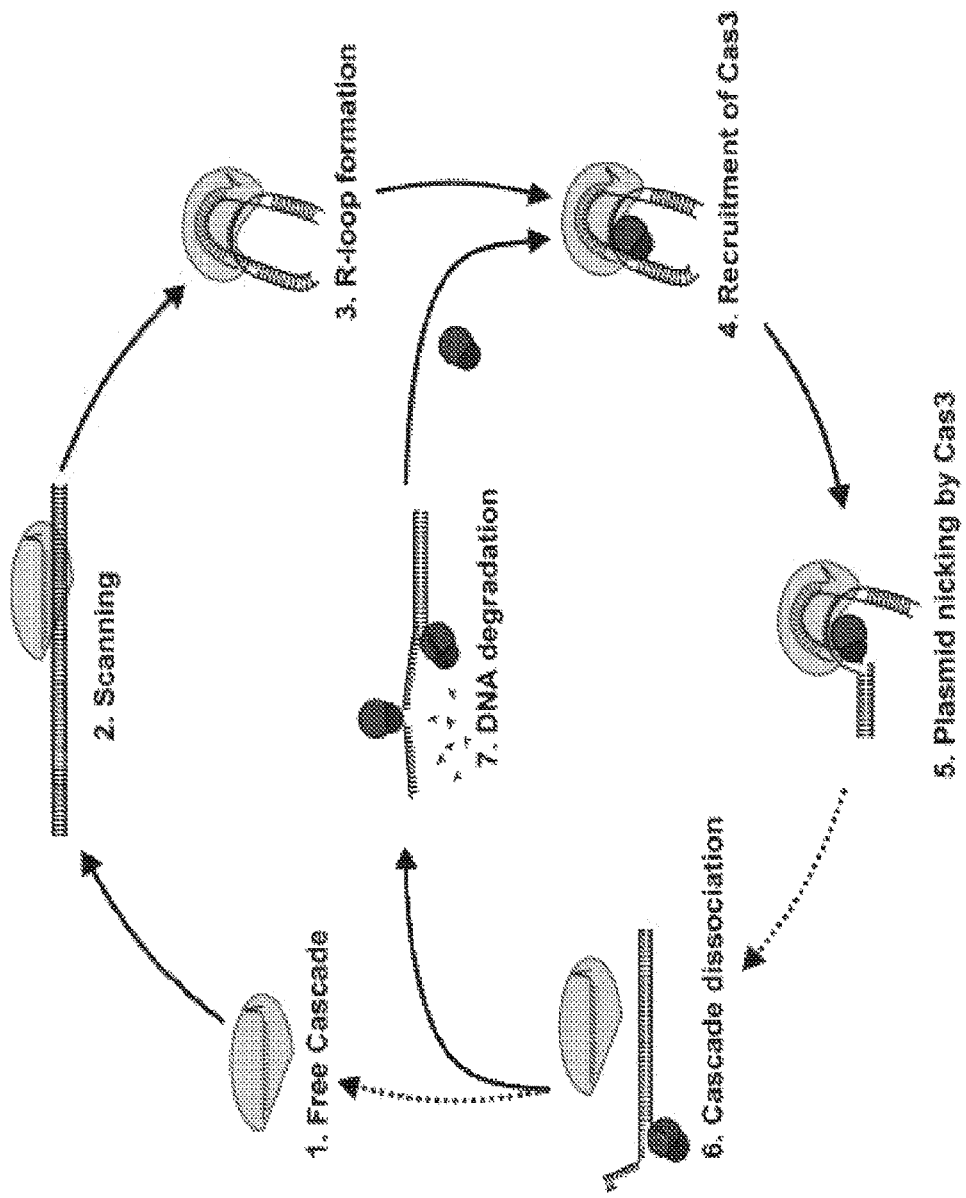
FIG. 7 shows a model of the CRISPR-interference type I pathway in *E. coli*. Steps that are not well-understood are depicted with dashed arrows. (1) Cascade (blue) carrying a crRNA (orange). (2) Cascade associates nonspecifically with the nSC plasmid DNA and scans for a protospacer (red), with protospacer adjacent motif (PAM) (yellow). (3) Sequence specific binding to a protospacer is achieved through base pairing between the crRNA and the complementary strand of the DNA, forming an R-loop. Upon binding, Cascade induces bending of the DNA, and Cascade itself undergoes conformational changes. (4) The Cse1 subunit of Cascade recruits the nuclease/helicase Cas3 (brown). This may be triggered by the conformational changes of Cascade and the target DNA. (5) The HD-domain (dark brown) of Cas3 catalyzes $Mg^{2+}$-dependent nicking of the target DNA at an unknown position, possibly within or near to the R-loop. (6) Plasmid nicking alters the topology of the target plasmid from nSC to relaxed OC, causing a reduced affinity of Cascade for the target. Dissociation of Cascade from the target may involve Cas3 helicase activity. Cascade may then remain associated with Cas3 or may be remobilized to locate new targets (7) Cas3 degrades the entire plasmid in an ATP-dependent manner as it progressively moves (in the 3' to 5' direction) along, unwinds and cleaves the target dsDNA. Exonucleolytic degradation takes place in the 3'-5' direction.
Figure 8:
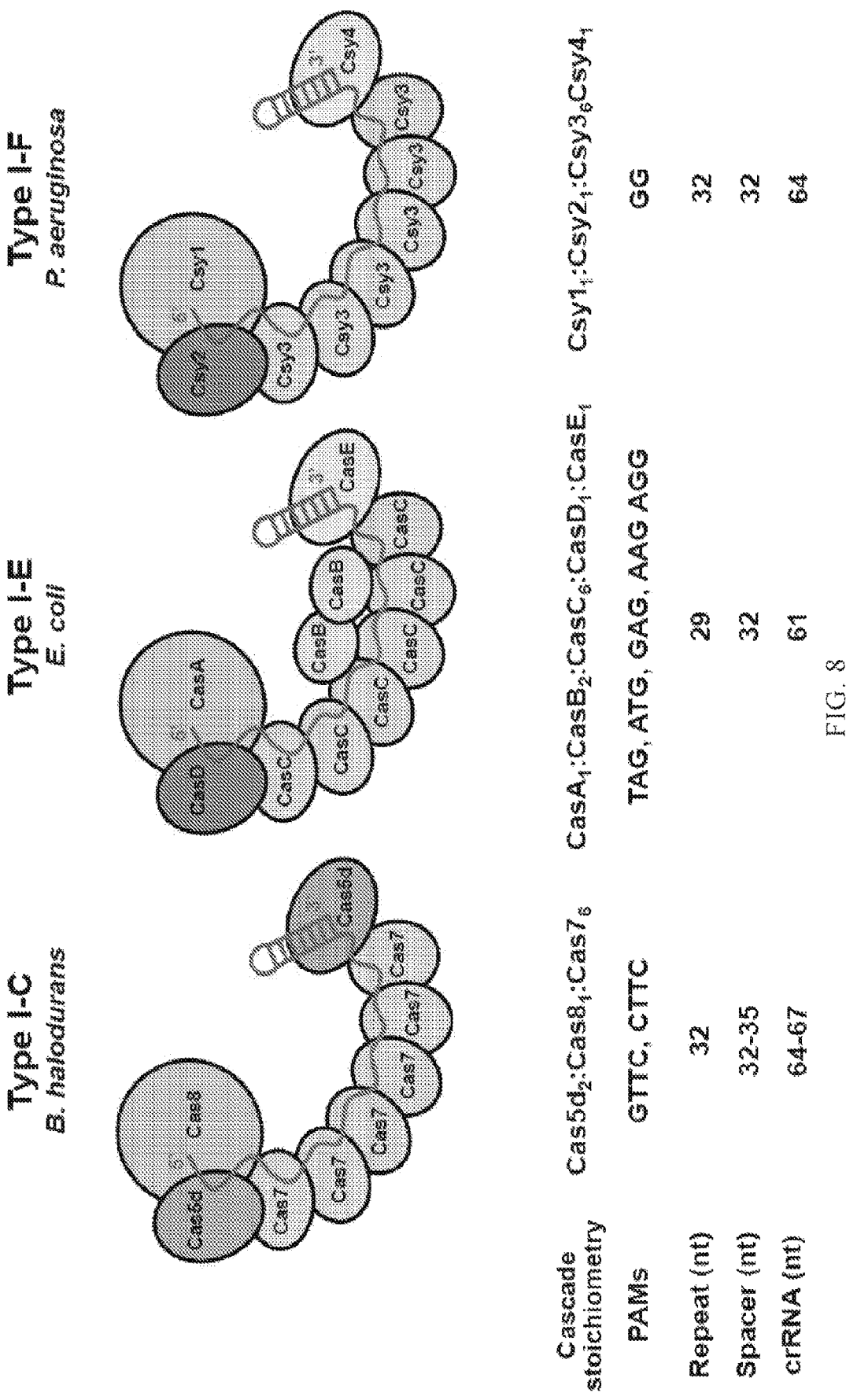
FIG. 8 shows a comparison of Type I CRISPR/Cas systems. The crRNP architecture is illustrated and colors indicate homology with conserved Cas proteins. The crRNA protospacer of the target and processed repeat ends are depicted as orange and blue, respectively.

The present invention is directed to compositions for genome editing, genomic alteration or altering gene expression of a target gene in a eukaryotic cell. The compositions may include a viral vector and a composition such as a Type I CRISPR/Cas system. The CRISPR system is a microbial nuclease system involved in defense against invading phages and plasmids that provides a form of acquired immunity. Three classes of CRISPR systems (Types I, II and III effector systems) are known. See FIGS. 1B and 1C. The Type I subtypes have different Cascade stoichiometry (FIGS. 1C, 2, and 8). The mechanism of Type I action is shown in FIGS. 4-7. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cascade forms a complex with the crRNA, and the protein-RNA pair recognizes its genomic target by complementary base pairing between the 5' end of the crRNA sequence and a predefined DNA sequence, known as the protospacer. This complex is directed to homologous loci of pathogen DNA via regions encoded within the crRNA, i.e., the protospacers, and protospacer-adjacent motifs (PAMs) within the pathogen genome. Base pairing occurs between the crRNA and the target DNA sequence leading to a conformational change. Cas3 dockets onto the DNA target and starts to degrade the target gene sequence. By simply exchanging the crRNA, the Cas3 can be directed to new genomic targets. CRISPR spacers are used to recognize and silence exogenous genetic elements in a manner analogous to RNAi in eukaryotic organisms.

Type I Clustered Regularly Interspaced Short Palindromic Repeats (CRISPR)/Cas systems consist of Cascade (a multimeric complex consisting of three to five proteins that processes crRNA arrays), Cas3 (a protein with nuclease, helicase, and exonuclease activity that is responsible for degradation of the target DNA), and crRNA (stabilizes Cascade complex and directs Cascade and Cas3 to DNA target). There are 6 different Type I subtypes; Type I-A, Type I-B, Type I-C, Type I-D, Type I-E, and Type I-F (see FIG. 1). In some embodiments, a recombinant polynucleotide sequence comprises, consists essentially of, consists of a polynucleotide sequence encoding a subset of type-1 Cascade polypeptides that function to process a CRISPR array and subsequently bind to a target DNA using the spacer of the processed CRISPR RNA (crRNA) as a guide.

In some embodiments, a recombinant polynucleotide of this invention includes a polynucleotide sequence encoding a subset of CRISPR-Cas or Cascade polypeptides, or functional fragments thereof, from a type I CRISPR-Cas system.

The present disclosure relates to a Type I CRISPR/Cas system composition for genome engineering at least one target gene in a eukaryotic cell. The composition includes at least one polynucleotide sequence encoding: (a) a Cascade complex; (b) a Cas3 polypeptide; and/or (c) at least one crRNA, wherein the crRNA targets a target nucleotide sequence from the at least one target gene. The Cascade complex comprises three or more Type I Cascade polypeptides, or functional fragments thereof. The at least one polynucleotide sequence is operably linked to a eukaryotic promoter and includes a nuclear localization signal. The at least one polynucleotide sequence is codon-optimized. In some embodiments, the Type I CRISPR/Cas system includes at least polynucleotide that encodes a Cascade complex and at least one crRNA, wherein the system does not include Cas3 protein. In some embodiments, the Type I CRISPR/Cas system includes at least one polynucleotide that encodes a Cascade complex, a Cas3 protein, and at least one crRNA. In some embodiments, the crRNA is part of a crRNA array.

In aspects of the invention, polypeptides of any known or later identified Type I CRISPR-Cas system can be used. For example, a Type I-A CRISPR-Cas system, a Type I-B CRISPR-Cas system, a Type I-C CRISPR-Cas system, a Type I-D CRISPR-Cas system, a Type I-E CRISPR-Cas system, and/or a Type I-F CRISPR-Cas system may be used.

As used herein, "Type I polypeptide," "Type I CRISPR system polypeptide" or "polypeptides of a Type I CRISPR system" refers to any of a Cas3 polypeptide, Cas3' polypeptide, a Cas3" polypeptide and any one or more of the Type I Clustered Regularly Interspaced Short Palindromic Repeats (CRISPR)-associated complex for antiviral defense ("Cascade") polypeptides. Thus, the term "Type I polypeptide" refers to the polypeptides that make up a Type I-A CRISPR-Cas system, a Type I-B CRISPR-Cas system, a Type I-C CRISPR-Cas system, a Type I-D CRISPR-Cas system, a Type I-E CRISPR-Cas system, and/or a Type I-F CRISPR-Cas system. Each Type-I CRISPR-Cas system comprises at least one Cas3 polypeptide. Cas3 polypeptides generally comprise both a helicase domain and an HD domain; however, in some Type I CRISPR-Cas systems, the helicase and HD domain are found in separate polypeptides, Cas3' and Cas3." In particular, Cas3' encodes the helicase domain whereas Cas3" encodes the HD domain. Consequently, because both domains are required for Cas3 function, Type I subtypes either encode Cas3 (I-C, I-D, I-E, I-F) or Cas3' and Cas3" (I-A, I-B).

As used herein, "Type I Cascade polypeptides" refers to a complex of polypeptides involved in processing of CRISPR arrays and subsequent binding to the target DNA in type I CRISPR-Cas systems. These polypeptides include, but are not limited to, the Cascade polypeptides of Type I subtypes I-A, I-B, I-C, I-D, I-E and I-F. Non-limiting examples of Type I-A polypeptides include Cas7 (Csa2), Cas8a1 (Csx13), Cas8a2 (Csx9), Cas5, Csa5, Cas6a, Cas3' and/or a Cas3". Non-limiting examples of Type I-B polypeptides include Cas6b, Cas8b (Csh1), Cas7 (Csh2) and/or Cas5. Non-limiting examples of Type-IC polypeptides include Cas5d, Cas8c (Csd1), and/or Cas7 (Csd2). Non-limiting examples of Type-ID polypeptides include Cas10d (Csc3), Csc2, Csc1, and/or Cas6d. Non-limiting examples of Type I-E polypeptides include Cse1 (CasA), Cse2 (CasB), Cas7 (CasC), Cas5 (CasD) and/or Cas6e (CasE). Non-limiting examples of Type I-F polypeptides include Cys1, Cys2, Cas7 (Cys3) and/or Cas6f (Csy4).

Accordingly, a Type I CRISPR-Cas system may comprise, consist essentially of, or consist of: (a) a nucleotide sequence encoding a Cas7 (Csa2) polypeptide, a nucleotide sequence encoding a Cas8a1 (Csx13) polypeptide or a Cas8a2 (Csx9) polypeptide, a nucleotide sequence encoding a Cas5 polypeptide, a nucleotide sequence encoding a Csa5 polypeptide, a nucleotide sequence encoding a Cas6a polypeptide, a nucleotide sequence encoding a Cas3' polypeptide, and a nucleotide sequence encoding a Cas3" polypeptide (Type I-A); (b) a nucleotide sequence encoding a Cas6b polypeptide, a nucleotide sequence encoding a Cas8b (Csh1) polypeptide, a nucleotide sequence encoding a Cas7 (Csh2) polypeptide, a nucleotide sequence encoding a Cas5 polypeptide, a nucleotide sequence encoding a Cas3' polypeptide, and a nucleotide sequence encoding a Cas3" polypeptide (Type I-B); (c) a nucleotide sequence encoding a Cas5d polypeptide, a nucleotide sequence encoding a Cas8c (Csd1) polypeptide, a nucleotide sequence encoding a Cas7 (Csd2) polypeptide and a nucleotide sequence encoding a Cas3 polypeptide (Type I-C); (d) a nucleotide sequence encoding a Cas10d (Csc3) polypeptide, a nucleotide sequence encoding a Csc2 polypeptide, a nucleotide sequence encoding a Csc1 polypeptide, a nucleotide sequence encoding a Cas6d polypeptide, and a nucleotide sequence encoding a Cas3 polypeptide (Type I-D); (e) a nucleotide sequence encoding a Cse1 (CasA) polypeptide, a nucleotide sequence encoding a Cse2 (CasB) polypeptide, a nucleotide sequence encoding a Cas7 (CasC) polypeptide, a nucleotide sequence encoding a Cas5 (CasD) polypeptide, a nucleotide sequence encoding a Cas6e (CasE) polypeptide, and a nucleotide sequence encoding a Cas3 polypeptide (Type I-E); and/or (f) a nucleotide sequence encoding a Cys1 polypeptide, a nucleotide sequence encoding a Cys2 polypeptide, a nucleotide sequence encoding a Cas7 (Cys3) polypeptide and a nucleotide sequence encoding a Cas6f polypeptide, and a nucleotide sequence encoding a Cas3 polypeptide (Type I-F).

In some embodiments of the invention, in a Type I CRISPR-Cas system, the Cas6 polypeptides (e.g., Cas6d, Cas6e, or Cas6f) may be omitted when a processed form of a CRISPR array is expressed.

a) Cascade

Type I CRISPR/Cas systems include, but are not limited to, the Cascade polypeptides of Type I subtypes 1-A, 1-B, 1-C, 1-D, 1-E and 1-F. Examples of Type I-A polypeptides include, but is not limited to, Cas7 (Csa2), Cas8a1 (Csx13), Cas8a2 (Csx9), Cas5, Csa5, Cas6a, Cas3' and/or a Cas3. Examples of Type I-B polypeptides include, but is not limited to, Cas6b, Cas8b (Csh1), Cas7 (Csh2) and/or Cas5. Examples of Type I-C polypeptides include, but is not limited to, Cas5d, Cas8c (Csd1), and/or Cas7 (Csd2). Examples of Type I-D polypeptides include, but is not limited to, Cas10d (Csc3), Csc2, Csc1, and/or Cas6d. Examples of Type I-E polypeptides include, but is not limited to, Cse1 (CasA), Cse2 (CasB), Cas7 (CasC), Cas5 (CasD) and/or Cas6e (CasE). Examples of Type I-F polypeptides include, but is not limited to, Csy1, Csy2, Cas7 (Csy3) and/or Cas6f (Csy4). In some embodiments, the Type I-C Cascade consists of CasSd (processes crRNA), Cas7, and Casa. In some embodiments, the Type I-E Cascade consists of CasA, CasB, Case, Caso (helps process crRNA), and CasE (helps process crRNA). In some embodiments, the Type I-F Cascade consists of Csy1, Csy2, Csy3, and Csy4 (processes crRNA). Other Cascade polypeptides are described in International Application Publication No. WO2015/155686, which is herein incorporated by reference. In some embodiments, at least one cascade polypeptide is encoded by a polynucleotide sequence of SEQ ID NO: 14, SEQ ID NO: 16, SEQ ID NO: 18, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31 b) Cascade Fusion Protein

The Type I CRISPR/Cas system may include a Cascade fusion protein. The Cascade fusion protein may comprise two heterologous polypeptide domains, a first polypeptide domain and a second polypeptide domain. In some embodiments, the first polypeptide domain comprises a Cascade polypeptide and the second polypeptide domain has an activity such as transcription activation activity, transcription repression activity, transcription release factor activity, histone modification activity, nuclease activity, nucleic acid association activity, methylase activity, or demethylase activity. In some embodiments, the first polypeptide domain comprises a Cascade polypeptide and the second polypeptide domain comprises a label or tag. In some embodiments, the second polypeptide domain is fused to the N-terminal end of the first polypeptide domain. In some embodiments, the second polypeptide domain is fused to the C-terminal end of the first polypeptide domain.

i) Transcription Activation Activity

The second polypeptide domain may have transcription activation activity, i.e., a transactivation domain. For example, the transactivation domain may include a VP16 protein, multiple VP16 proteins, such as a VP48 domain or VP64 domain, or p65 domain of NF kappa B transcription activator activity.

ii) Transcription Repression Activity

The second polypeptide domain may have transcription repression activity. The second polypeptide domain may have a Kruppel associated box activity, such as a KRAB domain, ERF repressor domain activity, Mxi1 repressor domain activity, SID4X repressor domain activity, Mad-SID repressor domain activity or TATA box binding protein activity. In some embodiments, the Cascade fusion protein may include an amino acid sequence of SEQ ID NO: 33, SEQ ID NO: 35, SEQ ID NO: 37, SEQ ID NO: 39 or SEQ ID NO: 41. In some embodiments, the Cascade fusion protein is encoded by a polynucleotide sequence of SEQ ID NO: 32, SEQ ID NO: 34, SEQ ID NO: 36, SEQ ID NO: 38, or SEQ ID NO: 40. In some embodiments, a modified lentiviral construct or vector includes the Cascade fusion protein that includes an amino acid sequence of SEQ ID NO: 33, SEQ ID NO: 35, SEQ ID NO: 37, SEQ ID NO: 39 or SEQ ID NO: 41. In some embodiments, a modified lentiviral construct or vector includes the Cascade fusion protein encoded by a polynucleotide sequence of SEQ ID NO: 32, SEQ ID NO: 34, SEQ ID NO: 36, SEQ ID NO: 38, or SEQ ID NO: 40. In some embodiments, the modified lentiviral construct or vector includes a polynucleotide sequence of any one of SEQ ID NO: 44, SEQ ID NO: 45, SEQ ID NO: 46, or SEQ ID NO: 47.

iii) Transcription Release Factor Activity

The second polypeptide domain may have transcription release factor activity. The second polypeptide domain may have eukaryotic release factor 1 (ERF1) activity or eukaryotic release factor 3 (ERF3) activity.

iv) Histone Modification Activity

The second polypeptide domain may have histone modification activity. The second polypeptide domain may have histone deacetylase, histone acetyltransferase, histone demethylase, or histone methyltransferase activity. The histone acetyltransferase may be p300 or CREB-binding protein (CBP) protein, or fragments thereof.

v) Nuclease Activity

The second polypeptide domain may have nuclease activity that is different from the nuclease activity of the Cas3 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

vi) Nucleic Acid Association Activity

The second polypeptide domain may have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

vii) Methylase Activity

The second polypeptide domain may have methylase activity, which involves transferring a methyl group to DNA, RNA, protein, small molecule, cytosine or adenine. The second polypeptide domain may include a DNA methyltransferase.

viii) Demethylase Activity

The second polypeptide domain may have demethylase activity. The second polypeptide domain may include an enzyme that remove methyl (CH3-) groups from nucleic acids, proteins (in particular histones), and other molecules. Alternatively, the second polypeptide may covert the methyl group to hydroxymethylcytosine in a mechanism for demethylating DNA. The second polypeptide may catalyze this reaction. For example, the second polypeptide that catalyzes this reaction may be Tet1.

ix) Tag or Label

The second polypeptide domain may comprise a tag or label. In some embodiments the tag may be an epitope tag. For examples, the epitope tag may include FLAG, such as FLAG (SEQ ID NO: 1) and 3×FLAG, HA (SEQ ID NO: 2), myc (SEQ ID NO: 3), V5 (SEQ ID NO: 4), E-tag (SEQ ID NO: 5), VSV-g (SEQ ID NO: 6), 6×His (SEQ ID NO: 7), and HSV (SEQ ID NO: 8).

c) Cas3

The Type I CRISPR/Cas system may include a Cas3 protein. Cas3 protein has nuclease, helicase, and exonuclease activity. The Cas3 protein may be from any bacterial or archaea species, such as B. halodurans (e.g. GenBank Accession No. BAB04055.1, etc.), E. coli (e.g. GenBank Accession No. AIN33136.1, AAC75803.1, etc.), or P. aeruginosa (e.g. GenBank Accession No. EOT14076.1, etc.). The Cas3 protein may be mutated so that the nuclease, helicase, and/or exonuclease activity is inactivated. In some embodiments, the Cas3 polypeptide may include an amino acid sequence of SEQ ID NO: 15, SEQ ID NO: 17, or SEQ ID NO: 19. In some embodiments, the Cas3 polypeptide is encoded by a polynucleotide sequence of SEQ ID NO: 14, SEQ ID NO: 16, or SEQ ID NO: 18.

d) crRNA

A "CRISPR array" or "CRISPR RNA" as used herein means a nucleic acid that comprises at least one spacer sequence and at least one repeat sequence, or a portion thereof, linked to the 5' end of the spacer sequence. The design of a CRISPR array of this invention will vary based on the planned use. The CRISPR arrays of this invention are synthetic, made by man and not found in nature. In some embodiments, a CRISPR array may comprise, from 5' to 3', a repeat sequence (full length or portion thereof ("handle")), a spacer sequence, and a repeat sequence (full length or portion thereof). In some embodiments, a CRISPR array may comprise, from 5' to 3', a repeat sequence (full length or portion thereof ("handle")) and a spacer sequence.

In some embodiments, a CRISPR array may comprise at least one spacer sequence having a 5' end and a 3' end and linked at its 3' end to the 5' end of at least one repeat sequence or a portion of the least one repeat sequence to form a "spacer-repeat sequence" having a 5' end and a 3' end. In other embodiments, a CRISPR array may comprise a "minimal CRISPR array," comprising a spacer having a 5' end and a 3' end and linked at its 5' end to a portion of a repeat sequence. In some embodiments, a CRISPR array may comprise a spacer-repeat sequence that comprises a further repeat sequence, or portion thereof, the further repeat sequence linked at its 3' end to the 5' end of a spacer-repeat sequence, thereby forming a "repeat-spacer-repeat sequence." In still further embodiments, a repeat-spacer-repeat sequence may be linked at the 3' end to at least one to up to about nine further spacer-repeat sequences (e.g., 1, 2, 3, 4, 5, 6, 7, 8, 9 additional consecutive spacer-repeat sequences). In such embodiments, each of the at least one up to nine additional consecutive spacer-repeat sequences, each having a 5' end and a 3' end, are linked at the 3' end to the 5' end of the next spacer-repeat sequence (e.g., a first spacer-repeat sequence linked at the 3' end to a second spacer-repeat sequence) and so on, to form, for example, a repeat-spacer-repeat-spacer-repeat with up to 10 spacer sequences alternating with up to 11 repeat sequences.

A CRISPR array of this invention can be "processed" or "unprocessed." An "unprocessed CRISPR array" may comprise at least one spacer linked at both the 5' end and at the 3' end to a full-length repeat sequence ("repeat-spacer-repeat" sequence). An unprocessed CRISPR array can comprise further spacer-repeat sequences linked to the 3' end of the repeat-spacer-repeat sequence (e.g., repeat-spacer-repeat-spacer-repeat-spacer-repeat and the like, up to about ten "spacer-repeat sequence" units). The design of a "processed CRISPR array will vary depending on its intended for use. Thus, in some embodiments, a "processed CRISPR array" can comprise a spacer sequence linked at its 5' end to the 3' end of a portion of consecutive nucleotides of a repeat sequence (e.g., "a handle"). In some embodiments, a processed CRISPR array can further comprise a full length repeat sequence or a portion of consecutive nucleotides of a repeat sequence, the full length repeat sequence or portion of a repeat sequence being linked at its 5' end to the 3' end of the spacer sequence.

In representative embodiments, an unprocessed CRISPR array can comprise a repeat sequence having a 5' end and a 3' end, and at least one spacer-repeat sequence having a 5' end and a 3' end, and the repeat sequence is linked at its 3' end to the 5' end of the at least one spacer-repeat sequence, wherein when more than one spacer-repeat sequence is present, the spacer-repeat sequences are consecutive to one another, each having a 5' end and a 3' end, and linked at the 3' end to the 5' end of the next spacer-repeat sequence. In some embodiments, an unprocessed CRISPR array, Type II crRNA or Type III crRNA may comprise up to nine additional consecutive spacer-repeat sequences, each having a 5' end and a 3' end and each linked at the 3' end to the 5' end of the next-spacer-repeat sequence. When processed, the leading repeat sequence is cleaved off, while the terminal repeat sequence is cleaved and retained with the spacer as part of Cascade.

In some aspects, a processed CRISPR array may be introduced with polypeptides of a Type I CRISPR-Cas system. In representative aspects, a processed Type I crRNA may comprise, consist essentially of, or consist of: (A) a first portion of a Type I repeat sequence having a 5' end and a 3' end; (B) a spacer sequence having a 5' end and a 3' end; and (C) (i) a full length Type I repeat sequence having a 5' end and a 3' end, or (ii) a second portion of a Type II repeat sequence having a 5' end and a 3' end, the second portion of the Type I repeat sequence comprising: (a) a portion of consecutive nucleotides of a Type I repeat sequence from the 5'-most end of the Type I repeat sequence through the hairpin (e.g., the hairpin having a 5' end and a 3' end and the second portion comprising a portion of consecutive nucleotides of a Type I repeat sequence from the 5'-most end of the Type I repeat sequence through the 3' end of the hairpin), or (b) a portion of consecutive nucleotides of a Type I repeat sequence from the 5'-most end of the Type I repeat sequence up to the base (5' end) of the stem loop (e.g., the stem loop having a 5' end and a 3' end and the second portion comprising a portion of consecutive nucleotides of a Type I repeat sequence from the 5'-most end of the Type I repeat sequence up to the 5' end of the stem loop), wherein the spacer sequence is linked at its 5' end to the 3' end of the first portion of a Type I repeat sequence and linked at its 3' end to the 5' end of the full length Type I repeat or the 5' end of the second portion of a Type I repeat. In some embodiments, the first portion of a Type I repeat comprises from about 5 consecutive nucleotides to about 10 (e.g., 5, 6, 7, 8, 9, 10) consecutive nucleotides from the 3'-most end of the Type I repeat sequence. In representative embodiments, the first portion of a Type I repeat comprises about 8 consecutive nucleotides from the 3'-most end of the Type I repeat sequence. In some embodiments, a spacer of a Type I crRNA may be at least about 70% complementary to a target nucleic acid. In some embodiments, the spacer sequence of a Type I crRNA may comprise, consist essentially of, or consist of a length of about 25-100 nucleotides. In aspects of the invention, the spacer guides the Type I CRISPR-Cas polypeptides to one strand of the target DNA and the Cas3 polypeptide to the opposite strand of the target DNA where the Cas3 polypeptide begins degradation of the target DNA and thus the chromosome in a 3' to 5' direction.

In some embodiments, the 5' region of a spacer sequence can be identical to a target DNA while the 3' region of the spacer can be substantially identical to the target DNA and therefore the overall complementarity of the spacer sequence to the target DNA is less than 100%. Thus, for example, the first 5, 6, 7, 8, 9, 10, 11, 12, 13, 14, 15, 16, and the like, nucleotides in the 3' region of, for example, a 20 nucleotide spacer sequence (seed region) can be 100% complementary to the target DNA, while the remaining nucleotides in the 5' region of the spacer sequence are substantially complementary (e.g., at least about 70% complementary) to the target DNA. In some embodiments, the first 5 to 12 nucleotides of the 3' end of the spacer sequence can be 100% complementary to the target DNA, while the remaining nucleotides in the 5' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA. In some embodiments, the 3' end of the spacer sequence can have about 75% to about 99% complementarity to the target DNA, while the remaining nucleotides in the 5' region of the spacer sequence can have at least about 50% to about 99% complementarity to the target DNA. In other embodiments, the first 7 to 10 nucleotides in the 3' end of the spacer sequence can have about 75% to about 99% complementarity to the target DNA, while the remaining nucleotides in the 5' region of the spacer sequence can have about 50% to about 99% complementarity to the target DNA. In other embodiments, the first 7 to 10 nucleotides in the 3' end of the spacer sequence can be fully (100%) complementary to the target DNA, while the remaining nucleotides in the 5' region of the spacer sequence can be substantially complementary (e.g., at least about 70% complementarity) to the target DNA. In representative embodiments, the first 10 nucleotides (within the seed region) of the spacer sequence can be 100% complementary to the target DNA, while the remaining nucleotides in the 5' region of the spacer sequence can be substantially complementary (e.g., at least about 70% complementary) to the target DNA. In an exemplary embodiment, the 5' region of a spacer sequence (e.g., the first 8 nucleotides at the 5' end, the first 10 nucleotides at the 5' end, the first 15 nucleotides at the 5' end, the first 20 nucleotides at the 5' end) can be about 75% identical or more (about 75% to about 100% identity) to a target DNA, while the remainder of the spacer sequence can be about 50% or more identical to the target DNA. Thus, for example, the first 8 nucleotides at the 5' end of a spacer sequence can be 100% identical to the target nucleotide sequence or it can have one or two mutations and therefore can be about 88% identical or about 75% identical to a target DNA, respectively, while the remainder of the spacer nucleotide sequence can be at least about 50% or more identical to the target DNA.

In some embodiments, a spacer sequence of this invention can be about 25 nucleotides to about 100 nucleotides in length for a CRISPR array (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein). In some particular embodiments, a spacer nucleotide sequence can be a length of about 25 to about 90 nucleotides, about 25 to about 80 nucleotides, about 25 to about 50 nucleotides, about 25 to about 40 nucleotides, about 25 to about 35 nucleotides, about 25 to about 30 nucleotides, at least about 25 nucleotides, at least about 30 nucleotides, at least about 35 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides in length, or more, and any value or range therein. In some embodiments, spacers of increased length exhibit greater specificity, where specificity is defined by the fraction of mismatches needed to disrupt targeting.

In representative embodiments, a spacer sequence of a Type I CRISPR spacer-repeat nucleic acid of the invention comprises at least about 25 consecutive nucleotides of a target DNA or target nucleic acid, wherein at the 3' end of the spacer at least about 10 consecutive nucleotides of the at least about 25 consecutive nucleotides comprise at least about 90% complementarity to the target nucleic acid, wherein the target nucleic acid is adjacent to a protospacer adjacent motif (PAM) sequence in the genome of a bacterium or archaeon of interest. The motif varies widely between Type I subtypes. For instance, the Type I-E system in *E. coli* recognizes a 4-base motif (read 5' to 3') that includes, but is not limited to, CTTN, CCTN, CTCN, CATN, TTTG, TATG, ATTG, and GTTV (where N is any nucleotide and V is any nucleotide except T). Separately, the 3-base motif (read 5' to 3') for the Type I-C system in *Bacillus halodurans* may be, for example, GAA, GAG, GGA, and AAA. The PAM is initially recognized by proteins within Cascade, DNA unwinding and evaluation of the base pairing between the CRISPR RNA spacer and the protospacer. Non-functional PAMs are never bound by Cascade, resulting in Cascade ignoring protospacers that are perfectly complementary to the CRISPR RNA spacer if flanked by this PAM. PAMs can be determined through bioinformatics analysis of the natural DNA targets of CRISPR arrays or through the experimental screening of potential PAM sequences through plasmid destruction.

Type I crRNA arrays include 61-67 nucleotide (nt) spacers complementary to a DNA target, flanked by 29-32 nt repeat sequences unique to each Type I subtype. Transcription of the crRNA array produces pre-crRNA that is processed via cleavage of a single site in each repeat sequence. The resulting mature crRNA includes of a 5' tail, the full-length spacer, and a 3' hairpin. The number of crRNA, singly or in a CRISPR array, administered to the cell may be at least 1 crRNA, at least 2 different crRNA, at least 3 different crRNA at least 4 different crRNA, at least 5 different crRNA, at least 6 different crRNA, at least 7 different crRNA, at least 8 different crRNA, at least 9 different crRNA, at least 10 different crRNAs, at least 11 different crRNAs, at least 12 different crRNAs, at least 13 different crRNAs, at least 14 different crRNAs, at least 15 different crRNAs, at least 16 different crRNAs, at least 17 different crRNAs, at least 18 different crRNAs, at least 18 different crRNAs, at least 20 different crRNAs, at least 25 different crRNAs, at least 30 different crRNAs, at least 35 different crRNAs, at least 40 different crRNAs, at least 45 different crRNAs, or at least 50 different crRNAs. The number of crRNA administered to the cell may be between at least 1 crRNA to at least 50 different crRNAs, at least 1 crRNA to at least 45 different crRNAs, at least 1 crRNA to at least 40 different crRNAs, at least 1 crRNA to at least 35 different crRNAs, at least 1 crRNA to at least 30 different crRNAs, at least 1 crRNA to at least 25 different crRNAs, at least 1 crRNA to at least 20 different crRNAs, at least 1 crRNA to at least 16 different crRNAs, at least 1 crRNA to at least 12 different crRNAs, at least 1 crRNA to at least 8 different crRNAs, at least 1 crRNA to at least 4 different crRNAs, at least 4 crRNAs to at least 50 different crRNAs, at least 4 different crRNAs to at least 45 different crRNAs, at least 4 different crRNAs to at least 40 different crRNAs, at least 4 different crRNAs to at least 35 different crRNAs, at least 4 different crRNAs to at least 30 different crRNAs, at least 4 different crRNAs to at least 25 different crRNAs, at least 4 different crRNAs to at least 20 different crRNAs, at least 4 different crRNAs to at least 16 different crRNAs, at least 4 different crRNAs to at least 12 different crRNAs, at least 4 different crRNAs to at least 8 different crRNAs, at least 8 different crRNAs to at least 50 different crRNAs, at least 8 different crRNAs to at least 45 different crRNAs, at least 8 different crRNAs to at least 40 different crRNAs, at least 8 different crRNAs to at least 35 different crRNAs, 8 different crRNAs to at least 30 different crRNAs, at least 8 different crRNAs to at least 25 different crRNAs, 8 different crRNAs to at least 20 different crRNAs, at least 8 different crRNAs to at least 16 different crRNAs, or 8 different crRNAs to at least 12 different crRNAs.

In some aspects, a target nucleotide sequence is located adjacent to or flanked by a PAM (protospacer adjacent motif). While PAMs are often specific to the particular CRISPR-Cas system, a PAM sequence can be determined by those skilled in the art through established experimental and computational approaches. Thus, for example, experimental approaches include targeting a sequence flanked by all possible nucleotides sequences and identifying sequence members that do not undergo targeting, such as through in vitro cleavage of target DNA or the transformation of target plasmid. In some aspects, a computational approach can include performing BLAST searches of natural spacers to identify the original target DNA sequences in bacteriophages or plasmids and aligning these sequences to determine conserved sequences adjacent to the target sequence.

The crRNA may comprise a complementary polynucleotide sequence of the target DNA sequence followed by a PAM sequence. The crRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. In some embodiments, the PAM sequence may be GTTC, CTTC, TAG, ATG, GAG, AAG, AGG, GG, CCA, CCT, CCG, CCT, CCA, TTC, ATG, and/or CC. The crRNA may target at least one of the promoter region, the enhancer region or the transcribed region of the target gene.

In another aspect, the present invention provides a recombinant CRISPR array comprising two or more repeat nucleotide sequences and one or more spacer nucleotide sequence(s), wherein each spacer nucleotide sequence in said CRISPR array is linked at its 5' end and at its 3' end to a repeat nucleotide sequence. Accordingly, the repeat nucleotide sequences and spacer nucleotide sequences of the CRISPR array alternate with each other, e.g., 5' to 3', repeat, spacer, repeat, and the like.

A "repeat sequence" as used herein, refers to, for example, any repeat sequence of a wild-type Type I CRISPR-Cas locus or a repeat sequence of a synthetic CRISPR array. A repeat sequence useful with this invention can be any known or later identified repeat sequence of a Type I CRISPR-Cas locus or it can be a synthetic repeat designed to function in a Type I CRISPR-Cas system. A repeat sequence may comprise a hairpin structure and/or a stem loop structure. Thus, in some embodiments, a repeat sequence can be identical to or substantially identical to a repeat sequence from a wild-type Type I CRISPR locus. A repeat sequence from a wild-type Type I CRISPR locus may be determined through established algorithms, such as using the CRISP-Rfinder offered through CRISPRdb (see, Grissa et al. *Nucleic Acids Res.* 35 (Web Server issue):W52-7). In some embodiments, a repeat sequence or portion thereof is linked to the 3' end of a spacer sequence. In other embodiments, a repeat sequence or portion thereof is linked to the 5' end of a spacer-repeat sequence, thereby forming a repeat-spacer-repeat sequence. In some embodiments, a repeat sequence comprises, consists essentially of, or consists of at least one nucleotide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides, or any range therein) depending on the particular repeat and whether the CRISPR array comprising the repeat is processed or unprocessed. In some embodiments, a repeat sequence comprises, consists essentially of, or consists of at least about one to about 40 nucleotides. In still other embodiments, a repeat sequence comprises, consists essentially of, or consists of at least about 8 nucleotides to about 40 nucleotides, or any range or value therein. In further embodiments, a repeat sequence can comprise, consist essentially of, or consist of about 10 nucleotides to about 40 nucleotides, about 15 nucleotides to about 40 nucleotides, about 20 nucleotides to about 40 nucleotides, about 25 nucleotides to about 40 nucleotides, about 1 to about 35 nucleotides, about 10 to about 35 nucleotides, about 15 to about 35 nucleotides, about 20 to about 35 nucleotides, about 25 to about 35 nucleotides, about 20 to about 30 nucleotides, and/or about 25 to about 30 nucleotides, or any range or value therein. In representative embodiments, a repeat sequence can comprise, consist essentially of, or consist of about 25 nucleotides to about 38 nucleotides, or any range or value therein. When more than one spacer sequence is present in a CRISPR array, each spacer nucleotide sequence is separated from another by a repeat sequence.

In some embodiments, a repeat sequence linked to the 5' or to the 3' end of a spacer sequence can comprise a portion of a repeat sequence (e.g., 1, 2, 3, 4, 5, 6, 7, 8, 9, 10, 11, 12, 13, 14, 15 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type repeat nucleotide sequence. In representative embodiments, a repeat sequence linked to the 5' end of a spacer sequence can be about eight consecutive nucleotides in length and have at least 90% identity (e.g., at least about 90%, 91%, 92%, 93%, 94%, 95%, 96%, 97%, 98%, 99%, or more) to the same region (e.g., 5' end) of a wild type repeat nucleotide sequence. In representative embodiments, a repeat sequence linked to the 3' end of a spacer sequence in a CRISPR array for Type I system can comprise a portion of consecutive nucleotides of a Type I repeat sequence from the 5'-most end through the hairpin of the Type I repeat sequence (e.g., to the 3' end of the hairpin of the repeat sequence). In further embodiments, a repeat sequence linked to the 3' end of a spacer sequence in a CRISPR array for Type I system can comprise a portion of consecutive nucleotides of a Type I repeat sequence from the 5'-most end up to the base of the stem loop of the Type I repeat sequence (e.g., up to the 5' end of the stem loop structure of the repeat sequence).

In some embodiments, the spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA. Thus, in some embodiments, the spacer sequence can have one, two, three, four, or five mismatches as compared to the target DNA where the mismatches can be contiguous or noncontiguous. In some embodiments, the spacer sequence can have 70% identity to a target DNA. In other embodiments, the spacer nucleotide sequence can have 80% identity to a target DNA. In still other embodiments, the spacer nucleotide sequence can have 85%, 90%, 95%, 96%, 97%, 98%, 99% identity, and the like, to a target nucleotide sequence of a target gene. In representative embodiments, the spacer sequence has 100% complementarity to the target DNA. In particular embodiments, a spacer sequence has complete identity or substantial identity over a region of a target nucleotide sequence that is at least about 25 nucleotides to about 100 nucleotides in length.

A recombinant CRISPR array of the invention can be of any length and include any number of spacer nucleotide sequences alternating with repeat nucleotide sequences, as described above, necessary to achieve the desired level of repression of expression (e.g., repression of transcription) of one or more target genes. In some embodiments, a CRISPR array can include 1 to about 100 spacer nucleotide sequences, each linked on its 5' end and its 3' end to a repeat nucleotide sequence. Thus, in some embodiments, a recombinant CRISPR array of the invention can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more, spacer nucleotide sequences.

A repeat nucleotide sequence of a CRISPR array of the invention can include a nucleotide sequence of any known repeat nucleotide sequence of a Type I CRISPR/Cas system. As described herein, a repeat nucleotide sequence can also be of a synthetic design comprising the secondary structure of a native repeat from a Type I CRISPR/Cas system (e.g., an internal hairpin).

In some embodiments, the at least one spacer nucleotide sequence can be linked at its 3' end to a repeat sequence and linked at its 5' end to about 1 to about 8, about 1 to about 10, about 1 to about 15 nucleotides from the 3' end of a repeat nucleotide sequence (e.g., a portion of a repeat nucleotide sequence). In other embodiments, the at least one spacer nucleotide sequence can be linked at its 5' end to about 2 to about 6, or about 2 to about 4 nucleotides from the 3' end of a repeat nucleotide sequence.

In representative embodiments, the recombinant CRISPER array includes two or more (e.g., 2, 3, 4, 5, 6, 7, 8, 9, 10, or more, as described herein) spacer nucleotide sequences, each spacer nucleotide sequence flanked on its 3' and its 5' end by a repeat nucleotide sequence, and the at least two of the two or more spacer nucleotide sequences of said recombinant CRISPR array can each include a nucleotide sequence that is complementary to a different target nucleotide sequence from a single target gene (e.g., a different region of the same target gene). By targeting at least two different regions of a single target gene, a CRISPR array can be used to modify repression (e.g., increase or decrease the level of repression) of the expression of said target gene. More specifically, a CRISPR array having multiple spacer nucleotide sequences each of which are complementary to a different non-overlapping target nucleotide sequence from a single gene, can provide stronger/ increased repression of expression of that target gene as compared with a CRISPR array having comparatively fewer spacer nucleotide sequences each of which are complementary to different target nucleotide sequences from a single target gene. The level of transcription repression can be further modified by designing a CRISPR array having spacer nucleotide sequences that are complementary to overlapping target nucleotide sequences within the same target gene. Overlapping spacer nucleotide sequences that are complementary to overlapping target nucleotide sequences within the same target gene can result in reduced repression of expression of that target gene as compared to a CRISPR array in which the spacer nucleotide sequences are complementary to different target nucleotide sequences within the same target gene but which said target nucleotide sequences do not overlap. That is, such overlapping spacer sequences have a reduced effect on repression of expression than spacer sequences that do not overlap. Without wishing to be bound to any particular theory it is believed that the overlapping sequences compete with one another, thereby reducing the level of repression as compared with non-overlapping sequences In addition to targeting different locations/regions on a single gene to modulate the repression of that gene, the length of the spacer or its complementarity to the target nucleotide sequence can be altered to modulate repression. Thus, for example, a shorter spacers or a spacer with less complementarity to a target nucleotide sequence will typically result in reduced repression as compared a longer spacer and/or a spacer with greater complementarity to a target nucleotide sequence, respectively.

Accordingly, in some embodiments, repression by a spacer can be increased by adding one or more nucleotides to the length of said spacer, said spacer resulting in increased repression when used with the recombinant nucleic acids of the invention as compared with the same spacer but without the additional nucleotides. In some embodiments, the length of the spacer can be increased by one to about 100 nucleotides, and/or any range or value therein (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more). In some embodiments, the length of the spacer can be increased by about 1 to about 40, about 5 to about 30, 10 to about 30, about 20 to about 30 nucleotides. In other embodiments, the length of the spacer can be increased by about 6 nucleotides, about 8 nucleotides, about 10 nucleotides, about 12 nucleotides, about 18 nucleotides, about 24 nucleotides, and the like.

In further embodiments, repression by a spacer can be decreased by reducing the length of said spacer by one or more nucleotides, said spacer resulting in decreased repression when used with the recombinant nucleic acids of the invention as compared with the same spacer but without a reduced number of nucleotides. Accordingly, in some embodiments, repression by a spacer can be decreased by decreasing the length of the spacer by 1 to about 100 nucleotides, and any range or value therein. In representative embodiments, the length of the spacer can be decreased by about 1 to about 40, about 5 to about 30, 10 to about 30, about 20 to about 30 nucleotides. In other embodiments, the length of the spacer can be decreased by about 6 nucleotides, about 8 nucleotides, about 10 nucleotides, about 12 nucleotides, about 18 nucleotides, about 24 nucleotides, and the like.

In further aspects, a spacer sequence of a CRISPR array of the invention can be complementary to a target nucleotide sequence that is from a coding strand or a plus (top) strand and/or from a non-coding strand or a minus (bottom) strand of a double stranded target gene. As demonstrated herein, designing a recombinant CRISPR array to include spacers targeting a coding/plus strand rather than a non-coding/ minus strand, and vice versa, provides further modulation of repression with targeting of coding/plus strands providing increased or greater repression as compared to targeting of non-coding/minus strands of the same target gene.

These variations of a spacer nucleotide sequence of a CRISPR array construct as described herein and other variations are possible and can be used to repress or modify repression of expression of a target gene. Any combination of the types of spacers described herein as well as other types of spacers can be used alone or in any combination for repressing expression or modulating the repression of expression of a target gene.

Variations in CRISPR array design can be used to achieve a desired level of repression of expression of a target gene. In other embodiments, a recombinant CRISPR array can be designed to include at least two spacer nucleotide sequences each of which include a nucleotide sequence that is complementary to a different target nucleotide sequence from a different target gene, thereby achieving repression of expression of different target genes using a single CRISPR array. Alternatively, different genes can be targeted for repression of expression using two or more recombinant CRISPR arrays. As would be readily understood, various recombinant CRISPR array designs can be constructed and introduced into a cell or an organism in single or in multiple recombinant CRISPR array constructs for use in repressing and/or modulating the expression of one or more target genes in said cell or organism. Thus, for example, various combinations of different types of spacer nucleotide sequences, as described herein, can be introduced on a single recombinant CRISPR array such that expression of one or more target genes can be repressed and/or modulated. Alternatively, in other embodiments, various spacer nucleotide sequences can be introduced on two or more recombinant CRISPR arrays for repressing or modulating expression of one or more target genes.

In some embodiments, a spacer nucleotide sequence of the recombinant CRISPR array of the invention can be fully identical to or substantially identical to a target nucleotide sequence, or complement thereof, from a target gene. In particular embodiments, the one or more spacer nucleotide sequence(s) can have at least about 50% identity to a target nucleotide sequence, or complement thereof. In other embodiments, the one or more spacer nucleotide sequence(s) can have at least about 70% identity to a target nucleotide sequence, or complement thereof. In further embodiments, the one or more spacer nucleotide sequence(s) can have at least about 80% identity to a target nucleotide sequence, or complement thereof. In still further embodiments, the one or more spacer nucleotide sequence(s) can have at least about 85%, 90%, 95%, 96%, 97%, 98%, 99% or 100% identity to a target nucleotide sequence, or complement thereof.

Therefore, a CRISPR array useful with this invention can be a processed CRISPR array or an unprocessed CRISPR array as described herein.

e) Eukaryotic Promoters

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase and directs the initiation of transcription. In general, promoters are found 5', or upstream, relative to the start of the coding region of the corresponding coding sequence. The promoter region may comprise other elements that act as regulators of gene expression. These include, but are not limited to, a -35 element consensus sequence and a -10 consensus sequence (Simpson. 1979. Proc. Natl. Acad. Sci. U.S.A. 76:3233-3237).

Promoters can include, for example, constitutive, inducible, temporally regulated, developmentally regulated, chemically regulated promoters for use in the preparation of recombinant nucleic acid constructs, polynucleotides, expression cassettes and vectors comprising the polynucleotides and recombinant nucleic acid constructs of the invention. These various types of promoters are known in the art.

Thus, in some embodiments, expression of a construct of the invention can be made constitutive, inducible, temporally regulated, developmentally regulated, chemically regulated promoters using the recombinant nucleic acid constructs of the invention operatively linked to the appropriate promoter functional in an organism of interest. In representative embodiments, repression can be made reversible using the recombinant nucleic acid constructs of the invention operatively linked to, for example, an inducible promoter functional in an organism of interest.

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Exemplary promoters useful with this invention include promoters functional in a eukaryote. Non-limiting examples of a eukaryote include a mammal, an insect, an amphibian, a reptile, a bird, a fish, a fungus, a plant, and/or a nematode.

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the RNAs and/or the polypeptides of the invention to be synthesized only when, for example, an organism is treated with the inducing chemicals. Depending upon the objective, the promoter may be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya et al. 2005. Nature 438:441-442).

Exemplary promoters include, but are not limited to, promoters functional in eukaryotes including, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE, including any fragment that has promoter activity.

Exemplary promoters useful with yeast can include a promoter from phosphoglycerate kinase (PGK), glyceraldehyde-3-phosphate dehydrogenase (GAP), triose phosphate isomerase (TPI), galactose-regulon (GAL1, GAL10), alcohol dehydrogenase (ADH1, ADH2), phosphatase (PH05), copper-activated metallothionine (CUP1), MFa1, PGK/a2 operator, TPI/a2 operator, GAP/GAL, PGK/GAL, GAP/ADH2, GAP/PH05, iso-1-cytochrome c/glucocorticoid response element (CYC/GRE), phosphoglycerate kinase/androgen response element (PGK ARE), transcription elongation factor EF-1a (TEF1), triose phosphate dehydrogenase (TDH3), phosphoglycerate kinase 1 (PGK1), pyruvate kinase 1 (PYK1), and/or hexose transporter (HXT7).

f) Nuclear Localization Signal

In further aspects, the nucleic acid constructs of the invention encoding the polypeptides Type I CRISPR-Cas systems may comprise one or more nuclear localization signals linked to the polynucleotides to move the polynucleotides from the cytoplasm into the nucleus. In some aspects, the Cascade polypeptides and the Cas3 polypeptides of the Type I CRISPR-Cas systems encoded by the nucleic acid constructs of the invention may comprise separate nuclear localization signals. Exemplary nuclear localization sequences include VQRKRQKLMP (SEQ ID NO: 80), SKKKKTKV (SEQ ID NO: 81), and/or GRKRKKRT (SEQ ID NO: 82).

Nuclear localization signal include, but are not limited to, the NLS sequence of SV40 Large T-antigen subunit (PKKKRKV (SEQ ID NO: 9), nucleoplasmin (AVKR-PAATKKAGQAKKKKLD (SEQ ID NO: 10), EGL-13 (MSRRRKANPTKLSENAKKLAKEVEN (SEQ ID NO: 11)), c-Myc (PAAKRVKLD (SEQ ID NO: 12)), TUS-protein (KLKIKRPVK (SEQ ID NO: 13)), the acidic M9 domain of hnRNP A1, the sequence KIPIK (SEQ ID NO: 83) in yeast transcription repressor Matα2, the complex signals of U snRNPs, or proline-tyrosine (PY)-NLSs.

g) Codon Optimization

In some embodiments, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. Such optimized sequences can provide enhanced expression, e.g., increased levels of protein expression, when introduced into a host cell. Examples of optimized sequences are disclosed in U.S. Pat. No. 7,728,118 and U.S. Pat. Appl. Publ. Nos. 2008/0070299, 2008/0090291, and 2006/0068395, each of which is incorporated by reference herein.

In some embodiments, the polynucleotide includes a nucleic acid sequence that is optimized for expression in a mammalian host cell. In some embodiments, an optimized polynucleotide no longer hybridizes to the corresponding non-optimized sequence, e.g., does not hybridize to the non-optimized sequence under medium or high stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often used when it is desired that nucleic acids that are not completely complementary to one another be hybridized or annealed together. The art knows well that numerous equivalent conditions can be employed to comprise medium or low stringency conditions.

Any polynucleotide of this invention (e.g., a heterologous polynucleotide encoding a Cas3 polypeptide (e.g., Cas3, Cas3', Cas3"), a Cascade polypeptide) can be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species-specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original nucleotide sequence. Thus, in representative embodiments of the invention, a polynucleotide of this invention can be codon optimized for expression in the particular organism/species of interest.

In some embodiments, the polynucleotide has less than 90%, e.g., less than 80%, nucleic acid sequence identity to the corresponding non-optimized sequence and optionally encodes a polypeptide having at least 60%, e.g., at least 65%, 70%, 75%, 80%, 85%, 90%, 95%, 96%, 97%, 98%, 99%, or 100%, amino acid sequence identity with the polypeptide encoded by the non-optimized sequence. Constructs, e.g., expression cassettes, and vectors comprising the isolated nucleic acid molecule, e.g., with optimized nucleic acid sequence, as well as kits comprising the isolated nucleic acid molecule, construct or vector are also provided.

A polynucleotide comprising a nucleic acid sequence encoding the Type I CRISPR/Cas system, a subcomponent or fragment thereof or a fusion thereof, is optionally optimized for expression in a particular host cell and also optionally operably linked to transcription regulatory sequences, e.g., one or more enhancers, a promoter, a transcription termination sequence or a combination thereof, to form an expression cassette.

In some embodiments, a nucleic acid sequence encoding the Type I CRISPR/Cas system of the invention, a subcomponent or fragment thereof or a fusion thereof, is optimized by replacing codons with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. Examples of undesirable structural attributes include, but are not limited to, restriction enzyme sites, eukaryotic sequence elements, vertebrate promoter modules and transcription factor binding sites, response elements, *E. coli* sequence elements, mRNA secondary structure. Thus, the optimized nucleic acid product may have an improved level of expression due to improved codon usage frequency, and a reduced risk of inappropriate transcriptional behavior due to a reduced number of undesirable transcription regulatory sequences.

An isolated and optimized nucleic acid molecule may have a codon composition that differs from that of the corresponding wild-type nucleic acid sequence at more than 30%, 35%, 40% or more than 45%, e.g., 50%, 55%, 60% or more of the codons. Exemplary codons for use in the invention are those which are employed more frequently than at least one other codon for the same amino acid in a particular organism and, in some embodiments, are also not low-usage codons in that organism and are not low-usage codons in the organism used to clone or screen for the expression of the nucleic acid molecule. Moreover, codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In some embodiments of the invention, the codons that are different are those employed more frequently in a mammal, while in still other embodiments, the codons that are different are those employed more frequently in a plant. Preferred codons for different organisms are known to the art. A particular type of mammal, e.g., a human, may have a different set of preferred codons than another type of mammal. Likewise, a particular type of plant may have a different set of preferred codons than another type of plant. In one embodiment of the invention, the majority of the codons that differ are ones that are preferred codons in a desired host cell. Preferred codons for organisms including mammals (e.g., humans) and plants are known to the art (e.g., Wada et al., Nucl. Acids Res., 18:2367 (1990); Murray et al., Nucl. Acids Res., 17:477 (1989)).

h) AAV/CRISPR Constructs

AAV may be used to deliver CRISPRs using various construct configurations For example, AAV may deliver the Cascade components, Cas3, and/or crRNA expression cassettes on separate vectors.

i) Modified Lentiviral Vector

The multiplex Type I CRISPR/Cas system includes a modified lentiviral vector. The modified lentiviral vector includes one or more polynucleotide sequences encoding Cascade proteins and/or Cas3 and a separate polynucleotide sequence encoding at least one crRNA. The one or more polynucleotide sequences may be operably linked to a eukaryotic promoter. The promoter may be a constitutive promoter, an inducible promoter, a repressible promoter, or a regulatable promoter.

Figure 49:
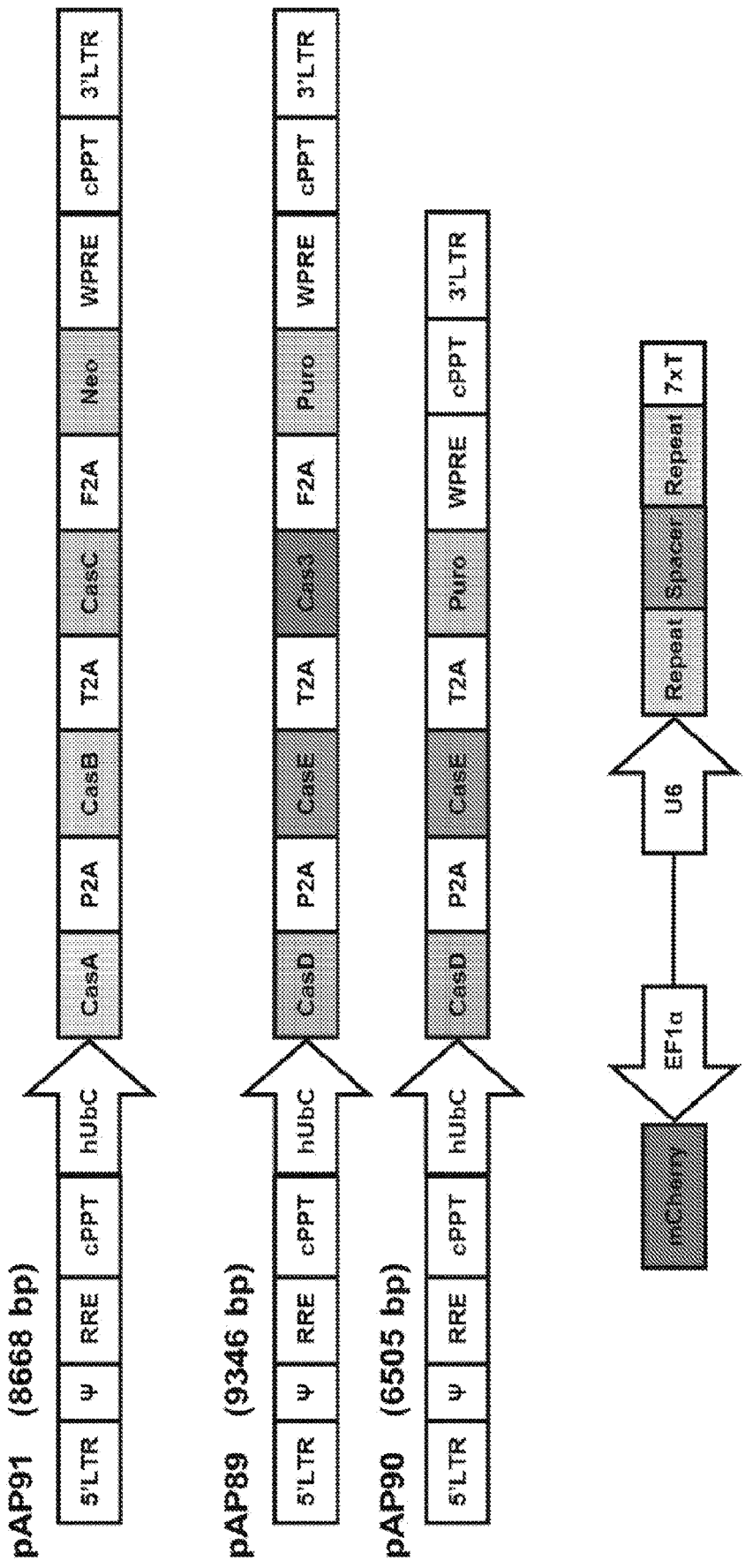
FIG. 49 shows Lentiviral Constructs.

The modified lentiviral vector may include a multicistronic polynucleotide sequence (see e.g., FIG. 49). In some embodiments, the multicistronic polynucleotide sequence includes polynucleotide sequences encoding two or more Cascade polypeptides. The coding sequences may be separated by at least one 2A peptide or IRES. For example, the multicistronic polynucleotide may include between 2 and 6, between 2 and 5, between 2 and 4, between 3 and 6, between 3 and 5, or between 4 and 6 Cascade polypeptides each separated by at least one 2A peptide or IRES.

The separate polynucleotide sequence encodes at least 1 crRNA. For example, the separate polynucleotide sequence may encode at least 1 crRNA, at least 2 crRNAs, at least 3 crRNAs, at least 4 crRNAs, at least 5 crRNAs, at least 6 crRNAs, at least 7 crRNAs, at least 8 crRNAs, at least 9 crRNAs, at least 10 crRNAs, at least 11 crRNA, at least 12 crRNAs, at least 13 crRNAs, at least 14 crRNAs, at least 15 crRNAs, at least 16 crRNAs, at least 17 crRNAs, at least 18 crRNAs, at least 19 crRNAs, at least 20 crRNAs, at least 25 crRNA, at least 30 crRNAs, at least 35 crRNAs, at least 40 crRNAs, at least 45 crRNAs, or at least 50 crRNAs. The separate polynucleotide sequence may encode between 1 crRNA and 50 crRNAs, between 1 crRNA and 45 crRNAs, between 1 crRNA and 40 crRNAs, between 1 crRNA and 35 crRNAs, between 1 crRNA and 30 crRNAs, between 1 crRNA and 25 different crRNAs, between 1 crRNA and 20 crRNAs, between 1 crRNA and 16 crRNAs, between 1 crRNA and 8 different crRNAs, between 4 different crRNAs and 50 different crRNAs, between 4 different crRNAs and 45 different crRNAs, between 4 different crRNAs and 40 different crRNAs, between 4 different crRNAs and 35 different crRNAs, between 4 different crRNAs and 30 different crRNAs, between 4 different crRNAs and 25 different crRNAs, between 4 different crRNAs and 20 different crRNAs, between 4 different crRNAs and 16 different crRNAs, between 4 different crRNAs and 8 different crRNAs, between 8 different crRNAs and 50 different crRNAs, between 8 different crRNAs and 45 different crRNAs, between 8 different crRNAs and 40 different crRNAs, between 8 different crRNAs and 35 different crRNAs, between 8 different crRNAs and 30 different crRNAs, between 8 different crRNAs and 25 different crRNAs, between 8 different crRNAs and 20 different crRNAs, between 8 different crRNAs and 16 different crRNAs, between 16 different crRNAs and 50 different crRNAs, between 16 different crRNAs and 45 different crRNAs, between 16 different crRNAs and 40 different crRNAs, between 16 different crRNAs and 35 different crRNAs, between 16 different crRNAs and 30 different crRNAs, between 16 different crRNAs and 25 different crRNAs, or between 16 different crRNAs and 20 different crRNAs. Each of the polynucleotide sequences encoding the different crRNAs may be operably linked to a eukaryotic promoter. The promoters that are operably linked to the different crRNAs may be the same promoter. The promoters that are operably linked to the different crRNAs may be different promoters. The promoter may be a constitutive promoter, an inducible promoter, a repressible promoter, or a regulatable promoter.

The at least one crRNA may bind to a target gene or loci. If more than one crRNA is included, each of the crRNAs binds to a different target region within one target loci or each of the crRNA binds to a different target region within different gene loci.

In some embodiments, the modified lentiviral vector can include a polynucleotide sequence of SEQ ID NO: 42 or SEQ ID NO: 43. In some embodiments, the modified lentiviral vector can include a polynucleotide sequence of any one of SEQ ID NO: 44, SEQ ID NO: 45, SEQ ID NO: 46, or SEQ ID NO: 47.

3. METHODS OF USES

Potential applications of the compositions are diverse across many areas of science and biotechnology. The disclosed compositions may be used to repair genetic mutations that cause disease. The disclosed compositions may be used to disrupt genes. The disclosed compositions may be used to introduce therapeutic genes to be expressed systemically. The disclosed compositions may be used to modulate mammalian gene expression. The disclosed compositions may be used to transdifferentiate or induce the differentiation of a cell or correct a mutant gene in a cell. Examples of activation of genes related to cell and gene therapy, genetic reprogramming, and regenerative medicine are provided. RNA-guided transcriptional activators may be used to reprogram cell lineage specification. Activation of endogenous genes encoding the key regulators of cell fate, rather than forced overexpression of these factors, may potentially lead to more rapid, efficient, stable, or specific methods for genetic reprogramming, transdifferentiation, and/or induced differentiation.

Thus, in some aspects, the Type I CRISPR-Cas system selected for introducing an insertion, deletion and/or mutation can be a Type I-A CRISPR-Cas system, a Type I-B CRISPR-Cas system, a Type I-C CRISPR-Cas system, a Type I-D CRISPR-Cas system, a Type I-E CRISPR-Cas system, or a Type I-F CRISPR-Cas system. In some aspects, when a Type I-D CRISPR-Cas system, a Type I-E CRISPR-Cas system or a Type I-F CRISPR-Cas system is used, the Cas6 polypeptides (e.g., Cas6d, Cas6e, or Cas6f, respectively) may be omitted. In a representative embodiment, the Type I CRISPR-Cas system selected for introducing an insertion, deletion and/or mutation is a Type I-C CRISPR-Cas system.

Thus, in some aspects, the Type I CRISPR-Cas system selected for degrading or deleting a chromosome, sequence specific killing, killing of a eukaryotic cell, killing of selected cells, deleting a target DNA, and/or treating a viral infection can be a Type I-A CRISPR-Cas system, a Type I-B CRISPR-Cas system, a Type I-C CRISPR-Cas system, a Type I-D CRISPR-Cas system, a Type I-E CRISPR-Cas system, or a Type I-F CRISPR-Cas system. In some aspects, when a Type I-D CRISPR-Cas system, a Type I-E CRISPR-Cas system or a Type I-F CRISPR-Cas system is used, the Cas6 polypeptides (e.g., Cas6d, Cas6e, or Cas6f, respectively) may be omitted. In a representative embodiment, the Type I CRISPR-Cas system selected for degrading or deleting a chromosome, sequence specific killing, killing of a eukaryotic cell, killing of selected cells, deleting a target DNA, and/or treating a viral infection is a Type I-C CRISPR-Cas system.

As known in the art, the selection of the Type I CRISPR-Cas system to introduce (e. g., Type I-A, Type I-B, Type I-C, Type I-D, Type I-E, or Type I-F) determines the selection of the repeat for the CRISPR array. Thus, if a Type I-E system is selected, a Type I-E repeat is selected for the CRISPR array that is introduced into a eukaryotic cell. The components of Type I CRISPR-Cas systems are well known (see, e.g., Gomaa et al. *mBio* 5(1): e00928-13 (2014); and Semenova et al. *Nucleic Acids Res.* 43(12):6049-61 (2015)).

The inventors have developed new methods for creating mutations, insertions and deletions in eukaryotic cells. The inventors have developed new methods for disabling or deleting chromosomes in eukaryotic cells as well as new methods for sequence specific killing of eukaryotic cells. These new methods comprise introducing into eukaryotic cells Type I CRISPR-Cas systems along with CRISPR arrays specifically designed to carry out these methods.

The present invention finds use in agricultural, veterinary and medical applications as well as research applications.

a) Method of Transcriptional Regulator

Type I systems can be re-purposed to regulate transcription in addition to edit genomes. Cascade functions with the crRNA to locate and bind to a complimentary DNA target sequence. The large subunit of Cascade (Casa for Type I-C, CasA for Type I-E, and Csy1 for Type I-F) is then responsible for recruiting Cas3 to degrade the target. Once Cas3 binds to the target, Cascade and the crRNA dissociate for additional genome scanning. Since Cascade is only released following recruitment of Cas3, binding of Cascade to the DNA target may be virtually permanent. Transcriptional regulation may be enhanced by generating various fusions on the Cascade molecules (examples include VP64 and p300 for activation, and KRAB for repression).

b) Methods of Activating Gene Expression

The present disclosure provides a mechanism for activating the expression of endogenous eukaryotic genes, such as mammalian genes, based on targeting a transcriptional activator to promoters via RNA using a Type I CRISPR/Cas system, as described above. This is fundamentally different from previously described methods based on engineering sequence-specific DNA-binding proteins and may provide opportunities for targeted gene regulation. The crRNAs can also be transfected directly to cells following in vitro transcription. Multiple crRNAs may target a single promoter or simultaneous target multiple promoters. Recognition of genomic target sites with RNAs, rather than proteins, may also circumvent limitations of targeting epigenetically modified sites, such as methylated DNA.

The method may include administering to a cell or subject a Type I CRISPR/Cas system, a polynucleotide or vector encoding said Type I CRISPR/Cas system, or DNA targeting systems or compositions of at least one Type I CRISPR/Cas system, as described above. The method may include administering a Type I CRISPR/Cas system, such as administering a Cascade fusion protein containing transcription activation domain or a nucleotide sequence encoding said Cascade fusion protein. The Cascade fusion protein may include a transcription activation domain such as a VP16 protein or a transcription co-activator such as a p300 protein.

c) Methods of Repressing Gene Expression

The present disclosure provides a mechanism for repressing the expression of endogenous genes, such as mammalian genes, based on targeting genomic regulatory elements, such as distal enhancers, via RNA using a Type I CRISPR/Cas system, as described above. The Cascade fusion protein may include a transcriptional repressor, such as the KRAB repressor.

d) Methods of Transdifferentiation or Induced Differentiation

The present disclosure provides a mechanism for transdifferentiating or inducing differentiation of cells by activating endogenous genes via RNA using a Type I CRISPR/Cas system, as described above.

(1) Transdifferentiation

The Type I CRISPR/Cas system may be used to transdifferentiate cells. Transdifferentiation, also known as lineage reprogramming or direct conversion, is a process where cells convert from one differentiated cell type to another without undergoing an intermediate pluripotent state or progenitor cell type. It is a type of metaplasia, which includes all cell fate switches, including the interconversion of stem cells. Transdifferentiation of cells has potential uses for disease modeling, drug discovery, gene therapy and regenerative medicine. Activation of endogenous genes using the Type I CRISPR/Cas system described above may lead to transdifferentiation of several cell types, such as fibroblasts, cardiomyocytes, hepatocytes, chondrocytes, mesenchymal progenitor cells, hematopoetic stem cells, or smooth muscle cells, into neuronal and myogenic phenotypes, respectively.

(2) Inducing Differentiation

The Type I CRISPR/Cas system may be used to induce differentiation of cells, such as stem cells, cardiomyocytes, hepatocytes, chondrocytes, mesenchymal progenitor cells, hematopoetic stem cells, or smooth muscle cells. For example, stem cells, such as embryonic stem cells or pluripotent stem cells, may be induced to differentiate into muscle cells or vascular endothelial cell, i.e., induce neuronal or myogenic differentiation.

e) Method of Inducing and Insertion, Deletion, or Mutation

In a first aspect, a method is provided for introducing an insertion, deletion, or mutation in a chromosome or extrachromosomal element of a eukaryotic cell by homologous recombination, comprising: introducing into the eukaryotic cell (A) (i) at least one nucleic acid construct encoding polypeptides of a Type I CRISPR-Cas system; and (ii) a CRISPR array comprising at least one spacer sequence that is complementary to a target DNA on the chromosome or extrachromosomal element; or (B) a protein-RNA complex comprising polypeptides of a Type I CRISPR-Cas system and a CRISPR array comprising at least one spacer sequence that is complementary to a target DNA on the chromosome or extrachromosomal element; and (C) a template comprising a single stranded DNA sequence or a double stranded DNA sequence, thereby introducing an insertion, deletion, or mutation in the chromosome or extrachromosomal element of the eukaryotic cell by homologous recombination. In some aspects, the template comprises single stranded DNA comprising (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising a length of zero to about 100,000 nucleotides. In other aspects, the template comprises double stranded DNA comprising (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of zero to about 100,000 base pairs.

In a second aspect, a method for introducing a deletion into a chromosome or extrachromosomal element of a eukaryotic cell is provided, comprising: introducing into the eukaryotic cell: (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; and (C) optionally, a template comprising a single stranded DNA sequence or a double stranded DNA sequence and an intervening sequence having zero nucleotides or base pairs, respectively, wherein the different target DNAs located on opposite strands of the chromosome or extrachromosomal element are each adjacent to a protospacer adjacent motif (PAM) and the at least two spacer sequences of the CRISPR array(s) guide the Type I CRISPR-Cas polypeptides to the two different target DNAs, thereby degrading the chromosome or extrachromosomal element between the two different target DNAs including the PAM adjacent to each of the two different target DNAs (convergent degradation) and introducing a deletion. In some aspects, the target DNA may be viral DNA that is incorporated into the eukaryotic chromosome or is an extrachromosomal element residing in the eukaryotic cell. In some aspects, the template comprises single stranded DNA comprising (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising zero nucleotides. In other aspects, the template comprises double stranded DNA comprising (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of zero base pairs.

In a third aspect, a method for introducing an insertion or mutation into a chromosome of a eukaryotic cell is provided, comprising: introducing into the eukaryotic cell (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary or extrachromosomal element to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; and (C) a template comprising a single stranded DNA sequence or a double stranded DNA sequence, wherein the different target DNAs located on opposite strands of the chromosome or extrachromosomal element are each adjacent to a protospacer adjacent motif (PAM) and the at least two spacer sequences of the CRISPR array(s) guide the Type I CRISPR-Cas polypeptides to the two different target DNAs, thereby degrading the chromosome or extrachromosomal element between the two different target DNAs including the PAM adjacent to each of the two different target DNAs (convergent degradation) and introducing an insertion or mutation. In some aspects, the template comprises single stranded DNA comprising (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising a length of one to about 100,000 nucleotides. In other aspects, the template comprises double stranded DNA comprising (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of one to about 100,000 base pairs.

In one aspect, the invention provides a method for disabling or deleting a chromosome in a eukaryotic cell comprising: introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA on the chromosome; or (B) a protein-RNA complex comprising polypeptides of a Type I CRISPR-Cas system and at least one CRISPR array comprising at least one spacer sequence that is complementary to a target DNA on the chromosome, thereby disabling or deleting the chromosome in the eukaryotic cell. In some aspects, the at least one nucleic acid construct and the CRISPR array may be introduced on one construct or on different constructs. In some aspects, the at least one nucleic acid construct may be operably linked to a promoter and to a polyA signal as known in the art. Accordingly, the at least one nucleic acid construct having a 5' end and a 3' end, may be operably linked at the 5' end to a promoter and at the 3' end to a polyA signal. In some aspects, the protein-RNA complex is generated through the overexpression and purification of the proteins in *E. coli* following established procedures and the production of the RNAs through chemical synthesis or in vitro transcription. The protein and RNA can be complexed in vitro by incubating the components together.

In some aspects, the at least one CRISPR array for use in disabling or deleting a chromosome may comprise an unprocessed CRISPR array or a processed CRISPR array as described herein. In some aspects, the at least one CRISPR array comprises one or more spacer sequences, wherein the one or more spacer sequences are complementary to a target DNA on a chromosome of the eukaryotic cell. In other aspects, the at least one CRISPR array comprises at least two spacer sequences, the at least two spacer sequences being complementary to different target DNAs that are on the same strand of the chromosome of the eukaryotic cell. In other aspects, the at least one CRISPR array comprises at least two CRISPR arrays each of which comprise at least one spacer sequence, wherein the at least one spacer sequence of each of the at least two CRISPR arrays are complementary to different target DNAs located on the same strand of the chromosome of the eukaryotic cell. In aspects of the invention, the spacer guides the Type I CRISPR-Cas polypeptides to one strand of the target DNA and the Cas3 polypeptide to the opposite strand of the target DNA where the Cas3 polypeptide begins degradation of the target DNA and thus the chromosome in a 3' to 5' direction.

The target DNA for disabling or deleting a chromosome can be any DNA on the chromosome that when targeted by the introduced Type I CRISPR-Cas system(s) results in the disabling or the deletion of the chromosome on which the target DNA is located. In some aspects, the target DNA for disabling or the deleting a chromosome can be in a telomere or a centromere of the chromosome that is to be disabled or deleted. In additional aspects, a target DNA for disabling or deleting a chromosome may be complementary to a mutation that is present in less than all of a pair or a group of homologous chromosomes (e.g., only one out of a pair; one to three out of a set of four homologous chromosomes, and the like) or only one of a pair of sister chromatids, thereby disabling or deleting less than all of a pair or a group of homologous chromosomes or only one of a pair of sister chromatids.

In some aspects, the chromosome that is to be disabled or deleted does not encode an essential gene.

In some aspects, the chromosome that is disabled or deleted is replaced with a synthetic chromosome. The chromosome contains all of the standard elements for stable replication, such telomeres and a centromere, as well as any essential genes encoded on the deleted chromosome.

In some embodiments, the chromosome that is disabled or deleted may be an extra chromosome (e.g., trisomy disorders such as trisomy 21, trisomy 18, trisomy 13). In some embodiments, an extra chromosome may be associated with a cancer cell. In some embodiments, the chromosome that is disabled or deleted may be a gender determining chromosome. In some embodiments, a method of disabling or deleting a gender determining chromosome can be used to control, for example, insect populations, by altering the sex ratios in the population. In other embodiments, disabling or deleting a chromosome can assist researchers in determining the function of the chromosome and the encoded genes of the chromosome.

In some aspects of this invention, disabling or deleting a chromosome in a eukaryotic cell may be used to kill the cell comprising the target DNA. Thus, for this purpose, in some aspects, a chromosome comprising the target DNA and that is to be disabled or deleted may comprise at least one essential gene, wherein disabling or deleting the chromosome kills the cell.

In further aspects, the chromosome that is disabled or deleted may be that of a eukaryotic organism that is infecting a prokaryotic culture. Thus, for example, a chromosome of a fungus infecting a bacterial culture can be disabled or deleted, wherein the chromosome of the fungus comprises an essential gene, thereby killing the cells of the fungus in the bacterial culture.

In some aspects, a target DNA for disabling or deleting a chromosome may be located up to about $10^7$ base pairs (e.g., about $10^6$, $10^5$, $10^4$, $10^3$, $10^2$, 10 base pairs) from an essential gene, thereby killing the cell by either disabling or deleting the chromosome comprising the essential gene or by disrupting or deleting the essential gene directly, with or without deleting or disabling the chromosome. Accordingly, in some aspects, the invention provides a method of killing a cell by disrupting or deleting an essential gene, comprising introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA on the chromosome; or (B) a protein-RNA complex comprising polypeptides of a Type I CRISPR-Cas system and at least one CRISPR array comprising at least one spacer sequence that is complementary to a target DNA on the chromosome, thereby disrupting or deleting an essential gene and killing the cell.

In some aspects, the first and second homology arms of a template of the invention can be fully complementary to regions of the chromosomal DNA flanking the site in the chromosome that is to be modified by homologous recombination. In some aspects, an intervening sequence can be fully complementary or substantially complementary (e.g., 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 10000 complementary) to the strand of the chromosome on which the target DNA is located. In some aspects, an intervening sequence is synthetic and is non-complementary or has limited complementarity to the strand of the chromosome on which the target DNA is located.

In some embodiments, when a template is present but does not include an intervening sequence (i.e., the template comprises zero nucleotides or base pairs) then a deletion is driven by homology-directed repair. When no template is present, the deletion is driven by non-homologous end joining (indel formation)

In some aspects, when introducing a deletion, the deletion that is introduced can be from about 10 base pairs to about $10^7$ base pairs (e.g., about 10, 20, 30, 40, 50, 60, 70, 80, 90, 100, 150, 20, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700, 000, 800,000, 900,000, $10^6$, $2\times10^6$, $3\times10^6$ $4\times10^6$ $5\times10^6$ $6\times10^6$, $7\times10^6$, $8\times10^6$, $9\times10^6$, $10^7$ base pairs and any range or value therein).

f) Method of Killing Selected Cells or Sequences

In some aspects, the invention provides a method of killing of selected cells in a population of eukaryotic cells, comprising introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA present in a subset of cells within a population of cells and not present in the other cells of the population; or (B) a protein-RNA complex comprising polypeptides of a Type I CRISPR-Cas system and at least one CRISPR array comprising at least one spacer sequence that is complementary to a target DNA present in a subset of cells in a population of cells and not present in the other cells of the population, thereby killing the subset of cells within the population of cells. In some aspects, the at least one nucleic acid construct and the CRISPR array may be introduced on one construct or on different constructs. In some aspects, the at least one nucleic acid construct may be operably linked to a promoter and to a polyA signal as known in the art. Accordingly, the at least one nucleic acid construct having a 5' end and a 3' end, may be operably linked at the 5' end to a promoter and at the 3' end to a polyA signal.

In a further aspect, the invention provides a method of sequence-specific killing of a eukaryotic cell, comprising: introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA encoding an essential gene; or (B) a protein-RNA complex comprising polypeptides of a Type I CRISPR-Cas system and at least one CRISPR array comprising at least one spacer sequence that is complementary to a target DNA encoding an essential gene, thereby disrupting or deleting the gene and killing the cell. In some aspects, the at least one nucleic acid construct and the CRISPR array may be introduced on one construct or on different constructs. In some aspects, the at least one nucleic acid construct may be operably linked to a promoter and to a polyA signal as known in the art. Accordingly, the at least one nucleic acid construct having a 5' end and a 3' end, may be operably linked at the 5' end to a promoter and at the 3' end to a polyA signal.

In some aspects the at least one CRISPR array for use in sequence specific killing may comprise an unprocessed CRISPR array or a processed CRISPR array as described herein. In some aspects, the at least one CRISPR array comprises one or more spacer sequences, wherein the one or more spacer sequences are complementary to a target DNA on a chromosome of the eukaryotic cell. In other aspects, the at least one CRISPR array comprises at least two spacer sequences, the at least two spacer sequences being complementary to different target DNAs that are on the same strand of the chromosome of the eukaryotic cell. In other aspects, the at least one CRISPR array comprises at least two CRISPR arrays each of which comprise at least one spacer sequence, wherein the at least one spacer sequence of each of the at least two CRISPR arrays are complementary to different target DNAs located on the same strand of the chromosome of the eukaryotic cell. In aspects of the invention, the spacer guides the Type I CRISPR-Cas polypeptides to one strand of the target DNA and the Cas3 polypeptide to the opposite strand of the target DNA where the Cas3 polypeptide begins degradation of the target DNA and thus the chromosome in a 3' to 5' direction.

In some aspects, the target DNA for sequence-specific killing may be in an essential gene. In some aspects, the target DNA may be in a telomere or a centromere of a chromosome of the eukaryotic cell. In other aspects, the target DNA for sequence-specific killing may be in a mutation in an essential gene of a eukaryotic cell. In representative aspects, a target DNA may be a sequence that includes a mutation that is present in a subset of cells in a population of cells that are otherwise genetically identical, thereby disabling or deleting the chromosome in the selected cells that is carrying the mutation (i.e., the target DNA), thereby killing the selected cells and leaving the cells without the mutation unaffected. In some embodiments, the mutation is located on a chromosome comprising an essential gene. Such methods may be used, for example, to target cancer cells in an otherwise healthy population of cells in a eukaryotic organism. In some embodiments, the target DNA may be present only in fungi but not in mammalian cells to ensure targeted killing.

In some aspects, the target DNA may be in a telomere or a centromere of a chromosome of the eukaryotic cell.

4. USES OF MULTIPLEX TYPE I CRISPR/CAS SYSTEM

The multiplex Type I CRISPR/Cas System takes advantage of the simplicity and low cost of crRNA design and may be helpful in exploiting advances in high-throughput genomic research using Type I CRISPR/Cas technology. The multiplex Type I CRISPR/Cas System may be used in the same ways as the Type I CRISPR/Cas System described above.

In addition to the described transcriptional activation and nuclease functionality, this system will be useful for expressing other novel Cascade-based effectors that control epigenetic modifications for diverse purposes, including interrogation of genome architecture and pathways of endogenous gene regulation. As endogenous gene regulation is a delicate balance between multiple enzymes, multiplexing Cascade systems with different functionalities will allow for examining the complex interplay among different regulatory signals. The vector described here should be compatible with aptamer-modified crRNAs and orthogonal Cascade to enable independent genetic manipulations using a single set of crRNAs.

The multiplex Type I CRISPR/Cas System may be used to activate at least one endogenous gene in a cell. The method includes contacting a cell with the modified lentiviral vector. The endogenous gene may be transiently activated or stably activated. The endogenous gene may be transiently repressed or stably repressed. The Cascade fusion protein may be expressed at similar levels to the crRNAs. The Cascade fusion protein may be expressed at different levels compared to the crRNAs. The cell may be a primary human cell.

The multiplex Type I CRISPR/Cas System may be used in a method of multiplex gene editing in a cell. The method includes contacting a cell with the modified lentiviral vector. The multiplex gene editing may include correcting a mutant gene or inserting a transgene. Correcting a mutant gene may include deleting, rearranging or replacing the mutant gene. Correcting the mutant gene may include nuclease-mediated non-homologous end joining or homology-directed repair. The multiplex gene editing may include deleting or correcting at least one gene, wherein the gene is an endogenous normal gene or a mutant gene. The multiplex gene editing may include deleting or correcting at least two genes. For example, at least two genes, at least three genes, at least four genes, at least five genes, at least six genes, at least seven genes, at least eight genes, at least nine genes, or at least ten genes may be deleted or corrected.

The multiplex Type I CRISPR/Cas System may be used in a method of multiplex modulation of gene expression in a cell. The method includes contacting a cell with the modified lentiviral vector. The method may include modulating the gene expression levels of at least one gene. The gene expression of the at least one target gene is modulated when gene expression levels of the at least one target gene are increased or decreased compared to normal gene expression levels for the at least one target gene. The gene expression levels may be RNA or protein levels.

5. METHODS OF CORRECTING A MUTANT GENE AND TREATING A SUBJECT

The present disclosure is also directed to a method of correcting a mutant gene in a subject. The method comprises administering to the subject the Type I CRISPR/Cas system, as described above. Use of the composition to deliver Type I CRISPR/Cas system to a cell may restore the expression of a full-functional or partially-functional protein with a repair template or donor DNA, which can replace the entire gene or the region containing the mutation. The Type I CRISPR/Cas system may be used to introduce site-specific double strand breaks at targeted genomic loci. Site-specific double-strand breaks are created when the Type I CRISPR/Cas system binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with a Type I CRISPR/Cas system without a repair template, which can efficiently correct the reading frame and restore the expression of a functional protein involved in a genetic disease. The disclosed Type I CRISPR/Cas system may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active Type I CRISPR/Cas system with an efficient gene editing method for the treatment of genetic diseases caused by mutations in nonessential coding regions that cause frameshifts, premature stop codons, aberrant splice donor sites or aberrant splice acceptor sites.

a) Nuclease Mediated Non-Homologous End Joining

Restoration of protein expression from an endogenous mutated gene may be through template-free NHEJ-mediated DNA repair. In contrast to a transient method targeting the target gene RNA, the correction of the target gene reading frame in the genome by a transiently expressed Type I CRISPR/Cas system may lead to permanently restored target gene expression by each modified cell and all of its progeny.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells. This provides a robust, permanent gene restoration alternative to oligonucleotide-based exon skipping or pharmacologic forced read-through of stop codons and could theoretically require as few as one drug treatment. NHEJ-based gene correction using a Type I CRISPR/Cas system, as well as other engineered nucleases including meganucleases and zinc finger nucleases, may be combined with other existing ex vivo and in vivo platforms for cell- and gene-based therapies, in addition to the plasmid electroporation approach described here. For example, delivery of a Type I CRISPR/Cas system by mRNA-based gene transfer or as purified cell permeable proteins could enable a DNA-free genome editing approach that would circumvent any possibility of insertional mutagenesis.

b) Homology-Directed Repair

Restoration of protein expression from an endogenous mutated gene may involve homology-directed repair. The method as described above further includes administrating a donor template to the cell. The donor template may include a nucleotide sequence encoding a full-functional protein or a partially-functional protein. For example, the donor template may include a miniaturized dystrophin construct, termed minidystrophin ("minidys"), a full-functional dystrophin construct for restoring a mutant dystrophin gene, or a fragment of the dystrophin gene that after homology-directed repair leads to restoration of the mutant dystrophin gene.

6. METHODS OF TREATING A DISEASE

The present disclosure is directed to a method of treating a subject in need thereof. The method comprises administering to a tissue of a subject the Type I CRISPR/Cas system in a eukaryotic cell or subject, as described above. The disease may be a genetic disease.

A "subject" of the invention includes any eukaryotic organism that has or is susceptible to an infection, disease or condition, for example, cancer or a viral infection. Thus, such a subject can be a mammal, an insect, an amphibian, a reptile, a bird, a fish, a fungus, a plant, or a nematode. Mammalian subjects include but are not limited to humans, non-human primates (e.g., gorilla, monkey, baboon, and chimpanzee, etc.), dogs, cats, goats, horses, pigs, cattle, sheep, and the like, and laboratory animals (e.g., rats, guinea pigs, mice, gerbils, hamsters, and the like). Avian subjects include but are not limited to chickens, ducks, turkeys, geese, quail, pheasants, and birds kept as pets (e.g., parakeets, parrots, macaws, cockatoos, *canaries*, and the like). Suitable subjects include both males and females and subjects of any age, including embryonic (e.g., in utero or in ovo), infant, juvenile, adolescent, adult and geriatric subjects. In some embodiments, a subject of this invention is a human.

A "subject in need" of the methods of the invention can be a subject known to have, suspected of having, or having an increased risk of developing an infection, disease, or condition, including secondary infections, caused by, for example, a virus.

In some embodiments, the subject is one that has a viral infection, has had a viral infection, or is at risk for a viral infection. A subject at risk for a viral infection can be one that is, for example, in a hospital and is thereby exposed to infectious viruses.

"Effective amount" as used herein refers to an amount of a nucleic acid construct, CRISPR array, and optionally, a template, or a protein-RNA complex of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of skill in the art by reference to the pertinent texts and literature and/or by using routine experimentation. In representative embodiments, an effective amount of a nucleic acid construct, CRISPR array, and optional templates, or a protein-RNA complex of the invention may be about 1 nM to 10 uM. In representative embodiments, an effective amount may be an amount that reduces the amount of cancer cells in a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein. In some embodiments, an effective amount may be an amount that reduces the amount of an infectious agent (e.g., a virus) in or on a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject. In some embodiments, a therapeutically effective amount of an at least one nucleic acid construct and a CRISPR array and optionally a template, or a protein-RNA complex of the invention may be about 1 nM to 10 uM. In representative embodiments, a therapeutically effective amount may be an amount that reduces the amount of an infectious agent (e.g., a virus) in or on a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein. In additional representative embodiments, an therapeutically effective amount may be an amount that reduces the amount of cancer cells in a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

Further, with respect to an infection, a disease or a condition, the terms "treat," "treating," or "treatment of" and the like refer to, e.g., elimination of or a decrease in the presence or amount of, for example, a virus, cells comprising viral DNA or cancer cells in a subject. Thus, by treating the infection, disease, and/or condition in the subject, the infection, disease, and/or condition is ameliorated, alleviated, severity reduced, symptoms reduced and the like as compared to a similar subject not treated with the chimeric constructs of this invention, thereby treating the infection, disease and/or condition. In some embodiments, the presence of a virus, cancer cell, or cell comprising viral DNA may be reduced by about 10% to about 100% (e.g., 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, or any value or range therein) following introduction of an at least one nucleic acid construct and a CRISPR array and optionally a template, or a protein-RNA complex of this invention.

In some embodiments, a subject in need of treatment may be identified by, for example, well-established hallmarks of an infection, such as fever, puls, culture of organisms, and the like, or a subject may be treated prior to infection to prevent or reduce the likelihood of infection in the subject.

The terms "prevent," "preventing," and "prevention" (and grammatical variations thereof) refer to prevention and/or delay of the onset of an infection, disease, condition and/or a clinical symptom(s) in a subject and/or a reduction in the severity of the onset of the infection, disease, condition and/or clinical symptom(s) relative to what would occur in the absence of carrying out the methods of the invention prior to the onset of the disease, disorder and/or clinical symptom(s).

A "prevention effective" amount as used herein is an amount of an at least one nucleic acid construct and a CRISPR array and optionally a template, or a protein-RNA complex of the invention that is sufficient to reduce a viral load by at least about 10% to about 100%, and any range or value therein.

a) Method of Treating for an Infectious Agent

In some aspects, a method of treating for an infectious agent (e.g., virus) in a subject in need thereof is provided, comprising: administering to the subject an effective amount of: A) (i) at least one nucleic acid construct encoding polypeptides of a Type I CRISPR-Cas system; and (ii) at least one CRISPR array comprising at least one spacer sequence that is complementary to a target DNA from the infectious agent that is present in a chromosome or on a extrachromosomal element in the eukaryotic cell; or (B) a protein-RNA complex comprising polypeptides of a Type I CRISPR-Cas system and at least one CRISPR array comprising at least one spacer sequence that is complementary to a target DNA from the infectious agent that is present in a chromosome or on a extrachromosomal element in the eukaryotic cell, thereby treating the viral infection. In particular aspects, a method of treating a viral infection in a subject in need thereof is provided, comprising: administering to the subject an effective amount of: A) (i) at least one nucleic acid construct encoding polypeptides of a Type I CRISPR-Cas system; and (ii) at least one CRISPR array comprising at least one spacer sequence that is complementary to a viral target DNA in a chromosome or on a extrachromosomal element in the eukaryotic cell; or (B) a protein-RNA complex comprising polypeptides of a Type I CRISPR-Cas system and at least one CRISPR array comprising at least one spacer sequence that is complementary to a viral target DNA in a chromosome or on a extrachromosomal element in the eukaryotic cell, thereby treating the viral infection. In some aspects, the at least one nucleic acid construct and the CRISPR array may be introduced on one construct or on different constructs. In some aspects, the at least one nucleic acid construct may be operably linked to a promoter and to a polyA signal as known in the art. Accordingly, the at least one nucleic acid construct having a 5' end and a 3' end, may be operably linked at the 5' end to a promoter and at the 3' end to a polyA signal. In some embodiments, the at least one nucleic acid construct and the at least one CRISPR array or the protein-RNA complex is provided as a pharmaceutical composition.

b) Method of Treating Viral Infection

In a fourth aspect, a method for treating a viral infection in a subject in need thereof is provided, comprising: administering to the subject an effective amount of (A) (i) at least one nucleic acid construct encoding polypeptides of a Type I CRISPR-Cas system; and (ii) a CRISPR array comprising at least one spacer sequence that is complementary to a target DNA on the chromosome or extrachromosomal element; or (B) a protein-RNA complex comprising polypeptides of a Type I CRISPR-Cas system and a CRISPR array comprising at least one spacer sequence that is complementary to a target DNA on the chromosome or extrachromosomal element; and (C) a template comprising a single stranded DNA sequence or a double stranded DNA sequence and an intervening sequence having zero nucleotides or base pairs, respectively, wherein the target DNA is DNA of a virus infecting the subject, thereby introducing a deletion by homologous recombination in the chromosome or extrachromosomal element of the eukaryotic cell, thereby treating the viral infection in the subject in need thereof. In some aspects, the template comprises single stranded DNA comprising (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising zero nucleotides. In other aspects, the template comprises double stranded DNA comprising (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of zero base pairs.

In a fifth aspect, a method for treating a viral infection in a subject in need thereof is provided, comprising: administering to the subject an effective amount of (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell, wherein the different target DNAs located on opposite strands of the chromosome or extrachromosomal element are each adjacent to a protospacer adjacent motif (PAM) and the at least two spacer sequences of the CRISPR array(s) are each complementary to DNA of a virus infecting the subject and guide the Type I CRISPR-Cas polypeptides to the two different target DNAs, thereby degrading the chromosome or extrachromosomal element between the two different target DNAs including the PAM adjacent to each of the two different target DNAs (convergent degradation), thereby treating the viral infection in the subject in need thereof. In some aspects, the template comprises single stranded DNA comprising (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising zero nucleotides. In other aspects, the template comprises double stranded DNA comprising (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of zero base pairs.

c) Method of Treating Cancer

In some aspects, a method of treating cancer in a subject in need thereof is provided, comprising: administering to the subject an effective amount of: A) (i) at least one nucleic acid construct encoding polypeptides of a Type I CRISPR-Cas system; and (ii) at least one CRISPR array comprising at least one spacer sequence that is complementary to a target DNA in a cancer cell (e.g., a mutation in an essential gene that is present in a cancer but not in the healthy cells); or (B) a protein-RNA complex comprising polypeptides of a Type I CRISPR-Cas system and at least one CRISPR array comprising at least one spacer sequence that is complementary to a target DNA in a cancer cell (e.g., a mutation in an essential gene that is present in a cancer but not in the healthy cells), thereby treating cancer in the subject. In some aspects, the at least one nucleic acid construct and the CRISPR array may be introduced on one construct or on different constructs. In some aspects, the at least one nucleic acid construct may be operably linked to a promoter and to a polyA signal as known in the art. Accordingly, the at least one nucleic acid construct having a 5' end and a 3' end, may be operably linked at the 5' end to a promoter and at the 3' end to a polyA signal. In some embodiments, the at least one nucleic acid construct and the at least one CRISPR array or the protein-RNA complex is provided as a pharmaceutical composition.

7. TARGET DNA

As used herein, a "target DNA," "target nucleotide sequence," "target region," or a "target region in the genome" refers to a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a CRISPR array of this invention. In some embodiments, a target region can be about 25 to about 100 consecutive nucleotides in length (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) which in Type I CRISPR-Cas systems is located immediately 3' to a PAM sequence in the genome of the organism.

A target nucleotide sequence or target DNA in a Type I system is located adjacent to or flanked by a PAM (protospacer adjacent motif). While PAMs are often specific to the particular Type I CRISPR-Cas system, a PAM sequence can be determined by those skilled in the art through established experimental and computational approaches. Thus, for example, experimental approaches include targeting a sequence flanked by all possible nucleotides sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, a target DNA can be in the genome of a eukaryotic cell (e.g., in a chromosome of the eukaryotic cell) or can be on an extrachromosomal element residing in the cell. In some aspects, the target DNA can be that of an infectious agent residing in the eukaryotic cell, as either incorporated into the chromosome of the eukaryotic cell or as, for example, an extrachromosomal element in the eukaryotic cell (e.g., a virus). In representative embodiments, the target DNA may be unique to a eukaryotic cell type (e.g., a mutation in a cancer cell), or unique to a species, genus, family or kingdom (e.g., a virus infecting a eukaryotic cell).

Thus, in some aspects, a target DNA may be DNA of an infectious agent that is either incorporated into a chromosome of a eukaryotic cell or resides on an extrachromosomal element in a eukaryotic cell. Accordingly, in some embodiments, the infectious agent may be a virus. Therefore, a target DNA may be that of any virus that incorporates its DNA into the chromosome of a eukaryotic cell or resides in a eukaryotic cell as an extrachromosomal element. Non-limiting examples of viruses that may be treated using the methods of this invention include a human immunodeficiency virus (HIV), a hepatitis C virus (HCV), and/or a human papillomavirus (HPV).

8. CONSTRUCTS AND PLASMIDS

The compositions, as described above, may comprise genetic constructs that encodes the Type I CRISPR/Cas system, as disclosed herein. The genetic construct, such as a plasmid, may comprise a nucleic acid that encodes the Type I CRISPR/Cas system. The compositions, as described above, may comprise genetic constructs that encodes the modified AAV vector and a nucleic acid sequence that encodes the Type I CRISPR/Cas system, as disclosed herein. The genetic construct, such as a plasmid, may comprise a nucleic acid that encodes the Type I CRISPR/Cas system. The compositions, as described above, may comprise genetic constructs that encodes the modified lentiviral vector, as disclosed herein. The genetic construct may be present in the cell as a functioning extrachromosomal molecule. The genetic construct may be a linear minichromosome including centromere, telomeres or plasmids or cosmids. In some embodiments, the genetic construct may include a modified lentiviral vector that includes a polynucleotide sequence of SEQ ID NO: 42 or SEQ ID NO: 43. In some embodiments, the genetic construct may include a modified lentiviral vector that includes a polynucleotide sequence of any one of SEQ ID NO: 44, SEQ ID NO: 45, SEQ ID NO: 46, or SEQ ID NO: 47. In some embodiments, the genetic construct may include a polynucleotide sequence of at least one of SEQ ID NO: 14, SEQ ID NO: 16, SEQ ID NO: 18, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 34, SEQ ID NO: 36, SEQ ID NO: 38, or SEQ ID NO:40.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the Cascade fusion protein in the cell of a mammal. The vector may be recombinant. The vector may comprise heterologous nucleic acid encoding the Cascade fusion protein. The vector may be a plasmid. The vector may be useful for transfecting cells with nucleic acid encoding the Cascade fusion protein, which the transformed host cell is cultured and maintained under conditions wherein expression of the Cascade fusion protein takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the Type I CRISPR/Cas system and may further comprise an initiation codon, which may be upstream of the Type I CRISPR/Cas system, and a stop codon, which may be downstream of the Type I CRISPR/Cas system. The initiation and termination codon may be in frame with the Type I CRISPR/Cas system. The vector may also comprise a promoter that is operably linked to the Type I CRISPR/Cas system. The promoter operably linked to the Type I CRISPR/Cas system may be a promoter from EF1alpha, simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the Type I CRISPR/Cas system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the Type I CRISPR/Cas system. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the Type I CRISPR/Cas system.

In some embodiments, the polynucleotides and polypeptides of the invention are "isolated." An "isolated" polynucleotide or an "isolated" polypeptide is a nucleotide sequence or polypeptide sequence that, by the hand of man, exists apart from its native environment and is therefore not a product of nature. An isolated polynucleotide or polypeptide may exist in a purified form that is at least partially separated from at least some of the other components of the naturally occurring organism or virus, for example, the cell or viral structural components or other polypeptides or polynucleotides commonly found associated with the polypeptide or polynucleotide. In representative embodiments, the isolated polynucleotide and/or the isolated polypeptide is at least about 1%, 5%, 10%, 20%, 30%, 40%, 50%, 60%, 70%, 80%, 90%, 95%, or more pure.

In other embodiments, an isolated polynucleotide or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, by the hand of man, they exist apart from their native environment and therefore are not products of nature, however, in some embodiments, they can be introduced into and exist in a recombinant host cell.

In further embodiments of the invention, polynucleotides comprising CRISPR arrays and/or polynucleotides encoding Cas polypeptides and/or Cascade polypeptides can be operatively associated with a variety of promoters, terminators and other regulatory elements for expression in various organisms or cells. Thus, in representative embodiments, at least one promoter and/or terminator can be operably linked to a polynucleotide of the invention. Any promoter useful with this invention can be used and includes, for example, promoters functional with the organism of interest including but not limited to constitutive, inducible, developmentally regulated, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid. Accordingly, in representative embodiments, a nucleic acid construct encoding polypeptides of a Type I CRISPR-Cas system and having a 5' end and a 3' end, can further comprise a promoter operably linked to 5' end of the at least one nucleic acid construct and a polyA signal operably linked to the 3 end of the at least one nucleic acid construct.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of the nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

In some aspects, the polynucleotides of Type I CRISPR-Cas systems that are introduced into a eukaryotic cell are operably linked to a promoter and/or to a polyA signal as known in the art. Therefore, in some aspects, the nucleic acid constructs of the invention encoding the polypeptides Type I CRISPR-Cas systems having a 5' end and a 3' end may be operably linked at the 5' end to a promoter and at the 3' end to a polyA signal. In some aspects, the nucleic acid constructs of the invention may comprise 2A peptide sequences and/or internal ribosomal entry sites as known in the art for assisting with transformation/transfection. In still further aspects, the Type I In some aspects, the nucleic acid constructs of the invention encoding the polypeptides Type I CRISPR-Cas systems may be introduced into a eukaryotic cell via a plasmid, a viral vector, or a nanoparticle.

In some embodiments, a nucleic acid comprising components of a heterologous Type I CRISPR-Cas system can be an "expression cassette" or can be comprised within an expression cassette. As used herein, "expression cassette" means a recombinant nucleic acid construct comprising one or more polynucleotides of the invention, wherein the recombinant nucleic acid construct is operably associated with at least one control sequence (e.g., a promoter). Thus, some aspects of the invention provide expression cassettes designed to express the polynucleotides of the invention.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). In some embodiments of this invention, terminators can be operably linked to a recombinant nucleic acid.

An expression cassette also can include a nucleotide sequence encoding a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or whether the marker is simply a trait that one can identify through observation or testing, such as by screening (e.g., fluorescence). Of course, many examples of suitable selectable markers are known in the art and can be used in the expression cassettes described herein.

In addition to expression cassettes, the recombinant polynucleotides described herein (e.g., polynucleotides comprising a CRISPR array, and polynucleotides encoding Cas polypeptides and/or Cascade polypeptides (i.e., Type I CRISPR-Cas polynucleotides), templates) can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a eukaryotic host either by integration into the cellular genome or exist as an extrachromosomal element (e.g., minichromosome). In some embodiments, the recombinant polynucleotides described herein may be delivered as a ribonucleoprotein complex.

Additionally included are shuttle vectors by which is meant a DNA vehicle capable, naturally or by design, of replication in two different host organisms, such as broad-host plasmids or shuttle vectors with multiple origins-of-replication. In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, a polynucleotide of this invention and/or expression cassettes comprising polynucleotides of this invention can be comprised in vectors as described herein and as known in the art. In some embodiments, the recombinant polynucleotides described herein may be delivered as a ribonucleoprotein complex.

9. PHARMACEUTICAL COMPOSITIONS

The composition may be in a pharmaceutical composition. The pharmaceutical composition may comprise about 1 ng to about 10 mg of DNA encoding the Type I CRISPR/Cas system or Type I CRISPR/Cas system protein component. The pharmaceutical composition may comprise about 1 ng to about 10 mg of the DNA of the modified AAV vector. The pharmaceutical composition may comprise about 1 ng to about 10 mg of the DNA of the modified lentiviral vector. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition of the present invention at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

As a further aspect, the invention provides pharmaceutical compositions and methods of administering the same to treat viral infections or cancer. The pharmaceutical composition may comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The compositions of the invention can optionally comprise medicinal agents, pharmaceutical agents, carriers, adjuvants, dispersing agents, diluents, and the like.

The nucleic acid constructs, CRISPR arrays, templates and/or protein-RNA complexes of the invention can be formulated for administration in a pharmaceutical carrier in accordance with known techniques. See, e.g., Remington, *The Science and Practice of Pharmacy* (21$^{st}$ Ed. 2005). In the manufacture of a pharmaceutical composition, the nucleic acid constructs, CRISPR arrays, templates and/or protein-RNA complexes are typically admixed with, inter alia, an acceptable carrier. The carrier can be a solid (including a powder) or a liquid, or both, and is preferably formulated with the compound as a unit-dose composition, for example, a tablet, which can contain from 0.01 or 0.5% to 95% or 99% by weight of the compound. One or more compounds can be incorporated in the compositions of the invention, which can be prepared by any of the well-known techniques of pharmacy.

A further aspect of the invention is a method of treating subjects in vivo, comprising administering to a subject a pharmaceutical composition comprising nucleic acid constructs, CRISPR arrays, optionally templates, and/or protein-RNA complexes of the invention in a pharmaceutically acceptable carrier, wherein the pharmaceutical composition is administered in a therapeutically effective amount. Administration of the compounds of the present invention to a eukaryotic subject in need thereof can be by any means known in the art for administering compounds.

The nucleic acid constructs, CRISPR arrays, and optionally templates, and/or protein-RNA complexes of the invention and compositions thereof include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). In some embodiments, the composition is delivered to the site of tissue infection. The most suitable route in any given case will depend on the nature and severity of the condition being treated and on the nature of the particular compound which is being used.

For oral administration, the nucleic acid constructs, CRISPR arrays, and optionally templates and/or protein-RNA complexes can be administered in solid dosage forms, such as capsules, tablets, and powders, or in liquid dosage forms, such as elixirs, syrups, and suspensions. The nucleic acid constructs, CRISPR arrays, and optionally templates and/or protein-RNA complexes can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the compound, which preparations are preferably isotonic with the blood of the intended recipient. These preparations can contain antioxidants, buffers, bacteriostats and solutes which render the composition isotonic with the blood of the intended recipient. Aqueous and non-aqueous sterile suspensions can include suspending agents and thickening agents. The compositions can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Compositions suitable for rectal administration are preferably presented as unit dose suppositories. These can be prepared by admixing the compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Compositions suitable for transdermal administration can be presented as discrete patches adapted to remain in intimate contact with the epidermis of the recipient for a prolonged period of time. Compositions suitable for transdermal administration can also be delivered by iontophoresis (see, for example, Tyle, *Pharm. Res.* 3:318 (1986)) and typically take the form of an optionally buffered aqueous solution of the compound. Suitable compositions comprise citrate or bis\tris buffer (pH 6) or ethanol/water and contain from 0.1 to 0.2M of the compound.

The nucleic acid constructs, CRISPR arrays, and optionally templates and/or protein-RNA complexes of the invention can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the nucleic acid constructs, CRISPR arrays, and optionally templates and/or protein-RNA complexes in a local rather than systemic manner, for example, in a depot or sustained-release composition.

Further, the present invention provides liposomal formulations of the nucleic acid constructs, CRISPR arrays, and optionally templates and/or protein-RNA complexes of the invention disclosed herein. The technology for forming liposomal suspensions is well known in the art. As aqueous-soluble material, using conventional liposome technology, the nucleic acid constructs, CRISPR arrays, and optionally templates and/or protein-RNA complexes of the invention can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. The liposomes which are produced can be reduced in size through the use of, for example, standard sonication and homogenization techniques. The liposomal compositions containing the compound disclosed herein can be lyophilized to produce a lyophilizate, which can be reconstituted with a pharmaceutically acceptable carrier, such as water, to regenerate a liposomal suspension.

A pharmaceutical composition comprising the nucleic acid constructs, CRISPR arrays, and optionally templates and/or protein-RNA complexes of the invention can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the composition is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxym ethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

In particular embodiments, the nucleic acid constructs, CRISPR arrays, and—optionally templates and/or protein-RNA complexes of the invention can be administered to the subject in a therapeutically effective amount, as that term is defined above. Dosages of pharmaceutically active compounds can be determined by methods known in the art, see, e.g., Remington, *The Science And Practice of Pharmacy* ($21^{th}$ Ed. 2005). The therapeutically effective dosage of any specific compound will vary somewhat from compound to compound, and patient to patient, and will depend upon the condition of the patient and the route of delivery. In one embodiment, the compound is administered at a dose of about 0.001 to about 10 mg/kg body weight, e.g., about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, or 10 mg/kg. In some instances, the dose can be even lower, e.g., as low as 0.0005 or 0.0001 mg/kg or lower. In some instances, the dose can be even higher, e.g., as high as 20, 50, 100, 500, or 1000 mg/kg or higher. The present invention encompasses every sub-range within the cited ranges and amounts.

10. METHODS OF DELIVERY

Provided herein is a method for delivering the pharmaceutical formulations, preferably compositions described above, for providing genetic constructs. The delivery of the compositions may be the transfection or electroporation of the composition as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product #D8537 (PBS), Invitrogen OptiMEM I (OM), or Amaxa Nucleofector solution V (N.V.). Transfections may include a transfection reagent, such as Lipofectamine 2000.

Upon delivery of the composition to the tissue, and thereupon the vector into the cells of the mammal, the transfected cells will express the fusion protein, such as a Type I CRISPR/Cas system containing the Cascade fusion protein. The composition may be administered to a mammal to alter gene expression or to re-engineer or alter the genome. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

"Introducing," "introduce," "introduced" (and grammatical variations thereof) in the context of a polynucleotide of interest (e.g., the Cas3 polypeptides, the Cascade polypeptide, CRISPR array) means presenting a polynucleotide of interest to a host organism or a cell of the organism (e.g., host cell such as a eukaryotic cell) in such a manner that the polynucleotide gains access to the interior of a cell and includes such terms as transformation" and/or "transfection." Where more than one polynucleotide is to be introduced these polynucleotides can be assembled as part of a single polynucleotide or nucleic acid construct, or as separate polynucleotide or nucleic acid constructs, and can be located on the same or different expression constructs or transformation vectors. Thus, in some aspects, a eukaryotic cell can be transformed or transfected with a Type I CRISPR-Cas system, thereby expressing the Cascade polypeptides and at least one Cas3 polypeptide, as well as at least one CRISPR array.

The terms "transformation" and "transfection" as used herein refer to the introduction of a heterologous polynucleotide into a cell (e.g., polynucleotides of heterologous Type I CRISPR-Cas systems, CRISPR arrays, templates). Such introduction into a cell may be stable or transient. Thus, in some embodiments, a host cell or host organism is stably transformed with a nucleic acid molecule of the invention (DNA or RNA (e.g., mRNA)) or a ribonucleoprotein complex. In other embodiments, a host cell or host organism is transiently transformed with a recombinant nucleic acid molecule of the invention (DNA or RNA (e.g., mRNA)) or a ribonucleoprotein complex.

"Transient transformation" in the context of a polynucleotide means that a polynucleotide is introduced into the cell and does not integrate into the genome of the cell and cannot be maintained through antibiotic selection or addictive systems.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plasmid genome, and therefore includes integration of the nucleic acid construct into, for example, the plasmid genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into a eukaryotic organism. Stable transformation of a cell can be detected by, for example, a Northern blot hybridization assay of RNA of the cell with nucleic acid sequences which specifically hybridize with a nucleotide sequence of a transgene introduced into the cell. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

The polynucleotides of the invention (e.g., Cas3 polypeptides, Cascade polypeptides, CRISPR arrays, templates) can be introduced into a eukaryotic cell by any method known to those of skill in the art. Exemplary methods of transformation include transformation via electroporation of competent cells, passive uptake by competent cells, chemical transformation of competent cells, as well as any other electrical, chemical, physical (mechanical) and/or biological mechanism that results in the introduction of nucleic acid into a cell, including any combination thereof. In some aspects, transformation of a cell may comprise nuclear transformation. In other aspects, transformation of a cell may comprise plastid transformation. Procedures for transforming eukaryotic organisms are well known and routine in the art and are described throughout the literature.

A nucleotide sequence (e.g., nucleotide sequences comprising the CRISPR nucleic acids and templates, and those encoding the CRISPR polypeptides), can therefore be introduced into a host cell in any number of ways that are well known in the art to generate a eukaryote comprising, for example, a Type I CRISPR-Cas system as described herein. The methods of the invention do not depend on a particular method for introducing one or more nucleotide sequences into an organism, only that they gain access to the interior of the cell. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events.

In additional aspects, a plant may be transformed with at least one nucleic acid construct comprising Type I CRISPR system and CRISPR array targeting nematodes and/or or fungi. The at least one nucleic acid construct and CRISPR array may be constitutively expressed or specifically expressed in various plant parts including leaves and/or roots. A nematode and/or fungus feeding on the transformed plant may then consume the at least one nucleic acid construct comprising Type I CRISPR system and CRISPR array targeting nematodes and/or fungi, thereby killing the nematode or fungus.

a) Type I CRISPR/Cas System

The vector encoding a Type I CRISPR/Cas system protein component, i.e., Cascade, the Cas3 protein, may be delivered to the mammal by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus. The nucleotide encoding a Type I CRISPR/Cas system protein component, i.e., Cascade, the Cas3 protein, may be introduced into a cell to genetically correct the target gene or alter gene expression of a gene, such as activate or repress endogenous genes.

11. ROUTES OF ADMINISTRATION

The compositions may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus.

12. CELL TYPES

Any of these delivery methods and/or routes of administration could be utilized with a myriad of eukaryotic cell types, for example, those cell types currently under investigation for cell-based therapies. Cell types may be fibroblasts, pluripotent stem cells, cardiomyocytes, hepatocytes, chondrocytes, mesenchymal progenitor cells, hematopoetic stem cells, smooth muscle cells, or K562 human erythroid leukemia cell line.

A eukaryotic cell useful with this invention can be any eukaryotic cell from any eukaryotic organism. Non-limiting examples of eukaryotic organisms include mammals, insects, amphibians, reptiles, birds, fish, fungi, plants, and/or nematodes.

13. KITS

Provided herein is a kit, which may be used for genome engineering in a eukaryotic cells. The kit comprises a composition, as described above, and instructions for using said composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions. The composition for modulating gene expression of a target gene in eukaryotic cells may include a modified AAV vector and a nucleotide sequence encoding Type I CRISPR/Cas system, as described above. The composition for modulating gene expression of a target gene in eukaryotic cells may include a modified lentiviral vector and a nucleotide sequence encoding Type I CRISPR/Cas system, as described above. The kit may further include donor DNA, a crRNA, or a transgene, as described above.

14. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein.

Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Type I-C, Type I-E, and Type I-F Systems for Eukaryotic Cells

Modifications to the Type I-C, Type I-E, and Type I-F systems were made for use as a molecular genome editing tool in eukaryotes. To express the Cascade and Cas3 proteins from these three systems in human cells, human codon optimized sequences were cloned into plasmids downstream of a CMV promoter and Kozak sequence. Unique epitope tags (3×Flag (FLAG=DYKDDDDK (SEQ ID NO: 1)), HA (HA=YPYDVPDYAC (SEQ ID NO: 2)), myc (myc=EQKLISEEDLC (SEQ ID NO: 3)), V5 (V5=GKPIPNPLLGLDST (SEQ ID NO: 4)), E-tag (E-tag=GAPVPYPDPLEPR (SEQ ID NO: 5)), VSV-g (VSV-g=YTDIEMNRLGK (SEQ ID NO: 6)), 6×His (6×HIS=HHHHHH (SEQ ID NO: 7)), and HSV (HSV=QPELAPEDPEDC (SEQ ID NO: 8))) were included for each system in the open reading frame for individual protein detection. In addition, nuclear localization signals (SV40 NLS; PKKKRKV (SEQ ID NO: 9)) were added to aid in transporting the bacterial proteins into eukaryotic nuclei. Expression of these constructs in transfected human embryonic kidney cells (HEK293T) was confirmed by western blot analysis, blotting with antibodies specific for each epitope tag. FlpIn293 cells containing GFP were generated (FIG. 15). The cascade polynucleotide sequences used were SEQ ID NOs: 20-22 for Type I-C system, SEQ ID NOs: 23-27 for Type I-E system, and SEQ ID NOs: 28-31 for Type I-F system. The Cas3 polynucleotide sequences used were SEQ ID NO: 14 (Type I-C), SEQ ID NO: 16 (Type I-E), and SEQ ID NO: 18 (Type I-F).

Figure 9:
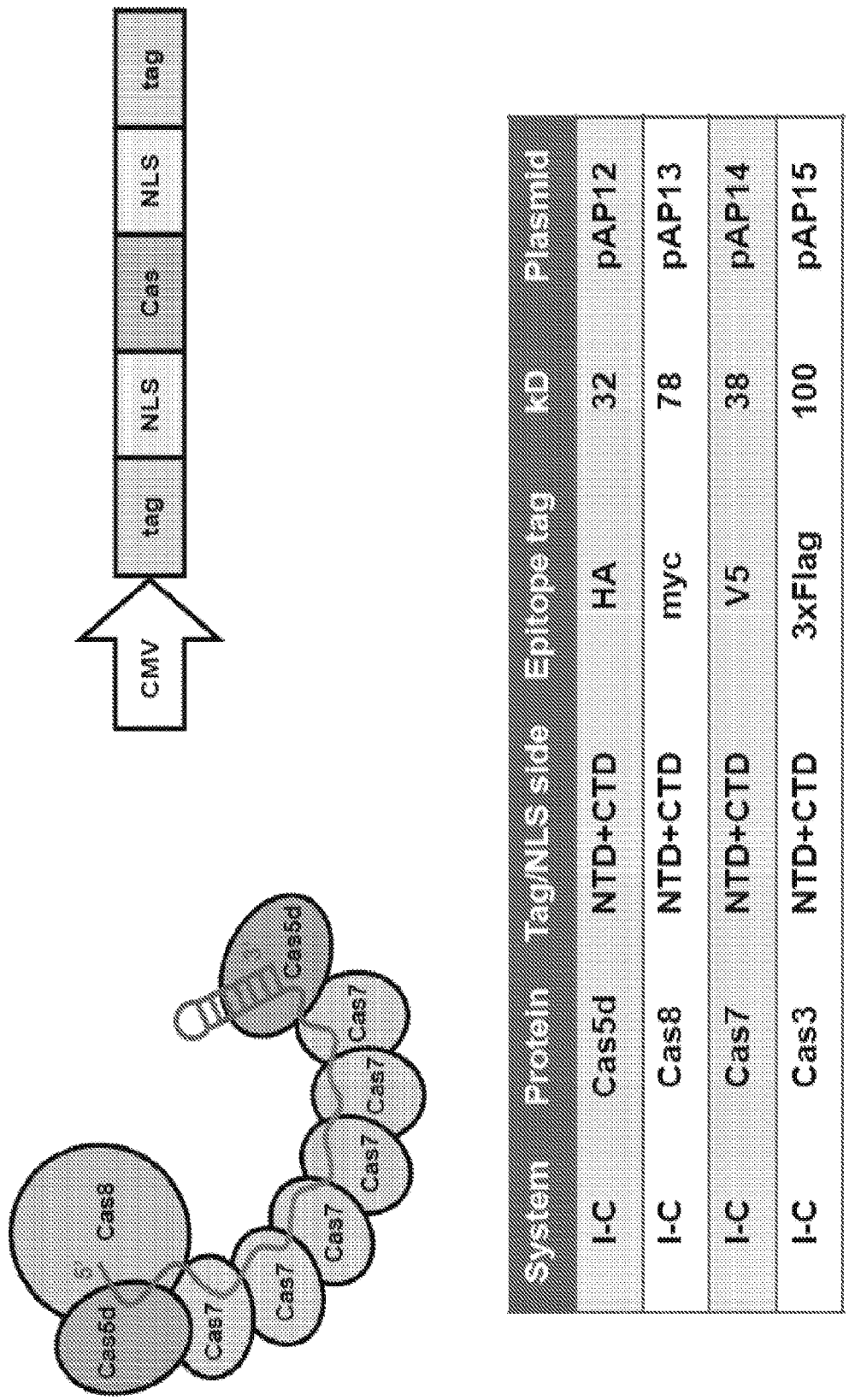
FIG. 9 shows the Type I-C constructs.
Figure 10:
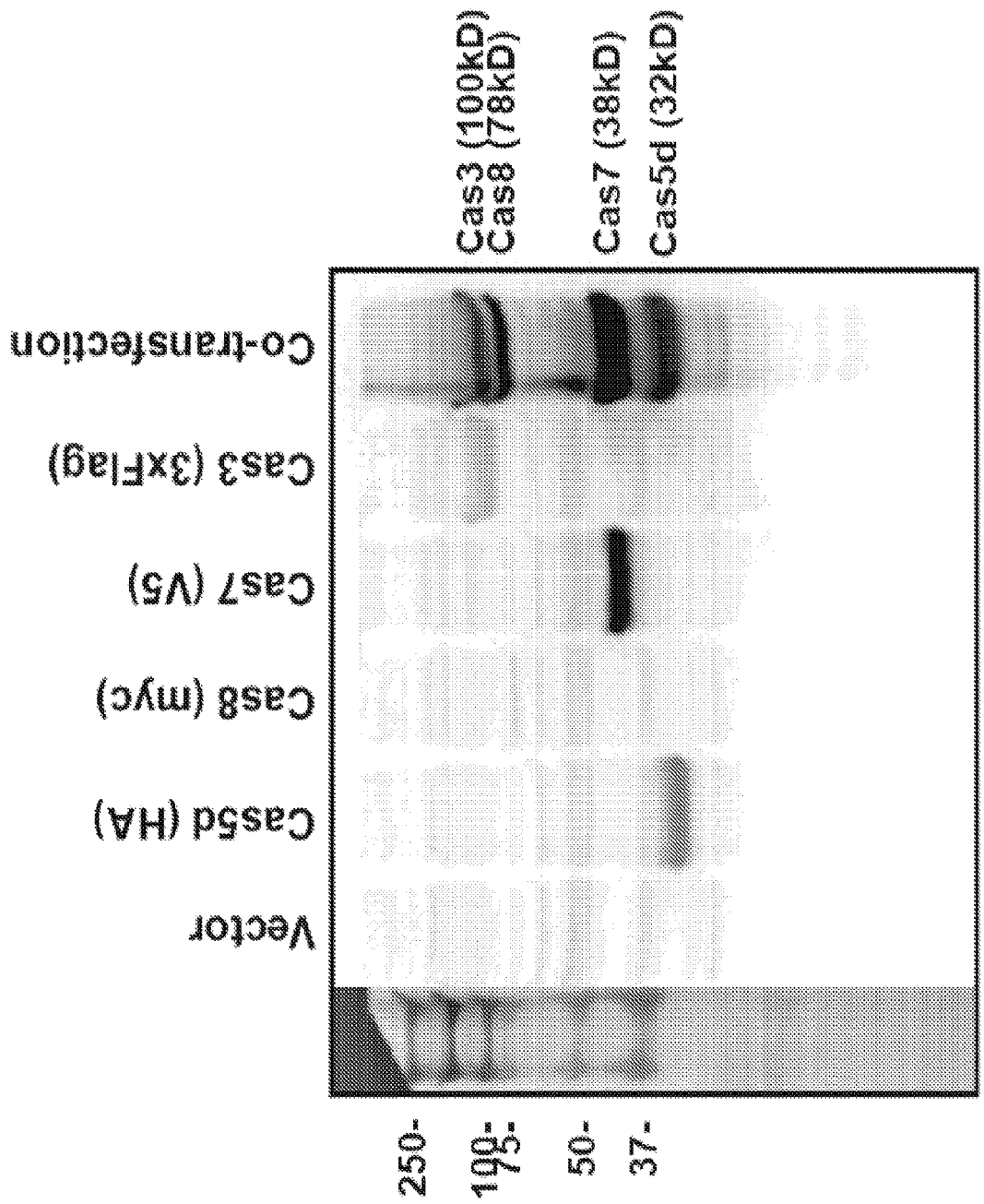
FIG. 10 shows the expression of Type I-C in HEK293T cells.
Figure 11:
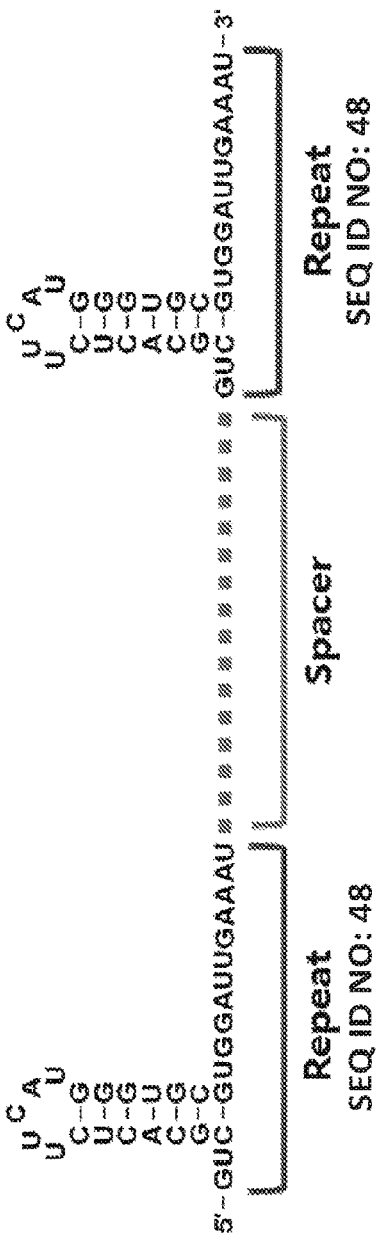
FIG. 11 shows the Type I-C crRNA production.
Figure 12:
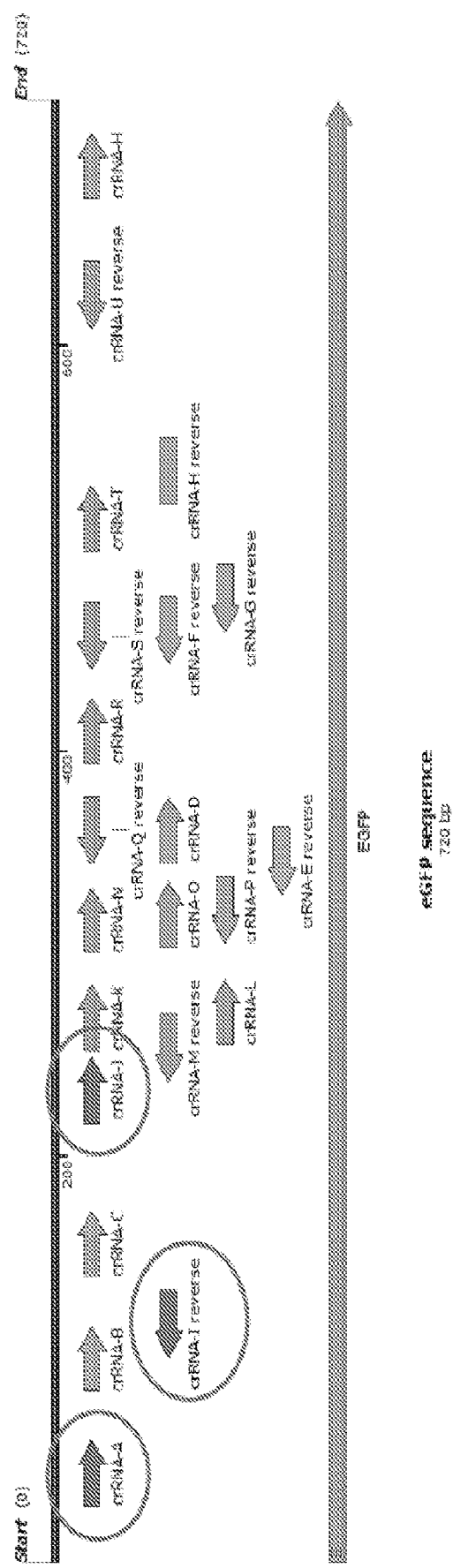
FIG. 12 shows the Type I-C crRNA targets in eGFP.
Figure 16:
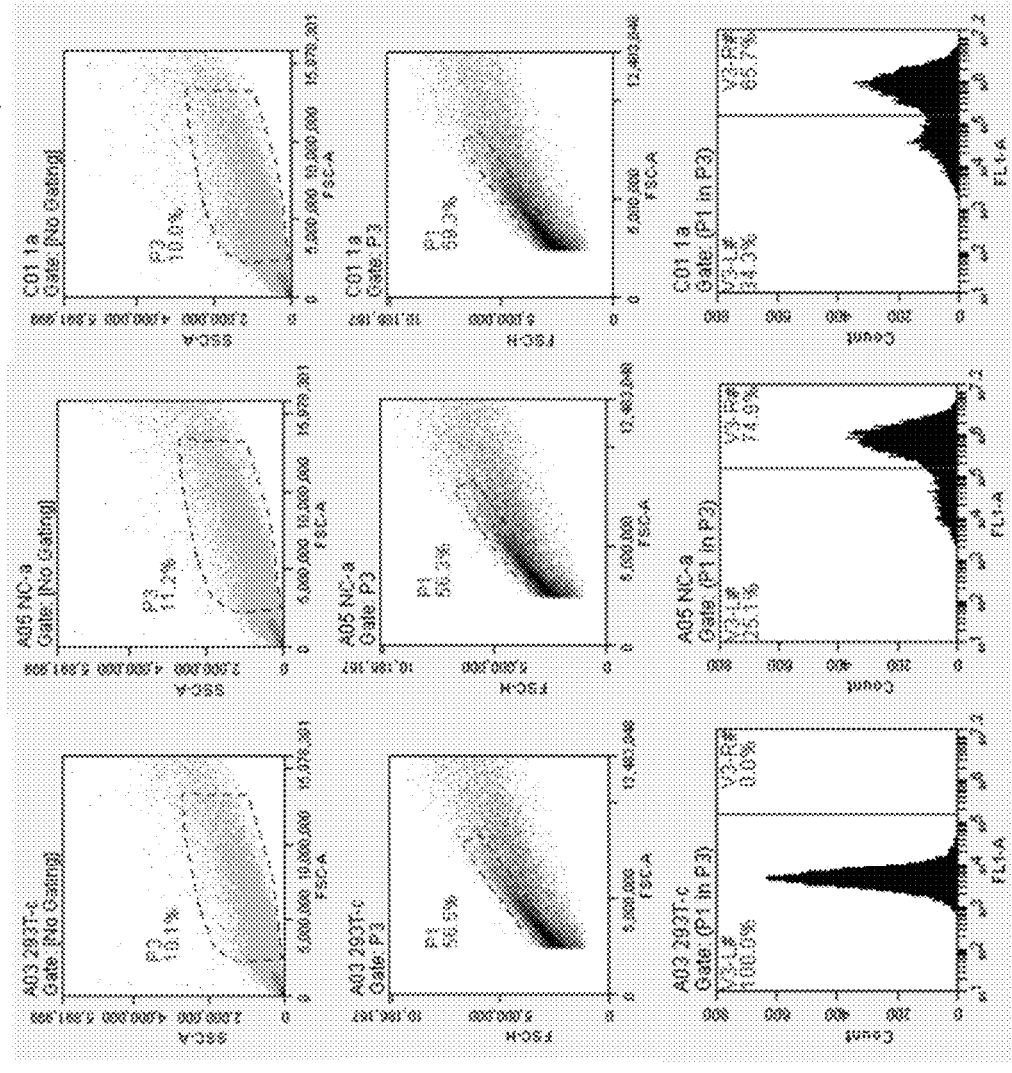
FIG. 16 shows flow analysis of targeting Type I-C Cascade/Cas3 to GFP.
Figure 17:
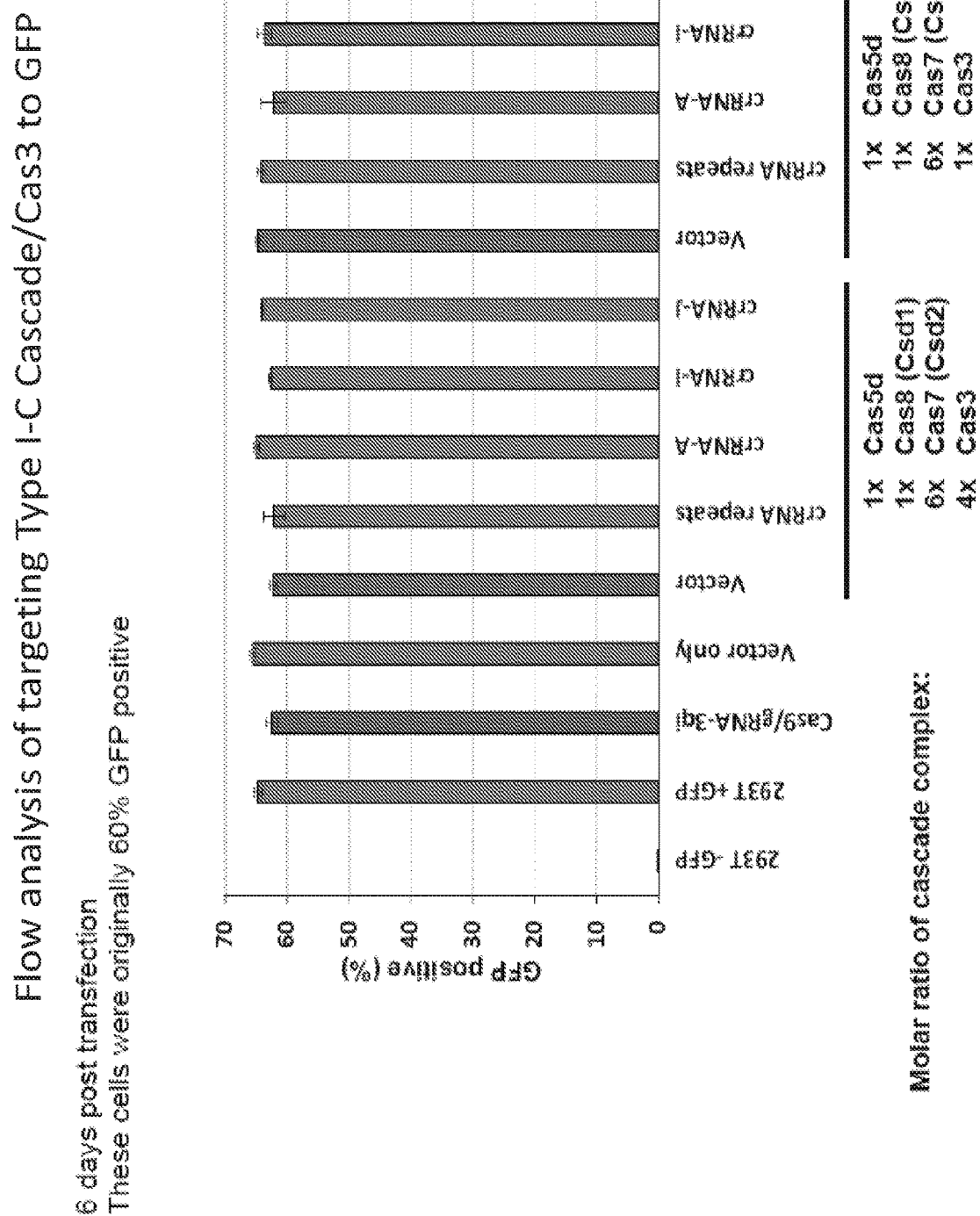
FIG. 17 shows flow analysis of targeting Type I-C Cascade/Cas3 to GFP.
Figure 18:
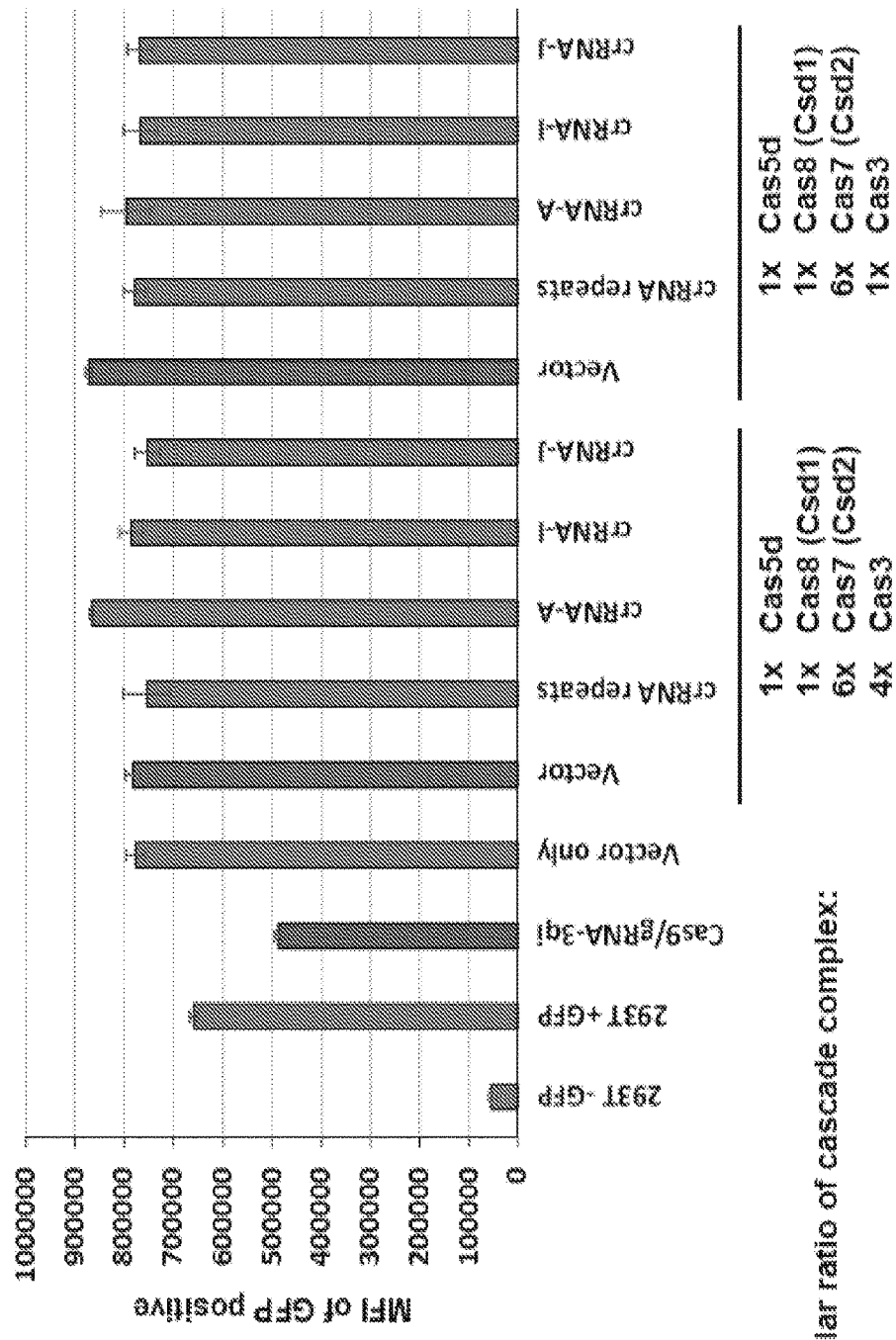
FIG. 18 shows flow analysis of targeting Type I-C Cascade/Cas3 to GFP.
Figure 19:
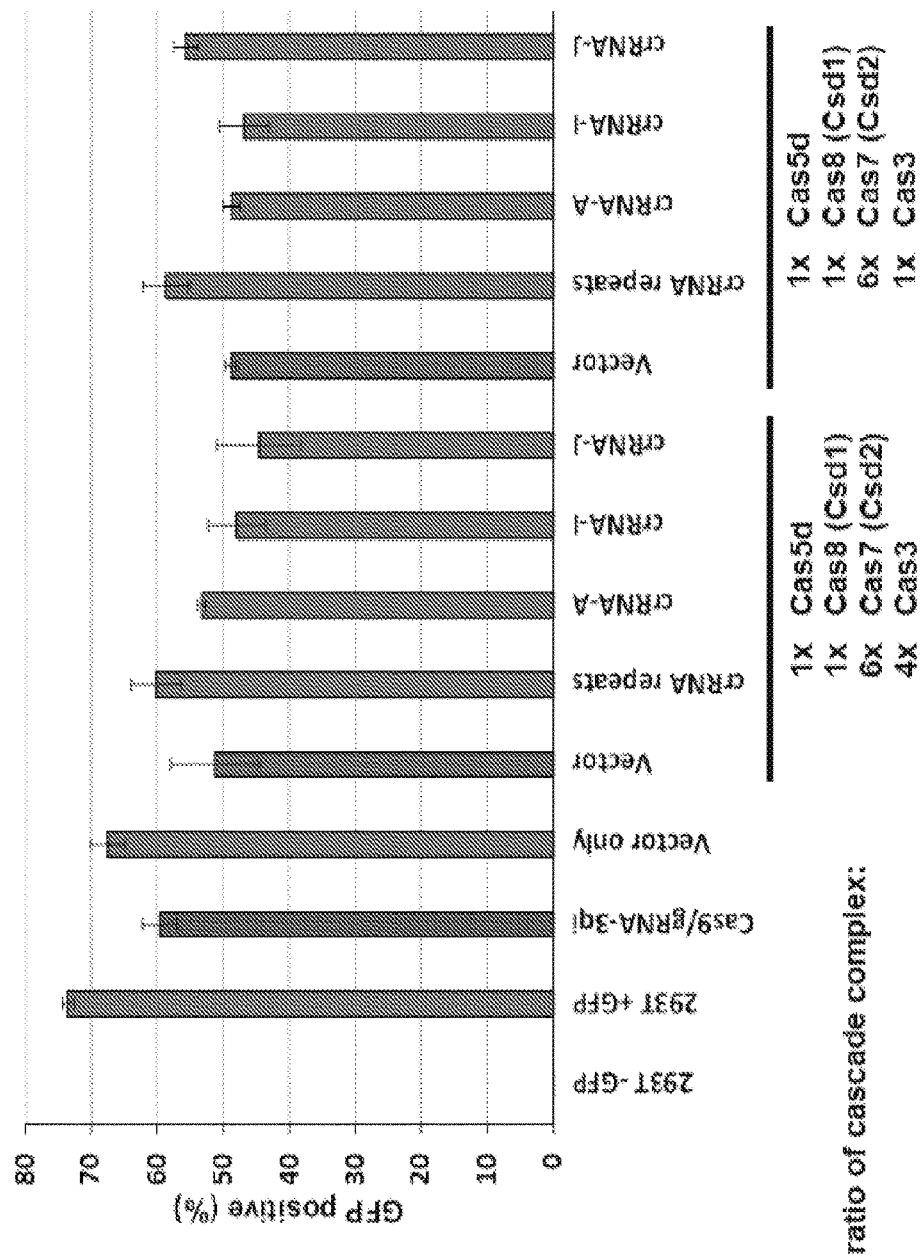
FIG. 19 shows flow analysis of targeting Type I-C Cascade/Cas3 to GFP.
Figure 20:
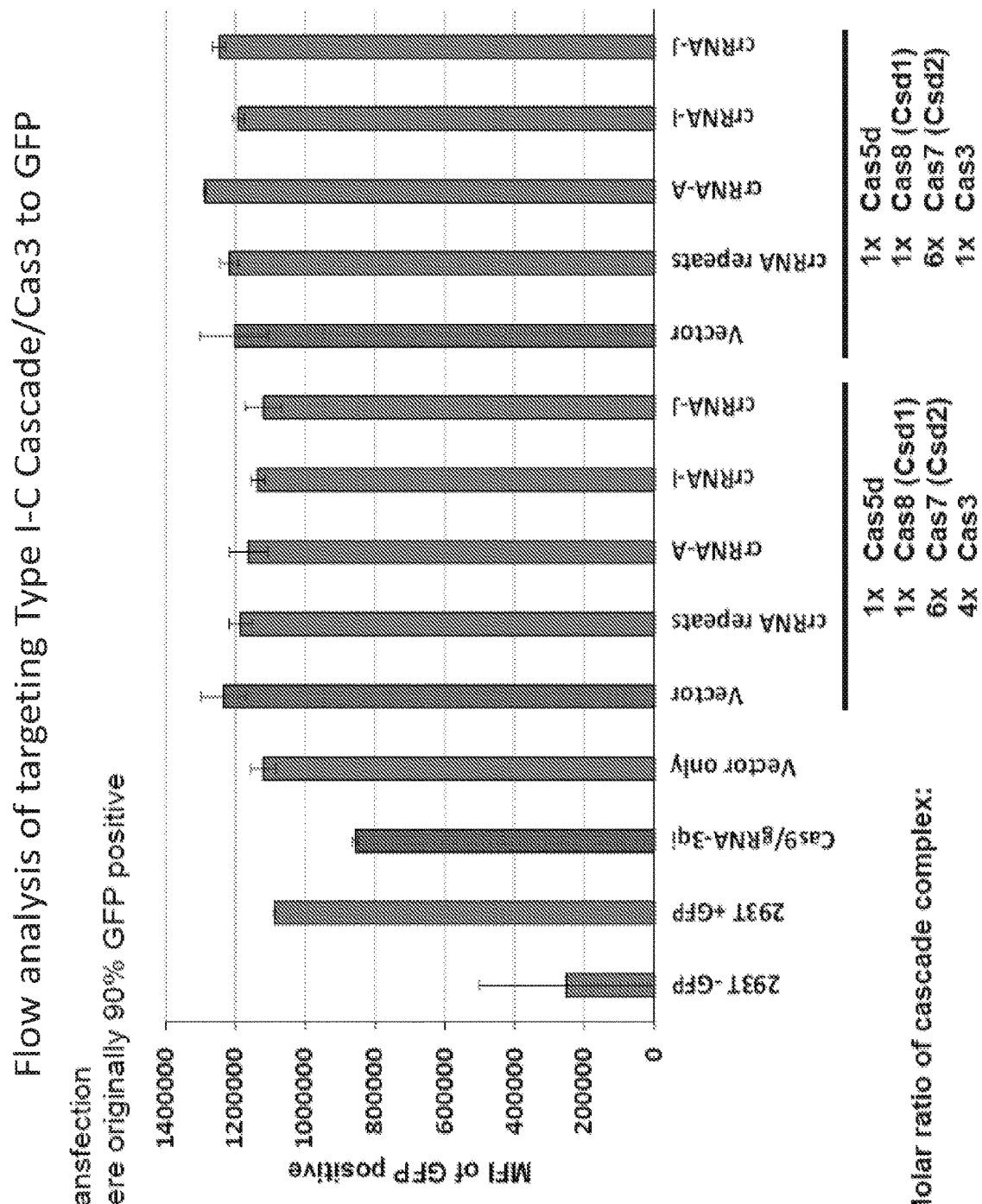
FIG. 20 shows flow analysis of targeting Type I-C Cascade/Cas3 to GFP.
Figure 21:
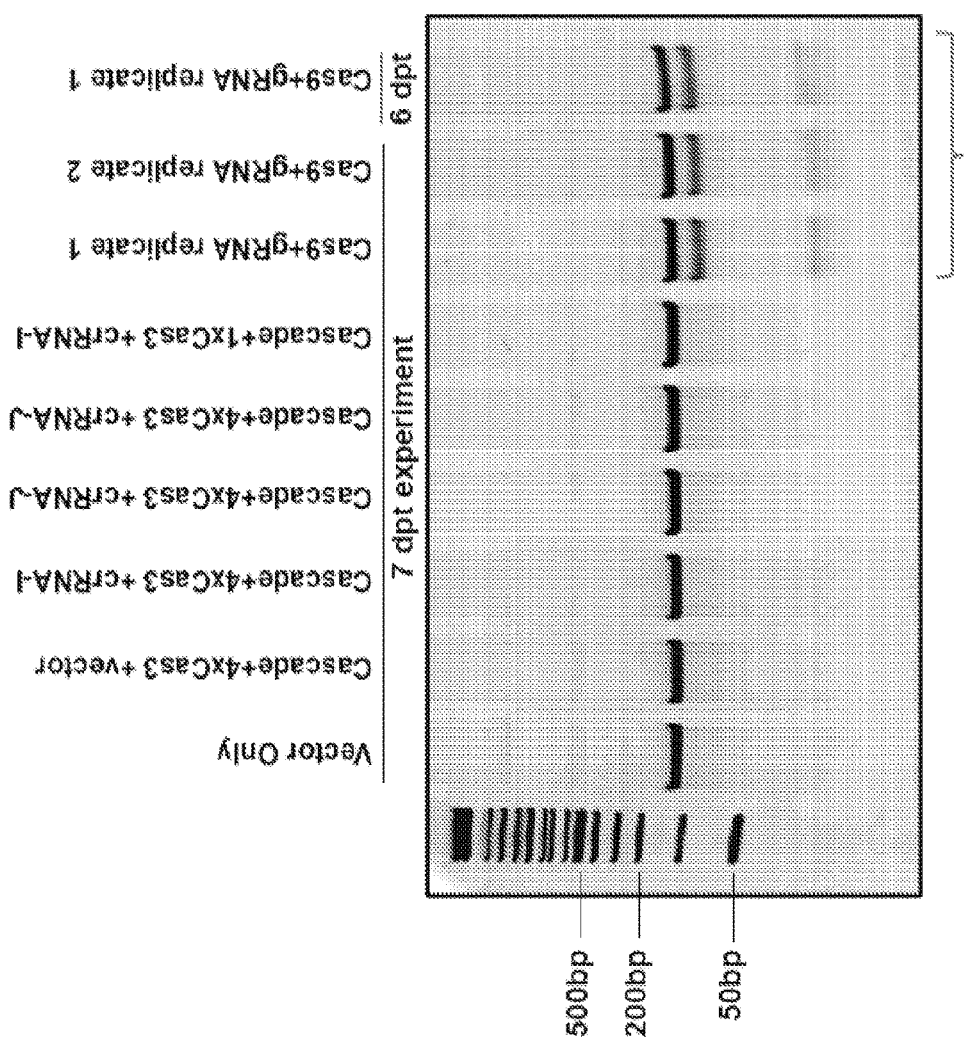
FIG. 21 shows flow analysis of targeting Type I-C Cascade/Cas3 to GFP.
Figure 22:
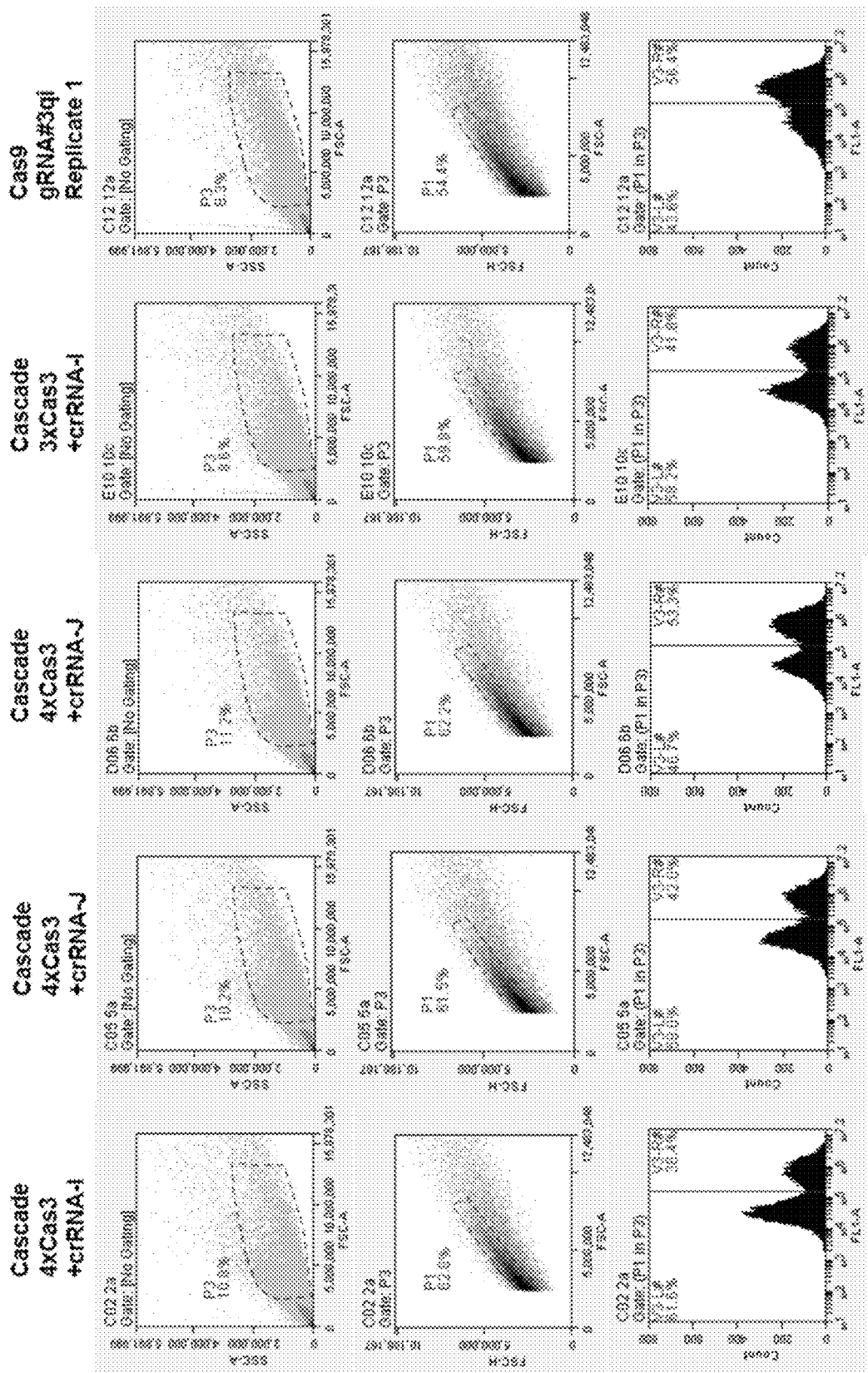
FIG. 22 shows flow analysis of targeting Type I-C Cascade/Cas3 to GFP.
Figure 23:
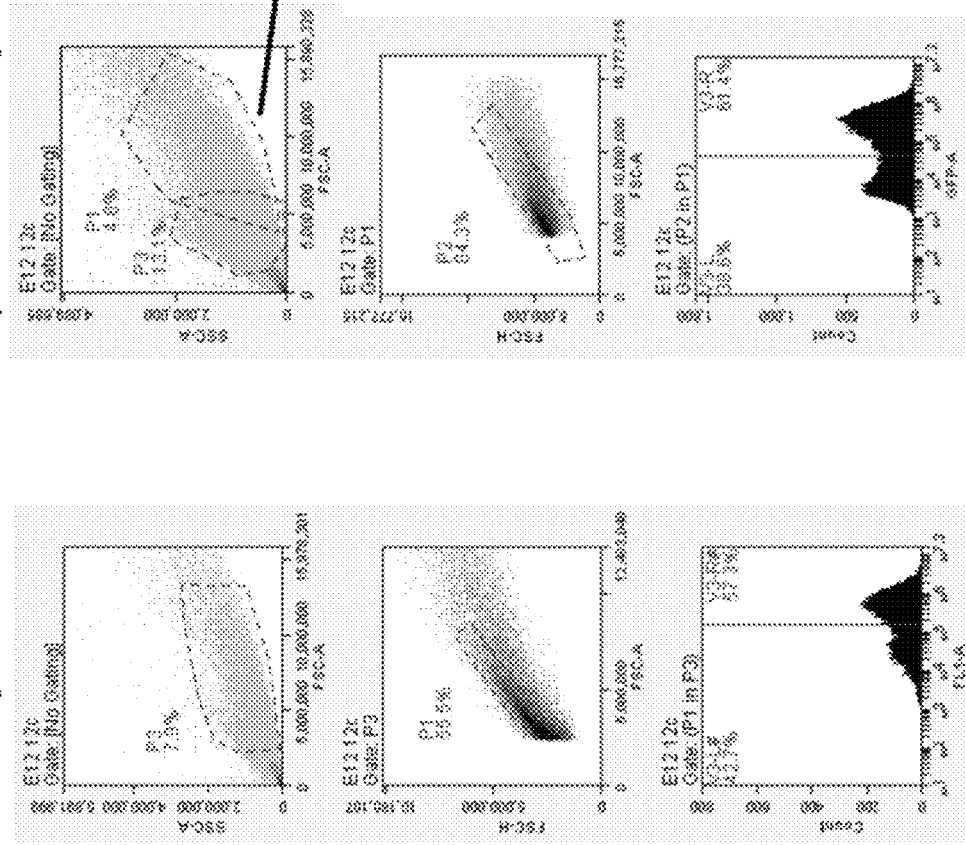
FIG. 23 shows flow analysis of targeting Type I-C Cascade/Cas3 to GFP.
Figure 24:
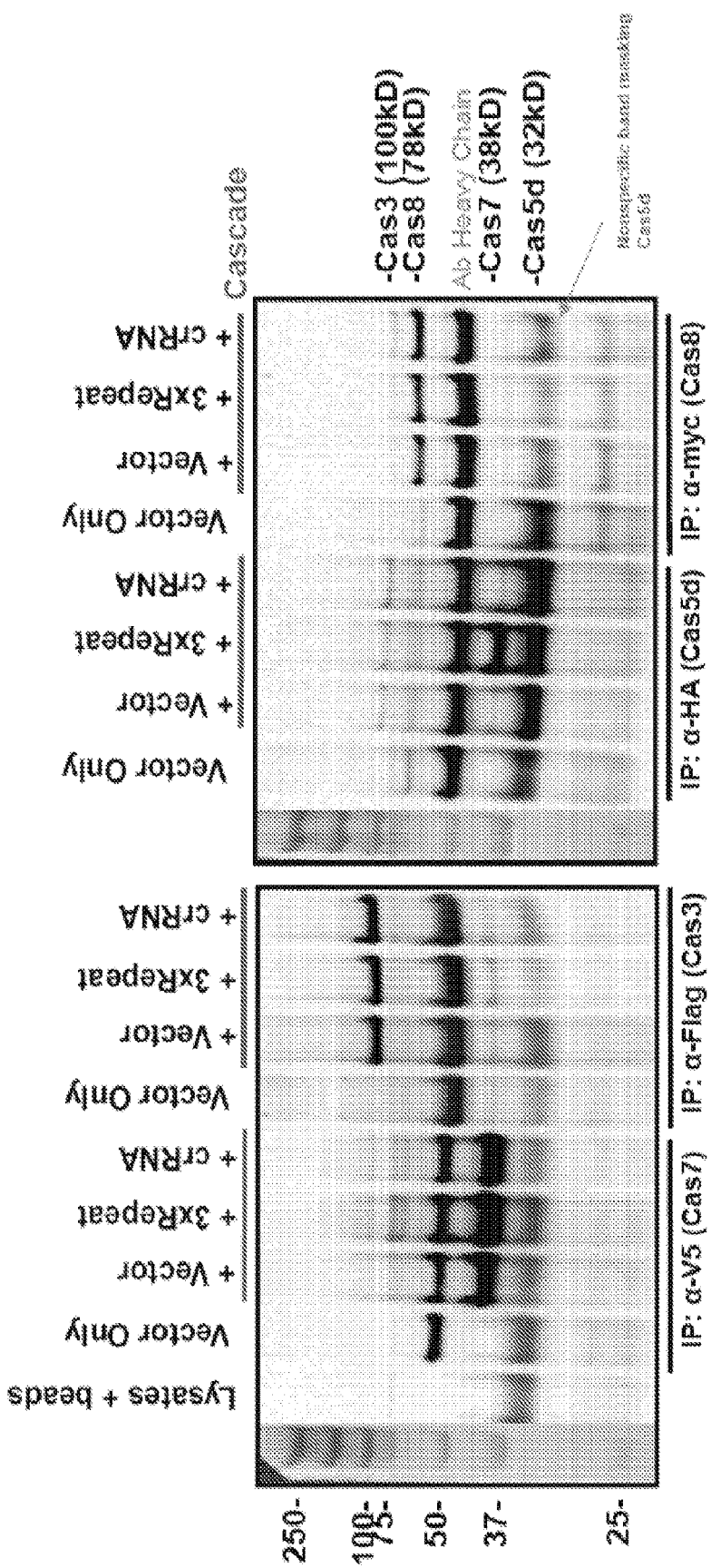
FIG. 24 shows Type I-C Cascade Co-Immunoprecipitation (Co-IP).
Figure 25:
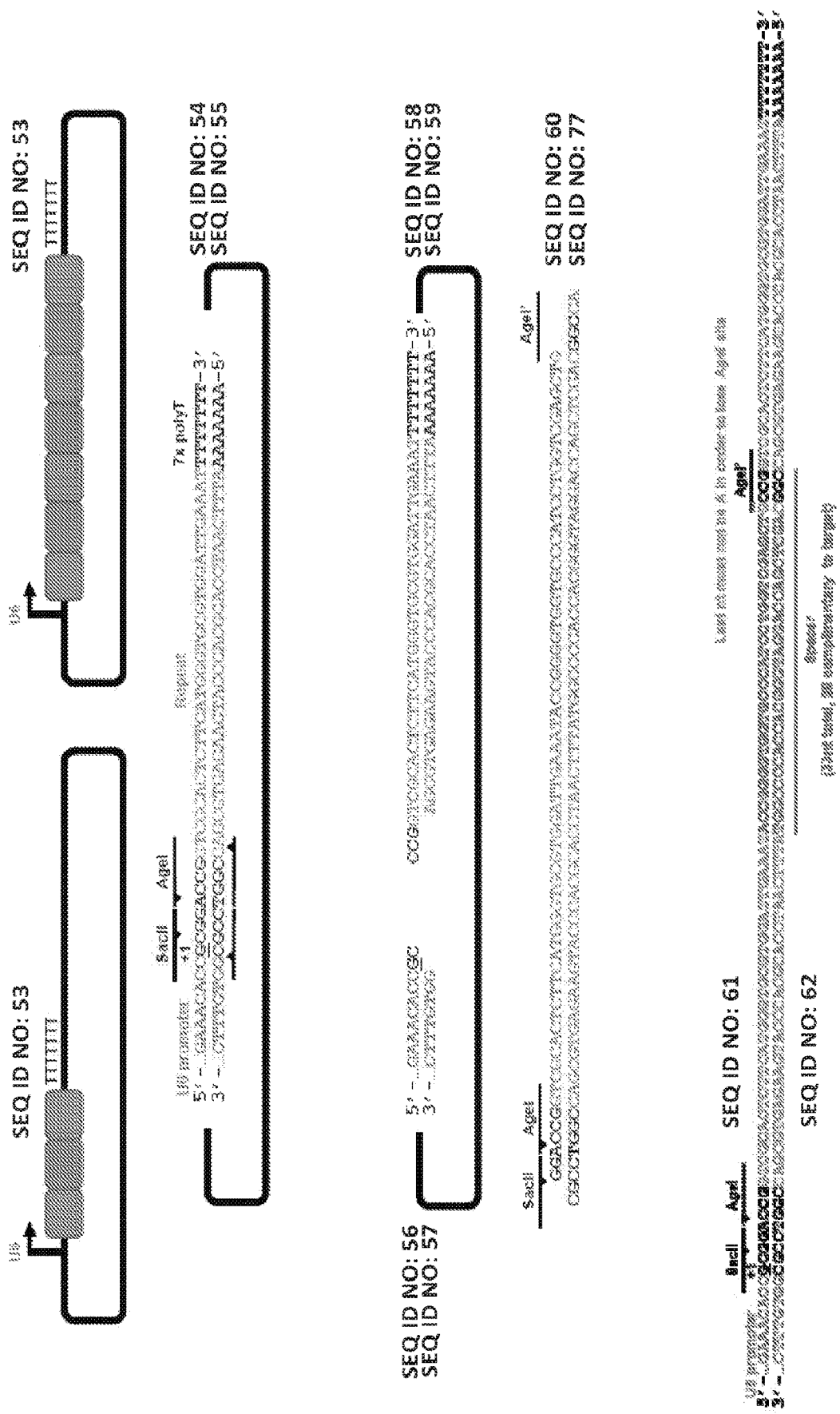
FIG. 25 shows the Type I-C crRNA repeat cloning vector (pAP68).
Figure 26:
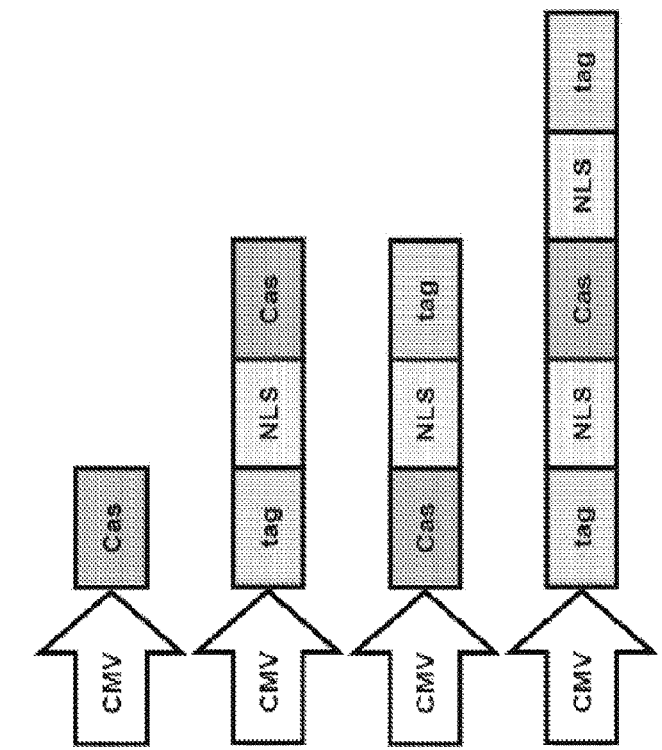
FIG. 26 shows Type I-C Constructs.
Figure 27:
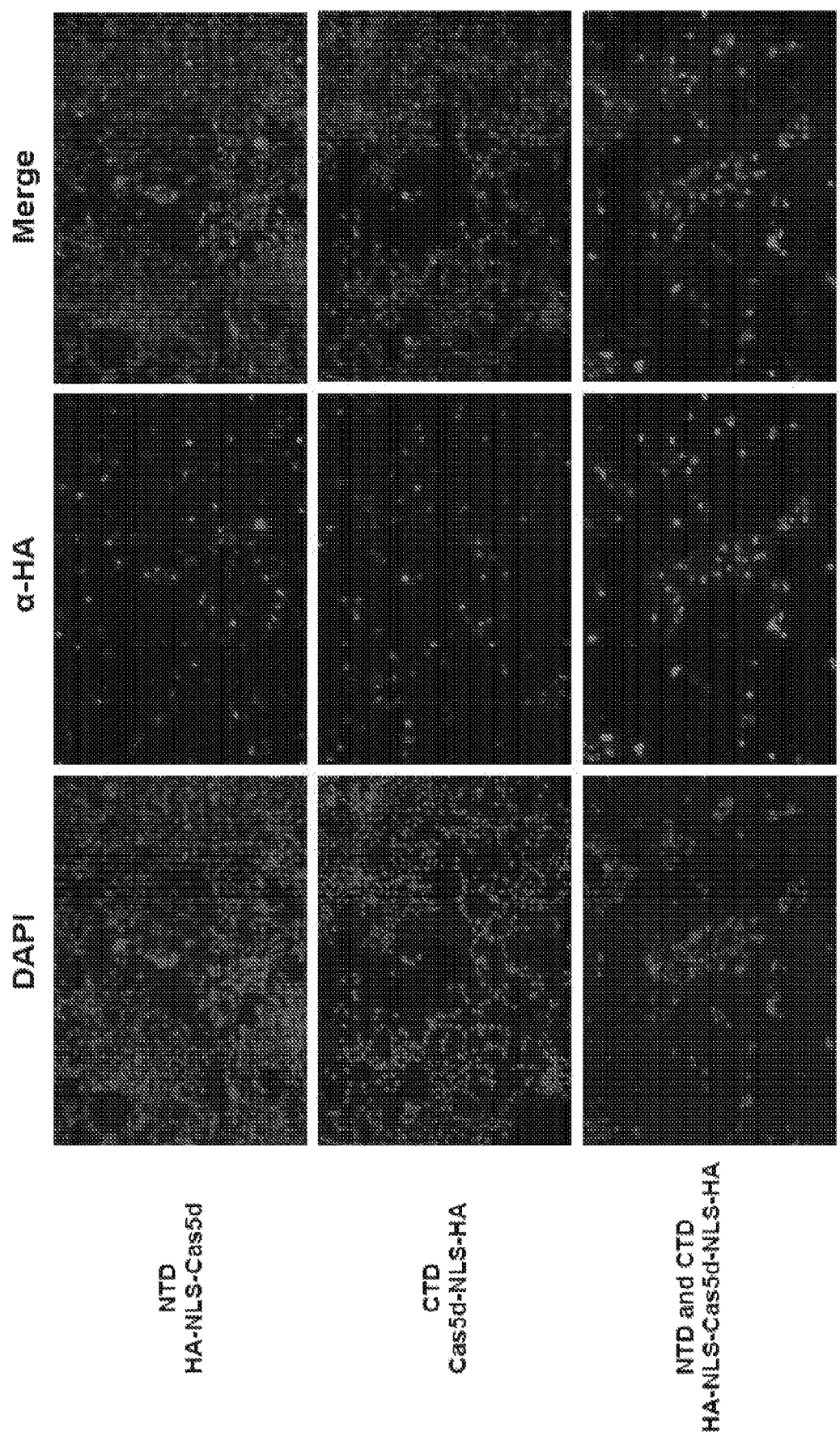
FIG. 27 shows α-hemagglutinin (α-HA) fluorescent imaging (red), DAPI nuclear staining (blue), and merged image of HEK293T cells transfected with Cas5 constructs.
Figure 28:
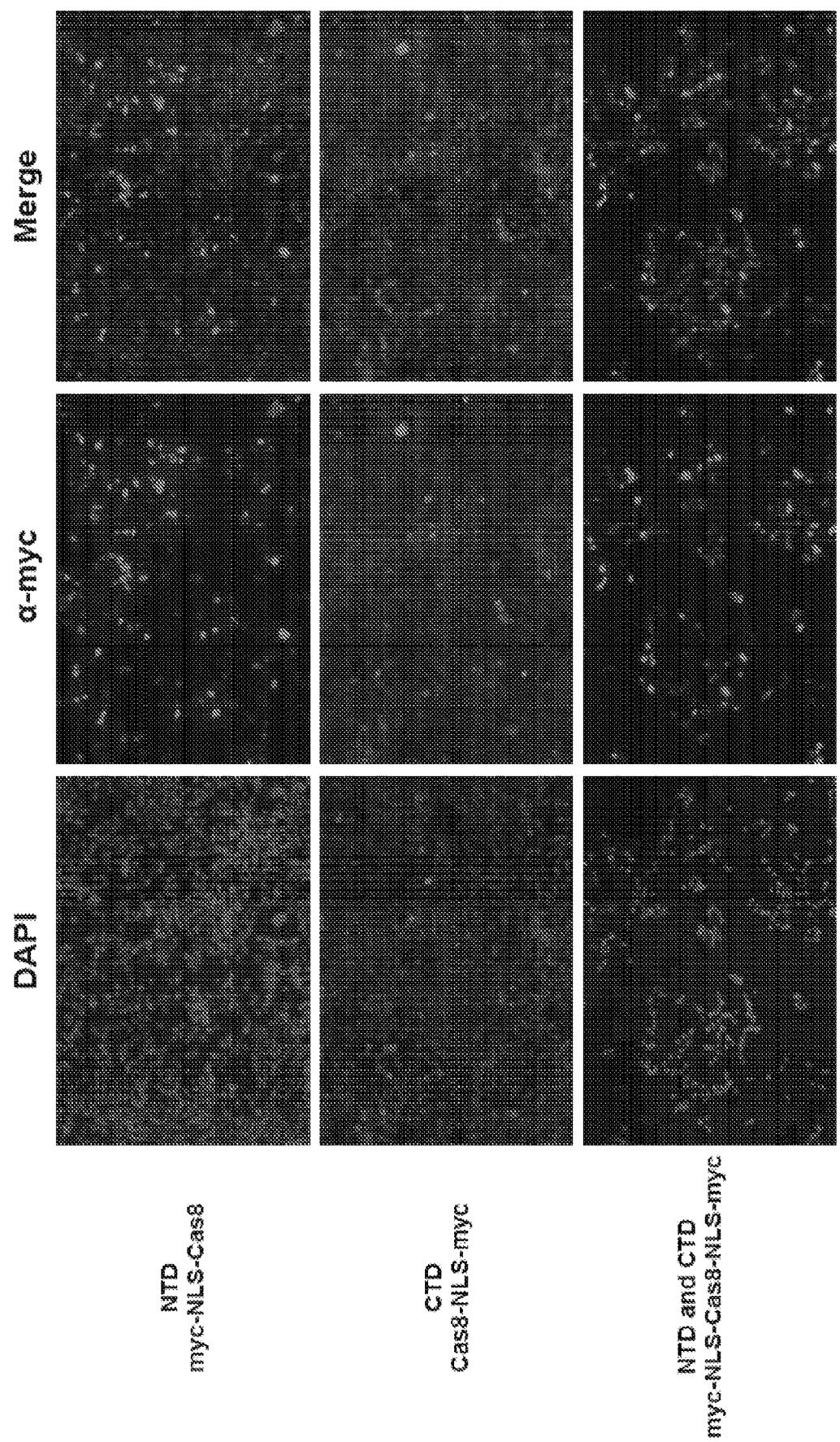
FIG. 28 shows α-myc fluorescent imaging (red), DAPI nuclear staining (blue), and merged image of HEK293T cells transfected with Cas8 constructs.
Figure 29:
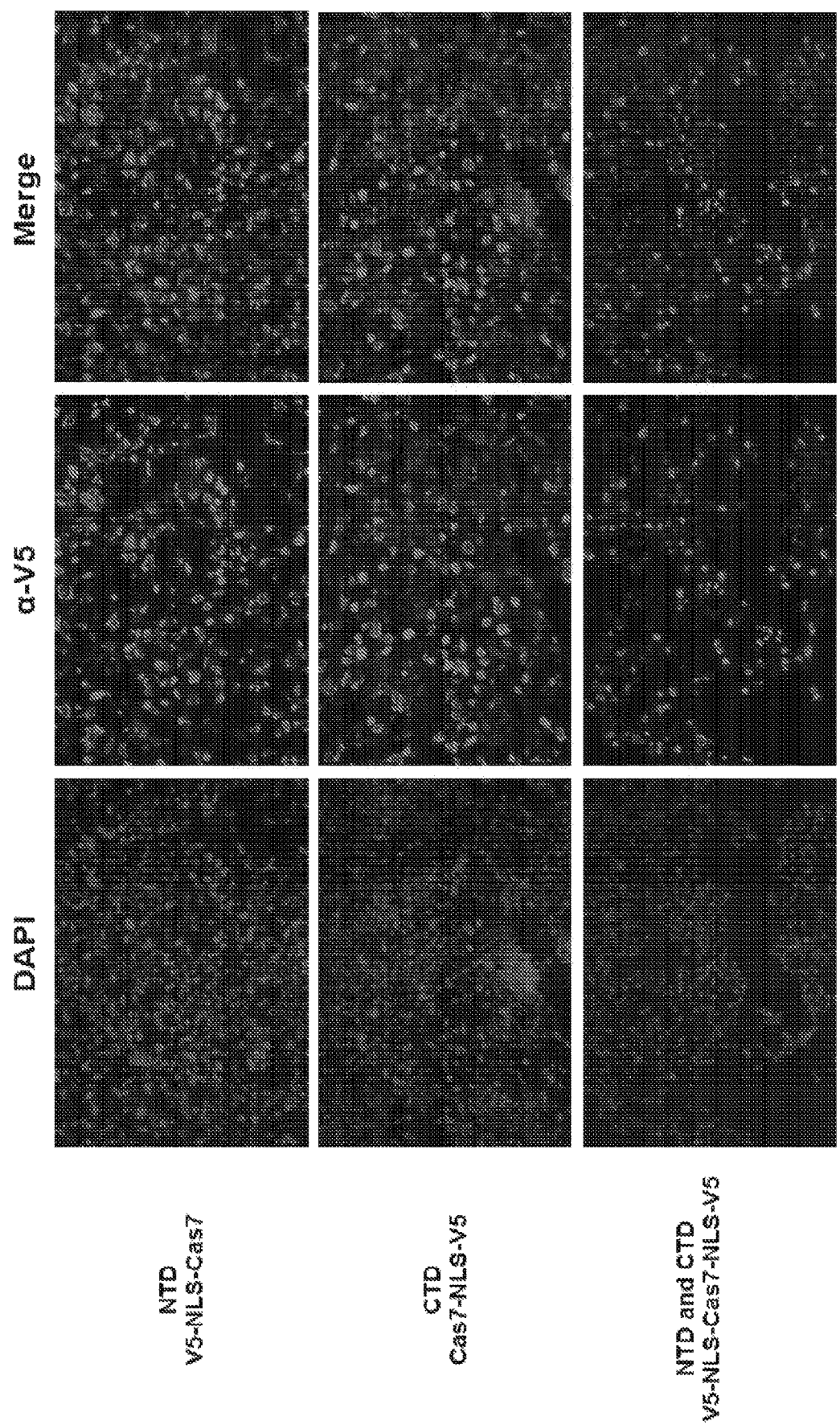
FIG. 29 shows α-V5 fluorescent imaging (red), DAPI nuclear staining (blue), and merged image of HEK293T cells transfected with Cas7 constructs.
Figure 30:
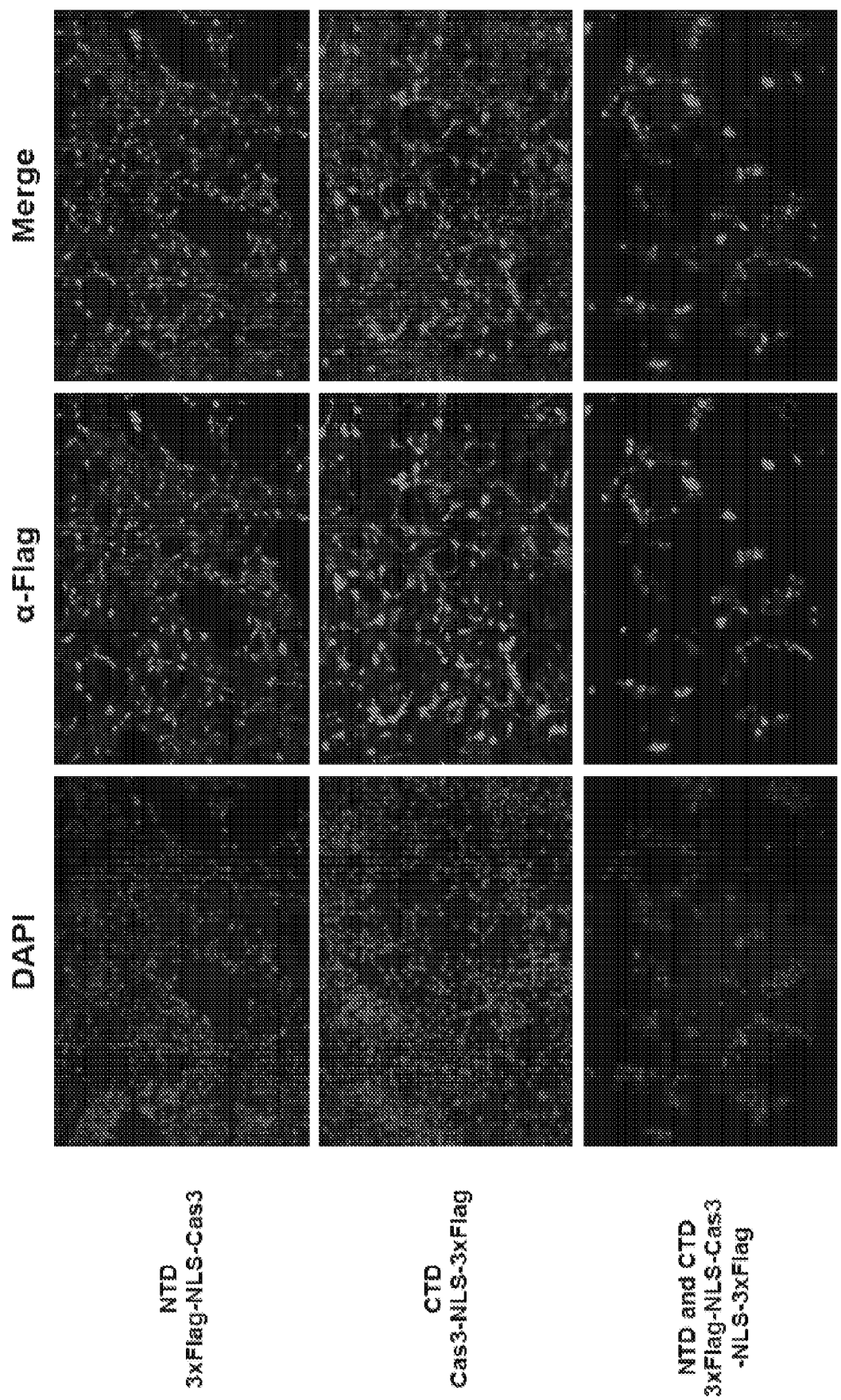
FIG. 30 shows α-Flag fluorescent imaging (red), DAPI nuclear staining (blue), and merged image of HEK293T cells transfected with Cas3 constructs
Figure 31:
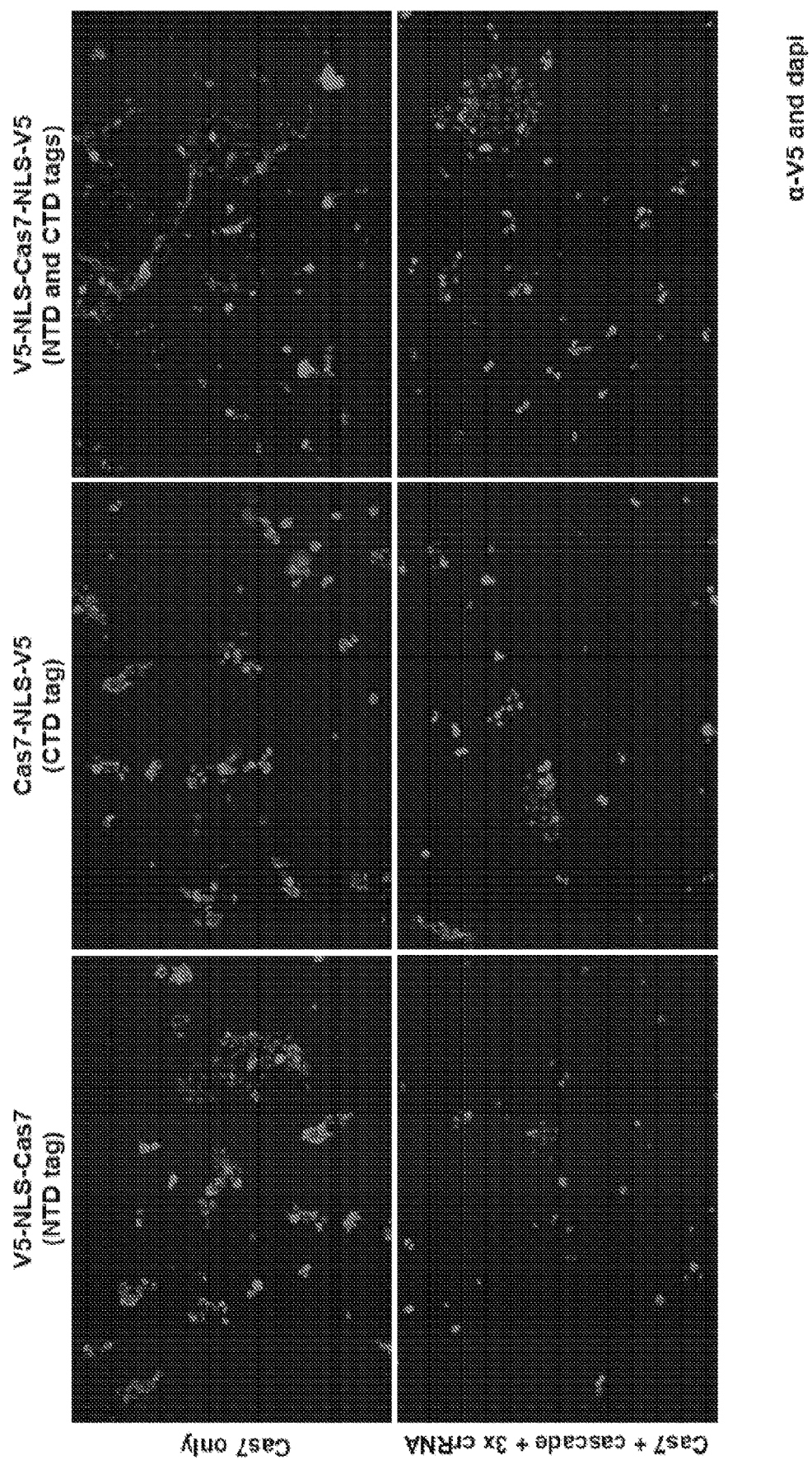
FIG. 31 shows the merged image of α-V5 fluorescent imaging (red) and DAPI nuclear staining (blue) of HEK293T cells transfected with Cas7 constructs with or without cascade and 3× crRNA construct.
Figure 32:
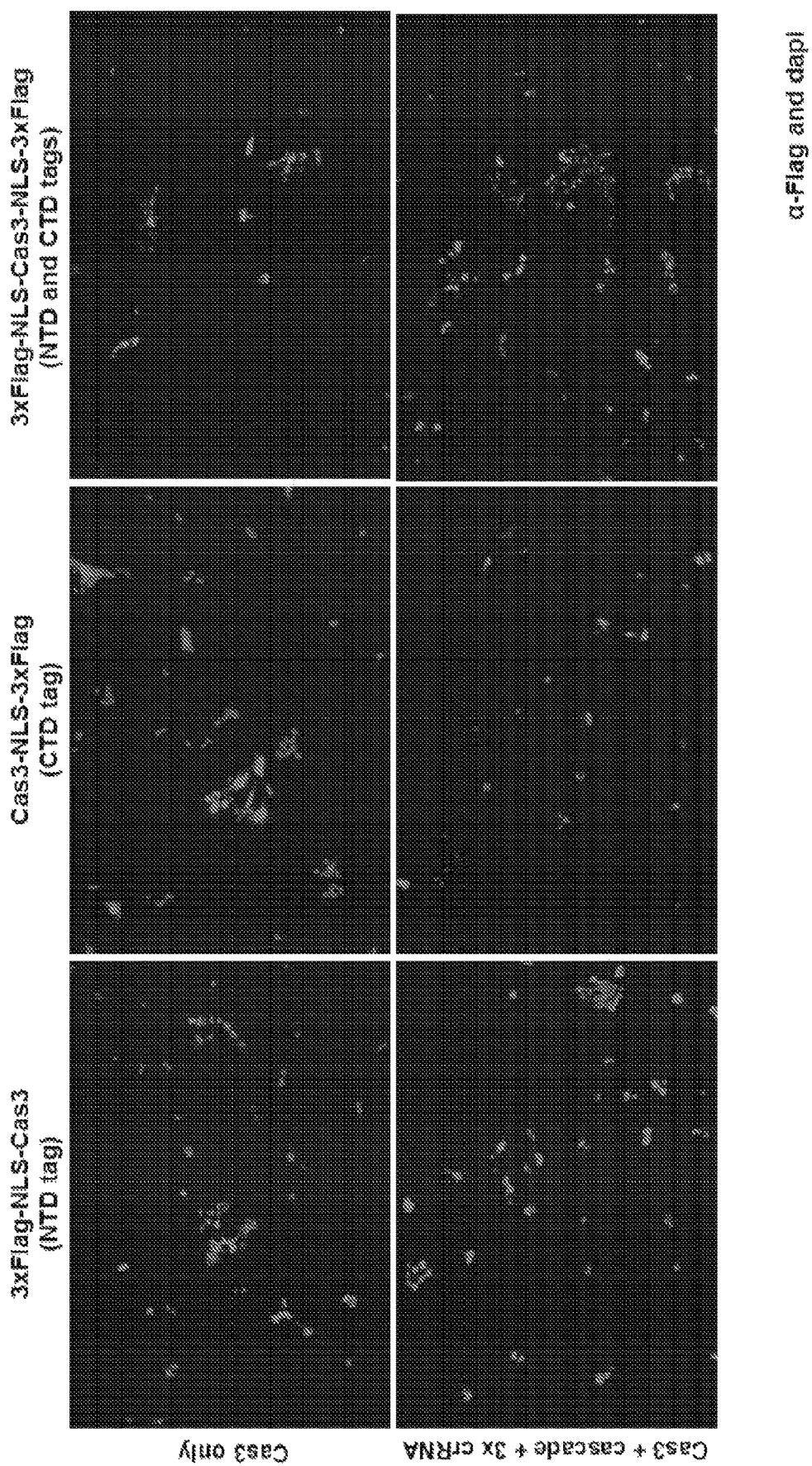
FIG. 32 shows the merged image of α-Flag fluorescent imaging (red) and DAPI nuclear staining (blue) of HEK293T cells transfected with Cas3 constructs with or without cascade and 3× crRNA construct.
Figure 33:
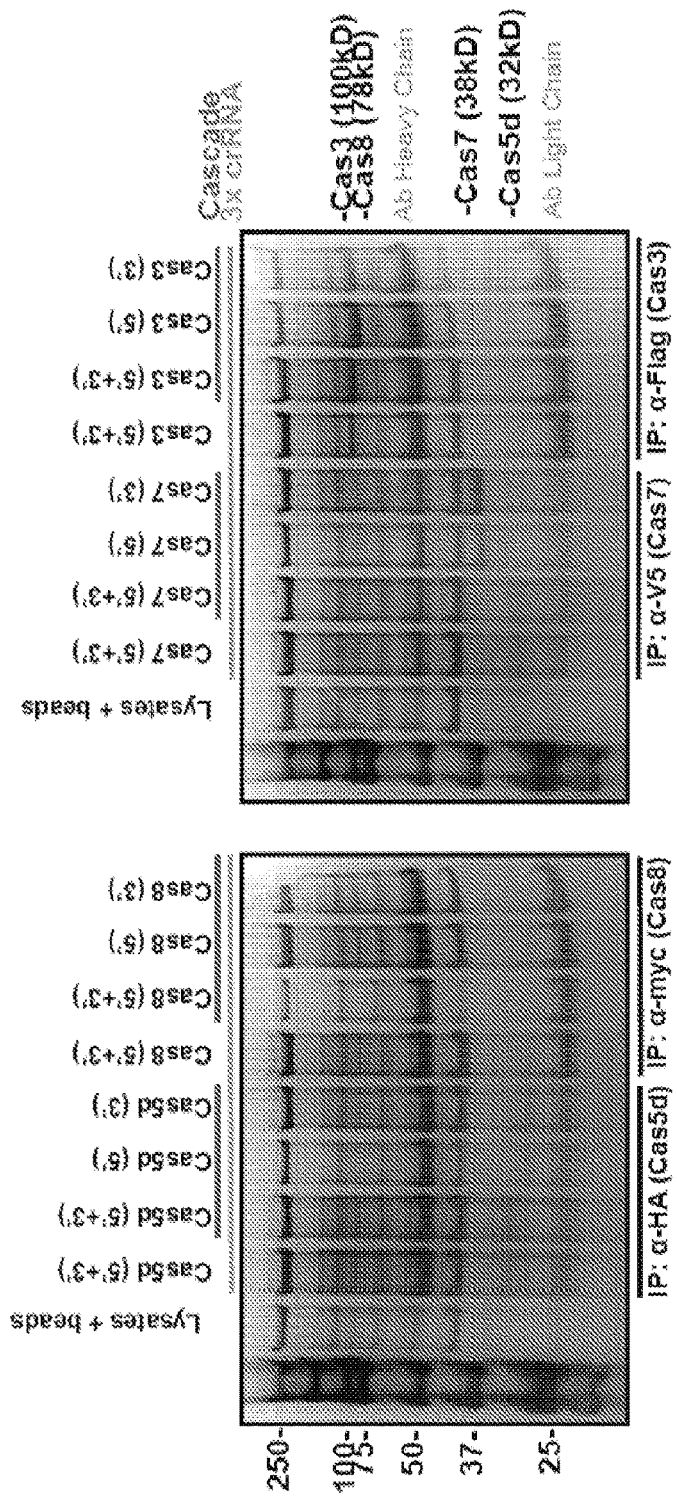
FIG. 33 shows Type I-C Cascade Co-Immunoprecipitation (Co-IP).
Figure 35:
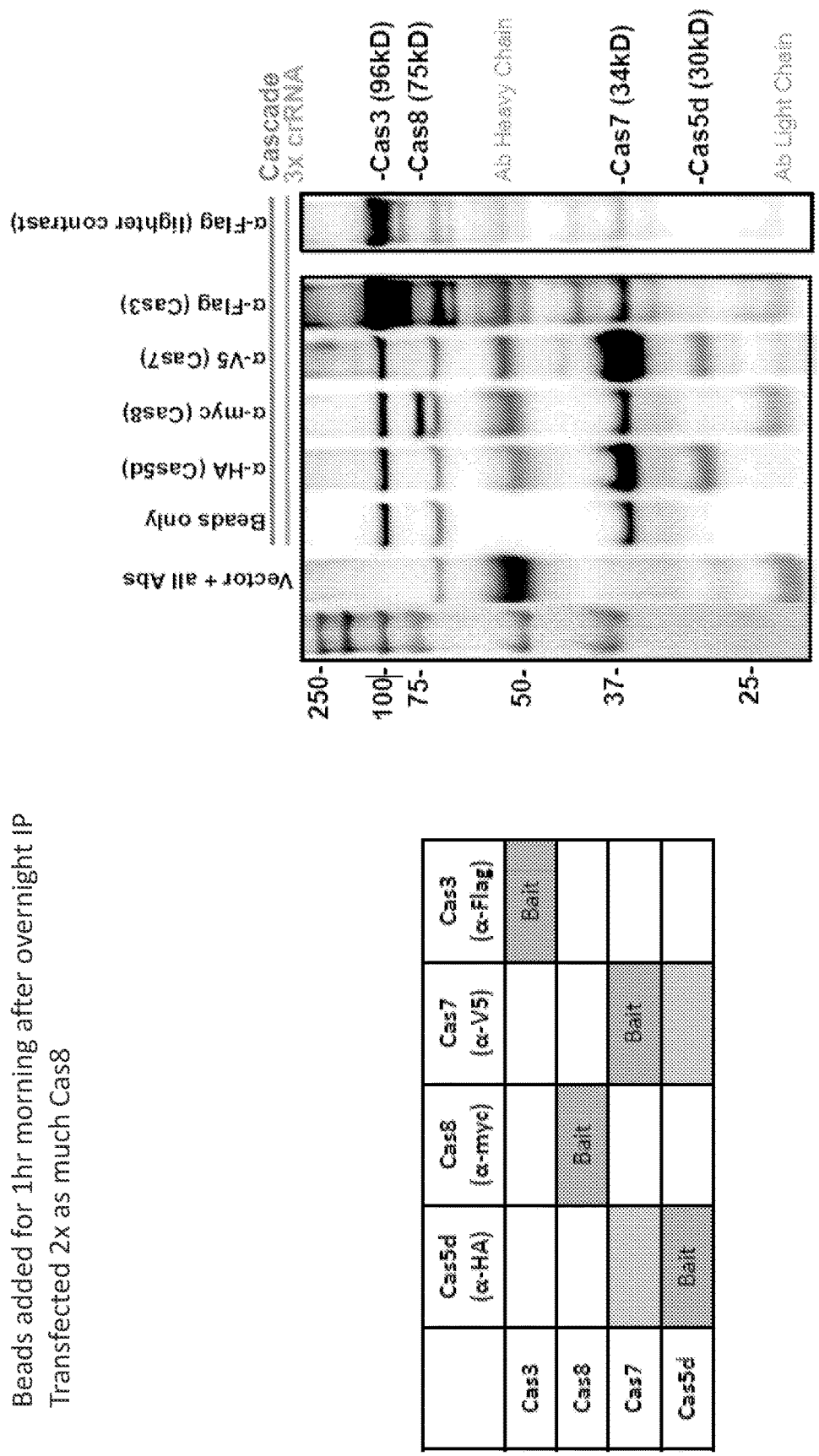
FIG. 35 shows Type I-C Cascade Co-IP with NTD constructs.
Figure 36:
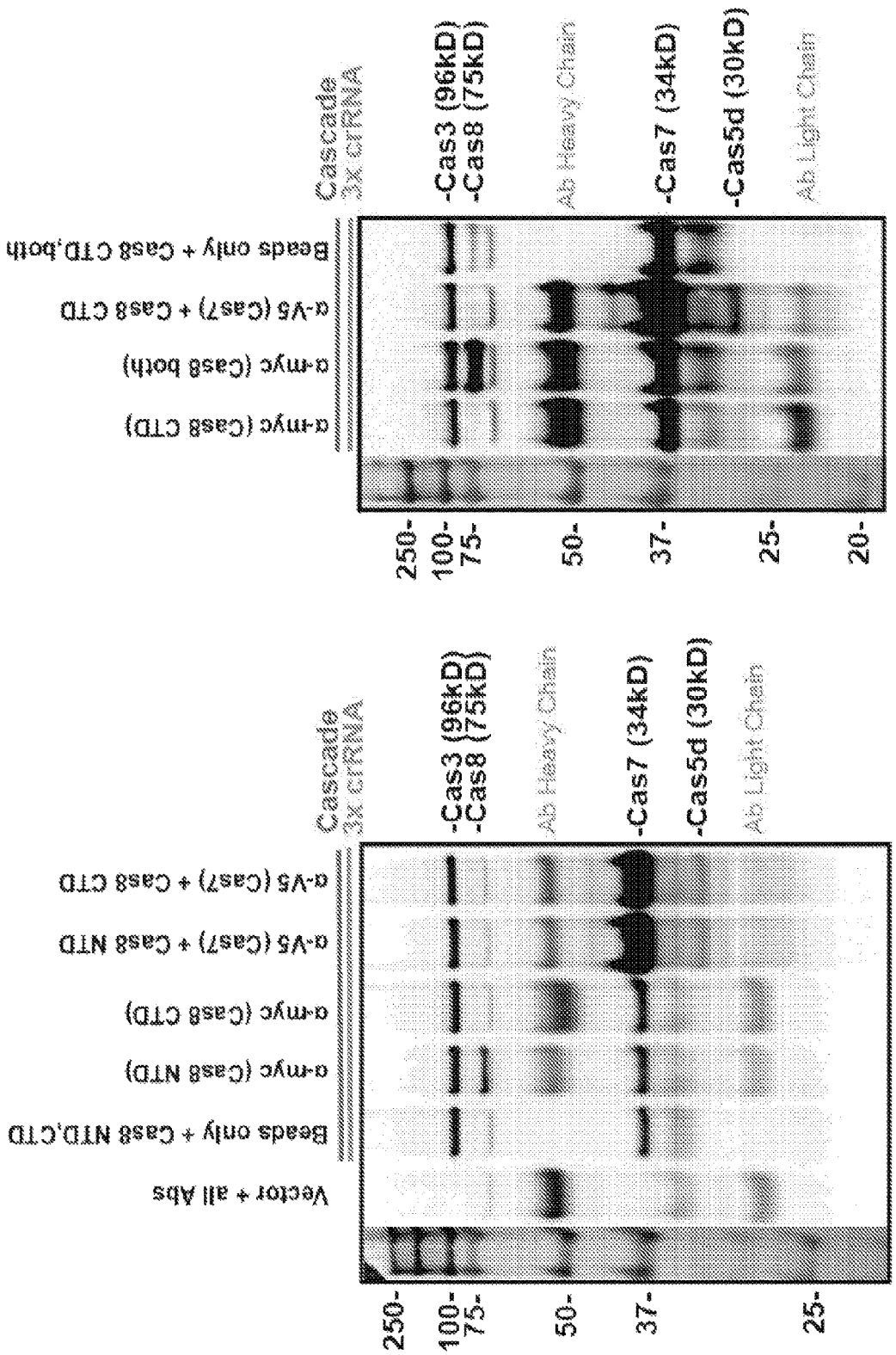
FIG. 36 shows Type I-C Cascade Co-IP with Cas8 constructs.

Type I-C: Type I-C constructs were generated as shown in FIGS. 9 and 35. See also FIG. 26. FIG. 25 shows the Type I-C crRNA repeat cloning vector (pAP68). The Type I-C Cas5d, Cas8, Cas7, and Cas3 proteins were expressed in HEK293T cells (FIG. 10). The localization of various constructs is shown in FIGS. 27-32. The crRNA and crRNA array for Type I-C is shown in FIGS. 11-14. Flow analysis of targeting Type I-C cascade/Cas3 to GFP using the HEK293T cells containing GFP was performed. FIGS. 16-23.

Figure 38:
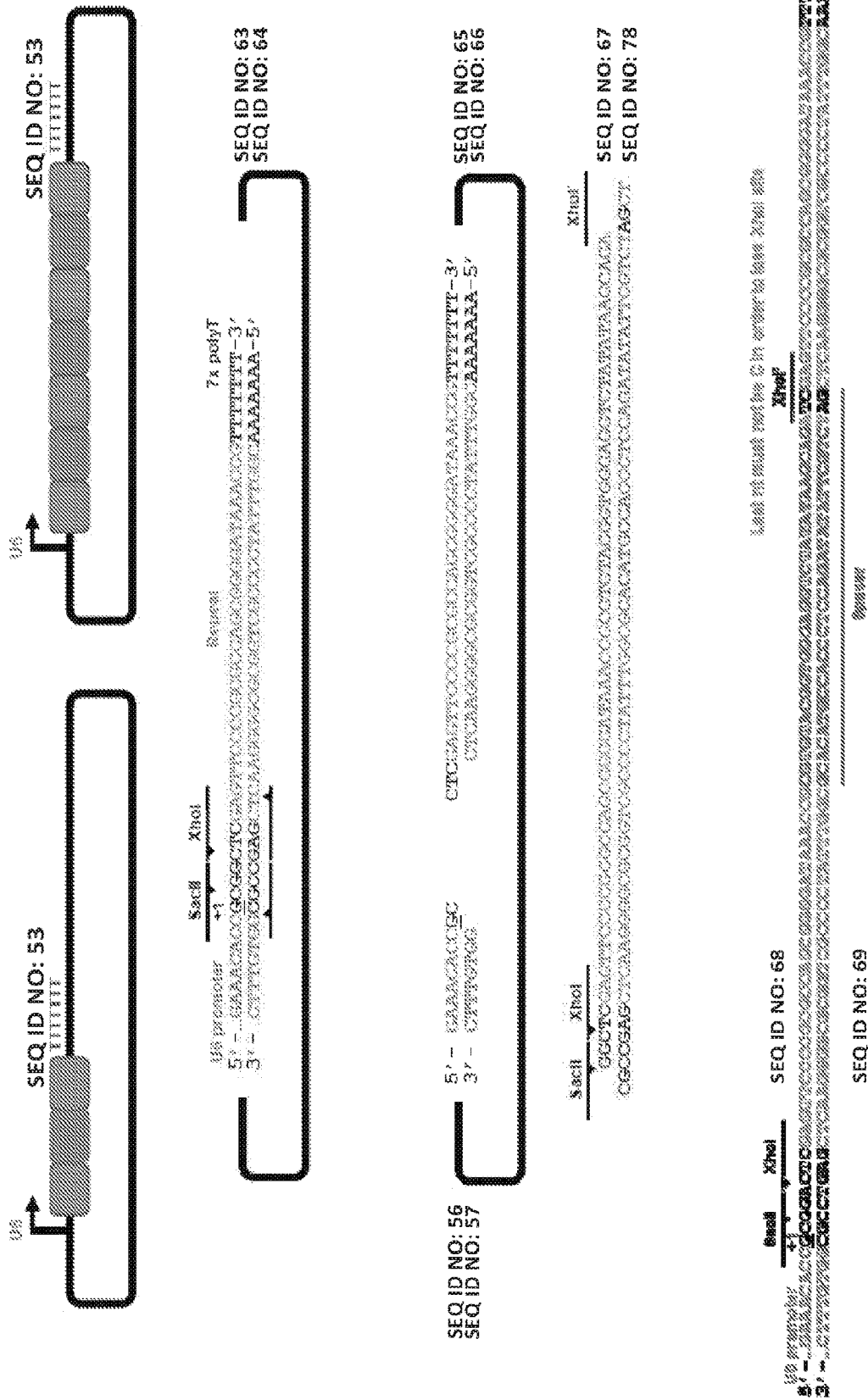
FIG. 38 shows Type I-E crRNA repeat cloning vector (pAP69).
Figure 39:
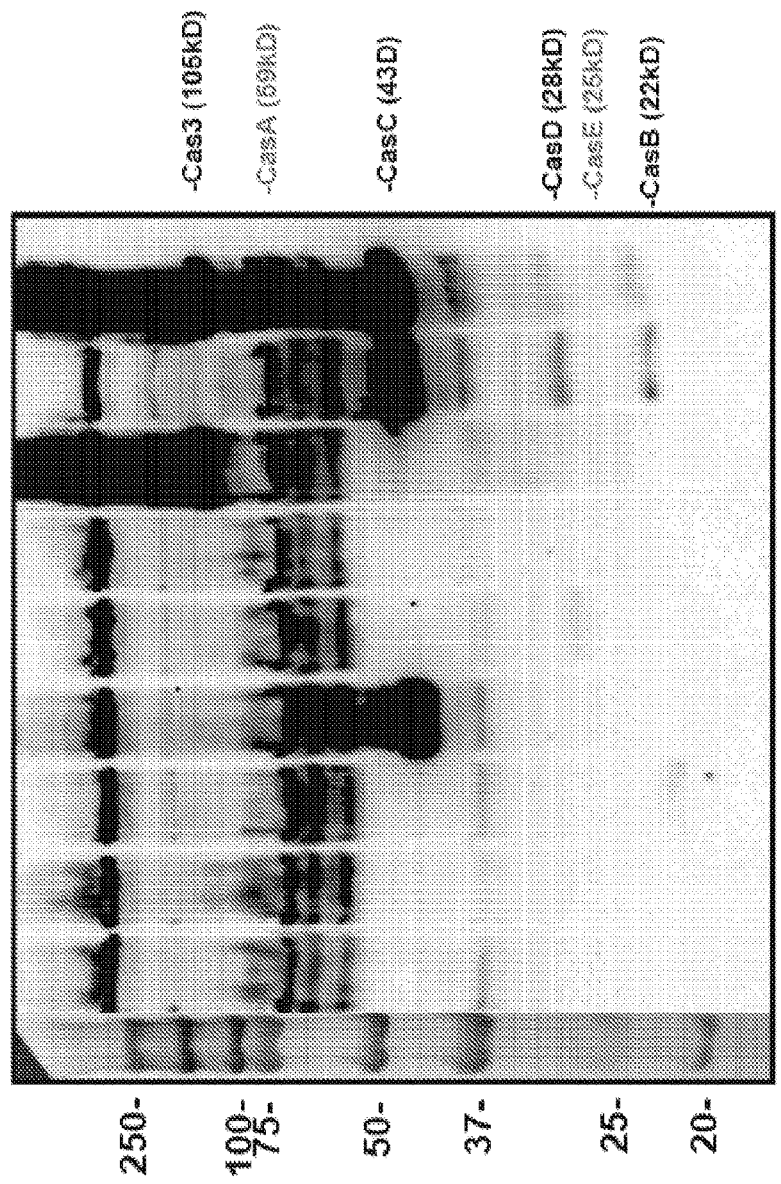
FIG. 39 shows Type I-E Cascade Expression in HEK293T Cells.
Figure 40:
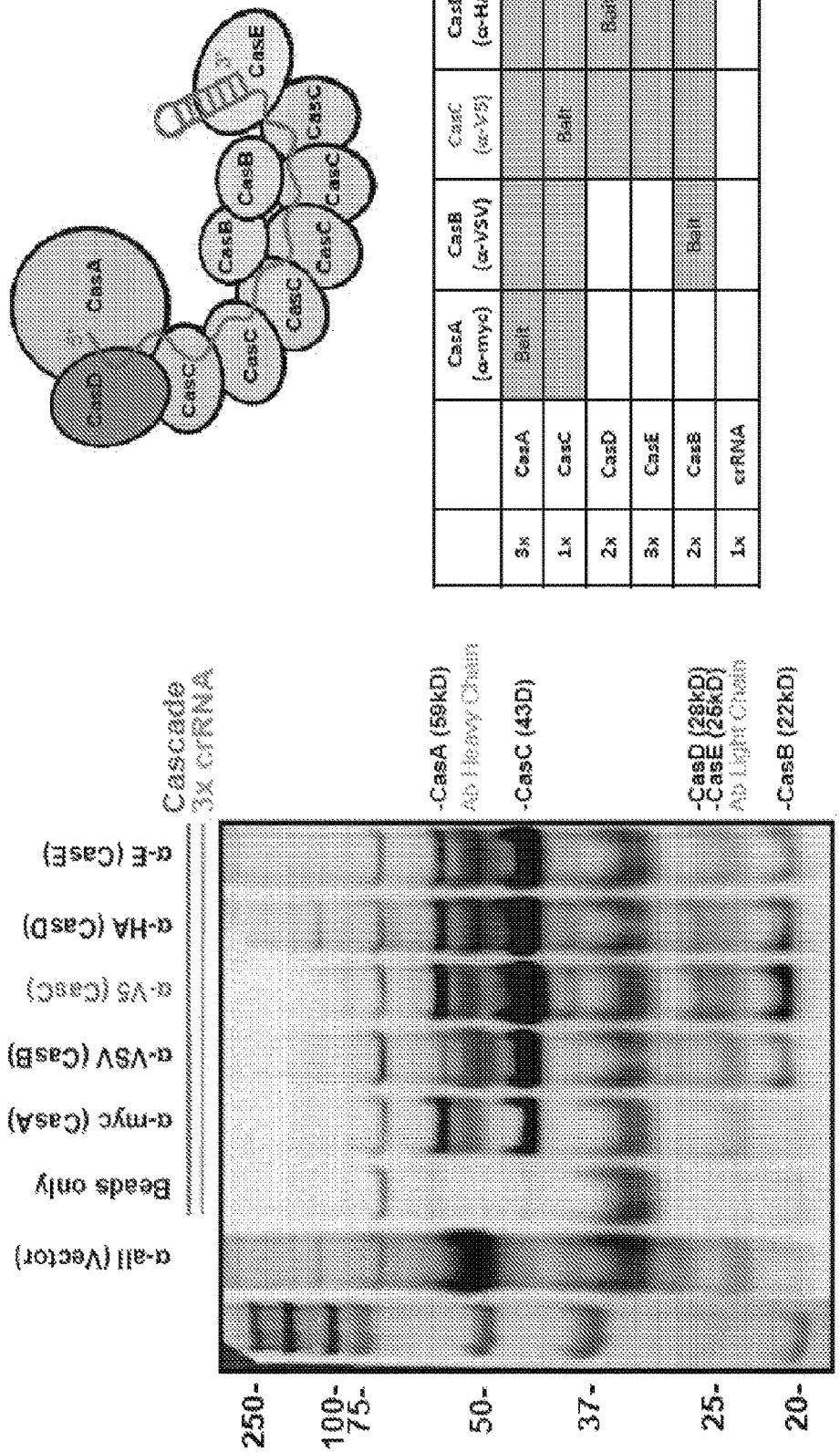
FIG. 40 shows Type I-E Cascade Co-IP shows complex formation.
Figure 41:
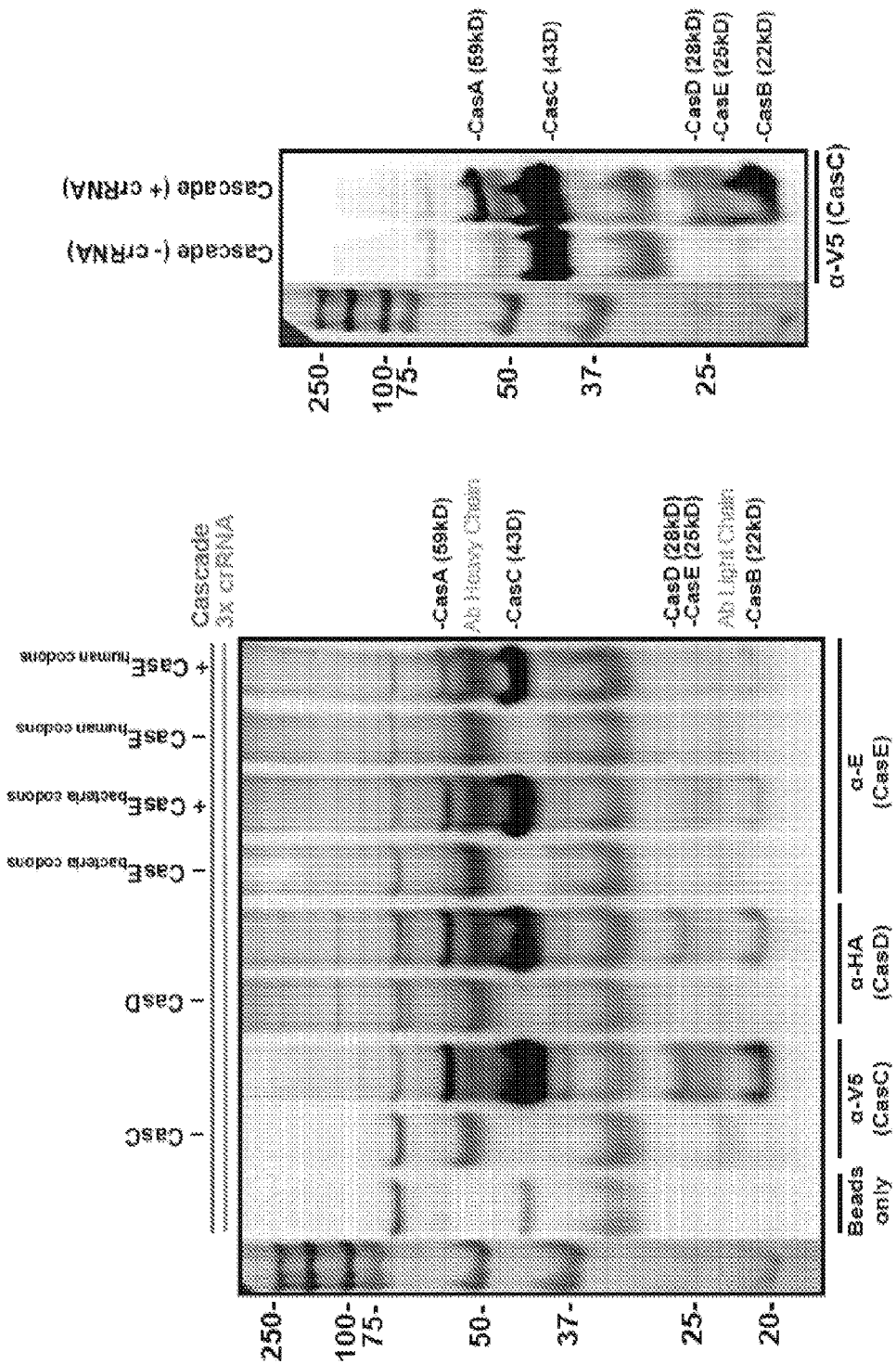
FIG. 41 shows Type I-E Cascade Co-IP antibody controls to confirm interaction and examining crRNA processing.
Figure 43:
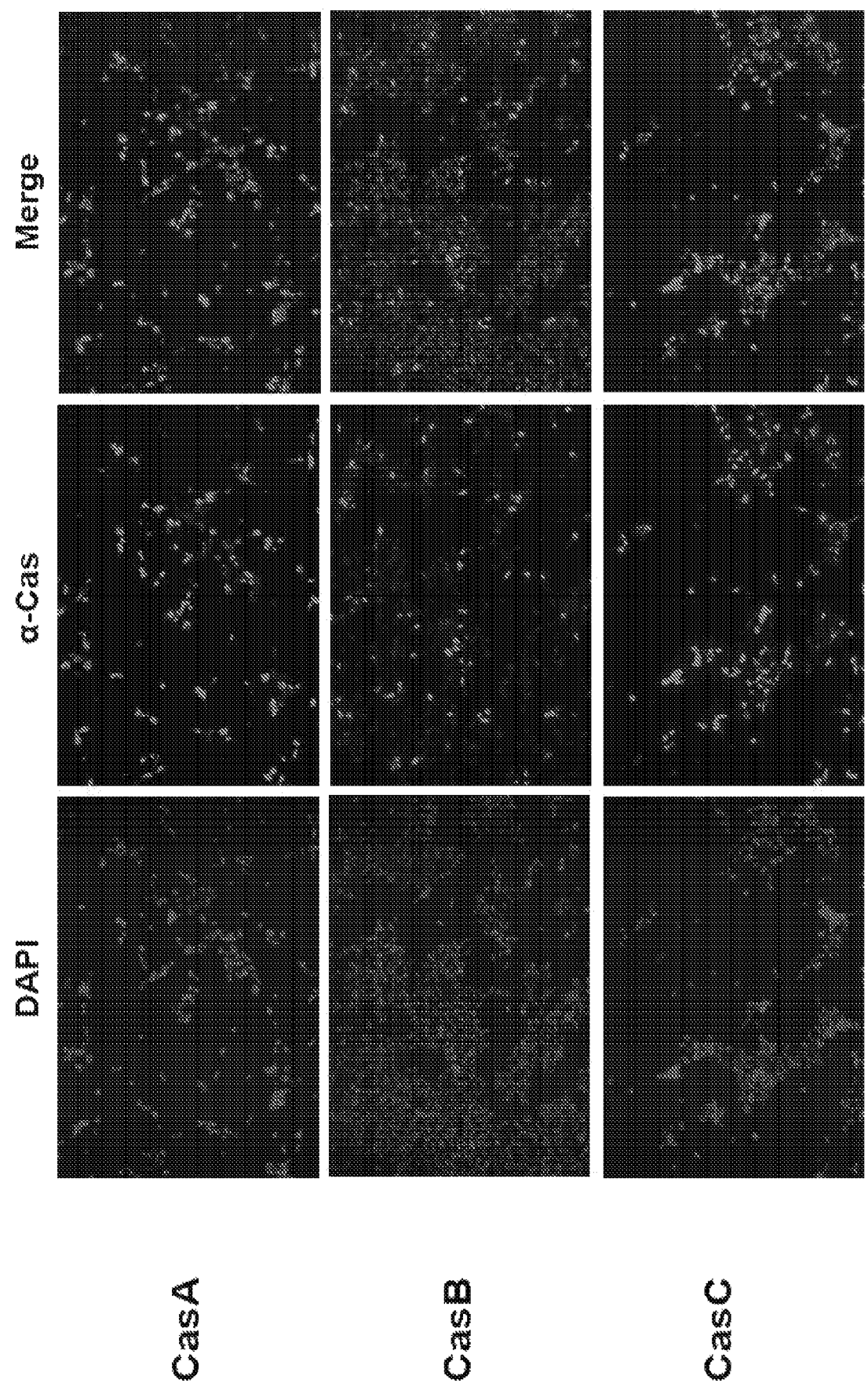
FIG. 43 shows α-Cas fluorescent imaging (red), DAPI nuclear staining (blue), and merged image of HEK293T cells transfected with CasA, CasB, and CasC constructs.
Figure 44:
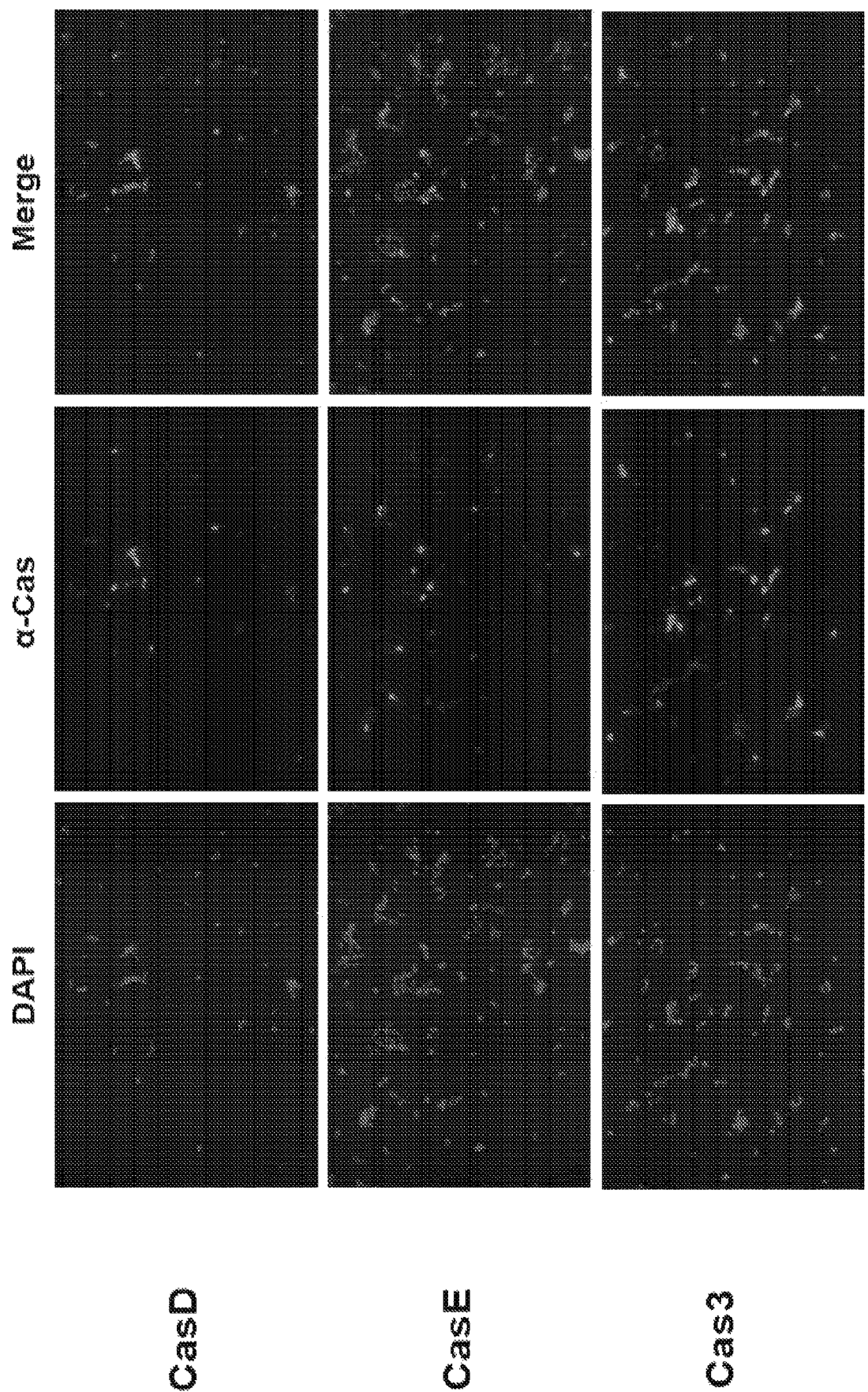
FIG. 44 shows α-Cas fluorescent imaging (red), DAPI nuclear staining (blue), and merged image of HEK293T cells transfected with CasD, CasE, and Cas3 constructs
Figure 46:
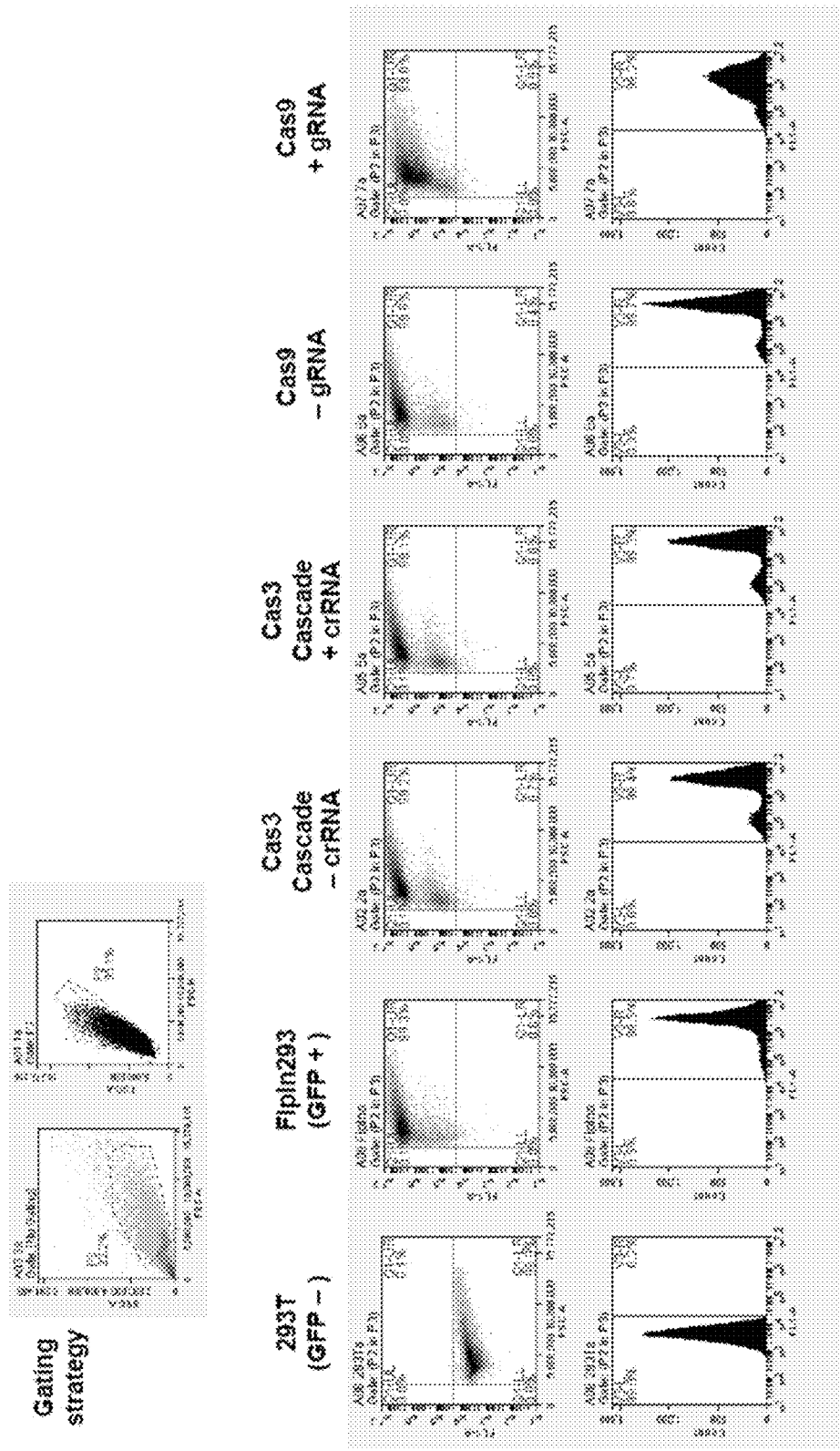
FIG. 46 shows flow analysis of targeting Type I-E Cascade/Cas3 to GFP.
Figure 47:
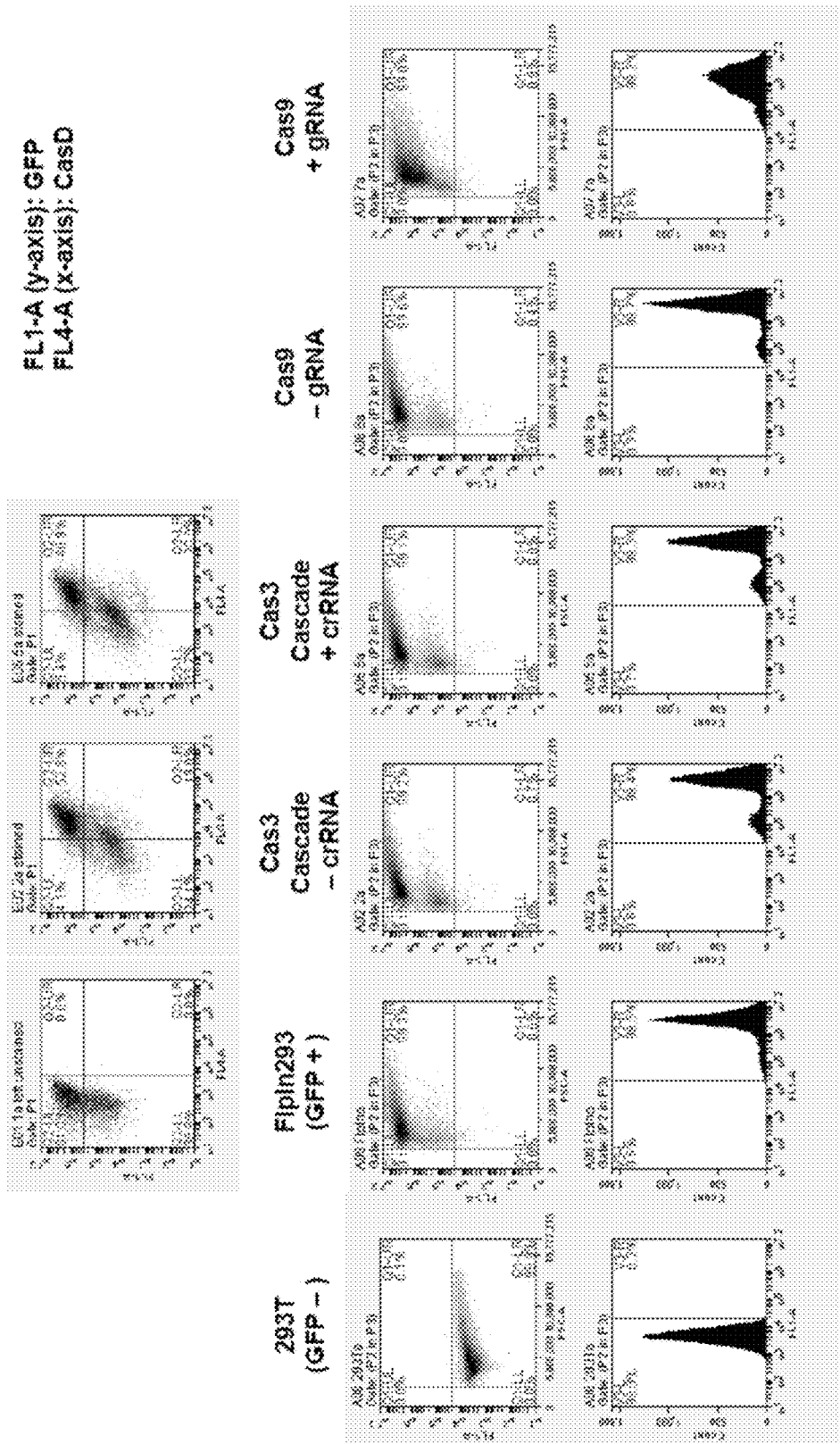
FIG. 47 shows flow analysis of targeting Type I-E Cascade/Cas3 to GFP.
Figure 48:
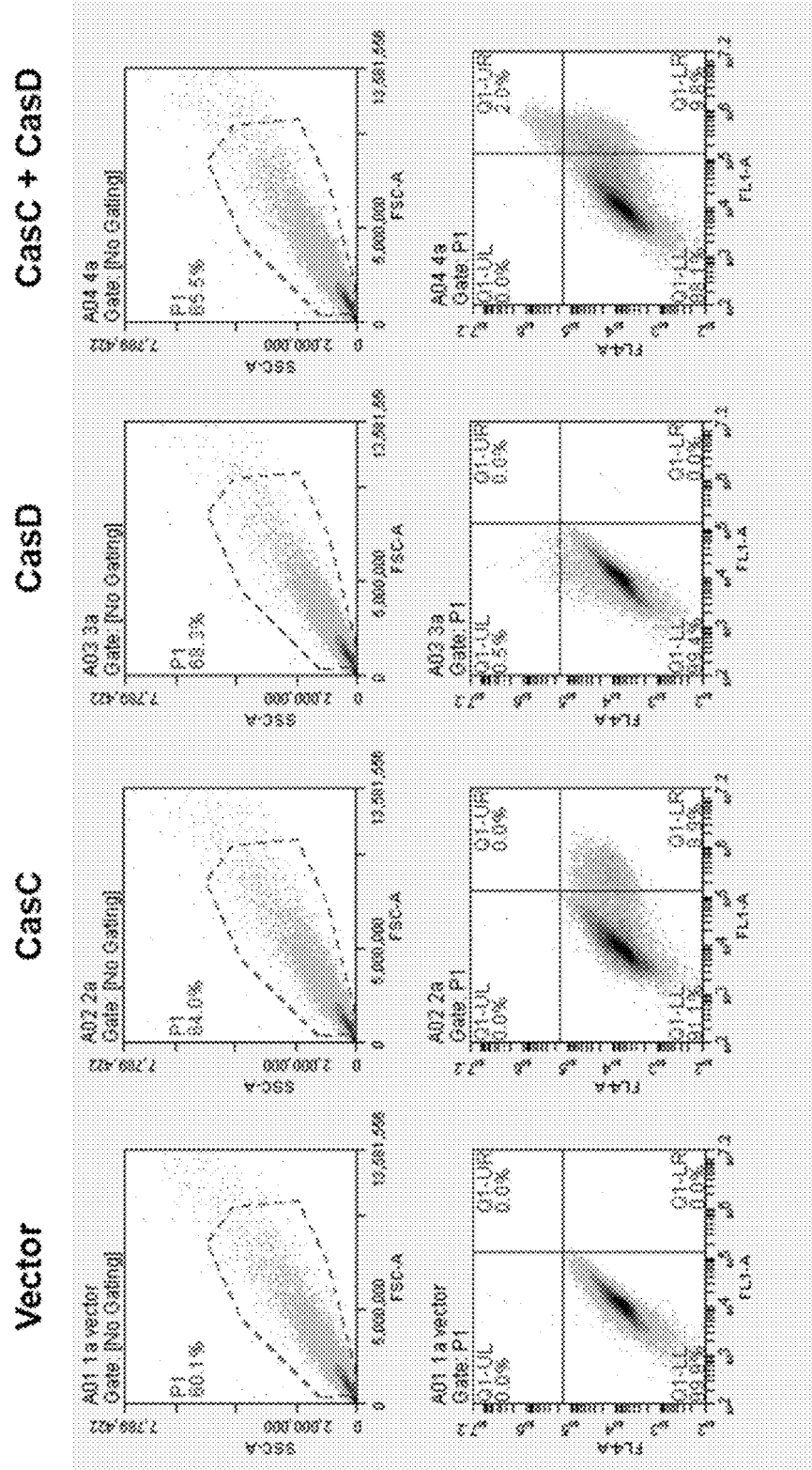
FIG. 48 shows flow analysis of Type I-E CasC and CasD co-transfections.

Type I-E: Type I-E constructs were generated as shown in FIGS. 37 and 40. FIG. 38 shows the Type I-E crRNA repeat cloning vector (pAP69). The Type I-E CasA, CasB, CasC, CasD, CasE, and Cas3 proteins were expressed in HEK293T cells (FIG. 39). The localization of various constructs is shown in FIGS. 43 and 44. Flow analysis of targeting Type I-E cascade/Cas3 to GFP using the HEK293T cells containing GFP was performed. FIGS. 46-48.

Figure 52:
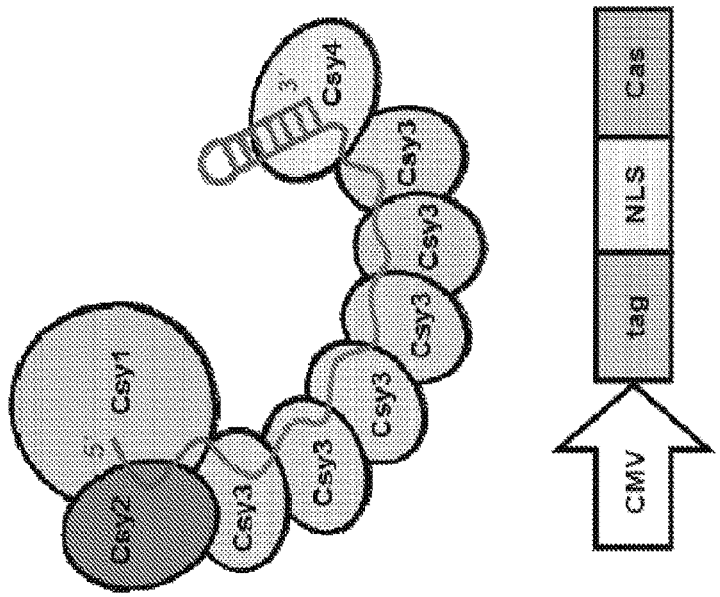
FIG. 52 shows Type I-F Constructs.
Figure 53:
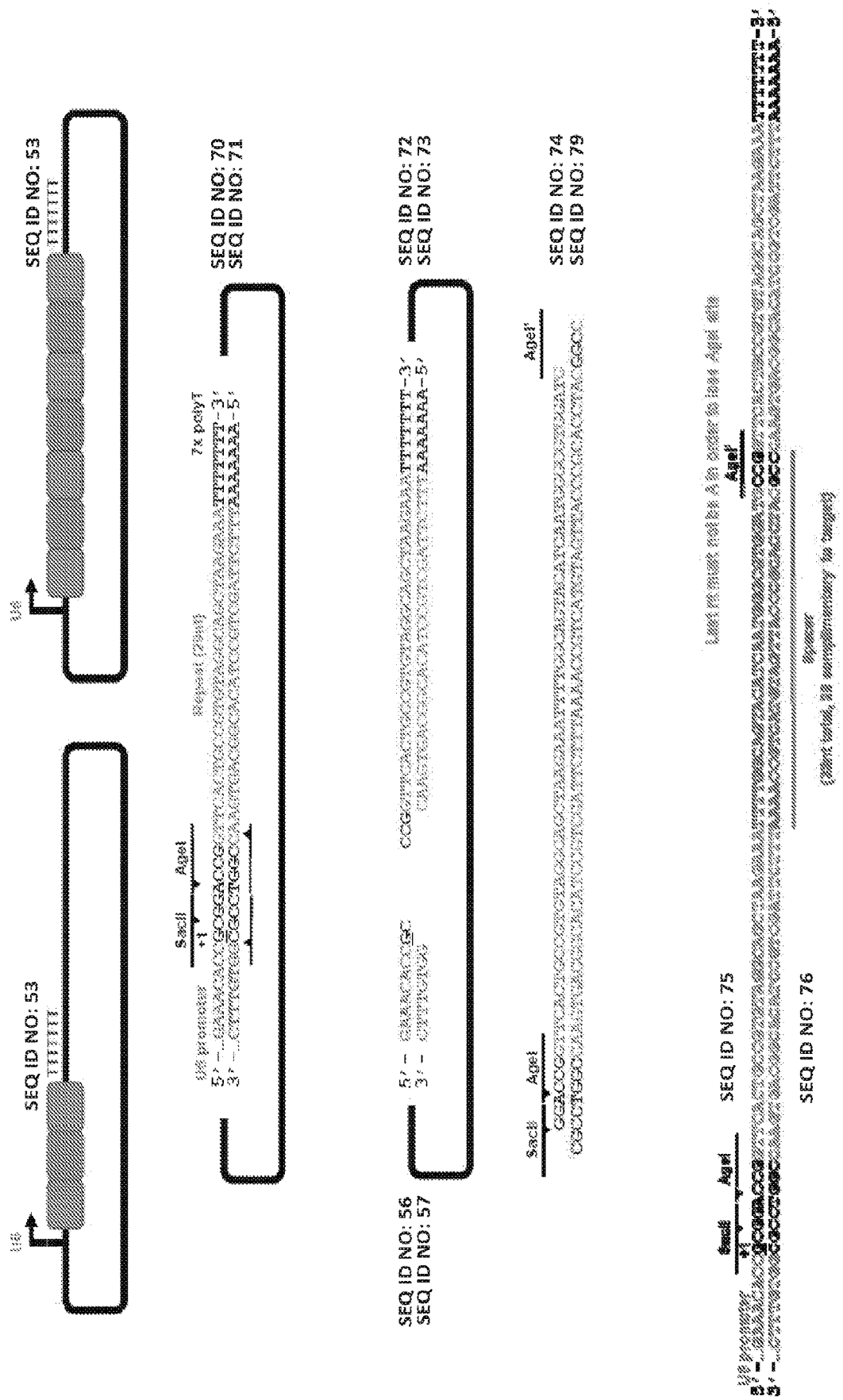
FIG. 53 shows Type I-F crRNA repeat cloning vector (pAP70).
Figure 54:
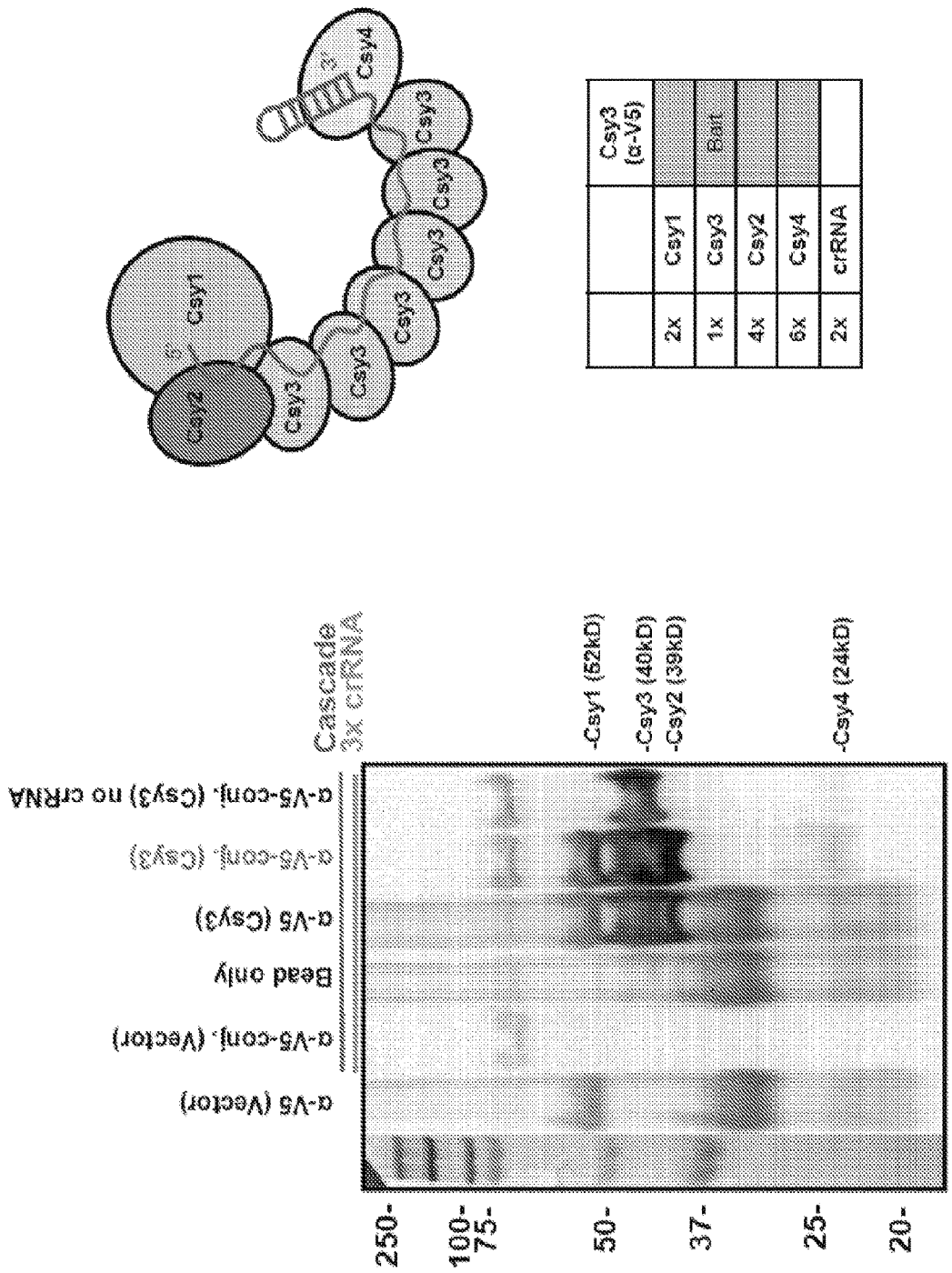
FIG. 54 shows Type I-F Cascade Co-IP shows Interactions.
Figure 55:
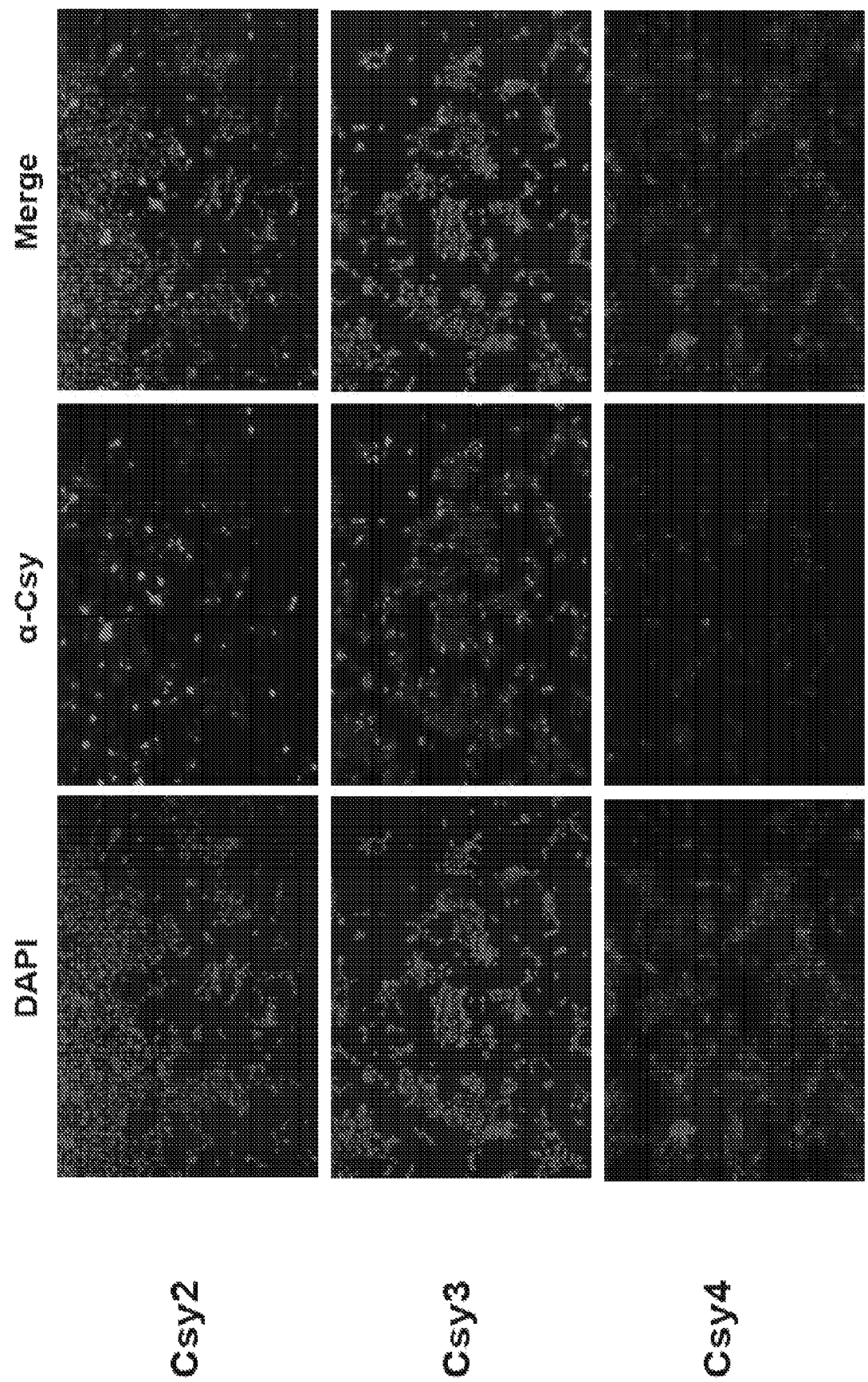
FIG. 55 shows α-Csy fluorescent imaging (red), DAPI nuclear staining (blue), and merged image of HEK293T cells transfected with Csy2, Csy3, and Csy4 constructs.
Figure 57A:
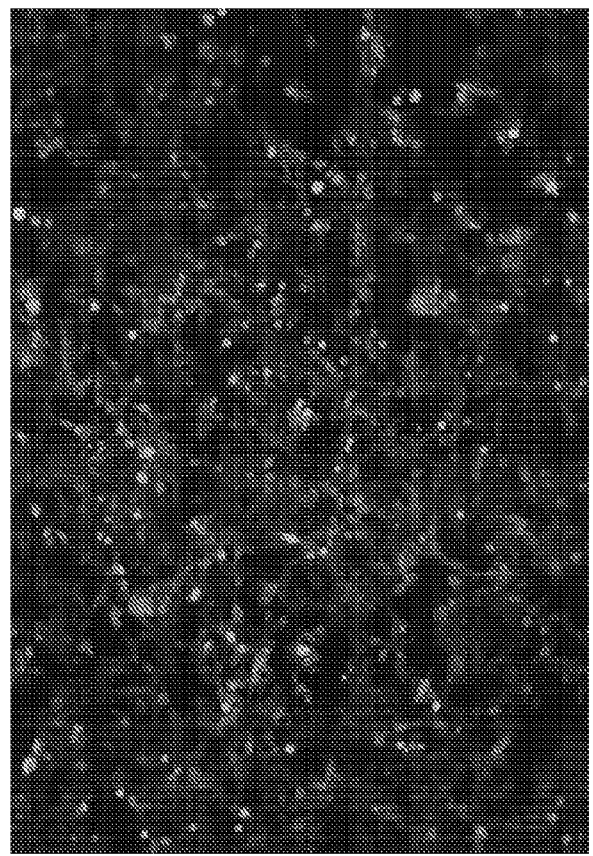
FIG. 57A shows GFP fluorescent images taken 1 dp transfection, where GFP=in the cell genome.
Figure 57B:
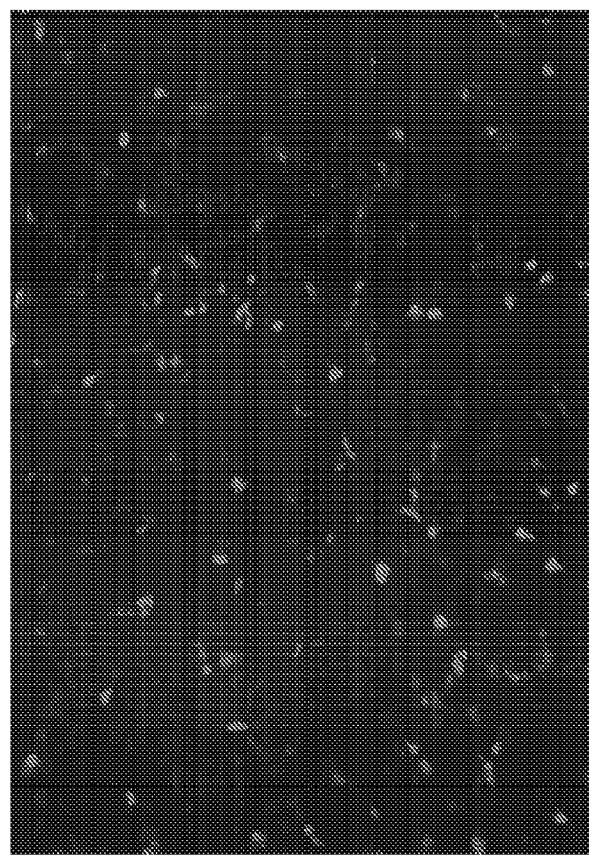
FIG. 57B shows mCherry fluorescent images taken 1 dp transfection, where mCherry=transfected crRNA.
Figures 58A, 58B:
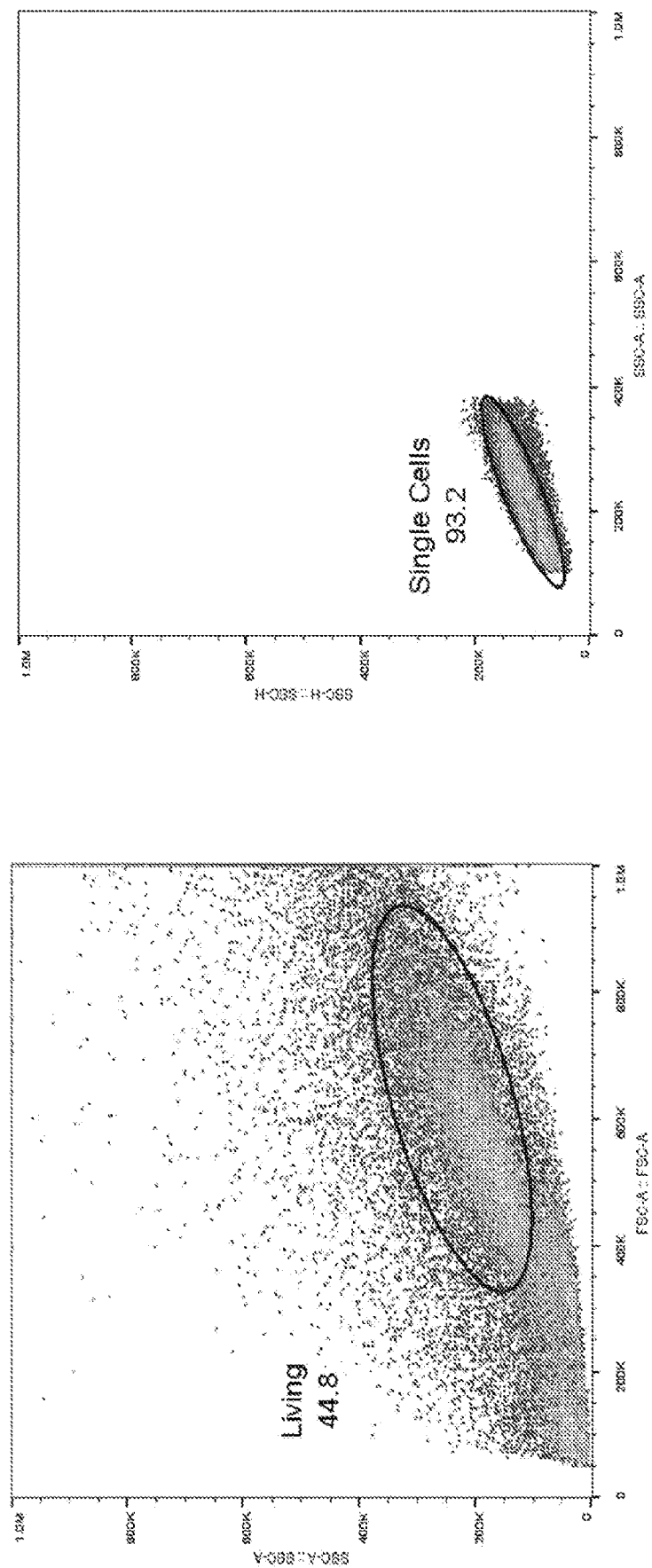
FIG. 58A shows the $1^{st}$ Gate=Live cells, where GFP+ control cells (94% GFP+) was used to establish this gate.
FIG. 58B shows the $2^{nd}$ Gate=singlets, where GFP+ control cells (94% GFP+) was used to establish this gate.
Figure 58C:
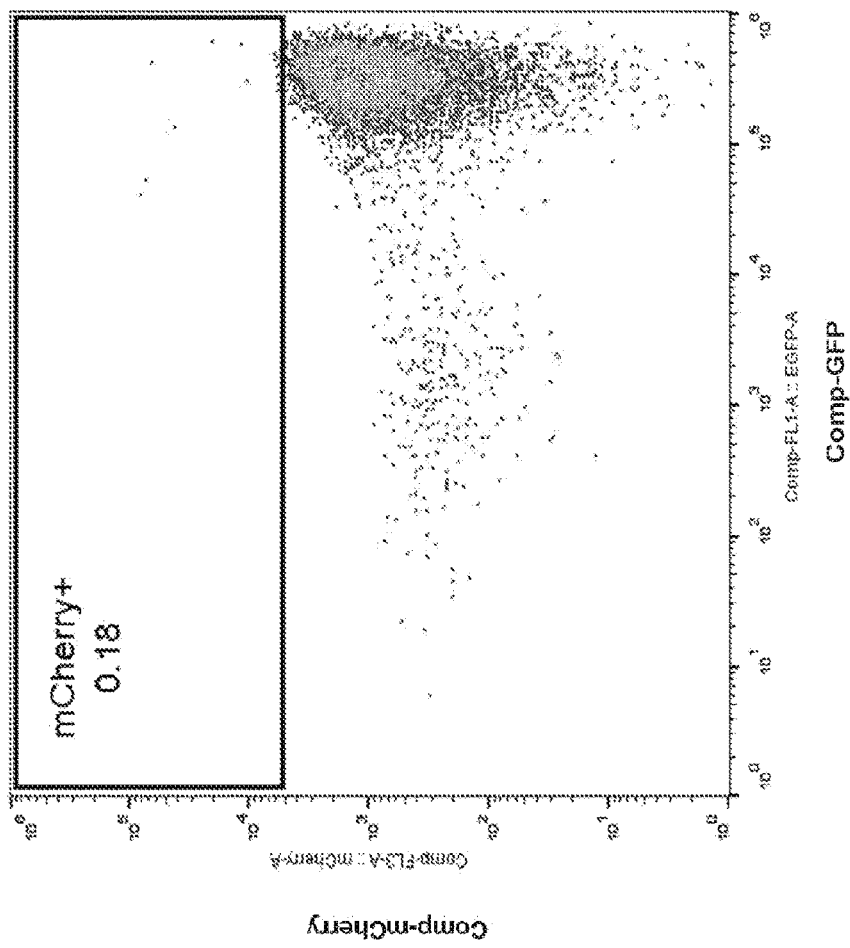
FIG. 58C shows the 3rd Gate=mCherry+, where GFP+ control cells (94% GFP+) was used to establish this gate.
Figure 59B:
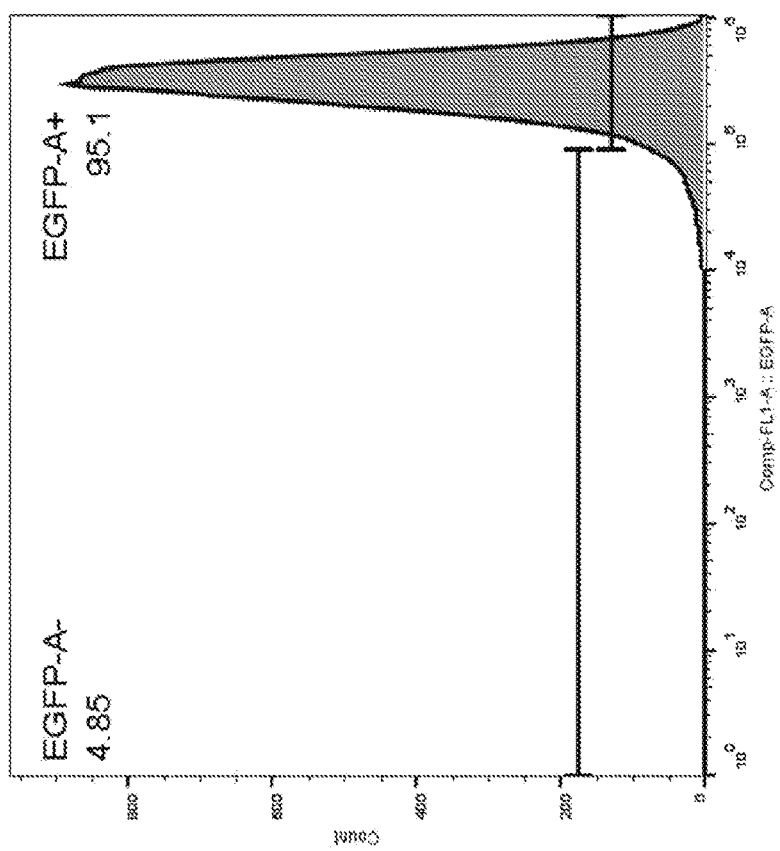
FIG. 59B shows crRNA transfection: mCherry-Vector.
Figure 59A:
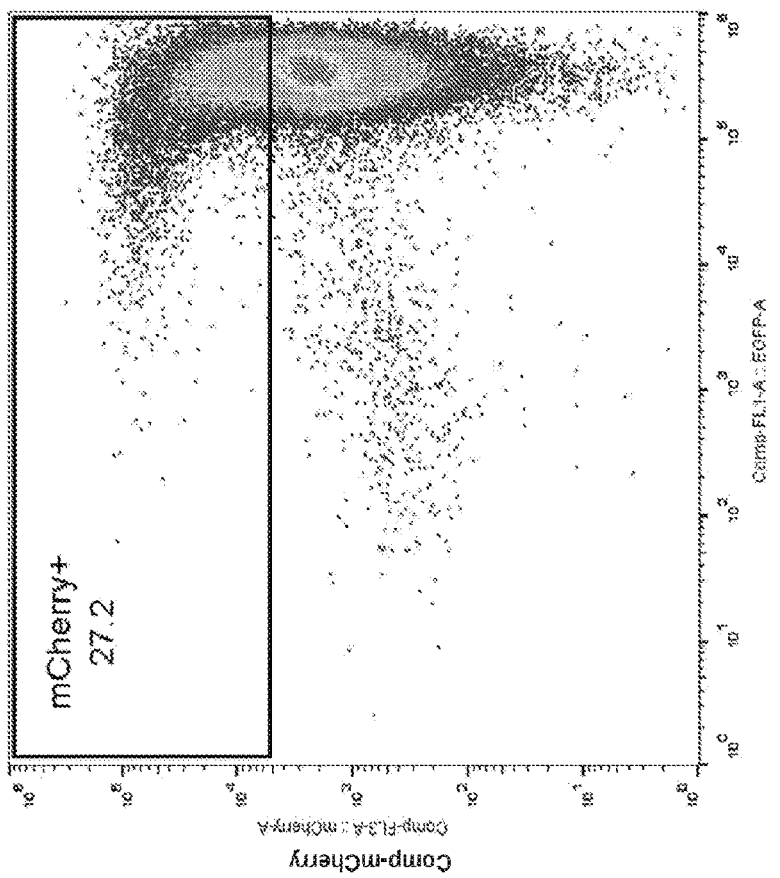
FIG. 59A shows crRNA transfection: mCherry-Vector.
Figure 59D:
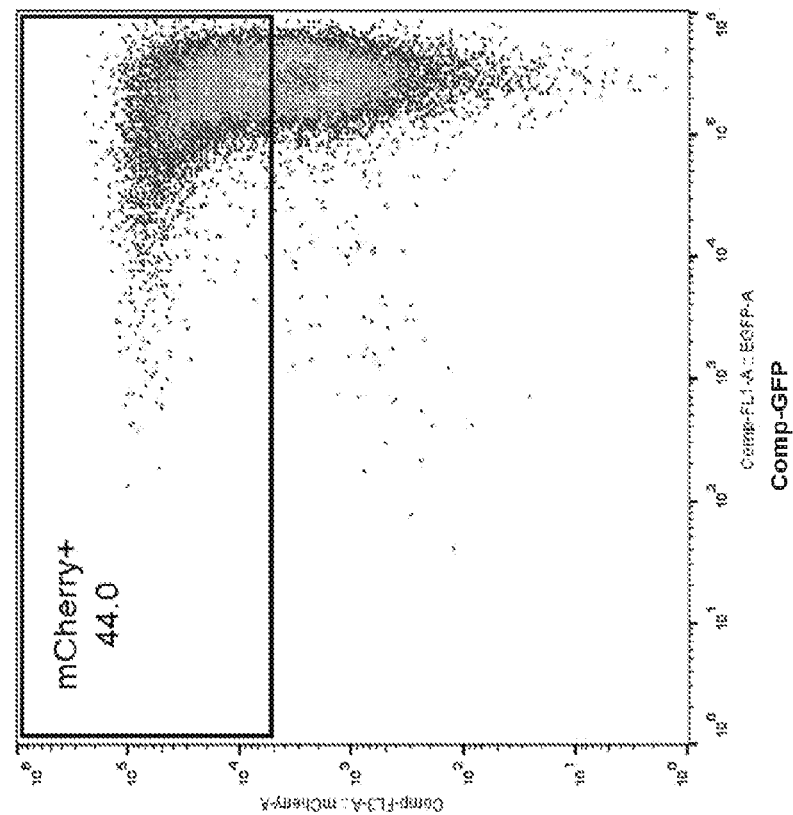
FIG. 59D shows crRNA transfection: mCherry-CMV target.
Figure 59C:
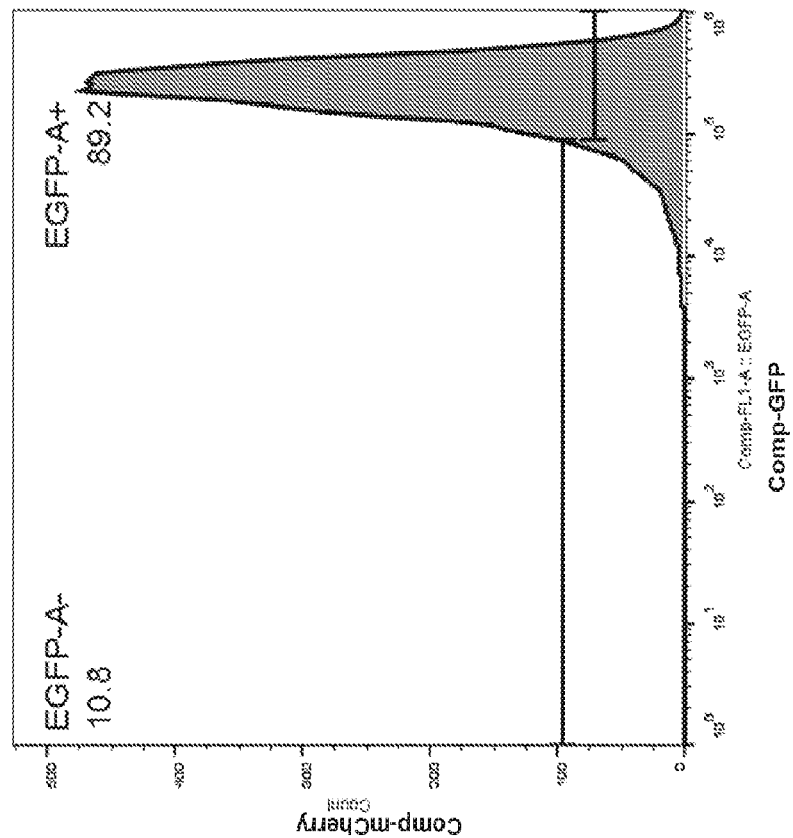
FIG. 59C shows crRNA transfection: mCherry-CMV target.
Figure 60A:
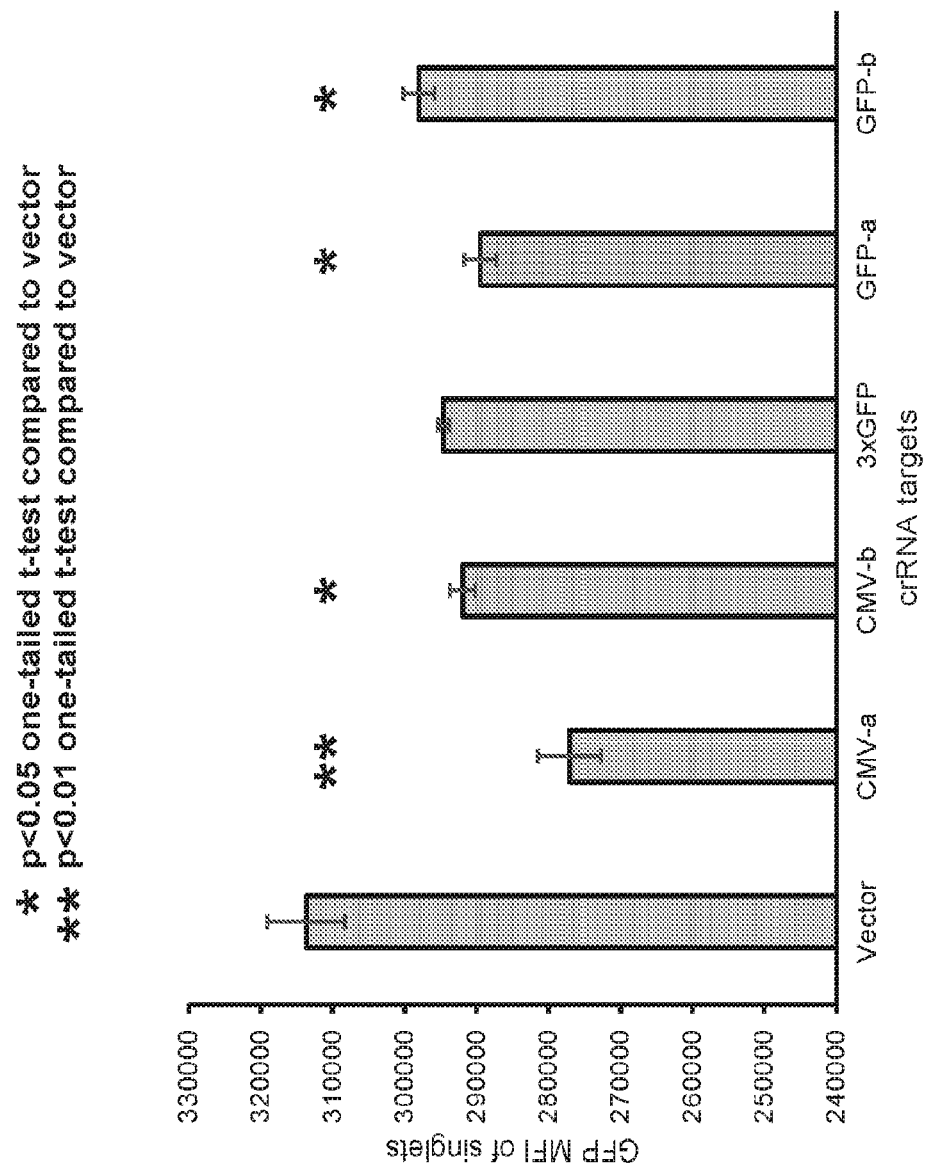
FIGS. 60A-60C show flow analysis of targeting Type I-E system to GFP.
Figure 60B:
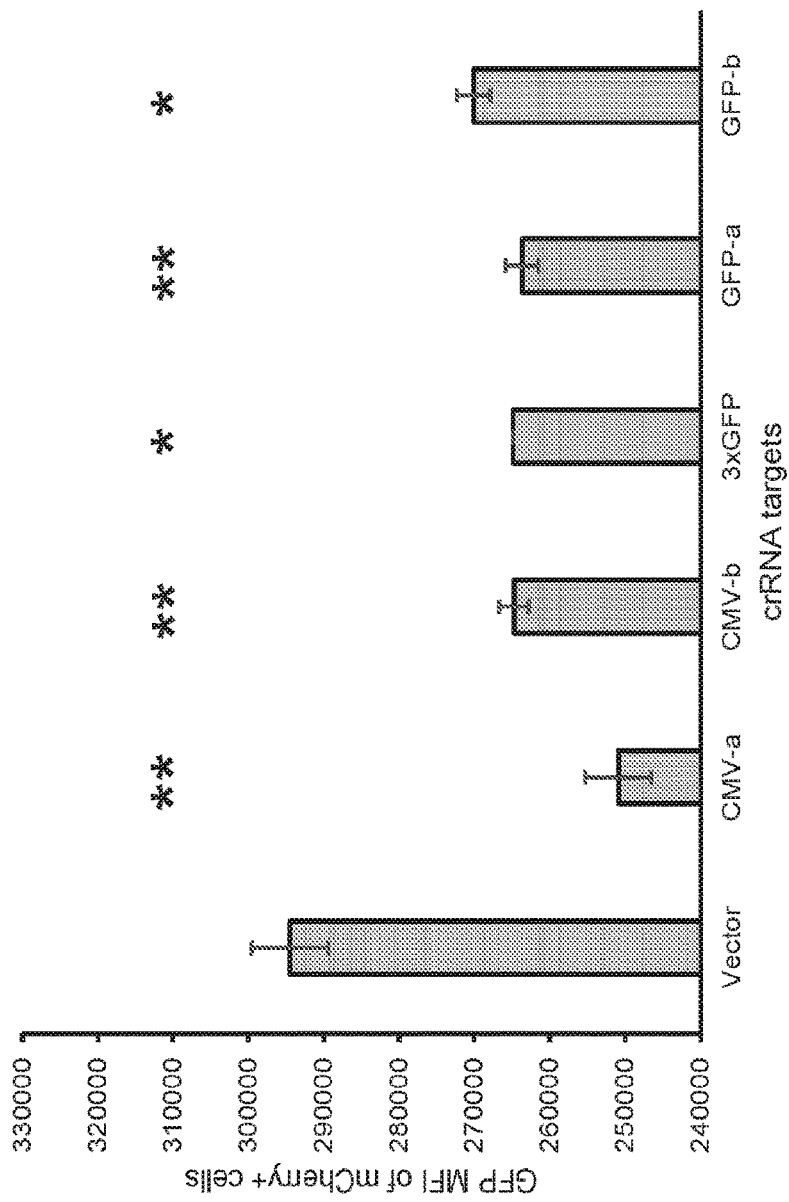
Figure 60C:
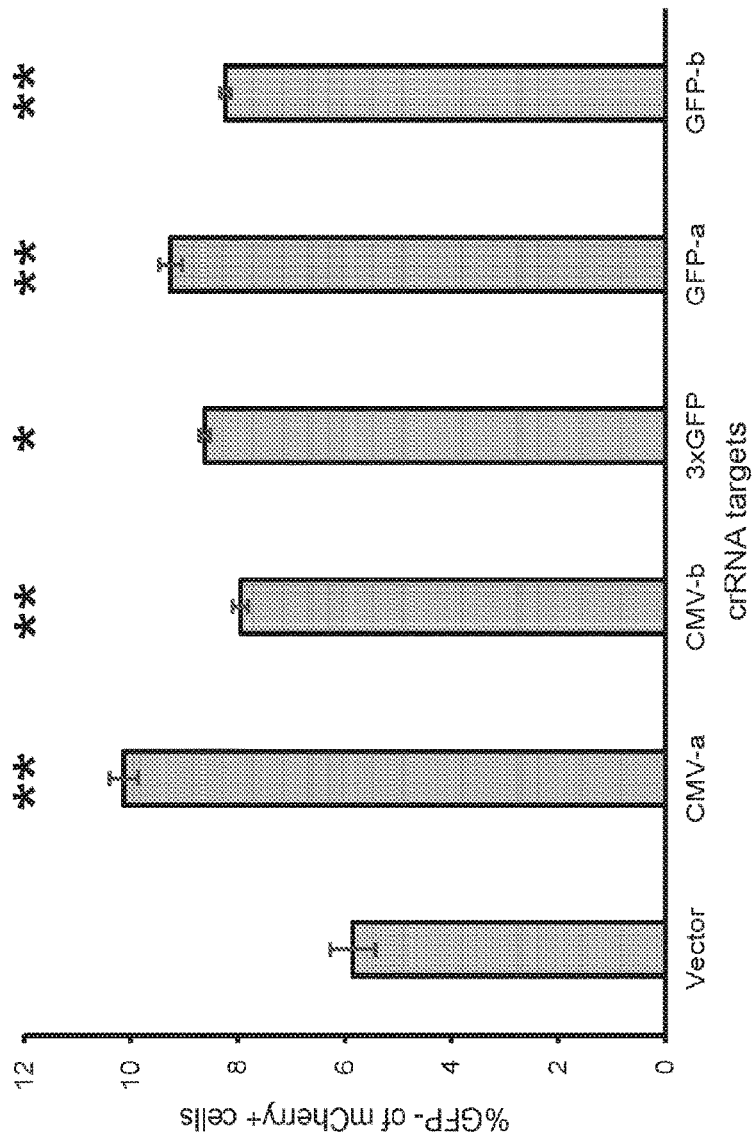
Figure 61:
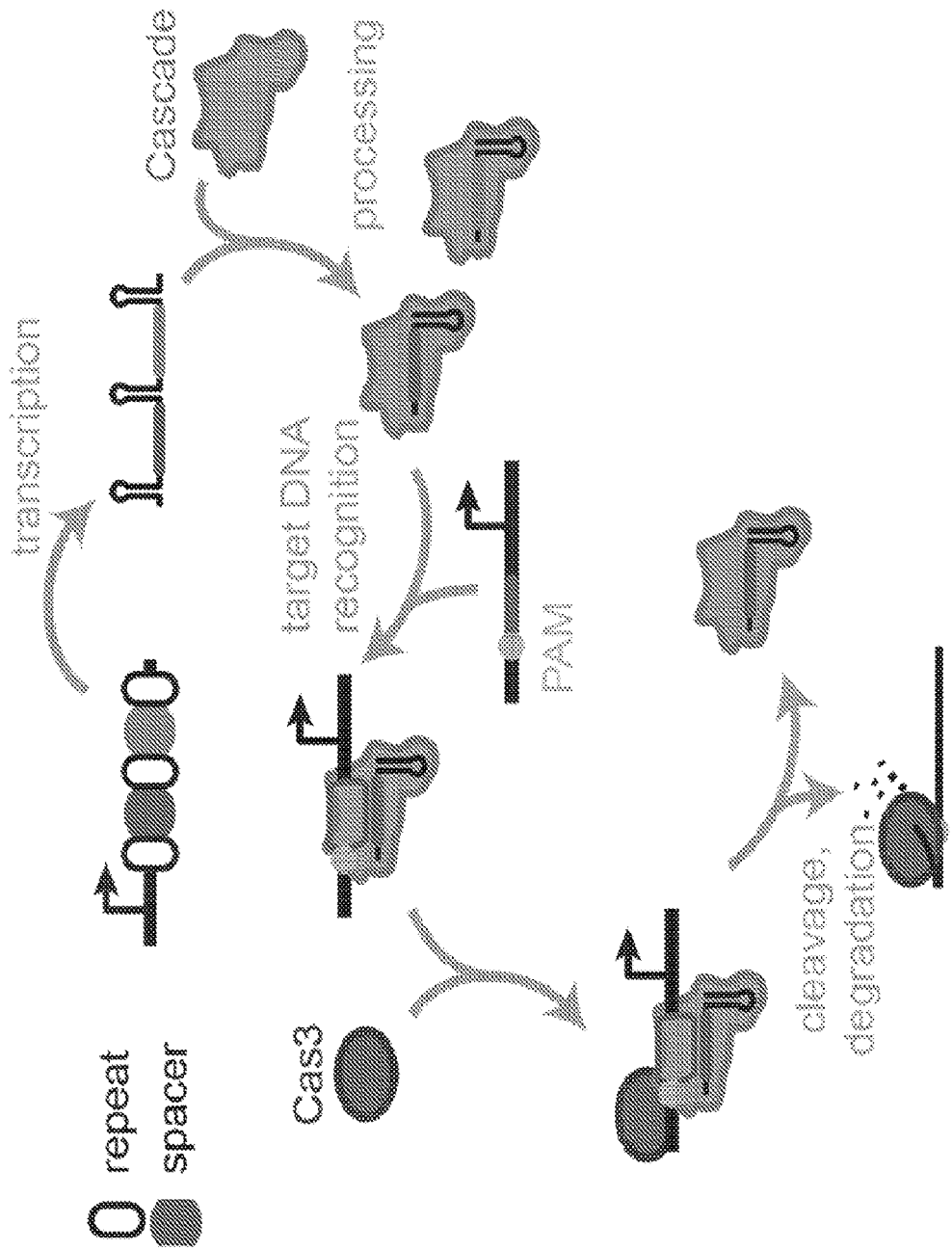
FIG. 61 provides an overview of DNA targeting by Type I CRISPR-Cas systems. The Cascade proteins process the CRISPR RNA and binding the target protospacer flanked by a protospacer adjacent motif (PAM). Cas3 (or Cas3' and Cas3") are then recruited and activated to cleave the non-target strand in the 3' to 5' direction.
Figure 62:
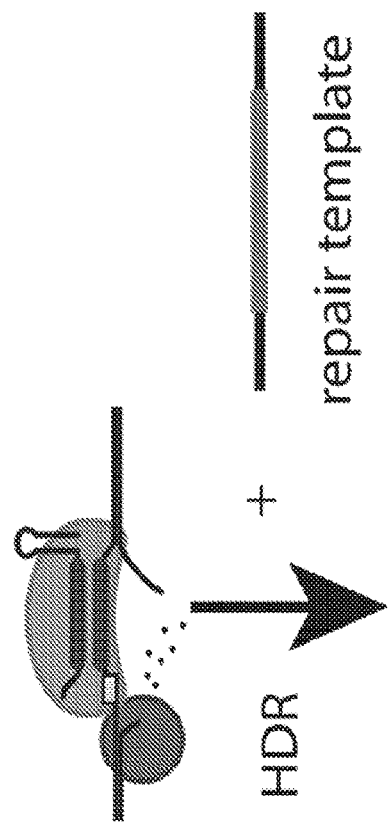
FIG. 62 provides an example of creating DNA insertions, deletions, and mutations through single-site targeting as claimed herein. Introducing a double-stranded or single-stranded DNA repair template when targeting a given sequence with the Type I CRISPR-Cas system can lead to homology-directed repair (HDR), resulting in an insertion, deletion, or mutation depending on the insertion sequence (medium grey).
Figure 63:
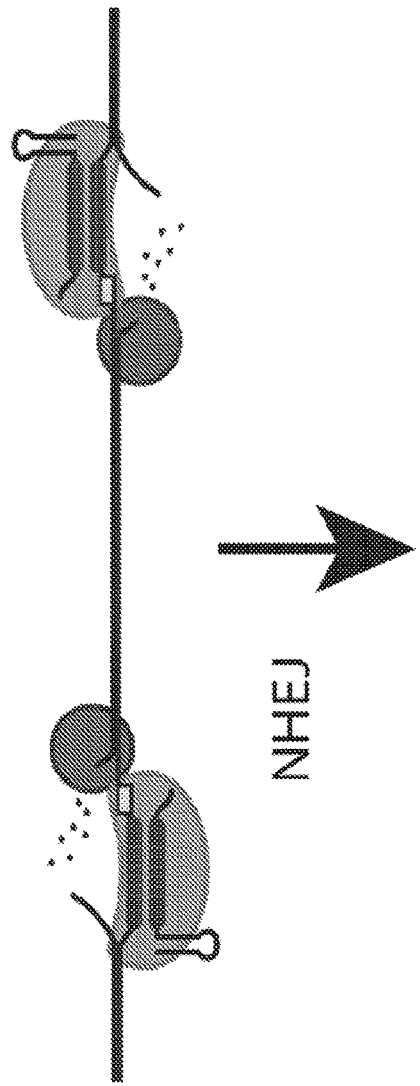
FIG. 63 provides an example of creating large, defined deletions as claimed herein. Targeting two locations on the same chromosome can generate a large deletion if Cas3 degradation is directed internally. This is accomplished by ensuring that the PAMs (light grey) are internal to the two protospacers. Upon degradation the cells can seal the two ends through non-homologous end joining (NHEJ).
Figure 64:
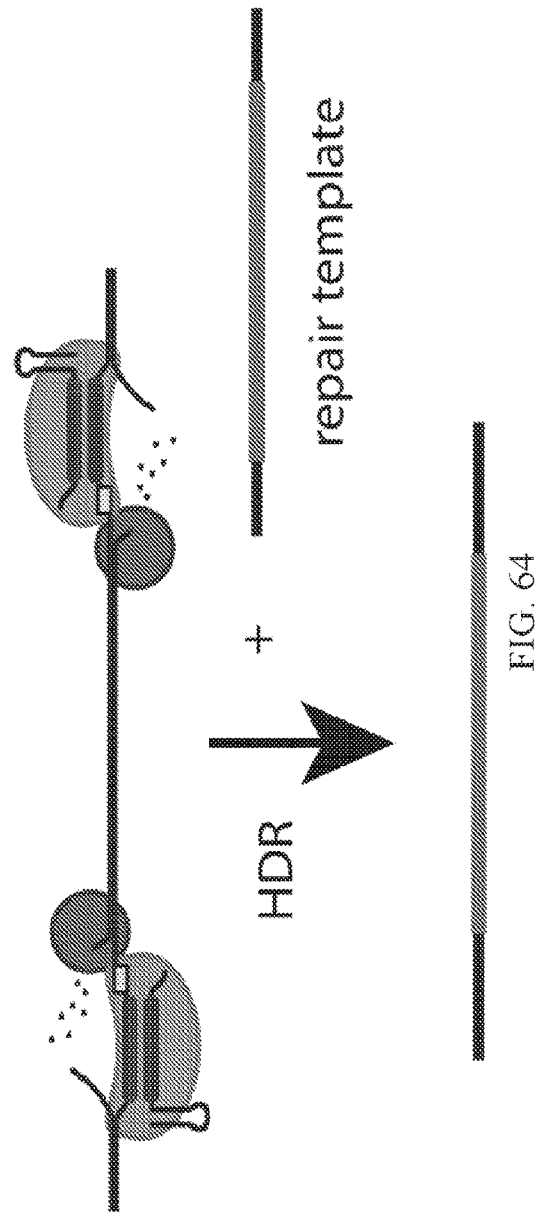
FIG. 64 provides an example of creating insertions, mutations, and deletions through dual-site targeting as claimed herein. Targeting two locations on the same chromosome can generate a large deletion if Cas3 degradation is directed internally. Introducing a repair template as part of DNA targeting can lead to homology-directed repair, resulting in an insertion, deletion, or mutation depending on the insertion sequence (medium grey).
Figure 65:
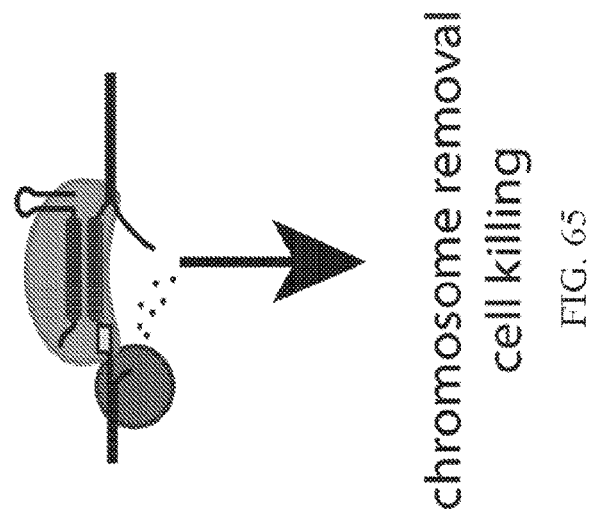
FIG. 65 provides an example of targeted chromosomal removal or cell killing as claimed herein. Targeting the Type I CRISPR-Cas system to a sequence within a chromosome leads to unidirectional degradation of the chromosomal DNA, thereby disabling the chromosome. If the chromosome encodes any essential genes, then chromosomal removal will lead to targeted cell killing.

Type I-F: Type I-F constructs were generated as shown in FIG. 52. FIG. 53 shows the Type I-F crRNA repeat cloning vector (pAP70). The Type I-F Csy1, Csy2, Csy3, Csy4, and Cas3 proteins were expressed in HEK293T cells. The localization of various constructs is shown in FIG. 55.

Alterations to the amino-terminal domain (NTD) or carboxyl-terminal domain (CTD) can disrupt a protein's functional activity, including its ability to interact with other molecules. Modifications were added to the N-terminal domain of the Type I-E and Type I-F proteins and cascade formation was confirmed by co-immunoprecipitation. See FIGS. 40-42 and FIG. 54. Constructs for the Type I-C system were generated with an epitope tag and NLS on the NTD, the CTD, and on both terminal domains. Co-immunoprecipitation of the Type I-C cascade was determined. See FIGS. 24, 33, 35, and 36. Following confirmation of protein interactions, Type I-C constructs with an NTD tag and NLS were used for subsequent experiments.

crRNA were expressed in eukaryotic cells. Sequences were cloned downstream of a U6 promoter. See FIG. 25. The processed crRNA sequences were cloned followed by a thymine-heptad repeat (7×T) tail. To generate crRNA arrays for processing by Cascade, repeat-spacer-repeat sequences were cloned followed by a 7×T tail. Plasmid vectors specific for each Type I subtype were generated to accelerate repeat-spacer-repeat cloning by including restriction enzyme sites downstream of the U6 promoter, followed by one copy of the repeat and a 7×T tail. These vectors can be used to add repeat-spacer sequences encoded on annealed oligomers, thus resulting in U6 promoter-repeat-spacer-repeat-7×T constructs. These plasmids can also be used to generate crRNA arrays by cloning in additional repeat-spacer-repeat sequences.

Example 2

Type I CRISPR/Cas Transcriptional Regulator System

Type I Cascade was re-purposed as a transcriptional regulator in eukaryotes by targeting promoters and enhancers. A CMV promoter and eGFP-coding sequence (pAP35) was integrated into the genome of FlpIn293 cells (FIG. 45). crRNA plasmids were generated with spacers to target the CMV promoter so that Cascade can sterically hinder the eukaryotic polymerase to block transcription. Following expression of Cascade and crRNA in the FlpIn293-GFP+ cells, GFP fluorescence will decrease.

To test that the constructs can be re-purposed to degrade DNA targets in eukaryotes, crRNA plasmids were generated with spacers to target the eGFP coding sequence. Following expression of Cascade, Cas3, and crRNA in the FlpIn293-GFP+ cells, a decrease in GFP fluorescence is expected to be measured due to degradation of the GFP-coding sequence by Cas3.

Example 3

Eukaryotic Genome Integration of Type I CRISPR-Cas System

Stable expression in eukaryotic cells was tested by integrating the Type I sequences into the eukaryotic genome. A lentiviral system was utilized for this purpose by cloning Cascade and Cas3 into two plasmid constructs. As shown in FIG. 49, the coding sequences were added downstream of an EGF1-alpha promoter, were separated by 2A sequences (P2A, T2A, and F2A), and followed by either neomycin or puromycin for selection of positively co-integrated cells. The wild-type Type I-E Cascade lentiviruses (pAP89-pAP91) were generated.

Example 4

Type I-E RNP In Vitro Activity

Figure 34:
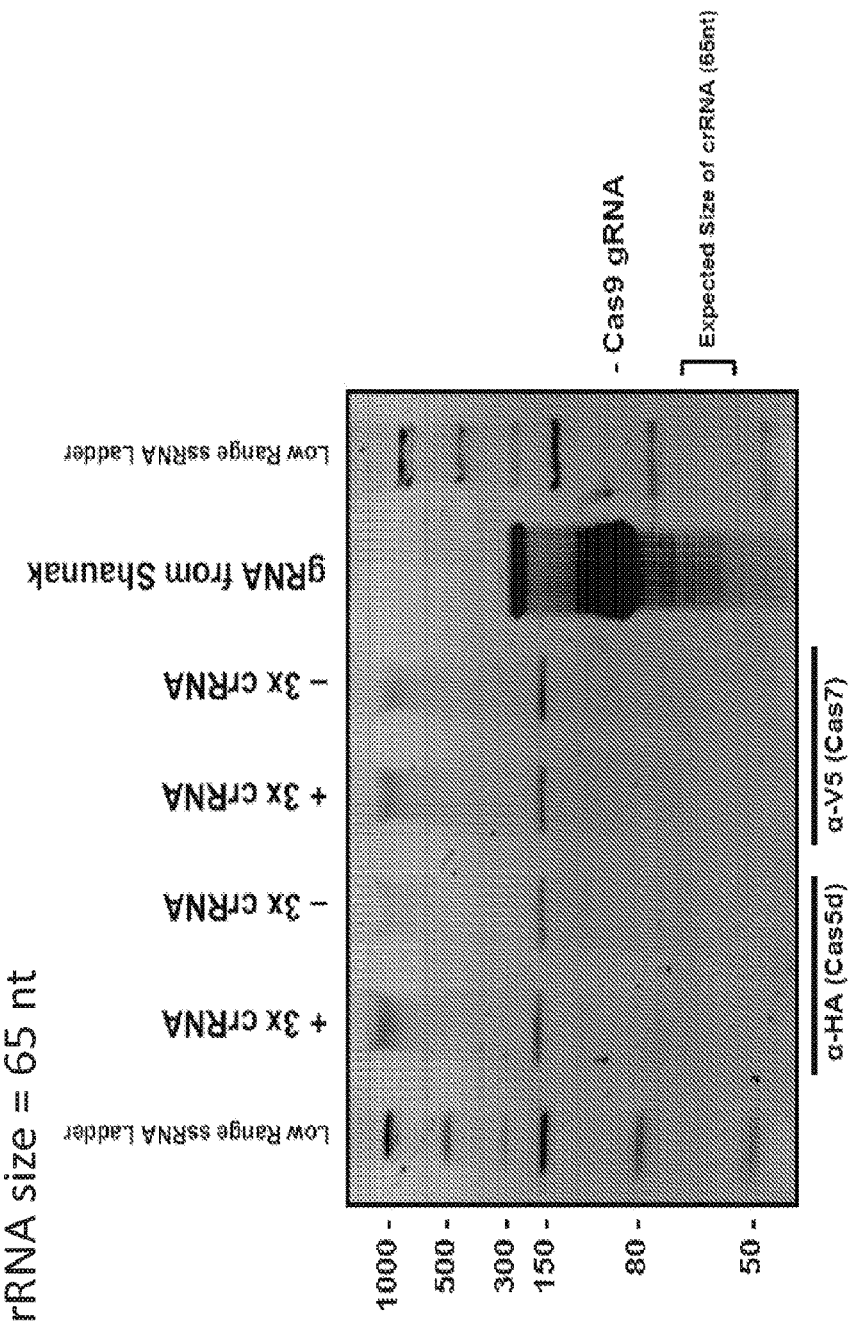
FIG. 34 shows Type I-C Cascade RNA-Immunoprecipitation (R-IP).

For Type II systems, electroporation of purified ribonucleoprotein (RNP) complexes into eukaryotic cells results in enhanced functional activity. To generate RNPs for the Type I constructs, Cas3 or Cascade with crRNA were expressed and purified from BL21 (DE3) bacterial cells, a strain that lacks active expression of the endogenous CRISPR/Cas molecules. See FIG. 51. Duet plasmid vectors were used for co-expression of the constructs since this system can be induced to express as many as eight sequences in bacterial cells. See FIG. 50. Following induction, Cas3 or Cascade with crRNA RNPs were extracted and purified. FIG. 34. Functional activity of these molecules were validated with target DNA in vitro, as described below. To use these constructs for transcriptional regulation and genome editing, the RNPs were electroporated into eukaryotic cells.

Figure 51:
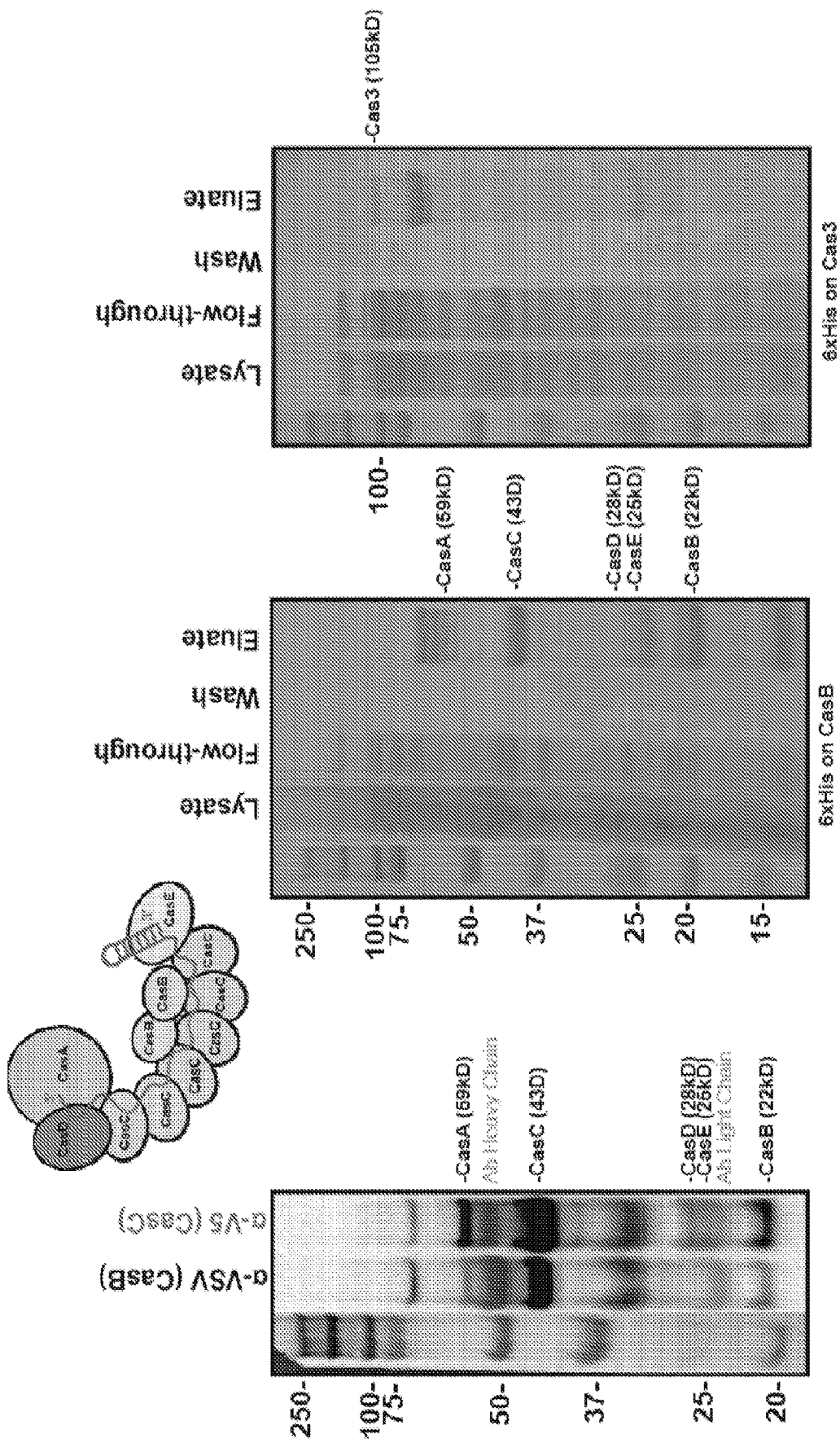
FIG. 51 shows Type I-E expression/purification from BL21(DE3) cells.

Type I-E in vitro Cas3 digestion of eGFP plasmid. To test the nuclease activity of Cas3 in vitro, Type I-E Cas3 and Cascade proteins in complex with the 3×GFP crRNA were purified as shown in FIGS. 50 and 51. The crRNA purified with both cascade complexes is a 3×repeat with different spacers targeted to GFP. To examine the Cas3 nuclease activity when Cascade is targeted to GFP, an in vitro digestion of a plasmid containing GFP was completed. The plasmid was 5744 bp. The digestion occurred for 45 min at 37° C. using a 1× reaction buffer of 20 mM HEPES (pH 7.5), 100 mM KCl, 100 μM $NiCl_2$, and 5 mM $MgCl_2$. See also Table 1.

TABLE 1

|  | 1 | 2 | 3 | 4 | 5 | 6 | 7 | 8 |
|---|---|---|---|---|---|---|---|---|
| DNA (pAP35) | 6 μg | 6 μg | 6 μg | 6 μg | 6 μg | 6 μg | 6 μg | 6 μg |
| 10x Rxn Buffer | 1x | 1x | 1x | 1x | 1x | 1x | 1x | 1x |
| Cascade (new anti-CasC purification) |  |  | 500 nM | 1000 nM | 1000 nM | 1000 nM | 1000 nM | 1000 nM |
| Cas3 |  | 500 nM |  |  | 250 nM | 500 nM | 250 nM | 500 nM |
| 10 mM ATP | 2 mM | 2 mM | 2 mM | 2 mM |  |  | 2 mM | 2 mM |

Figure 66:
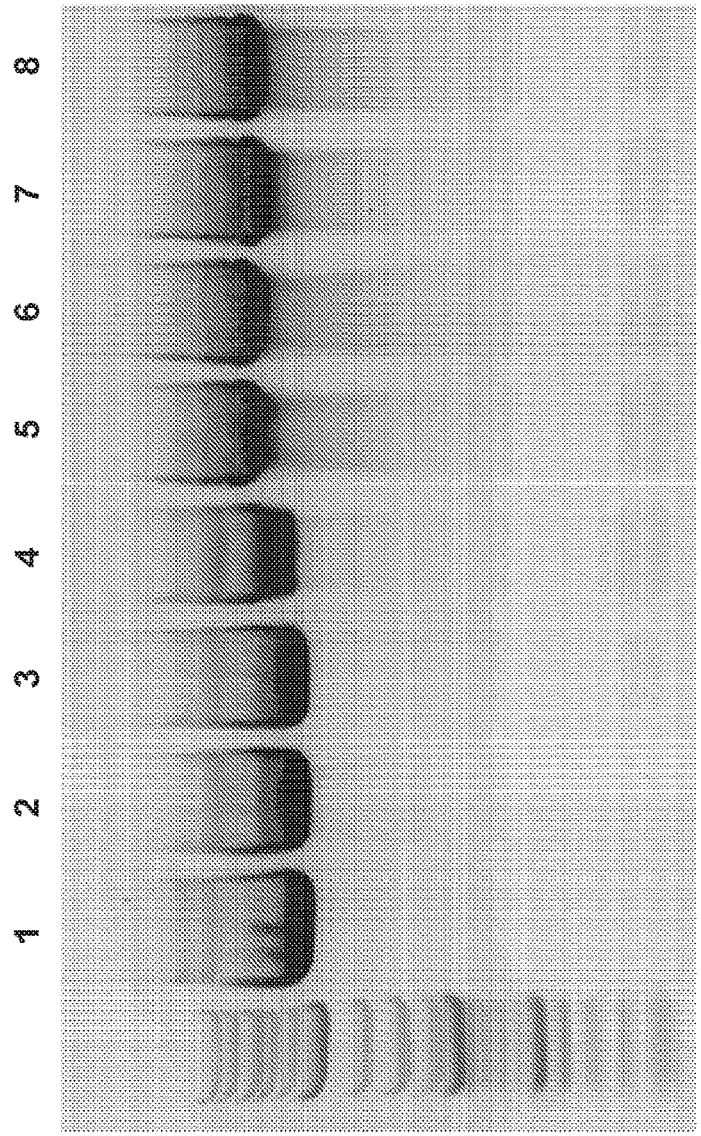
FIG. 66 shows an in vitro digestion of a GFP plasmid using the Type I-E system.

Following incubation of the RNPs with the plasmid DNA, nicking of the plasmid was observed. See FIG. 66. FIG. 66 shows an in vitro digestion of a GFP plasmid using the Type I-E system.

Example 5

Examining GFP knockdown using C.3 AP90/91 transduced FlpIn-GFP cells and transfected crRNA-mCherry constructs (3dpt, compensation included, done in triplicate biological samples). To generate the Type I-E cell line, lentiviruses were produced using pAP90 (SEQ ID NO: 42) and pAP91 (SEQ ID NO: 43) with a Type I-E system. Next, the FlpIn293-GFP+ cell line described above was co-transduced with these lentiviruses and a clone was expanded from the selected cell population. These cells were referred to as FlpIn293-GFP-AP90/AP91. To test that the Type I-E Cascade constructs can be re-purposed as a transcriptional regulator in eukaryotes by targeting promoters and open-reading frames, crRNA plasmids were generated with spacers to target the CMV promoter and eGFP coding sequence so that Cascade can sterically hinder the eukaryotic polymerase to block transcription. Following transfection of FlpIn293-GFP-AP90/AP91 cells for cascade and crRNA expression, GFP fluorescence decreased. See FIGS. 56-60.

Example 6

Targeted Killing of Cancer Cells

A cancer biopsy is sequenced in order to identify a mutation (e.g. a chromosomal inversion, point mutation, deletion) associated with the cancer cells but not the healthy cells. A CRISPR RNA is then designed to target these sequences such that the Type I system only targets the mutation. For instance, a chromosomal inversion could be specifically targeted by designing the CRISPR RNA to target the junction of the inversion. The Type I system and engineered CRISPR RNA could then be encoded in DNA that is delivered to the cancer cell using an established nanoparticle delivery vehicle or in an adeno-associated virus. Upon delivery to the cancer cells, the Type I system would be expected to degrade the chromosome with the inversion. If the identified chromosome harbors any essential genes, then the cancer cell will be killed. In contrast, the specific target sequence will not exist in the healthy cells, leaving these cells intact even upon delivery of the Type I system.

Example 7

Chromosomal Removal in a Trisomic Disorder

A lymphoid cell line from a person with Down's syndrome (trisomic chromosome 21) is used to remove the trisomic chromosome and study the impact on cell physiology. The trisomic chromosome is sequenced using next-generation sequencing techniques to identify single nucleotide polymorphisms (SNP's) present on only one of the chromosomes. This SNP is then specifically targeted (e.g. by ensuring that the SNP is within a selected PAM, and the non-SNP forms a non-functional PAM). In this setup, multiple SNPs on the same chromosome can be targeted at one time. The Type I system and the designed CRISPR array encoding spacers against each SNP can then be transfected into the cells. The impact on the polyploidy of chromosome 21 can then be determined by karyotyping. Our expectation is that the Type I system will selectively remove the third copy of chromosome 21 in some of the cells, resulting in a diploid cell line.

Example 8

Large Deletion for Humanizing a Mouse p53 Gene

Two CRISPR RNAs are designed to target the start codon and the stop codon of the p53 gene in mice. The targeting is oriented such that the PAMs are internal to the protospacers, leading to the internal degradation of the gene by Cas3. The expression plasmid is designed to encode the Type I system (e.g. the three Cascade genes and the cas3 gene for the Type I-C system from *Bacillus halodurans*) and a CRISPR array with the two targeting spacers. A separate plasmid is created encoding the human p53 gene with all introns removed along with 1,000 base pairs upstream and downstream of the mouse p53 gene. These plasmids are transfected into mouse embryonic stem cells followed by clonal expansion. The clones can then be individually screened for the presence of the human p53 gene. As a result, the Type I system allowed the replacement of an entire mouse gene with the human version.

Example 9

Targeted Removal of Human Papillomavirus (HPV)

A CRISPR RNA is designed to a target a site within the HPV genome that is distinct from the human genome. The Type I system and the CRISPR RNA are encoded within an adeno-associated virus delivery vehicle that are directly exposed to the cells. Alternatively the system can be encoded on a plasmid that is delivered through lipofection or using a nanoparticle delivery vehicle. Once inside the cell. The system is expected to degrade all copies of the HPV genome, resulting in clearance of the viral infection.

Example 10

Targeted Deletion of the Human Immunodeficiency Virus (HIV)

Two CRISPR RNAs are designed to target the long terminal repeats such that Cas3-mediated degradation is directed inward. The Type I system and the CRISPR array encoding both spacers can be inserted within an adeno-associated virus or in plasmid DNA. The construct can then be delivered to infected cells through ex vivo manipulation of infected CD4+ T-cells or introduction of the constructs into the blood stream. The construct can also include a repair template that would cut out the long terminal repeats. The expectation is that the construct will lead to the complete excision of the HIV DNA from the chromosome, thereby curing the CD4+ T-cells of the viral infection.

Example 11

Type I-E KRAB-Cascade Fusions

Figure 71:
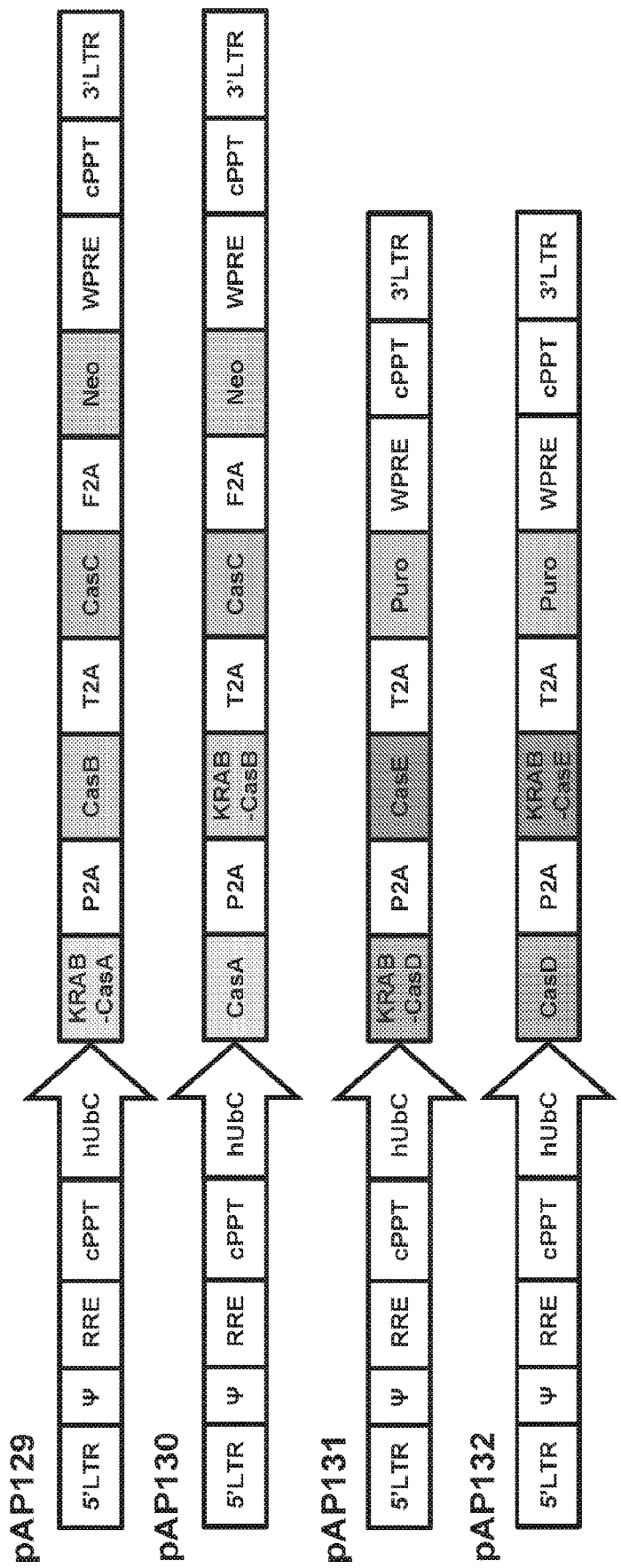
FIG. 71 shows Type I-E KRAB-Cascade lentiviral constructs.

A lentiviral system was utilized to stably express KRAB-Cascade in eukaryotic cells by integrating the sequences into the eukaryotic genome. FIG. 71 shows Type I-E KRAB-Cascade lentiviral constructs. As shown in FIG. 71, the coding sequences are added downstream of an EGF1-alpha promoter, are separated by 2A sequences (P2A, T2A, and F2A), and followed by either neomycin or puromycin for selection of positively co-integrated cells. The pAP129 nucleotide sequence (SEQ ID NO: 44), the pAP130 nucleotide sequence (SEQ ID NO: 45), the pAP131 nucleotide sequence (SEQ ID NO: 46), and the pAP132 nucleotide sequence (SEQ ID NO: 47) are schematically represented in FIG. 71.

Figure 67:
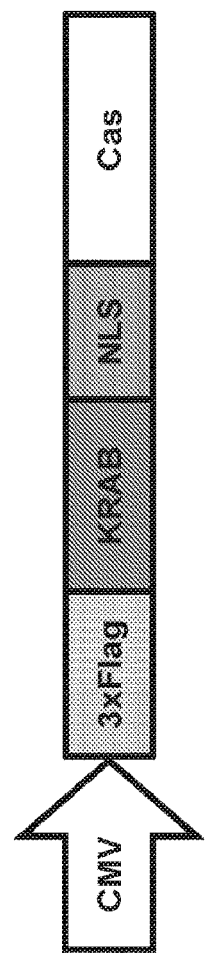
FIG. 67 shows Type I-E KRAB-Cascade constructs.

Design of Type I-E KRAB fusion constructs are shown in Table 2 and FIG. 67. FIG. 67 shows Type I-E KRAB-Cascade constructs.

TABLE 2

| Construct | Side | Tag | kD | Plasmid |
| --- | --- | --- | --- | --- |
| CasA | NTD | Myc | 59 | pAP62 |
| CasB | NTD | HSV | 22 | pAP86 |
| CasC | NTD | V5 | 43 | pAP64 |
| CasD | NTD | HA | 28 | pAP65 |
| CasE | NTD | E | 25 | pAP50 |
| KRAB-CasA | NTD | Flag | 72 | pAP104 |
| KRAB-CasB | NTD | Flag | 35 | pAP105 |
| KRAB-CasC | NTD | Flag | 56 | pAP106 |
| KRAB-CasD | NTD | Flag | 42 | pAP107 |
| KRAB-CasE | NTD | Flag | 39 | pAP108 |

Figure 68:
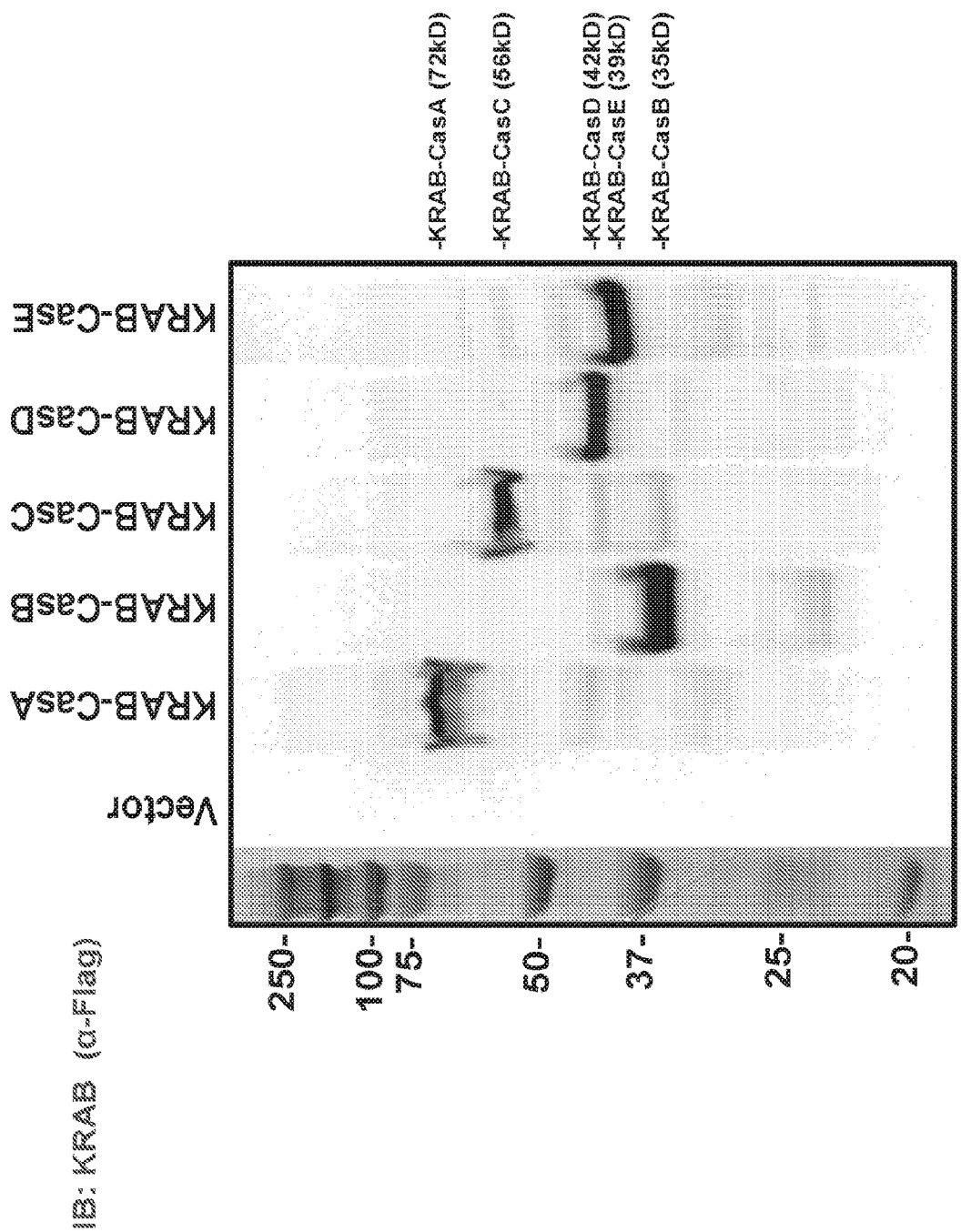
FIG. 68 shows the expression of Type I-E KRAB-Cascade in HEK293T cells.
Figures 69, 70:
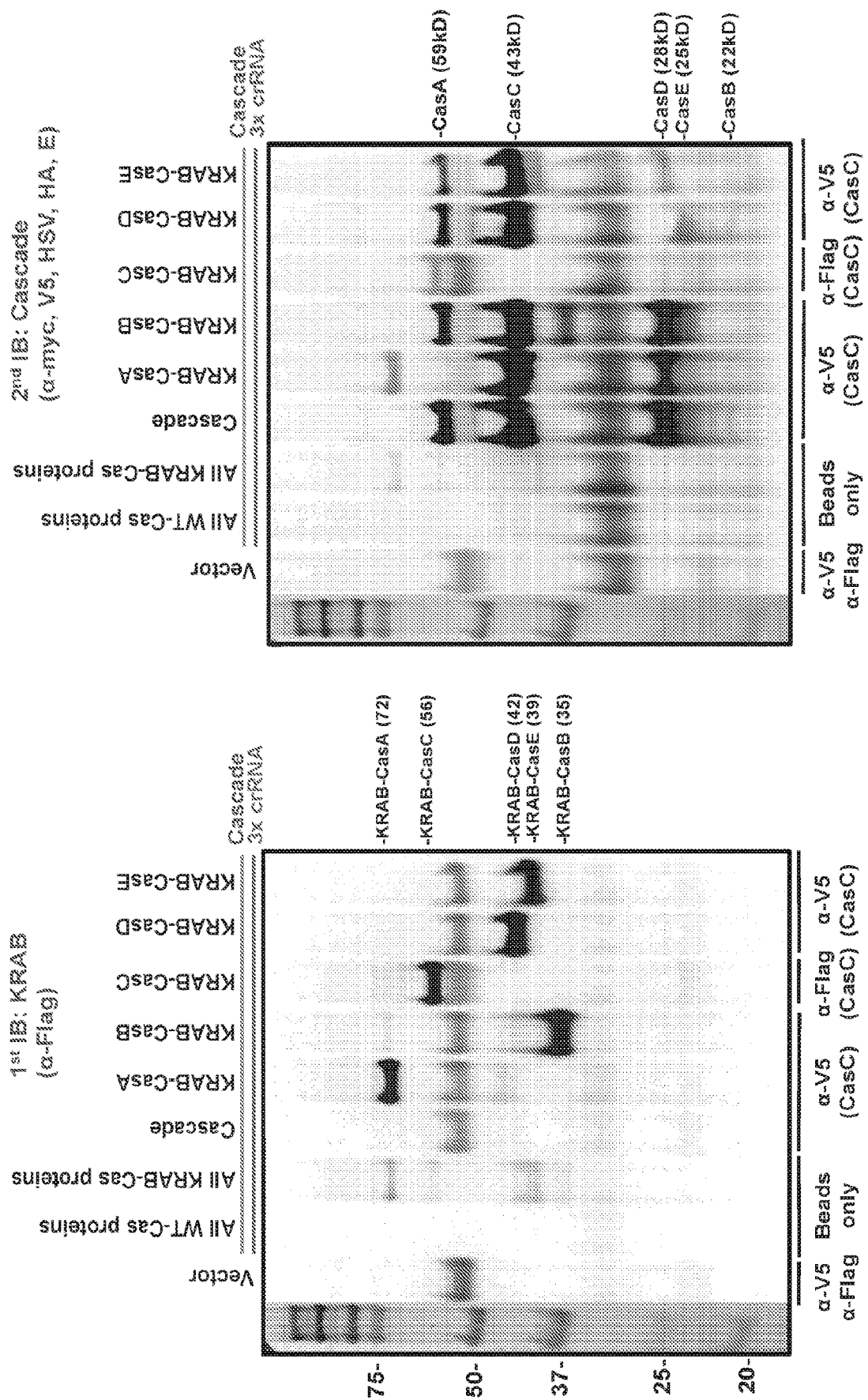
FIGS. 69 and 70 shows Type I-E KRAB-Cascade Co-IP.

FIG. 68 shows the expression of Type I-E KRAB-Cascade in HEK293T cells. FIGS. 69 and 70 show Type I-E KRAB-Cascade co-immunoprecipitation.

Example 12

Transcriptional Repression by KRAB-Cascade

To test transcriptional repression by KRAB-Cascade, the HS2 enhancer in the globin locus control region will be targeted. To more easily monitor transcriptional modulation of the HBE1 gene in this region, an endogenous reporter was generated in K562 cells by replacing the stop codon of HBE1 with a P2A-mCherry sequence via by CRISPR/Cas9-mediated genome editing. The K562-mCherry cells were transduced with the KRAB-Cascade lentiviral constructs (shown in FIG. 71) to make stable cell lines. The crRNA plasmids were cloned with spacers targeting the HS2 enhancer. Following stable cell line generation, the cells will be electroporated with the generated crRNA plasmids and the mCherry expression will be tested by flow cytometry analysis. A reduction in mCherry is expected.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clause:

Clause 1. A Type I CRISPR/Cas system composition for genome engineering at least one target gene in a eukaryotic cell, the composition comprising at least one polynucleotide sequence encoding: (a) a Cascade complex; (b) a Cas3 polypeptide; and/or (c) at least one crRNA, wherein the crRNA targets a target nucleotide sequence from the at least one target gene, wherein the Cascade complex comprises three or more Type I Cascade polypeptides, or functional fragments thereof, wherein the at least one polynucleotide sequence is operably linked to a eukaryotic promoter and comprises a nuclear localization signal, and the at least one polynucleotide sequence is codon-optimized.

Clause 2. The Type I CRISPR/Cas system composition of clause 1, wherein the at least one polynucleotide sequence encoding the Cascade complex comprises at least one polynucleotide sequence encoding one or more Cascade polypeptides of the Type I-A CRISPR/Cas system, the Type I-B CRISPR/Cas system, the Type I-C CRISPR/Cas system, the Type I-D CRISPR/Cas system, the Type I-E CRISPR/Cas system, or the Type I-F CRISPR/Cas system.

Clause 3. The Type I CRISPR/Cas system composition of clause 1 or 2, wherein the at least one polynucleotide sequence encoding the Cascade complex comprises: (i) a polynucleotide sequence encoding the a polynucleotide sequence encoding a Cas7 polypeptide, a polynucleotide sequence encoding a Cas8a1 polypeptide or a Cas8a2 polypeptide, a polynucleotide sequence encoding a Cas5 polypeptide, a polynucleotide sequence encoding a Csa5 polypeptide, a polynucleotide sequence encoding a Cas6a polypeptide, a polynucleotide sequence encoding a Cas3' polypeptide, and a polynucleotide sequence encoding a Cas3" polypeptide having no nuclease activity (Type I-A CRISPR/Cas system); (ii) a polynucleotide sequence encoding a Cas6b polypeptide, a polynucleotide sequence encoding a Cas8b polypeptide, a polynucleotide sequence encoding a Cas7 polypeptide and a polynucleotide sequence encoding a Cas5 polypeptide (Type 1-B CRISPR/Cas system); (iii) a polynucleotide sequence encoding a Cas5d polypeptide, a polynucleotide sequence encoding a Cas8c polypeptide, and a polynucleotide sequence encoding a Cas7 polypeptide (Type 1-C CRISPR/Cas system); (iv) a polynucleotide sequence encoding a Cas10d polypeptide, a polynucleotide sequence encoding a Csc2 polypeptide, a polynucleotide sequence encoding a Csc1 polypeptide, a polynucleotide sequence encoding a Cas6d polypeptide (Type 1-D CRISPR/Cas system); (v) a polynucleotide sequence encoding a Cse1 polypeptide, a polynucleotide sequence encoding a Cse2 polypeptide, a polynucleotide sequence encoding a Cas7 polypeptide, a polynucleotide sequence encoding a Cas5 polypeptide and a polynucleotide sequence encoding a Cas6e polypeptide (Type 1-E CRISPR/Cas system); (vi) a polynucleotide sequence encoding a Csy1 polypeptide, a polynucleotide sequence encoding a Csy2 polypeptide, a polynucleotide sequence encoding a Csy3 polypeptide and a polynucleotide sequence encoding a Csy4 polypeptide (Type 1-F CRISPR/Cas system).

Clause 4. The Type I CRISPR/Cas system composition of clause 3, wherein each of the polynucleotide sequences of (i)-(vi) is operably linked to a eukaryotic promoter, comprises a nuclear localization signal, and is operably linked to a terminator.

Clause 5. The Type I CRISPR/Cas system composition of any one of clauses 1-3, wherein two or more Type I Cascade polypeptides, or functional fragments thereof, are fused to form a single polypeptide.

Clause 6. The Type I CRISPR/Cas system composition of any one of clauses 1-3, wherein two or more Type I Cascade polypeptides are encoded by a multicistronic polynucleotide sequence and separated by at least one 2A peptide.

Clause 7. The Type I CRISPR/Cas system composition of clause 6, wherein a lentiviral vector comprises the multicistronic polynucleotide sequence.

Clause 8. The Type I CRISPR/Cas system composition of any one of clauses 1-4, wherein the at least one polynucleotide sequence encoding the Cascade complex comprises at least one polynucleotide sequence of SEQ ID NO: 14, SEQ ID NO: 16, SEQ ID NO: 18, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 34, SEQ ID NO: 36, SEQ ID NO: 38, or SEQ ID NO:40.

Clause 9. The Type I CRISPR/Cas system composition of any one of clauses 1-8, wherein at least one Cascade polypeptide is fused to a second polypeptide domain, wherein the second polypeptide domain has an activity selected from the group consisting of transcription activation activity, transcription repression activity, transcription release factor activity, histone modification activity, nuclease activity, nucleic acid association activity, methylase activity, and demethylase activity, or wherein the second polypeptide domain comprises a tag or label.

Clause 10. The Type I CRISPR/Cas system composition of clause 9, wherein the second polypeptide domain is fused to the N terminus and/or the C terminus of the at least one Cascade polypeptide.

Clause 11. The Type I CRISPR/Cas system composition of clause 9 or 10, wherein the second polypeptide domain has transcription activation activity.

Clause 12. The Type I CRISPR/Cas system composition of clause 11, wherein the second polypeptide domain comprises at least one VP16 transcription activation domain repeat.

Clause 13. The Type I CRISPR/Cas system composition of clause 11 or 12, wherein the second polypeptide domain comprises a p300 core domain, VP16 tetramer ("VP64"), or a p65 activation domain.

Clause 14. The Type I CRISPR/Cas system composition of clause 9 or 10, wherein the second polypeptide domain has transcription repression activity.

Clause 15. The Type I CRISPR/Cas system composition of clause 14, wherein the second polypeptide domain comprises a KRAB domain.

Clause 16. The Type I CRISPR/Cas system composition of clause 9 or 10, wherein the second polypeptide domain comprises an epitope tag.

Clause 17. The Type I CRISPR/Cas system composition of clause 16, wherein the epitope tag comprises FLAG (SEQ ID NO: 1), 3×FLAG, HA (SEQ ID NO: 2), myc (SEQ ID NO: 3), V5 (SEQ ID NO: 4), E-tag (SEQ ID NO: 5), VSV-g (SEQ ID NO: 6), 6×His (SEQ ID NO: 7), and HSV (SEQ ID NO: 8).

Clause 18. The Type I CRISPR/Cas system composition of any one of clauses 9-17, further comprising a linker connecting the Cascade polypeptide to the second polypeptide domain.

Clause 19. The Type I CRISPR/Cas system composition of any one of clauses 1-18, wherein the at least one polynucleotide sequence encoding the at least one crRNA comprises a recombinant CRISPR array comprising two or more repeat nucleotide sequences and one or more spacer nucleotide sequence(s), wherein each spacer nucleotide sequence in said CRISPR array is linked at its 5' end and at its 3' end to a repeat nucleotide sequence.

Clause 20. The Type I CRISPR/Cas system composition of clause 19, wherein the recombinant CRISPR array is operably linked to a eukaryotic promoter, comprises a nuclear localization signal, and is operably linked to a terminator.

Clause 21. The Type I CRISPR/Cas system of clause 19 or 20, wherein at least two of the one or more spacer nucleotide sequence(s) each comprise a nucleotide sequence that is complementary to a different target nucleotide sequence from a single target gene.

Clause 22. The Type I CRISPR/Cas system of any one of clauses 19-21, wherein at least two of the one or more spacer nucleotide sequence(s) each comprise a nucleotide sequence that is complementary to a different target nucleotide sequence from a different target gene.

Clause 23. The Type I CRISPR/Cas system of any one of clauses 19-22, wherein the target nucleotide sequence is located on a coding or a plus strand of a double stranded nucleotide sequence.

Clause 24. The Type I CRISPR/Cas system of any one of clauses 19-22, wherein the target nucleotide sequence is located on a non-coding or a minus strand of a double stranded nucleotide sequence.

Clause 25. The Type I CRISPR/Cas system of any one of clauses 19-24, wherein the target nucleotide sequence comprises all or a part of a nucleotide sequence encoding a promoter region of a gene or a complement thereof, an enhancer region of a gene or a complement thereof, or a transcribed region of a gene or a complement thereof.

Clause 26. The Type I CRISPR/Cas system of clause 25, wherein the target nucleotide sequence comprises an intron of a gene.

Clause 27. The Type I CRISPR/Cas system of clause 25, wherein the target nucleotide sequence comprises an exon of a gene.

Clause 28. The Type I CRISPR/Cas system of any one of clauses 1-27, wherein the Cas3 polypeptide comprises an amino acid sequence of SEQ ID NO: 15, SEQ ID NO: 17, or SEQ ID NO: 19.

Clause 29. The Type I CRISPR/Cas system of any one of clauses 1-28, wherein the at least one target gene is an endogenous gene or a transgene.

Clause 30. The Type I CRISPR/Cas system of any one of clauses 1-29, wherein the eukaryotic promoter comprises CMV or hUbC.

Clause 31. The Type I CRISPR/Cas system of any one of clauses 1-30, wherein the at least one polynucleotide sequence comprises a Kozak sequence.

Clause 32. The Type I CRISPR/Cas system of any one of clauses 1-31, wherein the nuclear localization signal comprises SV40 NLS (SEQ ID NO: 9).

Clause 33. An expression cassette or a vector comprising the Type I CRISPR/Cas system of any one of clauses 1-32 or subcomponents thereof.

Clause 34. A host cell comprising the Type I CRISPR/Cas system of any one of clauses 1-32 or the expression cassette or vector of clause 33.

Clause 35. A pharmaceutical composition comprising the Type I CRISPR/Cas system of any one of clauses 1-32, the expression cassette or vector of clause 33, or the host cell of clause 34.

Clause 36. A method of modulating the expression of a target gene in a eukaryotic cell, the method comprising introducing to a cell the Type I CRISPR/Cas system of any one of clauses 1-32 or the expression cassette or vector of clause 33.

Clause 37. The method of clause 36, wherein the gene expression is repressed.

Clause 38. The method of clause 36 or 37, wherein the Type I CRISPR/Cas system comprises at least one polynucleotide encoding a Cascade complex and at least one crRNA, with the proviso that the Type I CRISPR/Cas system does not comprise Cas3.

Clause 39. The method of clause 36 or 37, wherein the Type I CRISPR/Cas system comprises at least one polynucleotide encoding a Cascade complex, a Cas3 polypeptide, and at least one crRNA.

Clause 40. The method of clause 36, wherein the gene expression is induced.

Clause 41. The method of any one of clauses 36-40, wherein the Type I CRISPR/Cas system comprises two or more crRNAs.

Clause 42. The method of clause 41, wherein the Type I CRISPR/Cas system comprises between one and ten different crRNAs.

Clause 43. The method of clause 42, wherein the different crRNAs bind to different target nucleotide sequences within the target gene.

Clause 44. The method of clause 43, wherein the target nucleotide sequences are separated by at least one nucleotide.

Clause 45. The method of clause 43, wherein the target nucleotide sequences are separated by about 15 to about 700 base pairs.

Clause 46. The method of clause 42, wherein each of the different crRNAs bind to at least one different target genes.

Clause 47. The method of clause 46, wherein the different target genes are located on same chromosome.

Clause 48. The method of clause 46, wherein the different target genes are located on different chromosomes.

Clause 49. The method of any one of clauses 41-48, wherein at least one target nucleotide sequence is within a non-open chromatin region, an open chromatin region, a promoter region of the target gene, an enhancer region of the target gene, a transcribed region of the target gene, or a region upstream of a transcription start site of the target gene.

Clause 50. The method of any one of clauses 41-48, wherein at least one target nucleotide sequence is located between about 1 to about 1000 base pairs upstream of a transcription start site of a target gene.

Clause 51. The method of any one of clauses 41-48, wherein the Type I CRISPR/Cas system comprises two different crRNAs, three different crRNAs, four different crRNAs, five different crRNAs, six different crRNAs, seven different crRNAs, eight different crRNAs, nine different crRNAs, or ten different crRNAs.

Clause 52. The method of any one of clauses 41-51, wherein at least one target region is within an intron or an exon of a target gene.

Clause 53. The method of clause 37, wherein the endogenous gene is transiently repressed.

Clause 54. The method of clause 37, wherein the endogenous gene is stably repressed.

Clause 55. A method of activating an endogenous gene in a cell, the method comprising contacting a cell with the Type I CRISPR/Cas system of any one of clauses 1-32 or the expression cassette or vector of clause 33, wherein at least one Cascade polypeptide is fused to a second polypeptide domain having transcription activation activity.

Clause 56. The method of clause 55, wherein the endogenous gene is transiently activated.

Clause 57. The method of clause 55, wherein the endogenous gene is stably activated.

Clause 58. A method of correcting a mutant gene in a eukaryotic cell, the method comprising administering to a cell the Type I CRISPR/Cas system of any one of clauses 1-32 or the expression cassette or vector of clause 33.

Clause 59. The method of clause 58, wherein the correction of the mutant gene comprises homology-directed repair.

Clause 60. The method of clause 59, further comprising administering to the cell a donor DNA.

Clause 61. The method of clause 58, wherein the mutant gene comprises a frameshift mutation which causes a premature stop codon and a truncated gene product.

Clause 62. The method of clause 61, wherein the correction of the mutant gene comprises nuclease mediated non-homologous end joining.

Clause 63. The method of clause 58, wherein the correction of the mutant gene comprises a deletion of a premature stop codon, a disruption of a splice acceptor site, a deletion of one or more exons, or disruption of a splice donor sequence.

Clause 64. The method of clause 63, wherein the deletion of one or more exons results in the correction of the reading frame.

Clause 65. The method of any one of clauses 36-64, wherein the Type I CRISPR/Cas system is introduced on one or more expression cassettes or vectors.

Clause 66. The method of any one of clauses 36-65, wherein the Type I CRISPR/Cas system is delivered to the cell virally or non-virally.

Clause 67. The method of any one of clauses 36-65, wherein the target gene is an endogenous gene or a transgene.

Clause 68. A kit for modulating gene expression of at least one target gene in a eukaryotic cell, the kit comprising the Type I CRISPR/Cas system of any one of clauses 1-32, the expression cassette or vector of clause 33, or the host cell of clause 34.

Clause 69. A method for introducing an insertion, deletion, or mutation in a chromosome or extrachromosomal element of a eukaryotic cell by homologous recombination, comprising: introducing into the eukaryotic cell (A) (i) at least one nucleic acid construct encoding polypeptides of a Type I CRISPR-Cas system; and (ii) a CRISPR array comprising at least one spacer sequence that is complementary to a target DNA on the chromosome or extrachromosomal element; or (B) a protein-RNA complex comprising polypeptides of a Type I CRISPR-Cas system and a CRISPR array comprising at least one spacer sequence that is complementary to a target DNA on the chromosome or extrachromosomal element; and (C) a template comprising a single stranded DNA sequence or a double stranded DNA sequence, thereby introducing an insertion, deletion, or mutation in the chromosome or extrachromosomal element of the eukaryotic cell by homologous recombination.

Clause 70. A method for introducing a deletion into a chromosome or extrachromosomal element of a eukaryotic cell, comprising: introducing into the eukaryotic cell (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; and (C) optionally, a template comprising a single stranded DNA sequence or a double stranded DNA sequence and an intervening sequence having zero nucleotides or base pairs, respectively, wherein the different target DNAs located on opposite strands of the chromosome or extrachromosomal element are each adjacent to a protospacer adjacent motif (PAM) and the at least two spacer sequences of the CRISPR array(s) guide the Type I CRISPR-Cas polypeptides to the two different target DNAs, thereby degrading the chromosome or extrachromosomal element between the two different target DNAs including the PAM adjacent to each of the two different target DNAs (convergent degradation) and introducing a deletion.

Clause 71. A method for introducing an insertion or mutation into a chromosome of a eukaryotic cell, comprising: introducing into the eukaryotic cell (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary or extrachromosomal element to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; and (C) a template comprising a single stranded DNA sequence or a double stranded DNA sequence, wherein the different target DNAs located on opposite strands of the chromosome or extrachromosomal element are each adjacent to a protospacer adjacent motif (PAM) and the at least two spacer sequences of the CRISPR array(s) guide the Type I CRISPR-Cas polypeptides to the two different target DNAs, thereby degrading the chromosome or extrachromosomal element between the two different target DNAs including the PAM adjacent to each of the two different target DNAs (convergent degradation) and introducing an insertion or mutation.

Clause 72. A method for treating a viral infection in a subject in need thereof, comprising: administering to the subject an effective amount of (A) (i) at least one nucleic acid construct encoding polypeptides of a Type I CRISPR-Cas system; and (ii) a CRISPR array comprising at least one spacer sequence that is complementary to a target DNA on the chromosome or extrachromosomal element; or (B) a protein-RNA complex comprising polypeptides of a Type I CRISPR-Cas system and a CRISPR array comprising at least one spacer sequence that is complementary to a target DNA on the chromosome or extrachromosomal element; and (C) a template comprising a single stranded DNA sequence or a double stranded DNA sequence and an intervening sequence having zero nucleotides or base pairs, respectively, wherein the target DNA is DNA of a virus infecting the subject, thereby introducing a deletion by homologous recombination in the chromosome or extrachromosomal element of the eukaryotic cell, thereby treating the viral infection in the subject in need thereof.

Clause 73. A method for treating a viral infection in a subject in need thereof, comprising: administering to the subject an effective amount of: (A) (i) at least one nucleic acid construct encoding polypeptides of a Type I CRISPR-Cas system; and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; or (B) a protein-RNA complex comprising: (i) polypeptides of a Type I CRISPR-Cas system and (ii) (a) a CRISPR array comprising at least two spacer sequences, wherein the at least two spacer sequences are complementary to different target DNAs located on opposite strands of the chromosome or extrachromosomal element of the eukaryotic cell; or (b) at least two CRISPR arrays each comprising at least one spacer sequence, wherein the at least one spacer sequence of each of the two CRISPR arrays are complementary to different target DNAs located on opposite strands of the chromosome or extrachromosomal element of the eukaryotic cell; wherein the different target DNAs located on opposite strands of the chromosome or extrachromosomal element are each adjacent to a protospacer adjacent motif (PAM) and the at least two spacer sequences of the CRISPR array(s) are each complementary to DNA of a virus infecting the subject and guide the Type I CRISPR-Cas polypeptides to the two different target DNAs, thereby degrading the chromosome or extrachromosomal element between the two different target DNAs including the PAM adjacent to each of the two different target DNAs (convergent degradation), thereby treating the viral infection in the subject in need thereof.

Clause 74. The method of clause 70, wherein the target DNA is viral DNA that is incorporated into the eukaryotic chromosome or is an extrachromosomal element residing in the eukaryotic cell.

Clause 75. The method of any one of clause 69, wherein the template comprising single stranded DNA comprises (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising a length of zero to about 100,000 nucleotides.

Clause 76. The method of any one of clauses 70, 72 or 73, wherein the template comprising single stranded DNA comprises (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising zero nucleotides.

Clause 77. The method of any one of clause 71, wherein the template comprising single stranded DNA comprises (i) a first homology arm comprising a length of about 20 nucleotides to about 200 nucleotides; (ii) a second homology arm comprising a length of about 20 nucleotides to about 200 nucleotides; and (iii) an intervening synthetic nucleotide sequence (i.e., intervening sequence) located between the first and second homology arms and comprising a length of one to about 100,000 nucleotides.

Clause 78. The method of clause 69, wherein the template comprising double stranded DNA comprises (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of zero to about 100,000 base pairs.

Clause 79. The method of clauses 70, 72 or 73, wherein the template comprising double stranded DNA comprises (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of zero base pairs.

Clause 80. The method of clause 71, wherein the template comprising double stranded DNA comprises (i) a first homology arm comprising a length of about 100 base pairs to about 10,000 base pairs; (ii) a second homology arm comprising a length of about 100 base pairs to about 10,000 base pairs; and (iii) an intervening synthetic nucleotide sequence (i.e., intervening sequence) located between the first and second homology arms and comprising a length of one to about 100,000 base pairs.

Clause 81. The method of any one of clauses 69-80, wherein the CRISPR array comprises an unprocessed CRISPR array a repeat sequence, having a 5' end and a 3' end, and at least one spacer-repeat sequence, having a 5' end and a 3' end, and the repeat sequence is linked at its 3' end to the 5' end of the at least one spacer-repeat sequence, wherein when more than one spacer-repeat sequence is present, the spacer-repeat sequences are consecutive to one another, each having a 5' end and a 3' end, and linked at the 3' end to the 5' end of the next spacer-repeat sequence.

Clause 82. A method for disabling or deleting a chromosome in a eukaryotic cell comprising: introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA on the chromosome; or (B) a protein-RNA complex comprising polypeptides of a Type I CRISPR-Cas system and at least one CRISPR array comprising at least one spacer sequence that is complementary to a target DNA on the chromosome, thereby disabling or deleting the chromosome in the eukaryotic cell.

Clause 83. A method of killing of selected cells in a population of eukaryotic cells, comprising introducing into the eukaryotic cell: (A) (i) at least one nucleic acid construct encoding polypeptides of a Type I CRISPR-Cas system; and (ii) at least one CRISPR array comprising at least one spacer sequence that is complementary to a target DNA present on a chromosome of a subset of cells within a population of cells and not present in a chromosome of the other cells of the population; or (B) a protein-RNA complex comprising polypeptides of a Type I CRISPR-Cas system and at least one CRISPR array comprising at least one spacer sequence that is complementary to a target DNA present in a subset of cells in a population of cells and not present in the other cells of the population, thereby killing the subset of cells within the population of cells.

Clause 84. The method of clause 83, wherein the target DNA is a viral specific nucleic acid sequence or is a mutation or sequence specific to a cancer cell.

Clause 85. A method of sequence-specific killing of a eukaryotic cell, comprising: introducing into the organism cell: (A) (i) at least one nucleic acid construct encoding polypeptides of a Type I CRISPR-Cas system; and (ii) at least one CRISPR array comprising at least one spacer sequence that is complementary to a target DNA in an essential gene; or (B) a protein-RNA complex comprising polypeptides of a Type I CRISPR-Cas system and at least one CRISPR array comprising at least one spacer sequence that is complementary to a target DNA in an essential gene, thereby disrupting or deleting the gene and killing the cell.

Clause 86. A method for deleting a target DNA in a chromosome or on an extrachromosomal element in a eukaryotic cell, the method comprising introducing into the eukaryotic cell: (A) (i) at least one nucleic acid construct encoding polypeptides of a Type I CRISPR-Cas system; and (ii) at least one CRISPR array comprising at least one spacer sequence that is complementary to the target DNA on the chromosome or on the extrachromosomal element; or (B) a protein-RNA complex comprising polypeptides of a Type I CRISPR-Cas system and at least one CRISPR array comprising at least one spacer sequence that is complementary to the target DNA in the chromosome or on the extrachromosomal element, thereby deleting the target DNA in the chromosome or on the extrachromosomal element.

Clause 87. The method of any one of clauses 82-86, wherein the at least one CRISPR array comprises an unprocessed CRISPR array or a processed CRISPR array.

Clause 88. The method of clause 87, wherein the unprocessed CRISPR array comprises a repeat sequence having a 5' end and a 3' end, and at least one spacer-repeat sequence having a 5' end and a 3' end, and the repeat sequence is linked at its 3' end to the 5' end of the at least one spacer-repeat sequence, wherein when more than one spacer-repeat sequence is present, the spacer-repeat sequences are consecutive to one another, each having a 5' end and a 3' end, and linked at the 3' end to the 5' end of the next spacer-repeat sequence.

Clause 89. The method of any one of clauses 69-88, wherein the CRISPR array comprises a processed CRISPR array comprising: (A) a first portion of a Type I repeat sequence having a 5' end and a 3' end; (B) a spacer sequence having a 5' end and a 3' end; and (C) (i) a full length Type I repeat sequence having a 5' end and a 3' end, or (ii) a second portion of a Type I repeat sequence having a 5' end and a 3' end, the second portion of the Type I repeat sequence comprising: (a) a portion of consecutive nucleotides of a Type-I repeat sequence from the 5'-most end of the Type-I repeat sequence through the Type-I repeat sequence hairpin, or (b) a portion of consecutive nucleotides of a Type-I repeat sequence from the 5'-most end of the Type-I repeat sequence up to the base of the Type-I repeat sequence stem loop, wherein the spacer sequence is linked at its 5' end to the 3' end of the first portion of a Type I repeat sequence and linked at its 3' end to the 5' end of the full length Type-I repeat or the 5' end of the second portion of a Type-I repeat.

Clause 90. The method of any one of clauses 69-89, wherein the at least one CRISPR array comprises at least two spacer sequences, the at least two spacer sequences being complementary to different target DNAs that are on the same strand of the chromosome of the eukaryotic cell.

Clause 91. The method of any one of clauses 82 or 86-89, comprising introducing at least two CRISPR arrays each comprising at least one spacer sequence, wherein the at least one spacer sequence of each of the two CRISPR arrays are complementary to different target DNAs located on the same strand of the chromosome of the eukaryotic cell.

Clause 92. The method of clause 90 or clause 91, wherein the target DNA is in a telomere or a centromere of the chromosome of the eukaryotic cell.

Clause 93. The method of any one of clauses 82 or 86-92, wherein the target DNA is complementary to a mutation present in less than all of a pair or a group of homologous chromosomes (e.g., only one out of a pair; one to three out of a set of four homologous chromosomes, and the like) or in only one of a pair of sister chromatids, thereby disabling or deleting less than all of a pair or a group of homologous chromosomes or only one of a pair of sister chromatids.

Clause 94. The method of any one of clauses 82 or 87-93, wherein the chromosome does not encode an essential gene.

Clause 95. The method of any one of clauses 82 or 87-94, wherein the chromosome is replaced with a synthetic chromosome.

Clause 96. The method of any one of clauses 82, 83 or 86-92, wherein the chromosome comprises at least one essential gene and disabling or deleting the chromosome kills the cell.

Clause 97. The method of any one of clauses 82, 83, 87-93 or 96, wherein the target DNA is up to about $10^7$ base pairs from an essential gene, thereby either disabling or deleting the chromosome comprising the essential gene and killing the cell and/or disrupting or deleting the essential gene itself.

Clause 98. The method of any of one of clauses 69-97, wherein the Type I CRISPR-Cas system comprises: (a) a nucleotide sequence encoding a Cas7 (Csa2) polypeptide, a nucleotide sequence encoding a Cas8a1 (Csx13) polypeptide or a Cas8a2 (Csx9) polypeptide, a nucleotide sequence encoding a Cas5 polypeptide, a nucleotide sequence encoding a Csa5 polypeptide, a nucleotide sequence encoding a Cas6a polypeptide, a nucleotide sequence encoding a Cas3' polypeptide, and a nucleotide sequence encoding a Cas3" polypeptide (Type I-A); (b) a nucleotide sequence encoding a Cas6b polypeptide, a nucleotide sequence encoding a Cas8b (Csh1) polypeptide, a nucleotide sequence encoding a Cas7 (Csh2) polypeptide, a nucleotide sequence encoding a Cas5 polypeptide, a nucleotide sequence encoding a Cas3' polypeptide, and a nucleotide sequence encoding a Cas3" polypeptide (Type I-B); (c) a nucleotide sequence encoding a Cas5d polypeptide, a nucleotide sequence encoding a Cas8c (Csd1) polypeptide, a nucleotide sequence encoding a Cas7 (Csd2) polypeptide and a nucleotide sequence encoding a Cas3 polypeptide (Type I-C); (d) a nucleotide sequence encoding a Cas10d (Csc3) polypeptide, a nucleotide sequence encoding a Csc2 polypeptide, a nucleotide sequence encoding a Csc1 polypeptide, a nucleotide sequence encoding a Cas6d polypeptide, and a nucleotide sequence encoding a Cas3 polypeptide (Type I-D); (e) a nucleotide sequence encoding a Cse1 (CasA) polypeptide, a nucleotide sequence encoding a Cse2 (CasB) polypeptide, a nucleotide sequence encoding a Cas7 (CasC) polypeptide, a nucleotide sequence encoding a Cas5 (CasD) polypeptide, a nucleotide sequence encoding a Cas6e (CasE) polypeptide, and a nucleotide sequence encoding a Cas3 polypeptide (Type I-E); and/or (f) a nucleotide sequence encoding a Cys1 polypeptide, a nucleotide sequence encoding a Cys2 polypeptide, a nucleotide sequence encoding a Cas7 (Cys3) polypeptide and a nucleotide sequence encoding a Cas6f polypeptide, and a nucleotide sequence encoding a Cas3 polypeptide (Type I-F).

Clause 99. The method of any one of clauses 69-97, wherein the Type I CRISPR-Cas system comprises: a nucleotide sequence encoding a Cas5d polypeptide, a nucleotide sequence encoding a Cas8c (Csd1) polypeptide, a nucleotide sequence encoding a Cas7 (Csd2) polypeptide and a nucleotide sequence encoding a Cas3 polypeptide (Type I-C).

Clause 100. The method of any one of clauses 69-99, wherein the target DNA is immediately 3' to a protospacer adjacent motif (PAM).

Clause 101. The method of clause 100, wherein the PAM is a Type I-E CRISPR-Cas system PAM and is a 4 base motif (5' to 3') of CTTN, CCTN, CTCN, CATN, TTTG, TATG, ATTG, or GTTV (where N is any nucleotide and V is any nucleotide except T).

Clause 102. The method of clause 100, wherein the PAM is a Type I-C CRISPR-Cas system PAM and is 3-base motif (5' to 3') of GAA, GAG, GGA, or AAA.

Clause 103. The method of any one of clauses 69-102, wherein the eukaryotic cell is in a eukaryotic organism.

Clause 104. The method of clause 103, wherein the eukaryotic organism is a mammal, an insect, an amphibian, a reptile, a bird, a fish, a fungus, a plant, or a nematode.

Clause 105. The method of any one of clauses 69-104, wherein the at least one nucleic acid construct and the CRISPR array are introduced in one construct or in different constructs.

Clause 106. A modified lentiviral construct comprising a polynucleotide sequence of any one of SEQ ID NO: 42, SEQ ID NO: 43, SEQ ID NO: 44, SEQ ID NO: 45, SEQ ID NO: 46, or SEQ ID NO: 47.

APPENDIX

```
B. halodurans Cas3 (human codon optimized nucleotide sequence) (SEQ ID
NO: 14):
ATGTACATCGCACATATCCGGGAGGTTGATAAGGTGATTCAAACCTTGAAGGAGCATCTGTGTGGGGTGC
AGTGCCTGGCAGAGACCTTCGGCGCCAAGCTGCGGCTCCAGCATGTAGCGGGGCTCGCCGGGCTCCTCCA
TGACCTGGGAAAGTATACTAACGAGTTCAAGGACTATATATATAAAGCTGTCTTTGAGCCCGAGCTTGCT
GAGAAAAAGCGCGGTCAAGTTGACCATTCTACCGCCGGCGGTAGGCTTCTGTATCAAATGCTCCACGATC
GCGAAAATTCTTTCCACGAAAAGCTCCTGGCCGAGGTCGTGGGGAACGCAATTATATCTCACCACTCCAA
CCTGCAGGATTATATTTCCCCCACAATAGAGTCAAACTTCCTGACACGCGTACTCGAGAAGGAGCTGCCT
GAGTATGAGTCAGCTGTGGAAAGGTTTTTCCAAGAAGTGATGACAGAGCAGAACTTGCGCGCTATGTGG
CCAAAGCTGTGGACGAGATAAAGCAATTTACCGATAATTCTCCCACGCAGTCTTTTTTTCTCACCAAGTA
TATTTTTAGCTGCTTGATCGACGCTGATAGGACCAACACCCGGATGTTTGACGAGCAGGCAAGAGAGGAG
GAACCCACACAGCCTCAGCAGCTCTTCGAGCACTATCATCAGCAACTGCTGAATCACCTCGCTTCCCTGA
AGGAAAGTGACAGTGCTCAGAAGCCTATTAACGTGCTCCGGAGCGCCATGTCAGAGCAATGCGAATCCTT
TGCAATGCGCCCTAGTGGCATCTATACCCTGTCCATTCCCACCGGCGGCGGGAAAACATTGGCGAGTCTG
CGGTATGCCCTCAAACACGCTCAGGAGTACAACAAGCAGAGGATAATTTACATTGTCCCCTTCACCACCA
TTATTGAGCAGAATGCCCAGGAAGTTAGAAACATCCTCGGGGATGATGAGAATATTCTGGAGCACCACTC
CAACGTCGTTGAAGATAGTGAAAATGGCGATGAGCAAGAAGACGGCGTCATCACAAAGAAGGAGCGCCTC
AGACTGGCGAGAGATAACTGGGACAGACCTATCATCTTTACTACTTTGGTCCAGTTTCTGAACGTGTTTT
ATGCAAAGGGGAACAGGAACACAAGAAGGTTGCATAATCTCAGCCACTCCGTGCTGATATTCGATGAGGT
```

APPENDIX-continued

GCAGAAGGTTCCTACTAAATGTGTGTCATTGTTTAACGAGGCCCTGAACTTTCTTAAAGAGTTCGCACAT
TGCTCCATCCTCCTCTGTACGGCAACCCAGCCGACACTTGAAAACGTTAAGCACAGTCTGTTGAAGGATA
GGGATGGGGAGATAGTGCAGAATCTGACCGAGGTCTCCGAAGCCTTTAAACGCGTCGAAATCCTGGACAA
GACCGACCAGCCAATGACGAATGAGCGACTGGCAGAGTGGGTTCGAGATGAGGCACCTTCATGGGGCTCC
ACCTTGATTATCCTCAATACCAAGAAGGTCGTGAAGGATCTTTATGAGAAGCTTGAGGGAGGACCCCTGC
CCGTGTTTCACCTGTCAACTTCCATGTGTGCTGCTCATCGCAAAGACCAACTCGACGAAATACGCGCCCT
CCTGAAGGAAGGCACCCCTTTCATCTGTGTGACCACCCAGCTGATCGAGGCTGGTGTGGACGTCTCCTTT
AAATGCGTGATACGCTCTCTGGCTGGACTGGATAGCATAGCGCAGGCTGCCGGAAGATGCAATAGACATG
GCGAAGAGCAGTTGCAATATGTGTACGTGATTGACCACGCCGAAGAAACTCTGAGCAAATTGAAGGAGAT
AGAGGTGGGCCAGGAGATCGCTGGAAACGTCCTTGCACGCTTCAAAAAGAAAGCAGAAAAATATGAGGGC
AATTTGCTGTCTCAGGCTGCAATGCGAGAGTACTTCAGGTATTATTATTCCAAGATGGATGCCAACCTGA
ACTACTTTGTGAAAGAGGTGGACAAAGACATGACTAAGCTGCTCATGTCCCATGCAGTTGAAAACTCCTA
TGTAACTTATTATCAGAAGAACACCGGGACTCACTTCCCTCTTCTGTTGAATGGCAGCTACAAGACCGCC
GCTGACCACTTTAGAGTAATCGATCAGAACACCCACTTCCGCTATCGTCCCATACGGCGAGGGACAAGAC
TCATTGCACAGCTTAATAGCGGCGAGTGGGTGGACGATCTTTCTAAAGTGCTGAAAAAGGCTCAGCAGTA
TACCGTTAATCTGTATTCCCAGGAGATAGACCAGCTGAAGAAAGAGGGTGCAATCGTGATGCATCTTGAC
GGCATGGTCTACGAACTGAAAGAAAGTTGGTACTCCCACCAGTACGGGGTGGATTTCAAGGGTGAAGGGG
GGATGGATTTTATGAGTTTT

B. halodurans Cas3 (amino acid sequence) (SEQ ID NO: 15):
MYIAHIREVDKVIQTLKEHLCGVQCLAETFGAKLRLQHVAGLAGLLHDLGKYTNEFKDYIYKAVFEPELA
EKKRGQVDHSTAGGRLLYQMLHDRENSFHEKLLAEVVGNAIISHHSNLQDYISPTIESNELTRVLEKELP
EYESAVERFFQEVMTEAELARYVAKAVDEIKQFTDNSPTQSFFLTKYIFSCLIDADRTNTRMFDEQAREE
EPTQPQQLFEHYHQQLLNHLASLKESDSAQKPINVLRSAMSEQCESFAMRPSGIYTLSIPTGGGKTLASL
RYALKHAQEYNKQRIIYIVPFTTIIEQNAQEVRNILGDDENILEHHSNVVEDSENGDEQEDGVITKKERL
RLARDNWDRPIIFTTLVQFLNVFYAKGNRNTRRLHNLSHSVLIFDEVQKVPTKCVSLFNEALNFLKEFAH
CSILLCIATQPTLENVKHSLLKDRDGEIVQNLTEVSEAFKRVEILDKTDQPMTNERLAEWVRDEAPSNGS
TLIILNTKKVVKDLYEKLEGGPLPVFHLSTSMCAAHRKDQLDEIRALLKEGTPFICVTTQLIEAGVDVSF
KCVIRSLAGLDSIAQAAGRCNRHGEEQLQYVYVIDHAFETLSKLKEIEVGQETAGNVLARFKKKAEKYEG
NLLSQAAMREYFRYYYSKMDANLNYFVKEVDKDMTKLLMSHAVENSYVTYYQKNIGTHFPLLLNGSYKTA
ADHFRVIDQNTTSAIVPYGEGQDIIAQLNSGEWVDDLSKVLKKAQQYTVNLYSQEIDQLKKEGAIVMHLD
GMVYELKESWYSHQYGVDFKGEGGMDFMSF E. coli Cas3 (human codon optimized nucleotide sequence) (SEQ ID NO: 16):
ATGGAACCATTCAAGTACATTTGCCATTATTGGGGGAAGTCCTCAAAAAGTCTGACAAAGGGTAACGACA
TCCACCTGCTTATATATCACTGCCTGGACGTCGCCGCGGTAGCCGACTGTTGGTGGGACCAAAGTGTCGT
GCTTCAAAATACCTTTTGCCGAAACGAAATGTTGAGTAAGCAGCGCGTTAAAGCTTGGCTCCTTTTCTTT
ATAGCGTTGCATGACATCGGCAAGTTCGATATAAGATTCCAATACAAAAGTGCCGAGAGCTGGCTGAAGC
TCAACCCTGCTACTCCTTCTCTTAACGGGCCCTCAACACAGATGTGTCGGAAATTTAATCACGGCGCTGC
AGGGTTGTATTGGTTCAATCAGGACTCACTCAGCGAACAATCATTGGGCGATTTTTTTCTTTTTTCGAT
GCTGCTCCTCATCCATATGAATCTCGGTTTCCATGGGTAGAAGCCGTTACAGGGCATCACGGTTTTATAC
TTCATAGCCAAGATCAGGATAAATCACGGTGGGAGATGCCGGCTTCTCTTGCCAGCTATGCCGCCCAAGA
TAAGCAGGCCAGGGAAGAGTGGATTTCTGTTTTGGAAGCTTTGTTTCTGACTCCAGCCGGCCTTTCCATC
AATGACATACCCCCGATTGTTCATCACTTCTCGCAGGGTTCTGCAGTTTGGCTGATTGGTTGGGATCTT
GGACCACAACCAACACATTCTTGTTTAACGAGGACGCCCCCAGCGACATAAATGCGCTTCGAACCTATTT
CCAGGACCGCCAACAAGACGCTTCTCGGGTTCTTGAATTGTCAGGGCTCGTTAGCAACAAAAGGTGTTAC
GAAGGAGTCCATGCTCTTCTCGATAATGGATACCAGCCCCGGCAACTTCAAGTTTTGGTAGACGCCCTCC
CTGTGGCGCCTGGACTTACGGTCATAGAGGCCCCAACCGGATCTGGCAAAACCGAGACCGCATTGGCATA
TGCGTGGAAGTTGATAGATCAACAAATAGCCGACTCTGTCATTTTTGCACTAATAATCGCTTCGACACAA
AACGCCATGCTTACTAGGATGGAAGCATCTGCCTCTCACCTCTTCTCTTCCCCTAACCTTATCCTCGCGC
ATGGAAACTCCAGATTTAACCATTTGTTCCAAAGTATCAAGTCAAGGGCTATAACAGAGCAGGGACAAGA
AGAGGCATGGGTACAGTGTTGTCAGTGGCTCAGTCAGTCCAACAAGAAGGTCTTTTTGGGGCAGATTGGC
GTATGCACAATCGACCAAGTACTTATTTCTGTTCTGCCTGTCAAGCATAGATTCATTCGCGGCTTGGGAA
TAGGACGCTCCGTGCTCATAGTCGACGAAGTTCACGCTTATGATACGTATATGAACGGACTTTTGGAAGC
GGTTCTTAAGGCTCAGGCCGATGTAGGAGGCTCCGTTATTCTGTTGTCTGCAACACTCCCAATGAAACAA
AAACAAAAGTTGCTCGATACCTACGGCCTCCATACTGACCCCGTCGAAAACAATTCAGCCTACCCACTTA
TTAACTGGCGAGGTGTTAACGGAGCCCAAAGATTTGATCTCCTCGCACACCCCGAACAGCTCCCACCACG
GTTCTCCATTCAGCCGGAGCCGATATGTCTTGCGGACATGCTTCCTGATCTTACCATGCTTGAGCGGATG
ATTGCGGCGGCTAATGCTGGAGCTCAAGTATGCCTCATTTGCAATCGTGGATGTCGCACAGGTCTGCT
ATCAACGCCTGAAGGAGTTGAATAACACGCAAGTGGATATAGATCTGTTCCATGCTCGATTCACACTCAA
TGATCGACGCGAAAAAGAAAATCGGGTGATTAGTAATTTCGGAAAGAACGGCAAGCGAACAGTTGGCAGG
ATTCTCGTAGCCACCCAAGTTGTAGAACAGAGTCTGGACGTTGATTTTGATTGGCTCATAACGCAACACT
GTCCGGCAGACCTTCTGTTCCAAAGGTTGGGGAGACTCCACCGCCATCATCGGAAATACCGGCCCGCCGG
GTTCGAGATTCCTGTTGCTACCATTTTGCTCCCGGACGGGAGGGTTATGGCAGGCATGAACATATTTAC
TCAAATGTGCGGGTTATGTGGCGGACGCAACAACATATTGAAGAGCTCAACGGGCCTCTCTGTTCTTTC
CTGACGCATATAGGCAGTGGTTGGATAGTATATATGATGACGCGGAGAATGGACGAACCCGAGTGGGTTGG
AAACGGCATGGATAAATTTGAGTCCGCTGAGTGTGAGAAAAGGTTCAAGGCCAGAAAGGTATTGCAATGG
GCGGAGGAGTATTCTCTCCAGGACAATGATGAGACTATCCTCGCCGTAACGCGCGACGGAGAGATGTCAT
TGCCGCTTCTCCCGTACGTTCAAACTTCATCAGGTAAGCAACTTTTGGATGGACAAGTGTACGAGGATCT
GAGCCACGAGCAGCAGTACGAGGCGCTCGCACTCAATCGCGTGAACGATGCCCTTCACGTGGAAGCGGTCA
TTCAGTGAGGTTGTGGATGAAGACGGCCTCTTGTGGCTTGAAGGAAAGCAGAATTTGGATGGGTGGGTGT
GGCAAGGAAATAGCATCGTTATAACTTATACTGGAGACGAGGGGATGACACGCTGTGATCCCTGCGAACCC
TAAGTGA E. coli Cas3 (amino acid sequence) (SEQ ID NO: 17):
MEPFKYICHYWGKSSKSLTKGNDIHLLIYHCLDVAAVADCWWDQSVVLQNTFCRNEMLSKQRVKAWLLFF
IALHDIGKFDIRFQYKSAESWLKLNPATPSLNGPSTQMCRKFNHGAAGLYWFNQDSLSEQSLGDFFSFFD
AAPHPYESWFPWVEAVIGHHGFILHSQDQDKSRWEMPASLASYAAQDKQAREEWISVLEALFLTPAGLSI
NDIPPDCSSLLAGFCSLADWLGSWITTNTELFNEDAPSDINALRTYFQDRQQDASRVLELSGLVSNKRCY APPENDIX-continued EGVHALLDNGYQPRQLQVLVDALPVAPGLIVIEAPTGSGKTETALAYAWKLIDQQIADSVIFALPTQATA
NAMLTRMEASASHLFSSPNLILAHGNSRFNHLFQSIKSRAITEQGQEEAWVQCCQWLSQSNKKVFLGQIG
VCTIDQVLISVLPVKHRFIRGLGIGRSVLIVDEVHAYDTYMNGLLEAVLKAQADVGGSVILLSATLPMKQ
KQKLLDTYGLHTDPVENNSAYPLINWRGVNGAQRFDLLAHPEQLPPRFSIQPEPICLADMLPDLTMLERM
IAAANAGAQVCLICNLVDVAQVCYQRLKELNNTQVDIDLFHARFTLNDRREKENRVISNEGKNGKRNVGR
ILVATQVVEQSLDVDFDWLITQHCPADLLFQRLGRLHRHHRKYRPAGFEIPVATILLPDGEGYGRHEHIY
SNVRVMWRTQQHIEELNGASLFFPDAYRQWLDSIYDDAEMDEPEWVGNGMDKFESAECEKRFKARKVLQW
AEEYSLQDNDETILAVIRDGEMSLPLLPYVQTSSGKQLLDGQVYEDLSHEQQYEALALNRVNVPFTWKRS
FSEVVDEDGLLWLEGKQNLDGWVWQGNSIVITYTGDEGMTRVIPANPK*

P. aeruginosa Cas3 (bacteria codon nucleotide sequence) (SEQ ID NO: 18):
ATGAACATCCTGCTGGTGTCGCAATGCGAAAAGCGCGCCCTGAGCGAAACCCGCCGCATTCTCGACCAGT
TCGCCGAGCGCCGCGGCGAACGGACCTGGCAAACGCCCATCACTCAAGCCGGACTGGATACCCTGCGACG
CCTGCTGAAGAAAAGCGCACGGCGCAACACCGCCGTAGCCTGTCACTGGATCCGCGACCGCGACCACAGC
GAACTGCTGTGGATCGTCGGTGATGCCAGCCGCTTCAACGCCCAGGGTGCGGTGCCGACCAACAGGACCT
GCCGCGACATCCTGCGCAAGGAAGACGAGAACGACTGGCACAGCGCCGAAGACATCCGCCTGCTGACGGT
GATGGCAGCGCTGTTCCACGATATCGGCAAGGCCAGCCAGGCCTTCCAGGCCAAACTGCGGAACCGCGGC
AAACCGATGGCCGATGCCTATCGTCACGAATGGGTATCACTGCGCCTGTTCGAAGCCTTCGTTGGCCCAG
GCAGCAGCGACGAGGACTGGCTGAGGCGCCTGGCGGACAAGCGAGAGACGGGCGATGCCTGGCTGTCGCA
ACTGGCCAGGGACGACCGGCAATCCGCGCCACCCGGCCCGTTCCAGAAAAGCCGGCTACCGCCGCTCGCC
CAGGCGGTCGGCTGGTTGATCGTCAGCCATCATCGCCTGCCCAACGGGGACCATCGCGGCAGCGCCTCGC
TGGCACGCTTGCCGGCCCCCATCCAGAGCCAATGGTGCGGCGCACGCGACGCAGACGCAAAGAAAAGGC
CGCCTGCTGGCAGTTCCCCACGGCCTGCCCTTCGCCAGCGCCCATTGGCGCGCCAGGACAGCGCTATGC
GCGCAGAGCATGCTCGAGCGTCCCGGCCTGCTGGCTGGGGACCGGCCTTGTTGCATGATTCCTACGTCA
TGCATGTGTCCCGACTGATCCTGATGCTCGCGGACCACCACTATTCCAGTCTCCCTGCCGACTCCCGGCT
GGGCGACCCGAACTTCCCCTTGCACGCCAACACCGACCGGGACAGCGGCAAACTAAAGCAGCGCCTGGAC
GAACACCTGCTCGGCGTCGCCCTGCACAGTCGCAAGCTCGCCGGCACCCTGCCACGCCTGGAGCGACAAC
TACCGCGCCTTGCCCGGCACAAGGGCTTCACCCGCCGGGTCGAGCAGCCGCGCTTCCGCTGGCAGGACAA
GGCCTACGACTGCGCGATGGCCTGCCGCGAGCAGGCTATGGAGCATGGATTCTTCGGCCTCAACCTGGCG
TCGACCGGTTGCGGTAAGACCCTCGCCAACGGCCGTATCCTGTATGCGCTGGCCGATCCGCAACGGGCG
CGCGTTTCAGCATCGCTCTCGGCCTGCGCAGCTTGACCCTGCAAACCGGGCAGGCCTACCGCGAGCGGCT
CGGCCTGGGCGACGACGACCTCGCTATCCTGGTCGGCGGCAGCGCCGCCCGCGAACTGTTCGAAAAGCAG
CAGGAGCGCCTGGAGCGCAGCGGTAGCGAGTCAGCCCAGGAGCTGCTGGCGGAAAACAGCCATGTACACT
TCGCCGGCACGCTCGAGGACGGCCCTCTACGCGAGTGGCTCGGCAGGAACAGCGCGGGAAACCGCCTACT
CCAGGCGCCCATCCTGGCCTGCACCATCGACCACCTGATGCCCGCCAGCGAAAGCCTGCGCGGCGGACAC
CAGATAGCGCCACTGCTCCGCCTGATGACTTCCGACCTGGTGCTCGACGAGGTCGACGACTTCGATATCG
ACGACCTGCCCGCCCTGTCGCGGCTGGTGCACTGGGCCGGCCTGTTCGGCAGCCGCGTGCTGCTCTCCTC
CGCGACCCTGCCGCCGGCCTTGGTGCAGGGCCTGTTCGAGGCCTATCGCAGCGGCCGGGAAATCTTCCAG
CGCCATCGTGGCGCTCCCGGACGCGCTACGGAAATCCGCTGTGCCTGGTTCGACGAGTTCTCCAGCCAAT
CCAGCGCCCACGGCGCCGTAACCTCCTTCAGCGAAGCGCATGCGACCTTCGTCGCCCAGCGTCTGGCGAA
GCTCGAGCAACTGCCGCCACGTCGCCAGGCGCAGCTATGCACCGTGCATGCCGCTGGCGAGGCCCGTCCC
GCGCTGTGCCGCGAGTTGGCCGGGCAGATGAATACCTGGATGGCTGACCTGCATCGCTGCCATCACACCG
AACACCAAGGACGTCGCATCAGTTTCGGCCTGCTACGGCTGGCCAACATCGAACCCCTGATCGAACTGGC
CCAGGCCATCCTGCCCAGGGTGCGCCCGAGGGGTTGCATGTCCATCTGTGTGTCTACCATTCGCGGCAT
CCCCTTCTGGTCCGCTCGGCCATCGAGCGACAACTCGATGAACTGCTGAAGCGTTCGGACGACGACGCCG
CCGCGCTGTTCGCTCGTCCGACGCTGGCCAAGGCGCTCCAGGCCAGCACGGAGCGGGATCATCTGTTCGT
CGTACTCGCCTCGCCGGTGGCGGAGGTCGGTCGCGACCACGATTACGACTGGGCCATCGTCGAACCCTCC
TCCATGCGCTCGATCATCCAGTTGGCCGGGCGAATCCGCCGCCATCGCTCCGGCTTCAGCGGCGAGGCCA
ACCTATACCTGCTATCGCGCAATATCCGCTCGCTGGAAGGGCAGAATCCGGCGTTCCAGCGGCCCGGCTT
CGAGACCCCCGACTTCCCTCTTGACAGCCACGACCTGCACGACCTGCTCGACCCCGCCCTACTCGCCGC
ATCGACGCCAGCCCACGAATCGTCGAACCGTTCCCACTGTTCCCACGCAGCCGGTTGGTCGACCTGGAAC
ACCGACGCCTGCGCGCGCTGATGCTTGCCGACGACCCACCGTCGTCCCTGCTCGGCGTACCGCTCTGGTG
GCAAACCCCGGCATCGCTCAGCGGCGCCCTGCAAACCAGCCAACCATTTCGCGCAGGCGCCAAGGAGCGA
TGCTACGCCCTGCTGCCGGACGAGGACGACGAGGAGCGCTTGCATTTCAGCCGCTACGAAGAAGGGACCT
GGAGCAACCAGGACAACCTGTTGCGCAACCTCGACCTCACCTATGGCCCGGCCATCCAGACATGGGGCAC
GGTCAACTATCGGGAGGAGCTAGTCGCAATGGCCGGCCGCGAGGACCTCGACCTGCGCTGCAATGCGCCATG
CGCTACGGCGAGGTGAGATTGCGAGAAAACACCCAGGGATGGAGCTACCACCCTTATTTGGGGTTCAAGA
AATACAACTGA P. aeruginosa Cas3 (amino acid sequence) (SEQ ID NO: 19):
MNILLVSQCEKRALSETRRILDQFAERRGERTWQTPITQAGLDTLRRLLKKSARRNTAVACHWIRGRDHS
ELLWIVGDASRFNAQGAVPTNRTCRDILRKEDENDWHSAEDIRLLTVMAALFHDIGKASQAFQAKLRNRG
KPMADAYRHEWVSLRLFEAFVGPGSSDEDWLRRLADKRETGDAWLSQLARDDRQSAPPGPFQKSRLPPLA
QAVGWLIVSHHRLPNGDHRGSASLARLPAPIQSQWCGARDADAKEKAACWQFPHGLPFASAHWRARTALC
AQSMLERPGLLARGPALLHDSYVMHVSRLILMLADHHYSSLPADSRLGDPNFPLHANTDRDSGKLKQRLD
EHLLGVALHSRKLAGTLPRLERQLPRLARHKGFTRRVEQPRFRWQDKAYDCAMACREQAMEHGFFGLNLA
STGCGKTLANGRILYALADPQRGARFSIALGLRSLTLQTGQAYRERLGLGDDDLAILVGGSAARELFEKQ
QERLERSGSESAQELLAENSHVHFAGTLEDGPLREWLGRNSAGNRLLQAPILACTIDHLMPASESLRGGH
QIAPLLRLMTSDLVLDEVDDFDIDDLPALSRLVHWAGLEGSRVLLSSATLPPALVQGLFEAYRSGREIFQ
RHRGAPGRATEIRCAWFDEFSSQSSAHGAVTSFSEAHATEVAQRLAKLEQLPPRRQAQLCTVHAAGEARP
ALCRELAGQMNTWMADLHRCHHTEHQGRRISFGLLRLANIEPLIELAQAILAQGAPEGLHVHLCVYHSRH
PLLVRSAIERQLDELLKRSDDDAAALFARPTLAKALQASTERDHLFVVLASPVAEVGRDHDYDWAIVEPS
SMRSIIQLAGRIRRHRSGFSGEANLYLLSRNIRSLEGQNPAFQRPGFETPDFPLDSHDLHDLLDPALLAR
IDASPRIVEPFPLFPRSRLVDLEHRRLRALMLADDPPSSLLGVPLWWQTPASLSGALQTSQPFRAGAKER
CYALLPDFDDEERLHFSRYEEGTWSNQDNLLRNLDLTYGPRIQTWGTVNYREELVAMAGREDLDLRQCAM
RYGEVRLRENTQGWSYHPYLGFKKYN*

APPENDIX-continued

Type I-C Cas5d (human codon optimized cascade sequences) (SEQ ID NO: 20)
ATGGCCCGAAATGAGGTGCAGTTTGAACTTTTCGGCGATTACGCCCTCTTCACGGACCCACTGACCAAAA
TTGGCGGAGAGAAGCTGAGCTATTCAGTGCCTACGTACCAGGCACTGAAAGGCATCGCCGAATCAATTTA
TTGGAAACCAACCATTGTCTTCGTGATCGATGAACTGCGGGTGATGAAGCCAATCCAAATGGAGTCCAAG
GGGGTGCGGCCAATTGAATACGGAGGCGGCAATACATTGGCTCACTACACCTACCTGAAAGATGTCCACT
ATCAAGTCAAAGCGCATTTTGAGTTTAATCTCCACCGCCCCGACTTGGCCTTCGATAGAAATGAGGGGAA
GCATTACTCCATTCTTCAGAGATCACTGAAAGCGGGGGGAAGGAGGGACATCTTCCTGGGAGCACGGGAG
TGCCAGGGCTACGTGGCCCCATGTGAATTTGGTTCCGGAGACGGCTTTTATGACGGACAAGGAAAGTATC
ATCTTGGCACCATGGTGCACGGCTTCAACTACCCCGATGAAACTGGCCAGCATCAGTTGGACGTGCGGCT
GTGGTCAGCTGTGATGGAAAACGGGTATATTCAGTTCCCAAGACCAGAGGACTGCCCTATCGTCAGGCCC
GTCAAAGAAATGGAACCAAAGATTTTCAACCCAGATAATGTGCAGTCCGCAGAACAACTCCTCCATGACC
TCGGAGGCGAG Type I-C Case (human codon optimized cascade sequences) (SEQ ID NO: 21 )
ATGGCCAGTTGGCTCCTTCACCTGTACGAGACTTACGAAGCCAATCTGGATCAGGTGGGTAAAACCGTCA
AAAAGGGAGAGGATCGGGAATACACTCTGCTTCCAATCTCCCACACCACTCAGAACGCTCACATTGAAGT
GACCCTGGACGAGGACGGAGATTTTCTCAGGGCTAAAGCACTGACCAAAGAGTCTACCCTGATTCCCTGT
ACTGAGGAAGCTGCGAGTAGATCCGGATCCAAGGTGGCACCCTACCCCCTCCACGATAAGCTGTCTTACG
TTGCCGGCGACTTTGTCAAGTACGGAGGTAAGATAAAGAACCAGGACGATGCACCGTTTGACACTTACAT
CAAGAACCTTGGCGAATGGGCCAATAGTCCCTATGCGACTGAGAAGGTGAAGTGCATTTACACTTACCTC
AAGAAGGGACGGCTGATTGAGGACTTGGTGGACGCTGGGGTCCTTAAGTTGGACGAGAATCAGCAGCTTA
TAGAGAAGTGGGAGAAAAGGTACGAGGAGCTGCTGGGAGAAAAAGCCCGCAATTTTTAGCAGCGGGGCAAC
CGATCAGGCTTCCGCATTCGTGAGATTCAATGTCTTCCACCCCGAAAGTATTGATGACGTGTGGAAAGAC
AAAGAAATGTTTGACAGCTTTATCAGCTTTTATAATGATAAGCTCGGTGAGGAAGACATTTGCTTCGTCA
CCGGTAATCGACTCCCGAGCACCGAACGGCATGCTAATAAAATACGGCATGCAGCAGACAAGGCCAAGCT
GATCTCCGCAAACGATAACTCAGGCTTTACCTTCCGGGGTCGGTTCAAAACAAGTAGGGAAGCTGTCGGC
ATCAGTTACGAGGTTTCCCAAAAGGCTCATAATGCTCTGAAGTGGCTGATTCATAGGCAGAGCAAATCAA
TCGATGACCGGGTGTTCCTTGTCTGGAGCAATGATAATTCACTTGTGCCCAACCCAGACGAGGACGCCGT
TGACATTATGAAACACGCAAACCGAGAGCTGGAACGCGACCCTGATACCGGTCAGATTTCGCCGGCGAG
GTGAAGAAAGCCATCGGGGGATACCGAAGCGATTTGAACTACCAACCCGAGGTCCATATTCTTGTTCTTG
ATTCTGCAACAACTGGCCGGATGGCCGTGCTGTACTATAGAAGCCTGAATAAGGAACTGTATCTGAACAG
ACTGGAGGCCTGGCACGATTCTTGCGCCTGGGAACACCGGTACAGGCGCGATGAGAAAGAGTTCATTAGC
TTTTTATGGGCACCGGCCACGAAGGACATTGCCTTTGCAGCTTACGGGCAAGAGCTTCCGAAAAAGTGA
TCAAAGACCTTATGGAACGGATGCTTCCTTGCATCGTGGACGGACGCCGAGTCCCAAAAGACATAGTACG
GAGTGCTTTTCAGAGAGCGTCCAACCCAGTGTCTATGGAACGCTGGGAGTGGGAGAAAACTCTGAGCATT
ACTTGTGCCCTGATTCGGAAAATGCATATCGAACAAAAAGAAGAATGGGGGGTGCCCCTGGACAAATCCT
CAACCGATCGATCTTATCTTTTTGGGCGCCTCCTTGCCGTTGCTGACGTCCTGGAAAGGGGCGCCCTGGG
AAAGGACGAAACTCGGGCCACAAACGCTATTCGGTATATGAATAGCTACAGCAAAAACCCCGGAAGAACC
TGGAAAACAATACAGGAGTCATTGCAGCCCTACCAGGCTAAGCTGGGAACAAAAGCCACATACCCTGTCAA
AGCTTGTGGATGAGATTGGCGACCAGTTTGAGCCTGGTGACTTTAATAACAATCCATTGACTGAGCAGTA
TCTCTTGGGTTTTTACAGCCAGCGGCGGGAACTTTACGAGGAGGAGACAAATCAG Type I-C Cas7 (human codon optimized cascade sequences) (SEQ ID NO: 22)
ATGGCCACCATTCTTGATCACAAAATTGATTTCGCCGTTATTCTGAGCGTCACTAAGGCGAACCCAAATG
GTGACCCACTCAATGGCAACAGGCCGCGCCAGAATTATGATGGGCATGGCGAAATTTCTGACGTCGCCAT
AAAACGCAAGATCCGCAACCGCCTGCTCGACATGGAAGAGCCCATTTTTGTCCAGTCTGACGACCGCAAA
GCAGACTCTTTTAAGTCACTGCGGGACCGCGCTGATTCTAACCCCGAACTGGCAAAAATGCTGAAGGCCA
AAAATGCTAGTGTGGACGAATTTGCCAAAATAGCTTGCCAGGAATGGATGGACGTGAGGAGTTTCGGGCA
GGTGTTTGCGTTCAAAGGCTCAAATCTGTCAGTCGGCGTACGGGCCCAGTTAGCATTCACACTGCGACCC
TCTATCGATCCTATTGACATAGTGAGCACGCAGATCACTAAGAGTGTGAATAGTGTAACCGGGGACAAGA
GAAGTTCCGACACAATGGGTATGAAGCACCGGGTTGACTTCGGCGTCTATGTTTTCAAAGGGAGCATCAA
TACGCAGCTCGCAGAGAAGACTGGCTTCACAAACGAGGACGCCGAAAAAATCAAGCGGGCCCTGATTACT
CTGTTCGAAAATGATAGCTCTTCAGCCCGACCCGATGGGTCAATGGAGGTGCACAAAGTTTACTGGTGGG
AACACTCCAGCAAGCTTGGACAGTATAGTTCTGCTAAGGTGCACCGCAGCCTGAAATCGAATCTAAGAC
CGACACGCCTAAGAGCTTCGACGATTACGCTGTCAACTGTATGAACTGGACGGCCTCGGCGTGGAAGTG
ATCGACGGACAG Type I-E CasA (human codon optimized cascade sequences) (SEQ ID NO: 23)
ATGGCCAATCTCCTGATTGACAATTGGATCCCTGTGAGACCGAGGAACGGAGGGAAGGTTCAGATCATCA
ACCTGCAAAGTCTCTACTGTAGCAGAGATCAATGGCGACTCTCATTGCCCAGGGATGATATGGAATTGGC
GGCACTTGCACTCTTGGTATGTATTGGGCAGATCATCGCCCCTGCCAAGGATGATGTCGAGTTTAGGCAC
AGAATAATGAACCCTCTTACTGAAGATGAATTCCAGCAATTGATCGCCCTTGGATAGAATATGTTCTATT
TGAATCACGCCGAACATCCCTTCATGCAGACAAAAGGGGTTAAAGCAAATGATGTCACACCAATGGAGAA
GCTTTTGGCAGGTGTGTCAGGAGCAACCAACTGCGCTTTCGTTAACCAACCAGGCCAAGGTGAGGCGTTG
TGCGGGGGGTGCACGGCCATAGCGTTGTTTAATCAGGCGAACCAGGCTCCTGGCTTTGGAGGAGGATTCA
AGTCCGGTTTGCGCGGGGGTACACCCGTAACCACATTCGTTGCGGAATTGACCTCCGATCAACAGTCCCT
GTTGAACGTATTGACGTTGCCTAGACTTCAGAAGCAATTTCCAAACGAGTCTCACACTGAGAATCAACCG
ACTTGGATTAAGCCCATCAAGTCAAATGAAAGTATACCCGCGTCTTCTATTGGATTTGTTAGAGGACTTT
TTTGGCAGCCCGCTCACATAGAACTCTGTGATCCCATAGGCATTGGAAAGTGTTCTTGCTGTGGCCAAGA
GTCTAACCTTAGATATACGGGCTTTCTCAAGGAGAAGTTCACGTTCACCGTGAATGGACTTTGGCCACAT
CCCCATAGCCCGTGCTTGGTCACGGTCAAGAAGGGGGAGGTTGAAGAGAAATTTCTTGCGTTTTACACCAT
CCGCCCCATCCTGGACGCAAATATCTCGCGTCGTTGTGGATAAAATCATCCAGAACGAAAATGGTAACCG
CGTTGCCGCGGTAGTGAATCAATTCAGAAACATAGCACCACAGAGCCCGTTGGAGTTGGATAATGGGCGGG
TACCGCAATAATCAAGCTTCCATTCTCGAGCGACGCCATGACGTACTTATGTTTAACCAGGGGTGGCAGC
AATATGGTAACGTGATAAACGAGATAGTCACAGTCGGCCTCGGCTACAAAACTGCGTTGCGCAAAGCTCT APPENDIX-continued

```
GTATACGTTCGCGGAGGGTTTTAAGAATAAAGACTTTAAAGGCGCTGGGGTGAGTGTGCACGAGACGGCA
GAACGCCATTTCTATCGCCAGTCTGAACTCTTGATTCCCGACGTTCTGGCGAATGTCAATTTTTCCCAGG
CCGATGAGGTCATTGCGGATCTGCGAGATAAGCTTCACCAGTTGTGTGAGATGCTGTTCAACCAGTCTGT
GGCTCCTTATGCTCATCATCCCAAACTGATTTCAACTCTCGCTTTGGCAAGGGCTACGTTGTATAAACAC
CTTAGAGAACTGAAGCCACAGGGTGGTCCCAGCAATGGCTGA
```

Type I-E CasB (human codon optimized cascade sequences) (SEQ ID NO: 24)
```
ATGGCCGATGAAATAGACGCAATGGCTCTTTACCGAGCATGGCAACAGCTCGACAATGGATCTTGCGCCC
AAATACGGCGGGTAAGTGAACCCGATGAACTGCGAGATATCCCCGCATTCTACCGATTGGTTCAGCCGTT
TGGCTGGGAGAACCCACGGCACCAGCAGGCGCTTCTTAGGATGGTTTTTTGTCTTAGTGCCGGGAAAAAC
GTAATCCGCCATCAGGATAAGAAGTCCGAACAAACAACAGGGATTTCTCTGGGAAGAGCGCTTGCTAACA
GCGGCAGGATCAATGAACGCCGCATATTTCAGTTGATCCGAGCAGATCGGACTGCTGATATGGTCCAGCT
CAGGAGGCTCCTTACGCACGCAGAGCCAGTGTTGGATTGGCCACTCATGGCAAGAATGCTTACGTGGTGG
GGGAAGAGGGAAAGGCAGCAACTGCTTGAAGATTTTGTATTGACGACGAACAAAAACGCGTAA
```

Type I-E CasC (human codon optimized cascade sequences) (SEQ ID NO: 25)
```
ATGTCAAACTTCATTAATATCCACGTGCTTATCTCACACTCCCCTAGTTGCCTTAACAGAGACGATATGA
ACATGCAAAAGACGCAATTTTTGGCGGCAAAAGGAGAGTCAGAATTAGTAGCCAGAGCCTGAAGCGCGC
TATGAGGAAAAGCGGCTACTATGCTCAAACATTGGTGAAAGTTCAGTTGCGGACCATCCATCTCGCGCAG
TTGAGGGACGTCCTGCGACAGAAGCTTGGGGAAAGATTTGATCAGAAGATCATCGACAAAACGCTTGCCC
TTCTGTCCGGTAAATCAGTGGACGAAGCGGAGAAGATAAGTGCGGATGCTGTTACGCCATGGGTGGTAGG
TGAAATCGCGTGGTTTTGCGAGCAGGTAGCCAAGGCCGAAGCGGATAATTTGGATGATAAGAAACTGCTC
AAAGTCCTCAAAGAGGACATCGCGGCGATCCGGGTGAACCTTCAGCAGGGTGTTGATATTGCGCTCTCTG
GTCGGATGGCCACGTCTGGAATGATGACTGAACTGGGTAAGGTGGACGGAGCTATGTCTATAGCTCATGC
TATAACTACCCATCAGGTGGATTCTGACATAGACTGGTTCACGGCTGTCGACGATCTCCAGGAACAAGGA
TCCGCACACCTCGGCACGCAAGAATTTTCTTCTGGAGTGTTCTATAGGTATGCCAACATCAACCTTGCAC
AGCTCCAGGAAAACCTCGGTGGGGCAAGCCGGGAACAGGCTCTTGAAATAGCTACCCATGTGGTTCACAT
GCTGGCGACCGAAGTGCCAGGGGCCAAGCAGAGAACGTACGCCGCATTCAATCCGGCGGACATGGTCATG
GTGAATTTCTCTGATATGCCCTTGTCTATGGCAAATGCTTTCGAGAAGGCGGTCAAGGCAAAGGACGGTT
TTTTGCAACCCTCCATCCAAGCCTTTAATCAGTACTGGGATAGAGTAGCTAACGGGTATGGTCTCAATGG
CGCGGCTGCTCAGTTTTCTTTGTCCGATGTGGATCCGATAACGGCGCAGGTTAAACAGATGCCCACCTTG
GAACAACTCAAATCCTGGGTTAGAAACAATGGGGAGGCGTGA
```

Type I-E CasD (human codon optimized cascade sequences) (SEQ ID NO: 26)
```
ATGCGATCATACTTGATCCTGCGGCTTGCAGGTCCTATGCAAGCCTGGGGGCAACCTACCTTTGAAGGTA
CTCGGCCGACTGGCAGGTTCCCTACGCGGTCTGGTTTGCTCGGACTCCTCGGCGCCTGTTTGGGGATACA
AAGGGGATGACACTTCTTCCTTGCAGGCACTTTCCGAATCAGTCCAGTTCGCAGTGAGATGTGATGAACTC
ATACTGGACGACAGACGGGTGTCCGTAACTGGACTGAGGGACTATCATACTGTACTCGGCGCAAGAGAAG
ATTATCGAGGTCTTAAGTCACATGAGACTATTCAGACATGGAGGGAATATTTGTGACGCCTCCTTCAC
GGTGGCCCCTCTGGCTTACACCACATGCAACTATGGTGATCTCAGAGCTTGAGAAAGCCGTTCTTAAACCT
CGGTACACACCCATATCTGGGGAGGCGGTCTTGCCCACTTACCCACCCGCTTTTCTTGGGGACTTGTCAGG
CCAGCCGATCCACAGAAGGCCTTGCTGAACTATGAACCCGTTGGTGGCGATATATACAGTGAAGAGAGCGT
CACGGGCCATCACTTGAAGTTCACTGCTAGGGATGAGCCGATGATTACGCTCCCGAGACAGTTCGCTAGT
AGGGAATGGTACGTTATTAAGGGGGGAATGGACGTTTCCCAATGA
```

Type I-E CasE (SEQ ID NO: 27)
```
ATGTATCTCAGTAAAGTCATCATTGCCAGGGCCTGGAGCAGGGATCTTTACCAACTTCACCAGGGATTAT
GGCATTTATTTCCAAACAGACCGGATGCTGCTCGTGATTTTCTTTTTCATGTTGAGAAGCGAAACACACC
AGAAGGCTGTCATGTTTTATTGCAGTCAGCGCAAATGCCTGTTTCAACTGCCGTTGCGACAGTCATTAAA
ACTAAACAGGTTGAATTTCAACTTCAGGTTGGTGTTCCACTCTATTTTCGGCTTCGGGCAAATCCGATCA
AAACTATTCTCGACAATCAAAAGCGCCTGGACAGTAAAGGGAATATTAAACGCTGTCGGGTTCCGTTAAT
AAAAGAAGCAGAACAAATCGCGTGGTTGCAACGTAAATTGGGCAATGCGGCGCGCGTTGAAGATGTGCAT
CCCATATCGGAACGGCCACAGTATTTTTCTGGTGATGGTAAAAGTGGAAAGATCCAAACGGTTTGCTTTG
AAGGTGTGCTCACCATCAACGACGCGCCAGCGTTAATAGATCTTGTACAGCAAGGTATTGGGCCAGCTAA
ATCGATGGGATGTGGCTTGCTATCTTTGGCTCCACTGTGA
```

Type I-F Csy1 (human codon optimized cascade sequences) (SEQ ID NO: 28)
```
ATGACATCTCCATTGCCGACGCCTACCTGGCAGGAACTTAGACAATTTATCGAGAGTTTCATCCAGGAGC
GCCTCCAGGGGAAGCTGGACAAGTTGCAACCTGATGAGGACGATAAACGGCAAACTCTGTTGGCTACACA
CAGGCGAGAAGCGTGGCTTGCAGACGCGGCCCGAAGGGTCGGCCAACTCCAACTGGTTACCCACACCCTT
AAACCCATCCACCCCGACGCCGGGGCAGTAATCTGCACTCCCTCCCGCAAGCCCCTGGTCAACCCGGGT
TGGCTGGTTCCCACGAGCTTGGAGACAGACTGGTATCAGACGTTGTCGGAATGCAGCAGCTCTCGATGT
TTTTAAATTCCTGTCACTTCAGTATCAAGGAAAGAATCTCCATGCTTCACAGAAGACTCCGCTGAA
GCGCTGCAAGCGCTTAGCGATAACGCTGAGCAGGCTCGGGAGTGGCGCCAGGCATTCATCGGAATAACTA
CCGTCAAGGGGCCCCGGCAAGTCACTCTCTTGCTAAACAACTGTACTTTCCCCTGCCCGGGAGTGGTTA
CCATTTGTTGGCACCTCTGTTCCCTACCTCTCTTGTCCACCATGTCCACGCATTGCTGCGAGAAGCACGC
TTTGGCGACGCCGCCAAGGCAGCCAGGGAAGCTCGCTCTAGACAGGAGAGCTGGCCTCACGGGTTCTCAG
AGTACCCAAATTTGGCGATACAAAAATTCGGTGGTACAAAGCCGCAGAACATTTCCCAGCTTAATAATGA
AAGGCGGGGCGAGAATTGGCTCCTGCCATCCCTGCCGCTAATTGGCAGCGCCAAAATGTCAATGCCCCA
ATGAGACATTCCTCAGTGTTTGAACATGACTTTGGAAGAACGCCAGAGGTTAGTCGCCTCACCAGAACCC
TTCAACGGTTCCTTGCCAAGACAGTCCACAATAATCTTGCGATACGCCAGCGAAGGGCTCAGTTGGTGGC
GCAGATATGCGATGAAGCGCTTCAGTACGCCGCCCGCCTGCGAGAATTGGAACCGGATGGTCCGCCACT
CCTGGTTGCCAACTCCATGATGCAGAGCAGTTGTGGCTTGATCCCTTGCGCGCCCAGACAGATGAAACCT
TCCTGCAGCGCCGGCTCCGGGGTGATTGGCCTGCGGAAGTTGGCAACGCTTTGCTAACTGGTTGAATAG
AGCGGTTTCTTCAGACAGCCAAATACTTGGTTCACCTGAGGCCGCCCAGTGGTCCCAGGAGTTGAGTAAG
GAGCTGACGATGTTAAGGAGATACTTGAGGACGAAAGAGACTGA
```

APPENDIX-continued

Type I-F Csy2 (human codon optimized cascade sequences) (SEQ ID NO: 29)
ATGAGTGTCACAGACCCTGAAGCCTTGTTGCTTCTCCCCCGACTGAGTATCCAAATGCGAACGCTATAT
CTAGCCCTCTCACTTGGGGATTTCCCTCACCAGGGGCTTTTACTGGATTCGTACATGCGTTGCAGAGAAG
GGTCGGCATATCACTTGACATAGAGTTGGATGGTGTCGGCATCGTATGTCACCGATTTGAAGCACAGATA
AGCCAGCCTGCTGGTAAACGGACAAAGGTATTTAACTTGACACGCAATCCACTTAACAGAGATGGTTCCA
CCGCCGCGATCGTTGAAGAGGGGCGAGCCCACCTTGAGGTTAGTCTTTTGCTCGGAGTCCATGGCGATGG
ACTCGATGACCATCCGGCCCAGGAGATCGCCAGGCAGGTGCAAGAACAAGCGGGAGCCATGAGGTTGGCT
GGAGGTAGCATACTTCCCTGGTGTAATGAGCGGTTTCCCGCACCAAATGCAGAGCTGCTTATGCTCGGGG
GGAGCGACGAACAGAGAAGAAAGAATCAAAGGCGCCTGACTCGGAGGCTGTTGCCTGGATTTGCTCTTGT
TAGCAGGGAGGCTTTGCTCCAACAGCACCTGGAGACTCTCCGGACCACTCTTCCCGAAGCGACGACGCTC
GACGCTCTTCTGGACCTTTGTCGAATCAACTTTGAACCCCCAGCGACATCAAGTGAGGAAGAGGCTAGTC
CCCCAGATGCAGCATGGCAAGTACGAGACAAACCAGGCTGGCTCGTTCCTATCCCCGCCGGATATAATGC
GCTGAGCCCGCTTTATCTTCCCGGAGAAGTTCGCAACGCAAGAGACAGAGAGACACCGTTGAGGTTCGTA
GAGAACCTCTTTGGGCTTGGCGAATGGCTTTCTCCACATCGAGTAGCGGCCCTGTCTGATCTCCTGTGGT
ATCACCATGCCGAACCGGATAAGGGGCTTTACCGGTGGTCAACGCCTCGGTTTGTAGAGCACGCCATTGC
ATGA Type I-F Csy3 (human codon optimized cascade sequences) (SEQ ID NO: 30)
ATGAGCAAACCGATATTGAGCACAGCGTCTGTACTTGCCTTTGAACGAAAATTGGACCCCTCAGACGCCT
TGATGTCTGCCGGCGCCTGGGCACAACGAGACGCGTCCCAGGAGTGGCCTGCGGTGACTGTACGGGAGAA
GAGCGTGAGAGGGACTATCTCTAACCGGCTGAAGACCAAAGATAGAGACCCTGCCAAGCTGGATGCGTCT
ATTCAAAGCCCAAACTTGCAAACCGTGGACGTGGCCAATCTTCCGAGCGACGCTGATACACTGAAGGTAA
GATTTACGCTTAGGGTACTCGGCGGTGCTGGGACTCCGTCTGCATGCAATGATGCGGCGTATAGGGACAA
GCTGTTGCAGACTGTTGCAACATACGTCAATGATCAAGGCTTTGCAGAGCTTGCTAGGCGCTACGCTCAT
AATCTTGCCAACGCAAGGTTCCTGTGGAGGAATCGGGTTGGTGCAGAGGCCGTGGAGGTGAGAATTAATC
ACATAAGACAAGGCGAGGTGGCACGCGCGTGGCGGTTTGATGCTTTGGCCATCGGGCTGCGGGACTTCAA
AGCAGACGCCGAGTTGGACGCCCTTGCCGAGCTGATTGCATCTGGCCTTTCAGGGAGCGGGCATGTGCTT
CTTGAAGTCGTGGCCTTCGCTAGGATAGGAGACGGCCAAGAGGTATTTCATCACAAGAGTTGATTCTTG
ATAAGGGTGATAAAAAAGGACAAAAGTCCAAGACCCTCTACTCAGTGCGGGATGCGGCTGCGATTCACTC
CCAGAAAATAGGGAAACGCCTTGAGAACCATAGACACTTGGTATCCAGCAGCGCCGACGACTTGGACCCATT
GCAGTAGAACCTTATGGTTCCGTAACTAGCCAAGGAAAAGCCTATCGGCAGCCAAAGCAGAAACTTGACT
TTTATACCCTCCTTGACAACTGGGTTCTCCGGGATGAGGCACCGGCGGTCGAACAGCAACATTACGTCAT
CGCTAATCTCATCAGAGGCGGCGTGTTTGGTGAAGCTGAAGAGAAATGA Type I-F Csy4 (human codon optimized cascade sequences) (SEQ ID NO: 31)
ATGGACCACTACTTGGACATACGCCTGAGACCTGATCCAGAGTTTCCACCAGCCCAACTGATGTCCGTAT
TGTTCGGAAAGCTGCATCAGGCACTTGTGGCCCAGGGTGGAGATCGAATTGGCGTATCCTTTCCTGATTT
GGACGAATCACGCTCCCGACTTGGCGAGAGACTCCGAATCCATGCCGACGCCGACGACTTGCGGGCGTTG
CTCGCCAGGCCCTGGCTGGAGGGACTGAGGGATCACCTTCAATTTGGAGAACCTGCCGTCGTACCGCATC
CAACTCCCTATAGACAGGTCTCCAGAGTCCAGGCTAAAAGCAATCCAGAAAGATTGAGGCGCCGGTTGAT
GAGGCGGCACGACCTCTCCGAAGAAGAAGCACGCAAAAGAATCCCGGACACGGTGGCAAGAGCATTGGAT
CTGCCTTTTGTCACACTGCGGAGTCAGAGCACGGGGCAACACTTCCGACTTTTTATTCGCCACGGACCCT
TGCAGGTGACAGCAGAAGAAGGAGGGTTTACTTGTTATGGGCTTTCCAAAGGTGGGTTTGTTCCCTGGTT
CTGA KRAB-CasA (nucleotide) (SEQ ID NO: 32):
ATGGATTACAAGGACCATGACGGAGATTATAAGGACCACGACATAGACTATAAGGATGACGATGACAAAA
TGGCAGATGCTAAGTCACTGACTGCCTGGTCCCGGACACTGGTGACCTTCAAGGATGTGTTTGTGGACTT
CACCAGGGAGGAGTGGAAGCTGCTGGACACTGCTCAGCAGATCCTGTACAGAAATGTGATGCTGGAGAAC
TATAAGAACCTGGTTTCCTTGGGTTATCAGCTTACTAAGCCAGATGTGATCCTCCGGTTGGAGAAGGGAG
AAGAGCCCTGGCTGGTGGAGAGAGAAATTCACCAAGAGACCCATCCTGATTCAGAGACTGCATTTGAAAT
CAAATCATCAGTTCCGAAAAAGAAACGCAAAGTTGGATCCCCAAAGAAGAAACGCAAAGTGCGGGGCATG
GCCAATCTCCTGATTGACAATTGGATCCCTGTGAGACCAGGAACGGAGGGAAGGTTCAGATCATCAACC
TGCAAAGTCTCTACTGTAGCAGAGATCAATGGCGACTCTCATTGCCCAGGGATGATATGGAATTGGCGGC
ACTTGCACTCTTGGTATGTATTGGCAGATCATCGCCCCTGCCAAGGATGATGTCGAGTTTAGGCACAGA
ATAATGAACCCTCTTACTGAAGATGAATTCCAGCAATTGATCGCGCCTTGGATAGATATGTTCTATTTGA
ATCACGCCGAACATCCCOPTCATGCAGACAAAAGGGGTTAAAGCAAATGATGTCACACCAATGGAGAAGCT
TTTGGCAGGTGTGTCAGGAGCAACCAACTGCGCTTTCGTTAACCAACCAGGCCAAGGTGAGGCGTTGTGC
GGGGGGTGCACGGCCATAGCGTTGTTTAATCAGGCGAACCAGGCTCCTGGCTTTGGAGGAGGATTCAAGT
CCGGTTTGCGCGGGGGTACACCCGTAACCACATTCGTTCGCGGAATTGACCTCCGATCAACAGTCCTGTT
GAACGTATTGACGTTGCCTAGACTTCAGAAGCAATTTCCAAACGAGTCTCACACTGAGAATCAACCGACT
TGGATTAAGCCCATCAAGTCAAATGAAAGTATACCCGCGTCTTCTATTGGATTTGTTAGAGGACTTTTTT
GGCAGCCCGCTCACATAGAACTCTGTGATCCCATAGGCATTGGAAAGTGTTCTTGCTGTGGCCAAGAGTC
TAACCTTAGATATACGGGCTTTCTCAAGGAGAAGTTCACGTTCACCGTGAATGGACTTTGGCCACATCCC
CATAGCCCGTGCTTGGTCACGGTCAAGAAGGGGAGGTTGAAGAGAAATTTCTTGCGTTTACCACATCCG
CCCCATCCTGGACGCAAATATCTCGCGTCGTTGTGGATAAAATCATCCAGAACGAAAATGGTAACCGCGT
TGCCGCGGTAGTGAATCAATTCAGAAACATAGCACCACAGAGCCCGTTGGAGTTGATAATGGGCGGGTAC
CGCAATAATCAAGCTTCCATTCTCGAGCGACGCCATGACGTACTTATGTTTAACCAGGGGTGGCAGCAAT
ATGGTAACGTGATAAACGAGATAGTCACAGTCGGCCTCGGCTACAAAACTGCGTTGCGCAAAGCTCTGTA
TACGTTCGCGGAGGGTTTTAAGAATAAAGACTTTAAAGGCGCTGGGGTGAGTGTGCACGAGACGGCAGAA
CGCCATTTCTATCGCCAGTCTGAACTCTTGATTCCCGACGTTCTGGCGAATGTCAATTTTTCCCAGGCCG
ATGAGGTCATTGCGGATCTGCGAGATAAGCTTCACCAGTTGTGTGAGATGCTGTTCAACCAGTCTGTGGC
TCCTTATGCTCATCATCCCAAACTGATTTCAACTCTCGCTTTGGCAAGGGCTACGTTGTATAAACACCTT
AGAGAACTGAAGCCACAGGGTGGTCCCAGCAATGGCTGA APPENDIX-continued KRAB-CasA (amino acid) (SEQ ID NO: 33):
MDYKDHDGDYKDHDIDYKDDDDKMADAKSLTAWSRTLVTEKDVFVDFTREEWKLLDTAQQILYRNVMLEN
YKNLVSLGYQLTKPDVILRLEKGEEPWLVEREIHQETHPDSETAFEIKSSVPKKKRKVGSPEKKRKVRGM
ANLLIDNWIPVRPRNGGKVQIINLQSLYCSRDQWRLSLPRDDMELAALALLVCIGQIIAPAKDDVEFRHR
IMNPLTEDEFQQLIAPWIDMFYLNHAEHPFMQTKGVKANDVTPMEKLLAGVSGATNCAFVNQPGGQEALC
GGCTAIALFNQANQAPGFGGGFKSGLRGGTPVTTFVRGIDLRSTVLLNVLTLPRLQKQFPNESHTENQPT
WIKPIKSNESIPASSIGFVRGLFWQPAHIELCDPIGIGKCSCCGQESNLRYTGFLKEKFTFTVNGLWPHP
HSPCLVTVKKGEVEEKFLAFTTSAPSWTQISRVVVDKIIQNENGNRVAAVVNQFRNIAPQSPLELIMGGY
RNNQASILERRHDVLMFNQGWQQYGNVINEIVTVGLGYKTALRKALYTFAEGFKNKDFKGAGVSVHETAE
RHEYRQSELLIPDVLANVNFSQADEVIADLRDKLHQLCEMLFNQSVAPYAHHPKLISTLALARATLYKHL
RELKPQGGPSNG KRAB-CasB (nucleotide) (SEQ ID NO: 34):
ATGGATTACAAGGACCATGACGGAGATTATAAGGACCACGACATAGACTATAAGGATGACGATGACAAAA
TGGCAGATGCTAAGTCACTGACTGCCTGGTCCCGGACACTGGTGACCTTCAAGGATGTGTTTGTGGACTT
CACCAGGGAGGAGTGGAAGCTGCTGGACACTGCTCAGCAGATCCTGTACAGAAATGTGATGCTGGAGAAC
TATAAGAACCTGGTTTCCTTGGGTTATCAGCTTACTAAGCCAGATGTGATCCTCCGGTTGGAGAAGGGAG
AAGAGCCCTGGCTGGTGGAGAGAGAAATTCACCAAGAGACCCATCCTGATTCAGAGACTGCATTTGAAAT
CAAATCATCAGTTCCGAAAAAGAAACGCAAAGTTGGATCCCCAAAGAAGAAACGCAAGGTGCGCGGGATG
GCCGATGAAATAGACGCAATGGCTCTTTACCGAGCATGGCAACAGCTCGACAATGGATCTTGCGCCCAAA
TACGGCGGGTAAGTGAACCCGATGAACTGCGAGATATCCCCGCATTCTACCGATTGGTTCAGCCGTTTGG
CTGGGAGAACCCACGGCACCAGCAGGCGCTTCTTAGGATGGTTTTTTGTCTTAGTGCCGGGAAAAACGTA
ATCGCCCATCAGGATAAGAAGTCCGAACAAACAACAGGGATTTCTCTGGGAAGAGCGCTTGCTAACAGCG
GCAGGATCAATGAACGCCGCATATTTCAGTTGATCCGAGCAGATCGGACTGCTGATATGGTTCCAGCTCAG
GAGGCTCCTTACGCACGCAGAGCCAGTGTTGGATTGGCCACTCATGGCAAGAATGCTTACGTGGTGGGGG
AAGAGGGAAAGGCAGCAACTGCTTGAAGATTTTGTATTGACGACGAACAAAAACGCGTAA KRAB-CasB (amino acid) (SEQ ID NO: 35):
MDYKDHDGDYKDEDIDYKDDDDKMADAKSLTAWSRTLVTFKDVFVDFTREEWKLLDTAQQILYRNVMLEN
YKNLVSLGYQLTKPDVILRLEKGEEPWLVEREIHQETHPDSETAFEIKSSVPKKKRKVGSPKKKRKVRGM
ADEIDAMALYRAWQQLDNGSCAQIRRVSEPDELRDIPAFYRLVQPFGWENPRHQQALLRMVFCLSAGKNV
IRHQDKKSEQTTGISLGRALANSGRINERRIFQLIRADRTADMVQLRRLLTHAEPVLDWPLMARMLTWWG
KRERQQLLEDFVLTTNKNA KRAB-CasC (nucleotide) (SEQ ID NO: 36):
ATGGATTACAAGGACCATGACGGAGATTATAAGGACCACGACATAGACTATAAGGATGACGATGACAAAA
TGGCAGATGCTAAGTCACTGACTGCCTGGTCCCGGACACTGGTGACCTTCAAGGATGTGTTTGTGGACTT
CACCAGGGAGGAGTGGAAGCTGCTGGACACTGCTCAGCAGATCCTGTACAGAAATGTGATGCTGGAGAAC
TATAAGAACCTGGTTTCCTTGGGTTATCAGCTTACTAAGCCAGATGTGATCCTCCGGTTGGAGAAGGGAG
AAGAGCCCTGGCTGGTGGAGAGAGAAATTCACCAAGAGACCCATCCTGATTCAGAGACTGCATTTGAAAT
CAAATCATCAGTTCCGAAAAAGAAACGCAAAGTTGGATCCCCAAAGAAGAAACGCAAGGTGCGCGGGATG
TCAAACTTCATTAATATCCACGTGCTTATCTCACACTCCCCTAGTTGCCTTAACAGAGACGATATGAACA
TGCAAAAAGACGCAATTTTTGGCGGCAAAAGGAGAGTCAGAATTAGTAGCCAGAGCCTGAAGCGCGCTAT
GAGGAAAAGCGGCTACTATGCTCAAAACATTGGTGAAAGTTCATTGCGGACCATCCATCTCGCGCAGTTG
AGGGACGTCCTGCGACAGAAGCTTGGGGAAAGATTTGATCAGAAGATCATCGACAAAACGCTTGCCCTTC
TGTCCGGTAAATCAGTGGACGAAGCGGAGAAGATAAGTGCGGATGCTGTTACGCCATGGGTGGTAGGTGA
AATCGCGTGGTTTTGCGAGCAGGTAGCCAAGGCCGAAGCGGATAATTTGGATGATAAGAAACTGCTCAAA
GTCCTCAAAGAGGACATCGCGGCGATCCGGGTGAACCTTCAGCAGGGTGTTGATATTGCGCTCTCTGGTC
GGATGGCCACGTCTGGAATGATGACTGAACTGGGTAAGGTGGACGGAGCTATGTCTATAGCTCATGCTAT
AACTACCCATCAGGTGGATTCTGACATAGACTGGTTCACGGCTGTCGACGATCTCCAGGAACAAGGATCC
GCACACCTCGGCACGCAAGAATTTTCTTCTGGAGTGTTCTATAGGTATGCCAACATCAACCTTGCACAGC
TCCAGGAAAACCTCGGTGGGGCAAGCCGGGAACAGGCTCTTGAAATAGCTACCCATGTGGTTCACATGCT
GGCGACCGAAGTGCCAGGGGCCAAGCAGAGAACGTACGCCGCATTCAATCCGGCAGACATGGTCATGGTG
AATTTCTCTGATATGCCCTTGTCTATGGCAAATGCTTTCGAGAAGGCGGTCAAGGCAAAGGACGGTTTTT
TGCAACCCTCCATCCAAGCCTTTAATCAGTACTGGGATAGAGTAGCTAACGGGTATGGTCTCAATGGCGC
GGCTGCTCAGTTTTCTTTGTCCGATGTGGATCCGATAACGGCGCAGGTTAAACAGATGCCCACCTTGGAA
CAACTCAAATCCTGGGTTAGAAACAATGGGGAGGCGTGA KRAB-CasC (amino acid) (SEQ ID NO: 37):
MDYKDHDGDYKDEDIDYKDDDDKMADAKSLTAWSRTLVTEKDVEVDETREEWKLLDTAQQILYRNVMLEN
YKNLVSLGYQLTKPDVILRLEKGEEPWLVEREIHQETHPDSETAFEIKSSVPKKKRKVGSPKKKRKVRGM
SNFINIHVLISHSPSCLNRDDMNMQKDAIEGGKRRVRISSQSLKRAMRKSGYYAQNIGESSLRTIHLAQL
RDVLRQKLGERFDQKIIDKTLALLSGKSVDEAEKISADAVTPWVVGEIAWFCEQVAKAEADNLDDKKLLK
VLKEDIAAIRVNLQQGVDIALSGRMATSGMMTELGKVDGAMSIAHAITTHQVDSDIDWFTAVDDLQEQGS
AHLGTQEFSSGVEYRYANINLAQLQENLGGASREQALEIATHVVHMLATEVPGAKQRTYAAFNPADMVMV
NESDMPLSMANAFEKAVKAKDGFLQPSIQAFNQYWDRVANGYGLNGAAAQFSLSDVDPITAQVKQMPTLE
QLKSWVRNNGEA KRAB-CasD (nucleotide) (SEQ ID NO: 38):
ATGGATTACAAGGACCATGACGGAGATTATAAGGACCACGACATAGACTATAAGGATGACGATGACAAAA
TGGCAGATGCTAAGTCACTGACTGCCTGGTCCCGGACACTGGTGACCTTCAAGGATGTGTTTGTGGACTT
CACCAGGGAGGAGTGGAAGCTGCTGGACACTGCTCAGCAGATCCTGTACAGAAATGTGATGCTGGAGAAC
TATAAGAACCTGGTTTCCTTGGGTTATCAGCTTACTAAGCCAGATGTGATCCTCCGGTTGGAGAAGGGAG
AAGAGCCCTGGCTGGTGGAGAGAGAAATTCACCAAGAGACCCATCCTGATTCAGAGACTGCATTTGAAAT
CAAATCATCAGTTCCGAAAAAGAAACGCAAAGTTGGATCCCCAAAGAAGAAACGCAAGTACGGGGCATG
CGATCATACTTGATCCTGCGGCTTGCAGGTCCTATGCAAGCCTGGGGGCAACCTACCTTTGAAGGTACTC
GGCCGACTGGCAGGTTCCCTACGCGGTCTGGTTTGCTCGGACTCCTCGGCGCCTGTTTGGGGATACAAAG
GGATGACACTTCTTCCTTGCAGGCACTTTCCGAATCAGTCCAGTTCGCAGTGAGATGTGATGAACTCATA
CTGGACGACAGACGGGTGTCCGTAACTGGACTGAGGGACTATCATACTGTACTCGGCGCAAGAGAAGATT APPENDIX-continued

```
ATCGAGGTCTTAAGTCACATGAGACTATTCAGACATGGAGGGAATATTTGTGTGACGCCTCCTTCACGGT
GGCCCTCTGGCTTACACCACATGCAACTATGGTGATCTCAGAGCTTGAGAAAGCCGTTCTTAAACCTCGG
TACACACCATATCTGGGGAGGCGGTCTTGCCCACTTACCCACCCGCTTTTCTTGGGGACTTGTCAGGCCA
GCGATCCACAGAAGGCCTTGCTGAACTATGAACCCGTTGGTGGCGATATATACAGTGAAGAGAGCGTCAC
GGGCCATCACTTGAAGTTCACTGCTAGGGATGAGCCGATGATTACGCTCCCGAGACAGTTCGCTAGTAGG
GAATGGTACGTTATTAAGGGGGGAATGGACGTTTCCCAATGA

KRAB-CasD (amino acid) (SEQ ID NO: 39):
MDYKDHDGDYKDHDIDYKDDDDKMADAKSLTAWSRTLVTFKDVFVDFTREEWKLLDTAQQILYRNVMLEN
YKNLVSLGYQLTKPDVILRLEKGEEPWLVEREIHQETHPDSETAFEIKSSVPKKKRKVGSPKKKRKVRGM
RSYLILRLAGPMQAWGQPTFEGTRPTGREPTRSGLLGLLGACLGIQRDDTSSLQALSESVQFAVRCDELI
LDDRRVSVTGLRDYHTVLGAREDYRGLKSHETIQTWREYLCDASFTVALWLTPHATMVISELEKAVLKPR
YTPYLGRRSCPLTHPLFLGTCQASDPQKALLNYEPVGGDIYSEESVTGHHLKFTARDEPMITLPRQFASR
EWYVIKGGMDVSQ KRAB-CasE (nucleotide) (SEQ ID NO: 40):
ATGGATTACAAGGACCATGACGGAGATTATAAGGACCACGACATAGACTATAAGGATGACGATGACAAA
TGGCAGATGCTAAGTCACTGACTGCCTGGTCCCGGACACTGGTGACCTTCAAGGATGTGTTTGTGGACTT
CACCAGGGAGGAGTGGAAGCTGCTGGACACTGCTCAGCAGATCCTGTACAGAAATGTGATGCTGGAGAAC
TATAAGAACCTGGTTTCCTTGGGTTATCAGCTTACTAAGCCAGATGTGATCCTCCGGTTGGAGAAGGGAG
AAGAGCCCTGGCTGGTGGAGAGAGAAATTCACCAAGAGACCCATCCTGATTCAGAGACTGCATTTGAAAT
CAAATCATCAGTTCCGAAAAAGAAACGCAAAGTTGGATCCCCAAAGAAGAAACGCAAGGTGCGGGGCATG
TATCTCAGTAAAGTCATCATTGCCAGGGCCTGGAGCAGGGATCTTTACCAACTTCACCAGGGATTATGGC
ATTTATTTCCAAACAGACCGGATGCTGCTCGTGATTTTCTTTTTCATGTTGAGAAGCGAAACACACCAGA
AGGCTGTCATGTTTTATTGCAGTCAGCGCAAATGCCTGTTTCAACTGCCGTTGCGACAGTCATTAAACT
AAACAGGTTGAATTTCAACTTCAGGTTGGTGTTCCACTCTATTTTCGGCTTCGGGCAAATCCGATCAAA
CTATTCTCGACAATCAAAGCGCCTGGACAGTAAAGGGAATATTAAACGCTGTCGGGTTCCGTTAATAAA
AGAAGCAGAACAAATCGCGTGGTTGCAACGTAAATTGGGCAATGCGGCGCGCGTTGAAGATGTGCATCCC
ATATCGGAACGGCCACAGTATTTTCTGGTGATGGTAAAAGTGGAAAGATCCAAACGGTTTGCTTTGAAG
GTGTGCTCACCATCAACGACGCGCCAGCGTTAATAGATCTTGTACAGCAAGGTATTGGGCCAGCTAAATC
GATGGGATGTGGCTTGCTATCTTTGGCTCCACTGTGA KRAB-CasE (amino acid) (SEQ ID NO: 41):
MDYKDHDGDYKDHDIDYKDDDDKMADAKSLTAWSRTLVTFKDVFVDFTREEWKLLDTAQQILYRNVMLEN
YKNLVSLGYQLTKPDVILRLEKGEEPWLVEREIHQETHPDSETAFEIKSSVPKKKRKVGSPKKKRKVRGM
YLSKVIIARAWSRDLYQLHQGLWHLFPNRPDAARDFLFHVEKRNTPEGCHVLLQSAQMPVSTAVATVIKT
KQVEFQLQVGVPLYFRLRANPIKTILDNQKRLDSKGNIKRCRVPLIKEAEQIAWLQRKLGNAARVEDVHP
ISERPQYFSGDGKSGKIQTVCFEGVLTINDAPALIDLVQQGIGPAKSMGCGLLSLAPL
```

Lentiviral constructs to generate Type I-E cell lines (see also FIG. 49 for schematics of these constructs)[35]

```
pAP90 plasmid nucleotide sequence from LTR to LTR (SEQ ID NO: 42):
GGGTCTCTCTGGTTAGACCAGATCTGAGCCTGGGAGCTCTCTGGCTAACTAGGGAACCCACTGCTTAAGC

CTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGA

AAGGGAAACCAGAGGAGCTCTCTCGACGCAGGACTCGGCTTGCTGAAGCGCGCACGGCAAGAGGCGAGGG

GCGGCGACTGGTGAGTACGCCAAAAATTTTGACTAGCGGAGGCTAGAAGGAGAGATGGGTGCGAGAGC

GTCAGTATTAAGCGGGGAGAATTAGATCGCGATGGGAAAAAATTCGGTTAAGGCCAGGGGGAAAGAAAA

AATATAAATTAAAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAGGATCAGAAGAA

CTTAGATCATTATATAATACAGTAGCAACCCTCTATTGTGTGCATCAAAGGATAGAGATAAAAGACACCA

AGGAAGCTTTAGACAAGATAGAGGAAGAGCAAAACAAAAGTAAGACCACCGCACAGCAAGCGGCCGCTGA

TCTTCAGACCTGGAGGAGGAGATATGAGGGACAATTGGAGAAGTGAATTATATAAATATAAAGTAGTAAA

AATTGAACCATTAGGAGTAGCACCCACCAAGGCAAAGAGAAGAGTGGTGCAGAGAGAAAAAAGAGCAGTG

GGAATAGGAGCTTTGTTCCTTGGGTTCTTGGGAGCAGCAGGAAGCACTATGGGCGCAGCGTCAATGACGC

TGACGGTACAGGCCAGACAATTATTGTCTGGTATAGTGCAGCAGCAGAACAATTTGCTGAGGGCTATTGA

GGCGCAACAGCATCTGTTGCAACTCACAGTCTGGGGCATCAAGCAGCTCCAGGCAAGAATCCTGGCTGTG

GAAAGATACCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACCTGGATGGA
```

-continued

```
GTGGGACAGAGAAATTAACAATTACACAAGCTTAATACACTCCTTAATTGAAGAATCGCAAAACCAGCAA

GAAAAGAATGAACAAGAATTATTGGAATTAGATAAATGGGCAAGTTTGTGGAATTGGTTTAACATAACAA

ATTGGCTGTGGTATATAAAATTATTCATAATGATAGTAGGAGGCTTGGTAGGTTTAAGAATAGTTTTTGC

TGTACTTTCTATAGTGAATAGAGTTAGGCAGGGATATTCACCATTATCGTTTCAGACCCACCTCCCAACC

CCGAGGGGACCCGACAGGCCCGAAGGAATAGAAGAAGAAGGTGGAGAGAGAGACAGAGACAGATCCATTC

GATTAGTGAACGGATCGGCACTGCGTGCGCCAATTCTGCAGACAAATGGCAGTATTCATCCACAATTTTA

AAAGAAAAGGGGGGATTGGGGGGTACAGTGCAGGGGAAAGAATAGTAGACATAATAGCAACAGACATACA

AACTAAAGAATTACAAAAACAAATTACAAAAATTCAAAATTTTCGGGTTTATTACAGGGACAGCAGAGAT

CCAGTTTGGTTAATTAAGGGTGCAGCGGCCTCCGCGCCGGGTTTTGGCGCCTCCCGCGGGCGCCCCCCTC

CTCACGGCGAGCGCTGCCACGTCAGACGAAGGGCGCAGGAGCGTTCCTGATCCTTCCGCCCGGACGCTCA

GGACAGCGGCCCGCTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGGAAAAGTAGTCCCTT

CTCGGCGATTCTGCGGAGGGATCTCCGTGGGCGGTGAACGCCGATGATTATATAAGGACGCGCCGGGTG

TGGCACAGCTAGTTCCGTCGCAGCCGGGATTTGGGTCGCGGTTCTTGTTTGTGGATCGCTGTGATCGTCA

CTTGGTGAGTTGCGGGCTGCTGGGCTGGCCGGGGCTTTCGTGGCCGCCGGGCCGCTCGGTGGGACGGAAG

CGTGTGGAGAGACCGCCAAGGGCTGTAGTCTGGGTCCGCGAGCAAGGTTGCCCTGAACTGGGGGTTGGGG

GGAGCGCACAAAATGGCGGCTGTTCCCGAGTCTTGAATGGAAGACGCTTGTAAGGCGGGCTGTGAGGTCG

TTGAAACAAGGTGGGGGCATGGTGGGCGGCAAGAACCCAAGGTCTTGAGGCCTTCGCTAATGCGGGAAA

GCTCTTATTCGGGTGAGATGGGCTGGGGCACCATCTGGGGACCCTGACGTGAAGTTTGTCACTGACTGGA

GAACTCGGGTTTGTCGTCTGGTTGCGGGGGCGGCAGTTATGCGGTGCCGTTGGGCAGTGCACCCGTACCT

TTGGGAGCGCGCGCCTCGTCGTGTCGTGACGTCACCCGTTCTGTTGGCTTATAATGCAGGGTGGGGCCAC

CTGCCGGTAGGTGTGCGGTAGGCTTTTCTCCGTCGCAGGACGCAGGGTTCGGGCCTAGGGTAGGCTCTCC

TGAATCGACAGGCGCCGGACCTCTGGTGAGGGAGGGATAAGTGAGGCGTCAGTTTCTTTGGTCGGTTTT

ATGTACCTATCTTCTTAAGTAGCTGAAGCTCCGGTTTTGAACTATGCGCTCGGGGTTGGCGAGTGTGTTT

TGTGAAGTTTTTTAGGCACCTTTTGAAATGTAATCATTTGGGTCAATATGTAATTTTCAGTGTTAGACTA

GTAAATTGTCCGCTAAATTCTGGCCGTTTTTGGCTTTTTTGTTAGACGAAGCTTGGGCTGCAGGTCGACT

CTAGAGGATCCCCGGGTACCGGTCGCCACCGCCGCCACCATGGCCTATCCATATGATGTGCCAGATTATG

CCATGGCGCCGAAGAAAAGAGGAAAGTACGGGGCATGCGATCATACTTGATCCTGCGGCTTGCAGGTCC

TATGCAAGCCTGGGGGCAACCTACCTTTGAAGGTACTCGGCCGACTGGCAGGTTCCCTACGCGGTCTGGT

TTGCTCGGACTCCTCGGCGCCTGTTTGGGGATACAAAGGGATGACACTTCTTCCTTGCAGGCACTTTCCG

AATCAGTCCAGTTCGCAGTGAGATGTGATGAACTCATACTGGACGACAGACGGGTGTCCGTAACTGGACT

GAGGGACTATCATACTGTACTCGGCGCAAGAGAAGATTATCGAGGTCTTAAGTCACATGAGACTATTCAG

ACATGGAGGGAATATTTGTGTGACGCCTCCTTCACGGTGGCCCTCTGGCTTACACCACATGCAACTATGG

TGATCTCAGAGCTTGAGAAAGCCGTTCTTAAACCTCGGTACACACCATATCTGGGGAGGCGGTCTTGCCC

ACTTACCCACCCGCTTTTCTTGGGGACTTGTCAGGCCAGCGATCCACAGAAGGCCTTGCTGAACTATGAA

CCCGTTGGTGGCGATATATACAGTGAAGAGAGCGTCACGGGCCATCACTTGAAGTTCACTGCTAGGGATG

AGCCGATGATTACGCTCCCGAGACAGTTCGCTAGTAGGGAATGGTACGTTATTAAGGGGGGAATGGACGT

TTCCCAAGGAAGCGGAGCTACTAACTTCAGCCTGCTGAAGCAGGCTGGAGACGTGGAGGAGAACCCTGGA

CCTATGGGTGCCCCAGTTCCCTATCCCGACCCACTGGAGCCAAGGATGGCGCCTAAGAAGAAGCGCAAGG

TGCGGGCATGTATCTCAGTAAAGTCATCATTGCCAGGGCCTGGAGCAGGGATCTTTACCAACTTCACCA
```

-continued

```
GGGATTATGGCATTTATTTCCAAACAGACCGGATGCTGCTCGTGATTTTCTTTTTCATGTTGAGAAGCGA

AACACACCAGAAGGCTGTCATGTTTTATTGCAGTCAGCGCAAATGCCTGTTTCAACTGCCGTTGCGACAG

TCATTAAAACTAAACAGGTTGAATTTCAACTTCAGGTTGGTGTTCCACTCTATTTTCGGCTTCGGGCAAA

TCCGATCAAAACTATTCTCGACAATCAAAAGCGCCTGGACAGTAAAGGGAATATTAAACGCTGTCGGGTT

CCGTTAATAAAAGAAGCAGAACAAATCGCGTGGTTGCAACGTAAATTGGGCAATGCGGCGCGCGTTGAAG

ATGTGCATCCCATATCGGAACGGCCACAGTATTTTTCTGGTGATGGTAAAAGTGGAAAGATCCAAACGGT

TTGCTTTGAAGGTGTGCTCACCATCAACGACGCGCCAGCGTTAATAGATCTTGTACAGCAAGGTATTGGG

CCAGCTAAATCGATGGGATGTGGCTTGCTATCTTTGGCTCCACTGGGAAGCGGAGAGGGCAGAGGAAGTC

TTCTCACATGCGGTGACGTGGAGGAGAATCCTGGACCTATGACCGAGTACAAGCCCACGGTGCGCCTCGC

CACCCGCGACGACGTCCCCAGGGCCGTACGCACCCTCGCCGCCGCGTTCGCCGACTACCCCGCCACGCGC

CACACCGTCGATCCGGACCGCCACATCGAGCGGGTCACCGAGCTGCAAGAACTCTTCCTCACGCGCGTCG

GGCTCGACATCGGCAAGGTGTGGGTCGCGGACGACGGCGCCGCGGTGGCGGTCTGGACCACGCCGGAGAG

CGTCGAAGCGGGGGCGGTGTTCGCCGAGATCGGCCCGCGCATGGCCGAGTTGAGCGGTTCCCGGCTGGCC

GCGCAGCAACAGATGGAAGGCCTCCTGGCGCCGCACCGGCCCAAGGAGCCCGCGTGGTTCCTGGCCACCG

TCGGCGTCTCGCCCGACCACCAGGGCAAGGGTCTGGGCAGCGCCGTCGTGCTCCCCGGAGTGGAGGCGGC

CGAGCGCGCCGGGGTGCCCGCCTTCCTGGAGACCTCCGCGCCCCGCAACCTCCCCTTCTACGAGCGGCTC

GGCTTCACCGTCACCGCCGACGTCGAGGTGCCCGAAGGACCGCGCACCTGGTGCATGACCCGCAAGCCCG

GTGCCTGAGAATTCGATATCAAGCTTATCGATAATCAACCTCTGGATTACAAAATTTGTGAAAGATTGAC

TGGTATTCTTAACTATGTTGCTCCTTTTACGCTATGTGGATACGCTGCTTTAATGCCTTTGTATCATGCT

ATTGCTTCCCGTATGGCTTTCATTTTCTCCTCCTTGTATAAATCCTGGTTGCTGTCTCTTTATGAGGAGT

TGTGGCCCGTTGTCAGGCAACGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAATTCCGTGGTGTTGT

CGGGGAAATCATCGTCCTTTCCTTGGCTGCTCGCCTGTGTTGCCACCTGGATTCTGCGCGGGACGTCCTT

CTGCTACGTCCCTTCGGCCCTCAATCCAGCGGACCTTCCTTCCCGCGGCCTGCTGCCGGCTCTGCGGCCT

CTTCCGCGTCTTCGCCTTCGCCCTCAGACGAGTCGGATCTCCCTTTGGGCCGCCTCCCCGCATCGATACC

GTCGACCTCGAGACCTAGAAAAACATGGAGCAATCACAAGTAGCAATACAGCAGCTACCAATGCTGATTG

TGCCTGGCTAGAAGCACAAGAGGAGGAGGAGGTGGGTTTTCCAGTCACACCTCAGGTACCTTTAAGACCA

ATGACTTACAAGGCAGCTGTAGATCTTAGCCACTTTTTAAAAGAAAAGGGGGGACTGGAAGGGCTAATTC

ACTCCCAACGAAGACAAGATATCCTTGATCTGTGGATCTACCACACACAAGGCTACTTCCCTGATTGGCA

GAACTACACACCAGGGCCAGGGATCAGATATCCACTGACCTTTGGATGGTGCTACAAGCTAGTACCAGTT

GAGCAAGAGAAGGTAGAAGAAGCCAATGAAGGAGAGAACACCCGCTTGTTACACCCTGTGAGCCTGCATG

GGATGGATGACCCGGAGAGAGAAGTATTAGAGTGGAGGTTTGACAGCCGCCTAGCATTTCATCACATGGC

CCGAGAGCTGCATCCGGACTGTACTGGGTCTCTCTGGTTAGACCAGATCTGAGCCTGGGAGCTCTCTGGC

TAACTAGGGAACCCACTGCTTAAGCCTCAATAAAGCTTGCCTTGAGTGCTTCAAGTAGTGTGTGCCCGTC

TGTTGTGTGACTCTGGTAACTAGAGATCCCTCAGACCCTTTTAGTCAGTGTGGAAAATCTCTAGCA pAP91 plasmid nucleotide sequence from LTR to LTR (SEQ ID NO: 43):
GGGTCTCTCTGGTTAGACCAGATCTGAGCCTGGGAGCTCTCTGGCTAACTAGGGAACCCACTGCTTAAGC

CTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGA

AAGGGAAACCAGAGGAGCTCTCTCGACGCAGGACTCGGCTTGCTGAAGCGCGCACGGCAAGAGGCGAGGG
```

-continued

```
GCGGCGACTGGTGAGTACGCCAAAAATTTTGACTAGCGGAGGCTAGAAGGAGAGAGATGGGTGCGAGAGC

GTCAGTATTAAGCGGGGGAGAATTAGATCGCGATGGGAAAAAATTCGGTTAAGGCCAGGGGAAAGAAAA

AATATAAATTAAAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAGGATCAGAAGAA

CTTAGATCATTATATAATACAGTAGCAACCCTCTATTGTGTGCATCAAAGGATAGAGATAAAAGACACCA

AGGAAGCTTTAGACAAGATAGAGGAAGAGCAAAACAAAAGTAAGACCACCGCACAGCAAGCGGCCGCTGA

TCTTCAGACCTGGAGGAGGAGATATGAGGGACAATTGGAGAAGTGAATTATATAAATATAAAGTAGTAAA

AATTGAACCATTAGGAGTAGCACCCACCAAGGCAAAGAGAAGAGTGGTGCAGAGAGAAAAAAGAGCAGTG

GGAATAGGAGCTTTGTTCCTTGGGTTCTTGGGAGCAGCAGGAAGCACTATGGGCGCAGCGTCAATGACGC

TGACGGTACAGGCCAGACAATTATTGTCTGGTATAGTGCAGCAGCAGAACAATTTGCTGAGGGCTATTGA

GGCGCAACAGCATCTGTTGCAACTCACAGTCTGGGGCATCAAGCAGCTCCAGGCAAGAATCCTGGCTGTG

GAAAGATACCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACCTGGATGGA

GTGGGACAGAGAAATTAACAATTACACAAGCTTAATACACTCCTTAATTGAAGAATCGCAAAACCAGCAA

GAAAAGAATGAACAAGAATTATTGGAATTAGATAAATGGGCAAGTTTGTGGAATTGGTTTAACATAACAA

ATTGGCTGTGGTATATAAAATTATTCATAATGATAGTAGGAGGCTTGGTAGGTTTAAGAATAGTTTTTGC

TGTACTTTCTATAGTGAATAGAGTTAGGCAGGGATATTCACCATTATCGTTTCAGACCCACCTCCCAACC

CCGAGGGGACCCGACAGGCCCGAAGGAATAGAAGAAGAAGGTGGAGAGAGAGACAGAGACAGATCCATTC

GATTAGTGAACGGATCGGCACTGCGTGCGCCAATTCTGCAGACAAATGGCAGTATTCATCCACAATTTTA

AAAGAAAAGGGGGGATTGGGGGGTACAGTGCAGGGGAAAGAATAGTAGACATAATAGCAACAGACATACA

AACTAAAGAATTACAAAAACAAATTACAAAAATTCAAAATTTTCGGGTTTATTACAGGGACAGCAGAGAT

CCAGTTTGGTTAATTAAGGGTGCAGCGGCCTCCGCGCCGGGTTTTGGCGCCTCCCGCGGGCGCCCCCCTC

CTCACGGCGAGCGCTGCCACGTCAGACGAAGGGCGCAGGAGCGTTCCTGATCCTTCCGCCCGGACGCTCA

GGACAGCGGCCCGCTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGGAAAAGTAGTCCCTT

CTCGGCGATTCTGCGGAGGGATCTCCGTGGGGCGGTGAACGCCGATGATTATATAAGGACGCGCCGGGTG

TGGCACAGCTAGTTCCGTCGCAGCCGGGATTTGGGTCGCGGTTCTTGTTTGTGGATCGCTGTGATCGTCA

CTTGGTGAGTTGCGGGCTGCTGGGCTGGCCGGGGCTTTCGTGGCCGCCGGGCCGCTCGGTGGGACGGAAG

CGTGTGGAGAGACCGCCAAGGGCTGTAGTCTGGGTCCGCGAGCAAGGTTGCCCTGAACTGGGGGTTGGGG

GGAGCGCACAAAATGGCGGCTGTTCCCGAGTCTTGAATGGAAGACGCTTGTAAGGCGGGCTGTGAGGTCG

TTGAAACAAGGTGGGGGGCATGGTGGGCGGCAAGAACCCAAGGTCTTGAGGCCTTCGCTAATGCGGGAAA

GCTCTTATTCGGGTGAGATGGGCTGGGGCACCATCTGGGGACCCTGACGTGAAGTTTGTCACTGACTGGA

GAACTCGGGTTTGTCGTCTGGTTGCGGGGCGGCAGTTATGCGGTGCCGTTGGGCAGTGCACCCGTACCT

TTGGGAGCGCGCGCCTCGTCGTGTCGTGACGTCACCCGTTCTGTTGGCTTATAATGCAGGGTGGGGCCAC

CTGCCGGTAGGTGTGCGGTAGGCTTTTCTCCGTCGCAGGACGCAGGGTTCGGGCCTAGGGTAGGCTCTCC

TGAATCGACAGGCGCCGGACCTCTGGTGAGGGAGGGATAAGTGAGGCGTCAGTTTCTTTGGTCGGTTTT

ATGTACCTATCTTCTTAAGTAGCTGAAGCTCCGGTTTTGAACTATGCGCTCGGGGTTGGCGAGTGTGTTT

TGTGAAGTTTTTTAGGCACCTTTTGAAATGTAATCATTTGGGTCAATATGTAATTTTCAGTGTTAGACTA

GTAAATTGTCCGCTAAATTCTGGCCGTTTTTGGCTTTTTTGTTAGACGAAGCTTGGGCTGCAGGTCGACT

CTAGAGGATCCCCGGGTACCGGTCGCCACCGCCGCCACCATGGAGCAAAAATTGATCAGTGAAGAAGACC

TGATGGCACCAAAAAAGAAACGCAAAGTGCGGGGCATGGCCAATCTCCTGATTGACAATTGGATCCCTGT
```

-continued

```
GAGACCGAGGAACGGAGGGAAGGTTCAGATCATCAACCTGCAAAGTCTCTACTGTAGCAGAGATCAATGG

CGACTCTCATTGCCCAGGGATGATATGGAATTGGCGGCACTTGCACTCTTGGTATGTATTGGGCAGATCA

TCGCCCCTGCCAAGGATGATGTCGAGTTTAGGCACAGAATAATGAACCCTCTTACTGAAGATGAATTCCA

GCAATTGATCGCGCCTTGGATAGATATGTTCTATTTGAATCACGCCGAACATCCCTTCATGCAGACAAAA

GGGGTTAAAGCAAATGATGTCACACCAATGGAGAAGCTTTTGGCAGGTGTGTCAGGAGCAACCAACTGCG

CTTTCGTTAACCAACCAGGCCAAGGTGAGGCGTTGTGCGGGGGGTGCACGGCCATAGCGTTGTTTAATCA

GGCGAACCAGGCTCCTGGCTTTGGAGGAGGATTCAAGTCCGGTTTGCGCGGGGGTACACCCGTAACCACA

TTCGTTCGCGGAATTGACCTCCGATCAACAGTCCTGTTGAACGTATTGACGTTGCCTAGACTTCAGAAGC

AATTTCCAAACGAGTCTCACACTGAGAATCAACCGACTTGGATTAAGCCCATCAAGTCAAATGAAAGTAT

ACCCGCGTCTTCTATTGGATTTGTTAGAGGACTTTTTTGGCAGCCCGCTCACATAGAACTCTGTGATCCC

ATAGGCATTGGAAAGTGTTCTTGCTGTGGCCAAGAGTCTAACCTTAGATATACGGGCTTTCTCAAGGAGA

AGTTCACGTTCACCGTGAATGGACTTTGGCCACATCCCCATAGCCCGTGCTTGGTCACGGTCAAGAAGGG

GGAGGTTGAAGAGAAATTTCTTGCGTTTACCACATCCGCCCCATCCTGGACGCAAATATCTCGCGTCGTT

GTGGATAAAATCATCCAGAACGAAAATGGTAACCGCGTTGCCGCGGTAGTGAATCAATTCAGAAACATAG

CACCACAGAGCCCGTTGGAGTTGATAATGGGCGGGTACCGCAATAATCAAGCTTCCATTCTCGAGCGACG

CCATGACGTACTTATGTTTAACCAGGGGTGGCAGCAATATGGTAACGTGATAAACGAGATAGTCACAGTC

GGCCTCGGCTACAAAACTGCGTTGCGCAAAGCTCTGTATACGTTCGCGGAGGGTTTTAAGAATAAAGACT

TTAAAGGCGCTGGGGTGAGTGTGCACGAGACGGCAGAACGCCATTTCTATCGCCAGTCTGAACTCTTGAT

TCCCGACGTTCTGGCGAATGTCAATTTTTCCCAGGCCGATGAGGTCATTGCGGATCTGCGAGATAAGCTT

CACCAGTTGTGTGAGATGCTGTTCAACCAGTCTGTGGCTCCTTATGCTCATCATCCCAAACTGATTTCAA

CTCTCGCTTTGGCAAGGGCTACGTTGTATAAACACCTTAGAGAACTGAAGCCACAGGGTGGTCCCAGCAA

TGGCGGAAGCGGAGCTACTAACTTCAGCCTGCTGAAGCAGGCTGGAGACGTGGAGGAGAACCCTGGACCT

ATGGCCCAGCCAGAATTGGCACCTGAAGATCCCGAAGATATGGCGCCGAAGAAAAAGAGGAAAGTACGCG

GGATGGCCGATGAAATAGACGCAATGGCTCTTTACCGAGCATGGCAACAGCTCGACAATGGATCTTGCGC

CCAAATACGGCGGGTAAGTGAACCCGATGAACTGCGAGATATCCCCGCATTCTACCGATTGGTTCAGCCG

TTTGGCTGGGAGAACCCACGGCACCAGCAGGCGCTTCTTAGGATGGTTTTTTGTCTTAGTGCCGGGAAAA

ACGTAATCCGCCATCAGGATAAGAAGTCCGAACAAACAACAGGGATTTCTCTGGGAAGAGCGCTTGCTAA

CAGCGGCAGGATCAATGAACGCCGCATATTTCAGTTGATCCGAGCAGATCGGACTGCTGATATGGTCCAG

CTCAGGAGGCTCCTTACGCACGCAGAGCCAGTGTTGGATTGGCCACTCATGGCAAGAATGCTTACGTGGT

GGGGGAAGAGGGAAAGGCAGCAACTGCTTGAAGATTTTGTATTGACGACGAACAAGAACGCGGGAAGCGG

AGAGGGCAGAGGAAGTGTTCTCACATGCGGTGACGTGGAGGAGAATCCTGGACCTATGGGCAAGCCTATA

CCTAACCCTTTGCTCGGGCTGGACTCCACCATGGCTCCTAAGAAGAAGCGCAAGGTGAGAGGAATGTCAA

ACTTCATTAATATCCACGTGCTTATCTCACACTCCCCTAGTTGCCTTAACAGAGACGATATGAACATGCA

AAAAGACGCAATTTTTGGCGGCAAAAGGAGAGTCAGAATTAGTAGCCAGAGCCTGAAGCGCGCTATGAGG

AAAAGCGGCTACTATGCTCAAAACATTGGTGAAAGTTCATTGCGGACCATCCATCTCGCGCAGTTGAGGG

ACGTCCTGCGACAGAAGCTTGGGGAAAGATTTGATCAGAAGATCATCGACAAAACGCTTGCCCTTCTGTC

CGGTAAATCAGTGGACGAAGCGGAGAAGATAAGTGCGGATGCTGTTACGCCATGGGTGGTAGGTGAAATC

GCGTGGTTTTGCGAGCAGGTAGCCAAGGCCGAAGCGGATAATTTGGATGATAAGAAACTGCTCAAAGTCC

TCAAAGAGGACATCGCGGCGATCCGGGTGAACCTCAGCAGGGTGTTGATATTGCGCTCTCTGGTCGGAT

GGCCACGTCTGGAATGATGACTGAACTGGGTAAGGTGGACGGAGCTATGTCTATAGCTCATGCTATAACT
```

-continued

ACCCATCAGGTGGATTCTGACATAGACTGGTTCACGGCTGTCGACGATCTCCAGGAACAAGGATCCGCAC
ACCTCGGCACGCAAGAATTTTCTTCTGGAGTGTTCTATAGGTATGCCAACATCAACCTTGCACAGCTCCA
GGAAAACCTCGGTGGGGCAAGCCGGGAACAGGCTCTTGAAATAGCTACCCATGTGGTTCACATGCTGGCG
ACCGAAGTGCCAGGGGCCAAGCAGAGAACGTACGCCGCATTCAATCCGGCGGACATGGTCATGGTGAATT
TCTCTGATATGCCCTTGTCTATGGCAAATGCTTTCGAGAAGGCGGTCAAGGCAAAGGACGGTTTTTTGCA
ACCCTCCATCCAAGCCTTTAATCAGTACTGGGATAGAGTAGCTAACGGGTATGGTCTCAATGGCGCGGCT
GCTCAGTTTTCTTTGTCCGATGTGGATCCGATAACGGCGCAGGTTAAACAGATGCCCACCTTGGAACAAC
TCAAATCCTGGGTTAGAAACAATGGGGAGGCGGGAAGCGGAGTGAAACAGACTTTGAACTTTGACTTGCT
CAAGTTGGCAGGAGACGTGGAGTCCAACCCTGGACCTATGGGATCGGCCATTGAACAAGATGGATTGCAC
GCAGGTTCTCCGGCCGCTTGGGTGGAGAGGCTATTCGGCTATGACTGGGCACAACAGACAATCGGCTGCT
CTGATGCCGCCGTGTTCCGGCTGTCAGCGCAGGGGCGCCCGGTTCTTTTTGTCAAGACCGACCTGTCCGG
TGCCCTGAATGAACTGCAGGACGAGGCAGCGCGGCTATCGTGGCTGGCCACGACGGGCGTTCCTTGCGCA
GCTGTGCTCGACGTTGTCACTGAAGCGGGAAGGGACTGGCTGCTATTGGGCGAAGTGCCGGGGCAGGATC
TCCTGTCATCTCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACGTACTCGGATG
GAAGCCGGTCTTGTCGATCAGGATGATCTGGACGAAGAGCATCAGGGGCTCGCGCCAGCCGAACTGTTCG
CCAGGCTCAAGGCGCGCATGCCCGACGGCGATGATCTCGTCGTGACCCATGGCGATGCCTGCTTGCCGAA
TATCATGGTGGAAAATGGCCGCTTTTCTGGATTCATCGACTGTGGCCGGCTGGGTGTGGCGGACCGCTAT
CAGGACATAGCGTTGGCTACCCGTGATATTGCTGAAGAGCTTGGCGGCGAATGGGCTGACCGCTTCCTCG
TGCTTTACGGTATCGCCGCTCCCGATTCGCAGCGCATCGCCTTCTATCGCCTTCTTGACGAGTTCTTCTG
AGAATTCGATATCAAGCTTATCGATAATCAACCTCTGGATTACAAAATTTGTGAAAGATTGACTGGTATT
CTTAACTATGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAGGAGTTGTGGCC
CGTTGTCAGGCAACGTGGCGTGGTGTGCACTGTGTTTGCTGACGCAACCCCCACTGGTTGGGGCATTGCC
ACCACCTGTCAGCTCCTTTCCGGGACTTTCGCTTTCCCCCTCCCTATTGCCACGGCGGAACTCATCGCCG
CCTGCCTTGCCCGCTGCTGGACAGGGGCTCGGCTGTTGGGCACTGACAATTCCGTGGTGTTGTCGGGGAA
ATCATCGTCCTTTCCTTGGCTGCTCGCCTGTGTTGCCACCTGGATTCTGCGCGGGACGTCCTTCTGCTAC
GTCCOPTCGGCCCTCAATCCAGCGGACCTTCCTTCCCGCGGCCTGCTGCCGGCTCTGCGGCCTCTTCCGC
GTCTTCGCCTTCGCCCTCAGACGAGTCGGATCTCCCTTTGGGCCGCCTCCCCGCATCGATACCGTCGACC
TCGAGACCTAGAAAAACATGGAGCAATCACAAGTAGCAATACAGCAGCTACCAATGCTGATTGTGCCTGG
CTAGAAGCACAAGAGGAGGAGGAGGTGGGTTTTCCAGTCACACCTCAGGTACCTTTAAGACCAATGACTT
ACAAGGCAGCTGTAGATCTTAGCCACTTTTTAAAAGAAAAGGGGGGACTGGAAGGGCTAATTCACTCCCA
ACGAAGACAAGATATCCTTGATCTGTGGATCTACCACACACAAGGCTACTTCCCTGATTGGCAGAACTAC
ACACCAGGGCCAGGGATCAGATATCCACTGACCTTTGGATGGTGCTACAAGCTAGTACCAGTTGAGCAAG
AGAAGGTAGAAGAAGCCAATGAAGGAGAGAACACCCGCTTGTTACACCCTGTGAGCCTGCATGGGATGGA
TGACCCGGAGAGAGAAGTATTAGAGTGGAGGTTTGACAGCCGCCTAGCATTTCATCACATGGCCCGAGAG
CTGCATCCGGACTGTACTGGGTCTCTCTGGTTAGACCAGATCTGAGCCTGGGAGCTCTCTGGCTAACTAG
GGAACCCACTGCTTAAGCCTCAATAAAGCTTGCCTTGAGTGCTTCAAGTAGTGTGTGCCCGTCTGTTGTG
TGACTCTGGTAACTAGAGATCCCTCAGACCCTTTTAGTCAGTGTGGAAAATCTCTAGCA pAP129 nucleotide sequence-LTR to LTR (SEQ ID NO: 44):
GGGTCTCTCTGGTTAGACCAGATCTGAGCCTGGGAGCTCTCTGGCTAACTAGGGAACCCACTGCTTAAGC

CTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGA

AAGGGAAACCAGAGGAGCTCTCTCGACGCAGGACTCGGCTTGCTGAAGCGCGCACGGCAAGAGGCGAGGG

GCGGCGACTGGTGAGTACGCCAAAAATTTTGACTAGCGGAGGCTAGAAGGAGAGAGATGGGTGCGAGAGC

GTCAGTATTAAGCGGGGGAGAATTAGATCGCGATGGGAAAAAATTCGGTTAAGGCCAGGGGGAAAGAAAA

AATATAAATTAAAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAGGATCAGAAGAA

CTTAGATCATTATATAATACAGTAGCAACCCTCTATTGTGTGCATCAAAGGATAGAGATAAAAGACACCA

AGGAAGCTTTAGACAAGATAGAGGAAGAGCAAAACAAAAGTAAGACCACCGCACAGCAAGCGGCCGCTGA

TCTTCAGACCTGGAGGAGGAGATATGAGGGACAATTGGAGAAGTGAATTATATAAATATAAAGTAGTAAA

AATTGAACCATTAGGAGTAGCACCCACCAAGGCAAAGAGAAGAGTGGTGCAGAGAGAAAAAAGAGCAGTG

GGAATAGGAGCTTTGTTCCTTGGGTTCTTGGGAGCAGCAGGAAGCACTATGGGCGCAGCGTCAATGACGC

TGACGGTACAGGCCAGACAATTATTGTCTGGTATAGTGCAGCAGCAGAACAATTTGCTGAGGGCTATTGA

GGCGCAACAGCATCTGTTGCAACTCACAGTCTGGGGCATCAAGCAGCTCCAGGCAAGAATCCTGGCTGTG

GAAAGATACCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACCTGGATGGA

GTGGGACAGAGAAATTAACAATTACACAAGCTTAATACACTCCTTAATTGAAGAATCGCAAAACCAGCAA

GAAAAGAATGAACAAGAATTATTGGAATTAGATAAATGGGCAAGTTTGTGGAATTGGTTTAACATAACAA

ATTGGCTGTGGTATATAAAATTATTCATAATGATAGTAGGAGGCTTGGTAGGTTTAAGAATAGTTTTTGC

TGTACTTTCTATAGTGAATAGAGTTAGGCAGGGATATTCACCATTATCGTTTCAGACCCACCTCCCAACC

CCGAGGGGACCCGACAGGCCCGAAGGAATAGAAGAAGAAGGTGGAGAGAGAGACAGAGACAGATCCATTC

GATTAGTGAACGGATCGGCACTGCGTGCGCCAATTCTGCAGACAAATGGCAGTATTCATCCACAATTTTA

AAAGAAAAGGGGGGATTGGGGGGTACAGTGCAGGGGAAAGAATAGTAGACATAATAGCAACAGACATACA

AACTAAAGAATTACAAAAACAAATTACAAAAATTCAAAATTTTCGGGTTTATTACAGGGACAGCAGAGAT

CCAGTTTGGTTAATTAAGGGTGCAGCGGCCTCCGCGCCGGGTTTTGGCGCCTCCCGCGGGCGCCCCCCTC

CTCACGGCGAGCGCTGCCACGTCAGACGAAGGGCGCAGGAGCGTTCCTGATCCTTCCGCCCGGACGCTCA

GGACAGCGGCCCGCTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGGAAAAGTAGTCCCTT

CTCGGCGATTCTGCGGAGGGATCTCCGTGGGCGGTGAACGCCGATGATTATATAAGGACGCGCCGGGTG

TGGCACAGCTAGTTCCGTCGCAGCCGGGATTTGGGTCGCGGTTCTTGTTTGTGGATCGCTGTGATCGTCA

CTTGGTGAGTTGCGGGCTGCTGGGCTGGCCGGGGCTTTCGTGGCCGCCGGGCCGCTCGGTGGGACGGAAG

CGTGTGGAGAGACCGCCAAGGGCTGTAGTCTGGGTCCGCGAGCAAGGTTGCCCTGAACTGGGGGTTGGGG

GGAGCGCACAAAATGGCGGCTGTTCCCGAGTCTTGAATGGAAGACGCTTGTAAGGCGGGCTGTGAGGTCG

TTGAAACAAGGTGGGGGCATGGTGGGCGGCAAGAACCCAAGGTCTTGAGGCCTTCGCTAATGCGGGAAA

GCTCTTATTCGGGTGAGATGGCTGGGGCACCATCTGGGGACCCTGACGTGAAGTTTGTCACTGACTGGA

GAACTCGGGTTTGTCGTCTGGTTGCGGGGCGGCAGTTATGCGGTGCCGTTGGGCAGTGCACCCGTACCT

TTGGGAGCGCGCGCCTCGTCGTGTCGTGACGTCACCCGTTCTGTTGGCTTATAATGCAGGGTGGGGCCAC

CTGCCGGTAGGTGTGCGGTAGGCTTTTCTCCGTCGCAGGACGCAGGGTTCGGGCCTAGGGTAGGCTCTCC

TGAATCGACAGGCGCCGGACCTCTGGTGAGGGGAGGGATAAGTGAGGCGTCAGTTTCTTTGGTCGGTTTT

-continued

```
ATGTACCTATCTTCTTAAGTAGCTGAAGCTCCGGTTTTGAACTATGCGCTCGGGGTTGGCGAGTGTGTTT

TGTGAAGTTTTTTAGGCACCTTTTGAAATGTAATCATTTGGGTCAATATGTAATTTTCAGTGTTAGACTA

GTAAATTGTCCGCTAAATTCTGGCCGTTTTTGGCTTTTTTGTTAGACGAAGCTTGGGCTGCAGGTCGACT

CTAGAGGATCCCCGGGTACCGGTCGCCACCGCCGCCACCATGGATTACAAGGACCATGACGGAGATTATA

AGGACCACGACATAGACTATAAGGATGACGATGACAAAATGGCAGATGCTAAGTCACTGACTGCCTGGTC

CCGGACACTGGTGACCTTCAAGGATGTGTTTGTGGACTTCACCAGGGAGGAGTGGAAGCTGCTGGACACT

GCTCAGCAGATCCTGTACAGAAATGTGATGCTGGAGAACTATAAGAACCTGGTTTCCTTGGGTTATCAGC

TTACTAAGCCAGATGTGATCCTCCGGTTGGAGAAGGGAGAAGAGCCCTGGCTGGTGGAGAGAGAAATTCA

CCAAGAGACCCATCCTGATTCAGAGACTGCATTTGAAATCAAATCATCAGTTCCGAAAAAGAAACGCAAA

GTTGGATCCCCAAAGAAGAAACGCAAAGTGCGGGCATGGCCAATCTCCTGATTGACAATTGGATCCCTG

TGAGACCGAGGAACGGAGGGAAGGTTCAGATCATCAACCTGCAAAGTCTCTACTGTAGCAGAGATCAATG

GCGACTCTCATTGCCCAGGGATGATATGGAATTGGCGGCACTTGCACTCTTGGTATGTATTGGGCAGATC

ATCGCCCCTGCCAAGGATGATGTCGAGTTTAGGCACAGAATAATGAACCCTCTTACTGAAGATGAATTCC

AGCAATTGATCGCGCCTTGGATAGATATGTTCTATTTGAATCACGCCGAACATCCCTTCATGCAGACAAA

AGGGGTTAAAGCAAATGATGTCACACCAATGGAGAAGCTTTTGGCAGGTGTGTCAGGAGCAACCAACTGC

GCTTTCGTTAACCAACCAGGCCAAGGTGAGGCGTTGTGCGGGGGGTGCACGGCCATAGCGTTGTTTAATC

AGGCGAACCAGGCTCCTGGCTTTGGAGGAGGATTCAAGTCCGGTTTGCGCGGGGGTACACCCGTAACCAC

ATTCGTTCGCGGAATTGACCTCCGATCAACAGTCCTGTTGAACGTATTGACGTTGCCTAGACTTCAGAAG

CAATTTCCAAACGAGTCTCACACTGAGAATCAACCGACTTGGATTAAGCCCATCAAGTCAAATGAAAGTA

TACCCGCGTCTTCTATTGGATTTGTTAGAGGACTTTTTTGGCAGCCCGCTCACATAGAACTCTGTGATCC

CATAGGCATTGGAAAGTGTTCTTGCTGTGGCCAAGAGTCTAACCTTAGATATACGGGCTTTCTCAAGGAG

AAGTTCACGTTCACCGTGAATGGACTTTGGCCACATCCCCATAGCCCGTGCTTGGTCACGGTCAAGAAGG

GGGAGGTTGAAGAGAAATTTCTTGCGTTTACCACATCCGCCCCATCCTGGACGCAAATATCTCGCGTCGT

TGTGGATAAAATCATCCAGAACGAAAATGGTAACCGCGTTGCCGCGGTAGTGAATCAATTCAGAAACATA

GCACCACAGAGCCCGTTGGAGTTGATAATGGGCGGGTACCGCAATAATCAAGCTTCCATTCTCGAGCGAC

GCCATGACGTACTTATGTTTAACCAGGGGTGGCAGCAATATGGTAACGTGATAAACGAGATAGTCACAGT

CGGCCTCGGCTACAAAACTGCGTTGCGCAAAGCTCTGTATACGTTCGCGGAGGGTTTTAAGAATAAAGAC

TTTAAAGGCGCTGGGGTGAGTGTGCACGAGACGGCAGAACGCCATTTCTATCGCCAGTCTGAACTCTTGA

TTCCCGACGTTCTGGCGAATGTCAATTTTTCCCAGGCCGATGAGGTCATTGCGGATCTGCGAGATAAGCT

TCACCAGTTGTGTGAGATGCTGTTCAACCAGTCTGTGGCTCCTTATGCTCATCATCCCAAACTGATTTCA

ACTCTCGCTTTGGCAAGGGCTACGTTGTATAAACACCTTAGAGAACTGAAGCCACAGGGTGGTCCCAGCA

ATGGCGGAAGCGGAGCTACTAACTTCAGCCTGCTGAAGCAGGCTGGAGACGTGGAGGAGAACCCTGGACC

TATGGCCCAGCCAGAATTGGCACCTGAAGATCCCGAAGATATGGCGCCGAAGAAAAAGAGGAAAGTACGC

GGGATGGCCGATGAAATAGACGCAATGGCTCTTTACCGAGCATGGCAACAGCTCGACAATGGATCTTGCG

CCCAAATACGGCGGGTAAGTGAACCCGATGAACTGCGAGATATCCCCGCATTCTACCGATTGGTTCAGCC

GTTTGGCTGGGAGAACCCACGGCACCAGCAGGCGCTTCTTAGGATGGTTTTTTGTCTTAGTGCCGGGAAA

AACGTAATCCGCCATCAGGATAAGAAGTCCGAACAAACAACAGGGATTTCTCTGGGAAGAGCGCTTGCTA

ACAGCGGCAGGATCAATGAACGCCGCATATTTCAGTTGATCCGAGCAGATCGGACTGCTGATATGGTCCA

GCTCAGGAGGCTCCTTACGCACGCAGAGCCAGTGTTGGATTGGCCACTCATGGCAAGAATGCTTACGTGG

TGGGGGAAGAGGGAAAGGCAGCAACTGCTTGAAGATTTTGTATTGACGACGAACAAGAACGCGGGAAGCG
```

-continued

GAGAGGGCAGAGGAAGTCTTCTCACATGCGGTGACGTGGAGGAGAATCCTGGACCTATGGGCAAGCCTAT

ACCTAACCCTTTGCTCGGGCTGGACTCCACCATGGCTCCTAAGAAGAAGCGCAAGGTGAGAGGAATGTCA

AACTTCATTAATATCCACGTGCTTATCTCACACTCCCCTAGTTGCCTTAACAGAGACGATATGAACATGC

AAAAAGACGCAATTTTTGGCGGCAAAAGGAGAGTCAGAATTAGTAGCCAGAGCCTGAAGCGCGCTATGAG

GAAAAGCGGCTACTATGCTCAAAACATTGGTGAAAGTTCATTGCGGACCATCCATCTCGCGCAGTTGAGG

GACGTCCTGCGACAGAAGCTTGGGGAAAGATTTGATCAGAAGATCATCGACAAAACGCTTGCCCTTCTGT

CCGGTAAATCAGTGGACGAAGCGGAGAAGATAAGTGCGGATGCTGTTACGCCATGGGTGGTAGGTGAAAT

CGCGTGGTTTTGCGAGCAGGTAGCCAAGGCCGAAGCGGATAATTTGGATGATAAGAAACTGCTCAAAGTC

CTCAAAGAGGACATCGCGGCGATCCGGGTGAACCTTCAGCAGGGTGTTGATATTGCGCTCTCTGGTCGGA

TGGCCACGTCTGGAATGATGACTGAACTGGGTAAGGTGGACGGAGCTATGTCTATAGCTCATGCTATAAC

TACCCATCAGGTGGATTCTGACATAGACTGGTTCACGGCTGTCGACGATCTCCAGGAACAAGGATCCGCA

CACCTCGGCACGCAAGAATTTTCTTCTGGAGTGTTCTATAGGTATGCCAACATCAACCTTGCACAGCTCC

AGGAAAACCTCGGTGGGGCAAGCCGGGAACAGGCTCTTGAAATAGCTACCCATGTGGTTCACATGCTGGC

GACCGAAGTGCCAGGGGCCAAGCAGAGAACGTACGCCGCATTCAATCCGGCGGACATGGTCATGGTGAAT

TTCTCTGATATGCCCTTGTCTATGGCAAATGCTTTCGAGAAGGCGGTCAAGGCAAAGGACGGTTTTTTGC

AACCCTCCATCCAAGCCTTTAATCAGTACTGGGATAGAGTAGCTAACGGGTATGGTCTCAATGGCGCGGC

TGCTCAGTTTTCTTTGTCCGATGTGGATCCGATAACGGCGCAGGTTAAACAGATGCCCACCTTGGAACAA

CTCAAATCCTGGGTTAGAAACAATGGGGAGGCGGGAAGCGGAGTGAAACAGACTTTGAACTTTGACTTGC

TCAAGTTGGCAGGAGACGTGGAGTCCAACCCTGGACCTATGGGATCGGCCATTGAACAAGATGGATTGCA

CGCAGGTTCTCCGGCCGCTTGGGTGGAGAGGCTATTCGGCTATGACTGGGCACAACAGACAATCGGCTGC

TCTGATGCCGCCGTGTTCCGGCTGTCAGCGCAGGGGCGCCCGGTTCTTTTTGTCAAGACCGACCTGTCCG

GTGCCCTGAATGAACTGCAGGACGAGGCAGCGCGGCTATCGTGGCTGGCCACGACGGGCGTTCCTTGCGC

AGCTGTGCTCGACGTTGTCACTGAAGCGGGAAGGGACTGGCTGCTATTGGGCGAAGTGCCGGGGCAGGAT

CTCCTGTCATCTCACCTTGCTCCTGCCGAGAAAGTATCCATCATGGCTGATGCAATGCGGCGGCTGCATA

CGCTTGATCCGGCTACCTGCCCATTCGACCACCAAGCGAAACATCGCATCGAGCGAGCACGTACTCGGAT

GGAAGCCGGTCTTGTCGATCAGGATGATCTGGACGAAGAGCATCAGGGGCTCGCGCCAGCCGAACTGTTC

GCCAGGCTCAAGGCGCGCATGCCCGACGGCGATGATCTCGTCGTGACCCATGGCGATGCCTGCTTGCCGA

ATATCATGGTGGAAAATGGCCGCTTTTCTGGATTCATCGACTGTGGCCGGCTGGGTGTGGCGGACCGCTA

TCAGGACATAGCGTTGGCTACCCGTGATATTGCTGAAGAGCTTGGCGGCGAATGGGCTGACCGCTTCCTC

GTGCTTTACGGTATCGCCGCTCCCGATTCGCAGCGCATCGCCTTCTATCGCCTTCTTGACGAGTTCTTCT

GAGAATTCGATATCAAGCTTATCGATAATCAACCTCTGGATTACAAAATTTGTGAAAGATTGACTGGTAT

TCTTAACTATGTTGCTCCTTTTACGCTATGTGGATACGCTGCTTTAATGCCTTTGTATCATGCTATTGCT

TCCCGTATGGCTTTCATTTTCTCCTCCTTGTATAAATCCTGGTTGCTGTCTCTTTATGAGGAGTTGTGGC

CCGTTGTCAGGCAACGTGGCGTGGTGTGCACTGTGTTTGCTGACGCAACCCCCACTGGTTGGGGCATTGC

CACCACCTGTCAGCTCCTTTCCGGGACTTTCGCTTTCCCCCTCCCTATTGCCACGGCGGAACTCATCGCC

GCCTGCCTTGCCCGCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGACGTCCTTCTGCTA

CGTCCCTTCGGCCCTCAATCCAGCGGACCTTCCTTCCCGCGGCCTGCTGCCGGCTCTGCGGCCTCTTCCG

CGTCTTCGCCTTCGCCCTCAGACGAGTCGGATCTCCCTTTGGGCCGCCTCCCCGCATCGATACCGTCGAC

CTCGAGACCTAGAAAAACATGGAGCAATCACAAGTAGCAATACAGCAGCTACCAATGCTGATTGTGCCTG

GCTAGAAGCACAAGAGGAGGAGGAGGTGGGTTTTCCAGTCACACCTCAGGTACCTTTAAGACCAATGACT

TACAAGGCAGCTGTAGATCTTAGCCACTTTTTAAAAGAAAAGGGGGGACTGGAAGGGCTAATTCACTCCC

AACGAAGACAAGATATCCTTGATCTGTGGATCTACCACACACAAGGCTACTTCCCTGATTGGCAGAACTA

CACACCAGGGCCAGGGATCAGATATCCACTGACCTTTGGATGGTGCTACAAGCTAGTACCAGTTGAGCAA

GAGAAGGTAGAAGAAGCCAATGAAGGAGAGAACACCCGCTTGTTACACCCTGTGAGCCTGCATGGGATGG

ATGACCCGGAGAGAGAAGTATTAGAGTGGAGGTTTGACAGCCGCCTAGCATTTCATCACATGGCCCGAGA

GCTGCATCCGGACTGTACTGGGTCTCTCTGGTTAGACCAGATCTGAGCCTGGGAGCTCTCTGGCTAACTA

GGGAACCCACTGCTTAAGCCTCAATAAAGCTTGCCTTGAGTGCTTCAAGTAGTGTGTGCCCGTCTGTTGT

GTGACTCTGGTAACTAGAGATCCCTCAGACCCTTTTAGTCAGTGTGGAAAATCTCTAGCA pAP130 nucleotide sequence-LTR to LTR (SEQ ID NO: 45):
GGGTCTCTCTGGTTAGACCAGATCTGAGCCTGGGAGCTCTCTGGCTAACTAGGGAACCCACTGCTTAAGC

CTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGA

AAGGGAAACCAGAGGAGCTCTCTCGACGCAGGACTCGGCTTGCTGAAGCGCGCACGGCAAGAGGCGAGGG

GCGGCGACTGGTGAGTACGCCAAAAATTTTGACTAGCGGAGGCTAGAAGGAGAGAGATGGGTGCGAGAGC

GTCAGTATTAAGCGGGGGAGAATTAGATCGCGATGGGAAAAAATTCGGTTAAGGCCAGGGGGAAAGAAAA

AATATAAATTAAAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAGGATCAGAAGAA

CTTAGATCATTATATAATACAGTAGCAACCCTCTATTGTGTGCATCAAAGGATAGAGATAAAAGACACCA

AGGAAGCTTTAGACAAGATAGAGGAAGAGCAAAACAAAAGTAAGACCACCGCACAGCAAGCGGCCGCTGA

TCTTCAGACCTGGAGGAGGAGATATGAGGGACAATTGGAGAAGTGAATTATATAAATATAAAGTAGTAAA

AATTGAACCATTAGGAGTAGCACCCACCAAGGCAAAGAGAAGAGTGGTGCAGAGAGAAAAAAGAGCAGTG

GGAATAGGAGCTTTGTTCCTTGGGTTCTTGGGAGCAGCAGGAAGCACTATGGGCGCAGCGTCAATGACGC

TGACGGTACAGGCCAGACAATTATTGTCTGGTATAGTGCAGCAGCAGAACAATTTGCTGAGGGCTATTGA

GGCGCAACAGCATCTGTTGCAACTCACAGTCTGGGGCATCAAGCAGCTCCAGGCAAGAATCCTGGCTGTG

GAAAGATACCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACCTGGATGGA

GTGGGACAGAGAAATTAACAATTACACAAGCTTAATACACTCCTTAATTGAAGAATCGCAAAACCAGCAA

GAAAAGAATGAACAAGAATTATTGGAATTAGATAAATGGGCAAGTTTGTGGAATTGGTTTAACATAACAA

ATTGGCTGTGGTATATAAAATTATTCATAATGATAGTAGGAGGCTTGGTAGGTTTAAGAATAGTTTTTGC

TGTACTTTCTATAGTGAATAGAGTTAGGCAGGGATATTCACCATTATCGTTTCAGACCCACCTCCCAACC

CCGAGGGGACCCGACAGGCCCGAAGGAATAGAAGAAGAAGGTGGAGAGAGAGACAGAGACAGATCCATTC

GATTAGTGAACGGATCGGCACTGCGTGCGCCAATTCTGCAGACAAATGGCAGTATTCATCCACAATTTTA

AAAGAAAAGGGGGGATTGGGGGGTACAGTGCAGGGGAAAGAATAGTAGACATAATAGCAACAGACATACA

AACTAAAGAATTACAAAAACAAATTACAAAAATTCAAAATTTTCGGGTTTATTACAGGGACAGCAGAGAT

CCAGTTTGGTTAATTAAGGGTGCAGCGGCCTCCGCGCCGGGTTTTGGCGCCTCCCGCGGGCGCCCCCCTC

CTCACGGCGAGCGCTGCCACGTCAGACGAAGGGCGCAGGAGCGTTCCTGATCCTTCCGCCCGGACGCTCA

GGACAGCGGCCCGCTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGGAAAAGTAGTCCCTT

CTCGGCGATTCTGCGGAGGGATCTCCGTGGGGCGGTGAACGCCGATGATTATATAAGGACGCGCCGGGTG

TGGCACAGCTAGTTCCGTCGCAGCCGGGATTTGGGTCGCGGTTCTTGTTTGTGGATCGCTGTGATCGTCA

CTTGGTGAGTTGCGGGCTGCTGGGCTGGCCGGGGCTTTCGTGGCCGCCGGGCCGCTCGGTGGGACGGAAG

-continued

```
CGTGTGGAGAGACCGCCAAGGGCTGTAGTCTGGGTCCGCGAGCAAGGTTGCCCTGAACTGGGGGTTGGGG

GGAGCGCACAAAATGGCGGCTGTTCCCGAGTCTTGAATGGAAGACGCTTGTAAGGCGGGCTGTGAGGTCG

TTGAAACAAGGTGGGGGGCATGGTGGGCGGCAAGAACCCAAGGTCTTGAGGCCTTCGCTAATGCGGGAAA

GCTCTTATTCGGGTGAGATGGGCTGGGGCACCATCTGGGGACCCTGACGTGAAGTTTGTCACTGACTGGA

GAACTCGGGTTTGTCGTCTGGTTGCGGGGCGGCAGTTATGCGGTGCCGTTGGGCAGTGCACCCGTACCT

TTGGGAGCGCGCGCCTCGTCGTGTCGTGACGTCACCCGTTCTGTTGGCTTATAATGCAGGGTGGGGCCAC

CTGCCGGTAGGTGTGCGGTAGGCTTTTCTCCGTCGCAGGACGCAGGGTTCGGGCCTAGGGTAGGCTCTCC

TGAATCGACAGGCGCCGGACCTCTGGTGAGGGGAGGGATAAGTGAGGCGTCAGTTTCTTTGGTCGGTTTT

ATGTACCTATCTTCTTAAGTAGCTGAAGCTCCGGTTTTGAACTATGCGCTCGGGGTTGGCGAGTGTGTTT

TGTGAAGTTTTTTAGGCACCTTTTGAAATGTAATCATTTGGGTCAATATGTAATTTTCAGTGTTAGACTA

GTAAATTGTCCGCTAAATTCTGGCCGTTTTTGGCTTTTTTGTTAGACGAAGCTTGGGCTGCAGGTCGACT

CTAGAGGATCCCCGGGTACCGGTCGCCACCGCCGCCACCATGGAGCAAAAATTGATCAGTGAAGAAGACC

TGATGGCACCAAAAAAGAAACGCAAAGTGCGGGGCATGGCCAATCTCCTGATTGACAATTGGATCCCTGT

GAGACCGAGGAACGGAGGGAAGGTTCAGATCATCAACCTGCAAAGTCTCTACTGTAGCAGAGATCAATGG

CGACTCTCATTGCCCAGGGATGATATGGAATTGGCGGCACTTGCACTCTTGGTATGTATTGGGCAGATCA

TCGCCCCTGCCAAGGATGATGTCGAGTTTAGGCACAGAATAATGAACCCTCTTACTGAAGATGAATTCCA

GCAATTGATCGCGCCTTGGATAGATATGTTCTATTTGAATCACGCCGAACATCCCTTCATGCAGACAAAA

GGGGTTAAAGCAAATGATGTCACACCAATGGAGAAGCTTTTGGCAGGTGTGTCAGGAGCAACCAACTGCG

CTTTCGTTAACCAACCAGGTCAAGGTGAGGCGTTGTGCGGGGGGTGCACGGCCATAGCGTTGTTTAATCA

GGCGAACCAGGCTCCTGGCTTTGGAGGAGGATTCAAGTCCGGTTTGCGCGGGGGTACACCCGTAACCACA

TTCGTTCGCGGAATTGACCTCCGATCAACAGTCCTGTTGAACGTATTGACGTTGCCTAGACTTCAGAAGC

AATTTCCAAACGAGTCTCACACTGAGAATCAACCGACTTGGATTAAGCCCATCAAGTCAAATGAAAGTAT

ACCCGCGTCTTCTATTGGATTTGTTAGAGGACTTTTTTGGCAGCCCGCTCACATAGAACTCTGTGATCCC

ATAGGCATTGGAAAGTGTTCTTGCTGTGGCCAAGAGTCTAACCTTAGATATACGGGCTTTCTCAAGGAGA

AGTTCACGTTCACCGTGAATGGACTTTGGCCACATCCCCATAGCCCGTGCTTGGTCACGGTCAAGAAGGG

GGAGGTTGAAGAGAAATTTCTTGCGTTTACCACATCCGCCCCATCCTGGACGCAAATATCTCGCGTCGTT

GTGGATAAAATCATCCAGAACGAAAATGGTAACCGCGTTGCCGCGGTAGTGAATCAATTCAGAAACATAG

CACCACAGAGCCCGTTGGAGTTGATAATGGGCGGGTACCGCAATAATCAAGCTTCCATTCTCGAGCGACG

CCATGACGTACTTATGTTTAACCAGGGGTGGCAGCAATATGGTAACGTGATAAACGAGATAGTCACAGTC

GGCCTCGGCTACAAAACTGCGTTGCGCAAAGCTCTGTATACGTTCGCGGAGGGTTTTAAGAATAAAGACT

TTAAAGGCGCTGGGGTGAGTGTGCACGAGACGGCAGAACGCCATTTCTATCGCCAGTCTGAACTCTTGAT

TCCCGACGTTCTGGCGAATGTCAATTTTTCCCAGGCCGATGAGGTCATTGCGGATCTGCGAGATAAGCTT

CACCAGTTGTGTGAGATGCTGTTCAACCAGTCTGTGGCTCCTTATGCTCATCATCCCAAACTGATTTCAA

CTCTCGCTTTGGCAAGGGCTACGTTGTATAAACACCTTAGAGAACTGAAGCCACAGGGTGGTCCCAGCAA

TGGCGGAAGCGGAGCTACTAACTTCAGCCTGCTGAAGCAGGCTGGAGACGTGGAGGAGAACCCTGGACCT

ATGGATTACAAGGACCATGACGGAGATTATAAGGACCACGACATAGACTATAAGGATGACGATGACAAAA

TGGCAGATGCTAAGTCACTGACTGCCTGGTCCCGACACTGGTGACCTTCAAGGATGTGTTTGTGGACTT

CACCAGGGAGGAGTGGAAGCTGCTGGACACTGCTCAGCAGATCCTGTACAGAAATGTGATGCTGGAGAAC

TATAAGAACCTGGTTTCCTTGGGTTATCAGCTTACTAAGCCAGATGTGATCCTCCGGTTGGAGAAGGGAG

AAGAGCCCTGGCTGGTGGAGAGAGAAATTCACCAAGAGACCCATCCTGATTCAGAGACTGCATTTGAAAT
```

-continued
```
CAAATCATCAGTTCCGAAAAAGAAACGCAAAGTTGGATCCCCAAAGAAGAAACGCAAGGTGCGCGGGATG

GCCGATGAAATAGACGCAATGGCTCTTTACCGAGCATGGCAACAGCTCGACAATGGATCTTGCGCCCAAA

TACGGCGGGTAAGTGAACCCGATGAACTGCGAGATATCCCCGCATTCTACCGATTGGTTCAGCCGTTTGG

CTGGGAGAACCCACGGCACCAGCAGGCGCTTCTTAGGATGGTTTTTTGTCTTAGTGCCGGGAAAAACGTA

ATCCGCCATCAGGATAAGAAGTCCGAACAAACAACAGGGATTTCTCTGGGAAGAGCGCTTGCTAACAGCG

GCAGGATCAATGAACGCCGCATATTTCAGTTGATCCGAGCAGATCGGACTGCTGATATGGTCCAGCTCAG

GAGGCTCCTTACGCACGCAGAGCCAGTGTTGGATTGGCCACTCATGGCAAGAATGCTTACGTGGTGGGGG

AAGAGGGAAAGGCAGCAACTGCTTGAAGATTTTGTATTGACGACGAACAAGAACGCGGGAAGCGGAGAGG

GCAGAGGAAGTCTTCTCACATGCGGTGACGTGGAGGAGAATCCTGGACCTATGGGCAAGCCTATACCTAA

CCCTTTGCTCGGGCTGGACTCCACCATGGCTCCTAAGAAGAAGCGCAAGGTGAGAGGAATGTCAAACTTC

ATTAATATCCACGTGCTTATCTCACACTCCCCTAGTTGCCTTAACAGAGACGATATGAACATGCAAAAAG

ACGCAATTTTTGGCGGCAAAAGGAGAGTCAGAATTAGTAGCCAGAGCCTGAAGCGCGCTATGAGGAAAAG

CGGCTACTATGCTCAAAACATTGGTGAAAGTTCATTGCGGACCATCCATCTCGCGCAGTTGAGGGACGTC

CTGCGACAGAAGCTTGGGGAAAGATTTGATCAGAAGATCATCGACAAAACGCTTGCCCTTCTGTCCGGTA

AATCAGTGGACGAAGCGGAGAAGATAAGTGCGGATGCTGTTACGCCATGGGTGGTAGGTGAAATCGCGTG

GTTTTGCGAGCAGGTAGCCAAGGCCGAAGCGGATAATTTGGATGATAAGAAACTGCTCAAAGTCCTCAAA

GAGGACATCGCGGCGATCCGGGTGAACCTTCAGCAGGGTGTTGATATTGCGCTCTCTGGTCGGATGGCCA

CGTCTGGAATGATGACTGAACTGGGTAAGGTGGACGGAGCTATGTCTATAGCTCATGCTATAACTACCCA

TCAGGTGGATTCTGACATAGACTGGTTCACGGCTGTCGACGATCTCCAGGAACAAGGATCCGCACACCTC

GGCACGCAAGAATTTTCTTCTGGAGTGTTCTATAGGTATGCCAACATCAACCTTGCACAGCTCCAGGAAA

ACCTCGGTGGGCAAGCCGGGAACAGGCTCTTGAAATAGCTACCCATGTGGTTCACATGCTGGCGACCGA

AGTGCCAGGGGCCAAGGAGAGAACGTACGCCGCATTCAATCCGGCGGACATGGTCATGGTGAATTTCTCT

GATATGCCCTTGTCTATGGCAAATGCTTTCGAGAAGGCGGTCAAGGCAAAGGACGGTTTTTTGCAACCCT

CCATCCAAGCCTTTAATCAGTACTGGGATAGAGTAGCTAACGGGTATGGTCTCAATGGCGCGGCTGCTCA

GTTTTCTTTGTCCGATGTGGATCCGATAACGGCGCAGGTTAAACAGATGCCCACCTTGGAACAACTCAAA

TCCTGGGTTAGAAACAATGGGGAGGCGGGAAGCGGAGTGAAACAGACTTTGAACTTTGACTTGCTCAAGT

TGGCAGGAGACGTGGAGTCCAACCCTGGACCTATGGGATCGGCCATTGAACAAGATGGATTGCACGCAGG

TTCTCCGGCCGCTTGGGTGGAGAGGCTATTCGGCTATGACTGGGCACAACAGACAATCGGCTGCTCTGAT

GCCGCCGTGTTCCGGCTGTCAGCGCAGGGGCGCCCGGTTCTTTTTGTCAAGACCGACCTGTCCGGTGCCC

TGAATGAACTGCAGGACGAGGCAGCGCGGCTATCGTGGCTGGCCACGACGGGCGTTCCTTGCGCAGCTGT

GCTCGACGTTGTCACTGAAGCGGGAAGGGACTGGCTGCTATTGGGCGAAGTGCCGGGGCAGGATCTCCTG

TCATCTCACCTTGCTCCTGCCGAGAAAGTATCCATCATGGCTGATGCAATGCGGCGGCTGCATACGCTTG

ATCCGGCTACCTGCCCATTCGACCACCAAGCGAAACATCGCATCGAGCGAGCACGTACTCGGATGGAAGC

CGGTCTTGTCGATCAGGATGATCTGGACGAAGAGCATCAGGGGCTCGCGCCAGCCGAACTGTTCGCCAGG

CTCAAGGCGCGCATGCCCGACGGCGATGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGACCGCTATCAGGA

CATAGCGTTGGCTACCCGTGATATTGCTGAAGAGCTTGGCGGCGAATGGGCTGACCGCTTCCTCGTGCTT

TACGGTATCGCCGCTCCCGATTCGCAGCGCATCGCCTTCTATCGCCTTCTTGACGAGTTCTTCTGAGAAT

TCGATATCAAGCTTATCGATAATCAACCTCTGGATTACAAAATTTGTGAAAGATTGACTGGTATTCTTAA

CTATGTTGCTCCTTTTACGCTATGTGGATACGCTGCTTTAATGCCTTTGTATCATGCTATTGCTTCCCGT

ATGGCTTTCATTTTCTCCTCCTTGTATAAATCCTGGTTGCTGTCTCTTTATGAGGAGTTGTGGCCCGTTG
```

-continued

```
TCAGGCAACGTGGCGTGGTGTGCACTGTGTTTGCTGACGCAACCCCCACTGGTTGGGGCATTGCCACCAC
CTGTCAGCTCCTTTCCGGGACTTTCGCTTTCCCCCTCCCTATTGCCACGGCGGAACTCATCGCCGCCTGC
CTTGCCCGCTGCTGGACAGGGGCTCGGCTGTTGGGCACTGACAATTCCGTGGTGTTGTCGGGGAAATCAT
CGTCCTTTCCTTGGCTGCTCGCCTGTGTTGCCACCTGGATTCTGCGCGGGACGTCCTTCTGCTACGTCCC
TTCGGCCCTCAATCCAGCGGACCTTCCTTCCCGCGGCCTGCTGCCGGCTCTGCGGCCTCTTCCGCGTCTT
CGCCTTCGCCCTCAGACGAGTCGGATCTCCCTTTGGGCCGCCTCCCCGCATCGATACCGTCGACCTCGAG
ACCTAGAAAAACATGGAGCAATCACAAGTAGCAATACAGCAGCTACCAATGCTGATTGTGCCTGGCTAGA
AGCACAAGAGGAGGAGGAGGTGGGTTTTCCAGTCACACCTCAGGTACCTTTAAGACCAATGACTTACAAG
GCAGCTGTAGATCTTAGCCACTTTTTAAAAGAAAAGGGGGACTGGAAGGGCTAATTCACTCCCAACGAA
GACAAGATATCCTTGATCTGTGGATCTACCACACACAAGGCTACTTCCCTGATTGGCAGAACTACACACC
AGGGCCAGGGATCAGATATCCACTGACCTTTGGATGGTGCTACAAGCTAGTACCAGTTGAGCAAGAGAAG
GTAGAAGAAGCCAATGAAGGAGAGAACACCCGCTTGTTACACCCTGTGAGCCTGCATGGGATGGATGACC
CGGAGAGAGAAGTATTAGAGTGGAGGTTTGACAGCCGCCTAGCATTTCATCACATGGCCCGAGAGCTGCA
TCCGGACTGTACTGGGTCTCTCTGGTTAGACCAGATCTGAGCCTGGGAGCTCTCTGGCTAACTAGGGAAC
CCACTGCTTAAGCCTCAATAAAGCTTGCCTTGAGTGCTTCAAGTAGTGTGTGCCCGTCTGTTGTGTGACT
CTGGTAACTAGAGATCCCTCAGACCCTTTTAGTCAGTGTGGAAAATCTCTAGCA
``` pAP131 nucleotide sequence-LTR to LTR (SEQ ID NO: 46):
```
GGGTCTCTCTGGTTAGACCAGATCTGAGCCTGGGAGCTCTCTGGCTAACTAGGGAACCCACTGCTTAAGC
CTCAATAAAGCTTGCCTTGAGTGCTTCAAGTAGTGTGTGCCCGTCTGTTGTGTGACTCTGGTAACTAGAG
ATCCCTCAGACCCTTTTAGTCAGTGTGGAAAATCTCTAGCAGTGGCGCCCGAACAGGGACTTGAAAGCGA
AAGGGAAACCAGAGGAGCTCTCTCGACGCAGGACTCGGCTTGCTGAAGCGCGCACGGCAAGAGGCGAGGG
GCGGCGACTGGTGAGTACGCCAAAAATTTTGACTAGCGGAGGCTAGAAGGAGAGAGATGGGTGCGAGAGC
GTCAGTATTAAGCGGGGGAGAATTAGATCGCGATGGGAAAAAATTCGGTTAAGGCCAGGGGGAAAGAAAA
AATATAAATTAAAACATATAGTATGGGCAAGCAGGGAGCTAGAACGATTCGCAGTTAATCCTGGCCTGTT
AGAAACATCAGAAGGCTGTAGACAAATACTGGGACAGCTACAACCATCCCTTCAGACAGGATCAGAAGAA
CTTAGATCATTATATAATACAGTAGCAACCCTCTATTGTGTGCATCAAAGGATAGAGATAAAAGACACCA
AGGAAGCTTTAGACAAGATAGAGGAAGAGCAAAACAAAAGTAAGACCACCGCACAGCAAGCGGCCGCTGA
TCTTCAGACCTGGAGGAGCAGATATGAGGGAGAATTGGAGAAGTGAATTATATAAATATAAAGTAGTAAA
AATTGAACCATTAGGAGTAGCACCCACCAAGGCAAAGAGAAGAGTGGTGCAGAGAGAAAAAAGACCAGTG
GGAATAGGAGCTTTGTTCCTTGGGTTCTTGGGAGCAGCAGGAAGCACTATGGGCGCAGCGTCAATGACGC
TGACGGTACAGGCCAGACAATTATTGTCTGGTATAGTGCAGCAGCAGAACAATTTGCTGAGGGCTATTGA
GGCGCAACAGCATCTGTTGCAACTCACAGTCTGGGGCATCAAGCAGCTCCAGGCAAGAATCCTGGCTGTG
GAAAGATACCTAAAGGATCAACAGCTCCTGGGGATTTGGGGTTGCTCTGGAAAACTCATTTGCACCACTG
CTGTGCCTTGGAATGCTAGTTGGAGTAATAAATCTCTGGAACAGATTTGGAATCACACGACCTGGATGGA
GTGGGACAGAGAAATTAACAATTACACAAGCTTAATACACTCCTTAATTGAAGAATCGCAAAACCAGCAA
GAAAAGAATGAACAAGAATTATTGGAATTAGATAAATGGGCAAGTTTGTGGAATTGGTTTAACATAACAA
ATTGGCTGTGGTATATAAAATTATTCATAATGATAGTAGGAGGCTTGGTAGGTTTAAGAATAGTTTTTGC
TGTACTTTCTATAGTGAATAGAGTTAGGCAGGGATATTCACCATTATCGTTTCAGACCCACGTCCCAACC
CCGAGGGGACCCGACAGGCCCGAAGGAATAGAAGAAGAAGGTGGAGAGAGAGACAGAGACAGATCCATTC
GATTAGTGAACGGATCGGCACTGCGTGCGCCAATTCTGCAGACAAATGGCAGTATTCATCCACAATTTTA
AAAGAAAAGGGGGGATTGGGGGGTACAGTGCAGGGGAAAGAATAGTAGACATAATAGCAACAGACATACA
```

-continued

```
AACTAAAGAATTACAAAAACAAATTACAAAAATTCAAAATTTTCGCGTTTATTACAGGGACAGCAGAGAT

CCAGTTTGGTTAATTAAGGGTGCAGCGGCCTCCGCGCCGGGTTTTGGCGCCTCCCGCGGGCCCCCCCCTC

CTCACGGCGAGCGCTGCCACGTCAGACGAAGGGCGCAGGAGCGTTCCTGATCCTTCCGCCCGGACGCTCA

GGACAGCGGCCCGCTGCTCATAAGACTCGGCCTTAGAACCCCAGTATCAGCAGAAGGACATTTTAGGACG

GGACTTGGGTGACTCTAGCGCACTGGTTTTCTTTCCAGAGAGCGGAACAGGCGAGGAAAAGTAGTCCCTT

CTCGGCGATTCTGCGGAGGGATCTCCGTGGGGCGGTGAACGCCGATGATTATATAAGGACGCGCCGGGTG

TSGCACAGCTAGTTCCGTCGCAGCCGGGATTTGGGTCGCGGTTCTTGTTTGTGGATCGCTGTGATCGTCA

CTTGGTGAGTTGCGGGCTCCTGGGCTGGCCGGGGCTTTCGTGGCCCCGGGCCGCTCGGTGGGACGGAAG

CGTGTGGAGAGACCGCCAAGGGCTGTAGTCTGGGTCCGCGAGCAAGGTTGCCCTGAACTGGGGGTTGGGG

GGAGCGCAGGAAATGGCGGCTGTTCCCGAGTCTTGAATGGAAGACGCTTGTAAGGCGGGCTGTGAGGTCG

TTGAAACAACCTGGCGGGCATCCTCGCCCCCAACAACCCAAGGTCTTCACGCCTTCCCTAATCCCGGAAA

GCTCTTATTCCGCTGACATGGCCTGGCGCACCATCTGCGGACCCTGACCTGAACTTTCTCACTCACTGCA

GAACTCGGGTTTGTCGTCTGGTTGCGGGGCGGCAGTTATGCGGTGCCGTTGGGCAGTGCACCCGTACCT

TTGGGAGCGCGCGCCTCGTCGTGTCGTGACGTCACCCGTTCTGTTCGCTTATAATGCAGGGTGGGGCCAC

CTGCCGGTAGGTGTGCGGTAGGCTTTTCTCCGTCGCAGGACGCAGGGTTCGGGCCTAGGGTAGGCTCTCC

TSAATCGACAGGCGCCGGACCTCTGGTGAGGGGAGGGATAAGTGAGGCGTCAGTTTCTTTGGTCGGTTTT

ATGTACCTATCTTCTTAAGTAGCTGAAGCTCCGGTTTTGAACTATGCGCTCGGGGTTGGCGAGTGTGTTT

TGTGAAGTTTTTTAGGCACCTTTTGAAATGTAATCATTTGGGTCAATATGTAATTTTCAGTGTTAGACTA

GTAAATTGTCCGCTAAATTCTGGCCGTTTTTGGCTTTTTTGTTAGACGAAGCTTGGGCTGCAGGTCGACT

CTAGAGGATCCCCGGGTACCGGTCGCCACCGCCGCCACCATGGATTACAAGGACCATGACGGAGATTATA

AGGACCACGACATAGACTATAAGGATGACGATGACAAAATGGCAGATGCTAAGTCACTGACTGCCTGGTC

CCGGACACTGGTGACCTTCAAGGATGTGTTTGTGGACTTCACCAGGGAGGAGTGGAAGCTGCTGGACACT

GCTCAGCAGATCCTGTACAGAAATGTGATGCTGGAGAACTATAAGAACCTGGTTTCCTTGGGTTATCAGC

TTACTAAGCCAGATGTGATCCTCCGGTTGGAGAAGGGAGAAGAGCCCTGGCTGGTGCAGAGAGAAATTCA

CCAAGAGACCCATCCTGATTCAGAGACTGCATTTGAAATCAAATCATCAGTTCCGAAAAAGAAACGCAAA

GTTGGATCCCCAAAGAAGAAACGCAAAGTACGGGGCATGCGATCATACTTGATCCTCCGGCTTGCAGGTC

CTATGCAAGCCTGGGGGCAACCTACCTTTGAAGGTACTCGGCCGACTGGCAGGTTCCCTACGCGGTCTGG

TTTGCTCGGACTCCTCGGCGCCTGTTTGGGGATACAAAGGGATGACACTTCTTCCTTGCAGGCACTTTCC

GAATCAGTCCAGTTCGCAGTGAGATGTGATGAACTCATACTGGACGACAGACGGGTGTCCGTAACTGGAC

TGAGGGACTATCATACTGTACTCGGCGCAAGAGAAGATTATCGAGGTCTTAAGTCACATGAGACTATTCA

GACATGGAGGGAATATTTGTGTGACGCCTCCTTCACGGTGGCCCTCTGGCTTACACCACATGCAACTATG

GTGATCTCAGAGCTTGAGAAAGCCGTTCTTAAACCTCGGTACACACCATATCTGGGGAGGCGGTCTTGCC

CACTTACCCACCCGCTTTTCTTGGGGACTTGTCAGGCCAGCGATCCACAGAAGGCCTTGCTGAACTATGA

ACCCGTTGGTGGCGATATATACAGTGAAGAGAGCGTCACGGGCCATCACTTGAAGTTCACTGCTAGGGAT

GAGCCGATGTTTACGCTCCCGAGACAGTTCGCTAGTAGGGAATGGTACGTTATTAAGGGGGGAATGGACG

TTTCCCAAGGAAGCGGAGCTACTAACTTCAGCCTGCTGAAGCAGGCTGGAGACGTGCACGAGAACCCTGG

ACCTATGGGTGCCCCAGTTCCCTATCCCGACCCACTGGAGCCAAGGATGGCGCCTAAGAAGAAGCGCAAG

GTGCGGGGCATGTATCTCAGTAAAGTCATCATTGCCAGGGCCTGGAGCAGGGATCTTTACCAACTTCACC

AGGGATTATGGCATTTATTTCCAAACAGACCGGATGCTGCTCGTGATTTTCTTTTTCATGTTGAGAAGCG

AAACACACCAGAAGGCTGTCATGTTTTATTGCAGTCAGCGCAAATGCCTGTTTCAACTGCCGTTGCGACA
```

-continued

```
GTCATTAAAACTAAACAGGTTGAATTTCAACTTCAGGTTGGTGTTCCACTCTATTTTCGGCTTCGGGCAA

ATCCGATCAAAACTATTCTCGACAATCAAAAGCGCCTGGACAGTAAAGGGAATATTAAACGCTGTCGGGT

TCCGTTAATAAAAGAAGCAGAACAAATCGCGTGGTTGCAACGTAAATTGGGCAATGCGGCGCGCGTTGAA

GATGTGCATCCCATATCGGAACGGCCACAGTATTTTTCTGGTGATGGTAAAAGTGGAAAGATCCAAACGG

TTTGCTTTGAAGGTGTGCTCACCATCAACGACGCGCCAGCGTTAATAGATCTTGTACAGCAAGGTATTGG

GCCAGCTAAATCGATGGGATGTGGCTTGCTATCTTTGGCTCCACTGGGAAGCGGAGAGGGCAGAGGAAGT

CTTCTCACATGCGGTGACGTGGAGGAGAATCCTGGACCTATGACCGAGTACAAGCCCACGGTGCGCCTCG

CCACCCGCGACGACGTCCCCAGGGCCGTACGCACCCTCGCCGCCGCGTTCGCCGACTACCCCGCCACGCG

CCACACCGTCGATCCGGACCGCCACATCGAGCGGGTCACCGAGCTGCAAGAACTCTTCCTCACGCGCGTC

GGGCTCGACATCGGCAAGGTGTGGGTCGCGGACGACGGCGCCGCGGTGGCGGTCTGGACCACGCGGAGA

GCGTCGAAGCGGGGGCGGTGTTCGCCGAGATCGGCCCGCGCATGGCCGAGTTGAGCGGTTCCCGGCTGGC

CGCGCAGCAACAGATGGAAGGCCTCCTGGCGCCGCACCGGCCCAAGGAGCCCGCGTGGTTCCTGGCCACC

GTCGGCGTCTCGCCCGACCACCAGGGCAAGGGTCTGGGCAGCGCCGTCGTGCTCCCCGGAGTGGAGGCGG

CCGAGCGCGCCGGGGTGCCCGCCTTCCTGGAGACCTCCGCGCCCCGCAACCTCCCCTTCTACGAGCGGCT

CGGCTTCACCGTCACCGCCGACGTCGAGGTGCCCGAAGGACCGCGCACCTGGTGCATGACCCGCAAGCCC

GGTGCCTGAGAATTCGATATCAAGCTTATCGATAATCAACCTCTGGATTACAAAATTTGTGAAAGATTGA

CTGGTATTCTTAACTATGTTGCTCCTTTTACGCTATGTGGATACGCTGCTTTAATGCCTTTGTATCATGC

TATTGCTTCCCGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCCACTGGTTGGG

GCATTGCCACCACCTGTCAGCTCCTTTCCGGGACTTTCGCTTTCCCCCTCCCTATTGCCACGGCGGAACT

CATCGCCGCCTGCCTTGCCCGCTGCTGGACAGGGGCTCGGCTGTTGGGCACTGACAATTCCGTGGTGTTG

TCGGGGAAATCATCGTCCTTTCCTTGGCTGCTCGCCTGTGTTGCCACCTGGATTCTGCGCGGGACGTCCT

TCTGCTACGTCCOPTCGGCCCTCAATCCAGCGGACCTTCCTTCCCGCGGCCTGCTGCCGGCTCTGCGGCC

TCTTCCGCGTCTTCGCCTTCGCCCTCAGACGAGTCGGATCTCCCTTTGGGCCGCCTCCCCGCATCGATAC

CGTCGACCTCGAGACCTAGAAAAACATGGAGCAATCACAAGTAGCAATACAGCAGCTACCAATGCTGATT

GTGCCTGGCTAGAAGCACAAGAGGAGGAGGAGGTGGGTTTTCCAGTCACACCTCAGGTACCTTTAAGACC

AATGACTTACAAGGCAGCTGTAGATCTTAGCCACTTTTTAAAAGAAAAGGGGGGACTGGAAGGGCTAATT

CACTCCCAACGAAGACAAGATATCCTTGATCTGTGGATCTACCACACACAAGGCTACTTCCCTGATTGGC

AGAACTACACACCAGGGCCAGGGATCAGATATCCACTGACCTTTGGATGGTGCTACAAGCTAGTACCAGT

TGAGCAAGAGAAGGTAGAAGAAGCCAATGAAGGAGAGAACACCCGCTTGTTACACCCTGTGAGCCTGCAT

GGGATGGATGACCCGGAGAGAAGTATTAGAGTGGAGGTTTGACAGCCGCCTAGCATTTCATCACATGG

CCCGAGAGCTGCATCCGGACTGTACTGGGTCTCTCTGGTTAGACCAGATCTGAGCCTGGGAGCTCTCTGG

CTAACTAGGGAACCCACTGCTTAAGCCTCAATAAAGCTTGCCTTGAGTGCTTCAAGTAGTGTGTGCCCGT

CTGTTGTGTGACTCTGGTAACTAGAGATCCCTCAGACCCTTTTAGTCAGTGTGGAAAATCTCTAGCA
``` pAP132 nucleotide sequence-LTR to LTR (SEQ ID NO: 47):
```
GGGTCTCTCTGGTTAGACCAGATCTGAGCCTGGGAGCTCTCTGGCTAACTAGGGAACCCACTGCTTAAGC

CTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGA

AAGGGAAACCAGAGGAGCTCTCTCGACGCAGGACTCGGCTTGCTGAAGCGCGCACGGCAAGAGGCGAGGG

GCGGCGACTGGTGAGTACGCCAAAAATTTTGACTAGCGGAGGCTAGAAGGAGAGAGATGGGTGCGAGAGC

GTCAGTATTAAGCGGGGGAGAATTAGATCGCGATGGGAAAAAATTCGGTTAAGGCCAGGGGGAAAGAAAA
```

-continued

```
AATATAAATTAAAACATATAGTATGGGCAAGCAGGGAGCTAGAACGATTCGCAGTTAATCCTGGCCTGTT
AGAAACATCAGAAGGCTGTAGACAAATACTGGGACAGCTACAACCATCCCTTCAGACAGGATCAGAAGAA
CTTAGATCATTATATAATACAGTAGCAACCCTCTATTGTGTGCATCAAAGGATAGAGATAAAAGACACCA
AGGAAGCTTTAGACAAGATAGAGGAAGAGCAAAACAAAAGTAAGACCACCGCACAGCAAGCGGCCGCTGA
TCTTCAGACCTGGAGGAGGAGATATGAGGGACAATTGGAGAAGTGAATTATATAAATATAAAGTAGTAAA
AATTGAACCATTAGGAGTAGCACCCACCAAGGCAAAGAGAAGAGTGGTGCAGAGAGAAAAAAGAGCAGTG
GGAATAGGAGCTTTGTTCCTTGGGTTCTTGGGAGCAGCAGGAAGCACTATGGGCGCAGCGTCAATGACGC
TGACGGTACAGGCCAGACAATTATTGTCTGGTATAGTGCAGCAGCAGAACAATTTGCTGAGGGCTATTGA
GGCGCAACAGCATCTGTTGCAACTCACAGTCTGGGGCATCAAGCAGCTCCAGGCAAGAATCCTGGCTGTG
GAAAGATACCTAAAGGATCAACAGCTCCTGGGGATTTGGGGTTGCTCTGGAAAACTCATTTGCACCACTG
CTGTGCCTTGGAATGCTAGTTGGAGTAATAAATCTCTGGAACAGATTTGGAATCACACGACCTGGATGGA
GTGGACAGAGAAATTAACAATTACACAAGCTTAATACACTCCTTAATTGAAGAATCGCAAAACCAGCAA
GAAAAGAATGAACAAGAATTATTGGAATTAGATAAATGGGCAAGTTTGTGGAATTGGTTTAACATAACAA
ATTGGCTGTGGTATATAAAATTATTCATAATGATAGTAGGAGGCTTGGTAGGTTTAAGAATAGTTTTTGC
TGTACTTTCTATAGTGAATAGAGTTAGGCAGGGATATTCACCATTATCGTTTCAGACCCACCTCCCAACC
CCGAGGGGACCCGACAGGCCCGAAGGAATAGAAGAAGAAGGTGGAGAGAGAGACAGAGACAGATCCATTC
GATTAGTGAACGGATCGGCACTGCGTGCGCCAATTCTGCAGACAAATGGCAGTATTCATCCACAATTTTA
AAAGAAAGGGGGGATTGGGGGGTACAGTGCAGGGGAAAGAATAGTAGACATAATAGCAACAGACATACA
AACTAAAGAATTACAAAAACAAATTACAAAAATTCAAATTTTCGGGTTTATTACAGGGACAGCAGAGAT
CCAGTTTGGTTAATTAAGGGTGCAGCGGCCTCCGCGCCGGGTTTTGGCGCCTCCCGCGGGCGCCCCCCTC
CTCACGGCGAGCGCTGCCACGTCAGACGAAGGGCGCAGGAGCGTTCCTGATCCTTCCGCCCGGACGCTCA
GGACAGCGGCCCGCTGCTCATAAGACTCGGCCTTAGAACCCCAGTATCAGCAGAAGGACATTTTAGGACG
GGACTTGGGTGACTCTAGGGCACTGGTTTTCTTTCCAGAGAGCGGAACAGGCGAGGAAAAGTAGTCCCTT
CTCGGCGATTCTGCGGAGGGATCTCCGTGGGCGGTGAACGCCGATGATTATATAAGGACGCGCCGGGTG
TGGCACAGCTAGTTCCGTCGCAGCCGGGATTTGGGTCGCGGTTCTTGTTTGTGGATCGCTGTGATCGTCA
CTTGGTGAGTTGCGGGCTGCTGGGCTGGCCGGGGCTTTCGTGGCCGCCGGGCCGCTCGGTGGGACGGAAG
CGTGTGGAGAGACCGCCAAGGGCTGTAGTCTGGGTCCGCGAGCAAGGTTGCCCTGAACTGGGGGTTGGGG
GGAGCGCACAAAATGGCGGCTGTTCCCGAGTCTTGAATGGAAGACGCTTGTAAGGCGGGCTGTGAGGTCG
TTGAAACAAGGTGGGGGGCATGGTGGGCGGCAAGAACCCAAGGTCTTGAGGCCTTCGCTAATGCGGGAAA
GCTCTTATTCGGGTGAGATGGGCTGGGGCACCATCTGGGGACCCTGACGTGAAGTTTGTCACTGACTGGA
GAACTCGGGTTTGTCGTCTGGTTGCGGGGCGGCAGTTATGCGGTGCCGTTGGGCAGTGCACCCGTACCT
TTGGGAGCGCGCGCCTCGTCGTGTCGTGACGTCACCCGTTCTGTTGGCTTATAATGCAGGGTGGGGCCAC
CTGCCGGTAGGTGTGCGGTAGGCTTTTCTCCGTCGCAGGACGCAGGGTTCGGGCCTAGGGTAGGCTCTCC
TGAATCGACAGGCGCCGGACCTCTGGTGAGGGAGGGATAAGTGAGGCGTCAGTTTCTTTGGTCGGTTTT
ATGTACCTATCTTCTTAAGTAGCTGAAGCTCCGGTTTTGAACTATGCGCTCGGGTTGGCGAGTGTGTTT
TGTGAAGTTTTTTAGGCACCTTTTGAAATGTAATCATTTGGGTCAATATGTAATTTTCAGTGTTAGACTA
GTAAATTGTCCGCTAAATTCTGGCCGTTTTTGGCTTTTTTGTTAGACGAAGCTTGGGCTGCAGGTCGACT
CTAGAGGATCCCCGGGTACCGGTCGCCACCGCCGCCACCATGGCCTATCCATATGATGTGCCAGATTATG
CCATGGCGCCGAAGAAAAGAGGAAAGTACGGGGCATGCGATCATACTTGATCCTGCGGCTTGCAGGTCC
TATGCAAGCCTGGGGGCAACCTACCTTTGAAGGTACTCGGCCGACTGGCAGGTTCCCTACGCGGTCTGGT
TTGCTCGGACTCCTCGGCGCCTGTTTGGGGATACAAAGGGATGACACTTCTTCCTTGCAGGCACTTTCCG
```

-continued

```
AATCAGTCCAGTTCGCAGTGAGATGTGATGAACTCATACTGGACGACAGACGGGTGTCCGTAACTGGACT
GAGGGACTATCATACTGTACTCGGCGAAGAGAAGATTATCGAGGTCTTAAGTCACATGAGACTATTCAG
ACATGGAGGGAATATTTGTGTGACGCCTCCTTCACGGTGGCCCTCTGGCTTACACCACATGCAACTATGG
TGATCTCAGAGCTTGAGAAAGCCGTTCTTAAACCTCGGTACACACCATATCTGGGGAGGCGGTCTTGCCC
ACTTACCCACCCGCTTTTCTTGGGGACTTGTCAGGCCAGCGATCCACAGAAGGCCTTGCTGAACTATGAA
CCCGTTGGTGGCGATATATACAGTGAAGAGCGTCACGGGCCATCACTTGAAGTTCACTGCTAGGGATG
AGCCGATGATTACGCTCCCGAGACAGTTCGCTAGTAGGGAATGGTACGTTATTAAGGGGGGAATGGACGT
TTCCCAAGGAAGCGGAGCTACTAACTTCAGCCTGCTGAAGCAGGCTGGAGACGTGGAGGAGAACCCTGGA
CCTATGGATTACAAGGACCATGACGGAGATTATAAGGACCACGACATAGACTATAAGGATGACGATGACA
AAATGGCAGATGCTAAGTCACTGACTGCCTGGTCCCGGACACTGGTGACCTTCAAGGATGTGTTTGTGGA
CTTCACCAGGGAGGAGTGGAAGCTGCTGGACACTGCTCAGCAGATCCTGTACAGAAATGTGATGCTGGAG
AACTATAAGAACCTGGTTTCCTTGGGTTATCAGCTTACTAAGCCAGATGTGATCCTCCGGTTGGAGAAGG
GAGAAGAGCCCTGGCTGGTGGAGAGAGAAATTCACCAAGAGACCCATCCTGATTCAGAGACTGCATTTGA
AATCAAATCATCAGTTCCGAAAAAGAAACGCAAAGTTGGATCCCCAAAGAAGAAACGCAAGGTGCGGGGC
ATGTATCTCAGTAAAGTCATCATTGCCAGGGCCTGGAGCAGGGATCTTTACCAACTTCACCAGGGATTAT
GGCATTTATTTCCAAACAGACCGGATGCTGCTCGTGATTTTCTTTTTCATGTTGAGAAGCGAAACACACC
AGAAGGCTGTCATGTTTTATTGCAGTCAGCGCAAATGCCTGTTTCAACTGCCGTTGCGACAGTCATTAAA
ACTAAACAGGTTGAATTTCAACTTCAGGTTGGTGTTCCACTOTATTTTCGGCTTOGGGCAAATCCGATCA
AAACTATTCTCGACAATCAAAAGCGCCTGGACAGTAAAGGGAATATTAAACGCTGTCGGGTTCCGTTAAT
AAAAGAAGCAGAACAAATCGCGTGGTTGCAACGTAAATTGGGCAATGCGGCGCGCGTTGAAGATGTGCAT
CCCATATCGGAACGGCCACAGTATTTTTCTGGTGATGGTAAAAGTGGAAAGATCCAAACGGTTTGCTTTG
AAGGTGTGCTCACCATCAACGACGCGCCAGCGTTAATAGATOTTGTACAGCAAGGTATTGGGCCAGCTAA
ATCGATGGGATGTGGCTTGCTATCTTTGGCTCCACTGGGAAGCGGAGAGGGCAGAGGAAGTCTTCTCACA
TGCGGTGACGTGGAGGAGAATCCTGGACCTATGACCGAGTACAAGCCCACGGTGCGCCTCGCCACCCGCG
ACGACGTCCCCAGGGCCGTACGCACCCTCGCCGCCGCGTTCGCCGACTACCCCGCCACGCGCCACACCGT
CGATCCGGACCGCCACATCGAGCGGGTCACCGAGCTGCAAGAACTCTTCCTCACGCGCGTCGGGCTCGAC
ATCGGCAAGGTGTGGGTCGCGGACGACGGCGCCGCGGTGGCGGTCTGGACCACGCCGGAGAGCGTCGAAG
CGGGGGCGGTGTTCGCCGAGATCGGCCCGCGCATGGCCGAGTTGAGCGGTTCCCGGCTGGCCGCGCAGCA
ACAGATGGAAGGCCTCCTGGCGCCGCACCGGCCCAAGGAGCCCGCGTGGTTCCTGGCCACCGTCGGCGTC
TCGCCCGACCACCAGGGCAAGGGTCTGGGCAGCGCCGTCGTGCTCCCCGGAGTGGAGGCGGCCGAGCGCG
CCGGGGTGCCCGCCTTCCTGGAGACCTCCGCGCCCCGCAACCTCCCCTTCTACGAGCGGCTCGGCTTCAC
CGTCACCGCCGACGTCGAGGTGCCCGAAGGACCGCGCACCTGGTGCATGACCCGCAAGCCCGGTGCCTGA
GAATTCGATATCAAGCTTATCGATAATCAACCTCTGGATTACAAAATTTGTGAAAGATTGACTGGTATTC
TTAACTATGTTGCTCCTTTTACGCTATGTGGATACGCTGCTTTAATGCCTTTGTATCATGCTATTGCTTC
CCGTATGGCTTTCATTTTCTCCTCCTTGTATAAATCCTGGTTGCTGTCTCTTTATGAGGAGTTGTGGCCC
GTTGTCAGGCAACGTGGCGTGGTGTGCACTGTGTTTGCTGACGCAACCCCCACTGGTTGGGCATTGCCA
CCACCTGTCAGCTCCTTTCCGGGACTTTCGCTTTCCCCCTCCCTATTGCCACGGCGGAACTCATCGCCGC
CTGCCTTGCCCGCTGCTGGACAGGGGCTCGGCTGTTGGGCACTGACAATTCCGTGGTGTTGTCGGGGAAA
TCATCGTCCTTTCCTTGGCTGCTCGCCTGTGTTGCCACCTGGATTCTGCGCGGGACGTCCTTCTGCTACG
TCCCTTCGGCCCTCAATCCAGCGGACCTTCCTTCCCGCGGCCTGCTGCCGGCTCTGCGGCCTCTTCCGCG
```

-continued

```
TCTTCGCCTTCGCCCTCAGACGAGTCGGATCTCCCTTTGGGCCGCCTCCCCGCATCGATACCGTCGACCT

CGAGACCTAGAAAAACATGGAGCAATCACAAGTAGCAATACAGCAGCTACCAATGCTGATTGTGCCTGGC

TAGAAGCACAAGAGGAGGAGGAGGTGGGTTTTCCAGTCACACCTCAGGTACCTTTAAGACCAATGACTTA

CAAGGCAGCTGTAGATCTTAGCCACTTTTTAAAAGAAAAGGGGGACTGGAAGGGCTAATTCACTCCCAA

CGAAGACAAGATATCCTTGATCTGTGGATCTACCACACACAAGGCTACTTCCCTGATTGGCAGAACTACA

CACCAGGGCCAGGGATCAGATATCCACTGACCTTTGGATGGTGCTACAAGCTAGTACCAGTTGAGCAAGA

GAAGGTAGAAGAAGCCAATGAAGGAGAGAACACCCGCTTGTTACACCCTGTGAGCCTGCATGGGATGGAT

GACCCGGAGAGAGAAGTATTAGAGTGGAGGTTTGACAGCCGCCTAGCATTTCATCACATGGCCCGAGAGC

TGCATCCGGACTGTACTGGGTCTCTCTGGTTAGACCAGATCTGAGCCTGGGAGCTCTCTGGCTAACTAGG

GAACCCACTGCTTAAGCCTCAATAAAGCTTGCCTTGAGTGCTTCAAGTAGTGTGTGCCCGTCTGTTGTGT

GACTCTGGTAACTAGAGATCCCTCAGACCCTTTTAGTCAGTGTGGAAAATCTCTAGCA
```

What is claimed is:

1. A composition for genome engineering a target gene in a eukaryotic cell, the composition comprising:
   a. a polynucleotide sequence encoding:
      i. a Cascade complex comprising a Cse1 polypeptide, a Cse2 polypeptide, a Cas7 polypeptide, a Cas5 polypeptide, and a Cas6e polypeptide,
      wherein the polynucleotide sequence encoding the Cse1 polypeptide comprises the polynucleotide sequence of SEQ ID NO: 23, the polynucleotide sequence encoding the Cse2 polypeptide comprises the polynucleotide sequence of SEQ ID NO: 24, the polynucleotide sequence encoding the Cas7 polypeptide comprises the polynucleotide sequence of SEQ ID NO: 25, the polynucleotide sequence encoding the Cas5 polypeptide comprises the polynucleotide sequence of SEQ ID NO: 26, and the polynucleotide sequence encoding the Cas6e polypeptide comprises the polynucleotide sequence of SEQ ID NO: 27; and
      ii. a polypeptide domain, wherein the polypeptide domain comprises transcription activation activity, transcription repression activity, transcription release factor activity, histone modification activity, nuclease activity, nucleic acid association activity, methylase activity, or demethylase activity; and
   b. a pharmaceutically acceptable carrier.

2. The composition of claim 1, wherein the polypeptide domain is fused to a N terminus or a C terminus of the Cse1 polypeptide, the Cse2 polypeptide, the Cas7 polypeptide, the Cas5 polypeptide, or the Cas6e polypeptide of the Cascade complex.

3. The composition of claim 1, wherein the Cascade complex is associated with the polypeptide domain via a linker.

4. The composition of claim 1, wherein the polypeptide domain has transcription activation activity.

5. The composition of claim 4, wherein the polypeptide domain comprises at least one VP16 transcription activation domain repeat.

6. The composition of claim 4, wherein the polypeptide domain comprises a p300 core domain, VP16 tetramer ("VP64"), or a p65 activation domain.

7. The composition of claim 1, wherein the polypeptide domain has transcription repression activity.

8. The composition of claim 7, wherein the polypeptide domain comprises a KRAB domain.

9. The composition of claim 1, wherein the polypeptide domain has methylase activity.

10. The composition of claim 1, wherein the polypeptide domain has demethylase activity.

11. The composition of claim 1, wherein the polynucleotide sequence further encodes a Cas3 polypeptide.

12. The composition of claim 11, wherein the Cas3 polypeptide is mutated such that the helicase, and/or exonuclease activity is inactivated.

13. The composition of claim 1, wherein the polynucleotide sequence further encodes a crRNA, wherein the crRNA targets a target nucleotide sequence from the target gene.

14. The composition of claim 1, wherein the polynucleotide sequence is operably linked to a eukaryotic promoter.

15. The composition of claim 11, wherein the Cas3 polypeptide comprises the amino acid sequence of SEQ ID NO: 15, SEQ ID NO: 17, or SEQ ID NO: 19.

16. A method of killing a eukaryotic cell, the method comprising introducing into the eukaryotic cell the composition of claim 1.

17. The method of claim 16, wherein the polynucleotide sequence further encodes a Cas3 polypeptide.

* * * * *

UNITED STATES PATENT AND TRADEMARK OFFICE
CERTIFICATE OF CORRECTION

PATENT NO. : 11,970,710 B2
APPLICATION NO. : 15/766912
DATED : April 30, 2024
INVENTOR(S) : Gersbach et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 505 days.

Signed and Sealed this
Thirteenth Day of May, 2025

Coke Morgan Stewart
*Acting Director of the United States Patent and Trademark Office*